US008623999B2

(12) United States Patent
Steward et al.

(10) Patent No.: US 8,623,999 B2
(45) **Date of Patent: *Jan. 7, 2014**

(54) MODIFIED CLOSTRIDIAL TOXINS WITH ENHANCED TARGETING CAPABILITIES FOR ENDOGENOUS CLOSTRIDIAL TOXIN RECEPTOR SYSTEMS

(75) Inventors: Lance E. Steward, Irvine, CA (US); Ester Fernandez-Salas, Fullerton, CA (US); Joseph Francis, Aliso Viejo, CA (US); Shengwen Li, Irvine, CA (US); Marcella A. Gilmore, Santa Ana, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,422

(22) Filed: Feb. 27, 2012

(65) Prior Publication Data

US 2012/0178140 A1 Jul. 12, 2012

Related U.S. Application Data

(63) Continuation of application No. 11/908,349, filed as application No. PCT/US2006/008956 on Mar. 14, 2006, now Pat. No. 8,128,940.

(60) Provisional application No. 60/662,151, filed on Mar. 15, 2005, provisional application No. 60/661,953, filed on Mar. 15, 2005.

(51) Int. Cl.

| | |
|---|---|
| ***C07K 14/33*** | (2006.01) |
| ***C12N 15/63*** | (2006.01) |
| ***C07H 21/04*** | (2006.01) |

(52) U.S. Cl.

USPC .... 530/350; 435/69.7; 435/252.3; 435/320.1; 536/23.2

(58) Field of Classification Search

USPC .................. 424/239.1, 236.1; 536/23.7, 23.2; 514/21.2; 530/350; 435/252.7, 69.7, 435/252.3, 320.1

See application file for complete search history.

(56) References Cited

U.S. PATENT DOCUMENTS

| | | | | |
|---|---|---|---|---|
| 5,364,791 A | | 11/1994 | Vegeto | |
| 5,437,291 A | | 8/1995 | Pasricha | |
| 5,464,758 A | | 11/1995 | Gossen | |
| 5,514,578 A | | 5/1996 | Hogness | |
| 5,670,484 A | | 9/1997 | Binder | |
| 5,714,469 A | | 2/1998 | DeMarsh | |
| 5,814,618 A | | 9/1998 | Bujard | |
| 5,874,534 A | | 2/1999 | Vegeto | |
| 5,935,934 A | | 8/1999 | Vegeto | |
| 6,063,768 A | | 5/2000 | First | |
| 6,113,915 A | | 9/2000 | Aoki | |
| 6,139,845 A | | 10/2000 | Donovan | |
| 6,143,306 A | | 11/2000 | Donovan | |
| 6,245,531 B1 | | 6/2001 | Hogness | |
| 6,261,572 B1 | | 7/2001 | Donovan | |
| 6,265,379 B1 | | 7/2001 | Donovan | |
| 6,299,893 B1 | | 10/2001 | Schwartz | |
| 6,306,403 B1 | | 10/2001 | Donovan | |
| 6,319,505 B1 | | 11/2001 | Aoki | |
| 6,337,075 B1 | | 1/2002 | Donovan | |
| 6,358,917 B1 | | 3/2002 | Carruthers | |
| 6,358,926 B2 | | 3/2002 | Donovan | |
| 6,368,605 B1 | | 4/2002 | Donovan | |
| 6,416,765 B1 | | 7/2002 | Donovan | |
| 6,423,319 B1 | | 7/2002 | Brooks | |
| 6,458,365 B1 | | 10/2002 | Aoki | |
| 6,464,986 B1 | | 10/2002 | Aoki | |
| 6,565,870 B1 | | 5/2003 | Donovan | |
| 6,620,415 B2 | | 9/2003 | Donovan | |
| 6,623,742 B2 | | 9/2003 | Voet | |
| 6,641,820 B1 | | 11/2003 | Donovan | |
| 6,683,049 B1 | | 1/2004 | Aoki | |
| 6,740,321 B1 | | 5/2004 | Donovan | |
| 6,767,544 B2 | | 7/2004 | Brooks | |
| 6,776,992 B2 | | 8/2004 | Aoki | |
| 6,827,931 B1 | | 12/2004 | Donovan | |
| 6,838,434 B2 | | 1/2005 | Voet | |
| 6,869,610 B2 | | 3/2005 | Aoki | |
| 6,872,397 B2 | | 3/2005 | Aoki | |
| 7,811,584 B2 | * | 10/2010 | Steward et al. | 424/239.1 |
| 7,985,411 B2 | * | 7/2011 | Dolly et al. | 424/239.1 |
| 8,128,940 B2 | * | 3/2012 | Steward et al. | 424/239.1 |
| 8,273,865 B2 | * | 9/2012 | Steward et al. | 536/23.7 |

(Continued)

FOREIGN PATENT DOCUMENTS

| | | |
|---|---|---|
| WO | 2005-027917 | 3/2005 |
| WO | 2005-082096 | 9/2005 |
| WO | 2006-011966 | 2/2006 |

OTHER PUBLICATIONS

Arndt, Joseph et al, The Structure of the Neurotoxin-associated Protein HA33/A from *Clostridium botulinum* Suggests a Reoccurring β-Trefoil Fold in the Progenitor Toxin Complex, J. Mol. Biol., 2005, 1083-1093, 346.
Ausubel, Frederick et al, Current Protocols in Molecular Biology, John Wiley & Sons, 2004, 16 pages, 1.
Benihoud, Karim et al, Adenovirus Vectors for Gene Delivery, Current Opinion in Biotechnology, 1999, 440-447, 10.
Biewenga, Jeike et al, Plasmid-Mediated Gene Transfer in Neurons Using the Biolistics Technique, Journal of Neuroscience Methods, 1997, 67-75, 71.
Blesch, Armin, Lentiviral and MLV Based Retroviral Vectors for Ex Vivo and in Vivo Gene Transfer, Methods, 2004, 164-172, 33.
Brych, Stephen et al, Structure and Stability Effects of Mutations Designed to Increase the Primary Sequence Symmetry Within the Core Region of a β-Trefoil, Protein Science, 2001, 2587-2599, 10.
Bueler, Hansruedi, Adeno-Associated Viral Vectors for Gene Transfer and Gene Therapy, Biol. Chem., 1999, 613-622, 380 (6).
Burton, Edward et al, Gene Delivery Using Herpes Simplex Virus Vectors, DNA and Cell Biol., 2002, 915-936, 21 (12).

(Continued)

*Primary Examiner* — Chih-Min Kam

(74) *Attorney, Agent, or Firm* — Kenton Abel; Ted Chan; Debra Condino

(57) ABSTRACT

The specification discloses modified Clostridial toxins comprising a Clostridial toxin enzymatic domain, a Clostridial toxin translocation domain and an enhanced Clostridial toxin binding domain; polynucleotide molecules encoding such modified Clostridial toxins; and method of producing such modified Clostridial toxins.

3 Claims, 6 Drawing Sheets

(56) References Cited

U.S. PATENT DOCUMENTS

| | | | |
|---|---|---|---|
| 2002/0010138 | A1 | 1/2002 | Aoki |
| 2003/0027752 | A1 | 2/2003 | Steward |
| 2003/0211121 | A1 | 11/2003 | Donovan |
| 2003/0219462 | A1 | 11/2003 | Steward |
| 2004/0013692 | A1 | 1/2004 | Aoki |
| 2004/0037852 | A1 | 2/2004 | Aoki |
| 2004/0062776 | A1 | 4/2004 | Voet |
| 2004/0072276 | A1 | 4/2004 | Koltermann |
| 2004/0086531 | A1 | 5/2004 | Barron |
| 2004/0115139 | A1 | 6/2004 | Katz |
| 2004/0115727 | A1 | 6/2004 | Steward |
| 2004/0126396 | A1 | 7/2004 | Aoki |
| 2004/0151740 | A1 | 8/2004 | Aoki |
| 2004/0175399 | A1 | 9/2004 | Schiffman |
| 2004/0180061 | A1 | 9/2004 | Donovan |
| 2004/0220386 | A1 | 11/2004 | Steward |
| 2004/0234532 | A1 | 11/2004 | First |
| 2004/0253274 | A1 | 12/2004 | Voet |
| 2005/0031648 | A1 | 2/2005 | Brin |

OTHER PUBLICATIONS

De Jong, Lutea A.A. et al, Receptor-Ligand Binding Assays: Technologies and Applications, J of Chromatography B, 2005, 1-25, 829.
Depiereux, Eric et al, Match-Box: A Fundamentally New Algorithm for the Simultaneous Alignment of Several Protein Sequences, CABIOS, 1992, 501-509, 8 (5).
Dong, Min et al, Synaptotagmins I and II Mediate Entry of Botulinum Neurotoxin B Into Cells, J of Cell Biology, 2003, 1293-1303, 162 (7).
Doyle, A. et al, Cell & Tissue Culture: Laboratory Procedures, John Wiley & Sons, 1998, 18 pages, 1.
Edgar, Robert, Muscle: Multiple Sequence Alignment with High Accuracy and High Throughput, Nucleic Acids Research, 2004, 1792-1797, 32(5).
Ehrengruber, Markus, Alphaviral Gene Transfer in Neurobiology, Brain Res. Bull., 2002, 13-22, 59 (1).
Federico, Maurizio, From Lentiviruses to Lentivirus Vectors, Methods in Molecular Biology, 2003, 17 pages, 229.
Fernandez, Joseph et al, Gene Expression Systems: Using Nature for the Art of Expression, 1999, 8 pages, Academic Press.
Freshney, R., Culture of Animal Cells A Manual of Basic Technique, Wiley-Liss, 2004, 10 pages, 4.
Frolov, Ilya et al, Alphavirus-Based Expression Vectors: Strategies and Applications, Proc. Natl. Acad. Sci. USA, 1996, 11371-11377, 93 (21).
Ginalski, Krzysztof et al, Structure-Based Sequence Alignment for the β-Trefoil Subdomain of the Clostridial Neurotoxin Family Provides Residue Level Information About the Putative Ganglioside Binding Site, FEBS Letters, 2000, 119-124, 482.
Golzio, M. et al, In Vitro and In Vivo Electric Field-Mediated Permeabilization, Gene Transfer, and Expression, Methods, 2004, 126-135, 33 (2).
Goosen, Mattheus et al, Insect Cell Culture Engineering, Marcel Dekker, Inc., 1993, 4 Pages, 1.
Gotoh, Osamu, Significant Improvement in Accuracy of Multiple Protein Sequence Alignments by Iterative Refinement as Assessed by Reference to Structural Alignments, J. Mol. Biol., 1996, 823-838, 264.
Grandi, Paola et al, Targeting HSV Amplicon Vectors, Methods, 2004, 179-186, 33 (2).
Gresch, Oliver et al, New Non-Viral Method for Gene Transfer Into Primary Cells, Methods, 2004, 151-163, 33 (2).
Harlow, Ed. et al, Antibodies A Laboratory Manual, Cold Spring Harbor Lab., 1988, 3 pages, 1.
Harrison, Maureen et al, General Techniques of Cell Culture, 1997, 3 Pages, Cambridge University Press.
Hermens, Wim et al, Transient Gene Transfer to Neurons and Glia: Analysis of Adenoviral Vector Performance in the CNS and PNS, J of Neuroscience Methods, 1997, 85-98, 71 (1).
Higgins, S.J. et al, Protein Expression A Practical Approach, Oxford University, 1999, 8 pages, 1.
Humeau, Yann et al, How Botulinum and Tetanus Neurotoxins Block Neurotransmitter Release, Biochimie, 2000, 427-446, 82.
Huser, Andreas et al, Baculovirus Vectors: Novel Mammalian Cell Gene-Delivery Vehicles and Their Applications, Am J Pharmacogonomics, 2003, 53-63, 3(1).
Inoue, Kaoru et al, Structural Analysis by X-Ray Crystallography and Calorimetry of a Haemagglutinin Component (HA1) of the Progenitor Toxin From *Clostridium botulinum*, Microbiology, 2003, 3361-3370, 149 (12).
Johnson, Eric et al, *Clostridium botulinum* and Its Neurotoxins: a Metabolic and Cellular Perspective, Toxicon, 2001, 1703-1722, 39.
Jordan, Martin et al, Transfection of Adherent and Suspended Cells by Calcium Phosphate, Methods, 2004, 136-143, 33 (2).
Kim, Jaewon et al, Alternative Type I and I' Turn Conformations in the β8/β9 β-Hairpin of Human Acidic Fibroblast Growth Factor, Protein Science, 2002, 459-466, 11.
Kim, Jaewon et al, Sequence Swapping Does Not Result in Conformation Swapping for the β4/β5 and β8/β9 β-Hairpin Turns in Human Acidic Fibroblast Growth Factor, Protein Science, 2005, 351-359, 14.
Kortemme, Tanja et al, Computational Design of Protein-Protein Interactions, Current Opin. Chem. Biol., 2004, 91-97, 8 (1).
Kortemme, Tanja et al, Computational Redesign of Protein-Protein Interaction Specificity, Nature Structural & Molecular Biology, 2004, 371-379, 11 (4).
Kost, Thomas et al, Recombinant Baculoviruses as Mammalian Cell Gene-Delivery Vectors, Trends in Biotechnology, 2002, 173-180, 20 (4).
Lai, Chooi et al, Adenovirus and Adeno-Associated Virus Vectors, DNA Cell Biol., 2002, 895-913, 21 (12).
Lalli, Giovanna et al, The Journey of Tetanus and Botulinum Neurotoxins in Neurons, TRENDS in Microbiology, Sep. 2003, 431-437, 11 (9).
Lawrence, Charles et al, Detecting Subtle Sequence Signals: A Gibbs Sampling Strategy for Multiple Alignment, Science, Oct. 8, 1993, 208-214, 262 (5131).
Lipham, William, Cosmetic and Clinical Applications of Botulinum Toxin, Slack, 2004, 2 pages, 1.
Martin, Loic et al, Rational Design of a CD4 Mimic That Inhibits HIV-1 Entry and Exposes Cryptic Neutralization Epitopes, Nat. Biotechnol., 2003, 71-76, 21 (1).
Masters, John, Animal Cell Culture A Practical Approach, Oxford University, 2000, 7 pages, 3
Mizuguchi, Hiroyuki et al, Approaches for Generating Recombinant Adenovirus Vectors, Adv. Drug Del., 2001, 165-176, 52 (3).
Morgenstern, Burkhard et al, Multiple DNA and Protein Sequence Alignment Based on Segment-to-Segment Comparison, Proc Natl Acad Sci, Oct. 1996, 12098-12103, 93.
Naldini, Luigi et al, in Vivo Gene Delivery and Stable Transduction of Nondividing Cells by a Lentiviral Vector, Science, 1996, 263-267, 272.
Notredame, Cedric et al, T-Coffee: A Novel Method for Fast and Accurate Multiple Sequence Alignment, J. Mol. Biol., 2000, 205-217, 302.
O'Brien, John et al, Biolistic and Diolistic Transfection: Using the Gene Gun to Deliver DNA and Lipophilic Dyes Into Mammalian Cells, Methods, 2004, 121-125, 33 (2).
Orengo, Christine et al, Protein Superfamilies and Domain Superfolds, Nature, Dec. 1994, 631-634, 372.
Poeschla, Eric, Non-Primate Lentiviral Vectors, Current Opinion in Molecular Therapeutics, 2003, 529-540, 5(5).
Powers, C.J. et al, Fibroblast Growth Factors, Their Receptors and Signaling, Endocrine-Related Cancer, 2000, 165-197, 7.
Raffestin, Stephanie et al, Organization and Regulation of the Neurotoxin Genes in *Clostridium botulinum* and *Clostridium tetani*, Anaerobe, 2004, 93-100, 10.
Rai, Meena et al, Expression Systems for Production of Heterologous Proteins, Current Science, 2001, 1121-1128, 80 (9).
Recillas-Targa, Felix, Gene Transfer and Expression in Mammalian Cell Lines and Transgenic Animals, Methods in Molecular Biology, 2004, 417-433, 267.
Reuss, Bernhard et al, Fibroblast Growth Factors and Their Receptors in the Central Nervous System, Cell Tissue Res, 2003, 139-157, 313.

(56) References Cited

OTHER PUBLICATIONS

Rummel, Andreas et al, Synaptotagmins I and II Act as Nerve Cell Receptors for Botulinum Neurotoxin G, J . Biol. Chem., 2004, 30865-30870, 279 (29).
Rummel, Andreas et al, The Hcc-Domain of Botulinum Neurotoxins A and B Exhibits a Singular Ganglioside Binding Site Displaying Serotype Specific Carbohydrate Interaction, Molecular microbiology, 2004, 632-643m 51(3).
Sambrook, Joseph et al, Introducing Cloned Genes Into Cultured Mammalian Cells, Molecular Cloning, 2001, 16.1-16.62, 3rd Edition, vol. 3.
Sambrook, Joseph et al, Molecular Cloning A Laboratory Manual, 2001, 2 pages, 3rd Edition, vol. 1.
Sambrook, Joseph et al, Molecular Cloning: A Laboratory Manual, 2000, 17.90-17.94, 3rd Edition, vol. 3.
Sarkar, Casim et al, Rational Cytokine Design for Increased Lifetime and Enhanced Potency Using pH-Activated “Histidine Switching”, Nature Biotechnology, Sep. 2002, 908-913, 20.
Shimaoka, Motomu et al, Computational Design of an Integrin I Domain Stabilized in the Open High Affinity Conformation, Nat. Struct. Biol., 2000, 674-678, 7 (8).
Subramanian, Amarendran et al, Dialign-T: An Improved Algorithm for Segment-Based Multiple Sequence Alignment, BMC Bioinformatics, 2005, 13 Pages, 6(66).
Thompson, Julie et al, Clustal W: Improving the Sensitivity of Progressive Multiple Sequence Alignment Through Sequence Weighting, Position-Specific Gap Penalties and Weight Matrix Choice, Nucleic Acids Research, 1994, 4673-4680, 22(22).
Tonini, Tiziana et al, Transient Production of Retroviral- and Lentiviral-Based Vectors for the Transduction of Mammalian Cells, Methods in Molecular Biology, 2004, 141-148, 285.
Tuton, Kathryn et al, Botulinum and Tetanus Neurotoxins: Structure, Function and Therapeutic Utility, TRENDS in Biochemical Sciences, Nov. 2002, 552-558, 27(11).
Vlak, J.M. et al, Insect Cell Cultures: Fundamental and Applied Aspects, Kluwer Academic, 1996, 5 pages, 1.
Walle, Ivo et al, Align-m—a New Algorithm for Multiple Alignment of Highly Divergent Sequences, Bioinformatics, 2004, 1428-1435, 20 (9).
Wolkowicz, Roland et al, Lentiviral Vectors for the Delivery of DNA into Mammalian Cells, Methods in Molecular Biology, 2004, 391-411, 246.
Yuan, Ling et al, Laboratory-Directed Protein Evolution, Microbiol. Mol. Biol. Rev., 2005, 373-392, 69 (3).
Zhang, Chun et al, Polyethylenimine Strategies for Plasmid Delivery to Brain-Derived Cells, Methods, 2004, 144-150, 33 (2).
Zhou, Yu et al, Hemagglutinin-33 of Type a Botulinum Neurotoxin Complex Binds With Synaptotagmin II, FEBS Journal, 2005, 2717-2726, 272.

* cited by examiner

```
                              SEQUENCE LISTING


<160> NUMBER OF SEQ ID NOS: 86

<210> SEQ ID NO 1
<211> LENGTH: 1296
<212> TYPE: PRT
<213> ORGANISM: Clostridium botulinum serotype A

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110
```

```
Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540
```

```
Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
```

```
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295


<210> SEQ ID NO 2
<211> LENGTH: 1291
<212> TYPE: PRT
<213> ORGANISM: Clostridium botulinum serotype B

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
```

```
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480
```

```
Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910
```

```
Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
        995                 1000                1005

Asn Asn Leu Asn Asn Ala Lys Ile Tyr Ile Asn Gly Lys Leu Glu Ser
    1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
        1155                1160                1165

Leu Asp Phe Phe Asn Leu Asn Gln Glu Trp Arg Val Tyr Thr Tyr Lys
    1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
        1235                1240                1245

Val Phe Glu Glu Tyr Lys Asp Tyr Phe Cys Ile Ser Lys Trp Tyr Leu
    1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
                1285                1290
```

<210> SEQ ID NO 3
<211> LENGTH: 1291
<212> TYPE: PRT
<213> ORGANISM: Clostridium botulinum serotype C1

<400> SEQUENCE: 3

-continued

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
```

```
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845
```

```
Phe Ser Tyr Thr Asn Asn Ser Leu Leu Lys Asp Ile Ile Asn Glu Tyr
    850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
    930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
        995                 1000                1005

Phe Val Thr Val Thr Asn Asn Met Met Gly Asn Met Lys Ile Tyr Ile
    1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
                1045                1050                1055

Gly Leu Ile Thr Ser Asp Ser Asp Asn Ile Asn Met Trp Ile Arg Asp
            1060                1065                1070

Phe Tyr Ile Phe Ala Lys Glu Leu Asp Gly Lys Asp Ile Asn Ile Leu
        1075                1080                1085

Phe Asn Ser Leu Gln Tyr Thr Asn Val Val Lys Asp Tyr Trp Gly Asn
    1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
                1125                1130                1135

Arg Asn Asn Asn Asp Phe Asn Glu Gly Tyr Lys Ile Ile Ile Lys Arg
            1140                1145                1150

Ile Arg Gly Asn Thr Asn Asp Thr Arg Val Arg Gly Gly Asp Ile Leu
        1155                1160                1165

Tyr Phe Asp Met Thr Ile Asn Asn Lys Ala Tyr Asn Leu Phe Met Lys
    1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
                1205                1210                1215

Gln Ile Gln Pro Met Asn Asn Thr Tyr Tyr Tyr Ala Ser Gln Ile Phe
            1220                1225                1230

Lys Ser Asn Phe Asn Gly Glu Asn Ile Ser Gly Ile Cys Ser Ile Gly
        1235                1240                1245

Thr Tyr Arg Phe Arg Leu Gly Gly Asp Trp Tyr Arg His Asn Tyr Leu
    1250                1255                1260

Val Pro Thr Val Lys Gln Gly Asn Tyr Ala Ser Leu Leu Glu Ser Thr
1265                1270                1275                1280
```

```
Ser Thr His Trp Gly Phe Val Pro Val Ser Glu
                1285                1290


<210> SEQ ID NO 4
<211> LENGTH: 1276
<212> TYPE: PRT
<213> ORGANISM: Clostridium botulinum serotype D

<400> SEQUENCE: 4

Met Thr Trp Pro Val Lys Asp Phe Asn Tyr Ser Asp Pro Val Asn Asp
 1               5                  10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365
```

```
Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
```

```
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
    850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
        915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
        995                 1000                1005

Asn Asn Ile Met Gly Tyr Met Lys Leu Tyr Ile Asn Gly Glu Leu Lys
    1010                1015                1020

Gln Ser Gln Lys Ile Glu Asp Leu Asp Glu Val Lys Leu Asp Lys Thr
1025                1030                1035                1040

Ile Val Phe Gly Ile Asp Glu Asn Ile Asp Glu Asn Gln Met Leu Trp
                1045                1050                1055

Ile Arg Asp Phe Asn Ile Phe Ser Lys Glu Leu Ser Asn Glu Asp Ile
            1060                1065                1070

Asn Ile Val Tyr Glu Gly Gln Ile Leu Arg Asn Val Ile Lys Asp Tyr
        1075                1080                1085

Trp Gly Asn Pro Leu Lys Phe Asp Thr Glu Tyr Tyr Ile Ile Asn Asp
    1090                1095                1100

Asn Tyr Ile Asp Arg Tyr Ile Ala Pro Glu Ser Asn Val Leu Val Leu
1105                1110                1115                1120

Val Gln Tyr Pro Asp Arg Ser Lys Leu Tyr Thr Gly Asn Pro Ile Thr
                1125                1130                1135

Ile Lys Ser Val Ser Asp Lys Asn Pro Tyr Ser Arg Ile Leu Asn Gly
            1140                1145                1150

Asp Asn Ile Ile Leu His Met Leu Tyr Asn Ser Arg Lys Tyr Met Ile
        1155                1160                1165

Ile Arg Asp Thr Asp Thr Ile Tyr Ala Thr Gln Gly Gly Glu Cys Ser
    1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
                1205                1210                1215
```

Cys Ser Gln Ile Phe Ser Ser Phe Arg Glu Asn Thr Met Leu Leu Ala
1220 1225 1230

Asp Ile Tyr Lys Pro Trp Arg Phe Ser Phe Lys Asn Ala Tyr Thr Pro
1235 1240 1245

Val Ala Val Thr Asn Tyr Glu Thr Lys Leu Leu Ser Thr Ser Ser Phe
1250 1255 1260

Trp Lys Phe Ile Ser Arg Asp Pro Gly Trp Val Glu
1265 1270 1275

<210> SEQ ID NO 5
<211> LENGTH: 1252
<212> TYPE: PRT
<213> ORGANISM: Clostridium botulinum serotype E

<400> SEQUENCE: 5

Met Pro Lys Ile Asn Ser Phe Asn Tyr Asn Asp Pro Val Asn Asp Arg
1 5 10 15

Thr Ile Leu Tyr Ile Lys Pro Gly Gly Cys Gln Glu Phe Tyr Lys Ser
20 25 30

Phe Asn Ile Met Lys Asn Ile Trp Ile Ile Pro Glu Arg Asn Val Ile
35 40 45

Gly Thr Thr Pro Gln Asp Phe His Pro Pro Thr Ser Leu Lys Asn Gly
50 55 60

Asp Ser Ser Tyr Tyr Asp Pro Asn Tyr Leu Gln Ser Asp Glu Glu Lys
65 70 75 80

Asp Arg Phe Leu Lys Ile Val Thr Lys Ile Phe Asn Arg Ile Asn Asn
85 90 95

Asn Leu Ser Gly Gly Ile Leu Leu Glu Glu Leu Ser Lys Ala Asn Pro
100 105 110

Tyr Leu Gly Asn Asp Asn Thr Pro Asp Asn Gln Phe His Ile Gly Asp
115 120 125

Ala Ser Ala Val Glu Ile Lys Phe Ser Asn Gly Ser Gln Asp Ile Leu
130 135 140

Leu Pro Asn Val Ile Ile Met Gly Ala Glu Pro Asp Leu Phe Glu Thr
145 150 155 160

Asn Ser Ser Asn Ile Ser Leu Arg Asn Asn Tyr Met Pro Ser Asn His
165 170 175

Gly Phe Gly Ser Ile Ala Ile Val Thr Phe Ser Pro Glu Tyr Ser Phe
180 185 190

Arg Phe Asn Asp Asn Ser Met Asn Glu Phe Ile Gln Asp Pro Ala Leu
195 200 205

Thr Leu Met His Glu Leu Ile His Ser Leu His Gly Leu Tyr Gly Ala
210 215 220

Lys Gly Ile Thr Thr Lys Tyr Thr Ile Thr Gln Lys Gln Asn Pro Leu
225 230 235 240

Ile Thr Asn Ile Arg Gly Thr Asn Ile Glu Glu Phe Leu Thr Phe Gly
245 250 255

Gly Thr Asp Leu Asn Ile Ile Thr Ser Ala Gln Ser Asn Asp Ile Tyr
260 265 270

Thr Asn Leu Leu Ala Asp Tyr Lys Lys Ile Ala Ser Lys Leu Ser Lys
275 280 285

Val Gln Val Ser Asn Pro Leu Leu Asn Pro Tyr Lys Asp Val Phe Glu
290 295 300

Ala Lys Tyr Gly Leu Asp Lys Asp Ala Ser Gly Ile Tyr Ser Val Asn
305 310 315 320

-continued

```
Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750
```

-continued

```
Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                 1000                1005

Gly Asn Leu Ile Asp Gln Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Ser Asn Glu Pro Asn Thr Asn Ile Leu
            1060                1065                1070

Lys Asp Phe Trp Gly Asn Tyr Leu Leu Tyr Asp Lys Glu Tyr Tyr Leu
        1075                1080                1085

Leu Asn Val Leu Lys Pro Asn Asn Phe Ile Asp Arg Arg Lys Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
            1140                1145                1150

Val Ala Ser Lys Thr His Leu Phe Pro Leu Tyr Ala Asp Thr Ala Thr
        1155                1160                1165

Thr Asn Lys Glu Lys Thr Ile Lys Ile Ser Ser Ser Gly Asn Arg Phe
```

```
    1170                1175                1180

Asn Gln Val Val Val Met Asn Ser Val Gly Asn Asn Cys Thr Met Asn
1185                1190                1195                1200

Phe Lys Asn Asn Asn Gly Asn Asn Ile Gly Leu Leu Gly Phe Lys Ala
                1205                1210                1215

Asp Thr Val Val Ala Ser Thr Trp Tyr Tyr Thr His Met Arg Asp His
            1220                1225                1230

Thr Asn Ser Asn Gly Cys Phe Trp Asn Phe Ile Ser Glu Glu His Gly
        1235                1240                1245

Trp Gln Glu Lys
    1250


<210> SEQ ID NO 6
<211> LENGTH: 1274
<212> TYPE: PRT
<213> ORGANISM: Clostridium botulinum serotype F

<400> SEQUENCE: 6

Met Pro Val Ala Ile Asn Ser Phe Asn Tyr Asn Asp Pro Val Asn Asp
 1               5                  10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
```

```
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
        595                 600                 605

Ser Thr Val Asp Lys Ile Ala Asp Ile Ser Leu Ile Val Pro Tyr Val
    610                 615                 620

Gly Leu Ala Leu Asn Ile Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
            660                 665                 670

Asp Ser Tyr Glu Asn Lys Asn Lys Ala Ile Lys Ala Ile Asn Asn Ser
        675                 680                 685

Leu Ile Glu Arg Glu Ala Lys Trp Lys Glu Ile Tyr Ser Trp Ile Val
    690                 695                 700

Ser Asn Trp Leu Thr Arg Ile Asn Thr Gln Phe Asn Lys Arg Lys Glu
705                 710                 715                 720
```

```
Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
            740                 745                 750

Glu Ser Glu Tyr Asn Ile Asn Asn Ile Glu Glu Glu Leu Asn Lys Lys
        755                 760                 765

Val Ser Leu Ala Met Lys Asn Ile Glu Arg Phe Met Thr Glu Ser Ser
    770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
            820                 825                 830

Val Thr Ser Thr Leu Asn Ser Ser Ile Pro Phe Glu Leu Ser Ser Tyr
        835                 840                 845

Thr Asn Asp Lys Ile Leu Ile Ile Tyr Phe Asn Arg Leu Tyr Lys Lys
    850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                885                 890                 895

Tyr Ile Tyr Ser Thr Asn Arg Asn Gln Phe Gly Ile Tyr Asn Ser Arg
            900                 905                 910

Leu Ser Glu Val Asn Ile Ala Gln Asn Asn Asp Ile Ile Tyr Asn Ser
        915                 920                 925

Arg Tyr Gln Asn Phe Ser Ile Ser Phe Trp Val Arg Ile Pro Lys His
    930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                965                 970                 975

Cys Glu Ile Ile Trp Thr Leu Gln Asp Thr Ser Gly Asn Lys Glu Asn
            980                 985                 990

Leu Ile Phe Arg Tyr Glu Glu Leu Asn Arg Ile Ser Asn Tyr Ile Asn
        995                 1000                1005

Lys Trp Ile Phe Val Thr Ile Thr Asn Asn Arg Leu Gly Asn Ser Arg
    1010                1015                1020

Ile Tyr Ile Asn Gly Asn Leu Ile Val Glu Lys Ser Ile Ser Asn Leu
1025                1030                1035                1040

Gly Asp Ile His Val Ser Asp Asn Ile Leu Phe Lys Ile Val Gly Cys
                1045                1050                1055

Asp Asp Glu Thr Tyr Val Gly Ile Arg Tyr Phe Lys Val Phe Asn Thr
            1060                1065                1070

Glu Leu Asp Lys Thr Glu Ile Glu Thr Leu Tyr Ser Asn Glu Pro Asp
        1075                1080                1085

Pro Ser Ile Leu Lys Asn Tyr Trp Gly Asn Tyr Leu Leu Tyr Asn Lys
    1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
                1125                1130                1135

Ser Val Phe Leu Asn Tyr Lys Leu Tyr Glu Gly Val Glu Val Ile Ile
            1140                1145                1150
```

Arg Lys Asn Gly Pro Ile Asp Ile Ser Asn Thr Asp Asn Phe Val Arg
        1155                1160                1165

Lys Asn Asp Leu Ala Tyr Ile Asn Val Val Asp Arg Gly Val Glu Tyr
    1170                1175                1180

Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
                1205                1210                1215

Gly Asn Asn Cys Thr Met Asn Phe Gln Asn Asn Asn Gly Ser Asn Ile
            1220                1225                1230

Gly Leu Leu Gly Phe His Ser Asn Asn Leu Val Ala Ser Ser Trp Tyr
        1235                1240                1245

Tyr Asn Asn Ile Arg Arg Asn Thr Ser Ser Asn Gly Cys Phe Trp Ser
    1250                1255                1260

Ser Ile Ser Lys Glu Asn Gly Trp Lys Glu
1265                1270

<210> SEQ ID NO 7
<211> LENGTH: 1297
<212> TYPE: PRT
<213> ORGANISM: Clostridium botulinum serotype G

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

```
Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
```

-continued

```
        675                 680                 685

Asn Ala Leu Lys Lys Arg Asp Gln Lys Trp Thr Asp Met Tyr Gly Leu
    690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
        995                 1000                1005

Trp Phe Ser Ile Thr Ile Thr Asn Asp Arg Leu Gly Asn Ala Asn Ile
    1010                1015                1020

Tyr Ile Asn Gly Ser Leu Lys Lys Ser Glu Lys Ile Leu Asn Leu Asp
1025                1030                1035                1040

Arg Ile Asn Ser Ser Asn Asp Ile Asp Phe Lys Leu Ile Asn Cys Thr
                1045                1050                1055

Asp Thr Thr Lys Phe Val Trp Ile Lys Asp Phe Asn Ile Phe Gly Arg
            1060                1065                1070

Glu Leu Asn Ala Thr Glu Val Ser Ser Leu Tyr Trp Ile Gln Ser Ser
        1075                1080                1085

Thr Asn Thr Leu Lys Asp Phe Trp Gly Asn Pro Leu Arg Tyr Asp Thr
    1090                1095                1100
```

```
Gln Tyr Tyr Leu Phe Asn Gln Gly Met Gln Asn Ile Tyr Ile Lys Tyr
1105                1110                1115                1120

Phe Ser Lys Ala Ser Met Gly Glu Thr Ala Pro Arg Thr Asn Phe Asn
                1125                1130                1135

Asn Ala Ala Ile Asn Tyr Gln Asn Leu Tyr Leu Gly Leu Arg Phe Ile
            1140                1145                1150

Ile Lys Lys Ala Ser Asn Ser Arg Asn Ile Asn Asn Asp Asn Ile Val
        1155                1160                1165

Arg Glu Gly Asp Tyr Ile Tyr Leu Asn Ile Asp Asn Ile Ser Asp Glu
    1170                1175                1180

Ser Tyr Arg Val Tyr Val Leu Val Asn Ser Lys Glu Ile Gln Thr Gln
1185                1190                1195                1200

Leu Phe Leu Ala Pro Ile Asn Asp Asp Pro Thr Phe Tyr Asp Val Leu
                1205                1210                1215

Gln Ile Lys Lys Tyr Tyr Glu Lys Thr Thr Tyr Asn Cys Gln Ile Leu
            1220                1225                1230

Cys Glu Lys Asp Thr Lys Thr Phe Gly Leu Phe Gly Ile Gly Lys Phe
        1235                1240                1245

Val Lys Asp Tyr Gly Tyr Val Trp Asp Thr Tyr Asp Asn Tyr Phe Cys
    1250                1255                1260

Ile Ser Gln Trp Tyr Leu Arg Arg Ile Ser Glu Asn Ile Asn Lys Leu
1265                1270                1275                1280

Arg Leu Gly Cys Asn Trp Gln Phe Ile Pro Val Asp Glu Gly Trp Thr
                1285                1290                1295

Glu


<210> SEQ ID NO 8
<211> LENGTH: 1315
<212> TYPE: PRT
<213> ORGANISM: Clostridium teteni

<400> SEQUENCE: 8

Met Pro Ile Thr Ile Asn Asn Phe Arg Tyr Ser Asp Pro Val Asn Asn
 1               5                  10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
```

-continued

```
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605
```

```
Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
        995                 1000                1005

Gly Glu Val Arg Gln Ile Thr Phe Arg Asp Leu Pro Asp Lys Phe Asn
    1010                1015                1020

Ala Tyr Leu Ala Asn Lys Trp Val Phe Ile Thr Ile Thr Asn Asp Arg
1025                1030                1035                1040
```

```
Leu Ser Ser Ala Asn Leu Tyr Ile Asn Gly Val Leu Met Gly Ser Ala
                1045                1050                1055

Glu Ile Thr Gly Leu Gly Ala Ile Arg Glu Asp Asn Asn Ile Thr Leu
            1060                1065                1070

Lys Leu Asp Arg Cys Asn Asn Asn Asn Gln Tyr Val Ser Ile Asp Lys
        1075                1080                1085

Phe Arg Ile Phe Cys Lys Ala Leu Asn Pro Lys Glu Ile Glu Lys Leu
    1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
                1125                1130                1135

Ser Lys Asp Val Gln Leu Lys Asn Ile Thr Asp Tyr Met Tyr Leu Thr
            1140                1145                1150

Asn Ala Pro Ser Tyr Thr Asn Gly Lys Leu Asn Ile Tyr Tyr Arg Arg
        1155                1160                1165

Leu Tyr Asn Gly Leu Lys Phe Ile Ile Lys Arg Tyr Thr Pro Asn Asn
    1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
                1205                1210                1215

Ala Phe Asn Asn Leu Asp Arg Ile Leu Arg Val Gly Tyr Asn Ala Pro
            1220                1225                1230

Gly Ile Pro Leu Tyr Lys Lys Met Glu Ala Val Lys Leu Arg Asp Leu
        1235                1240                1245

Lys Thr Tyr Ser Val Gln Leu Lys Leu Tyr Asp Asp Lys Asn Ala Ser
    1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
                1285                1290                1295

Lys Ile Leu Gly Cys Asp Trp Tyr Phe Val Pro Thr Asp Glu Gly Trp
            1300                1305                1310

Thr Asn Asp
        1315


<210> SEQ ID NO 9
<211> LENGTH: 293
<212> TYPE: PRT
<213> ORGANISM: Clostridium botulinum serotype A

<400> SEQUENCE: 9

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45

Arg Leu Ile Tyr Asp Ser Asn Lys Ala Ala Tyr Lys Ile Lys Ser Met
    50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95
```

```
Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
    130                 135                 140

Tyr Ile Ile Ser Asp Leu Asn Asn Phe Thr Cys Lys Ile Ser Pro Ile
145                 150                 155                 160

Leu Asp Leu Asn Lys Val Val Gln Gln Val Asp Val Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Gly Gly Gln Thr Ala Asn Gly
            260                 265                 270

Thr Ala Ile Gln Val Phe Asn Tyr His Gly Asp Asp Asn Gln Lys Trp
        275                 280                 285

Asn Ile Arg Asn Pro
    290
```

```
<210> SEQ ID NO 10
<211> LENGTH: 293
<212> TYPE: PRT
<213> ORGANISM: Clostridium botulinum serotype A

<400> SEQUENCE: 10

Met Glu His Tyr Ser Val Ile Gln Asn Ser Leu Asn Asp Lys Ile Val
 1               5                  10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45

Arg Leu Ile Tyr Asp Ser Asn Lys Ala Ala Tyr Lys Ile Lys Ser Met
    50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
    130                 135                 140

Tyr Ile Ile Ser Asp Leu Asn Asn Phe Thr Cys Lys Ile Ser Pro Ile
145                 150                 155                 160

Leu Asp Arg Asn Lys Val Val Gln Gln Val Asp Met Thr Asn Leu Asn
                165                 170                 175
```

```
Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Asn Ser Gln Thr Ala Asn Gly
            260                 265                 270

Thr Ala Ile Gln Val Phe Asn Tyr His Gly Asp Asp Asn Gln Lys Trp
        275                 280                 285

Asn Ile Arg Asn Pro
    290


<210> SEQ ID NO 11
<211> LENGTH: 293
<212> TYPE: PRT
<213> ORGANISM: Clostridium botulinum serotype A

<400> SEQUENCE: 11

Met Glu His Tyr Ser Val Ile Gln Asn Ser Leu Asn Asp Lys Ile Val
 1               5                  10                  15

Thr Ile Ser Cys Arg Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45

Arg Ile Ile Tyr Asp Ser Asn Lys Ala Ala Tyr Lys Ile Lys Ser Met
    50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
    130                 135                 140

Tyr Ile Ile Ser Asp Phe Asn Asn Phe Thr Cys Lys Ile Ser Pro Ile
145                 150                 155                 160

Leu Asp Arg Asn Lys Val Val Gln Gln Val Ala Thr Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255
```

Asp Thr Thr Lys Ala Leu Asp Leu Tyr Asn Ser Gln Thr Ala Asn Gly
260 265 270

Thr Ala Ile Gln Val Phe Asn Ser Asn Gly Gly Asp Asn Gln Lys Trp
275 280 285

Asn Ile Arg Asn Pro
290

<210> SEQ ID NO 12
<211> LENGTH: 294
<212> TYPE: PRT
<213> ORGANISM: Clostridium botulinum serotype A

<400> SEQUENCE: 12

Met Glu His Tyr Ser Thr Ile Gln Asn Ser Leu Asn Asp Lys Ile Val
1 5 10 15

Thr Ile Ser Cys Lys Ala Asn Thr Asp Leu Phe Phe Tyr Gln Val Pro
20 25 30

Gly Asn Gly Asn Val Ser Leu Phe Gln Gln Thr Arg Asn Tyr Leu Glu
35 40 45

Arg Trp Arg Ile Ile Tyr Asp Ser Asn Lys Ala Ala Tyr Lys Ile Lys
50 55 60

Ser Met Asn Ile Tyr Asn Thr Asn Leu Val Leu Thr Trp Asn Ala Pro
65 70 75 80

Thr His Asn Ile Ser Ala Gln Gln Asp Ser Asn Ala Asp Asn Gln Tyr
85 90 95

Trp Leu Leu Leu Lys Asp Ile Gly Asn Asn Ser Phe Ile Ile Ala Ser
100 105 110

Tyr Lys Asn Pro Asn Leu Val Leu Tyr Ala Asp Thr Val Ala Arg Asn
115 120 125

Leu Lys Leu Ser Thr Leu Asn Asn Ser Ser Tyr Ile Lys Phe Ile Ile
130 135 140

Glu Asp Tyr Val Ile Ser Asp Phe Lys Asn Phe Thr Cys Arg Ile Ser
145 150 155 160

Pro Ile Leu Ala Gly Gly Lys Val Val Gln Gln Val Ser Met Thr Asn
165 170 175

Leu Ala Val Asn Leu Tyr Ile Trp Asn Asn Asp Leu Asn Gln Lys Trp
180 185 190

Thr Ile Ile Tyr Asn Glu Glu Lys Ala Ala Tyr Gln Phe Phe Asn Lys
195 200 205

Ile Leu Ser Asn Gly Val Leu Thr Trp Ile Phe Ser Asp Gly Asn Thr
210 215 220

Val Arg Val Ser Ser Ser Ala Gln Asn Asn Asp Ala Gln Tyr Trp Leu
225 230 235 240

Ile Asn Pro Val Ser Asp Asn Tyr Asp Arg Tyr Thr Ile Thr Asn Leu
245 250 255

Arg Asp Lys Thr Lys Val Leu Asp Leu Tyr Gly Gly Gln Thr Ala Asp
260 265 270

Gly Thr Thr Ile Gln Val Phe Asn Ser Asn Gly Gly Asp Asn Gln Ile
275 280 285

Trp Thr Met Ser Asn Pro
290

<210> SEQ ID NO 13
<211> LENGTH: 279
<212> TYPE: PRT
<213> ORGANISM: Clostridium botulinum serotype A

<400> SEQUENCE: 13

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45

Arg Leu Ile Tyr Asp Ser Asn Lys Ala Ala Tyr Lys Ile Lys Ser Met
    50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
    130                 135                 140

Tyr Ile Ile Ser Asp Leu Asn Asn Phe Thr Cys Lys Ile Ser Pro Ile
145                 150                 155                 160

Leu Asp Arg Asn Lys Val Val Gln Gln Val Asp Met Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Asn Ser Gln Thr Ala Asn Gly
            260                 265                 270

Thr Ala Ile Gln Val Phe Asn
        275

<210> SEQ ID NO 14
<211> LENGTH: 292
<212> TYPE: PRT
<213> ORGANISM: Clostridium botulinum serotype B

<400> SEQUENCE: 14

Met Glu His Tyr Ser Val Ile Gln Asn Ser Leu Asn Asp Glu Ile Val
1               5                   10                  15

Thr Ile Ser Cys Lys Ala Asp Thr Asn Leu Phe Phe Tyr Gln Thr Val
            20                  25                  30

Gly Asn Val Ser Leu Phe Gln Gln Thr Arg Asn Tyr Leu Glu Arg Trp
        35                  40                  45

Arg Leu Ile Tyr Asp Ala Asn Lys Ala Ala Tyr Lys Ile Lys Ser Met
    50                  55                  60

Asp Ser His Asn Thr Asn Leu Val Leu Thr Trp Asn Ala Pro Thr His
65                  70                  75                  80

-continued

Asn Ile Ser Ala Gln Gln Asp Ser Asn Ala Asp Asn Gln Tyr Trp Leu
85 90 95

Leu Leu Lys Asp Ile Gly Ser Asn Ser Phe Ile Ile Ala Ser Tyr Lys
100 105 110

Asn Pro Asn Leu Val Leu Tyr Ala Asp Thr Val Ala Arg Asn Leu Lys
115 120 125

Leu Ser Thr Leu Asn Asn Ser Ser Tyr Ile Lys Phe Ile Ile Glu Asp
130 135 140

Tyr Met Ile Ser Asp Phe Asn Asn Phe Thr Cys Lys Ile Ser Pro Ile
145 150 155 160

Leu Asp Ser Ser Lys Val Val Gln Gln Val Ala Met Thr Asp Leu Ser
165 170 175

Val Asn Leu Tyr Thr Trp Asp Tyr Gly Arg Asn Gln Lys Trp Thr Ile
180 185 190

Lys Tyr Asn Lys Glu Lys Ser Ala Tyr Gln Phe Phe Asn Thr Ile Leu
195 200 205

Ser Asn Gly Val Leu Thr Trp Ile Ser Ser Asn Gly Asn Thr Val Arg
210 215 220

Val Ser Ser Ile Ala Gln Asn Asn Asp Ala Gln Tyr Trp Leu Ile Asn
225 230 235 240

Pro Val Ser Asn Ala Tyr Glu Thr Tyr Thr Ile Thr Asn Leu His Asp
245 250 255

Thr Thr Lys Ala Leu Asp Leu Tyr Asn Ser Gln Thr Ala Asn Gly Thr
260 265 270

Thr Ile Gln Val Phe Asn Tyr His Gly Asp Asp Asn Gln Lys Trp Phe
275 280 285

Ile Arg Asn Pro
290

<210> SEQ ID NO 15
<211> LENGTH: 291
<212> TYPE: PRT
<213> ORGANISM: Clostridium botulinum serotype B

<400> SEQUENCE: 15

Met Glu His Tyr Ser Thr Ile Gln Asn Ser Leu Asn Asp Lys Ile Val
1 5 10 15

Thr Ile Ser Cys Lys Ala Asn Thr Asp Leu Phe Phe Tyr Gln Val Pro
20 25 30

Gly Asn Gly Asn Val Ser Leu Phe Gln Gln Thr Arg Asn Tyr Leu Glu
35 40 45

Arg Trp Arg Ile Ile Tyr Asp Ser Asn Lys Ala Ala Tyr Lys Ile Lys
50 55 60

Ser Met Asn Ile Tyr Asn Thr Asn Leu Val Leu Thr Trp Asn Ala Pro
65 70 75 80

Thr His Asn Ile Ser Ala Leu Gln Asp Ser Asn Ala Asp Asn Gln Tyr
85 90 95

Trp Leu Leu Leu Lys Asp Ile Gly Asn Asn Ser Phe Ile Ile Ala Ser
100 105 110

Tyr Lys Asn Pro Asn Leu Val Leu Tyr Ala Asp Thr Val Ala Arg Asn
115 120 125

Leu Lys Leu Ser Thr Leu Asn Asn Ser Ser Tyr Ile Lys Phe Ile Ile
130 135 140

Glu Asp Tyr Val Ile Ser Asp Phe Lys Asn Phe Thr Cys Arg Ile Ser
145 150 155 160

```
Pro Ile Leu Ala Gly Gly Lys Val Val Gln Gln Val Ser Met Thr Asn
                165                 170                 175

Leu Ala Val Asn Leu Tyr Ile Trp Asn Asn Asp Leu Asn Gln Lys Trp
            180                 185                 190

Thr Ile Ile Tyr Asn Glu Glu Lys Ala Ala Tyr Gln Phe Phe Asn Lys
        195                 200                 205

Ile Leu Ser Asn Gly Val Leu Thr Trp Ile Phe Ser Asp Gly Asn Thr
    210                 215                 220

Val Arg Val Ser Ser Ser Ala Gln Asn Asp Ala Gln Tyr Trp Leu Ile
225                 230                 235                 240

Asn Pro Val Ser Asp Asn Tyr Asp Arg Tyr Thr Ile Thr Asn Leu Arg
                245                 250                 255

Tyr Lys Thr Lys Val Leu Asp Leu Tyr Gly Gly Gln Thr Ala Asp Gly
            260                 265                 270

Thr Thr Ile Gln Val Phe Asn Ser Asn Gly Gly Asp Asn Gln Ile Trp
        275                 280                 285

Tyr Gly Leu
    290


<210> SEQ ID NO 16
<211> LENGTH: 286
<212> TYPE: PRT
<213> ORGANISM: Clostridium botulinum serotype C1

<400> SEQUENCE: 16

Met Ser Gln Thr Asn Ala Asn Asp Leu Arg Asn Asn Glu Val Phe Phe
 1               5                  10                  15

Ile Ser Pro Ser Asn Asn Thr Asn Lys Val Leu Asp Lys Ile Ser Gln
            20                  25                  30

Ser Glu Val Lys Leu Trp Asn Lys Leu Ser Gly Ala Asn Gln Lys Trp
        35                  40                  45

Arg Leu Ile Tyr Asp Thr Asn Lys Gln Ala Tyr Lys Ile Lys Val Met
    50                  55                  60

Asp Asn Thr Ser Leu Ile Leu Thr Trp Asn Ala Pro Leu Ser Ser Val
65                  70                  75                  80

Ser Val Lys Thr Asp Thr Asn Gly Asp Asn Gln Tyr Trp Tyr Leu Leu
                85                  90                  95

Gln Asn Tyr Ile Ser Arg Asn Val Ile Ile Arg Asn Tyr Met Asn Pro
            100                 105                 110

Asn Leu Val Leu Gln Tyr Asn Ile Asp Asp Thr Leu Met Val Ser Thr
        115                 120                 125

Gln Thr Ser Ser Ser Asn Gln Phe Phe Lys Phe Ser Asn Cys Ile Tyr
    130                 135                 140

Glu Ala Leu Asn Asn Arg Asn Cys Lys Leu Gln Thr Gln Leu Asn Ser
145                 150                 155                 160

Asp Arg Phe Leu Ser Lys Asn Leu Asn Ser Gln Ile Ile Val Leu Trp
                165                 170                 175

Gln Trp Phe Asp Ser Ser Arg Gln Lys Trp Ile Ile Glu Tyr Asn Glu
            180                 185                 190

Thr Lys Ser Ala Tyr Thr Leu Lys Cys Gln Glu Asn Asn Arg Tyr Leu
        195                 200                 205

Thr Trp Ile Gln Asn Ser Asn Asn Tyr Val Glu Thr Tyr Gln Ser Thr
    210                 215                 220

Asp Ser Leu Ile Gln Tyr Trp Asn Ile Asn Tyr Leu Asp Asn Asp Ala
225                 230                 235                 240
```

```
Ser Lys Tyr Ile Leu Tyr Asn Leu Gln Asp Thr Asn Arg Val Leu Asp
                245                 250                 255

Val Tyr Asn Ser Gln Ile Ala Asn Gly Thr His Val Ile Val Asp Ser
            260                 265                 270

Tyr His Gly Asn Thr Asn Gln Gln Trp Ile Ile Asn Leu Ile
        275                 280                 285
```

<210> SEQ ID NO 17
<211> LENGTH: 285
<212> TYPE: PRT
<213> ORGANISM: Clostridium botulinum serotype C1

<400> SEQUENCE: 17

```
Met Ser Gln Thr Asn Ala Asn Asp Leu Arg Asn Asn Glu Val Phe Phe
 1               5                  10                  15

Ile Ser Pro Ser Asn Asn Thr Asn Lys Val Leu Asp Lys Ile Ser Gln
            20                  25                  30

Ser Glu Val Lys Leu Trp Asn Lys Leu Ser Gly Ala Asn Gln Lys Trp
        35                  40                  45

Arg Leu Ile Tyr Asp Thr Asn Lys Gln Ala Tyr Lys Ile Lys Val Met
    50                  55                  60

Asp Asn Thr Ser Leu Ile Leu Thr Trp Asn Ala Pro Leu Ser Ser Val
65                  70                  75                  80

Ser Val Lys Thr Asp Thr Asn Gly Asp Asn Gln Tyr Trp Tyr Leu Leu
                85                  90                  95

Gln Asn Tyr Ile Ser Arg Asn Val Ile Ile Arg Asn Tyr Met Asn Pro
            100                 105                 110

Asn Leu Val Leu Gln Tyr Asn Ile Asp Asp Thr Leu Met Val Ser Thr
        115                 120                 125

Gln Thr Ser Ser Ser Asn Gln Phe Phe Lys Phe Ser Asn Cys Ile Tyr
    130                 135                 140

Glu Ser Phe Asn Asn Ser Thr Cys Lys Ile Gln Thr Ser Leu Thr Ile
145                 150                 155                 160

Lys Phe Ile Asp Lys Asn Gln Asn Ser Asn Asn Val Thr Ile Trp Ser
                165                 170                 175

Trp Asn Asn Gly Asp Asn Gln Lys Trp Lys Ile Leu Tyr Asn Glu Ser
            180                 185                 190

Lys Met Ala Tyr Thr Leu Thr Cys Ile Lys Asn Asn Glu Tyr Leu Thr
        195                 200                 205

Trp Phe Ser Ser Ile Gly Asn Asn Val Gly Thr Tyr Arg Thr Glu Gly
    210                 215                 220

Asn Asn Asp Gln Tyr Trp Phe Ile Asn Tyr Leu Asn Asn Asp Ala Ser
225                 230                 235                 240

Met Tyr Thr Ile Ser Asn Phe Ser Asn Gln Ser Lys Phe Leu Asp Val
                245                 250                 255

Val Asn Ser Gly Leu Ala Asp Gly Thr Asn Val Gln Val Trp Asp Ser
            260                 265                 270

Asn Gly Thr Ser Ala Gln Lys Trp Ile Ile Thr Arg Leu
        275                 280                 285
```

<210> SEQ ID NO 18
<211> LENGTH: 286
<212> TYPE: PRT
<213> ORGANISM: Clostridium botulinum serotype D

<400> SEQUENCE: 18

```
Met Ser Gln Thr Asn Ala Asn Asp Leu Arg Asn Asn Glu Val Phe Phe
```

-continued

```
1               5                   10                  15

Ile Ser Pro Ser Asn Asn Thr Asn Lys Val Leu Asp Lys Ile Ser Gln
            20                  25                  30

Ser Glu Val Lys Leu Trp Asn Lys Leu Ser Gly Ala Asn Gln Lys Trp
        35                  40                  45

Arg Leu Ile Tyr Asp Thr Asn Lys Gln Ala Tyr Thr Ile Lys Val Met
    50                  55                  60

Asp Asn Thr Ser Leu Ile Leu Thr Trp Asp Ala Pro Leu Ser Ser Val
65                  70                  75                  80

Ser Val Lys Thr Asp Thr Asn Thr Asn Asn Gln Tyr Trp Tyr Leu Leu
                85                  90                  95

Gln Asp Tyr Ile Ser Arg Asn Val Ile Leu Arg Asn Tyr Met Asn Pro
            100                 105                 110

Asn Leu Val Leu Gln Tyr Asn Thr Asp Asp Thr Leu Ile Val Ser Thr
        115                 120                 125

Gln Thr Asn Ser Asn Asn Gln Phe Phe Lys Phe Ser Asn Cys Ile Tyr
    130                 135                 140

Glu Ala Leu Asn Asn Arg Asn Cys Lys Leu Gln Thr Gln Leu Asn Ser
145                 150                 155                 160

Asp Arg Phe Leu Ser Lys Asn Leu Asn Ser Gln Ile Ile Val Leu Trp
                165                 170                 175

Gln Trp Phe Asp Ser Ser Arg Gln Lys Trp Thr Ile Glu Tyr Asn Glu
            180                 185                 190

Thr Lys Ser Ala Tyr Thr Leu Lys Cys Gln Glu Asn Asn Arg Tyr Leu
        195                 200                 205

Thr Trp Ile Gln Asn Ser Asn Asn Tyr Val Glu Thr Tyr Gln Ser Thr
    210                 215                 220

Asp Ser Leu Ile Gln Tyr Trp Asn Ile Asn Tyr Leu Asp Asn Asp Ala
225                 230                 235                 240

Ser Lys Tyr Ile Leu Tyr Asn Leu Gln Asp Thr Asn Arg Val Leu Asp
                245                 250                 255

Val Tyr Asn Ser Gln Thr Ala Asn Gly Thr His Val Ile Val Asp Ser
            260                 265                 270

Tyr His Gly Asn Thr Asn Gln Gln Trp Ile Ile Asn Leu Ile
        275                 280                 285


<210> SEQ ID NO 19
<211> LENGTH: 146
<212> TYPE: PRT
<213> ORGANISM: Clostridium botulinum serotype A

<400> SEQUENCE: 19

Met Ser Val Glu Arg Thr Phe Leu Pro Asn Gly Asn Tyr Asn Ile Lys
1               5                   10                  15

Ser Ile Phe Ser Gly Ser Leu Tyr Leu Asn Pro Val Ser Lys Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Asn Val Ala Glu Pro
    50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
```

100 105 110

Asp Ile Tyr Asp Thr Asn Glu Asn Ile Leu Ser Gln Pro Leu Leu Leu
115 120 125

Leu Pro Asn Phe Asp Ile Tyr Asn Ser Asn Gln Met Phe Lys Leu Glu
130 135 140

Lys Ile
145

<210> SEQ ID NO 20
<211> LENGTH: 146
<212> TYPE: PRT
<213> ORGANISM: Clostridium botulinum serotype B

<400> SEQUENCE: 20

Met Ser Ala Glu Arg Thr Phe Leu Pro Asn Gly Asn Tyr Asn Ile Lys
1 5 10 15

Ser Ile Phe Ser Gly Ser Leu Tyr Leu Ser Pro Val Ser Gly Ser Leu
20 25 30

Thr Phe Ser Asn Glu Ser Ser Ala Asn Asn Gln Lys Trp Asn Val Glu
35 40 45

Tyr Met Ala Glu Asn Arg Cys Phe Lys Ile Ser Asn Val Ala Glu Pro
50 55 60

Asn Lys Tyr Leu Ser Tyr Asp Asn Phe Gly Phe Ile Ser Leu Asp Ser
65 70 75 80

Leu Ser Asn Arg Cys Tyr Trp Phe Pro Ile Lys Ile Ala Val Asn Thr
85 90 95

Tyr Ile Met Leu Ser Leu Asn Lys Val Asn Glu Leu Asp Tyr Ala Trp
100 105 110

Asp Ile Tyr Asp Thr Asn Glu Asn Ile Leu Ser Gln Pro Leu Leu Leu
115 120 125

Leu Pro Asn Phe Asp Ile Tyr Asn Ser Asn Gln Met Phe Lys Leu Glu
130 135 140

Lys Ile
145

<210> SEQ ID NO 21
<211> LENGTH: 146
<212> TYPE: PRT
<213> ORGANISM: Clostridium botulinum serotype C1

<400> SEQUENCE: 21

Met Ser Ser Glu Arg Thr Phe Leu Pro Asn Gly Asn Tyr Lys Ile Lys
1 5 10 15

Ser Leu Phe Ser Asn Ser Leu Tyr Leu Thr Tyr Ser Ser Gly Ala Leu
20 25 30

Ser Phe Ser Asn Thr Ser Ser Leu Asp Asn Gln Lys Trp Lys Leu Glu
35 40 45

Tyr Ile Ser Ser Ser Asn Gly Phe Arg Phe Ser Asn Val Ala Glu Pro
50 55 60

Asn Lys Tyr Leu Ala Tyr Asn Asp Tyr Gly Phe Ile Tyr Leu Ser Ser
65 70 75 80

Ser Ser Asn Asn Ser Leu Trp Asn Pro Ile Lys Ile Ala Ile Asn Ser
85 90 95

Tyr Ile Ile Cys Thr Leu Ser Ile Val Asn Val Thr Asp Tyr Ala Trp
100 105 110

Thr Ile Tyr Asp Asn Asn Asn Asn Ile Thr Asp Gln Pro Ile Leu Asn
115 120 125

```
Leu Pro Asn Phe Asp Ile Asn Asn Ser Asn Gln Ile Leu Lys Leu Glu
    130                 135                 140

Lys Leu
145
```

<210> SEQ ID NO 22
<211> LENGTH: 146
<212> TYPE: PRT
<213> ORGANISM: Clostridium botulinum serotype D

<400> SEQUENCE: 22

```
Met Ser Ser Glu Arg Thr Phe Leu Pro Asn Gly Asn Tyr Lys Ile Lys
 1               5                  10                  15

Ser Leu Phe Ser Asp Ser Leu Tyr Leu Thr Tyr Ser Ser Gly Ser Leu
            20                  25                  30

Ser Phe Leu Asn Thr Ser Ser Leu Asp Asn Gln Lys Trp Lys Leu Glu
        35                  40                  45

Tyr Ile Ser Ser Ser Asn Gly Phe Arg Phe Ser Asn Val Ala Glu Pro
    50                  55                  60

Asn Lys Tyr Leu Ala Tyr Asn Asp Tyr Gly Phe Ile Tyr Leu Ser Ser
65                  70                  75                  80

Ser Ser Asn Asn Ser Leu Trp Asn Pro Ile Lys Ile Ala Ile Asn Ser
                85                  90                  95

Tyr Ile Ile Cys Thr Leu Ser Ile Val Asn Val Thr Asp Tyr Ala Trp
            100                 105                 110

Thr Ile Tyr Asp Asn Asn Asn Asn Ile Thr Asp Gln Pro Ile Leu Asn
        115                 120                 125

Leu Pro Asn Phe Asp Ile Asn Asn Ser Asn Gln Ile Leu Lys Leu Glu
    130                 135                 140

Lys Leu
145
```

<210> SEQ ID NO 23
<211> LENGTH: 1193
<212> TYPE: PRT
<213> ORGANISM: Clostridium botulinum serotype A

<400> SEQUENCE: 23

```
Met Asn Ile Asn Asp Asn Leu Ser Ile Asn Ser Pro Val Asp Asn Lys
 1               5                  10                  15

Asn Val Val Val Val Arg Ala Arg Lys Thr Asp Thr Val Phe Lys Ala
            20                  25                  30

Phe Lys Val Ala Pro Asn Ile Trp Val Ala Pro Glu Arg Tyr Tyr Gly
        35                  40                  45

Glu Ser Leu Ser Ile Asp Glu Glu Tyr Lys Val Asp Gly Gly Ile Tyr
    50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
    130                 135                 140
```

-continued

```
Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Thr Glu Ile Trp Phe Gln Pro Phe Leu Thr
        195                 200                 205

Tyr Lys Tyr Asp Glu Phe Tyr Ile Asp Pro Ala Ile Glu Leu Ile Lys
    210                 215                 220

Cys Leu Ile Lys Ser Leu Tyr Phe Leu Tyr Gly Ile Lys Pro Ser Asp
225                 230                 235                 240

Asp Leu Val Ile Pro Tyr Arg Leu Arg Ser Glu Leu Glu Asn Ile Glu
                245                 250                 255

Tyr Ser Gln Leu Asn Ile Val Asp Leu Leu Val Ser Gly Gly Ile Asp
            260                 265                 270

Pro Lys Phe Ile Asn Thr Asp Pro Tyr Trp Phe Thr Asp Asn Tyr Phe
        275                 280                 285

Ser Asn Ala Lys Lys Val Phe Glu Asp His Arg Asn Ile Tyr Glu Thr
    290                 295                 300

Glu Ile Glu Gly Asn Asn Ala Ile Gly Asn Asp Ile Lys Leu Arg Leu
305                 310                 315                 320

Lys Gln Lys Phe Arg Ile Asn Ile Asn Asp Ile Trp Glu Leu Asn Leu
                325                 330                 335

Asn Tyr Phe Ser Lys Glu Phe Ser Ile Met Met Pro Asp Arg Phe Asn
            340                 345                 350

Asn Ala Leu Lys His Phe Tyr Arg Lys Gln Tyr Tyr Lys Ile Asp Tyr
        355                 360                 365

Pro Glu Asn Tyr Ser Ile Asn Gly Phe Val Asn Gly Gln Ile Asn Ala
    370                 375                 380

Gln Leu Ser Leu Ser Asp Arg Asn Gln Asp Ile Ile Asn Lys Pro Glu
385                 390                 395                 400

Glu Ile Ile Asn Leu Leu Asn Gly Asn Asn Val Ser Leu Met Arg Ser
                405                 410                 415

Asn Ile Tyr Gly Asp Gly Leu Lys Ser Thr Val Asp Asp Phe Tyr Ser
            420                 425                 430

Asn Tyr Lys Ile Pro Tyr Asn Arg Ala Tyr Glu Tyr His Phe Asn Asn
        435                 440                 445

Ser Asn Asp Ser Ser Leu Asp Asn Val Asn Ile Gly Val Ile Asp Asn
    450                 455                 460

Ile Pro Glu Ile Ile Asp Val Asn Pro Tyr Lys Glu Asn Cys Asp Lys
465                 470                 475                 480

Phe Ser Pro Val Gln Lys Ile Thr Ser Thr Arg Glu Ile Asn Thr Asn
                485                 490                 495

Ile Pro Trp Pro Ile Asn Tyr Leu Gln Ala Gln Asn Thr Asn Asn Glu
            500                 505                 510

Lys Phe Ser Leu Ser Ser Asp Phe Val Glu Val Val Ser Ser Lys Asp
        515                 520                 525

Lys Ser Leu Val Tyr Ser Phe Leu Ser Asn Val Met Phe Tyr Leu Asp
    530                 535                 540

Ser Ile Lys Asp Asn Ser Pro Ile Asp Thr Asp Lys Lys Tyr Tyr Leu
545                 550                 555                 560

Trp Leu Arg Glu Ile Phe Arg Asn Tyr Ser Phe Asp Ile Thr Ala Thr
                565                 570                 575
```

-continued

```
Gln Glu Ile Asn Thr Asn Cys Gly Ile Asn Lys Val Val Thr Trp Phe
            580                 585                 590

Gly Lys Ala Leu Asn Ile Leu Asn Thr Ser Asp Ser Phe Val Glu Glu
        595                 600                 605

Phe Gln Asn Leu Gly Ala Ile Ser Leu Ile Asn Lys Lys Glu Asn Leu
    610                 615                 620

Ser Met Pro Ile Ile Glu Ser Tyr Glu Ile Pro Asn Asp Met Leu Gly
625                 630                 635                 640

Leu Pro Leu Asn Asp Leu Asn Glu Lys Leu Phe Asn Ile Tyr Ser Lys
                645                 650                 655

Asn Thr Ala Tyr Phe Lys Lys Ile Tyr Tyr Asn Phe Leu Asp Gln Trp
            660                 665                 670

Trp Thr Gln Tyr Tyr Ser Gln Tyr Phe Asp Leu Ile Cys Met Ala Lys
        675                 680                 685

Arg Ser Val Leu Ala Gln Glu Thr Leu Ile Lys Arg Ile Ile Gln Lys
    690                 695                 700

Lys Leu Ser Tyr Leu Ile Gly Asn Ser Asn Ile Ser Ser Asp Asn Leu
705                 710                 715                 720

Ala Leu Met Asn Leu Thr Thr Thr Asn Thr Leu Arg Asp Ile Ser Asn
                725                 730                 735

Glu Ser Gln Ile Ala Met Asn Asn Val Asp Ser Phe Leu Asn Asn Ala
            740                 745                 750

Ala Ile Cys Val Phe Glu Ser Asn Ile Tyr Pro Lys Phe Ile Ser Phe
        755                 760                 765

Met Glu Gln Cys Ile Asn Asn Ile Asn Ile Lys Thr Lys Glu Phe Ile
    770                 775                 780

Gln Lys Cys Thr Asn Ile Asn Glu Asp Glu Lys Leu Gln Leu Ile Asn
785                 790                 795                 800

Gln Asn Val Phe Asn Ser Leu Asp Phe Glu Phe Leu Asn Ile Gln Asn
                805                 810                 815

Met Lys Ser Leu Phe Ser Ser Glu Thr Ala Leu Leu Ile Lys Glu Glu
            820                 825                 830

Thr Trp Pro Tyr Glu Leu Val Leu Tyr Ala Phe Lys Glu Pro Gly Asn
        835                 840                 845

Asn Val Ile Gly Asp Ala Ser Gly Lys Asn Thr Ser Ile Glu Tyr Ser
    850                 855                 860

Lys Asp Ile Gly Leu Val Tyr Gly Ile Asn Ser Asp Ala Leu Tyr Leu
865                 870                 875                 880

Asn Gly Ser Asn Gln Ser Ile Ser Phe Ser Asn Asp Phe Phe Glu Asn
                885                 890                 895

Gly Leu Thr Asn Ser Phe Ser Ile Tyr Phe Trp Leu Arg Asn Leu Gly
            900                 905                 910

Lys Asp Thr Ile Lys Ser Lys Leu Ile Gly Ser Lys Glu Asp Asn Cys
        915                 920                 925

Gly Trp Glu Ile Tyr Phe Gln Asp Thr Gly Leu Val Phe Asn Met Ile
    930                 935                 940

Asp Ser Asn Gly Asn Glu Lys Asn Ile Tyr Leu Ser Asp Val Ser Asn
945                 950                 955                 960

Asn Ser Trp His Tyr Ile Thr Ile Ser Val Asp Arg Leu Lys Glu Gln
                965                 970                 975

Leu Leu Ile Phe Ile Asp Asp Asn Leu Val Ala Asn Glu Ser Ile Lys
            980                 985                 990

Glu Ile Leu Asn Ile Tyr Ser Ser Asn Ile Ile Ser Leu Leu Ser Glu
```

```
        995                 1000                1005

Asn Asn Pro Ser Tyr Ile Glu Gly Leu Thr Ile Leu Asn Lys Pro Thr
    1010                1015                1020

Thr Ser Gln Glu Val Leu Ser Asn Tyr Phe Glu Val Leu Asn Asn Ser
1025                1030                1035                1040

Tyr Ile Arg Asp Ser Asn Glu Glu Arg Leu Glu Tyr Asn Lys Thr Tyr
                1045                1050                1055

Gln Leu Tyr Asn Tyr Val Phe Ser Asp Lys Pro Ile Cys Glu Val Lys
            1060                1065                1070

Gln Asn Asn Asn Ile Tyr Leu Thr Ile Asn Asn Thr Asn Asn Leu Asn
        1075                1080                1085

Leu Gln Ala Ser Lys Phe Lys Leu Leu Ser Ile Asn Pro Asn Lys Gln
    1090                1095                1100

Tyr Val Gln Lys Leu Asp Glu Val Ile Ile Ser Val Leu Asp Asn Met
1105                1110                1115                1120

Glu Lys Tyr Ile Asp Ile Ser Glu Asp Asn Arg Leu Gln Leu Ile Asp
                1125                1130                1135

Asn Lys Asn Asn Ala Lys Lys Met Ile Ile Ser Asn Asp Ile Phe Ile
            1140                1145                1150

Ser Asn Cys Leu Thr Leu Ser Tyr Asn Gly Lys Tyr Ile Cys Leu Ser
        1155                1160                1165

Met Lys Asp Glu Asn His Asn Trp Met Ile Cys Asn Asn Asp Met Ser
    1170                1175                1180

Lys Tyr Leu Tyr Leu Trp Ser Phe Lys
1185                1190


<210> SEQ ID NO 24
<211> LENGTH: 1198
<212> TYPE: PRT
<213> ORGANISM: Clostridium botulinum serotype A

<400> SEQUENCE: 24

Met Asn Ile Asn Asp Asn Leu Ser Ile Asn Ser Pro Val Asp Asn Lys
 1               5                  10                  15

Asn Val Val Val Val Arg Ala Arg Lys Thr Asp Thr Val Phe Lys Ala
            20                  25                  30

Phe Lys Val Ala Pro Asn Ile Trp Val Ala Pro Glu Arg Tyr Tyr Gly
        35                  40                  45

Glu Ser Leu Ser Ile Asp Glu Glu Tyr Lys Val Asp Gly Gly Ile Tyr
    50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
    130                 135                 140

Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
```

-continued

```
            180                 185                 190

Asn Gly Met Gly Thr Met Thr Glu Ile Trp Phe Gln Pro Phe Leu Thr
        195                 200                 205

Tyr Lys Tyr Asp Glu Phe Tyr Ile Asp Pro Ala Ile Glu Leu Ile Lys
    210                 215                 220

Cys Leu Ile Lys Ser Leu Tyr Phe Leu Tyr Gly Ile Lys Pro Ser Asp
225                 230                 235                 240

Asp Leu Val Ile Pro Tyr Arg Leu Arg Ser Glu Leu Glu Asn Ile Glu
                245                 250                 255

Tyr Ser Gln Leu Asn Ile Val Asp Leu Leu Val Ser Gly Gly Ile Asp
            260                 265                 270

Pro Lys Phe Ile Asn Thr Asp Pro Tyr Trp Phe Ile Asp Asn Tyr Phe
        275                 280                 285

Ser Asn Ala Lys Lys Val Phe Glu Asp His Arg Asn Ile Tyr Glu Thr
    290                 295                 300

Glu Ile Glu Gly Asn Asn Ala Ile Gly Asn Asp Ile Lys Leu Arg Leu
305                 310                 315                 320

Lys Gln Lys Phe Arg Ile Asn Ile Asn Asp Ile Trp Glu Leu Asn Leu
                325                 330                 335

Asn Tyr Phe Ser Lys Glu Phe Ser Ile Met Met Pro Asp Arg Phe Asn
            340                 345                 350

Asn Ala Leu Lys His Phe Tyr Arg Lys Gln Tyr Tyr Lys Ile Asp Tyr
        355                 360                 365

Pro Glu Asn Tyr Ser Ile Asn Gly Phe Val Asn Gly Gln Ile Asn Ala
    370                 375                 380

Gln Leu Ser Leu Ser Asp Arg Asn Gln Asp Ile Ile Asn Lys Pro Glu
385                 390                 395                 400

Glu Ile Ile Asn Leu Leu Asn Gly Asn Asn Val Ser Leu Met Arg Ser
                405                 410                 415

Asn Ile Tyr Gly Asp Gly Leu Lys Ser Thr Val Asp Asp Phe Tyr Ser
            420                 425                 430

Asn Tyr Lys Ile Pro Tyr Asn Arg Ala Tyr Glu Tyr His Phe Asn Asn
        435                 440                 445

Ser Asn Asp Ser Ser Leu Asp Asn Val Asn Ile Gly Val Ile Asp Asn
    450                 455                 460

Ile Pro Glu Ile Ile Asp Val Asn Pro Tyr Lys Glu Asn Cys Asp Lys
465                 470                 475                 480

Phe Ser Pro Val Gln Lys Ile Thr Ser Thr Arg Glu Ile Asn Thr Asn
                485                 490                 495

Ile Pro Trp Pro Ile Asn Tyr Leu Gln Ala Gln Asn Thr Asn Asn Glu
            500                 505                 510

Lys Phe Ser Leu Ser Ser Asp Phe Val Glu Val Val Ser Ser Lys Asp
        515                 520                 525

Lys Ser Leu Val Tyr Ser Phe Leu Ser Asn Val Met Phe Tyr Leu Asp
    530                 535                 540

Ser Ile Lys Asp Asn Ser Pro Ile Asp Thr Asp Lys Lys Tyr Tyr Leu
545                 550                 555                 560

Trp Leu Arg Glu Ile Phe Arg Asn Tyr Ser Phe Asp Ile Thr Ala Thr
                565                 570                 575

Gln Glu Ile Asn Thr Asp Cys Gly Ile Asn Lys Val Val Thr Trp Phe
            580                 585                 590

Gly Lys Ala Leu Asn Ile Leu Asn Thr Ser Asp Ser Phe Val Glu Glu
        595                 600                 605
```

```
Phe Gln Asn Leu Gly Pro Ile Ser Leu Ile Asn Lys Lys Glu Asn Leu
    610                 615                 620

Ser Met Pro Lys Ile Glu Ile Asp Glu Ile Pro Asn Ser Met Leu Asn
625                 630                 635                 640

Leu Ser Phe Lys Asp Leu Ser Glu Asn Leu Phe Asn Ile Phe Ser Lys
                645                 650                 655

Asn Asn Ser Tyr Phe Glu Lys Ile Tyr Tyr Asp Phe Leu Asp Gln Trp
            660                 665                 670

Trp Thr Gln Tyr Tyr Ser Gln Tyr Phe Asp Leu Ile Cys Met Ala Lys
        675                 680                 685

Arg Ser Val Leu Ala Gln Glu Ser Leu Ile Lys Lys Ile Ile Gln Lys
    690                 695                 700

Lys Leu Ser Tyr Leu Ile Gly Asn Ser Asn Ile Ser Ser Asp Asn Leu
705                 710                 715                 720

Ala Leu Met Asn Leu Thr Thr Thr Asn Thr Leu Arg Asp Ile Ser Asn
                725                 730                 735

Glu Ser Gln Ile Ala Met Asn Asn Val Asn Asn Phe Leu Asn Asn Val
            740                 745                 750

Ala Ile Cys Val Phe Gln Thr Asn Ile Tyr Pro Lys Phe Ile Ser Phe
        755                 760                 765

Met Glu Gln Cys Ile Asn Asn Ile Asn Lys Asn Thr Arg Glu Phe Ile
    770                 775                 780

Gln Lys Cys Thr Asn Ile Thr Glu Asn Glu Lys Leu Gln Leu Ile Asn
785                 790                 795                 800

Gln Asn Ile Phe Ser Ser Leu Asp Phe Asp Phe Leu Asn Ile Glu Asn
                805                 810                 815

Leu Lys Ser Leu Phe Asn Ser Glu Thr Gly Leu Leu Ile Lys Glu Glu
            820                 825                 830

Thr Ser Pro Tyr Glu Leu Val Leu Tyr Ala Phe Gln Glu Pro Gly Asn
        835                 840                 845

Asn Ala Ile Gly Asp Ala Ser Gly Lys Asn Thr Ser Ile Glu Tyr Ser
    850                 855                 860

Lys Asp Ile Gly Leu Val Tyr Gly Ile Asn Ser Asp Ala Leu Tyr Leu
865                 870                 875                 880

Asn Gly Ser Asn Gln Ser Ile Ser Phe Ser Asn Asp Phe Phe Glu Asn
                885                 890                 895

Gly Leu Thr Asn Ser Phe Ser Ile Tyr Phe Trp Leu Arg Asn Leu Gly
            900                 905                 910

Lys Asp Thr Ile Lys Ser Lys Leu Ile Gly Ser Lys Glu Asp Asn Cys
        915                 920                 925

Gly Trp Glu Ile Tyr Phe Gln Asp Thr Gly Leu Val Phe Asn Met Ile
    930                 935                 940

Asp Ser Asn Gly Asn Glu Lys Asn Ile Tyr Leu Ser Asp Val Ser Asn
945                 950                 955                 960

Asn Ser Trp His Tyr Ile Thr Ile Ser Val Asp Arg Leu Lys Glu Gln
                965                 970                 975

Leu Leu Ile Phe Ile Asp Asp Asn Leu Val Ala Asn Glu Ser Ile Lys
            980                 985                 990

Glu Ile Leu Asn Ile Tyr Ser Ser Asn Thr Ile Ser Leu Val Asn Glu
        995                 1000                1005

Asn Asn Pro Ile Tyr Val Glu Gly Leu Ser Ile Leu Asn Arg Ser Ile
    1010                1015                1020

Thr Ser Glu Glu Val Val Asn Asn Tyr Phe Thr Tyr Leu Asn Asn Ser
1025                1030                1035                1040
```

```
Tyr Ile Arg Asp Ile Ser Gly Glu Arg Leu Glu Tyr Asn Lys Thr Tyr
                1045                1050                1055

Glu Leu Tyr Asn Tyr Val Phe Pro Glu Ser Ser Leu Tyr Glu Val Thr
            1060                1065                1070

Glu Asn Asn Asn Ile Tyr Leu Ser Ile Lys Asn Thr Asn Asn Leu Asn
        1075                1080                1085

Ile Gln Gly Ala Lys Phe Lys Leu Ile Asn Ile Asp Ala Asn Lys Gln
    1090                1095                1100

Tyr Val Gln Lys Trp Asp Glu Gly Val Val Cys Leu Leu Gly Asp Glu
1105                1110                1115                1120

Glu Lys Tyr Val Asp Ile Ser Ser Glu Asn Asn Arg Ile Gln Leu Val
                1125                1130                1135

Ser Ser Lys Asp Thr Ala Lys Arg Ile Ile Phe Asn Asn Asp Ile Phe
            1140                1145                1150

Arg Pro Asn Cys Leu Thr Phe Ala Tyr Asn Asn Lys Tyr Leu Ser Leu
        1155                1160                1165

Ser Leu Arg Asp Arg Asn Tyr Asn Trp Met Ile Cys Asn Asn Asn Asp
    1170                1175                1180

Asn Ile Pro Lys Ala Ala His Leu Trp Ala Leu Lys Gly Ile
1185                1190                1195


<210> SEQ ID NO 25
<211> LENGTH: 1197
<212> TYPE: PRT
<213> ORGANISM: Clostridium botulinum serotype B

<400> SEQUENCE: 25

Met Asn Ile Asn Asp Asn Leu Ser Ile Asn Ser Pro Val Asp Asn Lys
 1               5                  10                  15

Asn Val Val Val Val Arg Ala Arg Lys Thr Asp Thr Val Phe Lys Ala
            20                  25                  30

Phe Lys Val Ala Pro Asn Ile Trp Val Ala Pro Glu Arg Tyr Tyr Gly
        35                  40                  45

Glu Ser Leu Ser Ile Asp Glu Glu Tyr Lys Val Asp Gly Gly Ile Tyr
    50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
    130                 135                 140

Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Thr Glu Ile Trp Phe Gln Pro Phe Leu Thr
        195                 200                 205

Tyr Lys Tyr Asp Glu Phe Tyr Ile Asp Pro Ala Ile Glu Leu Ile Lys
    210                 215                 220
```

-continued

```
Cys Leu Ile Lys Ser Leu Tyr Phe Leu Tyr Gly Ile Lys Pro Ser Asp
225                 230                 235                 240

Asp Leu Val Ile Pro Tyr Arg Leu Arg Ser Glu Leu Glu Asn Ile Glu
                245                 250                 255

Tyr Ser Gln Leu Asn Ile Val Asp Leu Leu Val Ser Gly Gly Ile Asp
            260                 265                 270

Pro Lys Phe Ile Asn Thr Asp Pro Tyr Trp Phe Thr Asp Asn Tyr Phe
        275                 280                 285

Ser Asn Ala Lys Lys Val Phe Glu Asp His Arg Asn Ile Tyr Glu Thr
    290                 295                 300

Gln Ile Glu Gly Asn Asn Ala Ile Gly Asn Asp Ile Lys Leu Arg Leu
305                 310                 315                 320

Lys Gln Lys Phe Arg Ile Asn Ile Asn Asp Ile Trp Glu Leu Asn Leu
                325                 330                 335

Asn Tyr Phe Ser Lys Glu Phe Ser Ile Met Met Pro Asp Arg Phe Asn
            340                 345                 350

Asn Ala Leu Lys His Phe Tyr Arg Lys Gln Tyr Tyr Lys Ile Asp Tyr
        355                 360                 365

Pro Glu Asn Tyr Ser Ile Asn Gly Phe Val Asn Gly Gln Ile Asn Val
    370                 375                 380

Gln Leu Ser Leu Ser Asp Arg Asn Gln Asp Ile Ile Asn Lys Pro Glu
385                 390                 395                 400

Glu Ile Ile Asn Leu Leu Asn Gly Asn Asn Val Ser Leu Met Arg Ser
                405                 410                 415

Asn Ile Tyr Gly Asp Gly Leu Lys Ser Thr Val Asp Asp Phe Tyr Ser
            420                 425                 430

Asn Tyr Lys Ile Pro Tyr Asn Arg Ala Tyr Glu Tyr His Phe Asn Asn
        435                 440                 445

Ser Asn Asp Ser Ser Leu Asp Asn Val Asn Ile Gly Val Ile Asp Asn
    450                 455                 460

Ile Pro Glu Ile Ile Asp Val Asn Pro Tyr Lys Glu Asn Cys Asp Lys
465                 470                 475                 480

Phe Ser Pro Val Gln Lys Ile Thr Ser Thr Arg Glu Ile Asn Thr Asn
                485                 490                 495

Ile Pro Trp Pro Ile Asn Tyr Leu Gln Ala Gln Asn Thr Asn Asn Glu
            500                 505                 510

Lys Phe Ser Leu Ser Ser Asp Phe Val Glu Val Val Ser Ser Lys Asp
        515                 520                 525

Lys Ser Leu Val Tyr Ser Phe Leu Ser Asn Val Met Phe Tyr Leu Asp
    530                 535                 540

Ser Ile Lys Asp Asn Ser Pro Ile Asp Thr Asp Lys Lys Tyr Tyr Leu
545                 550                 555                 560

Trp Leu Arg Glu Ile Phe Arg Asn Tyr Ser Phe Asp Ile Thr Ala Thr
                565                 570                 575

Gln Glu Ile Asn Thr Asp Cys Gly Ile Asn Lys Val Val Thr Trp Phe
            580                 585                 590

Gly Lys Ala Leu Asn Ile Leu Asn Thr Ser Asp Ser Phe Val Glu Glu
        595                 600                 605

Phe Gln Asn Leu Gly Pro Ile Ser Leu Ile Asn Lys Lys Glu Asn Leu
    610                 615                 620

Ser Met Pro Ile Ile Glu Ile Tyr Gly Ile Pro Asn Asp Met Leu Gly
625                 630                 635                 640

Leu Pro Leu Asn Asp Leu Asn Glu Lys Leu Phe Asn Ile Tyr Leu Lys
```

```
                645                 650                 655

Asn Ile Leu Tyr Phe Lys Lys Val Tyr Phe Asn Phe Leu Asp Gln Trp
            660                 665                 670

Trp Thr Glu Tyr Tyr Ser Gln Tyr Phe Asp Leu Ile Cys Met Ala Lys
        675                 680                 685

Gln Ser Ile Leu Ala Gln Glu Lys Leu Ile Lys Gln Ile Ile Gln Asn
    690                 695                 700

Lys Leu Gln Asp Leu Phe Lys Ala Asp Ile Ser Met Asp Lys Leu Asn
705                 710                 715                 720

Leu Met Asn Leu Ala Thr Glu Lys Thr Phe Ile Asp Leu Ser Asn Glu
                725                 730                 735

Ser Gln Ile Ala Ile Asn Asn Ile Asn Asp Phe Leu Asn Lys Ser Ala
            740                 745                 750

Ile Cys Val Phe Asp Thr Asn Ile Tyr Pro Lys Phe Ile Ser Phe Met
        755                 760                 765

Glu Gln Cys Ile Asn Ser Val Asn Ser Asn Val Thr Ala Phe Ile Gln
    770                 775                 780

Lys Cys Thr Asn Ile Thr Glu Asp Glu Lys Leu Gln Leu Ile Lys Leu
785                 790                 795                 800

Asn Thr Phe Met Asn Ile Asp Phe Glu Phe Phe Asp Ile Gln Ser Ile
                805                 810                 815

Lys Asp Leu Ile Thr Ser Glu Thr Asp Leu Ile Lys Glu Glu Lys Glu
            820                 825                 830

Ser Asp Tyr Asn Leu Phe Leu Phe Thr Leu Gln Glu Asp Asn Asn Lys
        835                 840                 845

Val Ile Glu Asp Ile Ser Gly Lys Asn Thr Leu Val Lys Tyr Ser Asp
    850                 855                 860

Ser Ile Ser Leu Val Tyr Gly Val Asn Gly Asp Ala Leu Tyr Leu Lys
865                 870                 875                 880

Glu Pro Asp Glu Ser Val Ser Phe Ser Asn Lys Ala Phe Glu Asn Gly
                885                 890                 895

Leu Thr Asn Ser Phe Ser Ile Cys Phe Trp Leu Arg Asn Leu Gly Glu
            900                 905                 910

Asp Ile Ile Thr Ser Lys Leu Ile Glu Asn Lys Ala Asp Asn Cys Gly
        915                 920                 925

Trp Glu Ile Tyr Phe Glu Asn Asn Gly Leu Val Phe Ser Ile Val Asp
    930                 935                 940

Cys Asn Gly Asn Glu Glu Asn Ile Tyr Leu Ser Asp Val Ile Ser Lys
945                 950                 955                 960

Asn Trp Tyr Tyr Ile Ser Ile Ser Ile Asp Arg Leu Arg Asn Gln Leu
                965                 970                 975

Leu Ile Phe Ile Asn Asp Lys Leu Ile Ala Asn Gln Ser Ile Glu Gln
            980                 985                 990

Ile Leu Asn Ile Tyr Ser Ser Asn Thr Ile Ser Leu Val Asn Glu Asn
        995                 1000                1005

Asn Pro Ile Tyr Ile Glu Gly Leu Ser Ile Leu Asn Arg Ser Ile Thr
    1010                1015                1020

Ser Glu Glu Val Val Asn Asn Tyr Phe Ser Tyr Leu Asn Asn Ser Tyr
1025                1030                1035                1040

Ile Arg Asp Ile Ser Gly Glu Arg Leu Glu Tyr Asn Lys Thr Tyr Glu
                1045                1050                1055

Leu Tyr Asn Tyr Val Phe Pro Glu Asn Ser Leu Tyr Glu Val Thr Glu
            1060                1065                1070
```

```
Asn Asn Asn Ile Tyr Leu Ser Ile Lys Asp Thr Asn Asn Leu Asn Ile
        1075                1080                1085

Gln Gly Ala Lys Phe Lys Leu Ile Asn Ile Asp Ala Asn Lys Gln Tyr
    1090                1095                1100

Val Gln Lys Trp Asp Glu Gly Val Val Cys Leu Leu Gly Asp Glu Glu
1105                1110                1115                1120

Lys Tyr Val Asp Ile Ser Ser Glu Asn Asn Arg Ile Gln Leu Val Asn
                1125                1130                1135

Ser Lys Asp Thr Ala Lys Arg Ile Ile Phe Asn Asn Asp Ile Phe Met
            1140                1145                1150

Pro Asn Cys Leu Thr Phe Ala Tyr Asn Asn Lys Tyr Leu Ser Leu Ser
        1155                1160                1165

Leu Arg Asp Arg Asn Tyr Asn Trp Met Ile Cys Asn Asn Asn Asp Asn
    1170                1175                1180

Ile Pro Lys Ala Ala His Leu Trp Ala Leu Lys Gly Ile
1185                1190                1195


<210> SEQ ID NO 26
<211> LENGTH: 1193
<212> TYPE: PRT
<213> ORGANISM: Clostridium botulinum serotype B

<400> SEQUENCE: 26

Met Asp Ile Asn Asp Asp Leu Asn Ile Asn Ser Pro Val Asp Asn Lys
 1               5                  10                  15

Asn Val Val Ile Val Arg Ala Arg Lys Thr Asn Thr Phe Phe Lys Ala
            20                  25                  30

Phe Lys Val Ala Pro Asn Ile Trp Val Ala Pro Glu Arg Tyr Tyr Gly
        35                  40                  45

Glu Pro Leu His Ile Ala Glu Glu Tyr Lys Leu Asp Gly Gly Ile Tyr
    50                  55                  60

Asp Ser Asn Phe Leu Ser Gln Asp Ser Glu Arg Glu Asn Phe Leu Gln
65                  70                  75                  80

Ala Ile Ile Ile Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
            100                 105                 110

Ile Gly Gly Gly Tyr Ser Ser Pro Asn Ile Phe Thr Phe Gly Lys Thr
        115                 120                 125

Pro Arg Thr Asn Lys Lys Leu Asn Ser Leu Val Thr Ser Thr Ile Pro
    130                 135                 140

Phe Pro Phe Gly Gly Tyr Arg Glu Thr Asn Tyr Ile Glu Ser Gln Asn
145                 150                 155                 160

Asn Lys Asn Phe Tyr Ala Ser Asn Ile Ile Ile Phe Gly Pro Gly Ser
                165                 170                 175

Asn Ile Val Glu Asn Asn Val Ile Tyr Tyr Lys Lys Asn Asp Ala Glu
            180                 185                 190

Asn Gly Met Gly Thr Met Ala Glu Ile Val Phe Gln Pro Leu Leu Thr
        195                 200                 205

Tyr Lys Tyr Asn Lys Phe Tyr Ile Asp Pro Ala Met Glu Leu Thr Lys
    210                 215                 220

Cys Leu Ile Lys Ser Leu Tyr Phe Leu Tyr Gly Ile Lys Pro Ser Gly
225                 230                 235                 240

Asn Leu Val Val Pro Tyr Arg Leu Arg Thr Glu Leu Asp Asn Lys Gln
                245                 250                 255
```

-continued

```
Phe Ser Gln Leu Asn Ile Ile Asp Leu Leu Ile Ser Gly Gly Val Asp
            260                 265                 270

Leu Glu Phe Ile Asn Thr Asn Pro Tyr Trp Phe Thr Asn Ser Tyr Phe
        275                 280                 285

Pro Asn Ser Ile Lys Met Phe Glu Lys Tyr Lys Asn Ile Tyr Lys Thr
    290                 295                 300

Glu Ile Glu Gly Asn Asn Ala Ile Gly Asn Asp Ile Lys Leu Arg Leu
305                 310                 315                 320

Lys Gln Lys Phe Gln Ile Asn Val Gln Asp Ile Trp Asn Leu Asn Leu
                325                 330                 335

Asn Tyr Phe Cys Gln Ser Phe Asn Ser Ile Ile Pro Asp Arg Phe Ser
            340                 345                 350

Asn Ala Leu Lys His Phe Tyr Arg Lys Gln Tyr Tyr Thr Met Asp Tyr
        355                 360                 365

Thr Asp Asn Tyr Asn Ile Asn Gly Phe Val Asn Gly Gln Ile Asn Thr
    370                 375                 380

Lys Leu Pro Leu Ser Asn Lys Asn Thr Asn Ile Ile Ser Lys Pro Glu
385                 390                 395                 400

Lys Val Val Asn Leu Val Asn Glu Asn Asn Ile Ser Leu Met Lys Ser
                405                 410                 415

Asn Ile Tyr Gly Asp Gly Leu Lys Gly Thr Thr Glu Asp Phe Tyr Ser
            420                 425                 430

Thr Tyr Lys Ile Pro Tyr Asp Glu Glu Tyr Glu Tyr Arg Phe Asn Asp
        435                 440                 445

Ser Asp Asn Phe Pro Leu Asn Asn Ile Ser Ile Glu Glu Val Asp Ser
    450                 455                 460

Ile Pro Glu Ile Ile Asp Ile Asn Pro Tyr Lys Asp Asn Ser Asp Asn
465                 470                 475                 480

Leu Val Phe Thr Gln Ile Thr Ser Met Thr Glu Glu Val Thr Thr His
                485                 490                 495

Thr Ala Leu Ser Ile Asn Tyr Leu Gln Ala Gln Ile Thr Asn Asn Glu
            500                 505                 510

Asn Phe Thr Leu Ser Ser Asp Phe Ser Lys Val Val Ser Ser Lys Asp
        515                 520                 525

Lys Ser Leu Val Tyr Ser Phe Leu Asp Asn Leu Met Ser Tyr Leu Glu
    530                 535                 540

Thr Ile Lys Asn Asp Arg Pro Ile His Thr Asp Lys Lys Tyr Tyr Leu
545                 550                 555                 560

Trp Leu Lys Glu Val Phe Lys Asn Tyr Ser Phe Asp Ile Asn Leu Thr
                565                 570                 575

Gln Glu Ile Asp Ser Met Cys Gly Ile Asn Gln Val Val Leu Trp Phe
            580                 585                 590

Gly Lys Ala Leu Asn Ile Leu Asn Thr Ser Asn Ser Phe Val Glu Glu
        595                 600                 605

Tyr Gln Asp Ser Gly Ala Ile Ser Leu Ile Ser Lys Lys Asp Asn Leu
    610                 615                 620

Arg Glu Pro Asn Ile Glu Ile Asp Asp Ile Ser Asp Ser Leu Leu Gly
625                 630                 635                 640

Leu Ser Phe Lys Asp Leu Asn Asn Lys Leu Tyr Glu Ile Tyr Ser Lys
                645                 650                 655

Asn Ile Val Tyr Phe Lys Lys Ile Tyr Phe Ser Phe Leu Asp Gln Trp
            660                 665                 670

Trp Thr Gln Tyr Tyr Ser Gln Tyr Phe Asp Leu Ile Cys Met Ala Lys
        675                 680                 685
```

```
Lys Ser Ile Leu Ala Gln Glu Thr Leu Ile Lys Lys Ile Ile Gln Lys
    690                 695                 700

Lys Leu Ser Tyr Leu Ile Gly Asn Ser Asn Ile Ser Ser Asp Asn Leu
705                 710                 715                 720

Ala Leu Met Asn Leu Thr Thr Thr Asn Thr Leu Arg Asp Ile Ser Asn
                725                 730                 735

Glu Ser Gln Ile Ala Met Asn Asn Val Asp Ser Phe Leu Asn Ser Ala
            740                 745                 750

Ala Ile Cys Val Phe Glu Gly Asn Ile Tyr Pro Lys Phe Ile Ser Phe
        755                 760                 765

Met Glu Gln Cys Ile Asn Asn Ile Asn Lys Asn Thr Arg Glu Phe Ile
    770                 775                 780

Gln Lys Cys Thr Asn Ile Thr Glu Asn Glu Lys Leu Gln Leu Ile Asn
785                 790                 795                 800

Gln Asn Ile Phe Ser Ser Leu Asp Phe Asp Phe Leu Asn Ile Glu Asn
                805                 810                 815

Leu Lys Ser Leu Phe Ser Ser Glu Thr Ala Leu Leu Ile Lys Glu Glu
            820                 825                 830

Thr Ser Pro Tyr Glu Leu Val Leu Tyr Ala Phe Gln Glu Pro Asp Asn
        835                 840                 845

Asn Ala Ile Gly Asp Ala Ser Ala Lys Asn Thr Ser Ile Glu Tyr Ser
    850                 855                 860

Lys Asp Ile Asp Leu Val Tyr Gly Ile Asn Ser Asp Ala Leu Tyr Leu
865                 870                 875                 880

Asn Gly Ser Asn Gln Ser Ile Ser Phe Ser Asn Asp Phe Phe Glu Asn
                885                 890                 895

Gly Leu Thr Asn Ser Phe Ser Ile Tyr Phe Trp Leu Arg Asn Leu Gly
            900                 905                 910

Lys Asp Thr Ile Lys Ser Lys Leu Ile Gly Ser Lys Gly Asp Asn Cys
        915                 920                 925

Gly Trp Glu Ile Tyr Phe Gln Asp Thr Gly Leu Val Phe Asn Met Ile
    930                 935                 940

Asp Ser Asn Gly Asn Glu Lys Asn Ile Tyr Leu Ser Asp Val Ser Asn
945                 950                 955                 960

Asn Ser Trp His Tyr Ile Thr Ile Ser Val Asp Arg Leu Lys Glu Gln
                965                 970                 975

Leu Leu Ile Phe Ile Asp Asp Asn Leu Val Ala Asn Glu Ser Ile Lys
            980                 985                 990

Glu Ile Leu Asn Ile Tyr Ser Ser Asn Ile Ile Ser Leu Leu Ser Glu
        995                 1000                1005

Asn Asn Pro Ser Tyr Ile Glu Gly Leu Thr Ile Leu Asn Lys Pro Thr
    1010                1015                1020

Thr Ser Gln Glu Val Leu Asn Asn Tyr Phe Lys Val Leu Asn Asn Ser
1025                1030                1035                1040

Tyr Ile Arg Asp Ser Asn Glu Glu Arg Leu Glu Tyr Asn Lys Thr Tyr
                1045                1050                1055

Gln Leu Tyr Asn Tyr Val Phe Ser Asp Lys Pro Ile Cys Glu Val Lys
            1060                1065                1070

Gln Asn Asn Asn Ile Tyr Leu Thr Ile Asn Asn Thr Asn Asn Leu Asn
        1075                1080                1085

Leu Gln Pro Ser Lys Phe Lys Leu Leu Ser Ile Asn Pro Asn Lys Gln
    1090                1095                1100

Tyr Val Gln Lys Leu Asp Glu Val Ile Ile Ser Val Leu Gly Asn Met
```

1105 1110 1115 1120

Glu Lys Tyr Ile Asp Ile Ser Glu Asp Asn Arg Leu Gln Leu Ile Asp
1125 1130 1135

Asn Lys Asn Gly Ala Lys Lys Met Ile Ile Ser Asn Asp Met Phe Ile
1140 1145 1150

Ser Asn Cys Leu Thr Leu Ser Cys Gly Gly Lys Tyr Ile Cys Leu Ser
1155 1160 1165

Met Lys Asp Glu Asn His Asn Trp Met Ile Cys Asn Asn Asp Met Ser
1170 1175 1180

Lys Tyr Leu Tyr Leu Trp Ser Phe Lys
1185 1190

<210> SEQ ID NO 27
<211> LENGTH: 1196
<212> TYPE: PRT
<213> ORGANISM: Clostridium botulinum serotype C1

<400> SEQUENCE: 27

Met Asp Ile Asn Asp Asp Leu Asn Ile Asn Ser Pro Val Asp Asn Lys
1 5 10 15

Asn Val Val Ile Val Arg Ala Arg Lys Thr Asn Thr Phe Phe Lys Ala
20 25 30

Phe Lys Val Ala Pro Asn Ile Trp Val Ala Pro Glu Arg Tyr Tyr Gly
35 40 45

Glu Pro Leu Asp Ile Ala Glu Glu Tyr Lys Leu Asp Gly Gly Ile Tyr
50 55 60

Asp Ser Asn Phe Leu Ser Gln Asp Ser Glu Arg Glu Asn Phe Leu Gln
65 70 75 80

Ala Ile Ile Ile Leu Leu Lys Arg Ile Asn Asn Thr Ile Ser Gly Lys
85 90 95

Gln Leu Leu Ser Leu Ile Ser Thr Ala Ile Pro Phe Pro Tyr Gly Tyr
100 105 110

Ile Gly Gly Gly Tyr Ser Ser Pro Asn Ile Phe Thr Phe Gly Lys Thr
115 120 125

Pro Lys Ser Asn Lys Lys Leu Asn Ser Leu Val Thr Ser Thr Ile Pro
130 135 140

Phe Pro Phe Gly Gly Tyr Arg Glu Thr Asn Tyr Ile Glu Ser Gln Asn
145 150 155 160

Asn Lys Asn Phe Tyr Ala Ser Asn Ile Ile Ile Phe Gly Pro Gly Ser
165 170 175

Asn Ile Val Glu Asn Asn Val Ile Tyr Tyr Lys Lys Asn Asp Ala Glu
180 185 190

Asn Gly Met Gly Thr Met Ala Glu Ile Val Phe Gln Pro Leu Leu Thr
195 200 205

Tyr Lys Tyr Asn Lys Phe Tyr Ile Asp Pro Ala Met Glu Leu Thr Lys
210 215 220

Cys Leu Ile Lys Ser Leu Tyr Phe Leu Tyr Gly Ile Lys Pro Ser Asp
225 230 235 240

Asn Leu Val Val Pro Tyr Arg Leu Arg Thr Glu Leu Asp Asn Lys Gln
245 250 255

Phe Ser Gln Leu Asn Ile Ile Asp Leu Leu Ile Ser Gly Gly Val Asp
260 265 270

Leu Glu Phe Ile Asn Thr Asn Pro Tyr Trp Phe Thr Asn Ser Tyr Phe
275 280 285

Pro Asn Ser Ile Lys Met Phe Glu Lys Tyr Lys Asn Ile Tyr Lys Thr

-continued

```
    290                 295                 300

Glu Ile Glu Gly Asn Asn Ala Ile Gly Asn Asp Ile Lys Leu Arg Leu
305                 310                 315                 320

Lys Gln Lys Phe Gln Ile Asn Val Gln Asp Ile Trp Asn Leu Asn Leu
                325                 330                 335

Asn Tyr Phe Cys Gln Ser Phe Asn Ser Ile Ile Pro Asp Arg Phe Ser
            340                 345                 350

Asn Ala Leu Lys His Phe Tyr Arg Lys Gln Tyr Tyr Thr Met Asp Tyr
        355                 360                 365

Thr Asp Asn Tyr Asn Ile Asn Gly Phe Val Asn Gly Gln Ile Asn Thr
    370                 375                 380

Lys Leu Pro Leu Ser Asn Lys Asn Thr Asn Ile Ile Ser Lys Pro Glu
385                 390                 395                 400

Lys Val Val Asn Leu Val Asn Glu Asn Asn Ile Ser Leu Met Lys Ser
                405                 410                 415

Asn Ile Tyr Gly Asp Gly Leu Lys Gly Thr Thr Glu Asp Phe Tyr Ser
            420                 425                 430

Thr Tyr Lys Ile Pro Tyr Asn Glu Glu Tyr Glu Tyr Arg Phe Asn Asp
        435                 440                 445

Ser Asp Asn Phe Pro Leu Asn Asn Ile Ser Ile Glu Glu Val Asp Ser
    450                 455                 460

Ile Pro Glu Ile Ile Asp Ile Asn Pro Tyr Lys Asp Asn Ser Asp Asn
465                 470                 475                 480

Leu Val Phe Thr Gln Ile Thr Ser Met Thr Glu Glu Val Thr Thr His
                485                 490                 495

Thr Ala Leu Ser Ile Asn Tyr Leu Gln Ala Gln Ile Thr Asn Asn Glu
            500                 505                 510

Asn Phe Thr Leu Ser Ser Asp Phe Ser Lys Val Val Ser Ser Lys Asp
        515                 520                 525

Lys Ser Leu Val Tyr Ser Phe Leu Asp Asn Leu Met Ser Tyr Leu Glu
    530                 535                 540

Thr Ile Lys Asn Asp Gly Pro Ile Asp Thr Asp Lys Lys Tyr Tyr Leu
545                 550                 555                 560

Trp Leu Lys Glu Val Phe Lys Asn Tyr Ser Phe Asp Ile Asn Leu Thr
                565                 570                 575

Gln Glu Ile Asp Ser Met Cys Gly Ile Asn Glu Val Val Leu Trp Phe
            580                 585                 590

Gly Lys Ala Leu Asn Ile Leu Asn Thr Ser Asn Ser Phe Val Glu Glu
        595                 600                 605

Tyr Gln Asp Ser Gly Ala Ile Ser Leu Ile Ser Lys Lys Asp Asn Leu
    610                 615                 620

Arg Glu Pro Asn Ile Glu Ile Asp Asp Ile Ser Asp Ser Leu Leu Gly
625                 630                 635                 640

Leu Ser Phe Lys Asp Leu Asn Asn Lys Leu Tyr Glu Ile Tyr Ser Lys
                645                 650                 655

Asn Ile Val Tyr Phe Lys Lys Ile Tyr Phe Ser Phe Leu Asp Gln Trp
            660                 665                 670

Trp Thr Glu Tyr Tyr Ser Gln Tyr Phe Glu Leu Ile Cys Met Ala Lys
        675                 680                 685

Gln Ser Ile Leu Ala Gln Glu Ser Leu Val Lys Gln Ile Val Gln Asn
    690                 695                 700

Lys Phe Thr Asp Leu Ser Lys Ala Ser Ile Pro Pro Asp Thr Leu Lys
705                 710                 715                 720
```

-continued

```
Leu Ile Arg Glu Thr Thr Glu Lys Thr Phe Ile Asp Leu Ser Asn Glu
                725                 730                 735

Ser Gln Ile Ser Met Asn Arg Val Asp Asn Phe Leu Asn Lys Ala Ser
            740                 745                 750

Ile Cys Val Phe Val Glu Asp Ile Tyr Pro Lys Phe Ile Ser Tyr Met
        755                 760                 765

Glu Lys Tyr Ile Asn Asn Ile Asn Ile Lys Thr Arg Glu Phe Ile Gln
    770                 775                 780

Arg Cys Thr Asn Ile Asn Asp Asn Glu Lys Ser Ile Leu Ile Asn Ser
785                 790                 795                 800

Tyr Thr Phe Lys Thr Ile Asp Phe Lys Phe Leu Asp Ile Gln Ser Ile
                805                 810                 815

Lys Asn Phe Phe Asn Ser Gln Val Glu Gln Val Met Lys Glu Ile Leu
            820                 825                 830

Ser Pro Tyr Gln Leu Leu Leu Phe Ala Ser Lys Gly Pro Asn Ser Asn
        835                 840                 845

Ile Ile Glu Asp Ile Ser Gly Lys Asn Thr Leu Ile Gln Tyr Thr Glu
    850                 855                 860

Ser Ile Glu Leu Val Tyr Gly Val Asn Gly Glu Ser Leu Tyr Leu Lys
865                 870                 875                 880

Ser Pro Asn Glu Thr Ile Lys Phe Ser Asn Lys Phe Phe Thr Asn Gly
                885                 890                 895

Leu Thr Asn Asn Phe Thr Ile Cys Phe Trp Leu Arg Phe Thr Gly Lys
            900                 905                 910

Asn Asp Asp Lys Thr Arg Leu Ile Gly Asn Lys Val Asn Asn Cys Gly
        915                 920                 925

Trp Glu Ile Tyr Phe Glu Asp Asn Gly Leu Val Phe Glu Ile Ile Asp
    930                 935                 940

Ser Asn Gly Asn Gln Glu Ser Val Tyr Leu Ser Asn Ile Ile Asn Asp
945                 950                 955                 960

Asn Trp Tyr Tyr Ile Ser Ile Ser Val Asp Arg Leu Lys Asp Gln Leu
                965                 970                 975

Leu Ile Phe Ile Asn Asp Lys Asn Val Ala Asn Val Ser Ile Asp Gln
            980                 985                 990

Ile Leu Ser Ile Tyr Ser Thr Asn Ile Ile Ser Leu Val Asn Lys Asn
        995                 1000                1005

Asn Ser Ile Tyr Val Glu Glu Leu Ser Val Leu Asp Asn Pro Ile Thr
    1010                1015                1020

Ser Glu Glu Val Ile Arg Asn Tyr Phe Ser Tyr Leu Asp Asn Ser Tyr
1025                1030                1035                1040

Ile Arg Asp Ser Ser Lys Ser Leu Leu Glu Tyr Asn Lys Asn Tyr Gln
                1045                1050                1055

Leu Tyr Asn Tyr Val Phe Pro Glu Thr Ser Leu Tyr Glu Val Asn Asp
            1060                1065                1070

Asn Asn Lys Ser Tyr Leu Ser Leu Lys Asn Thr Asp Gly Ile Asn Ile
        1075                1080                1085

Ser Ser Val Lys Phe Lys Leu Ile Asn Ile Asp Glu Ser Lys Val Tyr
    1090                1095                1100

Val Gln Lys Trp Asp Glu Cys Ile Ile Cys Val Leu Asp Gly Thr Glu
1105                1110                1115                1120

Lys Tyr Leu Asp Ile Ser Pro Glu Asn Asn Arg Ile Gln Leu Val Ser
                1125                1130                1135

Ser Lys Asp Asn Ala Lys Lys Ile Thr Val Asn Thr Asp Leu Phe Arg
            1140                1145                1150
```

```
Pro Asp Cys Ile Thr Phe Ser Tyr Asn Asp Lys Tyr Phe Ser Leu Ser
        1155                1160                1165

Leu Arg Asp Gly Asp Tyr Asn Trp Met Ile Cys Asn Asp Asn Asn Lys
    1170                1175                1180

Val Pro Lys Gly Ala His Leu Trp Ile Leu Glu Ser
1185                1190                1195


<210> SEQ ID NO 28
<211> LENGTH: 1196
<212> TYPE: PRT
<213> ORGANISM: Clostridium botulinum serotype D

<400> SEQUENCE: 28

Met Asp Ile Asn Asp Asp Leu Asn Ile Asn Ser Pro Val Asp Asn Lys
1               5                   10                  15

Asn Val Val Ile Val Arg Ala Arg Lys Thr Asn Thr Phe Phe Lys Ala
            20                  25                  30

Phe Lys Val Ala Pro Asn Ile Trp Val Ala Pro Glu Arg Tyr Tyr Gly
        35                  40                  45

Glu Pro Leu Asp Ile Ala Glu Glu Tyr Lys Leu Asp Gly Gly Ile Tyr
    50                  55                  60

Asp Ser Asn Phe Leu Ser Gln Asp Ser Glu Arg Glu Asn Phe Leu Gln
65                  70                  75                  80

Ala Ile Ile Thr Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
            100                 105                 110

Val Gly Gly Gly Tyr Ser Ser Pro Asn Ile Phe Thr Phe Gly Lys Thr
        115                 120                 125

Pro Lys Ser Asn Lys Lys Leu Asn Ser Leu Val Thr Ser Thr Ile Pro
    130                 135                 140

Phe Pro Phe Gly Gly Tyr Arg Glu Thr Asn Tyr Ile Glu Ser Gln Asn
145                 150                 155                 160

Asn Lys Asn Phe Tyr Ala Ser Asn Ile Val Ile Phe Gly Pro Gly Ser
                165                 170                 175

Asn Ile Val Glu Asn Asn Val Ile Cys Tyr Lys Lys Asn Asp Ala Glu
            180                 185                 190

Asn Gly Met Gly Thr Met Ala Glu Ile Leu Phe Gln Pro Leu Leu Thr
        195                 200                 205

Tyr Lys Tyr Asn Lys Phe Tyr Ile Asp Pro Ala Met Glu Leu Thr Lys
    210                 215                 220

Cys Leu Ile Lys Ser Leu Tyr Phe Leu Tyr Gly Ile Lys Pro Ser Asp
225                 230                 235                 240

Asp Leu Val Val Pro Tyr Arg Leu Arg Thr Glu Leu Asp Asn Lys Gln
                245                 250                 255

Phe Ser Gln Leu Asn Ile Ile Asp Leu Leu Ile Ser Gly Gly Val Asp
            260                 265                 270

Leu Glu Phe Ile Asn Thr Asn Pro Tyr Trp Phe Thr Asn Ser Tyr Phe
        275                 280                 285

Ser Asn Ser Ile Lys Met Phe Glu Lys Tyr Lys Asn Ile Tyr Glu Thr
    290                 295                 300

Glu Ile Glu Gly Asn Asn Ala Ile Gly Asn Asp Ile Lys Leu Arg Leu
305                 310                 315                 320

Lys Gln Lys Phe Gln Asn Ser Val Gln Asp Ile Trp Asn Leu Asn Leu
                325                 330                 335
```

```
Asn Tyr Phe Ser Lys Glu Phe Asn Ser Ile Ile Pro Asp Arg Phe Ser
            340                 345                 350

Asn Ala Leu Lys His Phe Tyr Arg Lys Gln Tyr Tyr Thr Met Asp Tyr
        355                 360                 365

Gly Asp Asn Tyr Asn Ile Asn Gly Phe Val Asn Gly Gln Ile Asn Thr
    370                 375                 380

Lys Leu Pro Leu Ser Asp Lys Asn Thr Asn Ile Ile Ser Lys Pro Glu
385                 390                 395                 400

Lys Val Val Asn Leu Val Asn Ala Asn Asn Ile Ser Leu Met Lys Ser
                405                 410                 415

Asn Ile Tyr Gly Asp Gly Leu Lys Gly Thr Thr Glu Asp Phe Tyr Ser
            420                 425                 430

Thr Tyr Lys Ile Pro Tyr Asn Glu Glu Tyr Glu Tyr Arg Phe Asn Asp
        435                 440                 445

Ser Asp Asn Phe Pro Leu Asn Asn Ile Ser Ile Glu Glu Val Asp Ser
    450                 455                 460

Ile Pro Glu Ile Ile Asp Ile Asn Pro Tyr Lys Asp Asn Ser Asp Asp
465                 470                 475                 480

Leu Leu Phe Thr Gln Ile Thr Ser Thr Thr Glu Glu Val Ile Thr His
                485                 490                 495

Thr Ala Leu Pro Val Asn Tyr Leu Gln Ala Gln Ile Ile Thr Asn Glu
            500                 505                 510

Asn Phe Thr Leu Ser Ser Asp Phe Ser Lys Val Val Ser Ser Lys Asp
        515                 520                 525

Lys Ser Leu Val Tyr Ser Phe Leu Asp Asn Leu Met Ser Tyr Leu Glu
    530                 535                 540

Thr Ile Lys Asn Asp Gly Pro Ile Asp Thr Asp Lys Lys Tyr Tyr Leu
545                 550                 555                 560

Trp Leu Lys Glu Val Phe Lys Asn Tyr Ser Phe Asp Ile Asn Leu Thr
                565                 570                 575

Gln Glu Ile Asp Ser Ser Cys Gly Ile Asn Glu Val Val Ile Trp Phe
            580                 585                 590

Gly Lys Ala Leu Asn Ile Leu Asn Thr Ser Asn Ser Phe Val Glu Glu
        595                 600                 605

Tyr Gln Asn Ser Gly Pro Ile Ser Leu Ile Ser Lys Lys Asp Asn Leu
    610                 615                 620

Ser Glu Pro Asn Ile Glu Ile Asp Asp Ile Pro Asp Ser Leu Leu Gly
625                 630                 635                 640

Leu Ser Phe Lys Asp Leu Asn Asn Lys Leu Tyr Glu Ile Tyr Ser Lys
                645                 650                 655

Asn Arg Val Tyr Phe Arg Lys Ile Tyr Phe Asn Phe Leu Asp Gln Trp
            660                 665                 670

Trp Thr Glu Tyr Tyr Ser Gln Tyr Phe Glu Leu Ile Cys Met Ala Lys
        675                 680                 685

Gln Ser Ile Leu Ala Gln Glu Ser Val Val Lys Gln Ile Ile Gln Asn
    690                 695                 700

Lys Phe Thr Asp Leu Ser Lys Ala Ser Ile Pro Pro Asp Thr Leu Lys
705                 710                 715                 720

Leu Ile Lys Glu Thr Thr Glu Lys Thr Phe Ile Asp Leu Ser Asn Glu
                725                 730                 735

Ser Gln Ile Ser Met Asn Arg Val Asp Asn Phe Leu Asn Lys Ala Ser
            740                 745                 750

Ile Cys Val Phe Val Glu Asp Ile Tyr Pro Lys Phe Ile Ser Tyr Met
```

-continued

```
        755                 760                 765

Glu Lys Tyr Ile Asn Asn Ile Asn Ile Lys Thr Arg Glu Phe Ile Gln
    770                 775                 780

Arg Cys Thr Asn Ile Asn Asp Asn Glu Lys Ser Ile Leu Ile Asn Ser
785                 790                 795                 800

Tyr Thr Phe Lys Thr Ile Asp Phe Lys Phe Leu Asn Ile Gln Ala Ile
                805                 810                 815

Lys Asn Phe Phe Asn Ser Gln Val Glu Gln Val Met Lys Glu Met Leu
            820                 825                 830

Ser Pro Tyr Gln Leu Leu Leu Phe Ala Thr Arg Gly Pro Asn Ser Asn
        835                 840                 845

Ile Ile Glu Asp Ile Ser Gly Lys Asn Thr Leu Ile Gln Tyr Thr Glu
    850                 855                 860

Ser Val Glu Leu Val Tyr Gly Val Asn Gly Glu Ser Leu Tyr Leu Lys
865                 870                 875                 880

Ser Pro Asn Glu Thr Val Glu Phe Ser Asn Asn Phe Phe Thr Asn Gly
                885                 890                 895

Leu Thr Asn Asn Phe Thr Ile Cys Phe Trp Leu Arg Phe Thr Gly Lys
            900                 905                 910

Asp Asp Asp Lys Thr Arg Leu Ile Gly Asn Lys Val Asn Asn Cys Gly
        915                 920                 925

Trp Glu Ile Tyr Phe Glu Asp Asn Gly Leu Val Phe Glu Ile Ile Asp
    930                 935                 940

Ser Asn Gly Asn Gln Glu Ser Val Tyr Leu Ser Asn Val Ile Asn Asn
945                 950                 955                 960

Asn Trp Tyr Tyr Ile Ser Ile Ser Val Asp Arg Leu Lys Asp Gln Leu
                965                 970                 975

Leu Ile Phe Ile Asn Asp Lys Asn Val Ala Asn Val Ser Ile Glu Gln
            980                 985                 990

Ile Leu Asn Ile Tyr Ser Thr Asn Val Ile Ser Leu Val Asn Lys Asn
        995                 1000                1005

Asn Ser Ile Tyr Val Glu Glu Leu Ser Val Leu Asp Lys Pro Val Ala
    1010                1015                1020

Ser Glu Glu Val Ile Arg Asn Tyr Phe Ser Tyr Leu Asp Asn Ser Tyr
1025                1030                1035                1040

Ile Arg Asp Ser Ser Lys Ser Leu Leu Glu Tyr Asn Lys Asn Tyr Gln
                1045                1050                1055

Leu Tyr Asn Tyr Val Phe Pro Glu Thr Ser Leu Tyr Glu Val Asn Asp
            1060                1065                1070

Asn Asn Lys Ser Tyr Leu Ser Leu Lys Asn Thr Asp Gly Ile Asn Ile
        1075                1080                1085

Pro Ser Val Lys Phe Lys Leu Ile Asn Ile Asp Glu Ser Lys Gly Tyr
    1090                1095                1100

Val Gln Lys Trp Asp Glu Cys Ile Ile Cys Val Ser Asp Gly Thr Glu
1105                1110                1115                1120

Lys Tyr Leu Asp Ile Ser Pro Glu Asn Asn Arg Ile Gln Leu Val Ser
                1125                1130                1135

Ser Lys Asp Asn Ala Lys Lys Ile Thr Val Asn Thr Asp Leu Phe Arg
            1140                1145                1150

Pro Asp Cys Ile Thr Phe Ser Tyr Asn Asp Lys Tyr Phe Ser Leu Ser
        1155                1160                1165

Leu Arg Asp Gly Asp Tyr Asn Trp Met Ile Cys Asn Asp Asn Asn Lys
    1170                1175                1180
```

```
Val Pro Lys Gly Ala His Leu Trp Ile Leu Lys Ser
1185                1190                1195


<210> SEQ ID NO 29
<211> LENGTH: 1162
<212> TYPE: PRT
<213> ORGANISM: Clostridium botulinum serotype E

<400> SEQUENCE: 29

Met Lys Ile Asn Gly Asn Leu Asn Ile Asp Ser Pro Val Asp Asn Lys
 1               5                  10                  15

Asn Val Ala Ile Val Arg Ser Arg Asn Gln Met Phe Phe Lys Ala Phe
            20                  25                  30

Gln Val Ala Pro Asn Ile Trp Ile Val Pro Glu Arg Tyr Tyr Gly Glu
        35                  40                  45

Ser Leu Lys Ile Asn Glu Asp Gln Lys Phe Asp Gly Gly Ile Tyr Asp
    50                  55                  60

Ser Asn Phe Leu Ser Thr Asn Asn Glu Lys Asp Asp Phe Leu Gln Ala
65                  70                  75                  80

Thr Ile Lys Leu Leu Gln Arg Ile Asn Asn Asn Val Val Gly Ala Lys
                85                  90                  95

Leu Leu Ser Leu Ile Ser Thr Ala Ile Pro Phe Pro Tyr Glu Asn Asn
            100                 105                 110

Thr Glu Asp Tyr Arg Gln Thr Asn Tyr Leu Ser Ser Lys Asn Asn Glu
        115                 120                 125

His Tyr Tyr Thr Ala Asn Leu Val Ile Phe Gly Pro Gly Ser Asn Ile
    130                 135                 140

Ile Lys Asn Asn Val Ile Tyr Tyr Lys Lys Glu Tyr Ala Glu Ser Gly
145                 150                 155                 160

Met Gly Thr Met Leu Glu Ile Trp Phe Gln Pro Phe Leu Thr His Lys
                165                 170                 175

Tyr Asp Glu Phe Tyr Val Asp Pro Ala Leu Glu Leu Ile Lys Cys Leu
            180                 185                 190

Ile Lys Ser Leu Tyr Tyr Leu Tyr Gly Ile Lys Pro Asn Asp Asn Leu
        195                 200                 205

Asn Ile Pro Tyr Arg Leu Arg Asn Glu Phe Asn Ser Leu Glu Tyr Ser
    210                 215                 220

Glu Leu Asn Met Ile Asp Phe Leu Ile Ser Gly Gly Ile Asp Tyr Lys
225                 230                 235                 240

Leu Leu Asn Thr Asn Pro Tyr Trp Phe Ile Asp Lys Tyr Phe Ile Asp
                245                 250                 255

Thr Ser Lys Asn Phe Glu Lys Tyr Lys Asn Asp Tyr Glu Ile Lys Ile
            260                 265                 270

Lys Asn Asn Asn Tyr Ile Ala Asn Ser Ile Lys Leu Tyr Leu Glu Gln
        275                 280                 285

Lys Phe Lys Ile Asn Val Lys Asp Ile Trp Glu Leu Asn Leu Ser Tyr
    290                 295                 300

Phe Ser Lys Glu Phe Gln Ile Met Met Pro Glu Arg Tyr Asn Asn Ala
305                 310                 315                 320

Leu Asn His Tyr Tyr Arg Lys Glu Phe Tyr Val Ile Asp Tyr Phe Lys
                325                 330                 335

Asn Tyr Asn Ile Asn Gly Phe Lys Asn Gly Gln Ile Lys Thr Lys Leu
            340                 345                 350

Pro Leu Ser Lys Tyr Asn Lys Glu Ile Ile Asn Lys Pro Glu Leu Ile
        355                 360                 365
```

```
Val Asn Leu Ile Asn Gln Asn Asn Thr Val Leu Met Lys Ser Asn Ile
    370                 375                 380

Tyr Gly Asp Gly Leu Lys Gly Thr Val Asp Asn Phe Tyr Ser Asn Tyr
385                 390                 395                 400

Ile Ile Pro Tyr Asn Leu Asn Tyr Glu His Ser Ile Asn Tyr Phe Tyr
                405                 410                 415

Leu Asp Asn Val Asn Ile Glu Glu Ile Glu Lys Ile Pro Pro Ile Asn
            420                 425                 430

Asp Glu Asp Ile Tyr Pro Tyr Arg Lys Asn Ala Asp Thr Phe Ile Pro
        435                 440                 445

Val Tyr Asn Ile Thr Lys Ala Lys Glu Ile Asn Thr Thr Thr Pro Leu
    450                 455                 460

Pro Val Asn Tyr Leu Gln Ala Gln Met Ile Asp Ser Asn Asp Ile Asn
465                 470                 475                 480

Leu Ser Ser Asp Phe Leu Lys Val Ile Ser Ser Lys Gly Ser Leu Val
                485                 490                 495

Tyr Ser Phe Leu Asn Asn Thr Met Asp Tyr Leu Glu Phe Ile Lys Tyr
            500                 505                 510

Asp Lys Pro Ile Asp Thr Asp Lys Lys Tyr Tyr Lys Trp Leu Lys Ala
        515                 520                 525

Ile Phe Arg Asn Tyr Ser Leu Asp Ile Thr Glu Thr Gln Glu Ile Ser
    530                 535                 540

Asn Gln Phe Gly Asp Thr Lys Ile Ile Pro Trp Ile Gly Arg Ala Leu
545                 550                 555                 560

Asn Ile Leu Asn Thr Asn Asn Ser Phe Val Glu Glu Phe Lys Asn Leu
                565                 570                 575

Gly Pro Ile Ser Leu Ile Asn Lys Lys Glu Asn Ile Thr Ile Pro Lys
            580                 585                 590

Ile Lys Ile Asp Glu Ile Pro Ser Ser Met Leu Asn Phe Ser Phe Lys
        595                 600                 605

Asp Leu Ser Glu Asn Leu Phe Asn Ile Tyr Cys Lys Asn Asn Phe Tyr
    610                 615                 620

Leu Lys Lys Ile Tyr Tyr Asn Phe Leu Asp Gln Trp Trp Thr Gln Tyr
625                 630                 635                 640

Tyr Ser Gln Tyr Phe Asp Leu Ile Cys Met Ala Ser Lys Ser Val Leu
                645                 650                 655

Ala Gln Glu Lys Leu Ile Lys Lys Leu Ile Gln Lys Gln Leu Arg Tyr
            660                 665                 670

Leu Met Glu Asn Ser Asn Ile Ser Ser Thr Asn Leu Ile Leu Ile Asn
        675                 680                 685

Leu Thr Thr Thr Asn Thr Leu Arg Asp Ile Ser Asn Gln Ser Gln Ile
    690                 695                 700

Ala Ile Asn Asn Ile Asp Lys Phe Phe Asn Asn Ala Ala Met Cys Val
705                 710                 715                 720

Phe Glu Asn Asn Ile Tyr Pro Lys Phe Thr Ser Phe Met Glu Gln Cys
                725                 730                 735

Ile Lys Asn Ile Asn Lys Ser Thr Lys Glu Phe Ile Leu Lys Cys Thr
            740                 745                 750

Asn Ile Asn Glu Thr Glu Lys Ser His Leu Ile Met Gln Asn Ser Phe
        755                 760                 765

Ser Asn Leu Asp Phe Asp Phe Leu Asp Ile Gln Asn Met Lys Asn Leu
    770                 775                 780

Phe Asn Leu Tyr Thr Glu Leu Leu Ile Lys Glu Gln Thr Ser Pro Tyr
785                 790                 795                 800
```

```
Glu Leu Ser Leu Tyr Ala Phe Gln Glu Gln Asp Asn Asn Val Ile Gly
                805                 810                 815

Asp Thr Ser Gly Lys Asn Thr Leu Val Glu Tyr Pro Lys Asp Ile Gly
            820                 825                 830

Leu Val Tyr Gly Ile Asn Asn Asn Ala Ile His Leu Thr Gly Ala Asn
        835                 840                 845

Gln Asn Ile Lys Phe Thr Asn Asp Tyr Phe Glu Asn Gly Leu Thr Asn
    850                 855                 860

Asn Phe Ser Ile Tyr Phe Trp Leu Arg Asn Leu Lys Gln Asn Thr Ile
865                 870                 875                 880

Lys Ser Lys Leu Ile Gly Ser Lys Glu Asp Asn Cys Gly Trp Glu Ile
                885                 890                 895

Tyr Phe Glu Asn Asp Gly Leu Val Phe Asn Ile Ile Asp Ser Asn Gly
            900                 905                 910

Asn Glu Lys Asn Ile Tyr Leu Ser Asn Ile Ser Asn Lys Ser Trp His
        915                 920                 925

Tyr Ile Val Ile Ser Ile Asn Arg Leu Lys Asp Gln Leu Leu Ile Phe
    930                 935                 940

Ile Asp Asn Ile Leu Val Ala Asn Glu Asp Ile Lys Glu Ile Leu Asn
945                 950                 955                 960

Ile Tyr Ser Ser Asp Ile Ile Ser Leu Leu Ser Asp Asn Asn Asn Val
                965                 970                 975

Tyr Ile Glu Gly Leu Ser Val Leu Asn Lys Thr Ile Asn Ser Asn Glu
            980                 985                 990

Ile Leu Thr Asp Tyr Phe Ser Asp Leu Asn Asn Ser Tyr Ile Arg Asn
        995                 1000                1005

Phe Asp Glu Glu Ile Leu Gln Tyr Asn Arg Thr Tyr Glu Leu Phe Asn
    1010                1015                1020

Tyr Val Phe Pro Glu Ile Ala Ile Asn Lys Ile Glu Gln Asn Asn Asn
1025                1030                1035                1040

Ile Tyr Leu Ser Ile Asn Asn Glu Asn Asn Leu Asn Phe Lys Pro Leu
                1045                1050                1055

Lys Phe Lys Leu Leu Asn Thr Asn Pro Asn Lys Gln Tyr Val Gln Lys
            1060                1065                1070

Trp Asp Glu Val Ile Phe Ser Val Leu Asp Gly Thr Glu Lys Tyr Leu
        1075                1080                1085

Asp Ile Ser Thr Thr Asn Asn Arg Ile Gln Leu Val Asp Asn Lys Asn
    1090                1095                1100

Asn Ala Gln Ile Phe Ile Ile Asn Asn Asp Ile Phe Ile Ser Asn Cys
1105                1110                1115                1120

Leu Thr Leu Thr Tyr Asn Asn Val Asn Val Tyr Leu Ser Ile Lys Asn
                1125                1130                1135

Gln Asp Tyr Asn Trp Val Ile Cys Asp Leu Asn His Asp Ile Pro Lys
            1140                1145                1150

Lys Ser Tyr Leu Trp Ile Leu Lys Asn Ile
        1155                1160
```

<210> SEQ ID NO 30
<211> LENGTH: 1159
<212> TYPE: PRT
<213> ORGANISM: Clostridium botulinum serotype F

<400> SEQUENCE: 30

```
Met Lys Ile Asn Asn Asn Phe Asn Ile Asp Ser Leu Ile Asp Asn Arg
 1               5                  10                  15
```

```
Asp Val Ala Ile Val Arg Gly Arg Lys Thr Asp Thr Phe Phe Lys Val
            20                  25                  30

Phe Gln Val Ala Pro Asn Ile Trp Ile Ala Pro Glu Arg Tyr Tyr Gly
        35                  40                  45

Glu Ser Leu Asn Ile Asn Glu Asp Gln Lys Ser Asp Gly Gly Ile Tyr
    50                  55                  60

Asp Ser Asn Phe Leu Ser Thr Asn Asp Glu Lys Asp Glu Phe Leu Gln
65                  70                  75                  80

Ala Thr Val Lys Ile Leu Gln Arg Ile Asn Asn Asn Val Ile Gly Ala
                85                  90                  95

Lys Leu Leu Ser Leu Ile Ser Thr Ala Ile Pro Phe Pro Tyr Glu Tyr
            100                 105                 110

Lys Pro Gly Asp Tyr Arg Gln Thr Asn Tyr Leu Val Ser Lys Asp Asn
        115                 120                 125

Gln His Tyr Tyr Thr Ala Asn Leu Val Ile Phe Gly Pro Gly Thr Asn
    130                 135                 140

Ile Val Glu Asn Asn Ala Ile Tyr Tyr Lys Lys Glu Asp Ser Glu Asn
145                 150                 155                 160

Gly Met Gly Thr Met Ser Glu Ile Trp Phe Gln Pro Phe Leu Thr Tyr
                165                 170                 175

Lys Tyr Gly Gln Phe Tyr Val Asp Pro Ala Leu Glu Leu Ile Lys Cys
            180                 185                 190

Leu Ile Lys Ser Leu Tyr Tyr Leu Tyr Gly Ile Lys Pro Ser Asp Asp
        195                 200                 205

Leu Ser Ile Pro Tyr Arg Leu Arg Ser Glu Leu Asn Ser Phe Glu Tyr
    210                 215                 220

Ser Glu Leu Asp Met Ile Asp Phe Leu Ile Ser Gly Gly Thr Glu Tyr
225                 230                 235                 240

Lys Leu Leu Asp Thr Asn Pro Tyr Trp Phe Thr Asp Asn Tyr Phe Ile
                245                 250                 255

Asp Ala Pro Lys Asn Phe Glu Lys Tyr Lys Asn Asp Tyr Glu Thr Lys
            260                 265                 270

Ile Lys Asn Asn Asn Asp Ile Ala Asn Ser Ile Lys Leu Tyr Leu Glu
        275                 280                 285

Gln Lys Phe Lys Thr Asn Ala Gln Asp Ile Trp Glu Leu Asn Leu Ser
    290                 295                 300

Tyr Phe Ser Thr Glu Phe Glu Ile Met Met Pro Glu Ile Phe Asn Asn
305                 310                 315                 320

Ala Leu Asn His Tyr Tyr Arg Lys Glu Tyr Tyr Val Ile Asp Tyr Phe
                325                 330                 335

Lys Asn Tyr Asn Ile Asn Gly Phe Ile Asn Gly Gln Ile Lys Thr Ile
            340                 345                 350

Leu Pro Leu Ser Lys Tyr Asn Lys Asn Ile Ile Asn Lys Pro Glu Leu
        355                 360                 365

Val Val Asn Leu Ile Asn Glu Asn Asn Thr Val Leu Met Lys Ser Asn
    370                 375                 380

Val Tyr Gly Asp Gly Leu Lys Gly Thr Met Asp Asn Phe Tyr Ala Ala
385                 390                 395                 400

Tyr Lys Ile Pro Tyr Asn Ile Gly Asp Glu Tyr His Ile Asn Tyr Ser
                405                 410                 415

Tyr Leu Asn Asn Val Asn Val Glu Glu Ile Asn Asn Ile Pro Pro Ile
            420                 425                 430

Asn Asp Ala Asp Ile Tyr Pro Tyr Arg Lys Asn Ser Asp Pro Phe Ile
```

-continued

```
        435                 440                 445

Pro Val Tyr Asn Ile Thr Glu Thr Lys Glu Ile Asn Thr Thr Thr Pro
    450                 455                 460

Leu Ser Val Asn Tyr Leu Gln Ala Gln Val Thr Asn Ser Asn Asp Ile
465                 470                 475                 480

Ser Leu Ser Ser Asp Phe Ser Lys Val Ile Ser Ser Lys Asp Arg Ser
                485                 490                 495

Leu Val Tyr Ser Phe Leu Asp Asn Thr Ile Asp Tyr Leu Asp Ser Ile
            500                 505                 510

Lys Tyr Asp Glu Pro Ile Asp Thr Asp Lys Lys Tyr Tyr Leu Trp Leu
        515                 520                 525

Lys Glu Ile Phe Arg Asn Tyr Ser Phe Asp Met Thr Glu Thr Gln Glu
    530                 535                 540

Val Asn Thr Pro Cys Gly Ile Asn Lys Val Val Pro Trp Leu Gly Lys
545                 550                 555                 560

Ala Leu Asn Ile Leu Asn Thr Gly Asn Ser Phe Ile Glu Glu Phe Lys
                565                 570                 575

Ser Leu Gly Pro Ile Ser Leu Ile Asn Lys Lys Glu Asn Ile Thr Met
            580                 585                 590

Pro Lys Ile Glu Ile Asp Glu Ile Pro Asn Ser Met Leu Asn Leu Ser
        595                 600                 605

Phe Lys Asp Leu Ser Glu Asn Leu Phe Asn Arg Phe Ser Lys Asn Asn
    610                 615                 620

Ser Tyr Phe Glu Lys Ile Tyr Tyr Asp Phe Leu Asp Gln Trp Trp Thr
625                 630                 635                 640

Gln Tyr Tyr Ser Gln Tyr Phe Asp Leu Ile Cys Met Ala Lys Lys Ser
                645                 650                 655

Ile Leu Ala Gln Glu Thr Leu Ile Lys Lys Ile Ile Gln Lys Lys Leu
            660                 665                 670

Ser Tyr Leu Ile Gly Asn Ser Asn Ile Ser Ser Asp Asn Leu Ala Leu
        675                 680                 685

Met Asn Leu Thr Thr Thr Asn Thr Leu Arg Asp Ile Ser Asn Glu Ser
    690                 695                 700

Gln Ile Ala Met Asn Asn Val Asp Ser Phe Leu Asn Ser Ala Ala Ile
705                 710                 715                 720

Cys Val Phe Glu Gly Asn Ile Tyr Ser Lys Phe Ile Ser Phe Met Glu
                725                 730                 735

Gln Cys Ile Asn Asn Ile Asn Lys Asn Thr Arg Glu Phe Ile Gln Lys
            740                 745                 750

Cys Thr Asn Ile Thr Glu Asn Glu Lys Leu Gln Leu Ile Asn Gln Asn
        755                 760                 765

Ile Phe Ser Ser Leu Asp Phe Asp Phe Leu Asn Ile Glu Asn Leu Lys
    770                 775                 780

Ser Leu Phe Ser Ser Glu Thr Ala Leu Leu Ile Lys Glu Glu Thr Ser
785                 790                 795                 800

Pro Tyr Glu Leu Val Leu Tyr Ala Phe Gln Glu Pro Asp Asn Asn Ala
                805                 810                 815

Ile Gly Asp Ala Ser Ala Lys Asn Thr Ser Ile Glu Tyr Ser Lys Asp
            820                 825                 830

Ile Asp Leu Val Tyr Gly Ile Asn Ser Asp Ala Leu Tyr Leu Asn Gly
        835                 840                 845

Ser Asn Gln Ser Ile Ser Phe Ser Asn Asp Phe Phe Glu Asn Gly Leu
    850                 855                 860
```

Thr Asn Ser Phe Ser Ile Tyr Phe Trp Leu Arg Asn Leu Gly Lys Asp
865 870 875 880

Thr Ile Lys Tyr Lys Leu Ile Gly Ser Lys Glu Asp Asn Cys Gly Trp
885 890 895

Glu Ile Tyr Phe Gln Asp Thr Gly Leu Val Phe Asn Met Ile Asp Ser
900 905 910

Asn Gly Asn Glu Lys Asn Ile Tyr Leu Ser Asp Val Ser Asn Asn Ser
915 920 925

Trp His Tyr Ile Thr Ile Ser Val Asp Arg Leu Lys Glu Gln Leu Leu
930 935 940

Ile Phe Ile Asp Asp Asn Leu Val Ala Asn Glu Ser Ile Lys Glu Ile
945 950 955 960

Leu Asn Ile Tyr Ser Ser Asn Ile Ile Ser Leu Leu Ser Glu Asn Lys
965 970 975

Pro Ser Tyr Ile Glu Gly Leu Thr Ile Leu Asn Lys Pro Thr Thr Ser
980 985 990

Gln Glu Val Leu Asn Asn Tyr Phe Lys Val Leu Asn Asn Ser Tyr Ile
995 1000 1005

Arg Asp Ser Asn Glu Glu Arg Leu Glu Tyr His Lys Thr Tyr Gln Leu
1010 1015 1020

Asp Asn Tyr Val Phe Ser Asp Lys Pro Ile Cys Glu Val Lys Gln Asn
1025 1030 1035 1040

Asn Asn Ile Tyr Leu Thr Ile Asn Asn Thr Asn Asn Leu Asn Leu Gln
1045 1050 1055

Pro Ser Lys Phe Lys Leu Leu Ser Ile Asn Ser Asn Lys Gln Tyr Val
1060 1065 1070

Gln Lys Phe Asp Glu Val Ile Ile Ser Ile Leu Gly Asn Met Glu Lys
1075 1080 1085

Tyr Ile Asp Ile Ser Glu Asp Asn Arg Leu Gln Leu Ile Asp Asn Lys
1090 1095 1100

Asn Gly Ala Lys Lys Met Ile Ile Ser Asn Asp Met Phe Ile Ser Asn
1105 1110 1115 1120

Cys Leu Thr Leu Ser Cys Gly Gly Lys Tyr Ile Cys Leu Ser Met Lys
1125 1130 1135

Asp Glu Asn His Asn Trp Met Ile Cys Asn Asn Asp Met Ser Lys Tyr
1140 1145 1150

Leu Tyr Leu Trp Ser Phe Lys
1155

<210> SEQ ID NO 31
<211> LENGTH: 1165
<212> TYPE: PRT
<213> ORGANISM: Clostridium botulinum serotype F

<400> SEQUENCE: 31

Met Lys Ile Asn Asp Asp Leu Asn Ile Asn Ser Pro Val Asp Asn Lys
1 5 10 15

Asn Val Val Ile Val Arg Ala Arg Lys Thr Asn Ile Phe Phe Lys Ala
20 25 30

Phe Gln Val Ala Pro Asn Ile Trp Val Ala Pro Glu Arg Tyr Tyr Gly
35 40 45

Glu Pro Leu Asn Ile Ser Asp Gln Glu Lys Ser Asp Gly Gly Ile Tyr
50 55 60

Asp Glu Asn Phe Leu Lys Glu Asn Ser Glu Lys Glu Glu Phe Leu Gln
65 70 75 80

-continued

```
Ala Ile Ile Leu Leu Leu Lys Arg Ile Asn Asn Asn Ile Ile Gly Gln
                85                  90                  95

Lys Leu Leu Ser Leu Met Cys Thr Ser Ile Pro Phe Leu His Glu Tyr
            100                 105                 110

Lys Gln Gly Asp Tyr Arg Gln Ser Asn Tyr Leu Gly Ser Lys Asn Ser
        115                 120                 125

Glu Tyr Leu Tyr Ser Ala Asn Ile Val Ile Phe Gly Pro Gly Ser Asn
    130                 135                 140

Ile Val Lys Asn Asn Thr Ile Tyr Tyr Lys Lys Asn Phe Ala Glu Asn
145                 150                 155                 160

Gly Met Gly Thr Met Ala Glu Ile Leu Phe Gln Pro Phe Leu Thr Tyr
                165                 170                 175

Lys Tyr Asn Gln Phe Tyr Ala Asp Pro Ala Leu Glu Leu Ile Lys Cys
            180                 185                 190

Leu Ile Lys Ala Ile Tyr Phe Leu Tyr Gly Ile Lys Pro Asn Asp Asn
        195                 200                 205

Leu Asn Ile Pro Tyr Arg Leu Arg Asn Glu Phe Ser Asn Val Glu Tyr
    210                 215                 220

Ser Glu Leu Asn Ile Ile Asp Phe Leu Ile Ser Gly Gly Ile Asp Tyr
225                 230                 235                 240

Lys Phe Ile Asn Thr Asn Pro Tyr Trp Phe Ile Asp Asn Tyr Phe Ile
                245                 250                 255

Asp Val Pro Lys Val Phe Glu Lys His Lys Asn Asp Tyr Glu Ile Asn
            260                 265                 270

Ile Lys Asn Asn Ser Glu Ile Gly Thr Ser Ile Lys Leu Tyr Leu Glu
        275                 280                 285

Gln Lys Phe Lys Thr Asn Val Gln Asp Ile Trp Glu Leu Asn Leu Ser
    290                 295                 300

Tyr Phe Ser Lys Glu Phe Gln Ile Met Met Pro Glu Lys His Asn Asn
305                 310                 315                 320

Ala Leu Lys His Tyr Tyr Arg Lys Glu Tyr Tyr Lys Ile Asn Tyr Ser
                325                 330                 335

Lys Gln Tyr Asp Ile Asn Gly Phe Val Asn Gly Gln Ile Ala Thr Lys
            340                 345                 350

Leu Leu Leu Ser Glu Lys Asn Gln Tyr Ile Ile Asn Lys Pro Gln Leu
        355                 360                 365

Ile Ile Asn Leu Ile Asn Lys Ser Asn Asn Ser Leu Leu Met Lys Ser
    370                 375                 380

Asn Ile Tyr Gly Asp Gly Leu Asn Gly Thr Thr Asp Asn Phe Tyr Arg
385                 390                 395                 400

Asn Tyr Lys Ile Pro Asp Asn Ile Ala Tyr Gln Tyr His Pro Asn Asn
                405                 410                 415

Thr Tyr Leu Asp Asn Val Asn Ile Glu Glu Ile Asn Asn Ile Pro Gln
            420                 425                 430

Ile Thr Asp Ala Asp Ile Tyr Pro Tyr Thr Asn Asn Cys Asp Thr Phe
        435                 440                 445

Ile Pro Ile Tyr Asn Ile Thr Gln Ser Arg Glu Ile Asn Thr Thr Val
    450                 455                 460

Pro Tyr Ser Ile Asn Tyr Leu Gln Ser Gln Ile Met Asn Ser Asp Asp
465                 470                 475                 480

Ile Thr Leu Ser Ser Asp Phe Trp Glu Val Val Cys Ser Asn Asp Lys
                485                 490                 495

Ser Leu Val Tyr Ser Tyr Leu Asp Asn Val Ile Asn Tyr Leu Asp Ser
            500                 505                 510
```

```
Ile Lys Asn Asn Thr Pro Ile Asn Thr Asp Lys Lys Tyr Tyr Leu Trp
        515                 520                 525

Leu Lys Glu Ile Phe Arg Asn Tyr Ser Phe Asp Ile Thr Ala Thr Glu
    530                 535                 540

Glu Ile Thr Thr Glu Cys Gly Ile Asn Lys Ile Val Ser Trp Phe Gly
545                 550                 555                 560

Lys Ala Phe Asn Ile Leu Asn Thr Asp Asn Ser Phe Lys Ile Glu Phe
                565                 570                 575

Gln Asn Ser Gly Ala Ile Ala Leu Ile Asn Lys Lys Asp Asn Ile Ile
            580                 585                 590

Ile Pro Lys Ile Glu Ile Asp Glu Met Pro Asn Ser Met Leu Asn Leu
        595                 600                 605

Ser Phe Glu Asp Leu Asn Glu Gln Leu Tyr Ser Ile Tyr Ser Lys Asn
    610                 615                 620

Ile Thr Tyr Phe Lys Lys Ile Tyr Tyr Asn Phe Leu Asp Gln Trp Trp
625                 630                 635                 640

Thr Glu Tyr Tyr Ser Gln Tyr Phe Asp Leu Ile Cys Met Ala Lys Lys
                645                 650                 655

Ser Ile Leu Ala Gln Glu Asn Leu Ile Lys Lys Ile Ile Gln Lys Lys
            660                 665                 670

Ile Ser Tyr Leu Ile Gly Ala Ser Asn Ile Pro Asp Asp Ile Leu Ala
        675                 680                 685

Val Met Arg Leu Thr Thr Thr Asn Thr Leu Arg Asp Ile Ser Val Glu
    690                 695                 700

Ser Gln Ile Ala Met Asn Asn Leu Asn Asn Phe Leu Asn Lys Ala Ala
705                 710                 715                 720

Met Cys Val Phe Gln Ser Asn Ile Tyr Pro Lys Phe Ile Ser Phe Met
                725                 730                 735

Glu Gln Cys Ile Lys His Ile Asn Lys Ser Thr Lys Glu Phe Ile Gln
            740                 745                 750

Lys Cys Thr Asn Ile Asn Glu Thr Glu Lys Leu Gln Leu Ile Met Gln
        755                 760                 765

Asn Ser Phe Ser Asn Leu Asp Phe Asp Phe Leu Asp Ile Gln Asn Met
    770                 775                 780

Lys Asn Leu Phe Asn Ser Tyr Thr Glu Leu Leu Ile Lys Glu Gln Thr
785                 790                 795                 800

Ser Pro Tyr Glu Leu Ser Leu Tyr Ala Phe Glu Glu Gln Asp Asn Asn
                805                 810                 815

Val Ile Gly Asp Ala Ser Gly Lys Asn Thr Leu Val Glu Tyr Pro Lys
            820                 825                 830

Gly Ile Glu Leu Val Tyr Gly Ile Asn Asn Ser Ala Leu Tyr Leu Asn
        835                 840                 845

Gly Ser Asn Gln Ser Ile Ile Phe Thr Asn Asp Tyr Phe Glu Asn Gly
    850                 855                 860

Leu Thr Asn Ser Phe Ser Ile Tyr Phe Trp Leu Arg Asn Leu Gly Gln
865                 870                 875                 880

Asp Thr Ile Lys Ser Lys Leu Ile Gly Ser Lys Glu Tyr Asn Cys Gly
                885                 890                 895

Trp Glu Ile Tyr Phe Gln Glu Ile Gly His Val Phe Asn Met Ile Asp
            900                 905                 910

Ser Asn Gly Asn Glu Lys Asn Ile Tyr Leu Ser Asp Val Ser Asn Asn
        915                 920                 925

Ser Trp His Tyr Ile Thr Ile Ser Val Asp Arg Leu Lys Glu Gln Leu
```

```
    930                 935                 940

Leu Ile Phe Ile Asp Asp Asn Leu Val Val Asn Glu Ser Ile Lys Asp
945                 950                 955                 960

Ile Leu Asn Ile Tyr Ser Ser Asn Ile Ile Ser Leu Leu Ser Asp Asn
                965                 970                 975

Lys Ala Ser Tyr Ile Glu Gly Leu Thr Ile Leu Asn Lys Pro Thr Thr
            980                 985                 990

Gly Glu Glu Val Leu Arg Asn Tyr Phe Lys Asn Leu Asn Asn Ser Tyr
        995                 1000                1005

Val Arg Asp Ser Asn Asp Glu Arg Leu Glu Tyr Asn Lys Thr Tyr Gln
    1010                1015                1020

Leu Tyr Asp Tyr Val Phe Pro Asp Asn Pro Ile Cys Glu Val Lys Gln
1025                1030                1035                1040

Asp Asn Asn Ile Tyr Leu Thr Ile Asn Asn Ile Asn Asn Leu Asn Met
                1045                1050                1055

Lys Pro Cys Lys Phe Lys Leu Leu Ser Ile Asn Ser Asn Lys Gln Tyr
            1060                1065                1070

Val Gln Lys Trp Asp Glu Val Ile Ile Ser Val Leu Tyr Asp Thr Glu
        1075                1080                1085

Lys Tyr Val Cys Ile Ser Asn Glu Asn Asn Arg Val Lys Ile Ile Asp
    1090                1095                1100

Asn Lys Ile Met Gln Val Lys Phe Ile Ile Ser Asn Asp Ile Phe Ile
1105                1110                1115                1120

Ser Asn Cys Leu Thr His Ala His Asn Asn Lys Tyr Ile Cys Leu Ser
                1125                1130                1135

Met Lys Asp Glu Asn Tyr Asn Trp Met Ile Cys Asn Asn Glu Ser Asn
            1140                1145                1150

Ile Pro Lys Lys Ala Tyr Leu Trp Ile Leu Lys Glu Val
        1155                1160                1165


<210> SEQ ID NO 32
<211> LENGTH: 1198
<212> TYPE: PRT
<213> ORGANISM: Clostridium botulinum serotype G

<400> SEQUENCE: 32

Met Lys Ile Asn Ser Asn Leu Thr Ile Asn Ser Pro Ile Asp Asn Lys
 1               5                  10                  15

Asn Val Val Ile Val Arg Ala Arg Glu Thr Ser Lys Phe Phe Lys Ala
            20                  25                  30

Phe Lys Val Ala Pro Asn Ile Trp Val Ala Pro Glu Arg Tyr Tyr Gly
        35                  40                  45

Glu Ser Leu Ser Ile Glu Glu Ser Lys Lys Val Asn Gly Gly Val Tyr
    50                  55                  60

Asp Ser Asn Phe Leu Ser Gln Asn Asn Glu Lys Asp Lys Phe Leu Gln
65                  70                  75                  80

Ala Ile Ile Thr Leu Leu Lys Arg Ile Asn Ser Asn Ile Ala Gly Glu
                85                  90                  95

Lys Leu Leu Ser Leu Val Ser Thr Ala Ile Pro Phe Pro Tyr Gly Tyr
            100                 105                 110

Ile Gly Gly Gly Tyr Tyr Cys Pro Asn Ile Val Thr Phe Gly Ser Thr
        115                 120                 125

Ile Lys Tyr Asn Lys Lys Ile Asn Ser Leu Ile Ser Thr Thr Ile Pro
    130                 135                 140

Phe Pro Tyr Gly Gly Tyr Arg Glu Thr Asn Tyr Leu Ser Ser Lys Asp
```

```
145                 150                 155                 160

Thr Glu Asn Phe Tyr Ala Ala Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Ala Glu Ile Cys Phe Gln Pro Phe Leu Thr
        195                 200                 205

Tyr Lys Tyr Asp Gln Phe Tyr Val Asp Pro Ala Leu Glu Leu Met Glu
    210                 215                 220

Cys Leu Ile Lys Ser Leu Tyr Phe Leu Tyr Gly Ile Lys Pro Asn Asn
225                 230                 235                 240

Asn Leu Thr Val Pro Tyr Arg Leu Arg Asn Glu Leu Ser Asn Ile Glu
                245                 250                 255

Phe Ser Gln Leu Ser Ile Val Asp Leu Leu Ile Ser Gly Gly Ile Asp
            260                 265                 270

Ser Lys Phe Ile Asn Thr Asp Pro Tyr Trp Phe Ile Asp Ser Tyr Phe
        275                 280                 285

Ser Asn Ala Lys Thr Thr Phe Glu Glu His Lys Ser Ile Tyr Glu Thr
    290                 295                 300

Glu Ile Lys Gly Asn Asn Ala Ile Gly Asn Asp Ile Lys Leu Arg Leu
305                 310                 315                 320

Lys Gln Lys Phe Gln Thr Thr Val His Asp Ile Trp Gln Leu Asn Leu
                325                 330                 335

Asp Tyr Phe Ser Lys Glu Phe Gln Ile Met Met Pro Tyr Arg Phe Asn
            340                 345                 350

Asn Ala Leu Lys Tyr Tyr Tyr Arg Lys Glu Tyr Tyr Lys Ile Asp Tyr
        355                 360                 365

Pro Glu Lys Tyr Ser Ile Ala Gly Phe Val Asp Gly Gln Leu Asn Thr
    370                 375                 380

Gln Leu Ser Leu Ser Asp Lys Asn Gln Tyr Ile Ile Asn Lys Pro Glu
385                 390                 395                 400

Leu Ile Val Asn Leu Ile Ser Glu Asn Asn Ile Ser Leu Met Arg Ser
                405                 410                 415

Asn Ile Tyr Gly Asp Gly Leu Lys Tyr Thr Thr Asp Asn Phe Tyr Ser
            420                 425                 430

Thr Tyr Lys Ile Pro Tyr Asn Arg Ala Tyr Glu Tyr His Phe Asn Asn
        435                 440                 445

Ser Ser Thr Ser Ser Leu Glu Asn Val Asn Val Glu Glu Ile Ser Asn
    450                 455                 460

Ile Pro Glu Ile Ile Asp Ile Asn Pro Tyr Arg Glu Asn Ser Asp Ile
465                 470                 475                 480

Phe Ser Pro Val Glu Asn Ile Ile Glu Thr Lys Glu Val Asn Thr Lys
                485                 490                 495

Thr Pro Trp Pro Ile Asn Tyr Leu Gln Ala Gln Ile Pro Asn Asn Glu
            500                 505                 510

Glu Phe Thr Leu Ser Ser Asp Phe Ser Gln Val Val Ser Tyr Lys Thr
        515                 520                 525

Gln Ser Leu Val Tyr Ser Phe Leu Ser Asn Val Ile Ser Tyr Leu Asp
    530                 535                 540

Ser Val Lys Asp Thr Asn Pro Ile Asp Thr Asp Glu Lys Tyr Tyr Leu
545                 550                 555                 560

Trp Leu Arg Glu Ile Phe Arg Asn Tyr Ser Phe Asp Ile Thr Ala Ile
                565                 570                 575
```

```
Glu Glu Ile Asn Thr Ser Cys Gly Ile Asn Lys Val Val Ser Trp Phe
            580                 585                 590

Gly Lys Ala Leu Asn Ile Leu Asn Thr Ser Asn Ser Phe Val Lys Glu
        595                 600                 605

Phe Lys Asn Leu Gly Pro Ile Ser Leu Ile Asn Lys Lys Glu Asn Leu
    610                 615                 620

Ser Met Pro Ile Ile Glu Val Asn Glu Ile Pro Asn Asp Met Leu Gly
625                 630                 635                 640

Leu Ser Leu Lys Asp Leu Asn Glu Lys Leu Phe Asn Ile Tyr Leu Lys
                645                 650                 655

Asn Ile Leu Tyr Phe Lys Lys Val Tyr Phe Ser Phe Leu Asp Gln Trp
            660                 665                 670

Trp Thr Glu Tyr Tyr Ser Gln Tyr Phe Gly Leu Ile Cys Met Ala Lys
        675                 680                 685

Gln Ser Ile Leu Ala Gln Glu Asn Leu Ile Lys Lys Ile Val Gln Lys
    690                 695                 700

Lys Leu Ser Asp Leu Ser Lys Gln Ser Asn Ile Ser Asn Glu Lys Leu
705                 710                 715                 720

Asn Leu Met Asn Leu Thr Thr Glu Lys Thr Phe Ile Asp Leu Ser Asn
                725                 730                 735

Gln Ser Gln Ile Ala Met Asn Asn Ile Asn Asn Phe Leu Asn Lys Ala
            740                 745                 750

Ala Ile Cys Val Phe Glu Ser Asn Ile Tyr Pro Lys Phe Ile Ser Phe
        755                 760                 765

Met Glu Gln Tyr Ile Asn Asn Ile Asn Ile Lys Thr Thr Ala Phe Ile
    770                 775                 780

Arg Lys Cys Thr Asn Ile Thr Glu Lys Glu Lys Leu Gln Leu Ile Asn
785                 790                 795                 800

Gln Asn Thr Phe Asn Asn Leu Asp Phe Glu Phe Phe Asp Ile Gln Thr
                805                 810                 815

Ile Glu Asn Leu Leu Thr Ser Glu Thr Asn Leu Ile Ile Lys Glu Lys
            820                 825                 830

Thr Ser Pro Tyr Asp Leu Leu Leu Phe Ser Leu Gln Glu Ala Asp Arg
        835                 840                 845

Lys Val Ile Lys Asp Ile Ser Gly Lys Asp Thr Leu Val Gln Tyr Ser
    850                 855                 860

Asp Thr Ile Asp Leu Ser Tyr Gly Val Asn Gly Asp Ala Leu Tyr Leu
865                 870                 875                 880

Lys Glu Pro Asn Gln Ser Val Asn Phe Ser Asn Asn Ile Phe Glu Asn
                885                 890                 895

Gly Leu Thr Asn Ser Phe Ser Ile Cys Phe Trp Leu Arg Asn Leu Gly
            900                 905                 910

Gln Asp Asn Leu Ser Ser Asn Leu Ile Gly Asn Ile Val Asn Asn Cys
        915                 920                 925

Gly Trp Gln Ile Tyr Phe Glu Asn Asn Gly Leu Val Phe Ser Met Val
    930                 935                 940

Asp Cys Asn Gly Asn Glu Lys Asn Ile Tyr Leu Ser Asp Val Leu Ser
945                 950                 955                 960

Lys Tyr Trp Tyr Tyr Ile Ser Val Ser Val Asp Arg Leu Arg Asn Lys
                965                 970                 975

Leu Leu Ile Phe Ile Asn Asp Lys Leu Ile Val Asn Glu Ser Ile Glu
            980                 985                 990

Gln Ile Leu Asn Ile Tyr Ser Ser Asn Ile Ile Ser Leu Val Asn Glu
        995                 1000                1005
```

Asn Asn Pro Ile Cys Ile Glu Glu Leu Ser Ile Leu Asn Lys Ala Leu
    1010                1015                1020

Thr Ser Glu Glu Val Leu Asn Ser Tyr Phe Thr Asn Leu Asn Asn Ser
1025                1030                1035                1040

Tyr Ile Arg Asp Ser Tyr Gly Ala Arg Leu Glu Tyr Asn Lys Asn Tyr
                1045                1050                1055

Glu Leu Tyr Asn Tyr Val Phe Pro Glu Asn Ser Leu Tyr Glu Val Ile
            1060                1065                1070

Glu Asn Asn Asn Met Tyr Leu Ser Ile Lys Asn Ile Lys Asn Thr Asn
        1075                1080                1085

Ile Leu Gly Ala Lys Phe Lys Leu Ile Asn Thr Asp Glu Ser Lys Gln
    1090                1095                1100

Tyr Val Gln Lys Trp Asp Glu Val Ile Ile Cys Val Leu Gly Asp Thr
1105                1110                1115                1120

Glu Lys Tyr Ala Asp Ile Gln Ala Gly Asn Asn Arg Ile Gln Leu Val
                1125                1130                1135

Asn Ser Lys Asp Asn Ala Arg Lys Ile Ile Val Asn Asn Asn Ile Phe
            1140                1145                1150

Arg Pro Asn Cys Val Leu Phe Ser Tyr Asn Asn Lys Tyr Leu Ser Leu
        1155                1160                1165

Ser Leu Arg Asn Arg Asn Tyr Asn Trp Met Ile Cys Asn Asp Asn Ser
    1170                1175                1180

Phe Ile Pro Lys His Ala His Leu Trp Ile Leu Lys Lys Ile
1185                1190                1195

<210> SEQ ID NO 33
<211> LENGTH: 155
<212> TYPE: PRT
<213> ORGANISM: Homo sapiens

<400> SEQUENCE: 33

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 34
<211> LENGTH: 155
<212> TYPE: PRT
<213> ORGANISM: Homo sapiens

<400> SEQUENCE: 34

Met Ala Ala Gly Ser Ile Thr Thr Leu Pro Ala Leu Pro Glu Asp Gly
1 5 10 15

Gly Ser Gly Ala Phe Pro Pro Gly His Phe Lys Asp Pro Lys Arg Leu
20 25 30

Tyr Cys Lys Asn Gly Gly Phe Phe Leu Arg Ile His Pro Asp Gly Arg
35 40 45

Val Asp Gly Val Arg Glu Lys Ser Asp Pro His Ile Lys Leu Gln Leu
50 55 60

Gln Ala Glu Glu Arg Gly Val Val Ser Ile Lys Gly Val Cys Ala Asn
65 70 75 80

Arg Tyr Leu Ala Met Lys Glu Asp Gly Arg Leu Leu Ala Ser Lys Cys
85 90 95

Val Thr Asp Glu Cys Phe Phe Phe Glu Arg Leu Glu Ser Asn Asn Tyr
100 105 110

Asn Thr Tyr Arg Ser Arg Lys Tyr Thr Ser Trp Tyr Val Ala Leu Lys
115 120 125

Arg Thr Gly Gln Tyr Lys Leu Gly Ser Lys Thr Gly Pro Gly Gln Lys
130 135 140

Ala Ile Leu Phe Leu Pro Met Ser Ala Lys Ser
145 150 155

<210> SEQ ID NO 35
<211> LENGTH: 206
<212> TYPE: PRT
<213> ORGANISM: Homo sapiens

<400> SEQUENCE: 35

Met Ser Gly Pro Gly Thr Ala Ala Val Ala Leu Leu Pro Ala Val Leu
1 5 10 15

Leu Ala Leu Leu Ala Pro Trp Ala Gly Arg Gly Gly Ala Ala Ala Pro
20 25 30

Thr Ala Pro Asn Gly Thr Leu Glu Ala Glu Leu Glu Arg Arg Trp Glu
35 40 45

Ser Leu Val Ala Leu Ser Leu Ala Arg Leu Pro Val Ala Ala Gln Pro
50 55 60

Lys Glu Ala Ala Val Gln Ser Gly Ala Gly Asp Tyr Leu Leu Gly Ile
65 70 75 80

Lys Arg Leu Arg Arg Leu Tyr Cys Asn Val Gly Ile Gly Phe His Leu
85 90 95

Gln Ala Leu Pro Asp Gly Arg Ile Gly Gly Ala His Ala Asp Thr Arg
100 105 110

Asp Ser Leu Leu Glu Leu Ser Pro Val Glu Arg Gly Val Val Ser Ile
115 120 125

Phe Gly Val Ala Ser Arg Phe Phe Val Ala Met Ser Ser Lys Gly Lys
130 135 140

Leu Tyr Gly Ser Pro Phe Phe Thr Asp Glu Cys Thr Phe Lys Glu Ile
145 150 155 160

Leu Leu Pro Asn Asn Tyr Asn Ala Tyr Glu Ser Tyr Lys Tyr Pro Gly
165 170 175

Met Phe Ile Ala Leu Ser Lys Asn Gly Lys Thr Lys Lys Gly Asn Arg
180 185 190

Val Ser Pro Thr Met Lys Val Thr His Phe Leu Pro Arg Leu
195 200 205

<210> SEQ ID NO 36
<211> LENGTH: 204
<212> TYPE: PRT
<213> ORGANISM: Homo sapiens

<400> SEQUENCE: 36

Met Gly Ser Pro Arg Ser Ala Leu Ser Cys Leu Leu Leu His Leu Leu
1 5 10 15

Val Leu Cys Leu Gln Ala Gln His Val Arg Glu Gln Ser Leu Val Thr
20 25 30

Asp Gln Leu Ser Arg Arg Leu Ile Arg Thr Tyr Gln Leu Tyr Ser Arg
35 40 45

Thr Ser Gly Lys His Val Gln Val Leu Ala Asn Lys Arg Ile Asn Ala
50 55 60

Met Ala Glu Asp Gly Asp Pro Phe Ala Lys Leu Ile Val Glu Thr Asp
65 70 75 80

Thr Phe Gly Ser Arg Val Arg Val Arg Gly Ala Glu Thr Gly Leu Tyr
85 90 95

Ile Cys Met Asn Lys Lys Gly Lys Leu Ile Ala Lys Ser Asn Gly Lys
100 105 110

Gly Lys Asp Cys Val Phe Thr Glu Ile Val Leu Glu Asn Asn Tyr Thr
115 120 125

Ala Leu Gln Asn Ala Lys Tyr Glu Gly Trp Tyr Met Ala Phe Thr Arg
130 135 140

Lys Gly Arg Pro Arg Lys Gly Ser Lys Thr Arg Gln His Gln Arg Glu
145 150 155 160

Val His Phe Met Lys Arg Leu Pro Arg Gly His His Thr Thr Glu Gln
165 170 175

Ser Leu Arg Phe Glu Phe Leu Asn Tyr Pro Pro Phe Thr Arg Ser Leu
180 185 190

Arg Gly Ser Gln Arg Thr Trp Ala Pro Glu Pro Arg
195 200

<210> SEQ ID NO 37
<211> LENGTH: 208
<212> TYPE: PRT
<213> ORGANISM: Homo sapiens

<400> SEQUENCE: 37

Met Ala Pro Leu Gly Glu Val Gly Asn Tyr Phe Gly Val Gln Asp Ala
1 5 10 15

Val Pro Phe Gly Asn Val Pro Val Leu Pro Val Asp Ser Pro Val Leu
20 25 30

Leu Ser Asp His Leu Gly Gln Ser Glu Ala Gly Gly Leu Pro Arg Gly
35 40 45

Pro Ala Val Thr Asp Leu Asp His Leu Lys Gly Ile Leu Arg Arg Arg
50 55 60

Gln Leu Tyr Cys Arg Thr Gly Phe His Leu Glu Ile Phe Pro Asn Gly
65 70 75 80

Thr Ile Gln Gly Thr Arg Lys Asp His Ser Arg Phe Gly Ile Leu Glu
85 90 95

Phe Ile Ser Ile Ala Val Gly Leu Val Ser Ile Arg Gly Val Asp Ser
100 105 110

Gly Leu Tyr Leu Gly Met Asn Glu Lys Gly Glu Leu Tyr Gly Ser Glu
115 120 125

Lys Leu Thr Gln Glu Cys Val Phe Arg Glu Gln Phe Glu Glu Asn Trp

```
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205


<210> SEQ ID NO 38
<211> LENGTH: 216
<212> TYPE: PRT
<213> ORGANISM: Homo sapiens

<400> SEQUENCE: 38

Met Gly Ala Ala Arg Leu Leu Pro Asn Leu Thr Leu Cys Leu Gln Leu
 1               5                  10                  15

Leu Ile Leu Cys Cys Gln Thr Gln Gly Glu Asn His Pro Ser Pro Asn
            20                  25                  30

Phe Asn Gln Tyr Val Arg Asp Gln Gly Ala Met Thr Asp Gln Leu Ser
        35                  40                  45

Arg Arg Gln Ile Arg Glu Tyr Gln Leu Tyr Ser Arg Thr Ser Gly Lys
    50                  55                  60

His Val Gln Val Thr Gly Arg Arg Ile Ser Ala Thr Ala Glu Asp Gly
65                  70                  75                  80

Asn Lys Phe Ala Lys Leu Ile Val Glu Thr Asp Thr Phe Gly Ser Arg
                85                  90                  95

Val Arg Ile Lys Gly Ala Glu Ser Glu Lys Tyr Ile Cys Met Asn Lys
            100                 105                 110

Arg Gly Lys Leu Ile Gly Lys Pro Ser Gly Lys Ser Lys Asp Cys Val
        115                 120                 125

Phe Thr Glu Ile Val Leu Glu Asn Asn Tyr Thr Ala Phe Gln Asn Ala
    130                 135                 140

Arg His Glu Gly Trp Phe Met Ala Phe Thr Arg Gln Gly Arg Pro Arg
145                 150                 155                 160

Gln Ala Ser Arg Ser Arg Gln Asn Gln Arg Glu Ala His Phe Ile Lys
                165                 170                 175

Arg Leu Tyr Gln Gly Gln Leu Pro Phe Pro Asn His Ala Glu Lys Gln
            180                 185                 190

Lys Gln Phe Glu Phe Val Gly Ser Ala Pro Thr Arg Arg Thr Lys Arg
        195                 200                 205

Thr Arg Arg Pro Gln Pro Leu Thr
    210                 215


<210> SEQ ID NO 39
<211> LENGTH: 207
<212> TYPE: PRT
<213> ORGANISM: Homo sapiens

<400> SEQUENCE: 39

Met Tyr Ser Ala Pro Ser Ala Cys Thr Cys Leu Cys Leu His Phe Leu
 1               5                  10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45
```

```
Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205


<210> SEQ ID NO 40
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Bovine enterokinase cleavage site

<400> SEQUENCE: 40

Asp Asp Asp Asp Lys
 1               5


<210> SEQ ID NO 41
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 41

Glu Asn Leu Tyr Phe Gln Gly
 1               5


<210> SEQ ID NO 42
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 42

Glu Asn Leu Tyr Phe Gln Ser
 1               5


<210> SEQ ID NO 43
<211> LENGTH: 7
<212> TYPE: PRT
```

<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 43

Glu Asn Ile Tyr Thr Gln Gly
1               5

<210> SEQ ID NO 44
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 44

Glu Asn Ile Tyr Thr Gln Ser
1               5

<210> SEQ ID NO 45
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 45

Glu Asn Ile Tyr Leu Gln Gly
1               5

<210> SEQ ID NO 46
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 46

Glu Asn Ile Tyr Leu Gln Ser
1               5

<210> SEQ ID NO 47
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 47

Glu Asn Val Tyr Phe Gln Gly
1               5

<210> SEQ ID NO 48
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 48

Glu Asn Val Tyr Ser Gln Ser
1 5

<210> SEQ ID NO 49
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 49

Glu Asn Val Tyr Ser Gln Gly
1 5

<210> SEQ ID NO 50
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus cleavage site

<400> SEQUENCE: 50

Glu Asn Val Tyr Ser Gln Ser
1 5

<210> SEQ ID NO 51
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 51

Glu Ala Leu Phe Gln Gly Pro
1 5

<210> SEQ ID NO 52
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 52

Glu Val Leu Phe Gln Gly Pro
1 5

<210> SEQ ID NO 53
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 53

Glu Leu Leu Phe Gln Gly Pro
1 5

<210> SEQ ID NO 54
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 54

Asp Ala Leu Phe Gln Gly Pro
1 5

<210> SEQ ID NO 55
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 55

Asp Val Leu Phe Gln Gly Pro
1 5

<210> SEQ ID NO 56
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C cleavage site

<400> SEQUENCE: 56

Asp Leu Leu Phe Gln Gly Pro
1 5

<210> SEQ ID NO 57
<211> LENGTH: 98
<212> TYPE: PRT
<213> ORGANISM: Artificial Sequence
<220> FEATURE:
<221> NAME/KEY: SITE
<222> LOCATION: (1)...(98)
<223> OTHER INFORMATION: SUMO/ULP-1 cleavage site

<400> SEQUENCE: 57

Met Ala Asp Ser Glu Val Asn Gln Glu Ala Lys Pro Glu Val Lys Pro
1 5 10 15

Glu Val Lys Pro Glu Thr His Ile Asn Leu Lys Val Ser Asp Gly Ser
20 25 30

Ser Glu Ile Phe Phe Lys Ile Lys Lys Thr Thr Pro Leu Arg Arg Leu
35 40 45

Met Glu Ala Phe Ala Lys Arg Gln Gly Lys Glu Met Asp Ser Leu Arg
50 55 60

Phe Leu Tyr Asp Gly Ile Arg Ile Gln Ala Asp Gln Thr Pro Glu Asp
65 70 75 80

Leu Asp Met Glu Asp Asn Asp Ile Ile Glu Ala His Arg Glu Gln Ile
85 90 95

Gly Gly

<210> SEQ ID NO 58

<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 58

Gly Val Arg Gly
 1

<210> SEQ ID NO 59
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 59

Ser Ala Arg Gly
 1

<210> SEQ ID NO 60
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 60

Ser Leu Arg Gly
 1

<210> SEQ ID NO 61
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 61

Asp Gly Arg Ile
 1

<210> SEQ ID NO 62
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Thrombin cleavage site

<400> SEQUENCE: 62

Gln Gly Lys Ile
 1

<210> SEQ ID NO 63
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 63

Leu Val Pro Arg Gly Ser
1 5

<210> SEQ ID NO 64
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 64

Leu Val Pro Lys Gly Ser
1 5

<210> SEQ ID NO 65
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 65

Phe Ile Pro Arg Thr Phe
1 5

<210> SEQ ID NO 66
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 66

Val Leu Pro Arg Ser Phe
1 5

<210> SEQ ID NO 67
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 67

Ile Val Pro Arg Ser Phe
1 5

<210> SEQ ID NO 68
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 68

```
Ile Val Pro Arg Gly Tyr
 1               5


<210> SEQ ID NO 69
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 69

Val Val Pro Arg Gly Val
 1               5


<210> SEQ ID NO 70
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 70

Val Leu Pro Arg Leu Ile
 1               5


<210> SEQ ID NO 71
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 71

Val Met Pro Arg Ser Leu
 1               5


<210> SEQ ID NO 72
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Thrombin cleavage site

<400> SEQUENCE: 72

Met Phe Pro Arg Ser Leu
 1               5


<210> SEQ ID NO 73
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Coagulation Factor Xa cleavage site

<400> SEQUENCE: 73

Ile Asp Gly Arg
 1


<210> SEQ ID NO 74
```

-continued

<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Coagulation Factor Xa cleavage site

<400> SEQUENCE: 74

Ile Glu Gly Arg
1

<210> SEQ ID NO 75
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: Flexible spacer

<400> SEQUENCE: 75

Gly Gly Gly Gly Ser
1 5

<210> SEQ ID NO 76
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: Flexible spacer

<400> SEQUENCE: 76

Glu Ala Ala Ala Lys
1 5

<210> SEQ ID NO 77
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: FLAG epitope-binding region

<400> SEQUENCE: 77

Asp Tyr Lys Asp Asp Asp Asp Lys
1 5

<210> SEQ ID NO 78
<211> LENGTH: 9
<212> TYPE: PRT
<213> ORGANISM: Artificial Sequence
<220> FEATURE:
<221> NAME/KEY: PEPTIDE
<222> LOCATION: (1)...(9)
<223> OTHER INFORMATION: Human Influenza virus hemagluttinin (HA) epitope-binding region

<400> SEQUENCE: 78

Tyr Pro Tyr Asp Val Pro Asp Tyr Ala
1 5

<210> SEQ ID NO 79
<211> LENGTH: 10
<212> TYPE: PRT
<213> ORGANISM: Artificial Sequence
<220> FEATURE:

```
<221> NAME/KEY: PEPTIDE
<222> LOCATION: (1)...(10)
<223> OTHER INFORMATION: Human p62 c-Myc epitope-binding region

<400> SEQUENCE: 79

Glu Gln Lys Leu Ile Ser Glu Glu Asp Leu
 1               5                   10


<210> SEQ ID NO 80
<211> LENGTH: 11
<212> TYPE: PRT
<213> ORGANISM: Artificial Sequence
<220> FEATURE:
<221> NAME/KEY: PEPTIDE
<222> LOCATION: (1)...(11)
<223> OTHER INFORMATION: Vesicular Stomatitis Virus Glycoprotein (VSV-G)
      epitope-binding region

<400> SEQUENCE: 80

Tyr Thr Asp Ile Glu Met Asn Arg Leu Gly Lys
 1               5                   10


<210> SEQ ID NO 81
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Substance P epitope-binding region

<400> SEQUENCE: 81

Gln Phe Phe Gly Leu Met
 1               5


<210> SEQ ID NO 82
<211> LENGTH: 11
<212> TYPE: PRT
<213> ORGANISM: Artificial Sequence
<220> FEATURE:
<221> NAME/KEY: PEPTIDE
<222> LOCATION: (1)...(11)
<223> OTHER INFORMATION: Glycoprotein-D precursor of Herpes simplex
      virus epitope-binding region

<400> SEQUENCE: 82

Gln Pro Glu Leu Ala Pro Glu Asp Pro Glu Asp
 1               5                   10


<210> SEQ ID NO 83
<211> LENGTH: 14
<212> TYPE: PRT
<213> ORGANISM: Artificial Sequence
<220> FEATURE:
<221> NAME/KEY: PEPTIDE
<222> LOCATION: (1)...(14)
<223> OTHER INFORMATION: V5 epitope-binding region

<400> SEQUENCE: 83

Gly Lys Pro Ile Pro Asn Pro Leu Leu Gly Leu Asp Ser Thr
 1               5                   10


<210> SEQ ID NO 84
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: AU1 epitope-binding region
```

```
<400> SEQUENCE: 84

Asp Thr Tyr Arg Tyr Ile
 1               5


<210> SEQ ID NO 85
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: AU5 epitope-binding region

<400> SEQUENCE: 85

Thr Asp Phe Tyr Leu Lys
 1               5


<210> SEQ ID NO 86
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: HIS epitope-binding region

<400> SEQUENCE: 86

His His His His His His
 1               5
```

MODIFIED CLOSTRIDIAL TOXINS WITH ENHANCED TARGETING CAPABILITIES FOR ENDOGENOUS CLOSTRIDIAL TOXIN RECEPTOR SYSTEMS

This application is a continuation and claims priority pursuant to 35 U.S.C. §120 to U.S. patent application Ser. No. 11/908,349, filed Sep. 11, 2007, now U.S. Pat. No. 8,128,940, which is a national stage application under 35 U.S.C. §371 of PCT patent application PCT/US2006/008956, filed on Mar. 14, 2006 which claims the benefit of priority pursuant to 35 U.S.C. §119(e) to U.S. provisional patent application Ser. No. 60/662,151 filed on Mar. 15, 2005 and U.S. provisional patent application Ser. No. 60/661,953 filed on Mar. 15, 2005, each of which is hereby incorporated by reference in its entirety All of the patents and publications cited in this application are hereby incorporated by reference in their entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, Cosmetic and Clinical Applications of Botulinum Toxin (Slack, Inc., 2004). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder. In addition, Clostridial toxin therapies are proposed for treating neuromuscular disorders, see e.g., Kei Roger Aoki et al., Method for Treating Neuromuscular Disorders and Conditions with Botulinum Toxin Types A and B, U.S. Pat. No. 6,872,397 (Mar. 29, 2005); Rhett M. Schiffman, Methods for Treating Uterine Disorders, U.S. Patent Publication No. 2004/0175399 (Sep. 9, 2004); Richard L. Barron, Methods for Treating Ulcers and Gastroesophageal Reflux Disease, U.S. Patent Publication No. 2004/0086531 (May 7, 2004); and Kei Roger Aoki, et al., Method for Treating Dystonia with Botulinum Toxin C to G, U.S. Pat. No. 6,319,505 (Nov. 20, 2001); eye disorders, see e.g., Eric R. First, Methods and Compositions for Treating Eye Disorders, U.S. Patent Publication No. 2004/0234532 (Nov. 25, 2004); Kei Roger Aoki et al., Botulinum Toxin Treatment for Blepharospasm, U.S. Patent Publication No. 2004/0151740 (Aug. 5, 2004); and Kei Roger Aoki et al., Botulinum Toxin Treatment for Strabismus, U.S. Patent Publication No. 2004/0126396 (Jul. 1, 2004); pain, see e.g., Kei Roger Aoki et al., Pain Treatment by Peripheral Administration of a Neurotoxin, U.S. Pat. No. 6,869,610 (Mar. 22, 2005); Stephen Donovan, Clostridial Toxin Derivatives and Methods to Treat Pain, U.S. Pat. No. 6,641,820 (Nov. 4, 2003); Kei Roger Aoki, et al., Method for Treating Pain by Peripheral Administration of a Neurotoxin, U.S. Pat. No. 6,464,986 (Oct. 15, 2002); Kei Roger Aoki and Minglei Cui, Methods for Treating Pain, U.S. Pat. No. 6,113,915 (Sep. 5, 2000); Martin A. Voet, Methods for Treating Fibromyalgia, U.S. Pat. No. 6,623,742 (Sep. 23, 2003); Martin A. Voet, Botulinum Toxin Therapy for Fibromyalgia, U.S. Patent Publication No. 2004/0062776 (Apr. 1, 2004); and Kei Roger Aoki et al., Botulinum Toxin Therapy for Lower Back Pain, U.S. Patent Publication No. 2004/0037852 (Feb. 26, 2004); muscle injuries, see e.g., Gregory F. Brooks, Methods for Treating Muscle Injuries, U.S. Pat. No. 6,423,319 (Jul. 23, 2002); headache, see e.g., Martin Voet, Methods for Treating Sinus Headache, U.S. Pat. No. 6,838,434 (Jan. 4, 2005); Kei Roger Aoki et al., Methods for Treating Tension Headache, U.S. Pat. No. 6,776,992 (Aug. 17, 2004); and Kei Roger Aoki et al., Method for Treating Headache, U.S. Pat. No. 6,458,365 (Oct. 1, 2002); William J. Binder, Method for Reduction of Migraine Headache Pain, U.S. Pat. No. 5,714,469 (Feb. 3, 1998); cardiovascular diseases, see e.g., Gregory F. Brooks and Stephen Donovan, Methods for Treating Cardiovascular Diseases with Botulinum Toxin, U.S. Pat. No. 6,767,544 (Jul. 27, 2004); neurological disorders, see e.g., Stephen Donovan, Parkinson's Disease Treatment, U.S. Pat. No. 6,620,415 (Sep. 16, 2003); and Stephen Donovan, Method for Treating Parkinson's Disease with a Botulinum Toxin, U.S. Pat. No. 6,306,403 (Oct. 23, 2001); neuropsychiatric disorders, see e.g., Stephen Donovan, Botulinum Toxin Therapy for Neuropsychiatric Disorders, U.S. Patent Publication No. 2004/0180061 (Sep. 16, 2004); and Steven Donovan, Therapeutic Treatments for Neuropsychiatric Disorders, U.S. Patent Publication No. 2003/0211121 (Nov. 13, 2003); endocrine disorders, see e.g., Stephen Donovan, Method for Treating Endocrine Disorders, U.S. Pat. No. 6,827,931 (Dec. 7, 2004); Stephen Donovan, Method for Treating Thyroid Disorders with a Botulinum Toxin, U.S. Pat. No. 6,740,321 (May 25, 2004); Kei Roger Aoki et al., Method for Treating a Cholinergic Influenced Sweat Gland, U.S. Pat. No. 6,683,049 (Jan. 27, 2004); Stephen Donovan, Neurotoxin Therapy for Diabetes, U.S. Pat. No. 6,416,765 (Jul. 9, 2002); Stephen Donovan, Methods for Treating Diabetes, U.S. Pat. No. 6,337,075 (Jan. 8, 2002); Stephen Donovan, Method for Treating a Pancreatic Disorder with a Neurotoxin, U.S. Pat. No. 6,261,572 (Jul. 17, 2001); Stephen Donovan, Methods for Treating Pancreatic Disorders, U.S. Pat. No. 6,143,306 (Nov. 7, 2000); cancers, see e.g., Stephen Donovan, Methods for Treating Bone Tumors, U.S. Pat. No. 6,565,870 (May 20, 2003); Stephen Donovan, Method for Treating Cancer with a Neurotoxin to Improve Patient Function, U.S. Pat. No. 6,368,605 (Apr. 9, 2002); Stephen Donovan, Method for Treating Cancer with a Neurotoxin, U.S. Pat. No. 6,139,845 (Oct. 31, 2000); and Mitchell F. Brin and Stephen Donovan, Methods for Treating Diverse Cancers, U.S. Patent Publication No. 2005/0031648 (Feb. 10, 2005); otic disorders, see e.g., Stephen Donovan, Neurotoxin Therapy for Inner Ear Disorders, U.S. Pat. No. 6,358,926 (Mar. 19, 2002); and Stephen Donovan, Method for Treating Otic Disorders, U.S. Pat. No. 6,265,379 (Jul. 24, 2001); autonomic disorders, see, e.g., Pankai J. Pasricha and Anthony N. Kalloo, Method for Treating Gastrointestinal Muscle Disorders and Other Smooth Muscle Dysfunction, U.S. Pat. No. 5,437,291 (Aug. 1, 1995); as well as other disorders, see e.g., William J. Binder, Method for Treatment of Skin Lesions Associated with Cutaneous Cell-proliferative Disorders, U.S. Pat. No. 5,670,484 (Sep. 23, 1997); Eric R. First, Application of Botulinum Toxin to the Management of Neurogenic Inflammatory Disorders, U.S. Pat. No. 6,063,768 (May 16, 2000); Marvin Schwartz and Brian J. Freund, Method to Reduce Hair Loss and Stimulate Hair Growth, U.S. Pat. No. 6,299,893 (Oct. 9, 2001); Jean D. A. Carruthers and Alastair Carruthers, Cosmetic Use of Botulinum Toxin for Treatment of Downturned Mouth, U.S. Pat. No. 6,358,917 (Mar. 19, 2002); Stephen Donovan, Use of a Clostridial Toxin to Reduce Appetite, U.S. Patent Publication No. 2004/40253274 (Dec. 16, 2004); and Howard I. Katz and Andrew M. Blumenfeld, Botulinum Toxin Dental Therapies and Procedures, U.S. Patent Publication No. 2004/0115139 (Jun. 17, 2004); Kei Roger Aoki, et al., Treatment of Neuromuscular Disorders and Conditions with Different Botulinum, U.S. Patent Publication No. 2002/0010138 (Jan. 24, 2002); and Kei Roger Aoki, et al., Use of Botulinum Toxins for Treating Various Disorders and Conditions and Associated Pain, U.S. Patent Publication No. 2004/0013692 (Jan. 22, 2004). In addition, the expected use of Clostridial toxins, such as, e.g., BoNTs and TeNT, in therapeutic and cosmetic treatments of humans and other mammals is anticipated to expand to an ever widening range of diseases and ailments that can benefit from the properties of these toxins.

Clostridial toxin therapies are successfully used for many indications. Generally, administration of a Clostridial toxin treatment is well tolerated. However, toxin administration in some applications can be challenging because of the larger doses required to achieve a beneficial effect. Larger doses can increase the likelihood that the toxin may move through the interstitial fluids and the circulatory systems, such as, e.g., the cardiovascular system and the lymphatic system, of the body, resulting in the undesirable dispersal of the toxin to areas not targeted for toxin treatment. Such dispersal can lead to undesirable side effects, such as, e.g., inhibition of neurotransmitter release in neurons not targeted for treatment or paralysis of a muscle not targeted for treatment. For example, a patient administered a therapeutically effective amount of a BoNT/A treatment into the neck muscles for torticollis may develop dysphagia because of dispersal of the toxin into the oropharynx. Thus, there remains a need for improved Clostridial toxins that are effective at the site of treatment, but have negligible to minimal effects in areas not targeted for a toxin treatment.

The growing clinical, therapeutic and cosmetic use of Clostridial toxins in therapies requiring larger doses necessitates the pharmaceutical industry to develop modified Clostridial toxins that are effective at the target site of the application, but reduce or prevent the undesirable side-effects associated with the dispersal of the toxins to an unwanted location or locations. The present invention provides novel Clostridial toxins that reduce or prevent unwanted side-effects associated with toxin dispersal into non-targeted areas. These and related advantages are useful for various clinical, therapeutic and cosmetic applications, such as, e.g., the treatment of neuromuscular disorders, neuropathic disorders, eye disorders, pain, muscle injuries, headache, cardiovascular diseases, neuropsychiatric disorders, endocrine disorders, cancers, otic disorders and hyperkinetic facial lines, as well as, other disorders where a Clostridial toxin administration to a mammal can produce a beneficial effect.

BRIEF DESCRIPTION OF THE DRAWINGS

FIG. 1 shows a schematic of the current paradigm of neurotransmitter release and Clostridial toxin intoxication in a central and peripheral neuron.

FIG. 3 shows modified Clostridial toxins with an enhanced targeting domain located at the amino terminus of the modified toxin.

FIG. 4 shows modified Clostridial toxins with an enhanced targeting domain located between the other two domains.

FIG. 5 shows modified Clostridial toxins with an enhanced targeting domain located at the carboxyl terminus of the modified toxin.

DETAILED DESCRIPTION

Figure 1A:
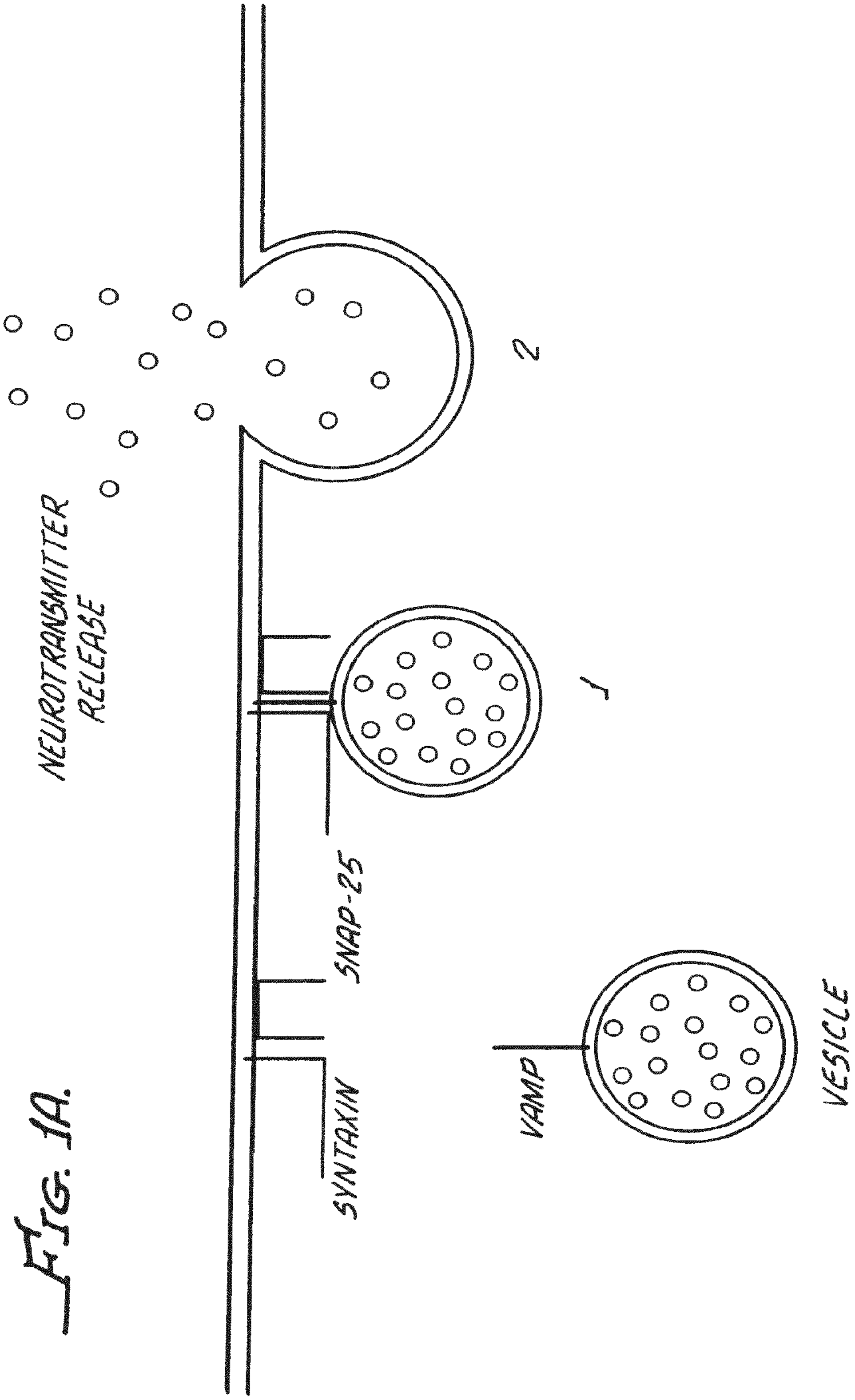
FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed.

The present invention discloses modified Clostridial toxins that exhibit enhanced binding activity for cells targeted by naturally-occurring Clostridial toxins. Enhanced binding activity is achieved by replacing a naturally-occurring binding domain of a Clostridial toxin with a binding domain showing enhanced binding activity for a Clostridial toxin target cell. This enhanced binding activity for a target cell should allow lower effective doses of a modified Clostridial toxin to be administered to an individual because more toxin will be delivered to a target cell. Thus modified Clostridial toxins with enhanced binding activity will reduce the undesirable dispersal of the toxin to areas not targeted for treatment, thereby reducing or preventing the undesirable side-effects associated with diffusion of a Clostridial toxin to an unwanted location.

Aspects of the present invention provide modified Clostridial toxins comprising a Clostridial toxin enzymatic domain, a Clostridial toxin translocation domain and an enhanced targeting domain, wherein the modified Clostridial toxin exhibits an enhanced targeting activity for a Clostridial toxin target cell relative to a naturally-occurring Clostridial toxin. It is envisioned that the location of the enhanced targeting domain in the modified Clostridial toxins of the present specification can be located at the amino terminus of the toxin, between the enzymatic and translocation domains or at the carboxyl terminus of the toxin. Thus, a modified Clostridial toxins disclosed in the present specification can comprise an amino to carboxyl domain arrangement of, e.g., an enhanced targeting domain, a Clostridial toxin translocation domain and a Clostridial toxin enzymatic domain; an enhanced targeting domain, a Clostridial toxin enzymatic domain and a Clostridial toxin translocation domain; a Clostridial toxin enzymatic domain, an enhanced targeting domain and a Clostridial toxin translocation domain; a Clostridial toxin translocation domain, an enhanced targeting domain and a Clostridial toxin enzymatic domain; a Clostridial toxin enzymatic domain, a Clostridial toxin translocation domain and an enhanced targeting domain; and a Clostridial toxin translocation domain, a Clostridial toxin enzymatic domain and an enhanced targeting domain.

Other aspects of the present invention provide polynucleotide molecules encoding modified Clostridial toxins comprising a Clostridial toxin enzymatic domain, a Clostridial toxin translocation domain and an enhanced targeting domain, wherein the modified Clostridial toxin exhibits an enhanced targeting activity for a Clostridial toxin target cell relative to a naturally-occurring Clostridial toxin. It is envisioned that the location of the enhanced targeting domain of the modified Clostridial toxins encoded by polynucleotide molecules of the present specification can be located at the amino terminus of the toxin, between the enzymatic and translocation domains or at the carboxyl terminus of the toxin. Thus, polynucleotide molecules disclosed in the present specification can encoded modified Clostridial toxins comprising an amino to carboxyl domain arrangement of, e.g., an enhanced targeting domain, a Clostridial toxin translocation domain and a Clostridial toxin enzymatic domain; an enhanced targeting domain, a Clostridial toxin enzymatic domain and a Clostridial toxin translocation domain; a Clostridial toxin enzymatic domain, an enhanced targeting domain and a Clostridial toxin translocation domain; a Clostridial toxin translocation domain, an enhanced targeting domain and a Clostridial toxin enzymatic domain; a Clostridial toxin enzymatic domain, a Clostridial toxin translocation domain and an enhanced targeting domain; and a Clostridial toxin translocation domain, a Clostridial toxin enzymatic domain and an enhanced targeting domain.

Other aspects of the present invention provide methods of producing a modified Clostridial toxin disclosed in the present specification, the method comprising the step of expressing in a cell a polynucleotide molecule encoding a modified Clostridial toxin comprising a Clostridial toxin enzymatic domain, a Clostridial toxin translocation domain and an enhanced targeting domain, wherein the modified Clostridial toxin exhibits an enhanced targeting activity for a Clostridial toxin target cell relative to a naturally-occurring Clostridial toxin. Other aspects of the present invention provide methods of producing a modified Clostridial toxin disclosed in the present specification, the method comprising the steps of introducing in a cell an expression construct comprising a polynucleotide molecule encoding a modified Clostridial toxin comprising a Clostridial toxin enzymatic domain, a Clostridial toxin translocation domain and an enhanced targeting domain, wherein the modified Clostridial toxin exhibits an enhanced targeting activity for a Clostridial toxin target cell relative to a naturally-occurring Clostridial toxin and expressing the expression construct in the cell.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). While all seven botulinum toxins (BoNT) serotypes have similar structure and pharmacological properties, each also displays heterogeneous bacteriological characteristics. In contrast, tetanus toxin (TeNT) is produced by a uniform group of *C. tetani*. Two other species of Clostridia, *C. baratii* and *C. butyricum*, also produce toxins similar to BoNT/F and BoNT/E, respectively.

Figure 2:
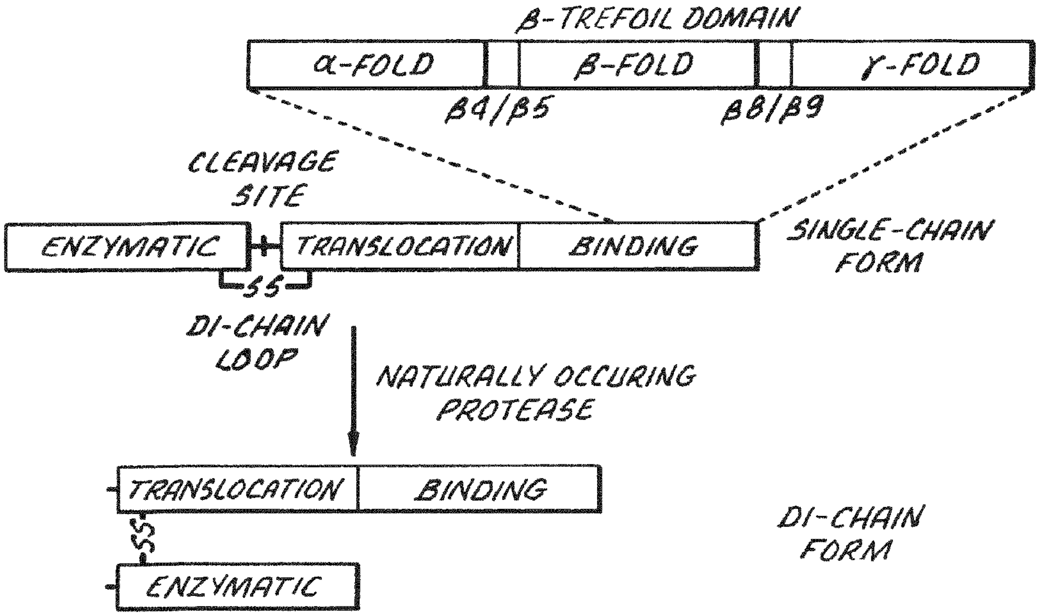
FIG. 2 shows the domain organization of naturally-occurring Clostridial toxins. The single chain form depicts the amino to carboxyl linear organization comprising an an enzymatic domain, a translocation domain, and a binding domain. The di-chain loop region located between the translocation and enzymatic domains is depicted by the double SS bracket. This region comprises an endogenous di-chain loop protease cleavage site that upon proteolytic cleavage with a naturally-occurring protease, such as, e.g., an endogenous Clostridial toxin protease or a naturally-occurring protease produced in the environment, converts the single chain form of the toxin into the di-chain form. Above the single-chain form, the $H_{CC}$ region of the Clostridial toxin binding domain is depicted. This region comprises the β-trefoil domain which comprises in a amino to carboxyl linear organization an α-fold, a β4/β5 hairpin turn, a β-fold, a β8/β9 hairpin turn and a γ-fold.

Clostridia toxins possess approximately 35% amino acid identity with each other and share the same functional domain organization and overall structural architecture. Clostridial toxins are each translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring protease produced in the environment (FIG. 2). This posttranslational processing yields a di-chain molecule comprising an approximately 50 kDa light chain (LC) and an approximately 100 kDa heavy chain (HC) held together by a single disulfide bond and non-covalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus (Table 1); 2) a translocation domain contained within the amino-terminal half of the HC ($H_N$) that facilitates release of the LC from intracellular vesicles into the cytoplasm of the target cell (Table 1); and 3) a binding domain found within the carboxyl-terminal half of the HC ($H_C$) that determines the binding activity and binding specificity of the toxin to the receptor complex located at the surface of the target cell (Table 1).

TABLE 1

Clostridial Toxin Reference Sequences and Regions

| Toxin | SEQ ID NO: | LC | $H_N$ | $H_C$ |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |
| BoNT/D | 4 | M1-R445 | D446-N862 | S863-E1276 |
| BoNT/E | 5 | M1-R422 | K423-K845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |

Figure 1B:
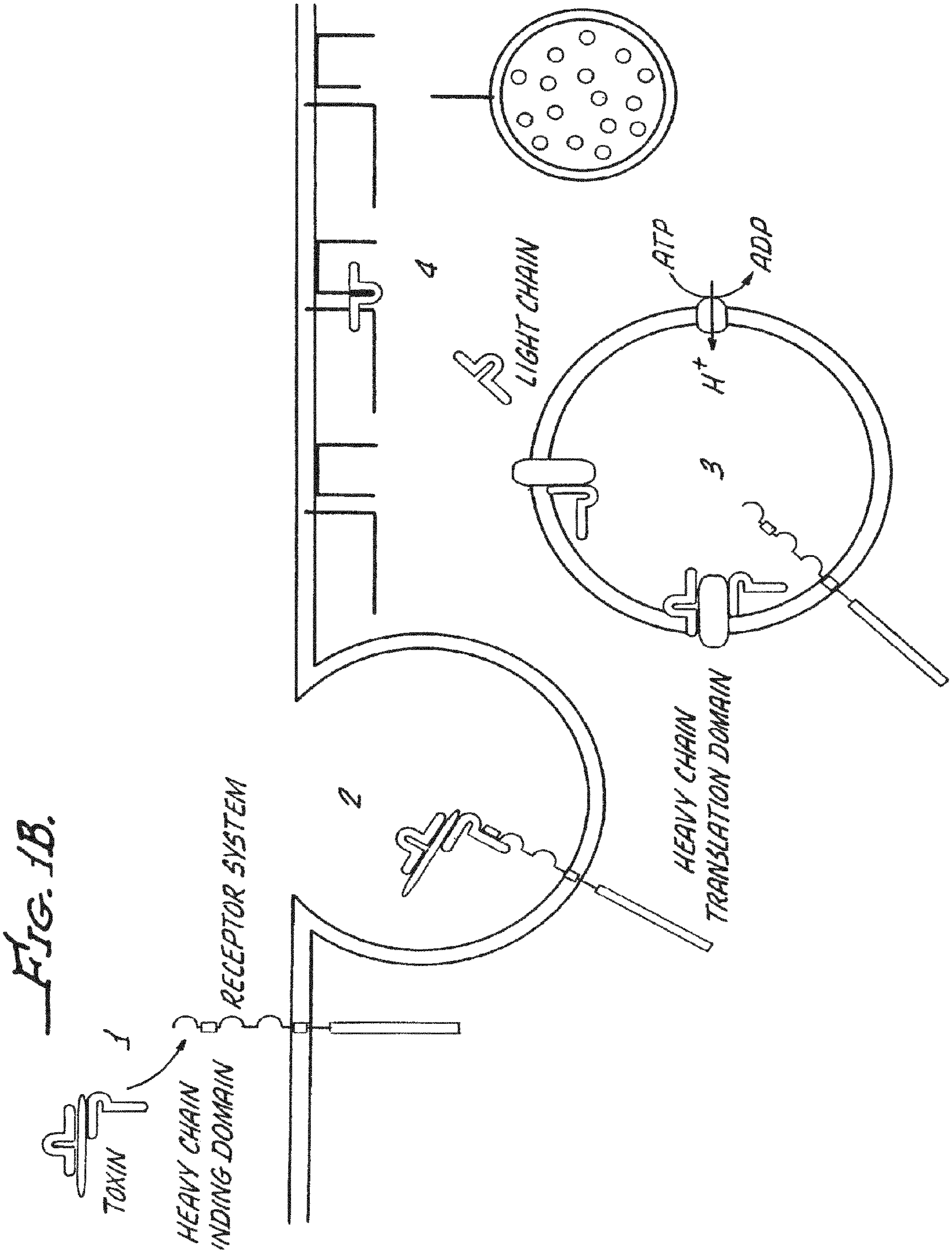
FIG. 1B shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events are thought to occur, including, e.g., changes in the internal pH of the vesicle, formation of a channel pore comprising the $H_N$ domain of the Clostridial toxin heavy chain, separation of the Clostridial toxin light chain from the heavy chain, and release of the active light chain and 4) enzymatic target modification, where the activate light chain of Clostridial toxin proteolytically cleaves its target SNARE substrate, such as, e.g., SNAP-25, VAMP or Syntaxin, thereby preventing vesicle docking and neurotransmitter release.

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (see FIG. 1). The process is initiated when the $H_C$ domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it appears to specifically targets one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release,* 82(5) Biochimie. 427-446 (2000); Kathryn Turton et al., *Botulinum and Tetanus Neurotoxins: Structure, Function and Therapeutic Utility,* 27(11) Trends Biochem. Sci. 552-558. (2002); Giovanna Lalli et al., *The Journey of Tetanus and Botulinum Neurotoxins in Neurons,* 11(9) Trends Microbiol. 431-437, (2003).

Aspects of the present invention provide, in part, a modified Clostridial toxin. As used herein, the term "modified Clostridial toxin" means any polypeptide that can execute the overall cellular mechanism whereby a Clostridial toxin enters a neuron and inhibits neurotransmitter release and encompasses the binding of a Clostridial toxin to a low or high affinity receptor complex, the internalization of the toxin, the translocation of the Clostridial toxin light chain into the cytoplasm and the enzymatic modification of a Clostridial toxin substrate. A modified Clostridial toxin disclosed in the present specification is distinguished from a naturally-occurring Clostridial toxin by the fact that a modified Clostridial toxin lacks the cell binding activity of a naturally-occurring binding domain found in a Clostridial toxin. Instead, a modified Clostridial toxin disclosed in the present specification comprises an enhanced targeting domain that determines the binding activity of the modified Clostridial toxin to an endogenous Clostridial toxin receptor system located at the surface of the target cell. By definition, a naturally-occurring Clostridial toxin lacks an enhanced targeting domain.

Aspects of the present invention provide, in part, a Clostridial toxin enzymatic domain. As used herein, the term "Clostridial toxin enzymatic domain" means any Clostridial toxin polypeptide that can execute the enzymatic target modification step of the intoxication process. Thus, a Clostridial toxin enzymatic domain specifically targets a Clostridial toxin substrate and encompasses the proteolytic cleavage of a Clostridial toxin substrate, such as, e.g., SNARE proteins like a SNAP-25 substrate, a VAMP substrate and a Syntaxin substrate. Non-limiting examples of a Clostridial toxin enzymatic domain include, e.g., a Clostridial toxin light chain region such as, e.g., a BoNT/A light chain region, a BoNT/B light chain region, a BoNT/C1 light chain region, a BoNT/D light chain region, a BoNT/E light chain region, a BoNT/F light chain region, a BoNT/G light chain region, and a TeNT light chain region.

A Clostridial toxin enzymatic domain includes, without limitation, naturally occurring Clostridial toxin light chain variants, such as, e.g., Clostridial toxin light chain isoforms and Clostridial toxin light chain subtypes; non-naturally occurring Clostridial toxin light chain variants, such as, e.g., conservative Clostridial toxin light chain variants, non-conservative Clostridial toxin light chain variants, Clostridial toxin light chain chimerics, active Clostridial toxin light chain fragments thereof, or any combination thereof.

As used herein, the term "Clostridial toxin light chain variant," whether naturally-occurring or non-naturally-occurring, means a Clostridial toxin light chain that has at least one amino acid change from the corresponding region of the disclosed reference sequences (see Table 1) and can be described in percent identity to the corresponding region of that reference sequence. Unless expressly indicated, all Clostridial toxin light chain variants disclosed in the present specification are capable of executing the enzymatic target modification step of the intoxication process. As non-limiting examples, a BoNT/A light chain variant comprising amino acids 1-448 of SEQ ID NO: 1 will have at least one amino acid difference, such as, e.g., an amino acid substitution, deletion or addition, as compared to the amino acid region 1-448 of SEQ ID NO: 1; a BoNT/B light chain variant comprising amino acids 1-441 of SEQ ID NO: 2 will have at least one amino acid difference, such as, e.g., an amino acid substitution, deletion or addition, as compared to the amino acid region 1-441 of SEQ ID NO: 2; a BoNT/C1 light chain variant comprising amino acids 1-449 of SEQ ID NO: 3 will have at least one amino acid difference, such as, e.g., an amino acid substitution, deletion or addition, as compared to the amino acid region 1-449 of SEQ ID NO: 3; a BoNT/D light chain variant comprising amino acids 1-445 of SEQ ID NO: 4 will have at least one amino acid difference, such as, e.g., an amino acid substitution, deletion or addition, as compared to the amino acid region 1-445 of SEQ ID NO: 4; a BoNT/E light chain variant comprising amino acids 1-422 of SEQ ID NO: 5 will have at least one amino acid difference, such as, e.g., an amino acid substitution, deletion or addition, as compared to the amino acid region 1-422 of SEQ ID NO: 5; a BoNT/F light chain variant comprising amino acids 1-439 of SEQ ID NO: 6 will have at least one amino acid difference, such as, e.g., an amino acid substitution, deletion or addition, as compared to the amino acid region 1-439 of SEQ ID NO: 6; a BoNT/G light chain variant comprising amino acids 1-446 of SEQ ID NO: 7 will have at least one amino acid difference, such as, e.g., an amino acid substitution, deletion or addition, as compared to the amino acid region 1-446 of SEQ ID NO: 7; and a TeNT light chain variant comprising amino acids 1-457 of SEQ ID NO: 8 will have at least one amino acid difference, such as, e.g., an amino acid substitution, deletion or addition, as compared to the amino acid region 1-457 of SEQ ID NO: 8.

It is recognized by those of skill in the art that within each serotype of Clostridial toxin there can be naturally occurring Clostridial toxin light chain variants that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific light chain subtypes showing approximately 95% amino acid identity when compared to another BoNT/A light chain subtype. As used herein, the term "naturally occurring Clostridial toxin light chain variant" means any Clostridial toxin light chain produced by a naturally-occurring process, including, without limitation, Clostridial toxin light chain isoforms produced from alternatively-spliced transcripts, Clostridial toxin light chain isoforms produced by spontaneous mutation and Clostridial toxin light chain subtypes. A naturally occurring Clostridial toxin light chain variant can function in substantially the same manner as the reference Clostridial toxin light chain on which the naturally occurring Clostridial toxin light chain variant is based, and can be substituted for the reference Clostridial toxin light chain in any aspect of the present invention. A naturally occurring Clostridial toxin light chain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial toxin light chain on which the naturally occurring Clostridial toxin light chain variant is based. A naturally occurring Clostridial toxin light chain variant can also substitute at least 10 contiguous amino acids, at least 15 contiguous amino acids, at least 20 contiguous amino acids, or at least 25 contiguous amino acids from the reference Clostridial toxin light chain on which the naturally occurring Clostridial toxin light chain variant is based, that possess at least 50% amino acid identity, 65% amino acid identity, 75% amino acid identity, 85% amino acid identity or 95% amino acid identity to the reference Clostridial toxin light chain on which the naturally occurring Clostridial toxin light chain variant is based.

A non-limiting examples of a naturally occurring Clostridial toxin light chain variant is a Clostridial toxin light chain isoform such as, e.g., a BoNT/A light chain isoform, a BoNT/B light chain isoform, a BoNT/C1 light chain isoform, a BoNT/D light chain isoform, a BoNT/E light chain isoform, a BoNT/F light chain isoform, a BoNT/G light chain isoform, and a TeNT light chain isoform. A Clostridial toxin light chain isoform can function in substantially the same manner as the reference Clostridial toxin light chain on which the Clostridial toxin light chain isoform is based, and can be substituted for the reference Clostridial toxin light chain in any aspect of the present invention.

Another non-limiting examples of a naturally occurring Clostridial toxin light chain variant is a Clostridial toxin light chain subtype such as, e.g., a light chain from subtype BoNT/A1, BoNT/A2, BoNT/A3 and BoNT/A4; a light chain from subtype BoNT/B1, BoNT/B2, BoNT/B bivalent and BoNT/B nonproteolytic; a light chain from subtype BoNT/C1-1 and BoNT/C1-2; a light chain from subtype BoNT/E1, BoNT/E2 and BoNT/E3; and a light chain from subtype BoNT/F1, BoNT/F2, BoNT/F3 and BoNT/F4. A Clostridial toxin light chain subtype can function in substantially the same manner as the reference Clostridial toxin light chain on which the Clostridial toxin light chain subtype is based, and can be substituted for the reference Clostridial toxin light chain in any aspect of the present invention.

As used herein, the term "non-naturally occurring Clostridial toxin light chain variant" means any Clostridial toxin light chain produced with the aid of human manipulation, including, without limitation, Clostridial toxin light chains produced by genetic engineering using random mutagenesis or rational design and Clostridial toxin light chains produced by chemical synthesis. Non-limiting examples of non-naturally occurring Clostridial toxin light chain variants include, e.g., conservative Clostridial toxin light chain variants, non-conservative Clostridial toxin light chain variants, Clostridial toxin light chain chimeric variants and active Clostridial toxin light chain fragments.

As used herein, the term "conservative Clostridial toxin light chain variant" means a Clostridial toxin light chain that has at least one amino acid substituted by another amino acid or an amino acid analog that has at least one property similar to that of the original amino acid from the reference Clostridial toxin light chain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin light chain variant can function in substantially the same manner as the reference Clostridial toxin light chain on which the conservative Clostridial toxin light chain variant is based, and can be substituted for the reference Clostridial toxin light chain in any aspect of the present invention. A conservative Clostridial toxin light chain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin light chain on which the conservative Clostridial toxin light chain variant is based. A conservative Clostridial toxin light chain variant can also substitute at least 10 contiguous amino acids, at least 15 contiguous amino acids, at least 20 contiguous amino acids, or at least 25 contiguous amino acids from the reference Clostridial toxin light chain on which the conservative Clostridial toxin light chain variant is based, that possess at least 50% amino acid identity, 65% amino acid identity, 75% amino acid identity, 85% amino acid identity or 95% amino acid identity to the reference Clostridial toxin light chain on which the conservative Clostridial toxin light chain variant is based. Non-limiting examples of a conservative Clostridial toxin light chain variant include, e.g., conservative BoNT/A light chain variants, conservative BoNT/B light chain variants, conservative BoNT/C1 light chain variants, conservative BoNT/D light chain variants, conservative BoNT/E light chain variants, conservative BoNT/F light chain variants, conservative BoNT/G light chain variants, and conservative TeNT light chain variants.

As used herein, the term "non-conservative Clostridial toxin light chain variant" means a Clostridial toxin light chain in which 1) at least one amino acid is deleted from the reference Clostridial toxin light chain on which the non-conservative Clostridial toxin light chain variant is based; 2) at least one amino acid added to the reference Clostridial toxin light chain on which the non-conservative Clostridial toxin light chain is based; or 3) at least one amino acid is substituted by another amino acid or an amino acid analog that does not share any property similar to that of the original amino acid from the reference Clostridial toxin light chain sequence (Table 1). A non-conservative Clostridial toxin light chain variant can function in substantially the same manner as the reference Clostridial toxin light chain on which the non-conservative Clostridial toxin light chain variant is based, and can be substituted for the reference Clostridial toxin light chain in any aspect of the present invention. A non-conservative Clostridial toxin light chain variant can delete one or more amino acids, two or more amino acids, three or more amino acids, four or more amino acids, five or more amino acids, and ten or more amino acids from the reference Clostridial toxin light chain on which the non-conservative Clostridial toxin light chain variant is based. A non-conservative Clostridial toxin light chain variant can add one or more amino acids, two or more amino acids, three or more amino acids, four or more amino acids, five or more amino acids, and ten or more amino acids to the reference Clostridial toxin light chain on which the non-conservative Clostridial toxin light chain variant is based. A non-conservative Clostridial toxin light chain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin light chain on which the non-conservative Clostridial toxin light chain variant is based. A non-conservative Clostridial toxin light chain variant can also substitute at least 10 contiguous amino acids, at least 15 contiguous amino acids, at least 20 contiguous amino acids, or at least 25 contiguous amino acids from the reference Clostridial toxin light chain on which the non-conservative Clostridial toxin light chain variant is based, that possess at least 50% amino acid identity, 65% amino acid identity, 75% amino acid identity, 85% amino acid identity or 95% amino acid identity to the reference Clostridial toxin light chain on which the non-conservative Clostridial toxin light chain variant is based. Non-limiting examples of a non-conservative Clostridial toxin light chain variant include, e.g., non-conservative BoNT/A light chain variants, non-conservative BoNT/B light chain variants, non-conservative BoNT/C1 light chain variants, non-conservative BoNT/D light chain variants, non-conservative BoNT/E light chain variants, non-conservative BoNT/F light chain variants, non-conservative BoNT/G light chain variants, and non-conservative TeNT light chain variants.

As used herein, the term "Clostridial toxin light chain chimeric" means a polypeptide comprising at least a portion of a Clostridial toxin light chain and at least a portion of at least one other polypeptide to form a toxin light chain with at least one property different from the reference Clostridial toxin light chains of Table 1, with the proviso that this Clostridial toxin light chain chimeric is still capable of specifically targeting the core components of the neurotransmitter release apparatus and thus participate in executing the overall cellular mechanism whereby a Clostridial toxin proteolytically cleaves a substrate. Such Clostridial toxin light chain chimerics are described in, e.g., Lance E. Steward et al., Leucine-based Motif and Clostridial Toxins, U.S. Patent Publication 2003/0027752 (Feb. 6, 2003); Lance E. Steward et al., Clostridial Neurotoxin Compositions and Modified Clostridial Neurotoxins, U.S. Patent Publication 2003/0219462 (Nov. 27, 2003); and Lance E. Steward et al., Clostridial Neurotoxin Compositions and Modified Clostridial Neurotoxins, U.S. Patent Publication 2004/0220386 (Nov. 4, 2004).

As used herein, the term "active Clostridial toxin light chain fragment" means any of a variety of Clostridial toxin fragments comprising the light chain can be useful in aspects of the present invention with the proviso that these light chain fragments can specifically target the core components of the neurotransmitter release apparatus and thus participate in executing the overall cellular mechanism whereby a Clostridial toxin proteolytically cleaves a substrate. The light chains of Clostridial toxins are approximately 420-460 amino acids in length and comprise an enzymatic domain (Table 1). Research has shown that the entire length of a Clostridial toxin light chain is not necessary for the enzymatic activity of the enzymatic domain. As a non-limiting example, the first eight amino acids of the BoNT/A light chain (residues 1-8 of SEQ ID NO: 1) are not required for enzymatic activity. As another non-limiting example, the first eight amino acids of the TeNT light chain (residues 1-8 of SEQ ID NO: 8) are not required for enzymatic activity. Likewise, the carboxyl-terminus of the light chain is not necessary for activity. As a non-limiting example, the last 32 amino acids of the BoNT/A light chain (residues 417-448 of SEQ ID NO: 1) are not required for enzymatic activity. As another non-limiting example, the last 31 amino acids of the TeNT light chain (residues 427-457 of SEQ ID NO: 8) are not required for enzymatic activity. Thus, aspects of this embodiment can include Clostridial toxin light chains comprising an enzymatic domain having a length of, e.g., at least 350 amino acids, at least 375 amino acids, at least 400 amino acids, at least 425 amino acids and at least 450 amino acids. Other aspects of this embodiment can include Clostridial toxin light chains comprising an enzymatic domain having a length of, e.g., at most 350 amino acids, at most 375 amino acids, at most 400 amino acids, at most 425 amino acids and at most 450 amino acids.

Any of a variety of sequence alignment methods can be used to determine percent identity of naturally-occurring Clostridial toxin light chain variants and non-naturally-occurring Clostridial toxin light chain variants, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice,* 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments,* 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences,* 8(5) CABIOS 501-509 (1992); Gibbs sampling, see, e.g., C. E. Lawrence et al., *Detecting Subtle Sequence Signals: A Gibbs Sampling Strategy for Multiple Alignment,* 262(5131) Science 208-214 (1993); Align-M, see, e.g., Ivo Van Walle et al., *Align-M—A New Algorithm for Multiple Alignment of Highly Divergent Sequences,* 20(9) Bioinformatics:1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison,* 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment,* 302(1) J. Mol. Biol. 205-217 (2000); MUSCLE, see, e.g., Robert C. Edgar, *MUSCLE: Multiple Sequence Alignment With High Score Accuracy and High Throughput,* 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment,* 6(1) BMC Bioinformatics 66 (2005).

Thus, in an embodiment, a modified Clostridial toxin disclosed in the present specification comprises a Clostridial toxin enzymatic domain. In an aspect of this embodiment, a Clostridial toxin enzymatic domain comprises a naturally occurring Clostridial toxin light chain variant, such as, e.g., a Clostridial toxin light chain isoform or a Clostridial toxin light chain subtype. In another aspect of this embodiment, a Clostridial toxin enzymatic domain comprises a non-naturally occurring Clostridial toxin light chain variant, such as, e.g., a conservative Clostridial toxin light chain variant, a non-conservative Clostridial toxin light chain variant, a Clostridial toxin chimeric light chain, an active Clostridial toxin light chain fragment, or any combination thereof.

In another embodiment, a Clostridial toxin enzymatic domain comprises a BoNT/A light chain. In an aspect of this embodiment, a BoNT/A light chain comprises amino acids 1-448 of SEQ ID NO: 1. In another aspect of this embodiment, a BoNT/A light chain comprises a naturally occurring BoNT/A light chain variant, such as, e.g., a light chain from a BoNT/A isoform or a light chain from a BoNT/A subtype. In another aspect of this embodiment, a BoNT/A light chain comprises amino acids 1-448 of a naturally occurring BoNT/A light chain variant of SEQ ID NO: 1, such as, e.g., amino acids 1-448 of a BoNT/A isoform of SEQ ID NO: 1 or amino acids 1-448 of a BoNT/A subtype of SEQ ID NO: 1. In still another aspect of this embodiment, a BoNT/A light chain comprises a non-naturally occurring BoNT/A light chain variant, such as, e.g., a conservative BoNT/A light chain variant, a non-conservative BoNT/A light chain variant, a BoNT/A chimeric light chain, an active BoNT/A light chain fragment, or any combination thereof. In still another aspect of this embodiment, a BoNT/A light chain comprises amino acids 1-448 of a non-naturally occurring BoNT/A light chain variant of SEQ ID NO: 1, such as, e.g., amino acids 1-448 of a conservative BoNT/A light chain variant of SEQ ID NO: 1, amino acids 1-448 of a non-conservative BoNT/A light chain variant of SEQ ID NO: 1, amino acids 1-448 of an active BoNT/A light chain fragment of SEQ ID NO: 1, or any combination thereof.

In other aspects of this embodiment, a BoNT/A light chain comprises a polypeptide having, e.g., at least 70% amino acid identity with amino acids 1-448 of SEQ ID NO: 1, at least 75% amino acid identity with amino acids 1-448 of SEQ ID NO: 1, at least 80% amino acid identity with amino acids 1-448 of SEQ ID NO: 1, at least 85% amino acid identity with amino acids 1-448 of SEQ ID NO: 1, at least 90% amino acid identity with amino acids 1-448 of SEQ ID NO: 1 or at least 95% amino acid identity with amino acids 1-448 of SEQ ID NO: 1. In yet other aspects of this embodiment, a BoNT/A light chain comprises a polypeptide having, e.g., at most 70% amino acid identity with amino acids 1-448 of SEQ ID NO: 1, at most 75% amino acid identity with amino acids 1-448 of SEQ ID NO: 1, at most 80% amino acid identity with amino acids 1-448 of SEQ ID NO: 1, at most 85% amino acid identity with amino acids 1-448 of SEQ ID NO: 1, at most 90% amino acid identity with amino acids 1-448 of SEQ ID NO: 1 or at most 95% amino acid identity with amino acids 1-448 of SEQ ID NO: 1.

In other aspects of this embodiment, a BoNT/A light chain comprises a polypeptide having, e.g., at most one, two, three, four, five, six, seven, eight, nine, 10, 20, 30, 40, 50, 100, or 200 non-contiguous amino acid substitutions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 non-contiguous amino acid substitutions relative to amino acids 1-448 of SEQ ID NO: 1. In yet other aspects of this embodiment, a BoNT/A light chain comprises a polypeptide having, e.g., at most one, two, three, four, five, six, seven, eight, nine, 10, 20, 30, 40, 50, 100 or 200 non-contiguous amino acid deletions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 non-contiguous amino acid deletions relative to amino acids 1-448 of SEQ ID NO: 1. In still other aspects of this embodiment, a BoNT/A light chain comprises a polypeptide having, e.g., at most one, two, three, four, five, six, seven, eight, nine, 10, 20, 30, 40, 50, 100 or 200 non-contiguous amino acid additions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 non-contiguous amino acid additions relative to amino acids 1-448 of SEQ ID NO: 1.

In other aspects of this embodiment, a BoNT/A light chain comprises a polypeptide having, e.g., at most one, two, three, four, five, six, seven, eight, nine, 10, 20, 30, 40, 50, 100 or 200 contiguous amino acid substitutions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 contiguous amino acid substitutions relative to amino acids 1-448 of SEQ ID NO: 1. In yet other aspects of this embodiment, a BoNT/A light chain comprises a polypeptide having, e.g., at most one, two, three, four, five, six, seven, eight, nine, 10, 20, 30, 40, 50, 100 or 200 contiguous amino acid deletions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 contiguous amino acid deletions relative to amino acids 1-448 of SEQ ID NO: 1. In still other aspects of this embodiment, a BoNT/A light chain comprises a polypeptide having, e.g., at most one, two, three, four, five, six, seven, eight, nine, 10, 20, 30, 40, 50, 100 or 200 contiguous amino acid additions relative to amino acids 1-448 of SEQ ID NO: 1. In other aspects of this embodiment, a BoNT/A light chain comprises a polypeptide having, e.g., at least one, two, three, four, five, six, seven, eight, nine, 10, 20, 30, 40, 50, 100 or 200 contiguous amino acid additions relative to amino acids 1-448 of SEQ ID NO: 1.

In another embodiment, a Clostridial toxin enzymatic domain comprises a BoNT/B light chain. In an aspect of this embodiment, a BoNT/B light chain comprises amino acids 1-441 of SEQ ID NO: 2. In another aspect of this embodiment, a BoNT/B light chain comprises a naturally occurring BoNT/B light chain variant, such as, e.g., a light chain from a BoNT/B isoform or a light chain from a BoNT/B subtype. In another aspect of this embodiment, a BoNT/B light chain comprises amino acids 1-441 of a naturally occurring BoNT/B light chain variant of SEQ ID NO: 2, such as, e.g., amino acids 1-441 of a BoNT/B isoform of SEQ ID NO: 2 or amino acids 1-441 of a BoNT/B subtype of SEQ ID NO: 2. In still another aspect of this embodiment, a BoNT/B light chain comprises a non-naturally occurring BoNT/B light chain variant, such as, e.g., a conservative BoNT/B light chain variant, a non-conservative BoNT/B light chain variant, a BoNT/B chimeric light chain, an active BoNT/B light chain fragment, or any combination thereof. In still another aspect of this embodiment, a BoNT/B light chain comprises amino acids 1-441 of a non-naturally occurring BoNT/B light chain variant of SEQ ID NO: 2, such as, e.g., amino acids 1-441 of a conservative BoNT/B light chain variant of SEQ ID NO: 2, amino acids 1-441 of a non-conservative BoNT/B light chain variant of SEQ ID NO: 2, amino acids 1-441 of an active BoNT/B light chain fragment of SEQ ID NO: 2, or any combination thereof.

In other aspects of this embodiment, a BoNT/B light chain comprises a polypeptide having, e.g., at least 70% amino acid identity with amino acids 1-441 of SEQ ID NO: 2, at least 75% amino acid identity with amino acids 1-441 of SEQ ID NO: 2, at least 80% amino acid identity with amino acids 1-441 of SEQ ID NO: 2, at least 85% amino acid identity with amino acids 1-441 of SEQ ID NO: 2, at least 90% amino acid identity with amino acids 1-441 of SEQ ID NO: 2 or at least 95% amino acid identity with amino acids 1-441 of SEQ ID NO: 2. In yet other aspects of this embodiment, a BoNT/B light chain comprises a polypeptide having, e.g., at most 70% amino acid identity with amino acids 1-441 of SEQ ID NO: 2, at most 75% amino acid identity with amino acids 1-441 of SEQ ID NO: 2, at most 80% amino acid identity with amino acids 1-441 of SEQ ID NO: 2, at most 85% amino acid identity with amino acids 1-441 of SEQ ID NO: 2, at most 90% amino acid identity with amino acids 1-441 of SEQ ID NO: 2 or at most 95% amino acid identity with amino acids 1-441 of SEQ ID NO: 2.

In other aspects of this embodiment, a BoNT/B light chain comprises a polypeptide having, e.g., at most one, two, three, four, five, six, seven, eight, nine, 10, 20, 30, 40, 50, 100, or 200 non-contiguous amino acid substitutions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 non-contiguous amino acid substitutions relative to amino acids 1-441 of SEQ ID NO: 2. In yet other aspects of this embodiment, a BoNT/B light chain comprises a polypeptide having, e.g., at most one, two, three, four, five, six, seven, eight, nine, 10, 20, 30, 40, 50, 100 or 200 non-contiguous amino acid deletions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 non-contiguous amino acid deletions relative to amino acids 1-441 of SEQ ID NO: 2. In still other aspects of this embodiment, a BoNT/B light chain comprises a polypeptide having, e.g., at most one, two, three, four, five, six, seven, eight, nine, 10, 20, 30, 40, 50, 100 or 200 non-contiguous amino acid additions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 non-contiguous amino acid additions relative to amino acids 1-441 of SEQ ID NO: 2.

In other aspects of this embodiment, a BoNT/B light chain comprises a polypeptide having, e.g., at most one, two, three, four, five, six, seven, eight, nine, 10, 20, 30, 40, 50, 100 or 200 contiguous amino acid substitutions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 contiguous amino acid substitutions relative to amino acids 1-441 of SEQ ID NO: 2. In yet other aspects of this embodiment, a BoNT/B light chain comprises a polypeptide having, e.g., at most one, two, three, four, five, six, seven, eight, nine, 10, 20, 30, 40, 50, 100 or 200 contiguous amino acid deletions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 contiguous amino acid deletions relative to amino acids 1-441 of SEQ ID NO: 2. In still other aspects of this embodiment, a BoNT/B light chain comprises a polypeptide having, e.g., at most one, two, three, four, five, six, seven, eight, nine, 10, 20, 30, 40, 50, 100 or 200 contiguous amino acid additions relative to amino acids 1-441 of SEQ ID NO: 2. In other aspects of this embodiment, a BoNT/B light chain comprises a polypeptide having, e.g., at least one, two, three, four, five, six, seven, eight, nine, 10, 20, 30, 40, 50, 100 or 200 contiguous amino acid additions relative to amino acids 1-441 of SEQ ID NO: 2.

In another embodiment, a Clostridial toxin enzymatic domain comprises a BoNT/C1 light chain. In an aspect of this embodiment, a BoNT/C1 light chain comprises amino acids 1-449 of SEQ ID NO: 3. In another aspect of this embodiment, a BoNT/C1 light chain comprises a naturally occurring BoNT/C1 light chain variant, such as, e.g., a light chain from a BoNT/C1 isoform or a light chain from a BoNT/C1 subtype. In another aspect of this embodiment, a BoNT/C1 light chain comprises amino acids 1-449 of a naturally occurring BoNT/C1 light chain variant of SEQ ID NO: 3, such as, e.g., amino acids 1-449 of a BoNT/C1 isoform of SEQ ID NO: 3 or amino acids 1-449 of a BoNT/C1 subtype of SEQ ID NO: 3. In still another aspect of this embodiment, a BoNT/C1 light chain comprises a non-naturally occurring BoNT/C1 light chain variant, such as, e.g., a conservative BoNT/C1 light chain variant, a non-conservative BoNT/C1 light chain variant, a BoNT/C1 chimeric light chain, an active BoNT/C1 light chain fragment, or any combination thereof. In still another aspect of this embodiment, a BoNT/C1 light chain comprises amino acids 1-449 of a non-naturally occurring BoNT/C1 light chain variant of SEQ ID NO: 3, such as, e.g., amino acids 1-449 of a conservative BoNT/C1 light chain variant of SEQ ID NO: 3, amino acids 1-449 of a non-conservative BoNT/C1 light chain variant of SEQ ID NO: 3, amino acids 1-449 of an active BoNT/C1 light chain fragment of SEQ ID NO: 3, or any combination thereof.

In other aspects of this embodiment, a BoNT/C1 light chain comprises a polypeptide having, e.g., at least 70% amino acid identity with amino acids 1-449 of SEQ ID NO: 3, at least 75% amino acid identity with amino acids 1-449 of SEQ ID NO: 3, at least 80% amino acid identity with amino acids 1-449 of SEQ ID NO: 3, at least 85% amino acid identity with amino acids 1-449 of SEQ ID NO: 3, at least 90% amino acid identity with amino acids 1-449 of SEQ ID NO: 3 or at least 95% amino acid identity with amino acids 1-449 of SEQ ID NO: 3. In yet other aspects of this embodiment, a BoNT/C1 light chain comprises a polypeptide having, e.g., at most 70% amino acid identity with amino acids 1-449 of SEQ ID NO: 3, at most 75% amino acid identity with amino acids 1-449 of SEQ ID NO: 3, at most 80% amino acid identity with amino acids 1-449 of SEQ ID NO: 3, at most 85% amino acid identity with amino acids 1-449 of SEQ ID NO: 3, at most 90% amino acid identity with amino acids 1-449 of SEQ ID NO: 3 or at most 95% amino acid identity with amino acids 1-449 of SEQ ID NO: 3.

In other aspects of this embodiment, a BoNT/C1 light chain comprises a polypeptide having, e.g., at most one, two, three, four, five, six, seven, eight, nine, 10, 20, 30, 40, 50, 100, or 200 non-contiguous amino acid substitutions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 non-contiguous amino acid substitutions relative to amino acids 1-449 of SEQ ID NO: 3. In yet other aspects of this embodiment, a BoNT/C1 light chain comprises a polypeptide having, e.g., at most one, two, three, four, five, six, seven, eight, nine, 10, 20, 30, 40, 50, 100 or 200 non-contiguous amino acid deletions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 non-contiguous amino acid deletions relative to amino acids 1-449 of SEQ ID NO: 3. In still other aspects of this embodiment, a BoNT/C1 light chain comprises a polypeptide having, e.g., at most one, two, three, four, five, six, seven, eight, nine, 10, 20, 30, 40, 50, 100 or 200 non-contiguous amino acid additions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 non-contiguous amino acid additions relative to amino acids 1-449 of SEQ ID NO: 3.

In other aspects of this embodiment, a BoNT/C1 light chain comprises a polypeptide having, e.g., at most one, two, three, four, five, six, seven, eight, nine, 10, 20, 30, 40, 50, 100 or 200 contiguous amino acid substitutions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 contiguous amino acid substitutions relative to amino acids 1-449 of SEQ ID NO: 3. In yet other aspects of this embodiment, a BoNT/C1 light chain comprises a polypeptide having, e.g., at most one, two, three, four, five, six, seven, eight, nine, 10, 20, 30, 40, 50, 100 or 200 contiguous amino acid deletions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 contiguous amino acid deletions relative to amino acids 1-449 of SEQ ID NO: 3. In still other aspects of this embodiment, a BoNT/C1 light chain comprises a polypeptide having, e.g., at most one, two, three, four, five, six, seven, eight, nine, 10, 20, 30, 40, 50, 100 or 200 contiguous amino acid additions relative to amino acids 1-449 of SEQ ID NO: 3. In other aspects of this embodiment, a BoNT/C1 light chain comprises a polypeptide having, e.g., at least one, two, three, four, five, six, seven, eight, nine, 10, 20, 30, 40, 50, 100 or 200 contiguous amino acid additions relative to amino acids 1-449 of SEQ ID NO: 3.

In another embodiment, a Clostridial toxin enzymatic domain comprises a BoNT/D light chain. In an aspect of this embodiment, a BoNT/D light chain comprises amino acids 1-445 of SEQ ID NO: 4. In another aspect of this embodiment, a BoNT/D light chain comprises a naturally occurring BoNT/D light chain variant, such as, e.g., a light chain from a BoNT/D isoform or a light chain from a BoNT/D subtype. In another aspect of this embodiment, a BoNT/D light chain comprises amino acids 1-445 of a naturally occurring BoNT/D light chain variant of SEQ ID NO: 4, such as, e.g., amino acids 1-445 of a BoNT/D isoform of SEQ ID NO: 4 or amino acids 1-445 of a BoNT/D subtype of SEQ ID NO: 4. In still another aspect of this embodiment, a BoNT/D light chain comprises a non-naturally occurring BoNT/D light chain variant, such as, e.g., a conservative BoNT/D light chain variant, a non-conservative BoNT/D light chain variant, a BoNT/D chimeric light chain, an active BoNT/D light chain fragment, or any combination thereof. In still another aspect of this embodiment, a BoNT/D light chain comprises amino acids 1-445 of a non-naturally occurring BoNT/D light chain variant of SEQ ID NO: 4, such as, e.g., amino acids 1-445 of a conservative BoNT/D light chain variant of SEQ ID NO: 4, amino acids 1-445 of a non-conservative BoNT/D light chain variant of SEQ ID NO: 4, amino acids 1-445 of an active BoNT/D light chain fragment of SEQ ID NO: 4, or any combination thereof.

In other aspects of this embodiment, a BoNT/D light chain comprises a polypeptide having, e.g., at least 70% amino acid identity with amino acids 1-445 of SEQ ID NO: 4, at least 75% amino acid identity with amino acids 1-445 of SEQ ID NO: 4, at least 80% amino acid identity with amino acids 1-445 of SEQ ID NO: 4, at least 85% amino acid identity with amino acids 1-445 of SEQ ID NO: 4, at least 90% amino acid identity with amino acids 1-445 of SEQ ID NO: 4 or at least 95% amino acid identity with amino acids 1-445 of SEQ ID NO: 4. In yet other aspects of this embodiment, a BoNT/D light chain comprises a polypeptide having, e.g., at most 70% amino acid identity with amino acids 1-445 of SEQ ID NO: 4, at most 75% amino acid identity with amino acids 1-445 of SEQ ID NO: 4, at most 80% amino acid identity with amino acids 1-445 of SEQ ID NO: 4, at most 85% amino acid identity with amino acids 1-445 of SEQ ID NO: 4, at most 90% amino acid identity with amino acids 1-445 of SEQ ID NO: 4 or at most 95% amino acid identity with amino acids 1-445 of SEQ ID NO: 4.

In other aspects of this embodiment, a BoNT/D light chain comprises a polypeptide having, e.g., at most one, two, three, four, five, six, seven, eight, nine, 10, 20, 30, 40, 50, 100, or 200 non-contiguous amino acid substitutions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 non-contiguous amino acid substitutions relative to amino acids 1-445 of SEQ ID NO: 4. In yet other aspects of this embodiment, a BoNT/D light chain comprises a polypeptide having, e.g., at most one, two, three, four, five, six, seven, eight, nine, 10, 20, 30, 40, 50, 100 or 200 non-contiguous amino acid deletions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 non-contiguous amino acid deletions relative to amino acids 1-445 of SEQ ID NO: 4. In still other aspects of this embodiment, a BoNT/D light chain comprises a polypeptide having, e.g., at most one, two, three, four, five, six, seven, eight, nine, 10, 20, 30, 40, 50, 100 or 200 non-contiguous amino acid additions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 non-contiguous amino acid additions relative to amino acids 1-445 of SEQ ID NO: 4.

In other aspects of this embodiment, a BoNT/D light chain comprises a polypeptide having, e.g., at most one, two, three, four, five, six, seven, eight, nine, 10, 20, 30, 40, 50, 100 or 200 contiguous amino acid substitutions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 contiguous amino acid substitutions relative to amino acids 1-445 of SEQ ID NO: 4. In yet other aspects of this embodiment, a BoNT/D light chain comprises a polypeptide having, e.g., at most one, two, three, four, five, six, seven, eight, nine, 10, 20, 30, 40, 50, 100 or 200 contiguous amino acid deletions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 contiguous amino acid deletions relative to amino acids 1-445 of SEQ ID NO: 4. In still other aspects of this embodiment, a BoNT/D light chain comprises a polypeptide having, e.g., at most one, two, three, four, five, six, seven, eight, nine, 10, 20, 30, 40, 50, 100 or 200 contiguous amino acid additions relative to amino acids 1-445 of SEQ ID NO: 4. In other aspects of this embodiment, a BoNT/D light chain comprises a polypeptide having, e.g., at least one, two, three, four, five, six, seven, eight, nine, 10, 20, 30, 40, 50, 100 or 200 contiguous amino acid additions relative to amino acids 1-445 of SEQ ID NO: 4.

In another embodiment, a Clostridial toxin enzymatic domain comprises a BoNT/E light chain. In an aspect of this embodiment, a BoNT/E light chain comprises amino acids 1-422 of SEQ ID NO: 5. In another aspect of this embodiment, a BoNT/E light chain comprises a naturally occurring BoNT/E light chain variant, such as, e.g., a light chain from a BoNT/E isoform or a light chain from a BoNT/E subtype. In another aspect of this embodiment, a BoNT/E light chain comprises amino acids 1-422 of a naturally occurring BoNT/E light chain variant of SEQ ID NO: 5, such as, e.g., amino acids 1-422 of a BoNT/E isoform of SEQ ID NO: 5 or amino acids 1-422 of a BoNT/E subtype of SEQ ID NO: 5. In still another aspect of this embodiment, a BoNT/E light chain comprises a non-naturally occurring BoNT/E light chain variant, such as, e.g., a conservative BoNT/E light chain variant, a non-conservative BoNT/E light chain variant, a BoNT/E chimeric light chain, an active BoNT/E light chain fragment, or any combination thereof. In still another aspect of this embodiment, a BoNT/E light chain comprises amino acids 1-422 of a non-naturally occurring BoNT/E light chain variant of SEQ ID NO: 5, such as, e.g., amino acids 1-422 of a conservative BoNT/E light chain variant of SEQ ID NO: 5, amino acids 1-422 of a non-conservative BoNT/E light chain variant of SEQ ID NO: 5, amino acids 1-422 of an active BoNT/E light chain fragment of SEQ ID NO: 5, or any combination thereof.

In other aspects of this embodiment, a BoNT/E light chain comprises a polypeptide having, e.g., at least 70% amino acid identity with amino acids 1-422 of SEQ ID NO: 5, at least 75% amino acid identity with amino acids 1-422 of SEQ ID NO: 5, at least 80% amino acid identity with amino acids 1-422 of SEQ ID NO: 5, at least 85% amino acid identity with amino acids 1-422 of SEQ ID NO: 5, at least 90% amino acid identity with amino acids 1-422 of SEQ ID NO: 5 or at least 95% amino acid identity with amino acids 1-422 of SEQ ID NO: 5. In yet other aspects of this embodiment, a BoNT/E light chain comprises a polypeptide having, e.g., at most 70% amino acid identity with amino acids 1-422 of SEQ ID NO: 5, at most 75% amino acid identity with amino acids 1-422 of SEQ ID NO: 5, at most 80% amino acid identity with amino acids 1-422 of SEQ ID NO: 5, at most 85% amino acid identity with amino acids 1-422 of SEQ ID NO: 5, at most 90% amino acid identity with amino acids 1-422 of SEQ ID NO: 5 or at most 95% amino acid identity with amino acids 1-422 of SEQ ID NO: 5.

In other aspects of this embodiment, a BoNT/E light chain comprises a polypeptide having, e.g., at most one, two, three, four, five, six, seven, eight, nine, 10, 20, 30, 40, 50, 100, or 200 non-contiguous amino acid substitutions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 non-contiguous amino acid substitutions relative to amino acids 1-422 of SEQ ID NO: 5. In yet other aspects of this embodiment, a BoNT/E light chain comprises a polypeptide having, e.g., at most one, two, three, four, five, six, seven, eight, nine, 10, 20, 30, 40, 50, 100 or 200 non-contiguous amino acid deletions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 non-contiguous amino acid deletions relative to amino acids 1-422 of SEQ ID NO: 5. In still other aspects of this embodiment, a BoNT/E light chain comprises a polypeptide having, e.g., at most one, two, three, four, five, six, seven, eight, nine, 10, 20, 30, 40, 50, 100 or 200 non-contiguous amino acid additions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 non-contiguous amino acid additions relative to amino acids 1-422 of SEQ ID NO: 5.

In other aspects of this embodiment, a BoNT/E light chain comprises a polypeptide having, e.g., at most one, two, three, four, five, six, seven, eight, nine, 10, 20, 30, 40, 50, 100 or 200 contiguous amino acid substitutions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 contiguous amino acid substitutions relative to amino acids 1-422 of SEQ ID NO: 5. In yet other aspects of this embodiment, a BoNT/E light chain comprises a polypeptide having, e.g., at most one, two, three, four, five, six, seven, eight, nine, 10, 20, 30, 40, 50, 100 or 200 contiguous amino acid deletions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 contiguous amino acid deletions relative to amino acids 1-422 of SEQ ID NO: 5. In still other aspects of this embodiment, a BoNT/E light chain comprises a polypeptide having, e.g., at most one, two, three, four, five, six, seven, eight, nine, 10, 20, 30, 40, 50, 100 or 200 contiguous amino acid additions relative to amino acids 1-422 of SEQ ID NO: 5. In other aspects of this embodiment, a BoNT/E light chain comprises a polypeptide having, e.g., at least one, two, three, four, five, six, seven, eight, nine, 10, 20, 30, 40, 50, 100 or 200 contiguous amino acid additions relative to amino acids 1-422 of SEQ ID NO: 5.

In another embodiment, a Clostridial toxin enzymatic domain comprises a BoNT/F light chain. In an aspect of this embodiment, a BoNT/F light chain comprises amino acids 1-439 of SEQ ID NO: 6. In another aspect of this embodiment, a BoNT/F light chain comprises a naturally occurring BoNT/F light chain variant, such as, e.g., a light chain from a BoNT/F isoform or a light chain from a BoNT/F subtype. In another aspect of this embodiment, a BoNT/F light chain comprises amino acids 1-439 of a naturally occurring BoNT/F light chain variant of SEQ ID NO: 6, such as, e.g., amino acids 1-439 of a BoNT/F isoform of SEQ ID NO: 6 or amino acids 1-439 of a BoNT/F subtype of SEQ ID NO: 6. In still another aspect of this embodiment, a BoNT/F light chain comprises a non-naturally occurring BoNT/F light chain variant, such as, e.g., a conservative BoNT/F light chain variant, a non-conservative BoNT/F light chain variant, a BoNT/F chimeric light chain, an active BoNT/F light chain fragment, or any combination thereof. In still another aspect of this embodiment, a BoNT/F light chain comprises amino acids 1-439 of a non-naturally occurring BoNT/F light chain variant of SEQ ID NO: 6, such as, e.g., amino acids 1-439 of a conservative BoNT/F light chain variant of SEQ ID NO: 6, amino acids 1-439 of a non-conservative BoNT/F light chain variant of SEQ ID NO: 6, amino acids 1-439 of an active BoNT/F light chain fragment of SEQ ID NO: 6, or any combination thereof.

In other aspects of this embodiment, a BoNT/F light chain comprises a polypeptide having, e.g., at least 70% amino acid identity with amino acids 1-439 of SEQ ID NO: 6, at least 75% amino acid identity with amino acids 1-439 of SEQ ID NO: 6, at least 80% amino acid identity with amino acids 1-439 of SEQ ID NO: 6, at least 85% amino acid identity with amino acids 1-439 of SEQ ID NO: 6, at least 90% amino acid identity with amino acids 1-439 of SEQ ID NO: 6 or at least 95% amino acid identity with amino acids 1-439 of SEQ ID NO: 6. In yet other aspects of this embodiment, a BoNT/F light chain comprises a polypeptide having, e.g., at most 70% amino acid identity with amino acids 1-439 of SEQ ID NO: 6, at most 75% amino acid identity with amino acids 1-439 of SEQ ID NO: 6, at most 80% amino acid identity with amino acids 1-439 of SEQ ID NO: 6, at most 85% amino acid identity with amino acids 1-439 of SEQ ID NO: 6, at most 90% amino acid identity with amino acids 1-439 of SEQ ID NO: 6 or at most 95% amino acid identity with amino acids 1-439 of SEQ ID NO: 6.

In other aspects of this embodiment, a BoNT/F light chain comprises a polypeptide having, e.g., at most one, two, three, four, five, six, seven, eight, nine, 10, 20, 30, 40, 50, 100, or 200 non-contiguous amino acid substitutions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 non-contiguous amino acid substitutions relative to amino acids 1-439 of SEQ ID NO: 6. In yet other aspects of this embodiment, a BoNT/F light chain comprises a polypeptide having, e.g., at most one, two, three, four, five, six, seven, eight, nine, 10, 20, 30, 40, 50, 100 or 200 non-contiguous amino acid deletions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 non-contiguous amino acid deletions relative to amino acids 1-439 of SEQ ID NO: 6. In still other aspects of this embodiment, a BoNT/F light chain comprises a polypeptide having, e.g., at most one, two, three, four, five, six, seven, eight, nine, 10, 20, 30, 40, 50, 100 or 200 non-contiguous amino acid additions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 non-contiguous amino acid additions relative to amino acids 1-439 of SEQ ID NO: 6.

In other aspects of this embodiment, a BoNT/F light chain comprises a polypeptide having, e.g., at most one, two, three, four, five, six, seven, eight, nine, 10, 20, 30, 40, 50, 100 or 200 contiguous amino acid substitutions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 contiguous amino acid substitutions relative to amino acids 1-439 of SEQ ID NO: 6. In yet other aspects of this embodiment, a BoNT/F light chain comprises a polypeptide having, e.g., at most one, two, three, four, five, six, seven, eight, nine, 10, 20, 30, 40, 50, 100 or 200 contiguous amino acid deletions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 contiguous amino acid deletions relative to amino acids 1-439 of SEQ ID NO: 6. In still other aspects of this embodiment, a BoNT/F light chain comprises a polypeptide having, e.g., at most one, two, three, four, five, six, seven, eight, nine, 10, 20, 30, 40, 50, 100 or 200 contiguous amino acid additions relative to amino acids 1-439 of SEQ ID NO: 6. In other aspects of this embodiment, a BoNT/F light chain comprises a polypeptide having, e.g., at least one, two, three, four, five, six, seven, eight, nine, 10, 20, 30, 40, 50, 100 or 200 contiguous amino acid additions relative to amino acids 1-439 of SEQ ID NO: 6.

In another embodiment, a Clostridial toxin enzymatic domain comprises a BoNT/G light chain. In an aspect of this embodiment, a BoNT/G light chain comprises amino acids 1-446 of SEQ ID NO: 7. In another aspect of this embodiment, a BoNT/G light chain comprises a naturally occurring BoNT/G light chain variant, such as, e.g., a light chain from a BoNT/G isoform or a light chain from a BoNT/G subtype. In another aspect of this embodiment, a BoNT/G light chain comprises amino acids 1-446 of a naturally occurring BoNT/G light chain variant of SEQ ID NO: 7, such as, e.g., amino acids 1-446 of a BoNT/G isoform of SEQ ID NO: 7 or amino acids 1-446 of a BoNT/G subtype of SEQ ID NO: 7. In still another aspect of this embodiment, a BoNT/G light chain comprises a non-naturally occurring BoNT/G light chain variant, such as, e.g., a conservative BoNT/G light chain variant, a non-conservative BoNT/G light chain variant, a BoNT/G chimeric light chain, an active BoNT/G light chain fragment, or any combination thereof. In still another aspect of this embodiment, a BoNT/G light chain comprises amino acids 1-446 of a non-naturally occurring BoNT/G light chain variant of SEQ ID NO: 7, such as, e.g., amino acids 1-446 of a conservative BoNT/G light chain variant of SEQ ID NO: 7, amino acids 1-446 of a non-conservative BoNT/G light chain variant of SEQ ID NO: 7, amino acids 1-446 of an active BoNT/G light chain fragment of SEQ ID NO: 7, or any combination thereof.

In other aspects of this embodiment, a BoNT/G light chain comprises a polypeptide having, e.g., at least 70% amino acid identity with amino acids 1-446 of SEQ ID NO: 7, at least 75% amino acid identity with amino acids 1-446 of SEQ ID NO: 7, at least 80% amino acid identity with amino acids 1-446 of SEQ ID NO: 7, at least 85% amino acid identity with amino acids 1-446 of SEQ ID NO: 7, at least 90% amino acid identity with amino acids 1-446 of SEQ ID NO: 7 or at least 95% amino acid identity with amino acids 1-446 of SEQ ID NO: 7. In yet other aspects of this embodiment, a BoNT/G light chain comprises a polypeptide having, e.g., at most 70% amino acid identity with amino acids 1-446 of SEQ ID NO: 7, at most 75% amino acid identity with amino acids 1-446 of SEQ ID NO: 7, at most 80% amino acid identity with amino acids 1-446 of SEQ ID NO: 7, at most 85% amino acid identity with amino acids 1-446 of SEQ ID NO: 7, at most 90% amino acid identity with amino acids 1-446 of SEQ ID NO: 7 or at most 95% amino acid identity with amino acids 1-446 of SEQ ID NO: 7.

In other aspects of this embodiment, a BoNT/G light chain comprises a polypeptide having, e.g., at most one, two, three, four, five, six, seven, eight, nine, 10, 20, 30, 40, 50, 100, or 200 non-contiguous amino acid substitutions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 non-contiguous amino acid substitutions relative to amino acids 1-446 of SEQ ID NO: 7. In yet other aspects of this embodiment, a BoNT/G light chain comprises a polypeptide having, e.g., at most one, two, three, four, five, six, seven, eight, nine, 10, 20, 30, 40, 50, 100 or 200 non-contiguous amino acid deletions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 non-contiguous amino acid deletions relative to amino acids 1-446 of SEQ ID NO: 7. In still other aspects of this embodiment, a BoNT/G light chain comprises a polypeptide having, e.g., at most one, two, three, four, five, six, seven, eight, nine, 10, 20, 30, 40, 50, 100 or 200 non-contiguous amino acid additions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 non-contiguous amino acid additions relative to amino acids 1-446 of SEQ ID NO: 7.

In other aspects of this embodiment, a BoNT/G light chain comprises a polypeptide having, e.g., at most one, two, three, four, five, six, seven, eight, nine, 10, 20, 30, 40, 50, 100 or 200 contiguous amino acid substitutions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 contiguous amino acid substitutions relative to amino acids 1-446 of SEQ ID NO: 7. In yet other aspects of this embodiment, a BoNT/G light chain comprises a polypeptide having, e.g., at most one, two, three, four, five, six, seven, eight, nine, 10, 20, 30, 40, 50, 100 or 200 contiguous amino acid deletions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 contiguous amino acid deletions relative to amino acids 1-446 of SEQ ID NO: 7. In still other aspects of this embodiment, a BoNT/G light chain comprises a polypeptide having, e.g., at most one, two, three, four, five, six, seven, eight, nine, 10, 20, 30, 40, 50, 100 or 200 contiguous amino acid additions relative to amino acids 1-446 of SEQ ID NO: 7. In other aspects of this embodiment, a BoNT/G light chain comprises a polypeptide having, e.g., at least one, two, three, four, five, six, seven, eight, nine, 10, 20, 30, 40, 50, 100 or 200 contiguous amino acid additions relative to amino acids 1-446 of SEQ ID NO: 7.

In another embodiment, a Clostridial toxin enzymatic domain comprises a TeNT light chain. In an aspect of this embodiment, a TeNT light chain comprises amino acids 1-457 of SEQ ID NO: 8. In another aspect of this embodiment, a TeNT light chain comprises a naturally occurring TeNT light chain variant, such as, e.g., a light chain from a TeNT isoform or a light chain from a TeNT subtype. In another aspect of this embodiment, a TeNT light chain comprises amino acids 1-457 of a naturally occurring TeNT light chain variant of SEQ ID NO: 8, such as, e.g., amino acids 1-457 of a TeNT isoform of SEQ ID NO: 8 or amino acids 1-457 of a TeNT subtype of SEQ ID NO: 8. In still another aspect of this embodiment, a TeNT light chain comprises a non-naturally occurring TeNT light chain variant, such as, e.g., a conservative TeNT light chain variant, a non-conservative TeNT light chain variant, a TeNT chimeric light chain, an active TeNT light chain fragment, or any combination thereof. In still another aspect of this embodiment, a TeNT light chain comprises amino acids 1-457 of a non-naturally occurring TeNT light chain variant of SEQ ID NO: 8, such as, e.g., amino acids 1-457 of a conservative TeNT light chain variant of SEQ ID NO: 8, amino acids 1-457 of a non-conservative TeNT light chain variant of SEQ ID NO: 8, amino acids 1-457 of an active TeNT light chain fragment of SEQ ID NO: 8, or any combination thereof.

In other aspects of this embodiment, a TeNT light chain comprises a polypeptide having, e.g., at least 70% amino acid identity with amino acids 1-457 of SEQ ID NO: 8, at least 75% amino acid identity with amino acids 1-457 of SEQ ID NO: 8, at least 80% amino acid identity with amino acids 1-457 of SEQ ID NO: 8, at least 85% amino acid identity with amino acids 1-457 of SEQ ID NO: 8, at least 90% amino acid identity with amino acids 1-457 of SEQ ID NO: 8 or at least 95% amino acid identity with amino acids 1-457 of SEQ ID NO: 8. In yet other aspects of this embodiment, a TeNT light chain comprises a polypeptide having, e.g., at most 70% amino acid identity with amino acids 1-457 of SEQ ID NO: 8, at most 75% amino acid identity with amino acids 1-457 of SEQ ID NO: 8, at most 80% amino acid identity with amino acids 1-457 of SEQ ID NO: 8, at most 85% amino acid identity with amino acids 1-457 of SEQ ID NO: 8, at most 90% amino acid identity with amino acids 1-457 of SEQ ID NO: 8 or at most 95% amino acid identity with amino acids 1-457 of SEQ ID NO: 8.

In other aspects of this embodiment, a TeNT light chain comprises a polypeptide having, e.g., at most one, two, three, four, five, six, seven, eight, nine, 10, 20, 30, 40, 50, 100, or 200 non-contiguous amino acid substitutions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 non-contiguous amino acid substitutions relative to amino acids 1-457 of SEQ ID NO: 8. In yet other aspects of this embodiment, a TeNT light chain comprises a polypeptide having, e.g., at most one, two, three, four, five, six, seven, eight, nine, 10, 20, 30, 40, 50, 100 or 200 non-contiguous amino acid deletions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 non-contiguous amino acid deletions relative to amino acids 1-457 of SEQ ID NO: 8. In still other aspects of this embodiment, a TeNT light chain comprises a polypeptide having, e.g., at most one, two, three, four, five, six, seven, eight, nine, 10, 20, 30, 40, 50, 100 or 200 non-contiguous amino acid additions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 non-contiguous amino acid additions relative to amino acids 1-457 of SEQ ID NO: 8.

In other aspects of this embodiment, a TeNT light chain comprises a polypeptide having, e.g., at most one, two, three, four, five, six, seven, eight, nine, 10, 20, 30, 40, 50, 100 or 200 contiguous amino acid substitutions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 contiguous amino acid substitutions relative to amino acids 1-457 of SEQ ID NO: 8. In yet other aspects of this embodiment, a TeNT light chain comprises a polypeptide having, e.g., at most one, two, three, four, five, six, seven, eight, nine, 10, 20, 30, 40, 50, 100 or 200 contiguous amino acid deletions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 contiguous amino acid deletions relative to amino acids 1-457 of SEQ ID NO: 8. In still other aspects of this embodiment, a TeNT light chain comprises a polypeptide having, e.g., at most one, two, three, four, five, six, seven, eight, nine, 10, 20, 30, 40, 50, 100 or 200 contiguous amino acid additions relative to amino acids 1-457 of SEQ ID NO: 8. In other aspects of this embodiment, a TeNT light chain comprises a polypeptide having, e.g., at least one, two, three, four, five, six, seven, eight, nine, 10, 20, 30, 40, 50, 100 or 200 contiguous amino acid additions relative to amino acids 1-457 of SEQ ID NO: 8.

Aspects of the present invention provide, in part, a Clostridial toxin translocation domain. As used herein, the term "Clostridial toxin translocation domain" means any Clostridial toxin polypeptide that can execute the translocation step of the intoxication process that mediates Clostridial toxin light chain translocation. Thus, a Clostridial toxin translocation domain facilitates the movement of a Clostridial toxin light chain across a membrane and encompasses the movement of a Clostridial toxin light chain through the membrane an intracellular vesicle into the cytoplasm of a cell. Non-limiting examples of a Clostridial toxin translocation domain include, e.g., a Clostridial toxin $H_N$ region such as, e.g., a BoNT/A $H_N$ region, a BoNT/B $H_N$ region, a BoNT/C1 $H_N$ region, a BoNT/D $H_N$ region, a BoNT/E $H_N$ region, a BoNT/F $H_N$ region, a BoNT/G $H_N$ region, and a TeNT $H_N$ region.

A Clostridial toxin translocation domain includes, without limitation, naturally occurring Clostridial toxin $H_N$ region variants, such as, e.g., Clostridial toxin $H_N$ region isoforms and Clostridial toxin $H_N$ region subtypes; non-naturally occurring Clostridial toxin $H_N$ region variants, such as, e.g., conservative Clostridial toxin $H_N$ region variants, non-conservative Clostridial toxin $H_N$ region variants, Clostridial toxin $H_N$ region chimerics, active Clostridial toxin $H_N$ region fragments thereof, or any combination thereof.

As used herein, the term "Clostridial toxin $H_N$ region variant," whether naturally-occurring or non-naturally-occurring, means a Clostridial toxin $H_N$ region that has at least one amino acid change from the corresponding region of the disclosed reference sequences (see Table 1) and can be described in percent identity to the corresponding region of that reference sequence. Unless expressly indicated, all Clostridial toxin $H_N$ region variants disclosed in the present specification are capable of executing the translocation step of the intoxication process that mediates Clostridial toxin light chain translocation. As non-limiting examples, a BoNT/A $H_N$ region variant comprising amino acids 449-871 of SEQ ID NO: 1 will have at least one amino acid difference, such as, e.g., an amino acid substitution, deletion or addition, as compared to the amino acid region 449-871 of SEQ ID NO: 1; a BoNT/B $H_N$ region variant comprising amino acids 442-858 of SEQ ID NO: 2 will have at least one amino acid difference, such as, e.g., an amino acid substitution, deletion or addition, as compared to the amino acid region 442-858 of SEQ ID NO: 2; a BoNT/C1 $H_N$ region variant comprising amino acids 450-866 of SEQ ID NO: 3 will have at least one amino acid difference, such as, e.g., an amino acid substitution, deletion or addition, as compared to the amino acid region 450-866 of SEQ ID NO: 3; a BoNT/D $H_N$ region variant comprising amino acids 446-862 of SEQ ID NO: 4 will have at least one amino acid difference, such as, e.g., an amino acid substitution, deletion or addition, as compared to the amino acid region 446-862 of SEQ ID NO: 4; a BoNT/E $H_N$ region variant comprising amino acids 423-845 of SEQ ID NO: 5 will have at least one amino acid difference, such as, e.g., an amino acid substitution, deletion or addition, as compared to the amino acid region 423-845 of SEQ ID NO: 5; a BoNT/F $H_N$ region variant comprising amino acids 440-864 of SEQ ID NO: 6 will have at least one amino acid difference, such as, e.g., an amino acid substitution, deletion or addition, as compared to the amino acid region 440-864 of SEQ ID NO: 6; a BoNT/G $H_N$ region variant comprising amino acids 447-863 of SEQ ID NO: 7 will have at least one amino acid difference, such as, e.g., an amino acid substitution, deletion or addition, as compared to the amino acid region 447-863 of SEQ ID NO: 7; and a TeNT $H_N$ region variant comprising amino acids 458-879 of SEQ ID NO: 8 will have at least one amino acid difference, such as, e.g., an amino acid substitution, deletion or addition, as compared to the amino acid region 458-879 of SEQ ID NO: 8.

It is recognized by those of skill in the art that within each serotype of Clostridial toxin there can be naturally occurring Clostridial toxin $H_N$ region variants that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific $H_N$ region subtypes showing approximately 87% amino acid identity when compared to another BoNT/A $H_N$ region subtype. As used herein, the term "naturally occurring Clostridial toxin $H_N$ region variant" means any Clostridial toxin $H_N$ region produced by a naturally-occurring process, including, without limitation, Clostridial toxin $H_N$ region isoforms produced from alternatively-spliced transcripts, Clostridial toxin $H_N$ region isoforms produced by spontaneous mutation and Clostridial toxin $H_N$ region subtypes. A naturally occurring Clostridial toxin $H_N$ region variant can function in substantially the same manner as the reference Clostridial toxin $H_N$ region on which the naturally occurring Clostridial toxin $H_N$ region variant is based, and can be substituted for the reference Clostridial toxin $H_N$ region in any aspect of the present invention. A naturally occurring Clostridial toxin $H_N$ region variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial toxin $H_N$ region on which the naturally occurring Clostridial toxin $H_N$ region variant is based. A naturally occurring Clostridial toxin $H_N$ region variant can also substitute at least 10 contiguous amino acids, at least 15 contiguous amino acids, at least 20 contiguous amino acids, or at least 25 contiguous amino acids from the reference Clostridial toxin $H_N$ region on which the naturally occurring Clostridial toxin $H_N$ region variant is based, that possess at least 50% amino acid identity, 65% amino acid identity, 75% amino acid identity, 85% amino acid identity or 95% amino acid identity to the reference Clostridial toxin $H_N$ region on which the naturally occurring Clostridial toxin $H_N$ region variant is based.

A non-limiting examples of a naturally occurring Clostridial toxin $H_N$ region variant is a Clostridial toxin $H_N$ region isoform such as, e.g., a BoNT/A $H_N$ region isoform, a BoNT/B $H_N$ region isoform, a BoNT/C1 $H_N$ region isoform, a BoNT/D $H_N$ region isoform, a BoNT/E $H_N$ region isoform, a BoNT/F $H_N$ region isoform, a BoNT/G $H_N$ region isoform, and a TeNT $H_N$ region isoform. A Clostridial toxin $H_N$ region isoform can function in substantially the same manner as the reference Clostridial toxin $H_N$ region on which the Clostridial toxin $H_N$ region isoform is based, and can be substituted for the reference Clostridial toxin $H_N$ region in any aspect of the present invention.

Another non-limiting examples of a naturally occurring Clostridial toxin $H_N$ region variant is a Clostridial toxin $H_N$ region subtype such as, e.g., a $H_N$ region from subtype BoNT/A1, BoNT/A2, BoNT/A3 and BoNT/A4; a $H_N$ region from subtype BoNT/B1, BoNT/B2, BoNT/B bivalent and BoNT/B nonproteolytic; a $H_N$ region from subtype BoNT/C1-1 and BoNT/C1-2; a $H_N$ region from subtype BoNT/E1, BoNT/E2 and BoNT/E3; and a $H_N$ region from subtype BoNT/F1, BoNT/F2, BoNT/F3 and BoNT/F4. A Clostridial toxin $H_N$ region subtype can function in substantially the same manner as the reference Clostridial toxin $H_N$ region on which the Clostridial toxin $H_N$ region subtype is based, and can be substituted for the reference Clostridial toxin $H_N$ region in any aspect of the present invention.

As used herein, the term "non-naturally occurring Clostridial toxin $H_N$ region variant" means any Clostridial toxin $H_N$ region produced with the aid of human manipulation, including, without limitation, Clostridial toxin $H_N$ regions produced by genetic engineering using random mutagenesis or rational design and Clostridial toxin $H_N$ regions produced by chemical synthesis. Non-limiting examples of non-naturally occurring Clostridial toxin $H_N$ region variants include, e.g., conservative Clostridial toxin $H_N$ region variants, non-conservative Clostridial toxin $H_N$ region variants, Clostridial toxin $H_N$ region chimeric variants and active Clostridial toxin $H_N$ region fragments.

As used herein, the term "conservative Clostridial toxin $H_N$ region variant" means a Clostridial toxin $H_N$ region that has at least one amino acid substituted by another amino acid or an amino acid analog that has at least one property similar to that of the original amino acid from the reference Clostridial toxin $H_N$ region sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin $H_N$ region variant can function in substantially the same manner as the reference Clostridial toxin $H_N$ region on which the conservative Clostridial toxin $H_N$ region variant is based, and can be substituted for the reference Clostridial toxin $H_N$ region in any aspect of the present invention. A conservative Clostridial toxin $H_N$ region variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin $H_N$ region on which the conservative Clostridial toxin $H_N$ region variant is based. A conservative Clostridial toxin $H_N$ region variant can also substitute at least 10 contiguous amino acids, at least 15 contiguous amino acids, at least 20 contiguous amino acids, or at least 25 contiguous amino acids from the reference Clostridial toxin $H_N$ region on which the conservative Clostridial toxin $H_N$ region variant is based, that possess at least 50% amino acid identity, 65% amino acid identity, 75% amino acid identity, 85% amino acid identity or 95% amino acid identity to the reference Clostridial toxin $H_N$ region on which the conservative Clostridial toxin $H_N$ region variant is based. Non-limiting examples of a conservative Clostridial toxin $H_N$ region variant include, e.g., conservative BoNT/A $H_N$ region variants, conservative BoNT/B $H_N$ region variants, conservative BoNT/C1 $H_N$ region variants, conservative BoNT/D $H_N$ region variants, conservative BoNT/E $H_N$ region variants, conservative BoNT/F $H_N$ region variants, conservative BoNT/G $H_N$ region variants, and conservative TeNT $H_N$ region variants.

As used herein, the term "non-conservative Clostridial toxin $H_N$ region variant" means a Clostridial toxin $H_N$ region in which 1) at least one amino acid is deleted from the reference Clostridial toxin $H_N$ region on which the non-conservative Clostridial toxin $H_N$ region variant is based; 2) at least one amino acid added to the reference Clostridial toxin $H_N$ region on which the non-conservative Clostridial toxin $H_N$ region is based; or 3) at least one amino acid is substituted by another amino acid or an amino acid analog that does not share any property similar to that of the original amino acid from the reference Clostridial toxin $H_N$ region sequence (Table 1). A non-conservative Clostridial toxin $H_N$ region variant can function in substantially the same manner as the reference Clostridial toxin $H_N$ region on which the non-conservative Clostridial toxin $H_N$ region variant is based, and can be substituted for the reference Clostridial toxin $H_N$ region in any aspect of the present invention. A non-conservative Clostridial toxin $H_N$ region variant can delete one or more amino acids, two or more amino acids, three or more amino acids, four or more amino acids, five or more amino acids, and ten or more amino acids from the reference Clostridial toxin $H_N$ region on which the non-conservative Clostridial toxin $H_N$ region variant is based. A non-conservative Clostridial toxin $H_N$ region variant can add one or more amino acids, two or more amino acids, three or more amino acids, four or more amino acids, five or more amino acids, and ten or more amino acids to the reference Clostridial toxin $H_N$ region on which the non-conservative Clostridial toxin $H_N$ region variant is based. A non-conservative Clostridial toxin $H_N$ region variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin $H_N$ region on which the non-conservative Clostridial toxin $H_N$ region variant is based. A non-conservative Clostridial toxin $H_N$ region variant can also substitute at least 10 contiguous amino acids, at least 15 contiguous amino acids, at least 20 contiguous amino acids, or at least 25 contiguous amino acids from the reference Clostridial toxin $H_N$ region on which the non-conservative Clostridial toxin $H_N$ region variant is based, that possess at least 50% amino acid identity, 65% amino acid identity, 75% amino acid identity, 85% amino acid identity or 95% amino acid identity to the reference Clostridial toxin $H_N$ region on which the non-conservative Clostridial toxin $H_N$ region variant is based. Non-limiting examples of a non-conservative Clostridial toxin $H_N$ region variant include, e.g., non-conservative BoNT/A $H_N$ region variants, non-conservative BoNT/B $H_N$ region variants, non-conservative BoNT/C1 $H_N$ region variants, non-conservative BoNT/D $H_N$ region variants, non-conservative BoNT/E $H_N$ region variants, non-conservative BoNT/F $H_N$ region variants, non-conservative BoNT/G $H_N$ region variants, and non-conservative TeNT $H_N$ region variants.

As used herein, the term "Clostridial toxin $H_N$ region chimeric" means a polypeptide comprising at least a portion of a Clostridial toxin $H_N$ region and at least a portion of at least one other polypeptide to form a toxin $H_N$ region with at least one property different from the reference Clostridial toxin $H_N$ regions of Table 1, with the proviso that this Clostridial toxin $H_N$ region chimeric is still capable of specifically targeting the core components of the neurotransmitter release apparatus and thus participate in executing the overall cellular mechanism whereby a Clostridial toxin proteolytically cleaves a substrate.

As used herein, the term "active Clostridial toxin $H_N$ region fragment" means any of a variety of Clostridial toxin fragments comprising the $H_N$ region can be useful in aspects of the present invention with the proviso that these active fragments can facilitate the release of the LC from intracellular vesicles into the cytoplasm of the target cell and thus participate in executing the overall cellular mechanism whereby a Clostridial toxin proteolytically cleaves a substrate. The $H_N$ regions from the heavy chains of Clostridial toxins are approximately 410-430 amino acids in length and comprise a translocation domain (Table 1). Research has shown that the entire length of a $H_N$ region from a Clostridial toxin heavy chain is not necessary for the translocating activity of the translocation domain. Thus, aspects of this embodiment can include Clostridial toxin $H_N$ regions comprising a translocation domain having a length of, e.g., at least 350 amino acids, at least 375 amino acids, at least 400 amino acids and at least 425 amino acids. Other aspects of this embodiment can include Clostridial toxin $H_N$ regions comprising translocation domain having a length of, e.g., at most 350 amino acids, at most 375 amino acids, at most 400 amino acids and at most 425 amino acids.

Any of a variety of sequence alignment methods can be used to determine percent identity of naturally-occurring Clostridial toxin $H_N$ region variants and non-naturally-occurring Clostridial toxin $H_N$ region variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a modified Clostridial toxin disclosed in the present specification comprises a Clostridial toxin translocation domain. In an aspect of this embodiment, a Clostridial toxin translocation domain comprises a naturally occurring Clostridial toxin $H_N$ region variant, such as, e.g., a Clostridial toxin $H_N$ region isoform or a Clostridial toxin $H_N$ region subtype. In another aspect of this embodiment, a Clostridial toxin translocation domain comprises a non-naturally occurring Clostridial toxin $H_N$ region variant, such as, e.g., a conservative Clostridial toxin $H_N$ region variant, a non-conservative Clostridial toxin $H_N$ region variant, a Clostridial toxin chimeric $H_N$ region, an active Clostridial toxin $H_N$ region fragment, or any combination thereof.

In another embodiment, a Clostridial toxin translocation domain comprises a BoNT/A $H_N$ region. In an aspect of this embodiment, a BoNT/A $H_N$ region comprises amino acids 449-871 of SEQ ID NO: 1. In another aspect of this embodiment, a BoNT/A $H_N$ region comprises a naturally occurring BoNT/A $H_N$ region variant, such as, e.g., a $H_N$ region from a BoNT/A isoform or a $H_N$ region from a BoNT/A subtype. In another aspect of this embodiment, a BoNT/A $H_N$ region comprises amino acids 449-871 of a naturally occurring BoNT/A $H_N$ region variant of SEQ ID NO: 1, such as, e.g., amino acids 449-871 of a BoNT/A isoform of SEQ ID NO: 1 or amino acids 449-871 of a BoNT/A subtype of SEQ ID NO: 1. In still another aspect of this embodiment, a BoNT/A $H_N$ region comprises a non-naturally occurring BoNT/A $H_N$ region variant, such as, e.g., a conservative BoNT/A $H_N$ region variant, a non-conservative BoNT/A $H_N$ region variant, a BoNT/A chimeric $H_N$ region, an active BoNT/A $H_N$ region fragment, or any combination thereof. In still another aspect of this embodiment, a BoNT/A $H_N$ region comprises amino acids 449-871 of a non-naturally occurring BoNT/A $H_N$ region variant of SEQ ID NO: 1, such as, e.g., amino acids 449-871 of a conservative BoNT/A $H_N$ region variant of SEQ ID NO: 1, amino acids 449-871 of a non-conservative BoNT/A $H_N$ region variant of SEQ ID NO: 1, amino acids 449-871 of an active BoNT/A $H_N$ region fragment of SEQ ID NO: 1, or any combination thereof.

In other aspects of this embodiment, a BoNT/A $H_N$ region comprises a polypeptide having, e.g., at least 70% amino acid identity with amino acids 449-871 of SEQ ID NO: 1, at least 75% amino acid identity with amino acids 449-871 of SEQ ID NO: 1, at least 80% amino acid identity with amino acids 449-871 of SEQ ID NO: 1, at least 85% amino acid identity with amino acids 449-871 of SEQ ID NO: 1, at least 90% amino acid identity with amino acids 449-871 of SEQ ID NO: 1 or at least 95% amino acid identity with amino acids 449-871 of SEQ ID NO: 1. In yet other aspects of this embodiment, a BoNT/A $H_N$ region comprises a polypeptide having, e.g., at most 70% amino acid identity with amino acids 449-871 of SEQ ID NO: 1, at most 75% amino acid identity with amino acids 449-871 of SEQ ID NO: 1, at most 80% amino acid identity with amino acids 449-871 of SEQ ID NO: 1, at most 85% amino acid identity with amino acids 449-871 of SEQ ID NO: 1, at most 90% amino acid identity with amino acids 449-871 of SEQ ID NO: 1 or at most 95% amino acid identity with amino acids 449-871 of SEQ ID NO: 1.

In other aspects of this embodiment, a BoNT/A $H_N$ region comprises a polypeptide having, e.g., at most one, two, three, four, five, six, seven, eight, nine, 10, 20, 30, 40, 50, 100, or 200 non-contiguous amino acid substitutions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 non-contiguous amino acid substitutions relative to amino acids 449-871 of SEQ ID NO: 1. In yet other aspects of this embodiment, a BoNT/A $H_N$ region comprises a polypeptide having, e.g., at most one, two, three, four, five, six, seven, eight, nine, 10, 20, 30, 40, 50, 100 or 200 non-contiguous amino acid deletions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 non-contiguous amino acid deletions relative to amino acids 449-871 of SEQ ID NO: 1. In still other aspects of this embodiment, a BoNT/A $H_N$ region comprises a polypeptide having, e.g., at most one, two, three, four, five, six, seven, eight, nine, 10, 20, 30, 40, 50, 100 or 200 non-contiguous amino acid additions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 non-contiguous amino acid additions relative to amino acids 449-871 of SEQ ID NO: 1.

In other aspects of this embodiment, a BoNT/A $H_N$ region comprises a polypeptide having, e.g., at most one, two, three, four, five, six, seven, eight, nine, 10, 20, 30, 40, 50, 100 or 200 contiguous amino acid substitutions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 contiguous amino acid substitutions relative to amino acids 449-871 of SEQ ID NO: 1. In yet other aspects of this embodiment, a BoNT/A $H_N$ region comprises a polypeptide having, e.g., at most one, two, three, four, five, six, seven, eight, nine, 10, 20, 30, 40, 50, 100 or 200 contiguous amino acid deletions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 contiguous amino acid deletions relative to amino acids 449-871 of SEQ ID NO: 1. In still other aspects of this embodiment, a BoNT/A $H_N$ region comprises a polypeptide having, e.g., at most one, two, three, four, five, six, seven, eight, nine, 10, 20, 30, 40, 50, 100 or 200 contiguous amino acid additions relative to amino acids 449-871 of SEQ ID NO: 1. In other aspects of this embodiment, a BoNT/A $H_N$ region comprises a polypeptide having, e.g., at least one, two, three, four, five, six, seven, eight, nine, 10, 20, 30, 40, 50, 100 or 200 contiguous amino acid additions relative to amino acids 449-871 of SEQ ID NO: 1.

In another embodiment, a Clostridial toxin translocation domain comprises a BoNT/B $H_N$ region. In an aspect of this embodiment, a BoNT/B $H_N$ region comprises amino acids 442-858 of SEQ ID NO: 2. In another aspect of this embodiment, a BoNT/B $H_N$ region comprises a naturally occurring BoNT/B $H_N$ region variant, such as, e.g., a $H_N$ region from a BoNT/B isoform or a $H_N$ region from a BoNT/B subtype. In another aspect of this embodiment, a BoNT/B $H_N$ region comprises amino acids 442-858 of a naturally occurring BoNT/B $H_N$ region variant of SEQ ID NO: 2, such as, e.g., amino acids 442-858 of a BoNT/B isoform of SEQ ID NO: 2 or amino acids 442-858 of a BoNT/B subtype of SEQ ID NO: 2. In still another aspect of this embodiment, a BoNT/B $H_N$ region comprises a non-naturally occurring BoNT/B $H_N$ region variant, such as, e.g., a conservative BoNT/B $H_N$ region variant, a non-conservative BoNT/B $H_N$ region variant, a BoNT/B chimeric $H_N$ region, an active BoNT/B $H_N$ region fragment, or any combination thereof. In still another aspect of this embodiment, a BoNT/B $H_N$ region comprises amino acids 442-858 of a non-naturally occurring BoNT/B $H_N$ region variant of SEQ ID NO: 2, such as, e.g., amino acids 442-858 of a conservative BoNT/B $H_N$ region variant of SEQ ID NO: 2, amino acids 442-858 of a non-conservative BoNT/B $H_N$ region variant of SEQ ID NO: 2, amino acids 442-858 of an active BoNT/B $H_N$ region fragment of SEQ ID NO: 2, or any combination thereof.

In other aspects of this embodiment, a BoNT/B $H_N$ region comprises a polypeptide having, e.g., at least 70% amino acid identity with amino acids 442-858 of SEQ ID NO: 2, at least 75% amino acid identity with amino acids 442-858 of SEQ ID NO: 2, at least 80% amino acid identity with amino acids 442-858 of SEQ ID NO: 2, at least 85% amino acid identity with amino acids 442-858 of SEQ ID NO: 2, at least 90% amino acid identity with amino acids 442-858 of SEQ ID NO: 2 or at least 95% amino acid identity with amino acids 442-858 of SEQ ID NO: 2. In yet other aspects of this embodiment, a BoNT/B $H_N$ region comprises a polypeptide having, e.g., at most 70% amino acid identity with amino acids 442-858 of SEQ ID NO: 2, at most 75% amino acid identity with amino acids 442-858 of SEQ ID NO: 2, at most 80% amino acid identity with amino acids 442-858 of SEQ ID NO: 2, at most 85% amino acid identity with amino acids 442-858 of SEQ ID NO: 2, at most 90% amino acid identity with amino acids 442-858 of SEQ ID NO: 2 or at most 95% amino acid identity with amino acids 442-858 of SEQ ID NO: 2.

In other aspects of this embodiment, a BoNT/B $H_N$ region comprises a polypeptide having, e.g., at most one, two, three, four, five, six, seven, eight, nine, 10, 20, 30, 40, 50, 100, or 200 non-contiguous amino acid substitutions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 non-contiguous amino acid substitutions relative to amino acids 442-858 of SEQ ID NO: 2. In yet other aspects of this embodiment, a BoNT/B $H_N$ region comprises a polypeptide having, e.g., at most one, two, three, four, five, six, seven, eight, nine, 10, 20, 30, 40, 50, 100 or 200 non-contiguous amino acid deletions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 non-contiguous amino acid deletions relative to amino acids 442-858 of SEQ ID NO: 2. In still other aspects of this embodiment, a BoNT/B $H_N$ region comprises a polypeptide having, e.g., at most one, two, three, four, five, six, seven, eight, nine, 10, 20, 30, 40, 50, 100 or 200 non-contiguous amino acid additions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 non-contiguous amino acid additions relative to amino acids 442-858 of SEQ ID NO: 2.

In other aspects of this embodiment, a BoNT/B $H_N$ region comprises a polypeptide having, e.g., at most one, two, three, four, five, six, seven, eight, nine, 10, 20, 30, 40, 50, 100 or 200 contiguous amino acid substitutions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 contiguous amino acid substitutions relative to amino acids 442-858 of SEQ ID NO: 2. In yet other aspects of this embodiment, a BoNT/B $H_N$ region comprises a polypeptide having, e.g., at most one, two, three, four, five, six, seven, eight, nine, 10, 20, 30, 40, 50, 100 or 200 contiguous amino acid deletions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 contiguous amino acid deletions relative to amino acids 442-858 of SEQ ID NO: 2. In still other aspects of this embodiment, a BoNT/B $H_N$ region comprises a polypeptide having, e.g., at most one, two, three, four, five, six, seven, eight, nine, 10, 20, 30, 40, 50, 100 or 200 contiguous amino acid additions relative to amino acids 442-858 of SEQ ID NO: 2. In other aspects of this embodiment, a BoNT/B $H_N$ region comprises a polypeptide having, e.g., at least one, two, three, four, five, six, seven, eight, nine, 10, 20, 30, 40, 50, 100 or 200 contiguous amino acid additions relative to amino acids 442-858 of SEQ ID NO: 2.

In another embodiment, a Clostridial toxin translocation domain comprises a BoNT/C1 $H_N$ region. In an aspect of this embodiment, a BoNT/C1 $H_N$ region comprises amino acids 450-866 of SEQ ID NO: 3. In another aspect of this embodiment, a BoNT/C1 $H_N$ region comprises a naturally occurring BoNT/C1 $H_N$ region variant, such as, e.g., a $H_N$ region from a BoNT/C1 isoform or a $H_N$ region from a BoNT/C1 subtype. In another aspect of this embodiment, a BoNT/C1 $H_N$ region comprises amino acids 450-866 of a naturally occurring BoNT/C1 $H_N$ region variant of SEQ ID NO: 3, such as, e.g., amino acids 450-866 of a BoNT/C1 isoform of SEQ ID NO: 3 or amino acids 450-866 of a BoNT/C1 subtype of SEQ ID NO: 3. In still another aspect of this embodiment, a BoNT/C1 $H_N$ region comprises a non-naturally occurring BoNT/C1 $H_N$ region variant, such as, e.g., a conservative BoNT/C1 $H_N$ region variant, a non-conservative BoNT/C1 $H_N$ region variant, a BoNT/C1 chimeric $H_N$ region, an active BoNT/C1 $H_N$ region fragment, or any combination thereof. In still another aspect of this embodiment, a BoNT/C1 $H_N$ region comprises amino acids 450-866 of a non-naturally occurring BoNT/C1 $H_N$ region variant of SEQ ID NO: 3, such as, e.g., amino acids 450-866 of a conservative BoNT/C1 $H_N$ region variant of SEQ ID NO: 3, amino acids 450-866 of a non-conservative BoNT/C1 $H_N$ region variant of SEQ ID NO: 3, amino acids 450-866 of an active BoNT/C1 $H_N$ region fragment of SEQ ID NO: 3, or any combination thereof.

In other aspects of this embodiment, a BoNT/C1 $H_N$ region comprises a polypeptide having, e.g., at least 70% amino acid identity with amino acids 450-866 of SEQ ID NO: 3, at least 75% amino acid identity with amino acids 450-866 of SEQ ID NO: 3, at least 80% amino acid identity with amino acids 450-866 of SEQ ID NO: 3, at least 85% amino acid identity with amino acids 450-866 of SEQ ID NO: 3, at least 90% amino acid identity with amino acids 450-866 of SEQ ID NO: 3 or at least 95% amino acid identity with amino acids 450-866 of SEQ ID NO: 3. In yet other aspects of this embodiment, a BoNT/C1 $H_N$ region comprises a polypeptide having, e.g., at most 70% amino acid identity with amino acids 450-866 of SEQ ID NO: 3, at most 75% amino acid identity with amino acids 450-866 of SEQ ID NO: 3, at most 80% amino acid identity with amino acids 450-866 of SEQ ID NO: 3, at most 85% amino acid identity with amino acids 450-866 of SEQ ID NO: 3, at most 90% amino acid identity with amino acids 450-866 of SEQ ID NO: 3 or at most 95% amino acid identity with amino acids 450-866 of SEQ ID NO: 3.

In other aspects of this embodiment, a BoNT/C1 $H_N$ region comprises a polypeptide having, e.g., at most one, two, three, four, five, six, seven, eight, nine, 10, 20, 30, 40, 50, 100, or 200 non-contiguous amino acid substitutions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 non-contiguous amino acid substitutions relative to amino acids 450-866 of SEQ ID NO: 3. In yet other aspects of this embodiment, a BoNT/C1 $H_N$ region comprises a polypeptide having, e.g., at most one, two, three, four, five, six, seven, eight, nine, 10, 20, 30, 40, 50, 100 or 200 non-contiguous amino acid deletions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 non-contiguous amino acid deletions relative to amino acids 450-866 of SEQ ID NO: 3. In still other aspects of this embodiment, a BoNT/C1 $H_N$ region comprises a polypeptide having, e.g., at most one, two, three, four, five, six, seven, eight, nine, 10, 20, 30, 40, 50, 100 or 200 non-contiguous amino acid additions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 non-contiguous amino acid additions relative to amino acids 450-866 of SEQ ID NO: 3.

In other aspects of this embodiment, a BoNT/C1 $H_N$ region comprises a polypeptide having, e.g., at most one, two, three, four, five, six, seven, eight, nine, 10, 20, 30, 40, 50, 100 or 200 contiguous amino acid substitutions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 contiguous amino acid substitutions relative to amino acids 450-866 of SEQ ID NO: 3. In yet other aspects of this embodiment, a BoNT/C1 $H_N$ region comprises a polypeptide having, e.g., at most one, two, three, four, five, six, seven, eight, nine, 10, 20, 30, 40, 50, 100 or 200 contiguous amino acid deletions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 contiguous amino acid deletions relative to amino acids 450-866 of SEQ ID NO: 3. In still other aspects of this embodiment, a BoNT/C1 $H_N$ region comprises a polypeptide having, e.g., at most one, two, three, four, five, six, seven, eight, nine, 10, 20, 30, 40, 50, 100 or 200 contiguous amino acid additions relative to amino acids 450-866 of SEQ ID NO: 3. In other aspects of this embodiment, a BoNT/C1 $H_N$ region comprises a polypeptide having, e.g., at least one, two, three, four, five, six, seven, eight, nine, 10, 20, 30, 40, 50, 100 or 200 contiguous amino acid additions relative to amino acids 450-866 of SEQ ID NO: 3.

In another embodiment, a Clostridial toxin translocation domain comprises a BoNT/D $H_N$ region. In an aspect of this embodiment, a BoNT/D $H_N$ region comprises amino acids 446-862 of SEQ ID NO: 4. In another aspect of this embodiment, a BoNT/D $H_N$ region comprises a naturally occurring BoNT/D $H_N$ region variant, such as, e.g., a $H_N$ region from a BoNT/D isoform or a $H_N$ region from a BoNT/D subtype. In another aspect of this embodiment, a BoNT/D $H_N$ region comprises amino acids 446-862 of a naturally occurring BoNT/D $H_N$ region variant of SEQ ID NO: 4, such as, e.g., amino acids 446-862 of a BoNT/D isoform of SEQ ID NO: 4 or amino acids 446-862 of a BoNT/D subtype of SEQ ID NO: 4. In still another aspect of this embodiment, a BoNT/D $H_N$ region comprises a non-naturally occurring BoNT/D $H_N$ region variant, such as, e.g., a conservative BoNT/D $H_N$ region variant, a non-conservative BoNT/D $H_N$ region variant, a BoNT/D chimeric $H_N$ region, an active BoNT/D $H_N$ region fragment, or any combination thereof. In still another aspect of this embodiment, a BoNT/D $H_N$ region comprises amino acids 446-862 of a non-naturally occurring BoNT/D $H_N$ region variant of SEQ ID NO: 4, such as, e.g., amino acids 446-862 of a conservative BoNT/D $H_N$ region variant of SEQ ID NO: 4, amino acids 446-862 of a non-conservative BoNT/D $H_N$ region variant of SEQ ID NO: 4, amino acids 446-862 of an active BoNT/D $H_N$ region fragment of SEQ ID NO: 4, or any combination thereof.

In other aspects of this embodiment, a BoNT/D $H_N$ region comprises a polypeptide having, e.g., at least 70% amino acid identity with amino acids 446-862 of SEQ ID NO: 4, at least 75% amino acid identity with amino acids 446-862 of SEQ ID NO: 4, at least 80% amino acid identity with amino acids 446-862 of SEQ ID NO: 4, at least 85% amino acid identity with amino acids 446-862 of SEQ ID NO: 4, at least 90% amino acid identity with amino acids 446-862 of SEQ ID NO: 4 or at least 95% amino acid identity with amino acids 446-862 of SEQ ID NO: 4. In yet other aspects of this embodiment, a BoNT/D $H_N$ region comprises a polypeptide having, e.g., at most 70% amino acid identity with amino acids 446-862 of SEQ ID NO: 4, at most 75% amino acid identity with amino acids 446-862 of SEQ ID NO: 4, at most 80% amino acid identity with amino acids 446-862 of SEQ ID NO: 4, at most 85% amino acid identity with amino acids 446-862 of SEQ ID NO: 4, at most 90% amino acid identity with amino acids 446-862 of SEQ ID NO: 4 or at most 95% amino acid identity with amino acids 446-862 of SEQ ID NO: 4.

In other aspects of this embodiment, a BoNT/D $H_N$ region comprises a polypeptide having, e.g., at most one, two, three, four, five, six, seven, eight, nine, 10, 20, 30, 40, 50, 100, or 200 non-contiguous amino acid substitutions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 non-contiguous amino acid substitutions relative to amino acids 446-862 of SEQ ID NO: 4. In yet other aspects of this embodiment, a BoNT/D $H_N$ region comprises a polypeptide having, e.g., at most one, two, three, four, five, six, seven, eight, nine, 10, 20, 30, 40, 50, 100 or 200 non-contiguous amino acid deletions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 non-contiguous amino acid deletions relative to amino acids 446-862 of SEQ ID NO: 4. In still other aspects of this embodiment, a BoNT/D $H_N$ region comprises a polypeptide having, e.g., at most one, two, three, four, five, six, seven, eight, nine, 10, 20, 30, 40, 50, 100 or 200 non-contiguous amino acid additions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 non-contiguous amino acid additions relative to amino acids 446-862 of SEQ ID NO: 4.

In other aspects of this embodiment, a BoNT/D $H_N$ region comprises a polypeptide having, e.g., at most one, two, three, four, five, six, seven, eight, nine, 10, 20, 30, 40, 50, 100 or 200 contiguous amino acid substitutions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 contiguous amino acid substitutions relative to amino acids 446-862 of SEQ ID NO: 4. In yet other aspects of this embodiment, a BoNT/D $H_N$ region comprises a polypeptide having, e.g., at most one, two, three, four, five, six, seven, eight, nine, 10, 20, 30, 40, 50, 100 or 200 contiguous amino acid deletions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 contiguous amino acid deletions relative to amino acids 446-862 of SEQ ID NO: 4. In still other aspects of this embodiment, a BoNT/D $H_N$ region comprises a polypeptide having, e.g., at most one, two, three, four, five, six, seven, eight, nine, 10, 20, 30, 40, 50, 100 or 200 contiguous amino acid additions relative to amino acids 446-862 of SEQ ID NO: 4. In other aspects of this embodiment, a BoNT/D $H_N$ region comprises a polypeptide having, e.g., at least one, two, three, four, five, six, seven, eight, nine, 10, 20, 30, 40, 50, 100 or 200 contiguous amino acid additions relative to amino acids 446-862 of SEQ ID NO: 4.

In another embodiment, a Clostridial toxin translocation domain comprises a BoNT/E $H_N$ region. In an aspect of this embodiment, a BoNT/E $H_N$ region comprises amino acids 423-845 of SEQ ID NO: 5. In another aspect of this embodiment, a BoNT/E $H_N$ region comprises a naturally occurring BoNT/E $H_N$ region variant, such as, e.g., a $H_N$ region from a BoNT/E isoform or a $H_N$ region from a BoNT/E subtype. In another aspect of this embodiment, a BoNT/E $H_N$ region comprises amino acids 423-845 of a naturally occurring BoNT/E $H_N$ region variant of SEQ ID NO: 5, such as, e.g., amino acids 423-845 of a BoNT/E isoform of SEQ ID NO: 5 or amino acids 423-845 of a BoNT/E subtype of SEQ ID NO: 5. In still another aspect of this embodiment, a BoNT/E $H_N$ region comprises a non-naturally occurring BoNT/E $H_N$ region variant, such as, e.g., a conservative BoNT/E $H_N$ region variant, a non-conservative BoNT/E $H_N$ region variant, a BoNT/E chimeric $H_N$ region, an active BoNT/E $H_N$ region fragment, or any combination thereof. In still another aspect of this embodiment, a BoNT/E $H_N$ region comprises amino acids 423-845 of a non-naturally occurring BoNT/E $H_N$ region variant of SEQ ID NO: 5, such as, e.g., amino acids 423-845 of a conservative BoNT/E $H_N$ region variant of SEQ ID NO: 5, amino acids 423-845 of a non-conservative BoNT/E $H_N$ region variant of SEQ ID NO: 5, amino acids 423-845 of an active BoNT/E $H_N$ region fragment of SEQ ID NO: 5, or any combination thereof.

In other aspects of this embodiment, a BoNT/E $H_N$ region comprises a polypeptide having, e.g., at least 70% amino acid identity with amino acids 423-845 of SEQ ID NO: 5, at least 75% amino acid identity with amino acids 423-845 of SEQ ID NO: 5, at least 80% amino acid identity with amino acids 423-845 of SEQ ID NO: 5, at least 85% amino acid identity with amino acids 423-845 of SEQ ID NO: 5, at least 90% amino acid identity with amino acids 423-845 of SEQ ID NO: 5 or at least 95% amino acid identity with amino acids 423-845 of SEQ ID NO: 5. In yet other aspects of this embodiment, a BoNT/E $H_N$ region comprises a polypeptide having, e.g., at most 70% amino acid identity with amino acids 423-845 of SEQ ID NO: 5, at most 75% amino acid identity with amino acids 423-845 of SEQ ID NO: 5, at most 80% amino acid identity with amino acids 423-845 of SEQ ID NO: 5, at most 85% amino acid identity with amino acids 423-845 of SEQ ID NO: 5, at most 90% amino acid identity with amino acids 423-845 of SEQ ID NO: 5 or at most 95% amino acid identity with amino acids 423-845 of SEQ ID NO: 5.

In other aspects of this embodiment, a BoNT/E $H_N$ region comprises a polypeptide having, e.g., at most one, two, three, four, five, six, seven, eight, nine, 10, 20, 30, 40, 50, 100, or 200 non-contiguous amino acid substitutions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 non-contiguous amino acid substitutions relative to amino acids 423-845 of SEQ ID NO: 5. In yet other aspects of this embodiment, a BoNT/E $H_N$ region comprises a polypeptide having, e.g., at most one, two, three, four, five, six, seven, eight, nine, 10, 20, 30, 40, 50, 100 or 200 non-contiguous amino acid deletions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 non-contiguous amino acid deletions relative to amino acids 423-845 of SEQ ID NO: 5. In still other aspects of this embodiment, a BoNT/E $H_N$ region comprises a polypeptide having, e.g., at most one, two, three, four, five, six, seven, eight, nine, 10, 20, 30, 40, 50, 100 or 200 non-contiguous amino acid additions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 non-contiguous amino acid additions relative to amino acids 423-845 of SEQ ID NO: 5.

In other aspects of this embodiment, a BoNT/E $H_N$ region comprises a polypeptide having, e.g., at most one, two, three, four, five, six, seven, eight, nine, 10, 20, 30, 40, 50, 100 or 200 contiguous amino acid substitutions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 contiguous amino acid substitutions relative to amino acids 423-845 of SEQ ID NO: 5. In yet other aspects of this embodiment, a BoNT/E $H_N$ region comprises a polypeptide having, e.g., at most one, two, three, four, five, six, seven, eight, nine, 10, 20, 30, 40, 50, 100 or 200 contiguous amino acid deletions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 contiguous amino acid deletions relative to amino acids 423-845 of SEQ ID NO: 5. In still other aspects of this embodiment, a BoNT/E $H_N$ region comprises a polypeptide having, e.g., at most one, two, three, four, five, six, seven, eight, nine, 10, 20, 30, 40, 50, 100 or 200 contiguous amino acid additions relative to amino acids 423-845 of SEQ ID NO: 5. In other aspects of this embodiment, a BoNT/E $H_N$ region comprises a polypeptide having, e.g., at least one, two, three, four, five, six, seven, eight, nine, 10, 20, 30, 40, 50, 100 or 200 contiguous amino acid additions relative to amino acids 423-845 of SEQ ID NO: 5.

In another embodiment, a Clostridial toxin translocation domain comprises a BoNT/F $H_N$ region. In an aspect of this embodiment, a BoNT/F $H_N$ region comprises amino acids 440-864 of SEQ ID NO: 6. In another aspect of this embodiment, a BoNT/F $H_N$ region comprises a naturally occurring BoNT/F $H_N$ region variant, such as, e.g., a $H_N$ region from a BoNT/F isoform or a $H_N$ region from a BoNT/F subtype. In another aspect of this embodiment, a BoNT/F $H_N$ region comprises amino acids 440-864 of a naturally occurring BoNT/F $H_N$ region variant of SEQ ID NO: 6, such as, e.g., amino acids 440-864 of a BoNT/F isoform of SEQ ID NO: 6 or amino acids 440-864 of a BoNT/F subtype of SEQ ID NO: 6. In still another aspect of this embodiment, a BoNT/F $H_N$ region comprises a non-naturally occurring BoNT/F $H_N$ region variant, such as, e.g., a conservative BoNT/F $H_N$ region variant, a non-conservative BoNT/F $H_N$ region variant, a BoNT/F chimeric $H_N$ region, an active BoNT/F $H_N$ region fragment, or any combination thereof. In still another aspect of this embodiment, a BoNT/F $H_N$ region comprises amino acids 440-864 of a non-naturally occurring BoNT/F $H_N$ region variant of SEQ ID NO: 6, such as, e.g., amino acids 440-864 of a conservative BoNT/F $H_N$ region variant of SEQ ID NO: 6, amino acids 440-864 of a non-conservative BoNT/F $H_N$ region variant of SEQ ID NO: 6, amino acids 440-864 of an active BoNT/F $H_N$ region fragment of SEQ ID NO: 6, or any combination thereof.

In other aspects of this embodiment, a BoNT/F $H_N$ region comprises a polypeptide having, e.g., at least 70% amino acid identity with amino acids 440-864 of SEQ ID NO: 6, at least 75% amino acid identity with amino acids 440-864 of SEQ ID NO: 6, at least 80% amino acid identity with amino acids 440-864 of SEQ ID NO: 6, at least 85% amino acid identity with amino acids 440-864 of SEQ ID NO: 6, at least 90% amino acid identity with amino acids 440-864 of SEQ ID NO: 6 or at least 95% amino acid identity with amino acids 440-864 of SEQ ID NO: 6. In yet other aspects of this embodiment, a BoNT/F $H_N$ region comprises a polypeptide having, e.g., at most 70% amino acid identity with amino acids 440-864 of SEQ ID NO: 6, at most 75% amino acid identity with amino acids 440-864 of SEQ ID NO: 6, at most 80% amino acid identity with amino acids 440-864 of SEQ ID NO: 6, at most 85% amino acid identity with amino acids 440-864 of SEQ ID NO: 6, at most 90% amino acid identity with amino acids 440-864 of SEQ ID NO: 6 or at most 95% amino acid identity with amino acids 440-864 of SEQ ID NO: 6.

In other aspects of this embodiment, a BoNT/F $H_N$ region comprises a polypeptide having, e.g., at most one, two, three, four, five, six, seven, eight, nine, 10, 20, 30, 40, 50, 100, or 200 non-contiguous amino acid substitutions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 non-contiguous amino acid substitutions relative to amino acids 440-864 of SEQ ID NO: 6. In yet other aspects of this embodiment, a BoNT/F $H_N$ region comprises a polypeptide having, e.g., at most one, two, three, four, five, six, seven, eight, nine, 10, 20, 30, 40, 50, 100 or 200 non-contiguous amino acid deletions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 non-contiguous amino acid deletions relative to amino acids 440-864 of SEQ ID NO: 6. In still other aspects of this embodiment, a BoNT/F $H_N$ region comprises a polypeptide having, e.g., at most one, two, three, four, five, six, seven, eight, nine, 10, 20, 30, 40, 50, 100 or 200 non-contiguous amino acid additions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 non-contiguous amino acid additions relative to amino acids 440-864 of SEQ ID NO: 6.

In other aspects of this embodiment, a BoNT/F $H_N$ region comprises a polypeptide having, e.g., at most one, two, three, four, five, six, seven, eight, nine, 10, 20, 30, 40, 50, 100 or 200 contiguous amino acid substitutions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 contiguous amino acid substitutions relative to amino acids 440-864 of SEQ ID NO: 6. In yet other aspects of this embodiment, a BoNT/F $H_N$ region comprises a polypeptide having, e.g., at most one, two, three, four, five, six, seven, eight, nine, 10, 20, 30, 40, 50, 100 or 200 contiguous amino acid deletions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 contiguous amino acid deletions relative to amino acids 440-864 of SEQ ID NO: 6. In still other aspects of this embodiment, a BoNT/F $H_N$ region comprises a polypeptide having, e.g., at most one, two, three, four, five, six, seven, eight, nine, 10, 20, 30, 40, 50, 100 or 200 contiguous amino acid additions relative to amino acids 440-864 of SEQ ID NO: 6. In other aspects of this embodiment, a BoNT/F $H_N$ region comprises a polypeptide having, e.g., at least one, two, three, four, five, six, seven, eight, nine, 10, 20, 30, 40, 50, 100 or 200 contiguous amino acid additions relative to amino acids 440-864 of SEQ ID NO: 6.

In another embodiment, a Clostridial toxin translocation domain comprises a BoNT/G $H_N$ region. In an aspect of this embodiment, a BoNT/G $H_N$ region comprises amino acids 447-863 of SEQ ID NO: 7. In another aspect of this embodiment, a BoNT/G $H_N$ region comprises a naturally occurring BoNT/G $H_N$ region variant, such as, e.g., a $H_N$ region from a BoNT/G isoform or a $H_N$ region from a BoNT/G subtype. In another aspect of this embodiment, a BoNT/G $H_N$ region comprises amino acids 447-863 of a naturally occurring BoNT/G $H_N$ region variant of SEQ ID NO: 7, such as, e.g., amino acids 447-863 of a BoNT/G isoform of SEQ ID NO: 7 or amino acids 447-863 of a BoNT/G subtype of SEQ ID NO: 7. In still another aspect of this embodiment, a BoNT/G $H_N$ region comprises a non-naturally occurring BoNT/G $H_N$ region variant, such as, e.g., a conservative BoNT/G $H_N$ region variant, a non-conservative BoNT/G $H_N$ region variant, a BoNT/G chimeric $H_N$ region, an active BoNT/G $H_N$ region fragment, or any combination thereof. In still another aspect of this embodiment, a BoNT/G $H_N$ region comprises amino acids 447-863 of a non-naturally occurring BoNT/G $H_N$ region variant of SEQ ID NO: 7, such as, e.g., amino acids 447-863 of a conservative BoNT/G $H_N$ region variant of SEQ ID NO: 7, amino acids 447-863 of a non-conservative BoNT/G $H_N$ region variant of SEQ ID NO: 7, amino acids 447-863 of an active BoNT/G $H_N$ region fragment of SEQ ID NO: 7, or any combination thereof.

In other aspects of this embodiment, a BoNT/G $H_N$ region comprises a polypeptide having, e.g., at least 70% amino acid identity with amino acids 447-863 of SEQ ID NO: 7, at least 75% amino acid identity with amino acids 447-863 of SEQ ID NO: 7, at least 80% amino acid identity with amino acids 447-863 of SEQ ID NO: 7, at least 85% amino acid identity with amino acids 447-863 of SEQ ID NO: 7, at least 90% amino acid identity with amino acids 447-863 of SEQ ID NO: 7 or at least 95% amino acid identity with amino acids 447-863 of SEQ ID NO: 7. In yet other aspects of this embodiment, a BoNT/G $H_N$ region comprises a polypeptide having, e.g., at most 70% amino acid identity with amino acids 447-863 of SEQ ID NO: 7, at most 75% amino acid identity with amino acids 447-863 of SEQ ID NO: 7, at most 80% amino acid identity with amino acids 447-863 of SEQ ID NO: 7, at most 85% amino acid identity with amino acids 447-863 of SEQ ID NO: 7, at most 90% amino acid identity with amino acids 447-863 of SEQ ID NO: 7 or at most 95% amino acid identity with amino acids 447-863 of SEQ ID NO: 7.

In other aspects of this embodiment, a BoNT/G $H_N$ region comprises a polypeptide having, e.g., at most one, two, three, four, five, six, seven, eight, nine, 10, 20, 30, 40, 50, 100, or 200 non-contiguous amino acid substitutions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 non-contiguous amino acid substitutions relative to amino acids 447-863 of SEQ ID NO: 7. In yet other aspects of this embodiment, a BoNT/G $H_N$ region comprises a polypeptide having, e.g., at most one, two, three, four, five, six, seven, eight, nine, 10, 20, 30, 40, 50, 100 or 200 non-contiguous amino acid deletions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 non-contiguous amino acid deletions relative to amino acids 447-863 of SEQ ID NO: 7. In still other aspects of this embodiment, a BoNT/G $H_N$ region comprises a polypeptide having, e.g., at most one, two, three, four, five, six, seven, eight, nine, 10, 20, 30, 40, 50, 100 or 200 non-contiguous amino acid additions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 non-contiguous amino acid additions relative to amino acids 447-863 of SEQ ID NO: 7.

In other aspects of this embodiment, a BoNT/G $H_N$ region comprises a polypeptide having, e.g., at most one, two, three, four, five, six, seven, eight, nine, 10, 20, 30, 40, 50, 100 or 200 contiguous amino acid substitutions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 contiguous amino acid substitutions relative to amino acids 447-863 of SEQ ID NO: 7. In yet other aspects of this embodiment, a BoNT/G $H_N$ region comprises a polypeptide having, e.g., at most one, two, three, four, five, six, seven, eight, nine, 10, 20, 30, 40, 50, 100 or 200 contiguous amino acid deletions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 contiguous amino acid deletions relative to amino acids 447-863 of SEQ ID NO: 7. In still other aspects of this embodiment, a BoNT/G $H_N$ region comprises a polypeptide having, e.g., at most one, two, three, four, five, six, seven, eight, nine, 10, 20, 30, 40, 50, 100 or 200 contiguous amino acid additions relative to amino acids 447-863 of SEQ ID NO: 7. In other aspects of this embodiment, a BoNT/G $H_N$ region comprises a polypeptide having, e.g., at least one, two, three, four, five, six, seven, eight, nine, 10, 20, 30, 40, 50, 100 or 200 contiguous amino acid additions relative to amino acids 447-863 of SEQ ID NO: 7.

In another embodiment, a Clostridial toxin translocation domain comprises a TeNT $H_N$ region. In an aspect of this embodiment, a TeNT $H_N$ region comprises amino acids 458-879 of SEQ ID NO: 8. In another aspect of this embodiment, a TeNT $H_N$ region comprises a naturally occurring TeNT $H_N$ region variant, such as, e.g., a $H_N$ region from a TeNT isoform or a $H_N$ region from a TeNT subtype. In another aspect of this embodiment, a TeNT $H_N$ region comprises amino acids 458-879 of a naturally occurring TeNT $H_N$ region variant of SEQ ID NO: 8, such as, e.g., amino acids 458-879 of a TeNT isoform of SEQ ID NO: 8 or amino acids 458-879 of a TeNT subtype of SEQ ID NO: 8. In still another aspect of this embodiment, a TeNT $H_N$ region comprises a non-naturally occurring TeNT $H_N$ region variant, such as, e.g., a conservative TeNT $H_N$ region variant, a non-conservative TeNT $H_N$ region variant, a TeNT chimeric $H_N$ region, an active TeNT $H_N$ region fragment, or any combination thereof. In still another aspect of this embodiment, a TeNT $H_N$ region comprises amino acids 458-879 of a non-naturally occurring TeNT $H_N$ region variant of SEQ ID NO: 8, such as, e.g., amino acids 458-879 of a conservative TeNT $H_N$ region variant of SEQ ID NO: 8, amino acids 458-879 of a non-conservative TeNT $H_N$ region variant of SEQ ID NO: 8, amino acids 458-879 of an active TeNT $H_N$ region fragment of SEQ ID NO: 8, or any combination thereof.

In other aspects of this embodiment, a TeNT $H_N$ region comprises a polypeptide having, e.g., at least 70% amino acid identity with amino acids 458-879 of SEQ ID NO: 8, at least 75% amino acid identity with amino acids 458-879 of SEQ ID NO: 8, at least 80% amino acid identity with amino acids 458-879 of SEQ ID NO: 8, at least 85% amino acid identity with amino acids 458-879 of SEQ ID NO: 8, at least 90% amino acid identity with amino acids 458-879 of SEQ ID NO: 8 or at least 95% amino acid identity with amino acids 458-879 of SEQ ID NO: 8. In yet other aspects of this embodiment, a TeNT $H_N$ region comprises a polypeptide having, e.g., at most 70% amino acid identity with amino acids 458-879 of SEQ ID NO: 8, at most 75% amino acid identity with amino acids 458-879 of SEQ ID NO: 8, at most 80% amino acid identity with amino acids 458-879 of SEQ ID NO: 8, at most 85% amino acid identity with amino acids 458-879 of SEQ ID NO: 8, at most 90% amino acid identity with amino acids 458-879 of SEQ ID NO: 8 or at most 95% amino acid identity with amino acids 458-879 of SEQ ID NO: 8.

In other aspects of this embodiment, a TeNT $H_N$ region comprises a polypeptide having, e.g., at most one, two, three, four, five, six, seven, eight, nine, 10, 20, 30, 40, 50, 100, or 200 non-contiguous amino acid substitutions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 non-contiguous amino acid substitutions relative to amino acids 458-879 of SEQ ID NO: 8. In yet other aspects of this embodiment, a TeNT $H_N$ region comprises a polypeptide having, e.g., at most one, two, three, four, five, six, seven, eight, nine, 10, 20, 30, 40, 50, 100 or 200 non-contiguous amino acid deletions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 non-contiguous amino acid deletions relative to amino acids 458-879 of SEQ ID NO: 8. In still other aspects of this embodiment, a TeNT $H_N$ region comprises a polypeptide having, e.g., at most one, two, three, four, five, six, seven, eight, nine, 10, 20, 30, 40, 50, 100 or 200 non-contiguous amino acid additions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 non-contiguous amino acid additions relative to amino acids 458-879 of SEQ ID NO: 8.

In other aspects of this embodiment, a TeNT $H_N$ region comprises a polypeptide having, e.g., at most one, two, three, four, five, six, seven, eight, nine, 10, 20, 30, 40, 50, 100 or 200 contiguous amino acid substitutions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 contiguous amino acid substitutions relative to amino acids 458-879 of SEQ ID NO: 8. In yet other aspects of this embodiment, a TeNT $H_N$ region comprises a polypeptide having, e.g., at most one, two, three, four, five, six, seven, eight, nine, 10, 20, 30, 40, 50, 100 or 200 contiguous amino acid deletions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 contiguous amino acid deletions relative to amino acids 458-879 of SEQ ID NO: 8. In still other aspects of this embodiment, a TeNT $H_N$ region comprises a polypeptide having, e.g., at most one, two, three, four, five, six, seven, eight, nine, 10, 20, 30, 40, 50, 100 or 200 contiguous amino acid additions relative to amino acids 458-879 of SEQ ID NO: 8. In other aspects of this embodiment, a TeNT $H_N$ region comprises a polypeptide having, e.g., at least one, two, three, four, five, six, seven, eight, nine, 10, 20, 30, 40, 50, 100 or 200 contiguous amino acid additions relative to amino acids 458-879 of SEQ ID NO: 8.

Aspects of the present invention provide, in part, an enhanced targeting domain. As used herein, the term "enhanced targeting domain" means any polypeptide that can selectively bind to an endogenous Clostridial toxin receptor system found on a Clostridial toxin target cell and initiate the overall internalization mechanism whereby a Clostridial toxin intoxicates a target cell with the proviso that an enhanced targeting domain is not a naturally-occurring binding domain from a naturally occurring Clostridial toxin. As used herein, the term "selectively" means having a highly preferred activity or effect. As used herein, the term "selectively bind" means a molecule is able to bind its target receptor system under physiological conditions, or in vitro conditions substantially approximating physiological conditions, to a statistically significantly greater degree relative to other, non-target receptor systems. Thus, with reference to an enhanced targeting domain of the present specification, there is a discriminatory binding of the enhanced targeting domain to an endogenous Clostridial toxin receptor system.

An enhanced targeting domain disclosed in the present specification facilitates the binding activity of the modified Clostridial toxins disclosed in the present specification to an endogenous Clostridial toxin receptor system located at the surface of a Clostridial toxin target cell. As used herein, the term “binding activity” means that one molecule is directly or indirectly contacting another molecule via at least one intermolecular or intramolecular force, including, without limitation, a covalent bond, an ionic bond, a metallic bond, a hydrogen bond, a hydrophobic interaction, a van der Waals interaction, and the like, or any combination thereof. “Bound” and “bind” are considered terms for binding.

As used herein, the term “binding affinity” means how strong a molecule’s binding activity is for a particular receptor system. In general, high binding affinity results from greater intermolecular force between a binding domain and its receptor system while low binding affinity involves less intermolecular force between the ligand and its receptor. High binding affinity involves a longer residence time for the binding domain at its receptor binding site than is the case for low binding affinity. As such, a molecule with a high binding affinity means a lower concentration of that molecule is required to maximally occupy the binding sites of a receptor system and trigger a physiological response. Conversely, low binding affinity means a relatively high concentration of a molecule is required before the receptor binding sites of a receptor system is maximally occupied and the maximum physiological response is achieved. Thus, modified Clostridial toxins with increased binding activity due to high binding affinity will allow administration of reduced doses of the toxin, thereby reducing or preventing unwanted side-effects associated with toxin dispersal into non-targeted areas.

As used herein, the term “binding specificity” means how specific a molecule’s binding activity is one particular receptor system. In general, high binding specificity results in a more exclusive interaction with one particular receptor system or subgroup of receptor systems while low binding specificity results in a more promiscuous interaction with a larger group of receptor systems. As such, a molecule with a high binding specificity means that molecule will occupy the binding sites of a particular receptor system and trigger a physiological response. Conversely, low binding specificity means a molecule will occupy the binding sites of a many receptor systems and trigger a multitude of physiological responses. Thus, modified Clostridial toxins with increased binding activity due to high binding specificity will only target a subgroup of Clostridial toxin target cells, thereby reducing the side effects associated with the targeting of all Clostridial toxin target cells.

It is envisioned that any and all enhanced targeting domains can be used to practice aspects of the present invention, including, without limitation, an enhanced targeting domain that increases binding affinity for an endogenous Clostridial toxin receptor system present on a naturally-occurring Clostridial toxin target cell; and an enhanced targeting domain that increases binding specificity for a subgroup of endogenous Clostridial toxin receptor systems present on a naturally-occurring Clostridial toxin target cell. As used herein, the term “Clostridial toxin target cell” means a cell that is a naturally occurring target cell for a naturally occurring Clostridial toxin, including, without limitation, motor neurons.

An example of an enhanced targeting domain that increases binding activity for an endogenous Clostridial toxin receptor system present on a naturally-occurring Clostridial toxin target cell, includes, without limitation, a modified Clostridial toxin binding domain with enhanced binding activity, such as, e.g., a modified BoNT/A binding domain with enhanced binding activity, a modified BoNT/B binding domain with enhanced binding activity, a modified BoNT/C1 binding domain with enhanced binding activity, a modified BoNT/D binding domain with enhanced binding activity, a modified BoNT/E binding domain with enhanced binding activity, a modified BoNT/F binding domain with enhanced binding activity, a modified BoNT/G binding domain with enhanced binding activity and a modified TeNT binding domain with enhanced binding activity. Examples of a modified Clostridial toxin binding domain that increase binding activity include, e.g., a modified Clostridial toxin binding domain that increases binding affinity for an endogenous Clostridial toxin receptor system present on a naturally-occurring Clostridial toxin target cell and a modified Clostridial toxin binding domain that increases binding specificity for a subgroup of endogenous Clostridial toxin receptor systems present on a naturally-occurring Clostridial toxin target cell.

The three-dimensional crystal structures of BoNT/A, BoNT/B and the $H_C$ domain of TeNT indicate that the three functional domains of Clostridial neurotoxins are structurally distinct. The HEXXH consensus motif of the light chain forms the tetrahedral zinc binding pocket of the catalytic site located in a deep cleft on the protein surface that is accessible by a channel. The structure of the $H_N$ and $H_C$ domains consists primarily of β-sheet topologies that are linked by a single α-helix. The cylindrical-shaped $H_N$ domain comprises two long amphipathic α-helices that resemble the coiled-coil motif found in some viral proteins. The $H_N$ domain also forms a long unstructured loop called the ‘translocation belt,’ which wraps around a large negatively charged cleft of the light chain that blocks access of the zinc atom to the catalytic-binding pocket of active site. The $H_C$ domain comprises two distinct structural features of roughly equal size that indicate function. The first, designated the $H_{CN}$ subdomain, is located in the amino half of the $H_C$ domain. The $H_{CN}$ subdomain forms a β-barrel, jelly-roll fold. The $H_{CC}$ subdomain is the second subdomain that comprises the $H_C$ domain. This carboxy-terminal subdomain comprises a modified β-trefoil domain which forms three distinct carbohydrate binding regions that resembles the carbohydrate binding moiety found in many sugar-binding proteins, such as, e.g., serum amyloid P, sialidase, cryia, insecticidal α-endotoxin and lectins. Biochemical studies indicate that the β-trefoil domain structure of the $H_{CC}$ subdomain appears to mediate the binding to specific carbohydrate containing components of the Clostridial toxin receptor system on the cell surface, see, e.g., Krzysztof Ginalski et al., *Structure-based Sequence Alignment for the Beta-Trefoil Subdomain of the Clostridial Neurotoxin Family Provides Residue Level Information About the Putative Ganglioside Binding Site,* 482(1-2) FEBS Lett. 119-124 (2000). The $H_C$ domain tilts away from the $H_N$ domain exposing the surface loops and making them accessible for binding. No contacts occur between the light chain and the $H_C$ domain.

Proteins containing the structural β-trefoil domain represents a diverse group of proteins, see, e.g., C. A. Orengo et al., *Protein Superfamilies and Domain Superfolds,* 372 Nature 631-634 (1994). The β-trefoil domain comprises a six-stranded β-barrel closed off at one end by three β-hairpin structures that exhibits a characteristic pseudo-threefold axis symmetry. The monomeric structural unit of this three-fold symmetry is referred to as the β-trefoil fold that contains four β-sheets organized as a pair of antiparallel β-sheets. Dividing each of these β-trefoil folds is a β-hairpin turn. Therefore, in a linear fashion, a β-trefoil domain comprises four β-sheets of the first β-trefoil fold (α-fold), a β-hairpin turn, four β-sheets of the second β-trefoil fold (β-fold), a second β-hairpin turn four β-sheets of the third β-trefoil fold (γ-fold) (FIG. 2). Because the first hairpin turn is located between the fourth and fifth β-sheets of the β-trefoil domain, it is designated the β4/β5 β-hairpin turn. Likewise, since the second hairpin turn is located between the eight and ninth β-sheets of the β-trefoil domain, it is designated the β8/β9 β-hairpin turn.

Continuing research has elucidated that β4/β5 and β8/β9 β-hairpin turns are important in conferring the proper pseudo-threefold axis symmetry observed in the β-trefoil domain. Additionally, this work has demonstrated that amino acid changes in these two β-hairpin turns can increase the stability of the β-trefoil domain, which in turn results in increased binding activity, see, e.g., Stephen R. Brych et al., *Structure and Stability Effects of Mutations Designed to Increase the Primary Sequence Symmetry Within the Core Region of a β-trefoil,* 10 Protein Sci. 2587-2599 (2001); Jaewon Kim et al., *Alternative Type I and I' Turn Conformations in the* β8/β9 *β-hairpin of Human Acidic Fibroblast Growth Factor,* 11 Protein Sci. 459-466 (2002); Jaewon Kim et al., *Sequence swapping Does Not Result in Conformation Swapping for the* β4/β5 *and* β8/β9 *β-hairpin Turns in Human Acidic Fibroblast Growth Factor,* 14 Protein Sci. 351-359 (2005). As a non-limiting example, replacement of an amino acid comprising either the β4/β5 hairpin turn or β8/β9 β-hairpin turn with a glycine results in increased stabilization of the β-trefoil domain. Therefore, replacement of amino acids located in the β4/β5 and β8/β9 β-hairpin turns of the β-trefoil domains present in the binding domain of Clostridial toxins will increase binding activity of such a modified Clostridial toxin by increasing the structural stability of the β-trefoil domain. The amino acid sequences comprising the β-trefoil domains found in various Clostridial toxins are shown in Table 2.

residues are Glu 1203, Phe 1252, Ser 1264, Tyr 1267 and Gly 1279, while in TeNT, these residues are Asp 1222, Thr 1270, Ser 1287, Tyr 1290 and Gly 1300. Additionally, tyrosine residues forming the hydrophilic wall of this pocket were also important (Trp 1266 of BoNT/A and Trp 1289 of TeNT) and tryptophan fluorescence quenching experiments indicated that Trp 1266 of BoNT/A bound carbohydrate molecules. In another studies, photoaffinity labeling experiments revealed that Gln 1270 of BoNT/A and His 1293 of TeNT were also involved in binding carbohydrate molecules. Mutagenesis experiments designed to assay loss-of-function binding activity mutations confirmed the importance of many of the residues described above for BoNT/A and TeNT and extended this analysis to BoNT/B (Glu 1190, His 1241, Typ 1262, Tyr 1263), see, e.g., Andreas Rummel et al., *The $H_{CC}$-Domain of Botulinum Neurotoxins A and B Exhibits a Singular Ganglioside Binding Site Displaying Serotype Specific Carbohydrate Interaction,* 51(3) Mol. Microbiol. 631-643 (2004).

As used herein, the term "Clostridial toxin binding domain" is synonomous with "Clostridial toxin $H_C$ region" and means any naturally occurring Clostridial toxin polypeptide that can execute the cell binding step of the intoxication process, including, e.g., the binding of the Clostridial toxin to a toxin-specific receptor system located on the plasma membrane surface of a target cell. As used herein, the term "modified Clostridial toxin binding domain" is synonomous with "modified Clostridial toxin $H_C$ region" and means a naturally occurring Clostridial toxin binding domain modified to enhance its cell binding activity for an endogenous Clostridial toxin receptor system, such as, e.g., a binding affinity or a binding specificity, to a statistically significantly degree relative to the unmodified naturally occurring Clostridial toxin binding domain from which the modified Clostridial toxin binding domain was derived. By definition, a modified Clostridial toxin binding domain has at least one amino acid change from the corresponding region of the disclosed refer-

TABLE 2

β-trefoil Domains of Clostridial Toxins

| Protein | SEQ ID NO: | Amino Acid Sequence Region of Carbohydrate Binding Moieties: α-fold | β4/β5 β-hairpin turn | β-fold | β8/β9 β-hairpin turn | γ-fold |
|---|---|---|---|---|---|---|
| BoNT/A | 1 | 1111-1162 | 1163-1178 | 1179-1223 | 1224-1236 | 1237-1296 |
| BoNT/B | 2 | 1098-1147 | 1148-1165 | 1166-1210 | 1211-1222 | 1223-1291 |
| BoNT/C1 | 3 | 1112-1150 | 1151-1166 | 1167-1218 | 1219-1229 | 1230-1291 |
| BoNT/D | 4 | 1099-1137 | 1138-1153 | 1154-1207 | 1208-1218 | 1219-1276 |
| BoNT/E | 5 | 1086-1129 | 1130-1146 | 1147-1190 | 1191-1198 | 1199-1252 |
| BoNT/F | 6 | 1106-1152 | 1153-1171 | 1172-1213 | 1214-1221 | 1222-1274 |
| BoNT/G | 7 | 1106-1153 | 1154-1172 | 1173-1218 | 1219-1230 | 1231-1297 |
| TeNT | 8 | 1128-1177 | 1178-1194 | 1195-1240 | 1241-1254 | 1255-1315 |

As is typical for proteins containing a β-trefoil fold, the overall amino acid sequence identity of the $H_{CC}$ subdomain between Clostridial toxins is low. However, key residues essential for binding activity have been identified by structural analysis and mutagenesis experiments, see, e.g., Krzysztof Ginalski et al., *Structure-based Sequence Alignment for the Beta-Trefoil Subdomain of the Clostridial Neurotoxin Family Provides Residue Level Information About the Putative Ganglioside Binding Site,* 482(1-2) FEBS Lett. 119-124 (2000). For example, analysis of the $H_{CC}$ subdomain structure by crystallography identified five highly conserved residues critical for forming a shallow surface pocket of a carbohydrate binding moiety. These polar residues make hydrogen bonds with the carbohydrate ring. In BoNT/A these five polar ence sequences (see Table 1) and can be described in percent identity to the corresponding region of that reference sequence. As non-limiting examples, a modified BoNT/A $H_C$ region comprising amino acids 872-1296 of SEQ ID NO: 1 will have at least one amino acid difference, such as, e.g., an amino acid substitution, deletion or addition, as compared to the amino acid region 872-1296 of SEQ ID NO: 1; a modified BoNT/B $H_C$ region comprising amino acids 859-1291 of SEQ ID NO: 2 will have at least one amino acid difference, such as, e.g., an amino acid substitution, deletion or addition, as compared to the amino acid region 859-1291 of SEQ ID NO: 2; a modified BoNT/C1 $H_C$ region comprising amino acids 867-1291 of SEQ ID NO: 3 will have at least one amino acid difference, such as, e.g., an amino acid substitution, deletion or addition, as compared to the amino acid region 867-1291 of SEQ ID NO: 3; a modified BoNT/D $H_C$ region comprising amino acids 863-1276 of SEQ ID NO: 4 will have at least one amino acid difference, such as, e.g., an amino acid substitution, deletion or addition, as compared to the amino acid region 863-1276 of SEQ ID NO: 4; a modified BoNT/E $H_C$ region comprising amino acids 846-1252 of SEQ ID NO: 5 will have at least one amino acid difference, such as, e.g., an amino acid substitution, deletion or addition, as compared to the amino acid region 846-1252 of SEQ ID NO: 5; a modified BoNT/F $H_C$ region comprising amino acids 865-1274 of SEQ ID NO: 6 will have at least one amino acid difference, such as, e.g., an amino acid substitution, deletion or addition, as compared to the amino acid region 865-1274 of SEQ ID NO: 6; a modified BoNT/G $H_C$ region comprising amino acids 864-1297 of SEQ ID NO: 7 will have at least one amino acid difference, such as, e.g., an amino acid substitution, deletion or addition, as compared to the amino acid region 864-1297 of SEQ ID NO: 7; and a modified TeNT $H_C$ region comprising amino acids 880-1315 of SEQ ID NO: 8 will have at least one amino acid difference, such as, e.g., an amino acid substitution, deletion or addition, as compared to the amino acid region 880-1315 of SEQ ID NO: 8.

As another non-limiting examples, a modified BoNT/A $H_C$ region comprising amino acids 1092-1296 of SEQ ID NO: 1 will have at least one amino acid difference, such as, e.g., an amino acid substitution, deletion or addition, as compared to the amino acid region 1092-1296 of SEQ ID NO: 1; a modified BoNT/B $H_C$ region comprising amino acids 1079-1291 of SEQ ID NO: 2 will have at least one amino acid difference, such as, e.g., an amino acid substitution, deletion or addition, as compared to the amino acid region 1079-1291 of SEQ ID NO: 2; a modified BoNT/C1 $H_C$ region comprising amino acids 1093-1291 of SEQ ID NO: 3 will have at least one amino acid difference, such as, e.g., an amino acid substitution, deletion or addition, as compared to the amino acid region 2093-1291 of SEQ ID NO: 3; a modified BoNT/D $H_C$ region comprising amino acids 1080-1276 of SEQ ID NO: 4 will have at least one amino acid difference, such as, e.g., an amino acid substitution, deletion or addition, as compared to the amino acid region 1080-1276 of SEQ ID NO: 4; a modified BoNT/E $H_C$ region comprising amino acids 1067-1252 of SEQ ID NO: 5 will have at least one amino acid difference, such as, e.g., an amino acid substitution, deletion or addition, as compared to the amino acid region 1067-1252 of SEQ ID NO: 5; a modified BoNT/F $H_C$ region comprising amino acids 1087-1274 of SEQ ID NO: 6 will have at least one amino acid difference, such as, e.g., an amino acid substitution, deletion or addition, as compared to the amino acid region 1087-1274 of SEQ ID NO: 6; a modified BoNT/G $H_C$ region comprising amino acids 1087-1297 of SEQ ID NO: 7 will have at least one amino acid difference, such as, e.g., an amino acid substitution, deletion or addition, as compared to the amino acid region 1087-1297 of SEQ ID NO: 7; and a modified TeNT $H_C$ region comprising amino acids 1109-1315 of SEQ ID NO: 8 will have at least one amino acid difference, such as, e.g., an amino acid substitution, deletion or addition, as compared to the amino acid region 1109-1315 of SEQ ID NO: 8.

It is also envisioned that any of a variety of modified Clostridial toxin $H_C$ region fragments comprising a binding domain with enhanced binding activity can be useful in aspects of the present invention with the proviso that these active fragments can provide enhanced binding activity of the toxin to the receptor system located at the surface of the target cell. The $H_C$ regions from the heavy chains of Clostridial toxins are approximately 400-440 amino acids in length and comprise a binding domain (Table 1). Research has shown that the entire length of a $H_C$ region from a Clostridial toxin heavy chain is not necessary for the binding activity of the binding domain. Thus, aspects of this embodiment can include Clostridial toxin $H_C$ regions comprising a binding domain having a length of, e.g., at least 350 amino acids, at least 375 amino acids, at least 400 amino acids and at least 425 amino acids. Other aspects of this embodiment can include Clostridial toxin $H_C$ regions comprising a binding domain having a length of, e.g., at most 350 amino acids, at most 375 amino acids, at most 400 amino acids and at most 425 amino acids.

Any of a variety of sequence alignment methods can be used to determine percent identity of a modified Clostridial toxin $H_C$ region relative to a naturally-occurring Clostridial toxin $H_C$ region, including, without limitation, global methods, local methods and hybrid methods, such as, e.g., segment approach methods. Protocols to determine percent identity are routine procedures within the scope of one skilled in the art and from the teaching herein.

One general approach well known to one skilled in the art on how to modify a Clostridial toxin binding domain in order to increase its binding activity for a naturally-occurring Clostridial toxin receptor system present on a naturally-occurring Clostridial toxin target cell involves changing specifically-identified amino acids. As described above, amino acids essential to binding activity have been identified and methods useful for determining which amino acid substitutions will enhance binding activity are known to one skilled in the art. For example, recent advances in computational protein design algorithims have markedly improved capabilities for generating novel proteins with optimized properties, including, enhanced stability, altered substrate specificity, improved binding affinity and optimized pharmacokinetics, see, e.g., Tanja Kortemme et al., Computational redesign of protein-protein interaction specificity, 11(4) Nat. Struct. Mol. Biol. 371-379 (2004); Tanja Kortemme and David Baker, Computational design of protein-protein interactions, 8(1) Curr. Opin. Chem. Biol. 91-97 (2004); Motomu Shimaoka et al., Computational design of an integrin I domain stabilized in the open high affinity conformation; 7(8) Nat. Struct. Biol. 674-678 (2000); Loïc Martin et al., *Rational Design of a CD*4 *Mimic that Inhibits HIV*-1 *Entry and Exposes Cryptic Neutralization Epitopes,* 21(1) Nat. Biotechnol. 71-76 (2003); and Casim A. Sarkar et al., *Rational Cytokine Design for Increased Lifetime and Enhanced Potency Using pH-activated "Histidine Switching,"* 20(9) Nat. Biotechnol. 908-913 (2002).

In addition, methods capable of altering an amino acid present in a Clostridial toxin binding domain, include, without limitation, site-directed mutagenesis, oligonucleotide-directed mutagenesis and site-specific mutagenesis. Non-limiting examples of specific mutagenesis protocols for making mutations in a Clostridial toxin are described in, e.g., Mutagenesis, pp. 13.1-13.105 (Sambrook and Russell, eds., Molecular Cloning A Laboratory Manual, Vol. 3, $3^{rd}$ ed. 2001). In addition, non-limiting examples of well-characterized mutagenesis protocols available from commercial vendors include, without limitation, Altered Sites® II in vitro Mutagenesis Systems (Promega Corp., Madison, Wis.); Erase-a-Base® System (Promega, Madison, Wis.); GeneTailor™ Site-Directed Mutagenesis System (Invitrogen, Inc., Carlsbad, Calif.); QuikChange® II Site-Directed Mutagenesis Kits (Stratagene, La Jolla, Calif.); and Transformer™ Site-Directed Mutagenesis Kit (BD-Clontech, Mountain View, Calif.).

Lastly, methods to test the binding activity of modified Clostridial toxins comprising a modified Clostridial toxin binding domain with enhanced binding activity are also well known to one skilled in the art, see, e.g., Lutea A. A. de Jong et al., *Receptor-Binding Assays: Technologies and Applications,* 829 J. Chromatogr. B 1-25 (2005). It is envisioned that heterogeneous assay types, homogeneous assay types and non-separating homogeneous assay types can be used to determine the binding activity of a modified Clostridial toxin with enhanced binding activity disclosed in the present specification. In a heterogeneous assay, the free ligand is separated from the bound ligand by, e.g., filtration, centrifugation or dialysis, before measurement of the binding activity. In a homogeneous assay, no separation of the free ligand from the bound ligand is required before measurement of the binding activity. In non-separating homogeneous assays, either the ligand or the receptor is immobilized on a solid phase support, in addition to the no separation aspect of all homogeneous assay. Non-limiting examples of heterogeneous, homogeneous and non-separating homogeneous assays include, e.g., radioactive heterogeneous assays, such as, e.g., filtration assays using radioactive energy transfer, SPA/flash plate assays using radioactive energy transfer; and non-radioactive heterogeneous assays, such as, e.g., filtration assays using fluorescence, FRET assays using fluorescence energy transfer, FP assays using light polarization, single-cell FMAT assays and flow cytometry. In addition, non-limiting examples of well-characterized receptor binding protocols available from commercial vendors include, without limitation, Homogeneous Time Resolved Fluorescense-based receptor binding assays (HTRF®; Cisbio International, Bedford, Mass.); DELFIA®-based receptor binding assays (PerkinElmer Lifesciences, Boston, Mass.); and AlphaScreen™-based receptor binding assays (PerkinElmer Lifesciences, Boston, Mass.).

It is further envisioned that the binding activity of a modified Clostridial toxin with enhanced binding activity disclosed in the present specification can be determined by affinity chromotography using immobilized receptors and interfacial optical assays, such as, e.g., total internal reflection fluorescence (TIRF) and surface plasmon resonance (SPR). Non-limiting examples of these assays include, e.g., FCS using diffusion mediated intensity fluctuations, SPR using a mass-dependent refractive index, TIRF using a mass-independent refractive index, microarrays using optical intensity changes and QAC using retention volume.

As another general approach well known to one skilled in the art on how to modify a Clostridial toxin binding domain in order to increase its binding activity for a naturally-occurring Clostridial toxin receptor system present on a naturally-occurring Clostridial toxin target cell involves directed-evolution methods, see, e.g., Andre Koltermann et al., Process for Generating Sequence-Specific Proteases by Directed Evolution and Uses Thereof, U.S. Patent Publication 2004/0072276 (Apr. 15, 2004); Lance E. Steward and Kei Roger Aoki, Evolved Clostridial Toxins with Altered Protease Activity, U.S. Patent Publication 2004/0115727 (Jun. 17, 2004); and L Yuan et al., Laboratory-directed protein evolution, 69(3) Microbiol. Mol. Biol. Rev. 373-392 (2005).

Often the first step of directed evolution is error-prone PCR amplification of the gene of interest or gene recombination when a family of related genes is available. In this case, the gene corresponding to full-length Clostridial toxin or the $H_C$ binding domain alone would be amplified under conditions that yield one to three amino acid substitutions per molecule. The protein would then be expressed and screened for the desired activity (i.e., receptor binding and/or enhanced activity). Any constructs with even a nominal improvement in receptor binding, regardless of the magnitude of the change, would be submitted for additional rounds of evolution. As a result of the random mutagenesis studies, any amino acids displaying improved binding or even dramatically reduced binding could then be submitted to saturation mutagenesis. This is a process in which the codon of interest it completely randomized so that different constructs containing each of the 20 amino acids substituted at the site of interest are generated.

For improvement of receptor binding characteristics, several different screening approaches could be utilized. If the receptor is known the soluble portion of the receptor can be expressed recombinantly for use in SPR binding assays. For example, the soluble portion of the receptor can be expressed as a fusion to streptavidin, polyhistidine tag, etc. and the receptor can then be immobilized on an appropriate sensor chip. Utilizing a SPR instrument, changes in local refractive index as a result of receptor binding are measured as a change in the SPR angle. The rates of change in the SPR angle can then be analyzed to determine association and dissociation phases and therefore equilibrium constants. This type of assay could be measured either with the full-length Clostridial toxin or the $H_C$ domain. Additionally, binding type assays relying on affinity pull-down experiments with affinity tagged receptors acting as a "bait molecule" could be used. The modified Clostridial toxin or $H_C$ domains could then be labeled with radioisotopes for analysis of the amount of target protein associated with the bait. Alternatively, radiolabeled ligands can be competed with Clostridial toxin or Hc domain variants that are not labeled.

If the receptor is not known, variants of full-length Clostridial toxins can be screened using cells that are known to be sensitive to treatment with native the Clostridial toxin. In this case there are several potential readouts for improved receptor binding, including the presence of the Clostridial toxin in the cell, measurement of cleaved SNARE protein by, e.g., Western blot or cell-based FRET activity assay, or inhibition of exocytosis, e.g., a neurotransmitter release assay.

Thus, in an embodiment, a modified Clostridial toxin disclosed in the present specification comprises a modified Clostridial toxin binding domain with enhanced binding activity. In an aspect of this embodiment, a modified Clostridial toxin binding domain comprises a modified Clostridial toxin $H_C$ region with enhanced binding activity or a modified Clostridial toxin $H_C$ region fragment with enhanced binding activity. In another aspect of this embodiment, a modified Clostridial toxin binding domain comprises a modified Clostridial toxin $H_{CC}$ region with enhanced binding activity or a modified Clostridial toxin $H_{CC}$ region fragment with enhanced binding activity.

In another embodiment, a modified Clostridial toxin binding domain with enhanced binding activity comprises a modified BoNT/A binding domain with enhanced binding activity. In an aspect of this embodiment, a modified BoNT/A binding domain with enhanced binding activity comprises a modified BoNT/A $H_C$ region with enhanced binding activity or a modified BoNT/A $H_C$ region fragment with enhanced binding activity. In another aspect of this embodiment, a modified BoNT/A binding domain with enhanced binding activity comprises a modified BoNT/A $H_{CC}$ region with enhanced binding activity or a modified BoNT/A $H_{CC}$ region fragment with enhanced binding activity.

In other aspects of this embodiment, a modified BoNT/A $H_C$ region with enhanced binding activity comprises a polypeptide having, e.g., at least 70% amino acid identity with amino acids 872-1296 of SEQ ID NO: 1, at least 75% amino acid identity with amino acids 872-1296 of SEQ ID NO: 1, at least 80% amino acid identity with amino acids 872-1296 of SEQ ID NO: 1, at least 85% amino acid identity with amino acids 872-1296 of SEQ ID NO: 1, at least 90% amino acid identity with amino acids 872-1296 of SEQ ID NO: 1 or at least 95% amino acid identity with amino acids 872-1296 of SEQ ID NO: 1. In yet other aspects of this embodiment, a modified BoNT/A $H_C$ region with enhanced binding activity comprises a polypeptide having, e.g., at most 70% amino acid identity with amino acids 872-1296 of SEQ ID NO: 1, at most 75% amino acid identity with amino acids 872-1296 of SEQ ID NO: 1, at most 80% amino acid identity with amino acids 872-1296 of SEQ ID NO: 1, at most 85% amino acid identity with amino acids 872-1296 of SEQ ID NO: 1, at most 90% amino acid identity with amino acids 872-1296 of SEQ ID NO: 1 or at most 95% amino acid identity with amino acids 872-1296 of SEQ ID NO: 1.

In other aspects of this embodiment, a modified BoNT/A $H_C$ region with enhanced binding activity comprises a polypeptide having, e.g., at most one, two, three, four, five, six, seven, eight, nine, 10, 20, 30, 40, 50, 100, or 200 non-contiguous amino acid substitutions relative to amino acids 872-1296 of SEQ ID NO: 1. In other aspects of this embodiment, a modified BoNT/A $H_C$ region with enhanced binding activity comprises a polypeptide having, e.g., at least one, two, three, four, five, six, seven, eight, nine, 10, 20, 30, 40, 50, 100 or 200 non-contiguous amino acid substitutions relative to amino acids 872-1296 of SEQ ID NO: 1. In yet other aspects of this embodiment, a modified BoNT/A $H_C$ region with enhanced binding activity comprises a polypeptide having, e.g., at most one, two, three, four, five, six, seven, eight, nine, 10, 20, 30, 40, 50, 100 or 200 non-contiguous amino acid deletions relative to amino acids 872-1296 of SEQ ID NO: 1. In other aspects of this embodiment, a modified BoNT/A $H_C$ region with enhanced binding activity comprises a polypeptide having, e.g., at least one, two, three, four, five, six, seven, eight, nine, 10, 20, 30, 40, 50, 100 or 200 non-contiguous amino acid deletions relative to amino acids 872-1296 of SEQ ID NO: 1. In still other aspects of this embodiment, a modified BoNT/A $H_C$ region with enhanced binding activity comprises a polypeptide having, e.g., at most one, two, three, four, five, six, seven, eight, nine, 10, 20, 30, 40, 50, 100 or 200 non-contiguous amino acid additions relative to amino acids 872-1296 of SEQ ID NO: 1. In other aspects of this embodiment, a modified BoNT/A $H_C$ region with enhanced binding activity comprises a polypeptide having, e.g., at least one, two, three, four, five, six, seven, eight, nine, 10, 20, 30, 40, 50, 100 or 200 non-contiguous amino acid additions relative to amino acids 872-1296 of SEQ ID NO: 1.

In other aspects of this embodiment, a modified BoNT/A $H_C$ region with enhanced binding activity comprises a polypeptide having, e.g., at most one, two, three, four, five, six, seven, eight, nine, 10, 20, 30, 40, 50, 100 or 200 contiguous amino acid substitutions relative to amino acids 872-1296 of SEQ ID NO: 1. In other aspects of this embodiment, a modified BoNT/A $H_C$ region with enhanced binding activity comprises a polypeptide having, e.g., at least one, two, three, four, five, six, seven, eight, nine, 10, 20, 30, 40, 50, 100 or 200 contiguous amino acid substitutions relative to amino acids 872-1296 of SEQ ID NO: 1. In yet other aspects of this embodiment, a modified BoNT/A $H_C$ region with enhanced binding activity comprises a polypeptide having, e.g., at most one, two, three, four, five, six, seven, eight, nine, 10, 20, 30, 40, 50, 100 or 200 contiguous amino acid deletions relative to amino acids 872-1296 of SEQ ID NO: 1. In other aspects of this embodiment, a modified BoNT/A $H_C$ region with enhanced binding activity comprises a polypeptide having, e.g., at least one, two, three, four, five, six, seven, eight, nine, 10, 20, 30, 40, 50, 100 or 200 contiguous amino acid deletions relative to amino acids 872-1296 of SEQ ID NO: 1. In still other aspects of this embodiment, a modified BoNT/A $H_C$ region with enhanced binding activity comprises a polypeptide having, e.g., at most one, two, three, four, five, six, seven, eight, nine, 10, 20, 30, 40, 50, 100 or 200 contiguous amino acid additions relative to amino acids 872-1296 of SEQ ID NO: 1. In other aspects of this embodiment, a modified BoNT/A $H_C$ region with enhanced binding activity comprises a polypeptide having, e.g., at least one, two, three, four, five, six, seven, eight, nine, 10, 20, 30, 40, 50, 100 or 200 contiguous amino acid additions relative to amino acids 872-1296 of SEQ ID NO: 1.

In another embodiment, a modified BoNT/A $H_C$ region with enhanced binding activity comprises a modified BoNT/A $H_C$ region with enhanced binding activity of comprising a modification of amino acids 1111-1296 of SEQ ID NO: 1. In another aspect of this embodiment, a modified BoNT/A $H_C$ region with enhanced binding activity comprises a modified α-fold motif of a β-trefoil domain of a BoNT/A binding domain, a modified β-fold motif of a β-trefoil domain of a BoNT/A binding domain, or a modified γ-fold motif of a β-trefoil domain of a BoNT/A binding domain. In another aspect of this embodiment, a modified BoNT/A $H_C$ region with enhanced binding activity comprises a modification to amino acids 1111-1162, amino acids 1179-1223, or amino acids 1237-1296 of SEQ ID NO: 1.

In other aspects of this embodiment, a modified BoNT/A $H_C$ region comprising a β-trefoil fold domain with enhanced binding activity comprises a polypeptide having, e.g., at least 70% amino acid identity with amino acids 1111-1162, amino acids 1179-1223, or amino acids 1237-1296 of SEQ ID NO: 1, at least 75% amino acid identity with amino acids 1111-1162, amino acids 1179-1223, or amino acids 1237-1296 of SEQ ID NO: 1, at least 80% amino acid identity with amino acids 1111-1162, amino acids 1179-1223, or amino acids 1237-1296 of SEQ ID NO: 1, at least 85% amino acid identity with amino acids 1111-1162, amino acids 1179-1223, or amino acids 1237-1296 of SEQ ID NO: 1, at least 90% amino acid identity with amino acids 1111-1162, amino acids 1179-1223, or amino acids 1237-1296 of SEQ ID NO: 1 or at least 95% amino acid identity with amino acids 1111-1162, amino acids 1179-1223, or amino acids 1237-1296 of SEQ ID NO: 1. In yet other aspects of this embodiment, a modified BoNT/A $H_C$ region comprising a β-trefoil fold domain with enhanced binding activity comprises a polypeptide having, e.g., at most 70% amino acid identity with amino acids 1111-1162, amino acids 1179-1223, or amino acids 1237-1296 of SEQ ID NO: 1, at most 75% amino acid identity with amino acids 1111-1162, amino acids 1179-1223, or amino acids 1237-1296 of SEQ ID NO: 1, at most 80% amino acid identity with amino acids 1111-1162, amino acids 1179-1223, or amino acids 1237-1296 of SEQ ID NO: 1, at most 85% amino acid identity with amino acids 1111-1162, amino acids 1179-1223, or amino acids 1237-1296 of SEQ ID NO: 1, at most 90% amino acid identity with amino acids 1111-1162, amino acids 1179-1223, or amino acids 1237-1296 of SEQ ID NO: 1 or at most 95% amino acid identity with amino acids 1111-1162, amino acids 1179-1223, or amino acids 1237-1296 of SEQ ID NO: 1.

In other aspects of this embodiment, a modified BoNT/A $H_C$ region comprising a β-trefoil fold domain with enhanced binding activity comprises a polypeptide having, e.g., at most one, two, three, four, five, six, seven, eight, nine, 10 or 20 non-contiguous amino acid substitutions relative to amino acids 1111-1162, amino acids 1179-1223, or amino acids 1237-1296 of SEQ ID NO: 1. In other aspects of this embodiment, a modified BoNT/A $H_C$ region comprises a polypeptide having, e.g., at least one, two, three, four, five, six, seven, eight, nine, 10 or 20 non-contiguous amino acid substitutions relative to amino acids 1111-1162, amino acids 1179-1223, or amino acids 1237-1296 of SEQ ID NO: 1. In yet other aspects of this embodiment, a modified BoNT/A $H_C$ region comprising a β-trefoil fold domain with enhanced binding activity comprises a polypeptide having, e.g., at most one, two, three, four, five, six, seven, eight, nine, 10 or 20 non-contiguous amino acid deletions relative to amino acids 1111-1162, amino acids 1179-1223, or amino acids 1237-1296 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine, 10 or 20 non-contiguous amino acid deletions relative to amino acids 1111-1162, amino acids 1179-1223, or amino acids 1237-1296 of SEQ ID NO: 1. In still other aspects of this embodiment, a modified BoNT/A $H_C$ region comprising a β-trefoil fold domain with enhanced binding activity comprises a polypeptide having, e.g., at most one, two, three, four, five, six, seven, eight, nine, 10 or 20 non-contiguous amino acid additions relative to amino acids 1111-1162, amino acids 1179-1223, or amino acids 1237-1296 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine, 10 or 20 non-contiguous amino acid additions relative to amino acids 1111-1162, amino acids 1179-1223, or amino acids 1237-1296 of SEQ ID NO: 1.

In other aspects of this embodiment, a modified BoNT/A $H_C$ region comprising a β-trefoil fold domain with enhanced binding activity comprises a polypeptide having, e.g., at most one, two, three, four, five, six, seven, eight, nine, 10 or 20 contiguous amino acid substitutions relative to amino acids 1111-1162, amino acids 1179-1223, or amino acids 1237-1296 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine, 10 or 20 contiguous amino acid substitutions relative to amino acids 1111-1162, amino acids 1179-1223, or amino acids 1237-1296 of SEQ ID NO: 1. In yet other aspects of this embodiment, a modified BoNT/A $H_C$ region comprising a β-trefoil fold domain with enhanced binding activity comprises a polypeptide having, e.g., at most one, two, three, four, five, six, seven, eight, nine, 10 or 20 contiguous amino acid deletions relative to amino acids 1111-1162, amino acids 1179-1223, or amino acids 1237-1296 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine, 10 or 20 contiguous amino acid deletions relative to amino acids 1111-1162, amino acids 1179-1223, or amino acids 1237-1296 of SEQ ID NO: 1. In still other aspects of this embodiment, a modified BoNT/A $H_C$ region comprising a β-trefoil fold domain with enhanced binding activity comprises a polypeptide having, e.g., at most one, two, three, four, five, six, seven, eight, nine, 10 or 20 contiguous amino acid additions relative to amino acids 1111-1162, amino acids 1179-1223, or amino acids 1237-1296 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine, 10 or 20 contiguous amino acid additions relative to amino acids 1111-1162, amino acids 1179-1223, or amino acids 1237-1296 of SEQ ID NO: 1.

In another embodiment, a modified BoNT/A $H_C$ region with enhanced binding activity comprises a modified BoNT/A $H_C$ region with enhanced binding activity of comprises a modified β4/β5 hairpin turn of a β-trefoil domain of a BoNT/A binding domain or a β8/β9 hairpin turn of a β-trefoil domain of a BoNT/A binding domain. In another aspect of this embodiment, a modified BoNT/A $H_C$ region with enhanced binding activity comprises a modification of amino acids 1163-1178 or amino acids 1224-1236 of SEQ ID NO: 1.

In other aspects of this embodiment, a modified BoNT/A $H_C$ region comprising a β-trefoil fold domain with enhanced binding activity comprises a polypeptide having, e.g., at least 70% amino acid identity with amino acids 1163-1178 or amino acids 1224-1236 of SEQ ID NO: 1, at least 75% amino acid identity with amino acids 1163-1178 or amino acids 1224-1236 of SEQ ID NO: 1, at least 80% amino acid identity with amino acids 1163-1178 or amino acids 1224-1236 of SEQ ID NO: 1, at least 85% amino acid identity with amino acids 1163-1178 or amino acids 1224-1236 of SEQ ID NO: 1, at least 90% amino acid identity with amino acids 1163-1178 or amino acids 1224-1236 of SEQ ID NO: 1 or at least 95% amino acid identity with amino acids 1163-1178 or amino acids 1224-1236 of SEQ ID NO: 1. In yet other aspects of this embodiment, a modified BoNT/A $H_C$ region comprising a β-trefoil fold domain with enhanced binding activity comprises a polypeptide having, e.g., at most 70% amino acid identity with amino acids 1163-1178 or amino acids 1224-1236 of SEQ ID NO: 1, at most 75% amino acid identity with amino acids 1163-1178 or amino acids 1224-1236 of SEQ ID NO: 1, at most 80% amino acid identity with amino acids 1163-1178 or amino acids 1224-1236 of SEQ ID NO: 1, at most 85% amino acid identity with amino acids 1163-1178 or amino acids 1224-1236 of SEQ ID NO: 1, at most 90% amino acid identity with amino acids 1163-1178 or amino acids 1224-1236 of SEQ ID NO: 1 or at most 95% amino acid identity with amino acids 1163-1178 or amino acids 1224-1236 of SEQ ID NO: 1.

In other aspects of this embodiment, a modified BoNT/A $H_C$ region comprising a β-trefoil fold domain with enhanced binding activity comprises a polypeptide having, e.g., at most one, two, three, four, five, six, seven, eight, nine or 10 non-contiguous amino acid substitutions relative to amino acids 1163-1178 or amino acids 1224-1236 of SEQ ID NO: 1. In other aspects of this embodiment, a modified BoNT/A $H_C$ region comprises a polypeptide having, e.g., at least one, two, three, four, five, six, seven, eight, nine or 10 non-contiguous amino acid substitutions relative to amino acids 1163-1178 or amino acids 1224-1236 of SEQ ID NO: 1. In other aspects of this embodiment, a non-contiguous amino acid substitution of any amino acid from amino acids 1163-1178 or amino acids 1224-1236 of SEQ ID NO: 1 can be replaced with glycine. In other aspects of this embodiment, a non-contiguous amino acid substitution of any hydrophobic amino acid from amino acids 1163-1178 or amino acids 1224-1236 of SEQ ID NO: 1 can be replaced with phenylalanine. In yet other aspects of this embodiment, a modified BoNT/A $H_C$ region comprising a β-trefoil fold domain with enhanced binding activity comprises a polypeptide having, e.g., at most one, two, three, four, five, six, seven, eight, nine or 10 non-contiguous amino acid deletions relative to amino acids 1163-1178 or amino acids 1224-1236 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine or 10 non-contiguous amino acid deletions relative to amino acids 1163-1178 or amino acids 1224-1236 of SEQ ID NO: 1. In still other aspects of this embodiment, a modified BoNT/A $H_C$ region comprising a β-trefoil fold domain with enhanced binding activity comprises a polypeptide having, e.g., at most one, two, three, four, five, six, seven, eight, nine or 10 non-contiguous amino acid additions relative to amino acids 1163-1178 or amino acids 1224-1236 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine or 10 non-contiguous amino acid additions relative to amino acids 1163-1178 or amino acids 1224-1236 of SEQ ID NO: 1.

In other aspects of this embodiment, a modified BoNT/A $H_C$ region comprising a β-trefoil fold domain with enhanced binding activity comprises a polypeptide having, e.g., at most one, two, three, four, five, six, seven, eight, nine or 10 contiguous amino acid substitutions relative to amino acids 1163-1178 or amino acids 1224-1236 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine or 10 contiguous amino acid substitutions relative to amino acids 1163-1178 or amino acids 1224-1236 of SEQ ID NO: 1. In other aspects of this embodiment, contiguous amino acid substitutions of amino acids from amino acids 1163-1178 or amino acids 1224-1236 of SEQ ID NO: 1 can be replaced with glycine. In other aspects of this embodiment, contiguous amino acid substitutions of hydrophobic amino acids from amino acids 1163-1178 or amino acids 1224-1236 of SEQ ID NO: 1 can be replaced with phenylalanine. In yet other aspects of this embodiment, a modified BoNT/A $H_C$ region comprising a β-trefoil fold domain with enhanced binding activity comprises a polypeptide having, e.g., at most one, two, three, four, five, six, seven, eight, nine or 10 contiguous amino acid deletions relative to amino acids 1163-1178 or amino acids 1224-1236 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine or 10 contiguous amino acid deletions relative to amino acids 1163-1178 or amino acids 1224-1236 of SEQ ID NO: 1. In still other aspects of this embodiment, a modified BoNT/A $H_C$ region comprising a β-trefoil fold domain with enhanced binding activity comprises a polypeptide having, e.g., at most one, two, three, four, five, six, seven, eight, nine or 10 contiguous amino acid additions relative to amino acids 1163-1178 or amino acids 1224-1236 of SEQ ID NO: 1. In other aspects of this embodiment, a modified BoNT/A $H_C$ region comprising a β-trefoil fold domain with enhanced binding activity comprises a polypeptide having, e.g., at least one, two, three, four, five, six, seven, eight, nine or 10 contiguous amino acid additions relative to amino acids 1163-1178 or amino acids 1224-1236 of SEQ ID NO: 1.

In other aspects of this embodiment, a modified BoNT/A $H_C$ region with enhanced binding activity comprises a substitution of amino acid Trp 1101, Gly 1102, Leu 1105, Tyr 1111, Tyr 1112, Gly 1158, Ile 1163, Asp 1179, Glu 1203, Phe 1252, Ser 1264, Trp 1266, Tyr 1267, Gln 1270, Gly 1279 or Trp 1282, or any combination thereof, the substitution enhancing the binding activity of the modified BoNT/A $H_C$ region. In other aspects of this embodiment, a modified BoNT/A $H_C$ region with enhanced binding activity comprises a deletion of amino acid Trp 1101, Gly 1102, Leu 1105, Tyr 1111, Tyr 1112, Gly 1158, Ile 1163, Asp 1179, Glu 1203, Phe 1252, Ser 1264, Trp 1266, Tyr 1267, Gln 1270, Gly 1279 or Trp 1282, or any combination thereof, the deletion enhancing the binding activity of the modified BoNT/A $H_C$ region.

In another embodiment, a modified Clostridial toxin binding domain with enhanced binding activity comprises a modified BoNT/B binding domain with enhanced binding activity. In an aspect of this embodiment, a modified BoNT/B binding domain with enhanced binding activity comprises a modified BoNT/B $H_C$ region with enhanced binding activity or a modified BoNT/B $H_C$ region fragment with enhanced binding activity. In another aspect of this embodiment, a modified BoNT/B binding domain with enhanced binding activity comprises a modified BoNT/B $H_{CC}$ region with enhanced binding activity or a modified BoNT/B $H_{CC}$ region fragment with enhanced binding activity.

In other aspects of this embodiment, a modified BoNT/B $H_C$ region with enhanced binding activity comprises a polypeptide having, e.g., at least 70% amino acid identity with amino acids 859-1291 of SEQ ID NO: 2, at least 75% amino acid identity with amino acids 859-1291 of SEQ ID NO: 2, at least 80% amino acid identity with amino acids 859-1291 of SEQ ID NO: 2, at least 85% amino acid identity with amino acids 859-1291 of SEQ ID NO: 2, at least 90% amino acid identity with amino acids 859-1291 of SEQ ID NO: 2 or at least 95% amino acid identity with amino acids 859-1291 of SEQ ID NO: 2. In yet other aspects of this embodiment, a modified BoNT/B $H_C$ region with enhanced binding activity comprises a polypeptide having, e.g., at most 70% amino acid identity with amino acids 859-1291 of SEQ ID NO: 2, at most 75% amino acid identity with amino acids 859-1291 of SEQ ID NO: 2, at most 80% amino acid identity with amino acids 859-1291 of SEQ ID NO: 2, at most 85% amino acid identity with amino acids 859-1291 of SEQ ID NO: 2, at most 90% amino acid identity with amino acids 859-1291 of SEQ ID NO: 2 or at most 95% amino acid identity with amino acids 859-1291 of SEQ ID NO: 2.

In other aspects of this embodiment, a modified BoNT/B $H_C$ region with enhanced binding activity comprises a polypeptide having, e.g., at most one, two, three, four, five, six, seven, eight, nine, 10, 20, 30, 40, 50, 100, or 200 non-contiguous amino acid substitutions relative to amino acids 859-1291 of SEQ ID NO: 2. In other aspects of this embodiment, a modified BoNT/B $H_C$ region with enhanced binding activity comprises a polypeptide having, e.g., at least one, two, three, four, five, six, seven, eight, nine, 10, 20, 30, 40, 50, 100 or 200 non-contiguous amino acid substitutions relative to amino acids 859-1291 of SEQ ID NO: 2. In yet other aspects of this embodiment, a modified BoNT/B $H_C$ region with enhanced binding activity comprises a polypeptide having, e.g., at most one, two, three, four, five, six, seven, eight, nine, 10, 20, 30, 40, 50, 100 or 200 non-contiguous amino acid deletions relative to amino acids 859-1291 of SEQ ID NO: 2. In other aspects of this embodiment, a modified BoNT/B $H_C$ region with enhanced binding activity comprises a polypeptide having, e.g., at least one, two, three, four, five, six, seven, eight, nine, 10, 20, 30, 40, 50, 100 or 200 non-contiguous amino acid deletions relative to amino acids 859-1291 of SEQ ID NO: 2. In still other aspects of this embodiment, a modified BoNT/B $H_C$ region with enhanced binding activity comprises a polypeptide having, e.g., at most one, two, three, four, five, six, seven, eight, nine, 10, 20, 30, 40, 50, 100 or 200 non-contiguous amino acid additions relative to amino acids 859-1291 of SEQ ID NO: 2. In other aspects of this embodiment, a modified BoNT/B $H_C$ region with enhanced binding activity comprises a polypeptide having, e.g., at least one, two, three, four, five, six, seven, eight, nine, 10, 20, 30, 40, 50, 100 or 200 non-contiguous amino acid additions relative to amino acids 859-1291 of SEQ ID NO: 2.

In other aspects of this embodiment, a modified BoNT/B $H_C$ region with enhanced binding activity comprises a polypeptide having, e.g., at most one, two, three, four, five, six, seven, eight, nine, 10, 20, 30, 40, 50, 100 or 200 contiguous amino acid substitutions relative to amino acids 859-1291 of SEQ ID NO: 2. In other aspects of this embodiment, a modified BoNT/B $H_C$ region with enhanced binding activity comprises a polypeptide having, e.g., at least one, two, three, four, five, six, seven, eight, nine, 10, 20, 30, 40, 50, 100 or 200 contiguous amino acid substitutions relative to amino acids 859-1291 of SEQ ID NO: 2. In yet other aspects of this embodiment, a modified BoNT/B $H_C$ region with enhanced binding activity comprises a polypeptide having, e.g., at most one, two, three, four, five, six, seven, eight, nine, 10, 20, 30, 40, 50, 100 or 200 contiguous amino acid deletions relative to amino acids 859-1291 of SEQ ID NO: 2. In other aspects of this embodiment, a modified BoNT/B $H_C$ region with enhanced binding activity comprises a polypeptide having, e.g., at least one, two, three, four, five, six, seven, eight, nine, 10, 20, 30, 40, 50, 100 or 200 contiguous amino acid deletions relative to amino acids 859-1291 of SEQ ID NO: 2. In still other aspects of this embodiment, a modified BoNT/B $H_C$ region with enhanced binding activity comprises a polypeptide having, e.g., at most one, two, three, four, five, six, seven, eight, nine, 10, 20, 30, 40, 50, 100 or 200 contiguous amino acid additions relative to amino acids 859-1291 of SEQ ID NO: 2. In other aspects of this embodiment, a modified BoNT/B $H_C$ region with enhanced binding activity comprises a polypeptide having, e.g., at least one, two, three, four, five, six, seven, eight, nine, 10, 20, 30, 40, 50, 100 or 200 contiguous amino acid additions relative to amino acids 859-1291 of SEQ ID NO: 2.

In another embodiment, a modified BoNT/B $H_C$ region with enhanced binding activity comprises a modified BoNT/B $H_C$ region with enhanced binding activity of comprising a modification of amino acids 1098-1291 of SEQ ID NO: 2. In another aspect of this embodiment, a modified BoNT/B $H_C$ region with enhanced binding activity comprises a modified α-fold motif of a β-trefoil domain of a BoNT/B binding domain, a modified β-fold motif of a β-trefoil domain of a BoNT/B binding domain, or a modified γ-fold motif of a β-trefoil domain of a BoNT/B binding domain. In another aspect of this embodiment, a modified BoNT/B $H_C$ region with enhanced binding activity comprises a modification to amino acids 1098-1147, amino acids 1166-1210, or amino acids 1223-1291 of SEQ ID NO: 2.

In other aspects of this embodiment, a modified BoNT/B $H_C$ region comprising a β-trefoil fold domain with enhanced binding activity comprises a polypeptide having, e.g., at least 70% amino acid identity with amino acids 1098-1147, amino acids 1166-1210, or amino acids 1223-1291 of SEQ ID NO: 2, at least 75% amino acid identity with amino acids 1098-1147, amino acids 1166-1210, or amino acids 1223-1291 of SEQ ID NO: 2, at least 80% amino acid identity with amino acids 1098-1147, amino acids 1166-1210, or amino acids 1223-1291 of SEQ ID NO: 2, at least 85% amino acid identity with amino acids 1098-1147, amino acids 1166-1210, or amino acids 1223-1291 of SEQ ID NO: 2, at least 90% amino acid identity with amino acids 1098-1147, amino acids 1166-1210, or amino acids 1223-1291 of SEQ ID NO: 2 or at least 95% amino acid identity with amino acids 1098-1147, amino acids 1166-1210, or amino acids 1223-1291 of SEQ ID NO: 2. In yet other aspects of this embodiment, a modified BoNT/B $H_C$ region comprising a β-trefoil fold domain with enhanced binding activity comprises a polypeptide having, e.g., at most 70% amino acid identity with amino acids 1098-1147, amino acids 1166-1210, or amino acids 1223-1291 of SEQ ID NO: 2, at most 75% amino acid identity with amino acids 1098-1147, amino acids 1166-1210, or amino acids 1223-1291 of SEQ ID NO: 2, at most 80% amino acid identity with amino acids 1098-1147, amino acids 1166-1210, or amino acids 1223-1291 of SEQ ID NO: 2, at most 85% amino acid identity with amino acids 1098-1147, amino acids 1166-1210, or amino acids 1223-1291 of SEQ ID NO: 2, at most 90% amino acid identity with amino acids 1098-1147, amino acids 1166-1210, or amino acids 1223-1291 of SEQ ID NO: 2 or at most 95% amino acid identity with amino acids 1098-1147, amino acids 1166-1210, or amino acids 1223-1291 of SEQ ID NO: 2.

In other aspects of this embodiment, a modified BoNT/B $H_C$ region comprising a β-trefoil fold domain with enhanced binding activity comprises a polypeptide having, e.g., at most one, two, three, four, five, six, seven, eight, nine, 10 or 20 non-contiguous amino acid substitutions relative to amino acids 1098-1147, amino acids 1166-1210, or amino acids 1223-1291 of SEQ ID NO: 2. In other aspects of this embodiment, a modified BoNT/B $H_C$ region comprises a polypeptide having, e.g., at least one, two, three, four, five, six, seven, eight, nine, 10 or 20 non-contiguous amino acid substitutions relative to amino acids 1098-1147, amino acids 1166-1210, or amino acids 1223-1291 of SEQ ID NO: 2. In yet other aspects of this embodiment, a modified BoNT/B $H_C$ region comprising a β-trefoil fold domain with enhanced binding activity comprises a polypeptide having, e.g., at most one, two, three, four, five, six, seven, eight, nine, 10 or 20 non-contiguous amino acid deletions relative to amino acids 1098-1147, amino acids 1166-1210, or amino acids 1223-1291 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine, 10 or 20 non-contiguous amino acid deletions relative to amino acids 1098-1147, amino acids 1166-1210, or amino acids 1223-1291 of SEQ ID NO: 2. In still other aspects of this embodiment, a modified BoNT/B $H_C$ region comprising a β-trefoil fold domain with enhanced binding activity comprises a polypeptide having, e.g., at most one, two, three, four, five, six, seven, eight, nine, 10 or 20 non-contiguous amino acid additions relative to amino acids 1098-1147, amino acids 1166-1210, or amino acids 1223-1291 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine, 10 or 20 non-contiguous amino acid additions relative to amino acids 1098-1147, amino acids 1166-1210, or amino acids 1223-1291 of SEQ ID NO: 2.

In other aspects of this embodiment, a modified BoNT/B $H_C$ region comprising a β-trefoil fold domain with enhanced binding activity comprises a polypeptide having, e.g., at most one, two, three, four, five, six, seven, eight, nine, 10 or 20 contiguous amino acid substitutions relative to amino acids 1098-1147, amino acids 1166-1210, or amino acids 1223-1291 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine, 10 or 20 contiguous amino acid substitutions relative to amino acids 1098-1147, amino acids 1166-1210, or amino acids 1223-1291 of SEQ ID NO: 2. In yet other aspects of this embodiment, a modified BoNT/B $H_C$ region comprising a β-trefoil fold domain with enhanced binding activity comprises a polypeptide having, e.g., at most one, two, three, four, five, six, seven, eight, nine, 10 or 20 contiguous amino acid deletions relative to amino acids 1098-1147, amino acids 1166-1210, or amino acids 1223-1291 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine, 10 or 20 contiguous amino acid deletions relative to amino acids 1098-1147, amino acids 1166-1210, or amino acids 1223-1291 of SEQ ID NO: 2. In still other aspects of this embodiment, a modified BoNT/B $H_C$ region comprising a β-trefoil fold domain with enhanced binding activity comprises a polypeptide having, e.g., at most one, two, three, four, five, six, seven, eight, nine, 10 or 20 contiguous amino acid additions relative to amino acids 1098-1147, amino acids 1166-1210, or amino acids 1223-1291 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine, 10 or 20 contiguous amino acid additions relative to amino acids 1098-1147, amino acids 1166-1210, or amino acids 1223-1291 of SEQ ID NO: 2.

In another embodiment, a modified BoNT/B $H_C$ region with enhanced binding activity comprises a modified BoNT/B $H_C$ region with enhanced binding activity of comprises a modified β4/β5 hairpin turn of a β-trefoil domain of a BoNT/B binding domain or a β8/β9 hairpin turn of a β-trefoil domain of a BoNT/B binding domain. In another aspect of this embodiment, a modified BoNT/B $H_C$ region with enhanced binding activity comprises a modification of amino acids 1148-1165 or amino acids 1211-1222 of SEQ ID NO: 2.

In other aspects of this embodiment, a modified BoNT/B $H_C$ region comprising a β-trefoil fold domain with enhanced binding activity comprises a polypeptide having, e.g., at least 70% amino acid identity with amino acids 1148-1165 or amino acids 1211-1222 of SEQ ID NO: 2, at least 75% amino acid identity with amino acids 1148-1165 or amino acids 1211-1222 of SEQ ID NO: 2, at least 80% amino acid identity with amino acids 1148-1165 or amino acids 1211-1222 of SEQ ID NO: 2, at least 85% amino acid identity with amino acids 1148-1165 or amino acids 1211-1222 of SEQ ID NO: 2, at least 90% amino acid identity with amino acids 1148-1165 or amino acids 1211-1222 of SEQ ID NO: 2 or at least 95% amino acid identity with amino acids 1148-1165 or amino acids 1211-1222 of SEQ ID NO: 2. In yet other aspects of this embodiment, a modified BoNT/B $H_C$ region comprising a β-trefoil fold domain with enhanced binding activity comprises a polypeptide having, e.g., at most 70% amino acid identity with amino acids 1148-1165 or amino acids 1211-1222 of SEQ ID NO: 2, at most 75% amino acid identity with amino acids 1148-1165 or amino acids 1211-1222 of SEQ ID NO: 2, at most 80% amino acid identity with amino acids 1148-1165 or amino acids 1211-1222 of SEQ ID NO: 2, at most 85% amino acid identity with amino acids 1148-1165 or amino acids 1211-1222 of SEQ ID NO: 2, at most 90% amino acid identity with amino acids 1148-1165 or amino acids 1211-1222 of SEQ ID NO: 2 or at most 95% amino acid identity with amino acids 1148-1165 or amino acids 1211-1222 of SEQ ID NO: 2.

In other aspects of this embodiment, a modified BoNT/B $H_C$ region comprising a β-trefoil fold domain with enhanced binding activity comprises a polypeptide having, e.g., at most one, two, three, four, five, six, seven, eight, nine or 10 non-contiguous amino acid substitutions relative to amino acids 1148-1165 or amino acids 1211-1222 of SEQ ID NO: 2. In other aspects of this embodiment, a modified BoNT/B $H_C$ region comprises a polypeptide having, e.g., at least one, two, three, four, five, six, seven, eight, nine or 10 non-contiguous amino acid substitutions relative to amino acids 1148-1165 or amino acids 1211-1222 of SEQ ID NO: 2. In other aspects of this embodiment, a non-contiguous amino acid substitution of any amino acid from amino acids 1148-1165 or amino acids 1211-1222 of SEQ ID NO: 2 can be replaced with glycine. In other aspects of this embodiment, a non-contiguous amino acid substitution of any hydrophobic amino acid from amino acids 1148-1165 or amino acids 1211-1222 of SEQ ID NO: 2 can be replaced with phenylalanine. In yet other aspects of this embodiment, a modified BoNT/B $H_C$ region comprising a β-trefoil fold domain with enhanced binding activity comprises a polypeptide having, e.g., at most one, two, three, four, five, six, seven, eight, nine or 10 non-contiguous amino acid deletions relative to amino acids 1148-1165 or amino acids 1211-1222 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine or 10 non-contiguous amino acid deletions relative to amino acids 1148-1165 or amino acids 1211-1222 of SEQ ID NO: 2. In still other aspects of this embodiment, a modified BoNT/B $H_C$ region comprising a β-trefoil fold domain with enhanced binding activity comprises a polypeptide having, e.g., at most one, two, three, four, five, six, seven, eight, nine or 10 non-contiguous amino acid additions relative to amino acids 1148-1165 or amino acids 1211-1222 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine or 10 non-contiguous amino acid additions relative to amino acids 1148-1165 or amino acids 1211-1222 of SEQ ID NO: 2.

In other aspects of this embodiment, a modified BoNT/B $H_C$ region comprising a β-trefoil fold domain with enhanced binding activity comprises a polypeptide having, e.g., at most one, two, three, four, five, six, seven, eight, nine or 10 contiguous amino acid substitutions relative to amino acids 1148-1165 or amino acids 1211-1222 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine or 10 contiguous amino acid substitutions relative to amino acids 1148-1165 or amino acids 1211-1222 of SEQ ID NO: 2. In other aspects of this embodiment, contiguous amino acid substitutions of amino acids from amino acids 1148-1165 or amino acids 1211-1222 of SEQ ID NO: 2 can be replaced with glycine. In other aspects of this embodiment, contiguous amino acid substitutions of hydrophobic amino acids from amino acids 1148-1165 or amino acids 1211-1222 of SEQ ID NO: 2 can be replaced with phenylalanine. In yet other aspects of this embodiment, a modified BoNT/B $H_C$ region comprising a β-trefoil fold domain with enhanced binding activity comprises a polypeptide having, e.g., at most one, two, three, four, five, six, seven, eight, nine or 10 contiguous amino acid deletions relative to amino acids 1148-1165 or amino acids 1211-1222 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine or 10 contiguous amino acid deletions relative to amino acids 1148-1165 or amino acids 1211-1222 of SEQ ID NO: 2. In still other aspects of this embodiment, a modified BoNT/B $H_C$ region comprising a β-trefoil fold domain with enhanced binding activity comprises a polypeptide having, e.g., at most one, two, three, four, five, six, seven, eight, nine or 10 contiguous amino acid additions relative to amino acids 1148-1165 or amino acids 1211-1222 of SEQ ID NO: 2. In other aspects of this embodiment, a modified BoNT/B $H_C$ region comprising a β-trefoil fold domain with enhanced binding activity comprises a polypeptide having, e.g., at least one, two, three, four, five, six, seven, eight, nine or 10 contiguous amino acid additions relative to amino acids 1148-1165 or amino acids 1211-1222 of SEQ ID NO: 2.

In other aspects of this embodiment, a modified BoNT/B $H_C$ region with enhanced binding activity comprises a substitution of amino acid Trp 1088, Gly 1089, Leu 1092, Tyr 1098, Tyr 1099, Gly 1142, Ile 1147, Asp 1165, Glu 1191, Ile 1240, Ser 1260, Trp 1262, Tyr 1263, Glu 1266, Gly 1277 or Trp 1280, or any combination thereof, the substitution enhancing the binding activity of the modified BoNT/B $H_C$ region. In other aspects of this embodiment, a modified BoNT/B $H_C$ region with enhanced binding activity comprises a deletion of amino acid Trp 1088, Gly 1089, Leu 1092, Tyr 1098, Tyr 1099, Gly 1142, Ile 1147, Asp 1165, Glu 1191, Ile 1240, Ser 1260, Trp 1262, Tyr 1263, Glu 1266, Gly 1277 or Trp 1280, or any combination thereof, the deletion enhancing the binding activity of the modified BoNT/B $H_C$ region.

In another embodiment, a modified Clostridial toxin binding domain with enhanced binding activity comprises a modified BoNT/C1 binding domain with enhanced binding activity. In an aspect of this embodiment, a modified BoNT/C1 binding domain with enhanced binding activity comprises a modified BoNT/C1 $H_C$ region with enhanced binding activity or a modified BoNT/C1 $H_C$ region fragment with enhanced binding activity. In another aspect of this embodiment, a modified BoNT/C1 binding domain with enhanced binding activity comprises a modified BoNT/C1 $H_{CC}$ region with enhanced binding activity or a modified BoNT/C1 $H_{CC}$ region fragment with enhanced binding activity.

In other aspects of this embodiment, a modified BoNT/C1 $H_C$ region with enhanced binding activity comprises a polypeptide having, e.g., at least 70% amino acid identity with amino acids 867-1291 of SEQ ID NO: 3, at least 75% amino acid identity with amino acids 867-1291 of SEQ ID NO: 3, at least 80% amino acid identity with amino acids 867-1291 of SEQ ID NO: 3, at least 85% amino acid identity with amino acids 867-1291 of SEQ ID NO: 3, at least 90% amino acid identity with amino acids 867-1291 of SEQ ID NO: 3 or at least 95% amino acid identity with amino acids 867-1291 of SEQ ID NO: 3. In yet other aspects of this embodiment, a modified BoNT/C1 $H_C$ region with enhanced binding activity comprises a polypeptide having, e.g., at most 70% amino acid identity with amino acids 867-1291 of SEQ ID NO: 3, at most 75% amino acid identity with amino acids 867-1291 of SEQ ID NO: 3, at most 80% amino acid identity with amino acids 867-1291 of SEQ ID NO: 3, at most 85% amino acid identity with amino acids 867-1291 of SEQ ID NO: 3, at most 90% amino acid identity with amino acids 867-1291 of SEQ ID NO: 3 or at most 95% amino acid identity with amino acids 867-1291 of SEQ ID NO: 3.

In other aspects of this embodiment, a modified BoNT/C1 $H_C$ region with enhanced binding activity comprises a polypeptide having, e.g., at most one, two, three, four, five, six, seven, eight, nine, 10, 20, 30, 40, 50, 100, or 200 non-contiguous amino acid substitutions relative to amino acids 867-1291 of SEQ ID NO: 3. In other aspects of this embodiment, a modified BoNT/C1 $H_C$ region with enhanced binding activity comprises a polypeptide having, e.g., at least one, two, three, four, five, six, seven, eight, nine, 10, 20, 30, 40, 50, 100 or 200 non-contiguous amino acid substitutions relative to amino acids 867-1291 of SEQ ID NO: 3. In yet other aspects of this embodiment, a modified BoNT/C1 $H_C$ region with enhanced binding activity comprises a polypeptide having, e.g., at most one, two, three, four, five, six, seven, eight, nine, 10, 20, 30, 40, 50, 100 or 200 non-contiguous amino acid deletions relative to amino acids 867-1291 of SEQ ID NO: 3. In other aspects of this embodiment, a modified BoNT/C1 $H_C$ region with enhanced binding activity comprises a polypeptide having, e.g., at least one, two, three, four, five, six, seven, eight, nine, 10, 20, 30, 40, 50, 100 or 200 non-contiguous amino acid deletions relative to amino acids 867-1291 of SEQ ID NO: 3. In still other aspects of this embodiment, a modified BoNT/C1 $H_C$ region with enhanced binding activity comprises a polypeptide having, e.g., at most one, two, three, four, five, six, seven, eight, nine, 10, 20, 30, 40, 50, 100 or 200 non-contiguous amino acid additions relative to amino acids 867-1291 of SEQ ID NO: 3. In other aspects of this embodiment, a modified BoNT/C1 $H_C$ region with enhanced binding activity comprises a polypeptide having, e.g., at least one, two, three, four, five, six, seven, eight, nine, 10, 20, 30, 40, 50, 100 or 200 non-contiguous amino acid additions relative to amino acids 867-1291 of SEQ ID NO: 3.

In other aspects of this embodiment, a modified BoNT/C1 $H_C$ region with enhanced binding activity comprises a polypeptide having, e.g., at most one, two, three, four, five, six, seven, eight, nine, 10, 20, 30, 40, 50, 100 or 200 contiguous amino acid substitutions relative to amino acids 867-1291 of SEQ ID NO: 3. In other aspects of this embodiment, a modified BoNT/C1 $H_C$ region with enhanced binding activity comprises a polypeptide having, e.g., at least one, two, three, four, five, six, seven, eight, nine, 10, 20, 30, 40, 50, 100 or 200 contiguous amino acid substitutions relative to amino acids 867-1291 of SEQ ID NO: 3. In yet other aspects of this embodiment, a modified BoNT/C1 $H_C$ region with enhanced binding activity comprises a polypeptide having, e.g., at most one, two, three, four, five, six, seven, eight, nine, 10, 20, 30, 40, 50, 100 or 200 contiguous amino acid deletions relative to amino acids 867-1291 of SEQ ID NO: 3. In other aspects of this embodiment, a modified BoNT/C1 $H_C$ region with enhanced binding activity comprises a polypeptide having, e.g., at least one, two, three, four, five, six, seven, eight, nine, 10, 20, 30, 40, 50, 100 or 200 contiguous amino acid deletions relative to amino acids 867-1291 of SEQ ID NO: 3. In still other aspects of this embodiment, a modified BoNT/C1 $H_C$ region with enhanced binding activity comprises a polypeptide having, e.g., at most one, two, three, four, five, six, seven, eight, nine, 10, 20, 30, 40, 50, 100 or 200 contiguous amino acid additions relative to amino acids 867-1291 of SEQ ID NO: 3. In other aspects of this embodiment, a modified BoNT/C1 $H_C$ region with enhanced binding activity comprises a polypeptide having, e.g., at least one, two, three, four, five, six, seven, eight, nine, 10, 20, 30, 40, 50, 100 or 200 contiguous amino acid additions relative to amino acids 867-1291 of SEQ ID NO: 3.

In another embodiment, a modified BoNT/C1 $H_C$ region with enhanced binding activity comprises a modified BoNT/C1 $H_C$ region with enhanced binding activity of comprising a modification of amino acids 1112-1291 of SEQ ID NO: 3. In another aspect of this embodiment, a modified BoNT/C1 $H_C$ region with enhanced binding activity comprises a modified α-fold motif of a β-trefoil domain of a BoNT/C1 binding domain, a modified β-fold motif of a β-trefoil domain of a BoNT/C1 binding domain, or a modified γ-fold motif of a β-trefoil domain of a BoNT/C1 binding domain. In another aspect of this embodiment, a modified BoNT/C1 $H_C$ region with enhanced binding activity comprises a modification to amino acids 1112-1150, amino acids 1167-1218, or amino acids 1230-1291 of SEQ ID NO: 3.

In other aspects of this embodiment, a modified BoNT/C1 $H_C$ region comprising a β-trefoil fold domain with enhanced binding activity comprises a polypeptide having, e.g., at least 70% amino acid identity with amino acids 1112-1150, amino acids 1167-1218, or amino acids 1230-1291 of SEQ ID NO: 3, at least 75% amino acid identity with amino acids 1112-1150, amino acids 1167-1218, or amino acids 1230-1291 of SEQ ID NO: 3, at least 80% amino acid identity with amino acids 1112-1150, amino acids 1167-1218, or amino acids 1230-1291 of SEQ ID NO: 3, at least 85% amino acid identity with amino acids 1112-1150, amino acids 1167-1218, or amino acids 1230-1291 of SEQ ID NO: 3, at least 90% amino acid identity with amino acids 1112-1150, amino acids 1167-1218, or amino acids 1230-1291 of SEQ ID NO: 3 or at least 95% amino acid identity with amino acids 1112-1150, amino acids 1167-1218, or amino acids 1230-1291 of SEQ ID NO: 3. In yet other aspects of this embodiment, a modified BoNT/C1 $H_C$ region comprising a β-trefoil fold domain with enhanced binding activity comprises a polypeptide having, e.g., at most 70% amino acid identity with amino acids 1112-1150, amino acids 1167-1218, or amino acids 1230-1291 of SEQ ID NO: 3, at most 75% amino acid identity with amino acids 1112-1150, amino acids 1167-1218, or amino acids 1230-1291 of SEQ ID NO: 3, at most 80% amino acid identity with amino acids 1112-1150, amino acids 1167-1218, or amino acids 1230-1291 of SEQ ID NO: 3, at most 85% amino acid identity with amino acids 1112-1150, amino acids 1167-1218, or amino acids 1230-1291 of SEQ ID NO: 3, at most 90% amino acid identity with amino acids 1112-1150, amino acids 1167-1218, or amino acids 1230-1291 of SEQ ID NO: 3 or at most 95% amino acid identity with amino acids 1112-1150, amino acids 1167-1218, or amino acids 1230-1291 of SEQ ID NO: 3.

In other aspects of this embodiment, a modified BoNT/C1 $H_C$ region comprising a β-trefoil fold domain with enhanced binding activity comprises a polypeptide having, e.g., at most one, two, three, four, five, six, seven, eight, nine, 10 or 20 non-contiguous amino acid substitutions relative to amino acids 1112-1150, amino acids 1167-1218, or amino acids 1230-1291 of SEQ ID NO: 3. In other aspects of this embodiment, a modified BoNT/C1 $H_C$ region comprises a polypeptide having, e.g., at least one, two, three, four, five, six, seven, eight, nine, 10 or 20 non-contiguous amino acid substitutions relative to amino acids 1112-1150, amino acids 1167-1218, or amino acids 1230-1291 of SEQ ID NO: 3. In yet other aspects of this embodiment, a modified BoNT/C1 $H_C$ region comprising a β-trefoil fold domain with enhanced binding activity comprises a polypeptide having, e.g., at most one, two, three, four, five, six, seven, eight, nine, 10 or 20 non-contiguous amino acid deletions relative to amino acids 1112-1150, amino acids 1167-1218, or amino acids 1230-1291 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine, 10 or 20 non-contiguous amino acid deletions relative to amino acids 1112-1150, amino acids 1167-1218, or amino acids 1230-1291 of SEQ ID NO: 3. In still other aspects of this embodiment, a modified BoNT/C1 $H_C$ region comprising a β-trefoil fold domain with enhanced binding activity comprises a polypeptide having, e.g., at most one, two, three, four, five, six, seven, eight, nine, 10 or 20 non-contiguous amino acid additions relative to amino acids 1112-1150, amino acids 1167-1218, or amino acids 1230-1291 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine, 10 or 20 non-contiguous amino acid additions relative to amino acids 1112-1150, amino acids 1167-1218, or amino acids 1230-1291 of SEQ ID NO: 3.

In other aspects of this embodiment, a modified BoNT/C1 $H_C$ region comprising a β-trefoil fold domain with enhanced binding activity comprises a polypeptide having, e.g., at most one, two, three, four, five, six, seven, eight, nine, 10 or 20 contiguous amino acid substitutions relative to amino acids 1112-1150, amino acids 1167-1218, or amino acids 1230-1291 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine, 10 or 20 contiguous amino acid substitutions relative to amino acids 1112-1150, amino acids 1167-1218, or amino acids 1230-1291 of SEQ ID NO: 3. In yet other aspects of this embodiment, a modified BoNT/C1 $H_C$ region comprising a β-trefoil fold domain with enhanced binding activity comprises a polypeptide having, e.g., at most one, two, three, four, five, six, seven, eight, nine, 10 or 20 contiguous amino acid deletions relative to amino acids 1112-1150, amino acids 1167-1218, or amino acids 1230-1291 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine, 10 or 20 contiguous amino acid deletions relative to amino acids 1112-1150, amino acids 1167-1218, or amino acids 1230-1291 of SEQ ID NO: 3. In still other aspects of this embodiment, a modified BoNT/C1 $H_C$ region comprising a β-trefoil fold domain with enhanced binding activity comprises a polypeptide having, e.g., at most one, two, three, four, five, six, seven, eight, nine, 10 or 20 contiguous amino acid additions relative to amino acids 1112-1150, amino acids 1167-1218, or amino acids 1230-1291 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine, 10 or 20 contiguous amino acid additions relative to amino acids 1112-1150, amino acids 1167-1218, or amino acids 1230-1291 of SEQ ID NO: 3.

In another embodiment, a modified BoNT/C1 $H_C$ region with enhanced binding activity comprises a modified BoNT/C1 $H_C$ region with enhanced binding activity of comprises a modified β4/β5 hairpin turn of a β-trefoil domain of a BoNT/C1 binding domain or a β8/β9 hairpin turn of a β-trefoil domain of a BoNT/C1 binding domain. In another aspect of this embodiment, a modified BoNT/C1 $H_C$ region with enhanced binding activity comprises a modification of amino acids 1151-1166 or amino acids 1219-1229 of SEQ ID NO: 3.

In other aspects of this embodiment, a modified BoNT/C1 $H_C$ region comprising a β-trefoil fold domain with enhanced binding activity comprises a polypeptide having, e.g., at least 70% amino acid identity with amino acids 1151-1166 or amino acids 1219-1229 of SEQ ID NO: 3, at least 75% amino acid identity with amino acids 1151-1166 or amino acids 1219-1229 of SEQ ID NO: 3, at least 80% amino acid identity with amino acids 1151-1166 or amino acids 1219-1229 of SEQ ID NO: 3, at least 85% amino acid identity with amino acids 1151-1166 or amino acids 1219-1229 of SEQ ID NO: 3, at least 90% amino acid identity with amino acids 1151-1166 or amino acids 1219-1229 of SEQ ID NO: 3 or at least 95% amino acid identity with amino acids 1151-1166 or amino acids 1219-1229 of SEQ ID NO: 3. In yet other aspects of this embodiment, a modified BoNT/C1 $H_C$ region comprising a β-trefoil fold domain with enhanced binding activity comprises a polypeptide having, e.g., at most 70% amino acid identity with amino acids 1151-1166 or amino acids 1219-1229 of SEQ ID NO: 3, at most 75% amino acid identity with amino acids 1151-1166 or amino acids 1219-1229 of SEQ ID NO: 3, at most 80% amino acid identity with amino acids 1151-1166 or amino acids 1219-1229 of SEQ ID NO: 3, at most 85% amino acid identity with amino acids 1151-1166 or amino acids 1219-1229 of SEQ ID NO: 3, at most 90% amino acid identity with amino acids 1151-1166 or amino acids 1219-1229 of SEQ ID NO: 3 or at most 95% amino acid identity with amino acids 1151-1166 or amino acids 1219-1229 of SEQ ID NO: 3.

In other aspects of this embodiment, a modified BoNT/C1 $H_C$ region comprising a β-trefoil fold domain with enhanced binding activity comprises a polypeptide having, e.g., at most one, two, three, four, five, six, seven, eight, nine or 10 non-contiguous amino acid substitutions relative to amino acids 1151-1166 or amino acids 1219-1229 of SEQ ID NO: 3. In other aspects of this embodiment, a modified BoNT/C1 $H_C$ region comprises a polypeptide having, e.g., at least one, two, three, four, five, six, seven, eight, nine or 10 non-contiguous amino acid substitutions relative to amino acids 1151-1166 or amino acids 1219-1229 of SEQ ID NO: 3. In other aspects of this embodiment, a non-contiguous amino acid substitution of any amino acid from amino acids 1151-1166 or amino acids 1219-1229 of SEQ ID NO: 3 can be replaced with glycine. In other aspects of this embodiment, a non-contiguous amino acid substitution of any hydrophobic amino acid from amino acids 1151-1166 or amino acids 1219-1229 of SEQ ID NO: 3 can be replaced with phenylalanine. In yet other aspects of this embodiment, a modified BoNT/C1 $H_C$ region comprising a β-trefoil fold domain with enhanced binding activity comprises a polypeptide having, e.g., at most one, two, three, four, five, six, seven, eight, nine or 10 non-contiguous amino acid deletions relative to amino acids 1151-1166 or amino acids 1219-1229 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine or 10 non-contiguous amino acid deletions relative to amino acids 1151-1166 or amino acids 1219-1229 of SEQ ID NO: 3. In still other aspects of this embodiment, a modified BoNT/C1 $H_C$ region comprising a β-trefoil fold domain with enhanced binding activity comprises a polypeptide having, e.g., at most one, two, three, four, five, six, seven, eight, nine or 10 non-contiguous amino acid additions relative to amino acids 1151-1166 or amino acids 1219-1229 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine or 10 non-contiguous amino acid additions relative to amino acids 1151-1166 or amino acids 1219-1229 of SEQ ID NO: 3.

In other aspects of this embodiment, a modified BoNT/C1 $H_C$ region comprising a β-trefoil fold domain with enhanced binding activity comprises a polypeptide having, e.g., at most one, two, three, four, five, six, seven, eight, nine or 10 contiguous amino acid substitutions relative to amino acids 1151-1166 or amino acids 1219-1229 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine or 10 contiguous amino acid substitutions relative to amino acids 1151-1166 or amino acids 1219-1229 of SEQ ID NO: 3. In other aspects of this embodiment, contiguous amino acid substitutions of amino acids from amino acids 1151-1166 or amino acids 1219-1229 of SEQ ID NO: 3 can be replaced with glycine. In other aspects of this embodiment, contiguous amino acid substitutions of hydrophobic amino acids from amino acids 1151-1166 or amino acids 1219-1229 of SEQ ID NO: 3 can be replaced with phenylalanine. In yet other aspects of this embodiment, a modified BoNT/C1 $H_C$ region comprising a β-trefoil fold domain with enhanced binding activity comprises a polypeptide having, e.g., at most one, two, three, four, five, six, seven, eight, nine or 10 contiguous amino acid deletions relative to amino acids 1151-1166 or amino acids 1219-1229 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine or 10 contiguous amino acid deletions relative to amino acids 1151-1166 or amino acids 1219-1229 of SEQ ID NO: 3. In still other aspects of this embodiment, a modified BoNT/C1 $H_C$ region comprising a β-trefoil fold domain with enhanced binding activity comprises a polypeptide having, e.g., at most one, two, three, four, five, six, seven, eight, nine or 10 contiguous amino acid additions relative to amino acids 1151-1166 or amino acids 1219-1229 of SEQ ID NO: 3. In other aspects of this embodiment, a modified BoNT/C1 $H_C$ region comprising a β-trefoil fold domain with enhanced binding activity comprises a polypeptide having, e.g., at least one, two, three, four, five, six, seven, eight, nine or 10 contiguous amino acid additions relative to amino acids 1151-1166 or amino acids 1219-1229 of SEQ ID NO: 3.

In other aspects of this embodiment, a modified BoNT/C1 $H_C$ region with enhanced binding activity comprises a substitution of amino acid Trp 1102, Gly 1103, Leu 1106, Tyr 1112, Tyr 1113, Gly 1145, Ile 1150, Asp 1166, Glu 1196, Ile 1247, Gly 1256, Trp 1258, Tyr 1259, His 1261, Gly 1281 or Trp 1284, or any combination thereof, the substitution enhancing the binding activity of the modified BoNT/C1 $H_C$ region. In other aspects of this embodiment, a modified BoNT/C1 $H_C$ region with enhanced binding activity comprises a deletion of amino acid Trp 1102, Gly 1103, Leu 1106, Tyr 1112, Tyr 1113, Gly 1145, Ile 1150, Asp 1166, Glu 1196, Ile 1247, Gly 1256, Trp 1258, Tyr 1259, His 1261, Gly 1281 or Trp 1284, or any combination thereof, the deletion enhancing the binding activity of the modified BoNT/C1 $H_C$ region.

In another embodiment, a modified Clostridial toxin binding domain with enhanced binding activity comprises a modified BoNT/D binding domain with enhanced binding activity. In an aspect of this embodiment, a modified BoNT/D binding domain with enhanced binding activity comprises a modified BoNT/D $H_C$ region with enhanced binding activity or a modified BoNT/D $H_C$ region fragment with enhanced binding activity. In another aspect of this embodiment, a modified BoNT/D binding domain with enhanced binding activity comprises a modified BoNT/D $H_{CC}$ region with enhanced binding activity or a modified BoNT/D $H_{CC}$ region fragment with enhanced binding activity.

In other aspects of this embodiment, a modified BoNT/D $H_C$ region with enhanced binding activity comprises a polypeptide having, e.g., at least 70% amino acid identity with amino acids 863-1276 of SEQ ID NO: 4, at least 75% amino acid identity with amino acids 863-1276 of SEQ ID NO: 4, at least 80% amino acid identity with amino acids 863-1276 of SEQ ID NO: 4, at least 85% amino acid identity with amino acids 863-1276 of SEQ ID NO: 4, at least 90% amino acid identity with amino acids 863-1276 of SEQ ID NO: 4 or at least 95% amino acid identity with amino acids 863-1276 of SEQ ID NO: 4. In yet other aspects of this embodiment, a modified BoNT/D $H_C$ region with enhanced binding activity comprises a polypeptide having, e.g., at most 70% amino acid identity with amino acids 863-1276 of SEQ ID NO: 4, at most 75% amino acid identity with amino acids 863-1276 of SEQ ID NO: 4, at most 80% amino acid identity with amino acids 863-1276 of SEQ ID NO: 4, at most 85% amino acid identity with amino acids 863-1276 of SEQ ID NO: 4, at most 90% amino acid identity with amino acids 863-1276 of SEQ ID NO: 4 or at most 95% amino acid identity with amino acids 863-1276 of SEQ ID NO: 4.

In other aspects of this embodiment, a modified BoNT/D $H_C$ region with enhanced binding activity comprises a polypeptide having, e.g., at most one, two, three, four, five, six, seven, eight, nine, 10, 20, 30, 40, 50, 100, or 200 non-contiguous amino acid substitutions relative to amino acids 863-1276 of SEQ ID NO: 4. In other aspects of this embodiment, a modified BoNT/D $H_C$ region with enhanced binding activity comprises a polypeptide having, e.g., at least one, two, three, four, five, six, seven, eight, nine, 10, 20, 30, 40, 50, 100 or 200 non-contiguous amino acid substitutions relative to amino acids 863-1276 of SEQ ID NO: 4. In yet other aspects of this embodiment, a modified BoNT/D $H_C$ region with enhanced binding activity comprises a polypeptide having, e.g., at most one, two, three, four, five, six, seven, eight, nine, 10, 20, 30, 40, 50, 100 or 200 non-contiguous amino acid deletions relative to amino acids 863-1276 of SEQ ID NO: 4. In other aspects of this embodiment, a modified BoNT/D $H_C$ region with enhanced binding activity comprises a polypeptide having, e.g., at least one, two, three, four, five, six, seven, eight, nine, 10, 20, 30, 40, 50, 100 or 200 non-contiguous amino acid deletions relative to amino acids 863-1276 of SEQ ID NO: 4. In still other aspects of this embodiment, a modified BoNT/D $H_C$ region with enhanced binding activity comprises a polypeptide having, e.g., at most one, two, three, four, five, six, seven, eight, nine, 10, 20, 30, 40, 50, 100 or 200 non-contiguous amino acid additions relative to amino acids 863-1276 of SEQ ID NO: 4. In other aspects of this embodiment, a modified BoNT/D $H_C$ region with enhanced binding activity comprises a polypeptide having, e.g., at least one, two, three, four, five, six, seven, eight, nine, 10, 20, 30, 40, 50, 100 or 200 non-contiguous amino acid additions relative to amino acids 863-1276 of SEQ ID NO: 4.

In other aspects of this embodiment, a modified BoNT/D $H_C$ region with enhanced binding activity comprises a polypeptide having, e.g., at most one, two, three, four, five, six, seven, eight, nine, 10, 20, 30, 40, 50, 100 or 200 contiguous amino acid substitutions relative to amino acids 863-1276 of SEQ ID NO: 4. In other aspects of this embodiment, a modified BoNT/D $H_C$ region with enhanced binding activity comprises a polypeptide having, e.g., at least one, two, three, four, five, six, seven, eight, nine, 10, 20, 30, 40, 50, 100 or 200 contiguous amino acid substitutions relative to amino acids 863-1276 of SEQ ID NO: 4. In yet other aspects of this embodiment, a modified BoNT/D $H_C$ region with enhanced binding activity comprises a polypeptide having, e.g., at most one, two, three, four, five, six, seven, eight, nine, 10, 20, 30, 40, 50, 100 or 200 contiguous amino acid deletions relative to amino acids 863-1276 of SEQ ID NO: 4. In other aspects of this embodiment, a modified BoNT/D $H_C$ region with enhanced binding activity comprises a polypeptide having, e.g., at least one, two, three, four, five, six, seven, eight, nine, 10, 20, 30, 40, 50, 100 or 200 contiguous amino acid deletions relative to amino acids 863-1276 of SEQ ID NO: 4. In still other aspects of this embodiment, a modified BoNT/D $H_C$ region with enhanced binding activity comprises a polypeptide having, e.g., at most one, two, three, four, five, six, seven, eight, nine, 10, 20, 30, 40, 50, 100 or 200 contiguous amino acid additions relative to amino acids 863-1276 of SEQ ID NO: 4. In other aspects of this embodiment, a modified BoNT/D $H_C$ region with enhanced binding activity comprises a polypeptide having, e.g., at least one, two, three, four, five, six, seven, eight, nine, 10, 20, 30, 40, 50, 100 or 200 contiguous amino acid additions relative to amino acids 863-1276 of SEQ ID NO: 4.

In another embodiment, a modified BoNT/D $H_C$ region with enhanced binding activity comprises a modified BoNT/D $H_C$ region with enhanced binding activity of comprising a modification of amino acids 1099-1276 of SEQ ID NO: 4. In another aspect of this embodiment, a modified BoNT/D $H_C$ region with enhanced binding activity comprises a modified α-fold motif of a β-trefoil domain of a BoNT/D binding domain, a modified β-fold motif of a β-trefoil domain of a BoNT/D binding domain, or a modified γ-fold motif of a β-trefoil domain of a BoNT/D binding domain. In another aspect of this embodiment, a modified BoNT/D $H_C$ region with enhanced binding activity comprises a modification to amino acids 1099-1137, amino acids 1154-1207, or amino acids 1219-1276 of SEQ ID NO: 4.

In other aspects of this embodiment, a modified BoNT/D $H_C$ region comprising a β-trefoil fold domain with enhanced binding activity comprises a polypeptide having, e.g., at least 70% amino acid identity with amino acids 1099-1137, amino acids 1154-1207, or amino acids 1219-1276 of SEQ ID NO: 4, at least 75% amino acid identity with amino acids 1099-1137, amino acids 1154-1207, or amino acids 1219-1276 of SEQ ID NO: 4, at least 80% amino acid identity with amino acids 1099-1137, amino acids 1154-1207, or amino acids 1219-1276 of SEQ ID NO: 4, at least 85% amino acid identity with amino acids 1099-1137, amino acids 1154-1207, or amino acids 1219-1276 of SEQ ID NO: 4, at least 90% amino acid identity with amino acids 1099-1137, amino acids 1154-1207, or amino acids 1219-1276 of SEQ ID NO: 4 or at least 95% amino acid identity with amino acids 1099-1137, amino acids 1154-1207, or amino acids 1219-1276 of SEQ ID NO: 4. In yet other aspects of this embodiment, a modified BoNT/D $H_C$ region comprising a β-trefoil fold domain with enhanced binding activity comprises a polypeptide having, e.g., at most 70% amino acid identity with amino acids 1099-1137, amino acids 1154-1207, or amino acids 1219-1276 of SEQ ID NO: 4, at most 75% amino acid identity with amino acids 1099-1137, amino acids 1154-1207, or amino acids 1219-1276 of SEQ ID NO: 4, at most 80% amino acid identity with amino acids 1099-1137, amino acids 1154-1207, or amino acids 1219-1276 of SEQ ID NO: 4, at most 85% amino acid identity with amino acids 1099-1137, amino acids 1154-1207, or amino acids 1219-1276 of SEQ ID NO: 4, at most 90% amino acid identity with amino acids 1099-1137, amino acids 1154-1207, or amino acids 1219-1276 of SEQ ID NO: 4 or at most 95% amino acid identity with amino acids 1099-1137, amino acids 1154-1207, or amino acids 1219-1276 of SEQ ID NO: 4.

In other aspects of this embodiment, a modified BoNT/D $H_C$ region comprising a β-trefoil fold domain with enhanced binding activity comprises a polypeptide having, e.g., at most one, two, three, four, five, six, seven, eight, nine, 10 or 20 non-contiguous amino acid substitutions relative to amino acids 1099-1137, amino acids 1154-1207, or amino acids 1219-1276 of SEQ ID NO: 4. In other aspects of this embodiment, a modified BoNT/D $H_C$ region comprises a polypeptide having, e.g., at least one, two, three, four, five, six, seven, eight, nine, 10 or 20 non-contiguous amino acid substitutions relative to amino acids 1099-1137, amino acids 1154-1207, or amino acids 1219-1276 of SEQ ID NO: 4. In yet other aspects of this embodiment, a modified BoNT/D $H_C$ region comprising a β-trefoil fold domain with enhanced binding activity comprises a polypeptide having, e.g., at most one, two, three, four, five, six, seven, eight, nine, 10 or 20 non-contiguous amino acid deletions relative to amino acids 1099-1137, amino acids 1154-1207, or amino acids 1219-1276 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine, 10 or 20 non-contiguous amino acid deletions relative to amino acids 1099-1137, amino acids 1154-1207, or amino acids 1219-1276 of SEQ ID NO: 4. In still other aspects of this embodiment, a modified BoNT/D $H_C$ region comprising a β-trefoil fold domain with enhanced binding activity comprises a polypeptide having, e.g., at most one, two, three, four, five, six, seven, eight, nine, 10 or 20 non-contiguous amino acid additions relative to amino acids 1099-1137, amino acids 1154-1207, or amino acids 1219-1276 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine, 10 or 20 non-contiguous amino acid additions relative to amino acids 1099-1137, amino acids 1154-1207, or amino acids 1219-1276 of SEQ ID NO: 4.

In other aspects of this embodiment, a modified BoNT/D $H_C$ region comprising a β-trefoil fold domain with enhanced binding activity comprises a polypeptide having, e.g., at most one, two, three, four, five, six, seven, eight, nine, 10 or 20 contiguous amino acid substitutions relative to amino acids 1099-1137, amino acids 1154-1207, or amino acids 1219-1276 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine, 10 or 20 contiguous amino acid substitutions relative to amino acids 1099-1137, amino acids 1154-1207, or amino acids 1219-1276 of SEQ ID NO: 4. In yet other aspects of this embodiment, a modified BoNT/D $H_C$ region comprising a β-trefoil fold domain with enhanced binding activity comprises a polypeptide having, e.g., at most one, two, three, four, five, six, seven, eight, nine, 10 or 20 contiguous amino acid deletions relative to amino acids 1099-1137, amino acids 1154-1207, or amino acids 1219-1276 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine, 10 or 20 contiguous amino acid deletions relative to amino acids 1099-1137, amino acids 1154-1207, or amino acids 1219-1276 of SEQ ID NO: 4. In still other aspects of this embodiment, a modified BoNT/D $H_C$ region comprising a β-trefoil fold domain with enhanced binding activity comprises a polypeptide having, e.g., at most one, two, three, four, five, six, seven, eight, nine, 10 or 20 contiguous amino acid additions relative to amino acids 1099-1137, amino acids 1154-1207, or amino acids 1219-1276 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine, 10 or 20 contiguous amino acid additions relative to amino acids 1099-1137, amino acids 1154-1207, or amino acids 1219-1276 of SEQ ID NO: 4.

In another embodiment, a modified BoNT/D $H_C$ region with enhanced binding activity comprises a modified BoNT/D $H_C$ region with enhanced binding activity of comprises a modified β4/β5 hairpin turn of a β-trefoil domain of a BoNT/D binding domain or a β8/β9 hairpin turn of a β-trefoil domain of a BoNT/D binding domain. In another aspect of this embodiment, a modified BoNT/D $H_C$ region with enhanced binding activity comprises a modification of amino acids 1138-1153 or amino acids 1208-1218 of SEQ ID NO: 4.

In other aspects of this embodiment, a modified BoNT/D $H_C$ region comprising a β-trefoil fold domain with enhanced binding activity comprises a polypeptide having, e.g., at least 70% amino acid identity with amino acids 1138-1153 or amino acids 1208-1218 of SEQ ID NO: 4, at least 75% amino acid identity with amino acids 1138-1153 or amino acids 1208-1218 of SEQ ID NO: 4, at least 80% amino acid identity with amino acids 1138-1153 or amino acids 1208-1218 of SEQ ID NO: 4, at least 85% amino acid identity with amino acids 1138-1153 or amino acids 1208-1218 of SEQ ID NO: 4, at least 90% amino acid identity with amino acids 1138-1153 or amino acids 1208-1218 of SEQ ID NO: 4 or at least 95% amino acid identity with amino acids 1138-1153 or amino acids 1208-1218 of SEQ ID NO: 4. In yet other aspects of this embodiment, a modified BoNT/D $H_C$ region comprising a β-trefoil fold domain with enhanced binding activity comprises a polypeptide having, e.g., at most 70% amino acid identity with amino acids 1138-1153 or amino acids 1208-1218 of SEQ ID NO: 4, at most 75% amino acid identity with amino acids 1138-1153 or amino acids 1208-1218 of SEQ ID NO: 4, at most 80% amino acid identity with amino acids 1138-1153 or amino acids 1208-1218 of SEQ ID NO: 4, at most 85% amino acid identity with amino acids 1138-1153 or amino acids 1208-1218 of SEQ ID NO: 4, at most 90% amino acid identity with amino acids 1138-1153 or amino acids 1208-1218 of SEQ ID NO: 4 or at most 95% amino acid identity with amino acids 1138-1153 or amino acids 1208-1218 of SEQ ID NO: 4.

In other aspects of this embodiment, a modified BoNT/D $H_C$ region comprising a β-trefoil fold domain with enhanced binding activity comprises a polypeptide having, e.g., at most one, two, three, four, five, six, seven, eight, nine or 10 non-contiguous amino acid substitutions relative to amino acids 1138-1153 or amino acids 1208-1218 of SEQ ID NO: 4. In other aspects of this embodiment, a modified BoNT/D $H_C$ region comprises a polypeptide having, e.g., at least one, two, three, four, five, six, seven, eight, nine or 10 non-contiguous amino acid substitutions relative to amino acids 1138-1153 or amino acids 1208-1218 of SEQ ID NO: 4. In other aspects of this embodiment, a non-contiguous amino acid substitution of any amino acid from amino acids 1138-1153 or amino acids 1208-1218 of SEQ ID NO: 4 can be replaced with glycine. In other aspects of this embodiment, a non-contiguous amino acid substitution of any hydrophobic amino acid from amino acids 1138-1153 or amino acids 1208-1218 of SEQ ID NO: 4 can be replaced with phenylalanine. In yet other aspects of this embodiment, a modified BoNT/D $H_C$ region comprising a β-trefoil fold domain with enhanced binding activity comprises a polypeptide having, e.g., at most one, two, three, four, five, six, seven, eight, nine or 10 non-contiguous amino acid deletions relative to amino acids 1138-1153 or amino acids 1208-1218 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine or 10 non-contiguous amino acid deletions relative to amino acids 1138-1153 or amino acids 1208-1218 of SEQ ID NO: 4. In still other aspects of this embodiment, a modified BoNT/D $H_C$ region comprising a β-trefoil fold domain with enhanced binding activity comprises a polypeptide having, e.g., at most one, two, three, four, five, six, seven, eight, nine or 10 non-contiguous amino acid additions relative to amino acids 1138-1153 or amino acids 1208-1218 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine or 10 non-contiguous amino acid additions relative to amino acids 1138-1153 or amino acids 1208-1218 of SEQ ID NO: 4.

In other aspects of this embodiment, a modified BoNT/D $H_C$ region comprising a β-trefoil fold domain with enhanced binding activity comprises a polypeptide having, e.g., at most one, two, three, four, five, six, seven, eight, nine or 10 contiguous amino acid substitutions relative to amino acids 1138-1153 or amino acids 1208-1218 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine or 10 contiguous amino acid substitutions relative to amino acids 1138-1153 or amino acids 1208-1218 of SEQ ID NO: 4. In other aspects of this embodiment, contiguous amino acid substitutions of amino acids from amino acids 1138-1153 or amino acids 1208-1218 of SEQ ID NO: 4 can be replaced with glycine. In other aspects of this embodiment, contiguous amino acid substitutions of hydrophobic amino acids from amino acids 1138-1153 or amino acids 1208-1218 of SEQ ID NO: 4 can be replaced with phenylalanine. In yet other aspects of this embodiment, a modified BoNT/D $H_C$ region comprising a β-trefoil fold domain with enhanced binding activity comprises a polypeptide having, e.g., at most one, two, three, four, five, six, seven, eight, nine or 10 contiguous amino acid deletions relative to amino acids 1138-1153 or amino acids 1208-1218 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine or 10 contiguous amino acid deletions relative to amino acids 1138-1153 or amino acids 1208-1218 of SEQ ID NO: 4. In still other aspects of this embodiment, a modified BoNT/D $H_C$ region comprising a β-trefoil fold domain with enhanced binding activity comprises a polypeptide having, e.g., at most one, two, three, four, five, six, seven, eight, nine or 10 contiguous amino acid additions relative to amino acids 1138-1153 or amino acids 1208-1218 of SEQ ID NO: 4. In other aspects of this embodiment, a modified BoNT/D $H_C$ region comprising a β-trefoil fold domain with enhanced binding activity comprises a polypeptide having, e.g., at least one, two, three, four, five, six, seven, eight, nine or 10 contiguous amino acid additions relative to amino acids 1138-1153 or amino acids 1208-1218 of SEQ ID NO: 4.

In other aspects of this embodiment, a modified BoNT/D $H_C$ region with enhanced binding activity comprises a substitution of amino acid Trp 1089, Gly 1090, Leu 1093, Tyr 1099, Tyr 1100, Gly 1132, Ile 1137, Asp 1153, Asn 1186, Lys 1236, Trp 1238, Arg 1239, Phe 1242, Ser 1262 or Trp 1265, or any combination thereof, the substitution enhancing the binding activity of the modified BoNT/D $H_C$ region. In other aspects of this embodiment, a modified BoNT/D $H_C$ region with enhanced binding activity comprises a deletion of amino acid Trp 1089, Gly 1090, Leu 1093, Tyr 1099, Tyr 1100, Gly 1132, Ile 1137, Asp 1153, Asn 1186, Lys 1236, Trp 1238, Arg 1239, Phe 1242, Ser 1262 or Trp 1265, or any combination thereof, the deletion enhancing the binding activity of the modified BoNT/D $H_C$ region.

In another embodiment, a modified Clostridial toxin binding domain with enhanced binding activity comprises a modified BoNT/E binding domain with enhanced binding activity. In an aspect of this embodiment, a modified BoNT/E binding domain with enhanced binding activity comprises a modified BoNT/E $H_C$ region with enhanced binding activity or a modified BoNT/E $H_C$ region fragment with enhanced binding activity. In another aspect of this embodiment, a modified BoNT/E binding domain with enhanced binding activity comprises a modified BoNT/E $H_{CC}$ region with enhanced binding activity or a modified BoNT/E $H_{CC}$ region fragment with enhanced binding activity.

In other aspects of this embodiment, a modified BoNT/E $H_C$ region with enhanced binding activity comprises a polypeptide having, e.g., at least 70% amino acid identity with amino acids 846-1252 of SEQ ID NO: 5, at least 75% amino acid identity with amino acids 846-1252 of SEQ ID NO: 5, at least 80% amino acid identity with amino acids 846-1252 of SEQ ID NO: 5, at least 85% amino acid identity with amino acids 846-1252 of SEQ ID NO: 5, at least 90% amino acid identity with amino acids 846-1252 of SEQ ID NO: 5 or at least 95% amino acid identity with amino acids 846-1252 of SEQ ID NO: 5. In yet other aspects of this embodiment, a modified BoNT/E $H_C$ region with enhanced binding activity comprises a polypeptide having, e.g., at most 70% amino acid identity with amino acids 846-1252 of SEQ ID NO: 5, at most 75% amino acid identity with amino acids 846-1252 of SEQ ID NO: 5, at most 80% amino acid identity with amino acids 846-1252 of SEQ ID NO: 5, at most 85% amino acid identity with amino acids 846-1252 of SEQ ID NO: 5, at most 90% amino acid identity with amino acids 846-1252 of SEQ ID NO: 5 or at most 95% amino acid identity with amino acids 846-1252 of SEQ ID NO: 5.

In other aspects of this embodiment, a modified BoNT/E $H_C$ region with enhanced binding activity comprises a polypeptide having, e.g., at most one, two, three, four, five, six, seven, eight, nine, 10, 20, 30, 40, 50, 100, or 200 non-contiguous amino acid substitutions relative to amino acids 846-1252 of SEQ ID NO: 5. In other aspects of this embodiment, a modified BoNT/E $H_C$ region with enhanced binding activity comprises a polypeptide having, e.g., at least one, two, three, four, five, six, seven, eight, nine, 10, 20, 30, 40, 50, 100 or 200 non-contiguous amino acid substitutions relative to amino acids 846-1252 of SEQ ID NO: 5. In yet other aspects of this embodiment, a modified BoNT/E $H_C$ region with enhanced binding activity comprises a polypeptide having, e.g., at most one, two, three, four, five, six, seven, eight, nine, 10, 20, 30, 40, 50, 100 or 200 non-contiguous amino acid deletions relative to amino acids 846-1252 of SEQ ID NO: 5. In other aspects of this embodiment, a modified BoNT/E $H_C$ region with enhanced binding activity comprises a polypeptide having, e.g., at least one, two, three, four, five, six, seven, eight, nine, 10, 20, 30, 40, 50, 100 or 200 non-contiguous amino acid deletions relative to amino acids 846-1252 of SEQ ID NO: 5. In still other aspects of this embodiment, a modified BoNT/E $H_C$ region with enhanced binding activity comprises a polypeptide having, e.g., at most one, two, three, four, five, six, seven, eight, nine, 10, 20, 30, 40, 50, 100 or 200 non-contiguous amino acid additions relative to amino acids 846-1252 of SEQ ID NO: 5. In other aspects of this embodiment, a modified BoNT/E $H_C$ region with enhanced binding activity comprises a polypeptide having, e.g., at least one, two, three, four, five, six, seven, eight, nine, 10, 20, 30, 40, 50, 100 or 200 non-contiguous amino acid additions relative to amino acids 846-1252 of SEQ ID NO: 5.

In other aspects of this embodiment, a modified BoNT/E $H_C$ region with enhanced binding activity comprises a polypeptide having, e.g., at most one, two, three, four, five, six, seven, eight, nine, 10, 20, 30, 40, 50, 100 or 200 contiguous amino acid substitutions relative to amino acids 846-1252 of SEQ ID NO: 5. In other aspects of this embodiment, a modified BoNT/E $H_C$ region with enhanced binding activity comprises a polypeptide having, e.g., at least one, two, three, four, five, six, seven, eight, nine, 10, 20, 30, 40, 50, 100 or 200 contiguous amino acid substitutions relative to amino acids 846-1252 of SEQ ID NO: 5. In yet other aspects of this embodiment, a modified BoNT/E $H_C$ region with enhanced binding activity comprises a polypeptide having, e.g., at most one, two, three, four, five, six, seven, eight, nine, 10, 20, 30, 40, 50, 100 or 200 contiguous amino acid deletions relative to amino acids 846-1252 of SEQ ID NO: 5. In other aspects of this embodiment, a modified BoNT/E $H_C$ region with enhanced binding activity comprises a polypeptide having, e.g., at least one, two, three, four, five, six, seven, eight, nine, 10, 20, 30, 40, 50, 100 or 200 contiguous amino acid deletions relative to amino acids 846-1252 of SEQ ID NO: 5. In still other aspects of this embodiment, a modified BoNT/E $H_C$ region with enhanced binding activity comprises a polypeptide having, e.g., at most one, two, three, four, five, six, seven, eight, nine, 10, 20, 30, 40, 50, 100 or 200 contiguous amino acid additions relative to amino acids 846-1252 of SEQ ID NO: 5. In other aspects of this embodiment, a modified BoNT/E $H_C$ region with enhanced binding activity comprises a polypeptide having, e.g., at least one, two, three, four, five, six, seven, eight, nine, 10, 20, 30, 40, 50, 100 or 200 contiguous amino acid additions relative to amino acids 846-1252 of SEQ ID NO: 5.

In another embodiment, a modified BoNT/E $H_C$ region with enhanced binding activity comprises a modified BoNT/E $H_C$ region with enhanced binding activity of comprising a modification of amino acids 1086-1252 of SEQ ID NO: 5. In another aspect of this embodiment, a modified BoNT/E $H_C$ region with enhanced binding activity comprises a modified α-fold motif of a β-trefoil domain of a BoNT/E binding domain, a modified β-fold motif of a β-trefoil domain of a BoNT/E binding domain, or a modified γ-fold motif of a β-trefoil domain of a BoNT/E binding domain. In another aspect of this embodiment, a modified BoNT/E $H_C$ region with enhanced binding activity comprises a modification to amino acids 1086-1129, amino acids 1147-1190, or amino acids 1199-1252 of SEQ ID NO: 5.

In other aspects of this embodiment, a modified BoNT/E $H_C$ region comprising a β-trefoil fold domain with enhanced binding activity comprises a polypeptide having, e.g., at least 70% amino acid identity with amino acids 1086-1129, amino acids 1147-1190, or amino acids 1199-1252 of SEQ ID NO: 5, at least 75% amino acid identity with amino acids 1086-1129, amino acids 1147-1190, or amino acids 1199-1252 of SEQ ID NO: 5, at least 80% amino acid identity with amino acids 1086-1129, amino acids 1147-1190, or amino acids 1199-1252 of SEQ ID NO: 5, at least 85% amino acid identity with amino acids 1086-1129, amino acids 1147-1190, or amino acids 1199-1252 of SEQ ID NO: 5, at least 90% amino acid identity with amino acids 1086-1129, amino acids 1147-1190, or amino acids 1199-1252 of SEQ ID NO: 5 or at least 95% amino acid identity with amino acids 1086-1129, amino acids 1147-1190, or amino acids 1199-1252 of SEQ ID NO: 5. In yet other aspects of this embodiment, a modified BoNT/E $H_C$ region comprising a β-trefoil fold domain with enhanced binding activity comprises a polypeptide having, e.g., at most 70% amino acid identity with amino acids 1086-1129, amino acids 1147-1190, or amino acids 1199-1252 of SEQ ID NO: 5, at most 75% amino acid identity with amino acids 1086-1129, amino acids 1147-1190, or amino acids 1199-1252 of SEQ ID NO: 5, at most 80% amino acid identity with amino acids 1086-1129, amino acids 1147-1190, or amino acids 1199-1252 of SEQ ID NO: 5, at most 85% amino acid identity with amino acids 1086-1129, amino acids 1147-1190, or amino acids 1199-1252 of SEQ ID NO: 5, at most 90% amino acid identity with amino acids 1086-1129, amino acids 1147-1190, or amino acids 1199-1252 of SEQ ID NO: 5 or at most 95% amino acid identity with amino acids 1086-1129, amino acids 1147-1190, or amino acids 1199-1252 of SEQ ID NO: 5.

In other aspects of this embodiment, a modified BoNT/E $H_C$ region comprising a β-trefoil fold domain with enhanced binding activity comprises a polypeptide having, e.g., at most one, two, three, four, five, six, seven, eight, nine, 10 or 20 non-contiguous amino acid substitutions relative to amino acids 1086-1129, amino acids 1147-1190, or amino acids 1199-1252 of SEQ ID NO: 5. In other aspects of this embodiment, a modified BoNT/E $H_C$ region comprises a polypeptide having, e.g., at least one, two, three, four, five, six, seven, eight, nine, 10 or 20 non-contiguous amino acid substitutions relative to amino acids 1086-1129, amino acids 1147-1190, or amino acids 1199-1252 of SEQ ID NO: 5. In yet other aspects of this embodiment, a modified BoNT/E $H_C$ region comprising a β-trefoil fold domain with enhanced binding activity comprises a polypeptide having, e.g., at most one, two, three, four, five, six, seven, eight, nine, 10 or 20 non-contiguous amino acid deletions relative to amino acids 1086-1129, amino acids 1147-1190, or amino acids 1199-1252 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine, 10 or 20 non-contiguous amino acid deletions relative to amino acids 1086-1129, amino acids 1147-1190, or amino acids 1199-1252 of SEQ ID NO: 5. In still other aspects of this embodiment, a modified BoNT/E $H_C$ region comprising a β-trefoil fold domain with enhanced binding activity comprises a polypeptide having, e.g., at most one, two, three, four, five, six, seven, eight, nine, 10 or 20 non-contiguous amino acid additions relative to amino acids 1086-1129, amino acids 1147-1190, or amino acids 1199-1252 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine, 10 or 20 non-contiguous amino acid additions relative to amino acids 1086-1129, amino acids 1147-1190, or amino acids 1199-1252 of SEQ ID NO: 5.

In other aspects of this embodiment, a modified BoNT/E $H_C$ region comprising a β-trefoil fold domain with enhanced binding activity comprises a polypeptide having, e.g., at most one, two, three, four, five, six, seven, eight, nine, 10 or 20 contiguous amino acid substitutions relative to amino acids 1086-1129, amino acids 1147-1190, or amino acids 1199-1252 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine, 10 or 20 contiguous amino acid substitutions relative to amino acids 1086-1129, amino acids 1147-1190, or amino acids 1199-1252 of SEQ ID NO: 5. In yet other aspects of this embodiment, a modified BoNT/E $H_C$ region comprising a β-trefoil fold domain with enhanced binding activity comprises a polypeptide having, e.g., at most one, two, three, four, five, six, seven, eight, nine, 10 or 20 contiguous amino acid deletions relative to amino acids 1086-1129, amino acids 1147-1190, or amino acids 1199-1252 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine, 10 or 20 contiguous amino acid deletions relative to amino acids 1086-1129, amino acids 1147-1190, or amino acids 1199-1252 of SEQ ID NO: 5. In still other aspects of this embodiment, a modified BoNT/E $H_C$ region comprising a β-trefoil fold domain with enhanced binding activity comprises a polypeptide having, e.g., at most one, two, three, four, five, six, seven, eight, nine, 10 or 20 contiguous amino acid additions relative to amino acids 1086-1129, amino acids 1147-1190, or amino acids 1199-1252 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine, 10 or 20 contiguous amino acid additions relative to amino acids 1086-1129, amino acids 1147-1190, or amino acids 1199-1252 of SEQ ID NO: 5.

In another embodiment, a modified BoNT/E $H_C$ region with enhanced binding activity comprises a modified BoNT/E $H_C$ region with enhanced binding activity of comprises a modified β4/β5 hairpin turn of a β-trefoil domain of a BoNT/E binding domain or a β8/β9 hairpin turn of a β-trefoil domain of a BoNT/E binding domain. In another aspect of this embodiment, a modified BoNT/E $H_C$ region with enhanced binding activity comprises a modification of amino acids 1130-1146 or amino acids 1191-1198 of SEQ ID NO: 5.

In other aspects of this embodiment, a modified BoNT/E $H_C$ region comprising a β-trefoil fold domain with enhanced binding activity comprises a polypeptide having, e.g., at least 70% amino acid identity with amino acids 1130-1146 or amino acids 1191-1198 of SEQ ID NO: 5, at least 75% amino acid identity with amino acids 1130-1146 or amino acids 1191-1198 of SEQ ID NO: 5, at least 80% amino acid identity with amino acids 1130-1146 or amino acids 1191-1198 of SEQ ID NO: 5, at least 85% amino acid identity with amino acids 1130-1146 or amino acids 1191-1198 of SEQ ID NO: 5, at least 90% amino acid identity with amino acids 1130-1146 or amino acids 1191-1198 of SEQ ID NO: 5 or at least 95% amino acid identity with amino acids 1130-1146 or amino acids 1191-1198 of SEQ ID NO: 5. In yet other aspects of this embodiment, a modified BoNT/E $H_C$ region comprising a β-trefoil fold domain with enhanced binding activity comprises a polypeptide having, e.g., at most 70% amino acid identity with amino acids 1130-1146 or amino acids 1191-1198 of SEQ ID NO: 5, at most 75% amino acid identity with amino acids 1130-1146 or amino acids 1191-1198 of SEQ ID NO: 5, at most 80% amino acid identity with amino acids 1130-1146 or amino acids 1191-1198 of SEQ ID NO: 5, at most 85% amino acid identity with amino acids 1130-1146 or amino acids 1191-1198 of SEQ ID NO: 5, at most 90% amino acid identity with amino acids 1130-1146 or amino acids 1191-1198 of SEQ ID NO: 5 or at most 95% amino acid identity with amino acids 1130-1146 or amino acids 1191-1198 of SEQ ID NO: 5.

In other aspects of this embodiment, a modified BoNT/E $H_C$ region comprising a β-trefoil fold domain with enhanced binding activity comprises a polypeptide having, e.g., at most one, two, three, four, five, six, seven, eight, nine or 10 non-contiguous amino acid substitutions relative to amino acids 1130-1146 or amino acids 1191-1198 of SEQ ID NO: 5. In other aspects of this embodiment, a modified BoNT/E $H_C$ region comprises a polypeptide having, e.g., at least one, two, three, four, five, six, seven, eight, nine or 10 non-contiguous amino acid substitutions relative to amino acids 1130-1146 or amino acids 1191-1198 of SEQ ID NO: 5. In other aspects of this embodiment, a non-contiguous amino acid substitution of any amino acid from amino acids 1130-1146 or amino acids 1191-1198 of SEQ ID NO: 5 can be replaced with glycine. In other aspects of this embodiment, a non-contiguous amino acid substitution of any hydrophobic amino acid from amino acids 1130-1146 or amino acids 1191-1198 of SEQ ID NO: 5 can be replaced with phenylalanine. In yet other aspects of this embodiment, a modified BoNT/E $H_C$ region comprising a β-trefoil fold domain with enhanced binding activity comprises a polypeptide having, e.g., at most one, two, three, four, five, six, seven, eight, nine or 10 non-contiguous amino acid deletions relative to amino acids 1130-1146 or amino acids 1191-1198 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine or 10 non-contiguous amino acid deletions relative to amino acids 1130-1146 or amino acids 1191-1198 of SEQ ID NO: 5. In still other aspects of this embodiment, a modified BoNT/E $H_C$ region comprising a β-trefoil fold domain with enhanced binding activity comprises a polypeptide having, e.g., at most one, two, three, four, five, six, seven, eight, nine or 10 non-contiguous amino acid additions relative to amino acids 1130-1146 or amino acids 1191-1198 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine or 10 non-contiguous amino acid additions relative to amino acids 1130-1146 or amino acids 1191-1198 of SEQ ID NO: 5.

In other aspects of this embodiment, a modified BoNT/E $H_C$ region comprising a β-trefoil fold domain with enhanced binding activity comprises a polypeptide having, e.g., at most one, two, three, four, five, six, seven, eight, nine or 10 contiguous amino acid substitutions relative to amino acids 1130-1146 or amino acids 1191-1198 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine or 10 contiguous amino acid substitutions relative to amino acids 1130-1146 or amino acids 1191-1198 of SEQ ID NO: 5. In other aspects of this embodiment, contiguous amino acid substitutions of amino acids from amino acids 1130-1146 or amino acids 1191-1198 of SEQ ID NO: 5 can be replaced with glycine. In other aspects of this embodiment, contiguous amino acid substitutions of hydrophobic amino acids from amino acids 1130-1146 or amino acids 1191-1198 of SEQ ID NO: 5 can be replaced with phenylalanine. In yet other aspects of this embodiment, a modified BoNT/E $H_C$ region comprising a β-trefoil fold domain with enhanced binding activity comprises a polypeptide having, e.g., at most one, two, three, four, five, six, seven, eight, nine or 10 contiguous amino acid deletions relative to amino acids 1130-1146 or amino acids 1191-1198 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine or 10 contiguous amino acid deletions relative to amino acids 1130-1146 or amino acids 1191-1198 of SEQ ID NO: 5. In still other aspects of this embodiment, a modified BoNT/E $H_C$ region comprising a β-trefoil fold domain with enhanced binding activity comprises a polypeptide having, e.g., at most one, two, three, four, five, six, seven, eight, nine or 10 contiguous amino acid additions relative to amino acids 1130-1146 or amino acids 1191-1198 of SEQ ID NO: 5. In other aspects of this embodiment, a modified BoNT/E $H_C$ region comprising a β-trefoil fold domain with enhanced binding activity comprises a polypeptide having, e.g., at least one, two, three, four, five, six, seven, eight, nine or 10 contiguous amino acid additions relative to amino acids 1130-1146 or amino acids 1191-1198 of SEQ ID NO: 5.

In other aspects of this embodiment, a modified BoNT/E $H_C$ region with enhanced binding activity comprises a substitution of amino acid Trp 1076, Gly 1077, Leu 1080, Tyr 1086, Tyr 1087, Gly 1124, Ile 1129, Asp 1146, Glu 1172, Phe 1213, Ser 1221, Trp 1223, Tyr 1224, His 1227, Gly 1236 or Trp 1239, or any combination thereof, the substitution enhancing the binding activity of the modified BoNT/E $H_C$ region. In other aspects of this embodiment, a modified BoNT/E $H_C$ region with enhanced binding activity comprises a deletion of amino acid Trp 1076, Gly 1077, Leu 1080, Tyr 1086, Tyr 1087, Gly 1124, Ile 1129, Asp 1146, Glu 1172, Phe 1213, Ser 1221, Trp 1223, Tyr 1224, His 1227, Gly 1236 or Trp 1239, or any combination thereof, the deletion enhancing the binding activity of the modified BoNT/E $H_C$ region.

In another embodiment, a modified Clostridial toxin binding domain with enhanced binding activity comprises a modified BoNT/F binding domain with enhanced binding activity. In an aspect of this embodiment, a modified BoNT/F binding domain with enhanced binding activity comprises a modified BoNT/F $H_C$ region with enhanced binding activity or a modified BoNT/F $H_C$ region fragment with enhanced binding activity. In another aspect of this embodiment, a modified BoNT/F binding domain with enhanced binding activity comprises a modified BoNT/F $H_{CC}$ region with enhanced binding activity or a modified BoNT/F $H_{CC}$ region fragment with enhanced binding activity.

In other aspects of this embodiment, a modified BoNT/F $H_C$ region with enhanced binding activity comprises a polypeptide having, e.g., at least 70% amino acid identity with amino acids 865-1274 of SEQ ID NO: 6, at least 75% amino acid identity with amino acids 865-1274 of SEQ ID NO: 6, at least 80% amino acid identity with amino acids 865-1274 of SEQ ID NO: 6, at least 85% amino acid identity with amino acids 865-1274 of SEQ ID NO: 6, at least 90% amino acid identity with amino acids 865-1274 of SEQ ID NO: 6 or at least 95% amino acid identity with amino acids 865-1274 of SEQ ID NO: 6. In yet other aspects of this embodiment, a modified BoNT/F $H_C$ region with enhanced binding activity comprises a polypeptide having, e.g., at most 70% amino acid identity with amino acids 865-1274 of SEQ ID NO: 6, at most 75% amino acid identity with amino acids 865-1274 of SEQ ID NO: 6, at most 80% amino acid identity with amino acids 865-1274 of SEQ ID NO: 6, at most 85% amino acid identity with amino acids 865-1274 of SEQ ID NO: 6, at most 90% amino acid identity with amino acids 865-1274 of SEQ ID NO: 6 or at most 95% amino acid identity with amino acids 865-1274 of SEQ ID NO: 6.

In other aspects of this embodiment, a modified BoNT/F $H_C$ region with enhanced binding activity comprises a polypeptide having, e.g., at most one, two, three, four, five, six, seven, eight, nine, 10, 20, 30, 40, 50, 100, or 200 non-contiguous amino acid substitutions relative to amino acids 865-1274 of SEQ ID NO: 6. In other aspects of this embodiment, a modified BoNT/F $H_C$ region with enhanced binding activity comprises a polypeptide having, e.g., at least one, two, three, four, five, six, seven, eight, nine, 10, 20, 30, 40, 50, 100 or 200 non-contiguous amino acid substitutions relative to amino acids 865-1274 of SEQ ID NO: 6. In yet other aspects of this embodiment, a modified BoNT/F $H_C$ region with enhanced binding activity comprises a polypeptide having, e.g., at most one, two, three, four, five, six, seven, eight, nine, 10, 20, 30, 40, 50, 100 or 200 non-contiguous amino acid deletions relative to amino acids 865-1274 of SEQ ID NO: 6. In other aspects of this embodiment, a modified BoNT/F $H_C$ region with enhanced binding activity comprises a polypeptide having, e.g., at least one, two, three, four, five, six, seven, eight, nine, 10, 20, 30, 40, 50, 100 or 200 non-contiguous amino acid deletions relative to amino acids 865-1274 of SEQ ID NO: 6. In still other aspects of this embodiment, a modified BoNT/F $H_C$ region with enhanced binding activity comprises a polypeptide having, e.g., at most one, two, three, four, five, six, seven, eight, nine, 10, 20, 30, 40, 50, 100 or 200 non-contiguous amino acid additions relative to amino acids 865-1274 of SEQ ID NO: 6. In other aspects of this embodiment, a modified BoNT/F $H_C$ region with enhanced binding activity comprises a polypeptide having, e.g., at least one, two, three, four, five, six, seven, eight, nine, 10, 20, 30, 40, 50, 100 or 200 non-contiguous amino acid additions relative to amino acids 865-1274 of SEQ ID NO: 6.

In other aspects of this embodiment, a modified BoNT/F $H_C$ region with enhanced binding activity comprises a polypeptide having, e.g., at most one, two, three, four, five, six, seven, eight, nine, 10, 20, 30, 40, 50, 100 or 200 contiguous amino acid substitutions relative to amino acids 865-1274 of SEQ ID NO: 6. In other aspects of this embodiment, a modified BoNT/F $H_C$ region with enhanced binding activity comprises a polypeptide having, e.g., at least one, two, three, four, five, six, seven, eight, nine, 10, 20, 30, 40, 50, 100 or 200 contiguous amino acid substitutions relative to amino acids 865-1274 of SEQ ID NO: 6. In yet other aspects of this embodiment, a modified BoNT/F $H_C$ region with enhanced binding activity comprises a polypeptide having, e.g., at most one, two, three, four, five, six, seven, eight, nine, 10, 20, 30, 40, 50, 100 or 200 contiguous amino acid deletions relative to amino acids 865-1274 of SEQ ID NO: 6. In other aspects of this embodiment, a modified BoNT/F $H_C$ region with enhanced binding activity comprises a polypeptide having, e.g., at least one, two, three, four, five, six, seven, eight, nine, 10, 20, 30, 40, 50, 100 or 200 contiguous amino acid deletions relative to amino acids 865-1274 of SEQ ID NO: 6. In still other aspects of this embodiment, a modified BoNT/F $H_C$ region with enhanced binding activity comprises a polypeptide having, e.g., at most one, two, three, four, five, six, seven, eight, nine, 10, 20, 30, 40, 50, 100 or 200 contiguous amino acid additions relative to amino acids 865-1274 of SEQ ID NO: 6. In other aspects of this embodiment, a modified BoNT/F $H_C$ region with enhanced binding activity comprises a polypeptide having, e.g., at least one, two, three, four, five, six, seven, eight, nine, 10, 20, 30, 40, 50, 100 or 200 contiguous amino acid additions relative to amino acids 865-1274 of SEQ ID NO: 6.

In another embodiment, a modified BoNT/F $H_C$ region with enhanced binding activity comprises a modified BoNT/F $H_C$ region with enhanced binding activity of comprising a modification of amino acids 1106-1274 of SEQ ID NO: 6. In another aspect of this embodiment, a modified BoNT/F $H_C$ region with enhanced binding activity comprises a modified α-fold motif of a β-trefoil domain of a BoNT/F binding domain, a modified β-fold motif of a β-trefoil domain of a BoNT/F binding domain, or a modified γ-fold motif of a β-trefoil domain of a BoNT/F binding domain. In another aspect of this embodiment, a modified BoNT/F $H_C$ region with enhanced binding activity comprises a modification to amino acids 1106-1152, amino acids 1172-1213, or amino acids 1222-1274 of SEQ ID NO: 6.

In other aspects of this embodiment, a modified BoNT/F $H_C$ region comprising a β-trefoil fold domain with enhanced binding activity comprises a polypeptide having, e.g., at least 70% amino acid identity with amino acids 1106-1152, amino acids 1172-1213, or amino acids 1222-1274 of SEQ ID NO: 6, at least 75% amino acid identity with amino acids 1106-1152, amino acids 1172-1213, or amino acids 1222-1274 of SEQ ID NO: 6, at least 80% amino acid identity with amino acids 1106-1152, amino acids 1172-1213, or amino acids 1222-1274 of SEQ ID NO: 6, at least 85% amino acid identity with amino acids 1106-1152, amino acids 1172-1213, or amino acids 1222-1274 of SEQ ID NO: 6, at least 90% amino acid identity with amino acids 1106-1152, amino acids 1172-1213, or amino acids 1222-1274 of SEQ ID NO: 6 or at least 95% amino acid identity with amino acids 1106-1152, amino acids 1172-1213, or amino acids 1222-1274 of SEQ ID NO: 6. In yet other aspects of this embodiment, a modified BoNT/F $H_C$ region comprising a β-trefoil fold domain with enhanced binding activity comprises a polypeptide having, e.g., at most 70% amino acid identity with amino acids 1106-1152, amino acids 1172-1213, or amino acids 1222-1274 of SEQ ID NO: 6, at most 75% amino acid identity with amino acids 1106-1152, amino acids 1172-1213, or amino acids 1222-1274 of SEQ ID NO: 6, at most 80% amino acid identity with amino acids 1106-1152, amino acids 1172-1213, or amino acids 1222-1274 of SEQ ID NO: 6, at most 85% amino acid identity with amino acids 1106-1152, amino acids 1172-1213, or amino acids 1222-1274 of SEQ ID NO: 6, at most 90% amino acid identity with amino acids 1106-1152, amino acids 1172-1213, or amino acids 1222-1274 of SEQ ID NO: 6 or at most 95% amino acid identity with amino acids 1106-1152, amino acids 1172-1213, or amino acids 1222-1274 of SEQ ID NO: 6.

In other aspects of this embodiment, a modified BoNT/F $H_C$ region comprising a β-trefoil fold domain with enhanced binding activity comprises a polypeptide having, e.g., at most one, two, three, four, five, six, seven, eight, nine, 10 or 20 non-contiguous amino acid substitutions relative to amino acids 1106-1152, amino acids 1172-1213, or amino acids 1222-1274 of SEQ ID NO: 6. In other aspects of this embodiment, a modified BoNT/F $H_C$ region comprises a polypeptide having, e.g., at least one, two, three, four, five, six, seven, eight, nine, 10 or 20 non-contiguous amino acid substitutions relative to amino acids 1106-1152, amino acids 1172-1213, or amino acids 1222-1274 of SEQ ID NO: 6. In yet other aspects of this embodiment, a modified BoNT/F $H_C$ region comprising a β-trefoil fold domain with enhanced binding activity comprises a polypeptide having, e.g., at most one, two, three, four, five, six, seven, eight, nine, 10 or 20 non-contiguous amino acid deletions relative to amino acids 1106-1152, amino acids 1172-1213, or amino acids 1222-1274 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine, 10 or 20 non-contiguous amino acid deletions relative to amino acids 1106-1152, amino acids 1172-1213, or amino acids 1222-1274 of SEQ ID NO: 6. In still other aspects of this embodiment, a modified BoNT/F $H_C$ region comprising a β-trefoil fold domain with enhanced binding activity comprises a polypeptide having, e.g., at most one, two, three, four, five, six, seven, eight, nine, 10 or 20 non-contiguous amino acid additions relative to amino acids 1106-1152, amino acids 1172-1213, or amino acids 1222-1274 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine, 10 or 20 non-contiguous amino acid additions relative to amino acids 1106-1152, amino acids 1172-1213, or amino acids 1222-1274 of SEQ ID NO: 6.

In other aspects of this embodiment, a modified BoNT/F $H_C$ region comprising a β-trefoil fold domain with enhanced binding activity comprises a polypeptide having, e.g., at most one, two, three, four, five, six, seven, eight, nine, 10 or 20 contiguous amino acid substitutions relative to amino acids 1106-1152, amino acids 1172-1213, or amino acids 1222-1274 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine, 10 or 20 contiguous amino acid substitutions relative to amino acids 1106-1152, amino acids 1172-1213, or amino acids 1222-1274 of SEQ ID NO: 6. In yet other aspects of this embodiment, a modified BoNT/F $H_C$ region comprising a β-trefoil fold domain with enhanced binding activity comprises a polypeptide having, e.g., at most one, two, three, four, five, six, seven, eight, nine, 10 or 20 contiguous amino acid deletions relative to amino acids 1106-1152, amino acids 1172-1213, or amino acids 1222-1274 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine, 10 or 20 contiguous amino acid deletions relative to amino acids 1106-1152, amino acids 1172-1213, or amino acids 1222-1274 of SEQ ID NO: 6. In still other aspects of this embodiment, a modified BoNT/F $H_C$ region comprising a β-trefoil fold domain with enhanced binding activity comprises a polypeptide having, e.g., at most one, two, three, four, five, six, seven, eight, nine, 10 or 20 contiguous amino acid additions relative to amino acids 1106-1152, amino acids 1172-1213, or amino acids 1222-1274 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine, 10 or 20 contiguous amino acid additions relative to amino acids 1106-1152, amino acids 1172-1213, or amino acids 1222-1274 of SEQ ID NO: 6.

In another embodiment, a modified BoNT/F $H_C$ region with enhanced binding activity comprises a modified BoNT/F $H_C$ region with enhanced binding activity of comprises a modified β4/β5 hairpin turn of a β-trefoil domain of a BoNT/F binding domain or a β8/β9 hairpin turn of a β-trefoil domain of a BoNT/F binding domain. In another aspect of this embodiment, a modified BoNT/F $H_C$ region with enhanced binding activity comprises a modification of amino acids 1153-1171 or amino acids 1214-1221 of SEQ ID NO: 6.

In other aspects of this embodiment, a modified BoNT/F $H_C$ region comprising a β-trefoil fold domain with enhanced binding activity comprises a polypeptide having, e.g., at least 70% amino acid identity with amino acids 1153-1171 or amino acids 1214-1221 of SEQ ID NO: 6, at least 75% amino acid identity with amino acids 1153-1171 or amino acids 1214-1221 of SEQ ID NO: 6, at least 80% amino acid identity with amino acids 1153-1171 or amino acids 1214-1221 of SEQ ID NO: 6, at least 85% amino acid identity with amino acids 1153-1171 or amino acids 1214-1221 of SEQ ID NO: 6, at least 90% amino acid identity with amino acids 1153-1171 or amino acids 1214-1221 of SEQ ID NO: 6 or at least 95% amino acid identity with amino acids 1153-1171 or amino acids 1214-1221 of SEQ ID NO: 6. In yet other aspects of this embodiment, a modified BoNT/F $H_C$ region comprising a β-trefoil fold domain with enhanced binding activity comprises a polypeptide having, e.g., at most 70% amino acid identity with amino acids 1153-1171 or amino acids 1214-1221 of SEQ ID NO: 6, at most 75% amino acid identity with amino acids 1153-1171 or amino acids 1214-1221 of SEQ ID NO: 6, at most 80% amino acid identity with amino acids 1153-1171 or amino acids 1214-1221 of SEQ ID NO: 6, at most 85% amino acid identity with amino acids 1153-1171 or amino acids 1214-1221 of SEQ ID NO: 6, at most 90% amino acid identity with amino acids 1153-1171 or amino acids 1214-1221 of SEQ ID NO: 6 or at most 95% amino acid identity with amino acids 1153-1171 or amino acids 1214-1221 of SEQ ID NO: 6.

In other aspects of this embodiment, a modified BoNT/F $H_C$ region comprising a β-trefoil fold domain with enhanced binding activity comprises a polypeptide having, e.g., at most one, two, three, four, five, six, seven, eight, nine or 10 non-contiguous amino acid substitutions relative to amino acids 1153-1171 or amino acids 1214-1221 of SEQ ID NO: 6. In other aspects of this embodiment, a modified BoNT/F $H_C$ region comprises a polypeptide having, e.g., at least one, two, three, four, five, six, seven, eight, nine or 10 non-contiguous amino acid substitutions relative to amino acids 1153-1171 or amino acids 1214-1221 of SEQ ID NO: 6. In other aspects of this embodiment, a non-contiguous amino acid substitution of any amino acid from amino acids 1153-1171 or amino acids 1214-1221 of SEQ ID NO: 6 can be replaced with glycine. In other aspects of this embodiment, a non-contiguous amino acid substitution of any hydrophobic amino acid from amino acids 1153-1171 or amino acids 1214-1221 of SEQ ID NO: 6 can be replaced with phenylalanine. In yet other aspects of this embodiment, a modified BoNT/F $H_C$ region comprising a β-trefoil fold domain with enhanced binding activity comprises a polypeptide having, e.g., at most one, two, three, four, five, six, seven, eight, nine or 10 non-contiguous amino acid deletions relative to amino acids 1153-1171 or amino acids 1214-1221 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine or 10 non-contiguous amino acid deletions relative to amino acids 1153-1171 or amino acids 1214-1221 of SEQ ID NO: 6. In still other aspects of this embodiment, a modified BoNT/F $H_C$ region comprising a β-trefoil fold domain with enhanced binding activity comprises a polypeptide having, e.g., at most one, two, three, four, five, six, seven, eight, nine or 10 non-contiguous amino acid additions relative to amino acids 1153-1171 or amino acids 1214-1221 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine or 10 non-contiguous amino acid additions relative to amino acids 1153-1171 or amino acids 1214-1221 of SEQ ID NO: 6.

In other aspects of this embodiment, a modified BoNT/F $H_C$ region comprising a β-trefoil fold domain with enhanced binding activity comprises a polypeptide having, e.g., at most one, two, three, four, five, six, seven, eight, nine or 10 contiguous amino acid substitutions relative to amino acids 1153-1171 or amino acids 1214-1221 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine or 10 contiguous amino acid substitutions relative to amino acids 1153-1171 or amino acids 1214-1221 of SEQ ID NO: 6. In other aspects of this embodiment, contiguous amino acid substitutions of amino acids from amino acids 1153-1171 or amino acids 1214-1221 of SEQ ID NO: 6 can be replaced with glycine. In other aspects of this embodiment, contiguous amino acid substitutions of hydrophobic amino acids from amino acids 1153-1171 or amino acids 1214-1221 of SEQ ID NO: 6 can be replaced with phenylalanine. In yet other aspects of this embodiment, a modified BoNT/F $H_C$ region comprising a β-trefoil fold domain with enhanced binding activity comprises a polypeptide having, e.g., at most one, two, three, four, five, six, seven, eight, nine or 10 contiguous amino acid deletions relative to amino acids 1153-1171 or amino acids 1214-1221 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine or 10 contiguous amino acid deletions relative to amino acids 1153-1171 or amino acids 1214-1221 of SEQ ID NO: 6. In still other aspects of this embodiment, a modified BoNT/F $H_C$ region comprising a β-trefoil fold domain with enhanced binding activity comprises a polypeptide having, e.g., at most one, two, three, four, five, six, seven, eight, nine or 10 contiguous amino acid additions relative to amino acids 1153-1171 or amino acids 1214-1221 of SEQ ID NO: 6. In other aspects of this embodiment, a modified BoNT/F $H_C$ region comprising a β-trefoil fold domain with enhanced binding activity comprises a polypeptide having, e.g., at least one, two, three, four, five, six, seven, eight, nine or 10 contiguous amino acid additions relative to amino acids 1153-1171 or amino acids 1214-1221 of SEQ ID NO: 6.

In other aspects of this embodiment, a modified BoNT/F $H_C$ region with enhanced binding activity comprises a substitution of amino acid Trp 1096, Gly 1097, Leu 1100, Tyr 1106, Tyr 1107, Gly 1147, Ile 1152, Asp 1171, Glu 1195, Phe 1237, Ser 1245, Trp 1247, Tyr 1248, Asn 1251, Gly 1260 or Trp 1263, or any combination thereof, the substitution enhancing the binding activity of the modified BoNT/F $H_C$ region. In other aspects of this embodiment, a modified BoNT/F $H_C$ region with enhanced binding activity comprises a deletion of amino acid Trp 1096, Gly 1097, Leu 1100, Tyr 1106, Tyr 1107, Gly 1147, Ile 1152, Asp 1171, Glu 1195, Phe 1237, Ser 1245, Trp 1247, Tyr 1248, Asn 1251, Gly 1260 or Trp 1263, or any combination thereof, the deletion enhancing the binding activity of the modified BoNT/F $H_C$ region.

In another embodiment, a modified Clostridial toxin binding domain with enhanced binding activity comprises a modified BoNT/G binding domain with enhanced binding activity. In an aspect of this embodiment, a modified BoNT/G binding domain with enhanced binding activity comprises a modified BoNT/G $H_C$ region with enhanced binding activity or a modified BoNT/G $H_C$ region fragment with enhanced binding activity. In another aspect of this embodiment, a modified BoNT/G binding domain with enhanced binding activity comprises a modified BoNT/G $H_{CC}$ region with enhanced binding activity or a modified BoNT/G $H_{CC}$ region fragment with enhanced binding activity.

In other aspects of this embodiment, a modified BoNT/G $H_C$ region with enhanced binding activity comprises a polypeptide having, e.g., at least 70% amino acid identity with amino acids 864-1297 of SEQ ID NO: 7, at least 75% amino acid identity with amino acids 864-1297 of SEQ ID NO: 7, at least 80% amino acid identity with amino acids 864-1297 of SEQ ID NO: 7, at least 85% amino acid identity with amino acids 864-1297 of SEQ ID NO: 7, at least 90% amino acid identity with amino acids 864-1297 of SEQ ID NO: 7 or at least 95% amino acid identity with amino acids 864-1297 of SEQ ID NO: 7. In yet other aspects of this embodiment, a modified BoNT/G $H_C$ region with enhanced binding activity comprises a polypeptide having, e.g., at most 70% amino acid identity with amino acids 864-1297 of SEQ ID NO: 7, at most 75% amino acid identity with amino acids 864-1297 of SEQ ID NO: 7, at most 80% amino acid identity with amino acids 864-1297 of SEQ ID NO: 7, at most 85% amino acid identity with amino acids 864-1297 of SEQ ID NO: 7, at most 90% amino acid identity with amino acids 864-1297 of SEQ ID NO: 7 or at most 95% amino acid identity with amino acids 864-1297 of SEQ ID NO: 7.

In other aspects of this embodiment, a modified BoNT/G $H_C$ region with enhanced binding activity comprises a polypeptide having, e.g., at most one, two, three, four, five, six, seven, eight, nine, 10, 20, 30, 40, 50, 100, or 200 non-contiguous amino acid substitutions relative to amino acids 864-1297 of SEQ ID NO: 7. In other aspects of this embodiment, a modified BoNT/G $H_C$ region with enhanced binding activity comprises a polypeptide having, e.g., at least one, two, three, four, five, six, seven, eight, nine, 10, 20, 30, 40, 50, 100 or 200 non-contiguous amino acid substitutions relative to amino acids 864-1297 of SEQ ID NO: 7. In yet other aspects of this embodiment, a modified BoNT/G $H_C$ region with enhanced binding activity comprises a polypeptide having, e.g., at most one, two, three, four, five, six, seven, eight, nine, 10, 20, 30, 40, 50, 100 or 200 non-contiguous amino acid deletions relative to amino acids 864-1297 of SEQ ID NO: 7. In other aspects of this embodiment, a modified BoNT/G $H_C$ region with enhanced binding activity comprises a polypeptide having, e.g., at least one, two, three, four, five, six, seven, eight, nine, 10, 20, 30, 40, 50, 100 or 200 non-contiguous amino acid deletions relative to amino acids 864-1297 of SEQ ID NO: 7. In still other aspects of this embodiment, a modified BoNT/G $H_C$ region with enhanced binding activity comprises a polypeptide having, e.g., at most one, two, three, four, five, six, seven, eight, nine, 10, 20, 30, 40, 50, 100 or 200 non-contiguous amino acid additions relative to amino acids 864-1297 of SEQ ID NO: 7. In other aspects of this embodiment, a modified BoNT/G $H_C$ region with enhanced binding activity comprises a polypeptide having, e.g., at least one, two, three, four, five, six, seven, eight, nine, 10, 20, 30, 40, 50, 100 or 200 non-contiguous amino acid additions relative to amino acids 864-1297 of SEQ ID NO: 7.

In other aspects of this embodiment, a modified BoNT/G $H_C$ region with enhanced binding activity comprises a polypeptide having, e.g., at most one, two, three, four, five, six, seven, eight, nine, 10, 20, 30, 40, 50, 100 or 200 contiguous amino acid substitutions relative to amino acids 864-1297 of SEQ ID NO: 7. In other aspects of this embodiment, a modified BoNT/G $H_C$ region with enhanced binding activity comprises a polypeptide having, e.g., at least one, two, three, four, five, six, seven, eight, nine, 10, 20, 30, 40, 50, 100 or 200 contiguous amino acid substitutions relative to amino acids 864-1297 of SEQ ID NO: 7. In yet other aspects of this embodiment, a modified BoNT/G $H_C$ region with enhanced binding activity comprises a polypeptide having, e.g., at most one, two, three, four, five, six, seven, eight, nine, 10, 20, 30, 40, 50, 100 or 200 contiguous amino acid deletions relative to amino acids 864-1297 of SEQ ID NO: 7. In other aspects of this embodiment, a modified BoNT/G $H_C$ region with enhanced binding activity comprises a polypeptide having, e.g., at least one, two, three, four, five, six, seven, eight, nine, 10, 20, 30, 40, 50, 100 or 200 contiguous amino acid deletions relative to amino acids 864-1297 of SEQ ID NO: 7. In still other aspects of this embodiment, a modified BoNT/G $H_C$ region with enhanced binding activity comprises a polypeptide having, e.g., at most one, two, three, four, five, six, seven, eight, nine, 10, 20, 30, 40, 50, 100 or 200 contiguous amino acid additions relative to amino acids 864-1297 of SEQ ID NO: 7. In other aspects of this embodiment, a modified BoNT/G $H_C$ region with enhanced binding activity comprises a polypeptide having, e.g., at least one, two, three, four, five, six, seven, eight, nine, 10, 20, 30, 40, 50, 100 or 200 contiguous amino acid additions relative to amino acids 864-1297 of SEQ ID NO: 7.

In another embodiment, a modified BoNT/G $H_C$ region with enhanced binding activity comprises a modified BoNT/G $H_C$ region with enhanced binding activity of comprising a modification of amino acids 1106-1297 of SEQ ID NO: 7. In another aspect of this embodiment, a modified BoNT/G $H_C$ region with enhanced binding activity comprises a modified α-fold motif of a β-trefoil domain of a BoNT/G binding domain, a modified β-fold motif of a β-trefoil domain of a BoNT/G binding domain, or a modified γ-fold motif of a β-trefoil domain of a BoNT/G binding domain. In another aspect of this embodiment, a modified BoNT/G $H_C$ region with enhanced binding activity comprises a modification to amino acids 1106-1153, amino acids 1173-1218, or amino acids 1231-1297 of SEQ ID NO: 7.

In other aspects of this embodiment, a modified BoNT/G $H_C$ region comprising a β-trefoil fold domain with enhanced binding activity comprises a polypeptide having, e.g., at least 70% amino acid identity with amino acids 1106-1153, amino acids 1173-1218, or amino acids 1231-1297 of SEQ ID NO: 7, at least 75% amino acid identity with amino acids 1106-1153, amino acids 1173-1218, or amino acids 1231-1297 of SEQ ID NO: 7, at least 80% amino acid identity with amino acids 1106-1153, amino acids 1173-1218, or amino acids 1231-1297 of SEQ ID NO: 7, at least 85% amino acid identity with amino acids 1106-1153, amino acids 1173-1218, or amino acids 1231-1297 of SEQ ID NO: 7, at least 90% amino acid identity with amino acids 1106-1153, amino acids 1173-1218, or amino acids 1231-1297 of SEQ ID NO: 7 or at least 95% amino acid identity with amino acids 1106-1153, amino acids 1173-1218, or amino acids 1231-1297 of SEQ ID NO: 7. In yet other aspects of this embodiment, a modified BoNT/G $H_C$ region comprising a β-trefoil fold domain with enhanced binding activity comprises a polypeptide having, e.g., at most 70% amino acid identity with amino acids 1106-1153, amino acids 1173-1218, or amino acids 1231-1297 of SEQ ID NO: 7, at most 75% amino acid identity with amino acids 1106-1153, amino acids 1173-1218, or amino acids 1231-1297 of SEQ ID NO: 7, at most 80% amino acid identity with amino acids 1106-1153, amino acids 1173-1218, or amino acids 1231-1297 of SEQ ID NO: 7, at most 85% amino acid identity with amino acids 1106-1153, amino acids 1173-1218, or amino acids 1231-1297 of SEQ ID NO: 7, at most 90% amino acid identity with amino acids 1106-1153, amino acids 1173-1218, or amino acids 1231-1297 of SEQ ID NO: 7 or at most 95% amino acid identity with amino acids 1106-1153, amino acids 1173-1218, or amino acids 1231-1297 of SEQ ID NO: 7.

In other aspects of this embodiment, a modified BoNT/G $H_C$ region comprising a β-trefoil fold domain with enhanced binding activity comprises a polypeptide having, e.g., at most one, two, three, four, five, six, seven, eight, nine, 10 or 20 non-contiguous amino acid substitutions relative to amino acids 1106-1153, amino acids 1173-1218, or amino acids 1231-1297 of SEQ ID NO: 7. In other aspects of this embodiment, a modified BoNT/G $H_C$ region comprises a polypeptide having, e.g., at least one, two, three, four, five, six, seven, eight, nine, 10 or 20 non-contiguous amino acid substitutions relative to amino acids 1106-1153, amino acids 1173-1218, or amino acids 1231-1297 of SEQ ID NO: 7. In yet other aspects of this embodiment, a modified BoNT/G $H_C$ region comprising a β-trefoil fold domain with enhanced binding activity comprises a polypeptide having, e.g., at most one, two, three, four, five, six, seven, eight, nine, 10 or 20 non-contiguous amino acid deletions relative to amino acids 1106-1153, amino acids 1173-1218, or amino acids 1231-1297 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine, 10 or 20 non-contiguous amino acid deletions relative to amino acids 1106-1153, amino acids 1173-1218, or amino acids 1231-1297 of SEQ ID NO: 7. In still other aspects of this embodiment, a modified BoNT/G $H_C$ region comprising a β-trefoil fold domain with enhanced binding activity comprises a polypeptide having, e.g., at most one, two, three, four, five, six, seven, eight, nine, 10 or 20 non-contiguous amino acid additions relative to amino acids 1106-1153, amino acids 1173-1218, or amino acids 1231-1297 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine, 10 or 20 non-contiguous amino acid additions relative to amino acids 1106-1153, amino acids 1173-1218, or amino acids 1231-1297 of SEQ ID NO: 7.

In other aspects of this embodiment, a modified BoNT/G $H_C$ region comprising a β-trefoil fold domain with enhanced binding activity comprises a polypeptide having, e.g., at most one, two, three, four, five, six, seven, eight, nine, 10 or 20 contiguous amino acid substitutions relative to amino acids 1106-1153, amino acids 1173-1218, or amino acids 1231-1297 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine, 10 or 20 contiguous amino acid substitutions relative to amino acids 1106-1153, amino acids 1173-1218, or amino acids 1231-1297 of SEQ ID NO: 7. In yet other aspects of this embodiment, a modified BoNT/G $H_C$ region comprising a β-trefoil fold domain with enhanced binding activity comprises a polypeptide having, e.g., at most one, two, three, four, five, six, seven, eight, nine, 10 or 20 contiguous amino acid deletions relative to amino acids 1106-1153, amino acids 1173-1218, or amino acids 1231-1297 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine, 10 or 20 contiguous amino acid deletions relative to amino acids 1106-1153, amino acids 1173-1218, or amino acids 1231-1297 of SEQ ID NO: 7. In still other aspects of this embodiment, a modified BoNT/G $H_C$ region comprising a β-trefoil fold domain with enhanced binding activity comprises a polypeptide having, e.g., at most one, two, three, four, five, six, seven, eight, nine, 10 or 20 contiguous amino acid additions relative to amino acids 1106-1153, amino acids 1173-1218, or amino acids 1231-1297 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine, 10 or 20 contiguous amino acid additions relative to amino acids 1106-1153, amino acids 1173-1218, or amino acids 1231-1297 of SEQ ID NO: 7.

In another embodiment, a modified BoNT/G $H_C$ region with enhanced binding activity comprises a modified BoNT/G $H_C$ region with enhanced binding activity of comprises a modified β4/β5 hairpin turn of a β-trefoil domain of a BoNT/G binding domain or a β8/β9 hairpin turn of a β-trefoil domain of a BoNT/G binding domain. In another aspect of this embodiment, a modified BoNT/G $H_C$ region with enhanced binding activity comprises a modification of amino acids 1154-1172 or amino acids 1219-1230 of SEQ ID NO: 7.

In other aspects of this embodiment, a modified BoNT/G $H_C$ region comprising a β-trefoil fold domain with enhanced binding activity comprises a polypeptide having, e.g., at least 70% amino acid identity with amino acids 1154-1172 or amino acids 1219-1230 of SEQ ID NO: 7, at least 75% amino acid identity with amino acids 1154-1172 or amino acids 1219-1230 of SEQ ID NO: 7, at least 80% amino acid identity with amino acids 1154-1172 or amino acids 1219-1230 of SEQ ID NO: 7, at least 85% amino acid identity with amino acids 1154-1172 or amino acids 1219-1230 of SEQ ID NO: 7, at least 90% amino acid identity with amino acids 1154-1172 or amino acids 1219-1230 of SEQ ID NO: 7 or at least 95% amino acid identity with amino acids 1154-1172 or amino acids 1219-1230 of SEQ ID NO: 7. In yet other aspects of this embodiment, a modified BoNT/G $H_C$ region comprising a β-trefoil fold domain with enhanced binding activity comprises a polypeptide having, e.g., at most 70% amino acid identity with amino acids 1154-1172 or amino acids 1219-1230 of SEQ ID NO: 7, at most 75% amino acid identity with amino acids 1154-1172 or amino acids 1219-1230 of SEQ ID NO: 7, at most 80% amino acid identity with amino acids 1154-1172 or amino acids 1219-1230 of SEQ ID NO: 7, at most 85% amino acid identity with amino acids 1154-1172 or amino acids 1219-1230 of SEQ ID NO: 7, at most 90% amino acid identity with amino acids 1154-1172 or amino acids 1219-1230 of SEQ ID NO: 7 or at most 95% amino acid identity with amino acids 1154-1172 or amino acids 1219-1230 of SEQ ID NO: 7.

In other aspects of this embodiment, a modified BoNT/G $H_C$ region comprising a β-trefoil fold domain with enhanced binding activity comprises a polypeptide having, e.g., at most one, two, three, four, five, six, seven, eight, nine or 10 non-contiguous amino acid substitutions relative to amino acids 1154-1172 or amino acids 1219-1230 of SEQ ID NO: 7. In other aspects of this embodiment, a modified BoNT/G $H_C$ region comprises a polypeptide having, e.g., at least one, two, three, four, five, six, seven, eight, nine or 10 non-contiguous amino acid substitutions relative to amino acids 1154-1172 or amino acids 1219-1230 of SEQ ID NO: 7. In other aspects of this embodiment, a non-contiguous amino acid substitution of any amino acid from amino acids 1154-1172 or amino acids 1219-1230 of SEQ ID NO: 7 can be replaced with glycine. In other aspects of this embodiment, a non-contiguous amino acid substitution of any hydrophobic amino acid from amino acids 1154-1172 or amino acids 1219-1230 of SEQ ID NO: 7 can be replaced with phenylalanine. In yet other aspects of this embodiment, a modified BoNT/G $H_C$ region comprising a β-trefoil fold domain with enhanced binding activity comprises a polypeptide having, e.g., at most one, two, three, four, five, six, seven, eight, nine or 10 non-contiguous amino acid deletions relative to amino acids 1154-1172 or amino acids 1219-1230 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine or 10 non-contiguous amino acid deletions relative to amino acids 1154-1172 or amino acids 1219-1230 of SEQ ID NO: 7. In still other aspects of this embodiment, a modified BoNT/G $H_C$ region comprising a β-trefoil fold domain with enhanced binding activity comprises a polypeptide having, e.g., at most one, two, three, four, five, six, seven, eight, nine or 10 non-contiguous amino acid additions relative to amino acids 1154-1172 or amino acids 1219-1230 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine or 10 non-contiguous amino acid additions relative to amino acids 1154-1172 or amino acids 1219-1230 of SEQ ID NO: 7.

In other aspects of this embodiment, a modified BoNT/G $H_C$ region comprising a β-trefoil fold domain with enhanced binding activity comprises a polypeptide having, e.g., at most one, two, three, four, five, six, seven, eight, nine or 10 contiguous amino acid substitutions relative to amino acids 1154-1172 or amino acids 1219-1230 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine or 10 contiguous amino acid substitutions relative to amino acids 1154-1172 or amino acids 1219-1230 of SEQ ID NO: 7. In other aspects of this embodiment, contiguous amino acid substitutions of amino acids from amino acids 1154-1172 or amino acids 1219-1230 of SEQ ID NO: 7 can be replaced with glycine. In other aspects of this embodiment, contiguous amino acid substitutions of hydrophobic amino acids from amino acids 1154-1172 or amino acids 1219-1230 of SEQ ID NO: 7 can be replaced with phenylalanine. In yet other aspects of this embodiment, a modified BoNT/G $H_C$ region comprising a β-trefoil fold domain with enhanced binding activity comprises a polypeptide having, e.g., at most one, two, three, four, five, six, seven, eight, nine or 10 contiguous amino acid deletions relative to amino acids 1154-1172 or amino acids 1219-1230 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine or 10 contiguous amino acid deletions relative to amino acids 1154-1172 or amino acids 1219-1230 of SEQ ID NO: 7. In still other aspects of this embodiment, a modified BoNT/G $H_C$ region comprising a β-trefoil fold domain with enhanced binding activity comprises a polypeptide having, e.g., at most one, two, three, four, five, six, seven, eight, nine or 10 contiguous amino acid additions relative to amino acids 1154-1172 or amino acids 1219-1230 of SEQ ID NO: 7. In other aspects of this embodiment, a modified BoNT/G $H_C$ region comprising a β-trefoil fold domain with enhanced binding activity comprises a polypeptide having, e.g., at least one, two, three, four, five, six, seven, eight, nine or 10 contiguous amino acid additions relative to amino acids 1154-1172 or amino acids 1219-1230 of SEQ ID NO: 7.

In other aspects of this embodiment, a modified BoNT/G $H_C$ region with enhanced binding activity comprises a substitution of amino acid Trp 1096, Gly 1097, Leu 1100, Tyr 1106, Tyr 1107, Gly 1148, Ile 1153, Asp 1172, Gln 1198, Ile 1245, Ser 1266, Trp 1268, Tyr 1269, Arg 1272, Gly 1283 or Trp 1285, or any combination thereof, the substitution enhancing the binding activity of the modified BoNT/G $H_C$ region. In other aspects of this embodiment, a modified BoNT/G $H_C$ region with enhanced binding activity comprises a deletion of amino acid Trp 1096, Gly 1097, Leu 1100, Tyr 1106, Tyr 1107, Gly 1148, Ile 1153, Asp 1172, Gln 1198, Ile 1245, Ser 1266, Trp 1268, Tyr 1269, Arg 1272, Gly 1283 or Trp 1285, or any combination thereof, the deletion enhancing the binding activity of the modified BoNT/G $H_C$ region.

In another embodiment, a modified Clostridial toxin binding domain with enhanced binding activity comprises a modified TeNT binding domain with enhanced binding activity. In an aspect of this embodiment, a modified TeNT binding domain with enhanced binding activity comprises a modified TeNT $H_C$ region with enhanced binding activity or a modified TeNT $H_C$ region fragment with enhanced binding activity. In another aspect of this embodiment, a modified TeNT binding domain with enhanced binding activity comprises a modified TeNT $H_{CC}$ region with enhanced binding activity or a modified TeNT $H_{CC}$ region fragment with enhanced binding activity.

In other aspects of this embodiment, a modified TeNT $H_C$ region with enhanced binding activity comprises a polypeptide having, e.g., at least 70% amino acid identity with amino acids 880-1315 of SEQ ID NO: 8, at least 75% amino acid identity with amino acids 880-1315 of SEQ ID NO: 8, at least 80% amino acid identity with amino acids 880-1315 of SEQ ID NO: 8, at least 85% amino acid identity with amino acids 880-1315 of SEQ ID NO: 8, at least 90% amino acid identity with amino acids 880-1315 of SEQ ID NO: 8 or at least 95% amino acid identity with amino acids 880-1315 of SEQ ID NO: 8. In yet other aspects of this embodiment, a modified TeNT $H_C$ region with enhanced binding activity comprises a polypeptide having, e.g., at most 70% amino acid identity with amino acids 880-1315 of SEQ ID NO: 8, at most 75% amino acid identity with amino acids 880-1315 of SEQ ID NO: 8, at most 80% amino acid identity with amino acids 880-1315 of SEQ ID NO: 8, at most 85% amino acid identity with amino acids 880-1315 of SEQ ID NO: 8, at most 90% amino acid identity with amino acids 880-1315 of SEQ ID NO: 8 or at most 95% amino acid identity with amino acids 880-1315 of SEQ ID NO: 8.

In other aspects of this embodiment, a modified TeNT $H_C$ region with enhanced binding activity comprises a polypeptide having, e.g., at most one, two, three, four, five, six, seven, eight, nine, 10, 20, 30, 40, 50, 100, or 200 non-contiguous amino acid substitutions relative to amino acids 880-1315 of SEQ ID NO: 8. In other aspects of this embodiment, a modified TeNT $H_C$ region with enhanced binding activity comprises a polypeptide having, e.g., at least one, two, three, four, five, six, seven, eight, nine, 10, 20, 30, 40, 50, 100 or 200 non-contiguous amino acid substitutions relative to amino acids 880-1315 of SEQ ID NO: 8. In yet other aspects of this embodiment, a modified TeNT $H_C$ region with enhanced binding activity comprises a polypeptide having, e.g., at most one, two, three, four, five, six, seven, eight, nine, 10, 20, 30, 40, 50, 100 or 200 non-contiguous amino acid deletions relative to amino acids 880-1315 of SEQ ID NO: 8. In other aspects of this embodiment, a modified TeNT $H_C$ region with enhanced binding activity comprises a polypeptide having, e.g., at least one, two, three, four, five, six, seven, eight, nine, 10, 20, 30, 40, 50, 100 or 200 non-contiguous amino acid deletions relative to amino acids 880-1315 of SEQ ID NO: 8. In still other aspects of this embodiment, a modified TeNT $H_C$ region with enhanced binding activity comprises a polypeptide having, e.g., at most one, two, three, four, five, six, seven, eight, nine, 10, 20, 30, 40, 50, 100 or 200 non-contiguous amino acid additions relative to amino acids 880-1315 of SEQ ID NO: 8. In other aspects of this embodiment, a modified TeNT $H_C$ region with enhanced binding activity comprises a polypeptide having, e.g., at least one, two, three, four, five, six, seven, eight, nine, 10, 20, 30, 40, 50, 100 or 200 non-contiguous amino acid additions relative to amino acids 880-1315 of SEQ ID NO: 8.

In other aspects of this embodiment, a modified TeNT $H_C$ region with enhanced binding activity comprises a polypeptide having, e.g., at most one, two, three, four, five, six, seven, eight, nine, 10, 20, 30, 40, 50, 100 or 200 contiguous amino acid substitutions relative to amino acids 880-1315 of SEQ ID NO: 8. In other aspects of this embodiment, a modified TeNT $H_C$ region with enhanced binding activity comprises a polypeptide having, e.g., at least one, two, three, four, five, six, seven, eight, nine, 10, 20, 30, 40, 50, 100 or 200 contiguous amino acid substitutions relative to amino acids 880-1315 of SEQ ID NO: 8. In yet other aspects of this embodiment, a modified TeNT $H_C$ region with enhanced binding activity comprises a polypeptide having, e.g., at most one, two, three, four, five, six, seven, eight, nine, 10, 20, 30, 40, 50, 100 or 200 contiguous amino acid deletions relative to amino acids 880-1315 of SEQ ID NO: 8. In other aspects of this embodiment, a modified TeNT $H_C$ region with enhanced binding activity comprises a polypeptide having, e.g., at least one, two, three, four, five, six, seven, eight, nine, 10, 20, 30, 40, 50, 100 or 200 contiguous amino acid deletions relative to amino acids 880-1315 of SEQ ID NO: 8. In still other aspects of this embodiment, a modified TeNT $H_C$ region with enhanced binding activity comprises a polypeptide having, e.g., at most one, two, three, four, five, six, seven, eight, nine, 10, 20, 30, 40, 50, 100 or 200 contiguous amino acid additions relative to amino acids 880-1315 of SEQ ID NO: 8. In other aspects of this embodiment, a modified TeNT $H_C$ region with enhanced binding activity comprises a polypeptide having, e.g., at least one, two, three, four, five, six, seven, eight, nine, 10, 20, 30, 40, 50, 100 or 200 contiguous amino acid additions relative to amino acids 880-1315 of SEQ ID NO: 8.

In another embodiment, a modified TeNT $H_C$ region with enhanced binding activity comprises a modified TeNT $H_C$ region with enhanced binding activity of comprising a modification of amino acids 1128-1315 of SEQ ID NO: 8. In another aspect of this embodiment, a modified TeNT $H_C$ region with enhanced binding activity comprises a modified α-fold motif of a β-trefoil domain of a TeNT binding domain, a modified β-fold motif of a β-trefoil domain of a TeNT binding domain, or a modified γ-fold motif of a β-trefoil domain of a TeNT binding domain. In another aspect of this embodiment, a modified TeNT $H_C$ region with enhanced binding activity comprises a modification to amino acids 1128-1177, amino acids 1195-1240, or amino acids 1255-1315 of SEQ ID NO: 8.

In other aspects of this embodiment, a modified TeNT $H_C$ region comprising a β-trefoil fold domain with enhanced binding activity comprises a polypeptide having, e.g., at least 70% amino acid identity with amino acids 1128-1177, amino acids 1195-1240, or amino acids 1255-1315 of SEQ ID NO: 8, at least 75% amino acid identity with amino acids 1128-1177, amino acids 1195-1240, or amino acids 1255-1315 of SEQ ID NO: 8, at least 80% amino acid identity with amino acids 1128-1177, amino acids 1195-1240, or amino acids 1255-1315 of SEQ ID NO: 8, at least 85% amino acid identity with amino acids 1128-1177, amino acids 1195-1240, or amino acids 1255-1315 of SEQ ID NO: 8, at least 90% amino acid identity with amino acids 1128-1177, amino acids 1195-1240, or amino acids 1255-1315 of SEQ ID NO: 8 or at least 95% amino acid identity with amino acids 1128-1177, amino acids 1195-1240, or amino acids 1255-1315 of SEQ ID NO: 8. In yet other aspects of this embodiment, a modified TeNT $H_C$ region comprising a β-trefoil fold domain with enhanced binding activity comprises a polypeptide having, e.g., at most 70% amino acid identity with amino acids 1128-1177, amino acids 1195-1240, or amino acids 1255-1315 of SEQ ID NO: 8, at most 75% amino acid identity with amino acids 1128-1177, amino acids 1195-1240, or amino acids 1255-1315 of SEQ ID NO: 8, at most 80% amino acid identity with amino acids 1128-1177, amino acids 1195-1240, or amino acids 1255-1315 of SEQ ID NO: 8, at most 85% amino acid identity with amino acids 1128-1177, amino acids 1195-1240, or amino acids 1255-1315 of SEQ ID NO: 8, at most 90% amino acid identity with amino acids 1128-1177, amino acids 1195-1240, or amino acids 1255-1315 of SEQ ID NO: 8 or at most 95% amino acid identity with amino acids 1128-1177, amino acids 1195-1240, or amino acids 1255-1315 of SEQ ID NO: 8.

In other aspects of this embodiment, a modified TeNT $H_C$ region comprising a β-trefoil fold domain with enhanced binding activity comprises a polypeptide having, e.g., at most one, two, three, four, five, six, seven, eight, nine, 10 or 20 non-contiguous amino acid substitutions relative to amino acids 1128-1177, amino acids 1195-1240, or amino acids 1255-1315 of SEQ ID NO: 8. In other aspects of this embodiment, a modified TeNT $H_C$ region comprises a polypeptide having, e.g., at least one, two, three, four, five, six, seven, eight, nine, 10 or 20 non-contiguous amino acid substitutions relative to amino acids 1128-1177, amino acids 1195-1240, or amino acids 1255-1315 of SEQ ID NO: 8. In yet other aspects of this embodiment, a modified TeNT $H_C$ region comprising a β-trefoil fold domain with enhanced binding activity comprises a polypeptide having, e.g., at most one, two, three, four, five, six, seven, eight, nine, 10 or 20 non-contiguous amino acid deletions relative to amino acids 1128-1177, amino acids 1195-1240, or amino acids 1255-1315 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine, 10 or 20 non-contiguous amino acid deletions relative to amino acids 1128-1177, amino acids 1195-1240, or amino acids 1255-1315 of SEQ ID NO: 8. In still other aspects of this embodiment, a modified TeNT $H_C$ region comprising a β-trefoil fold domain with enhanced binding activity comprises a polypeptide having, e.g., at most one, two, three, four, five, six, seven, eight, nine, 10 or 20 non-contiguous amino acid additions relative to amino acids 1128-1177, amino acids 1195-1240, or amino acids 1255-1315 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine, 10 or 20 non-contiguous amino acid additions relative to amino acids 1128-1177, amino acids 1195-1240, or amino acids 1255-1315 of SEQ ID NO: 8.

In other aspects of this embodiment, a modified TeNT $H_C$ region comprising a β-trefoil fold domain with enhanced binding activity comprises a polypeptide having, e.g., at most one, two, three, four, five, six, seven, eight, nine, 10 or 20 contiguous amino acid substitutions relative to amino acids 1128-1177, amino acids 1195-1240, or amino acids 1255-1315 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine, 10 or 20 contiguous amino acid substitutions relative to amino acids 1128-1177, amino acids 1195-1240, or amino acids 1255-1315 of SEQ ID NO: 8. In yet other aspects of this embodiment, a modified TeNT $H_C$ region comprising a β-trefoil fold domain with enhanced binding activity comprises a polypeptide having, e.g., at most one, two, three, four, five, six, seven, eight, nine, 10 or 20 contiguous amino acid deletions relative to amino acids 1128-1177, amino acids 1195-1240, or amino acids 1255-1315 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine, 10 or 20 contiguous amino acid deletions relative to amino acids 1128-1177, amino acids 1195-1240, or amino acids 1255-1315 of SEQ ID NO: 8. In still other aspects of this embodiment, a modified TeNT $H_C$ region comprising a β-trefoil fold domain with enhanced binding activity comprises a polypeptide having, e.g., at most one, two, three, four, five, six, seven, eight, nine, 10 or 20 contiguous amino acid additions relative to amino acids 1128-1177, amino acids 1195-1240, or amino acids 1255-1315 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine, 10 or 20 contiguous amino acid additions relative to amino acids 1128-1177, amino acids 1195-1240, or amino acids 1255-1315 of SEQ ID NO: 8.

In another embodiment, a modified TeNT $H_C$ region with enhanced binding activity comprises a modified TeNT $H_C$ region with enhanced binding activity of comprises a modified β4/β5 hairpin turn of a β-trefoil domain of a TeNT binding domain or a β8/β9 hairpin turn of a β-trefoil domain of a TeNT binding domain. In another aspect of this embodiment, a modified TeNT $H_C$ region with enhanced binding activity comprises a modification of amino acids 1178-1194 or amino acids 1241-1254 of SEQ ID NO: 8.

In other aspects of this embodiment, a modified TeNT $H_C$ region comprising a β-trefoil fold domain with enhanced binding activity comprises a polypeptide having, e.g., at least 70% amino acid identity with amino acids 1178-1194 or amino acids 1241-1254 of SEQ ID NO: 8, at least 75% amino acid identity with amino acids 1178-1194 or amino acids 1241-1254 of SEQ ID NO: 8, at least 80% amino acid identity with amino acids 1178-1194 or amino acids 1241-1254 of SEQ ID NO: 8, at least 85% amino acid identity with amino acids 1178-1194 or amino acids 1241-1254 of SEQ ID NO: 8, at least 90% amino acid identity with amino acids 1178-1194 or amino acids 1241-1254 of SEQ ID NO: 8 or at least 95% amino acid identity with amino acids 1178-1194 or amino acids 1241-1254 of SEQ ID NO: 8. In yet other aspects of this embodiment, a modified TeNT $H_C$ region comprising a β-trefoil fold domain with enhanced binding activity comprises a polypeptide having, e.g., at most 70% amino acid identity with amino acids 1178-1194 or amino acids 1241-1254 of SEQ ID NO: 8, at most 75% amino acid identity with amino acids 1178-1194 or amino acids 1241-1254 of SEQ ID NO: 8, at most 80% amino acid identity with amino acids 1178-1194 or amino acids 1241-1254 of SEQ ID NO: 8, at most 85% amino acid identity with amino acids 1178-1194 or amino acids 1241-1254 of SEQ ID NO: 8, at most 90% amino acid identity with amino acids 1178-1194 or amino acids 1241-1254 of SEQ ID NO: 8 or at most 95% amino acid identity with amino acids 1178-1194 or amino acids 1241-1254 of SEQ ID NO: 8.

In other aspects of this embodiment, a modified TeNT $H_C$ region comprising a β-trefoil fold domain with enhanced binding activity comprises a polypeptide having, e.g., at most one, two, three, four, five, six, seven, eight, nine or 10 non-contiguous amino acid substitutions relative to amino acids 1178-1194 or amino acids 1241-1254 of SEQ ID NO: 8. In other aspects of this embodiment, a modified TeNT $H_C$ region comprises a polypeptide having, e.g., at least one, two, three, four, five, six, seven, eight, nine or 10 non-contiguous amino acid substitutions relative to amino acids 1178-1194 or amino acids 1241-1254 of SEQ ID NO: 8. In other aspects of this embodiment, a non-contiguous amino acid substitution of any amino acid from amino acids 1178-1194 or amino acids 1241-1254 of SEQ ID NO: 8 can be replaced with glycine. In other aspects of this embodiment, a non-contiguous amino acid substitution of any hydrophobic amino acid from amino acids 1178-1194 or amino acids 1241-1254 of SEQ ID NO: 8 can be replaced with phenylalanine. In yet other aspects of this embodiment, a modified TeNT $H_C$ region comprising a β-trefoil fold domain with enhanced binding activity comprises a polypeptide having, e.g., at most one, two, three, four, five, six, seven, eight, nine or 10 non-contiguous amino acid deletions relative to amino acids 1178-1194 or amino acids 1241-1254 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine or 10 non-contiguous amino acid deletions relative to amino acids 1178-1194 or amino acids 1241-1254 of SEQ ID NO: 8. In still other aspects of this embodiment, a modified TeNT $H_C$ region comprising a β-trefoil fold domain with enhanced binding activity comprises a polypeptide having, e.g., at most one, two, three, four, five, six, seven, eight, nine or 10 non-contiguous amino acid additions relative to amino acids 1178-1194 or amino acids 1241-1254 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine or 10 non-contiguous amino acid additions relative to amino acids 1178-1194 or amino acids 1241-1254 of SEQ ID NO: 8.

In other aspects of this embodiment, a modified TeNT $H_C$ region comprising a β-trefoil fold domain with enhanced binding activity comprises a polypeptide having, e.g., at most one, two, three, four, five, six, seven, eight, nine or 10 contiguous amino acid substitutions relative to amino acids 1178-1194 or amino acids 1241-1254 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine or 10 contiguous amino acid substitutions relative to amino acids 1178-1194 or amino acids 1241-1254 of SEQ ID NO: 8. In other aspects of this embodiment, contiguous amino acid substitutions of amino acids from amino acids 1178-1194 or amino acids 1241-1254 of SEQ ID NO: 8 can be replaced with glycine. In other aspects of this embodiment, contiguous amino acid substitutions of hydrophobic amino acids from amino acids 1178-1194 or amino acids 1241-1254 of SEQ ID NO: 8 can be replaced with phenylalanine. In yet other aspects of this embodiment, a modified TeNT $H_C$ region comprising a β-trefoil fold domain with enhanced binding activity comprises a polypeptide having, e.g., at most one, two, three, four, five, six, seven, eight, nine or 10 contiguous amino acid deletions relative to amino acids 1178-1194 or amino acids 1241-1254 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine or 10 contiguous amino acid deletions relative to amino acids 1178-1194 or amino acids 1241-1254 of SEQ ID NO: 8. In still other aspects of this embodiment, a modified TeNT $H_C$ region comprising a β-trefoil fold domain with enhanced binding activity comprises a polypeptide having, e.g., at most one, two, three, four, five, six, seven, eight, nine or 10 contiguous amino acid additions relative to amino acids 1178-1194 or amino acids 1241-1254 of SEQ ID NO: 8. In other aspects of this embodiment, a modified TeNT $H_C$ region comprising a β-trefoil fold domain with enhanced binding activity comprises a polypeptide having, e.g., at least one, two, three, four, five, six, seven, eight, nine or 10 contiguous amino acid additions relative to amino acids 1178-1194 or amino acids 1241-1254 of SEQ ID NO: 8.

In other aspects of this embodiment, a modified TeNT $H_C$ region with enhanced binding activity comprises a substitution of amino acid Trp 1118, Gly 1119, Leu 1122, Tyr 1128, Tyr 1129, Gly 1172, Ile 1177, Asp 1194, Asp 1222, Thr 1270, Ser 1287, Trp 1289, Tyr 1290, His 1293, Gly 1300 or Trp 1303, or any combination thereof, the substitution enhancing the binding activity of the modified TeNT $H_C$ region. In other aspects of this embodiment, a modified TeNT $H_C$ region with enhanced binding activity comprises a deletion of amino acid Trp 1118, Gly 1119, Leu 1122, Tyr 1128, Tyr 1129, Gly 1172, Ile 1177, Asp 1194, Asp 1222, Thr 1270, Ser 1287, Trp 1289, Tyr 1290, His 1293, Gly 1300 or Trp 1303, or any combination thereof, the deletion enhancing the binding activity of the modified TeNT $H_C$ region.

Another example of an enhanced targeting domain that increases binding activity for an endogenous Clostridial toxin receptor system present on a naturally-occurring Clostridial toxin target cell, includes, without limitation, non-toxin associated proteins of Clostridial toxins, such as, e.g., non-toxic non-hemagglutinin (NTNH), hemagglutinin-17 (HA-17), hemagglutinin-33 (HA-33) and hemagglutinin-70 (HA-70). In vivo, Clostridial bacteria produce a toxin complex comprising the approximately 150-kDa Clostridial toxin and other proteins collectively called nontoxin associated proteins (NAPs). Identified NAPs include proteins possessing hemaglutination activity, such, e.g., a hemagglutinin of approximately 17-kDa (HA-17), a hemagglutinin of approximately 33-kDa (HA-33) and a hemagglutinin of approximately 70-kDa (HA-70); as well as non-toxic non-hemagglutinin (NTNH), a protein of approximately 130-kDa, see, e.g., Eric A. Johnson and Marite Bradshaw, *Clostridial botulinum and its Neurotoxins: A Metabolic and Cellular Perspective,* 39 Toxicon 1703-1722 (2001); and Stephanie Raffestin et al., *Organization and Regulation of the Neurotoxin Genes in Clostridium botulinum and Clostridium tetani,* 10 Anaerobe 93-100 (2004). The toxin complex is important for the intoxication process because it provides protection from adverse environmental conditions, resistance to protease digestion, and appears to facilitate internalization and activation of the toxin.

Recent crystallography experiments have revealed that HA-17, HA-33 and NTNH from various Clostridial bacteria contain a region comprising β-trefoil domains very similar to the single β-trefoil domain present in the binding domain of Clostridial toxins, see, e.g., Kaoru Inoue et al., *Structural Analysis by X-Ray Crystallography and calorimtry of a Haemagglutinin Component (HA1) of the Progenitor Toxin from Clostridium botulinum,* 149 Microbiol. 3361-3370 (2003); and Joseph W. Arndt et al., *The Structure of the Neurotoxin-Associated Protein HA33/A from Clostridial botulinum Suggests a Reoccurring β-trefoil Fold in the Progenitor Toxin Complex,* 346 J. Mol. Biol. 1083-1093 (2005). For example, HA-33 from *Clostridium botulinum* serotype A has two β-trefoil domains, each of which consists of three potential carbohydrate binding moieties or β-trefoil folds, designated 1α (amino acids 10-55 of SEQ ID NO: 9), 1β (amino acids 56-102 of SEQ ID NO: 9) and 1γ (amino acids 103-144 of SEQ ID NO: 9) for the first β-trefoil domain and 2α (amino acids 151-197 of SEQ ID NO: 9), 2β (amino acids 198-245 of SEQ ID NO: 9) and 2γ (amino acids 246-293 of SEQ ID NO: 9) for the second β-trefoil domain. Mutations in conserved amino acids of the carbohydrate binding moiety result in a loss of carbohydrate binding, see, e.g., Kaoru Inoue et al., *Structural Analysis by X-Ray Crystallography and calorimetry of a Haemagglutinin Component (HA1) of the Progenitor Toxin from Clostridium botulinum,* 149 Microbiol. 3361-3370 (2003).

These β-trefoil domains are also found in the HA-33 proteins produced by *Clostridium botulinum* serotype B, serotype C1 and serotype D and sequence alignments revealed that amino acids essential for overall carbohydrate binding are conserved. The amino acids predicted to be essential for carbohydrate binding are as follows Asp 263, Tyr 265, Gln 268, Gln 276, Phe 278 and Gln 286 of HA-33/A1 of SEQ ID NO: 9, HA-33/A2 of SEQ ID NO: 10, HA-33/A3 of SEQ ID NO: 11, HA-33/A5 of SEQ ID NO: 12 and HA-33/B2 of SEQ ID NO: 15; Asp 264, Tyr 266, Gln 269, Gln 277, Phe 279 and Gln 287 of HA-33/A4 of SEQ ID NO: 12; Asp 262, Tyr 264, Gln 267, Gln 275, Phe 277 and Gln 285 of HA-33/B1 of SEQ ID NO: 14; Asp 255, Val 257, Gly 260, Gln 268, Typ 270 and Gln 278 of HA-33/C1 of SEQ ID NO: 16; and Asp 256, Tyr 258, Gln 261, Ise 269, Asp 271 and Gln 279 of HA-33/C2 of SEQ ID NO: 17 and HA-33/D of SEQ ID NO: 18. Immunoaffinity column chromatography and pull-down assays have shown that HA-33 can bind synaptotagmin II, a putative Clostridial toxin receptor, see, e.g., Yu Zhou et al., *Haemagglutinin-33 of Type Q Botulinum Neurotoxin Complex Binds with Synaptotagmin II,* 272 FEBS Lett. 2717-2726 (2005). The amino acid sequences comprising the β-trefoil domains found in various Clostridial HA-33 proteins are shown in Tables 3 and 4.

TABLE 3

β-trefoil Domains of Clostridial HA-33 Proteins

| | | Amino Acid Sequence Region of Carbohydrate Binding Moieties | | | | |
|---|---|---|---|---|---|---|
| Protein | SEQ ID NO: | 1α-fold | 1β4/β5 β-hairpin turn | 1β-fold | 1β8/β9 β-hairpin turn | 1γ-fold |
| HA-33/A1 | 9 | 10-54 | 55-59 | 60-100 | 101-104 | 105-144 |
| HA-33/A2 | 10 | 10-54 | 55-59 | 60-100 | 101-104 | 105-144 |
| HA-33/A3 | 11 | 10-54 | 55-59 | 60-100 | 101-104 | 105-144 |
| HA-33/A4 | 12 | 10-56 | 57-61 | 62-102 | 103-106 | 107-146 |
| HA-33/A5 | 13 | 10-54 | 55-59 | 60-100 | 101-104 | 105-144 |
| HA-33/B1 | 14 | 10-54 | 55-59 | 60-100 | 101-104 | 105-144 |
| HA-33/B2 | 15 | 10-56 | 57-61 | 62-102 | 103-106 | 107-146 |
| HA-33/C1-1 | 16 | 10-54 | 55-59 | 60-98 | 99-102 | 103-141 |
| HA-33/C1-2 | 17 | 10-54 | 55-59 | 60-98 | 99-102 | 103-141 |
| HA-33/D1 | 18 | 10-54 | 55-59 | 60-98 | 99-102 | 103-141 |

TABLE 4

| β-trefoil Domains of Clostridial HA-33 Proteins | | | | | | |
|---|---|---|---|---|---|---|
| | | Amino Acid Sequence Region of Carbohydrate Binding Moieties | | | | |
| Protein | SEQ ID NO: | 2α-fold | 2β4/β5 β-hairpin turn | 2β-fold | 2β8/β9 β-hairpin turn | 2γ-fold |
| HA-33/A1 | 9 | 151-195 | 196-199 | 200-242 | 243-248 | 249-293 |
| HA-33/A2 | 10 | 151-195 | 196-199 | 200-242 | 243-248 | 249-293 |
| HA-33/A3 | 11 | 151-195 | 196-199 | 200-242 | 243-248 | 249-293 |
| HA-33/A4 | 12 | 153-197 | 198-201 | 202-243 | 244-249 | 250-294 |
| HA-33/A5 | 13 | 151-195 | 196-199 | 200-242 | 243-248 | 249-279 |
| HA-33/B1 | 14 | 151-195 | 196-199 | 200-241 | 242-247 | 248-292 |
| HA-33/B2 | 15 | 153-197 | 198-201 | 200-242 | 243-248 | 249-291 |
| HA-33/C1-1 | 16 | 148-190 | 191-194 | 195-234 | 235-240 | 241-285 |
| HA-33/C1-2 | 17 | 148-190 | 191-194 | 195-235 | 236-241 | 242-286 |
| HA-33/D1 | 18 | 148-190 | 191-194 | 195-235 | 236-241 | 242-286 |

Further analysis of the β-trefoil domain sequence of HA-33 also identified β-trefoil domains in HA-17 and NTNH, see, e.g., Joseph W. Arndt et al., *The Structure of the Neurotoxin-Associated Protein HA33/A from Clostridial botulinum Suggests a Reoccurring β-trefoil Fold in the Progenitor Toxin Complex,* 346 J. Mol. Biol. 1083-1093 (2005). The HA-17 comprises a single β-trefoil domain containing three carbohydrate binding moieties or β-trefoil folds. The carbohydrate binding moieties of HA-17 exhibits the greatest sequence similarity with the 2γ carbohydrate binding moiety of HA-33. These β-trefoil domains are also found in the HA-17 proteins produced by *Clostridium botulinum* serotype B, serotype C1 and serotype D and sequence alignments revealed that amino acids essential for overall carbohydrate binding are conserved. The amino acids predicted to be essential for carbohydrate binding are as follows Tyr 110, Typ 112, Tyr 115, Pro 130, Phe 132 and Asn 138 of HA-17/A of SEQ ID NO: 19, HA-17/B of SEQ ID NO: 20, HA-17/C1 of SEQ ID NO: 21 and HA-17/D of SEQ ID NO: 22. The amino acid sequences comprising the β-trefoil domains found in various Clostridial HA-17 proteins are shown in Table 5.

TABLE 5

| β-trefoil Domains of Clostridial HA-17 Proteins | | | | | | |
|---|---|---|---|---|---|---|
| | | Amino Acid Sequence Region of Carbohydrate Binding Moieties | | | | |
| Protein | SEQ ID NO: | α-fold | β4/β5 β-hairpin turn | β-fold | β8/β9 β-hairpin turn | γ-fold |
| HA-17/A | 19 | 9-50 | 51-54 | 55-91 | 92-94 | 95-146 |
| HA-17/B | 20 | 9-50 | 51-54 | 55-91 | 92-94 | 95-146 |
| HA-17/C1 | 21 | 9-50 | 51-54 | 55-91 | 92-94 | 95-146 |
| HA-17/D | 22 | 9-50 | 51-54 | 55-91 | 92-94 | 95-146 |

NTNH from various Clostridial bacteria shows significant sequence similarity to the β-trefoil domains present in the cell binding domain of BoNT/A and TeNT. The high degree of structural similarity is interesting in light of the low sequence similarity between NTNH and the Clostridial toxins. Furthermore, since NTNH of the various serotypes have greater sequence similarity than the Clostridial toxins, it is likely that the NTNH produced by other Clostridial strains will also have β-trefoil domains exhibiting high structural similarity with the binding domains of Clostridial toxins. The β-trefoil domains of various Clostridial NTNHs are as follows: amino acids 1050-1193 of NTNH/A1 of SEQ ID NO: 23; amino acids 1050-1198 of NTNH/A2 of SEQ ID NO: 24; amino acids 1050-1193 of NTNH/A3 of SEQ ID NO: 25; amino acids 1049-1197 of NTNH/B of SEQ ID NO: 26; amino acids 1049-1196 of NTNH/C1 of SEQ ID NO: 27; amino acids 1049-1196 of NTNH/D of SEQ ID NO: 28; amino acids 1014-1162 of NTNH/E of SEQ ID NO: 29; amino acids 1016-1159 of NTNH/F1 of SEQ ID NO: 30; amino acids 1017-1165 of NTNH/F2 of SEQ ID NO: 31; and amino acids 1050-1198 of NTNH/G of SEQ ID NO: 32. The amino acid sequences comprising the β-trefoil domains found in various Clostridial NTNH proteins are shown in Table 6.

The β-trefoil domains present in the Clostridial toxin, HA-33, HA-17 and NTNH collectively form nearly half the mass of a Clostridial toxin complex and underlies the apparent importance of carbohydrate binding in the cell binding step of the intoxication process. This observation is further enhanced by the fact that a Clostridial toxin alone is not as effective in intoxicating a cell as the entire toxin complex. One potential explanation for this enhanced binding activity is the presence, both in type and in quantity, of the β-trefoil domains present in HA-33, HA-17 and NTNH. Therefore, the high prediction of structural similarity of the β-trefoil domains present in HA-33, HA-17 and NTNH relative to the β-trefoil domain found in Clostridial toxins provides a potential source of binding domains useful for developing modified Clostridial toxins with enhanced binding activity. As a non-limiting example, a carbohydrate binding moiety or a β-trefoil fold from HA-33, HA-17 or NTNH can be substituted for the naturally occurring carbohydrate binding moiety present in a Clostridial toxin. As another non-limiting example, a carbohydrate binding moiety or a β-trefoil fold from HA-33, HA-17 or NTNH can be added in addition to the naturally occurring carbohydrate binding moiety present in a Clostridial toxin. As yet another non-limiting example, a multiple carbohydrate binding moieties or a β-trefoil folds from HA-33, HA-17 or NTNH can be substituted for the naturally occurring carbohydrate binding moiety present in a Clostridial toxin. As still another non-limiting example, multiple carbohydrate binding moieties or a β-trefoil folds from HA-33, HA-17 or NTNH can be added in addition to the naturally occurring carbohydrate binding moiety present in a Clostridial toxin. As another non-limiting example, multiple carbohydrate binding moieties or a β-trefoil folds from a Clostridial toxin binding domain can be added in addition to the naturally occurring carbohydrate binding moiety present in a Clostridial toxin.

TABLE 6

β-trefoil Domains of Clostridial NTNH Proteins

| Protein | SEQ ID NO: | Amino Acid Sequence Region of Carbohydrate Binding Moieties | | | | |
|---|---|---|---|---|---|---|
| | | α-fold | β4/β5 β-hairpin turn | β-fold | β8/β9 β-hairpin turn | γ-fold |
| NTNH/A1 | 23 | 1050-1097 | 1098-1110 | 1111-1138 | 1139-1148 | 1149-1194 |
| NTNH/A2 | 24 | 1050-1097 | 1098-1110 | 1111-1139 | 1140-1148 | 1149-1199 |
| NTNH/A3 | 25 | 1050-1097 | 1098-1110 | 1111-1138 | 1139-1148 | 1149-1194 |
| NTNH/B | 26 | 1049-1096 | 1097-1109 | 1110-1138 | 1139-1147 | 1148-1198 |
| NTNH/C1 | 27 | 1049-1096 | 1097-1109 | 1110-1138 | 1139-1147 | 1148-1197 |
| NTNH/D | 28 | 1049-1096 | 1097-1109 | 1110-1138 | 1139-1147 | 1148-1197 |
| NTNH/E | 29 | 1014-1061 | 1062-1074 | 1075-1103 | 1104-1113 | 1114-1163 |
| NTNH/F1 | 30 | 1016-1063 | 1064-1076 | 1077-1104 | 1105-1114 | 1115-1160 |
| NTNH/F2 | 31 | 1017-1064 | 1065-1077 | 1078-1106 | 1107-1116 | 1117-1166 |
| NTNH/G | 32 | 1050-1097 | 1098-1110 | 1111-1139 | 1140-1149 | 1150-1199 |

As used herein, the term "Non-toxin Associated Protein" is synonymous with "NAP" and means a Clostridial NAP with selective binding activity, such as, e.g., a binding affinity or a binding specificity, for an endogenous Clostridial toxin receptor system. It is envisioned that both naturally occurring NAPs as well as NAPs with enhanced binding activity can be used to practice aspects of the present invention. As used herein, the term "NAP with enhanced binding activity" means a Clostridial NAP with enhanced binding activity for an endogenous Clostridial toxin receptor system, such as, e.g., a binding affinity or a binding specificity, to a statistically significantly degree relative to an unmodified naturally occurring Clostridial toxin binding domain from a Clostridial toxin. By definition, a NAP with enhanced binding activity has at least one amino acid change from the corresponding region of the disclosed reference sequences (see Table 3-6) and can be described in percent identity to the corresponding region of that reference sequence.

Any of a variety of sequence alignment methods can be used to determine percent identity of a modified Clostridial NAP relative to a naturally-occurring Clostridial NAP, including, without limitation, global methods, local methods and hybrid methods, such as, e.g., segment approach methods. Protocols to determine percent identity are routine procedures within the scope of one skilled in the art and from the teaching herein.

Approaches well known to one skilled in the art on how to modify a Clostridial NAP in order to increase its binding activity for an endogenous Clostridial toxin receptor system present on a naturally-occurring Clostridial toxin target cell. As described above, one approach involves identifying amino acids using computational protein design algorithims; changing specifically-identified amino acids using, without limitation, site-directed mutagenesis, oligonucleotide-directed mutagenesis and site-specific mutagenesis; and testing the binding activity of modified Clostridial toxins comprising a modified Clostridial NAP with enhanced binding activity using, e.g., heterogeneous assays, homogeneous assays and non-separating homogeneous assays. It is further envisioned that the binding activity of a modified Clostridial toxin with enhanced binding activity disclosed in the present specification can be determined by affinity chromotography using immobilized receptors and interfacial optical assays. In another approach described above, a binding activity of a modified Clostridial NAP for a naturally-occurring Clostridial toxin receptor system present on a naturally-occurring Clostridial toxin target cell can be achieved using directed-evolution methods.

A Clostridial NAP includes, without limitation, naturally occurring Clostridial NAP variants, such as, e.g., Clostridial NAP isoforms and Clostridial NAP subtypes; non-naturally occurring Clostridial NAP variants, such as, e.g., conservative Clostridial NAP variants, non-conservative Clostridial NAP variants, Clostridial NAP chimerics, active Clostridial NAP fragments thereof, or any combination thereof.

As used herein, the term "Clostridial NAP variant," whether naturally-occurring or non-naturally-occurring, means a Clostridial NAP that has at least one amino acid change from the corresponding region of the disclosed reference sequences (see Tables 3-6) and can be described in percent identity to the corresponding region of that reference sequence. Unless expressly indicated, all Clostridial NAP variants disclosed in the present specification are capable of executing the cell binding step of the intoxication process.

It is recognized by those of skill in the art that within each Clostridial bacterium there can be naturally occurring Clostridial NAP variants that differ somewhat in their amino acid sequence, and also in the nucleic acids encoding these proteins. For example, there are presently five Clostridial botulinum serotype A HA-33 variants, HA-33/A1, HA-33/A2, HA-33/A3, HA-33/A4 and HA-33/A5 (Tables 3 and 4), with specific HA-33 variants showing various degrees of amino acid divergence when compared to another HA-33 variant. As another example, there are presently three Clostridial botulinum serotype A NTNH-33 variants, NTNH/A1, NTNH/A2 and NTNH/A3 (Table 6), with specific NTNH variant showing various degrees of amino acid divergence when compared to another NTNH variant. As used herein, the term "naturally occurring Clostridial NAP variant" means any Clostridial NAP produced by a naturally-occurring process, including, without limitation, Clostridial NAP isoforms produced from alternatively-spliced transcripts, Clostridial NAP isoforms produced by spontaneous mutation and Clostridial NAP subtypes. A naturally occurring Clostridial NAP variant can function in substantially the same manner as the reference Clostridial NAP on which the naturally occurring Clostridial NAP variant is based, and can be substituted for the reference Clostridial NAP in any aspect of the present invention. A naturally occurring Clostridial NAP variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial NAP on which the naturally occurring Clostridial NAP variant is based. A naturally occurring Clostridial NAP variant can also substitute at least 10 contiguous amino acids, at least 15 contiguous amino acids, at least 20 contiguous amino acids, or at least 25 contiguous amino acids from the reference Clostridial NAP on which the naturally occurring Clostridial NAP variant is based, that possess at least 50% amino acid identity, 65% amino acid identity, 75% amino acid identity, 85% amino acid identity or 95% amino acid identity to the reference Clostridial NAP on which the naturally occurring Clostridial NAP variant is based.

A non-limiting examples of a naturally occurring Clostridial NAP variant is a Clostridial NAP isoform such as, e.g., a Clostridial botulinum serotype A HA-33 isoform, a Clostridial botulinum serotype B HA-33 isoform, a Clostridial botulinum serotype C1 HA-33 isoform, a Clostridial botulinum serotype D HA-33 isoform, a Clostridial botulinum serotype A HA-17 isoform, a Clostridial botulinum serotype B HA-17 isoform, a Clostridial botulinum serotype C1 HA-17 isoform, a Clostridial botulinum serotype D HA-17 isoform, a Clostridial botulinum serotype A NTNH isoform, a Clostridial botulinum serotype B NTNH isoform, a Clostridial botulinum serotype C1 NTNH isoform, a Clostridial botulinum serotype D NTNH isoform, a Clostridial botulinum serotype E NTNH isoform, a Clostridial botulinum serotype F NTNH isoform and a Clostridial botulinum serotype G NTNH isoform. A Clostridial NAP isoform can function in substantially the same manner as the reference Clostridial NAP on which the Clostridial NAP isoform is based, and can be substituted for the reference Clostridial NAP in any aspect of the present invention.

Another non-limiting examples of a naturally occurring Clostridial NAP variant is a Clostridial NAP subtype such as, e.g., a Clostridial botulinum serotype A HA-33 subtype, a Clostridial botulinum serotype B HA-33 subtype, a Clostridial botulinum serotype C1 HA-33 subtype, a Clostridial botulinum serotype D HA-33 subtype, a Clostridial botulinum serotype A HA-17 subtype, a Clostridial botulinum serotype B HA-17 subtype, a Clostridial botulinum serotype C1 HA-17 subtype, a Clostridial botulinum serotype D HA-17 subtype, a Clostridial botulinum serotype A NTNH subtype, a Clostridial botulinum serotype B NTNH subtype, a Clostridial botulinum serotype C1 NTNH subtype, a Clostridial botulinum serotype D NTNH subtype, a Clostridial botulinum serotype E NTNH subtype, a Clostridial botulinum serotype F NTNH subtype and a Clostridial botulinum serotype G NTNH subtype. A Clostridial NAP subtype can function in substantially the same manner as the reference Clostridial NAP on which the Clostridial NAP subtype is based, and can be substituted for the reference Clostridial NAP in any aspect of the present invention.

As used herein, the term "non-naturally occurring Clostridial NAP variant" means any Clostridial NAP produced with the aid of human manipulation, including, without limitation, Clostridial NAPs produced by genetic engineering using random mutagenesis or rational design and Clostridial NAPs produced by chemical synthesis. Non-limiting examples of non-naturally occurring Clostridial NAP variants include, e.g., conservative Clostridial NAP variants, non-conservative Clostridial NAP variants, Clostridial NAP chimeric variants and active Clostridial NAP fragments.

As used herein, the term "conservative Clostridial NAP variant" means a Clostridial NAP that has at least one amino acid substituted by another amino acid or an amino acid analog that has at least one property similar to that of the original amino acid from the reference Clostridial NAP sequence (see Tables 3-6). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial NAP variant can function in substantially the same manner as the reference Clostridial NAP on which the conservative Clostridial NAP variant is based, and can be substituted for the reference Clostridial NAP in any aspect of the present invention. A conservative Clostridial NAP variant may substitute one or more amino acids, two or more amino acids, three or more amino acids, four or more amino acids, five or more amino acids, ten or more amino acids, 20 or more amino acids, 30 or more amino acids, 40 or more amino acids or 50 or more amino acids from the reference Clostridial NAP on which the conservative Clostridial NAP variant is based. A conservative Clostridial NAP variant can also substitute at least 10 contiguous amino acids, at least 15 contiguous amino acids, at least 20 contiguous amino acids, or at least 25 contiguous amino acids from the reference Clostridial NAP on which the conservative Clostridial NAP variant is based, that possess at least 50% amino acid identity, 65% amino acid identity, 75% amino acid identity, 85% amino acid identity or 95% amino acid identity to the reference Clostridial NAP on which the conservative Clostridial NAP variant is based. Non-limiting examples of a conservative Clostridial NAP variant include, e.g., a conservative Clostridial botulinum serotype A HA-33 variant, a conservative Clostridial botulinum serotype B HA-33 variant, a conservative Clostridial botulinum serotype C1 HA-33 variant, a conservative Clostridial botulinum serotype D HA-33 variant, a conservative Clostridial botulinum serotype A HA-17 variant, a conservative Clostridial botulinum serotype B HA-17 variant, a conservative Clostridial botulinum serotype C1 HA-17 variant, a conservative Clostridial botulinum serotype D HA-17 variant, a conservative Clostridial botulinum serotype A NTNH variant, a conservative Clostridial botulinum serotype B NTNH variant, a conservative Clostridial botulinum serotype C1 NTNH variant, a conservative Clostridial botulinum serotype D NTNH variant, a conservative Clostridial botulinum serotype E NTNH variant, a conservative Clostridial botulinum serotype F NTNH variant and a conservative Clostridial botulinum serotype G NTNH variant.

As used herein, the term "non-conservative Clostridial NAP variant" means a Clostridial NAP in which 1) at least one amino acid is deleted from the reference Clostridial NAP on which the non-conservative Clostridial NAP variant is based; 2) at least one amino acid added to the reference Clostridial NAP on which the non-conservative Clostridial NAP is based; or 3) at least one amino acid is substituted by another amino acid or an amino acid analog that does not share any property similar to that of the original amino acid from the reference Clostridial NAP sequence (see Tables 3-6). A non-conservative Clostridial NAP variant can function in substantially the same manner as the reference Clostridial NAP on which the non-conservative Clostridial NAP variant is based, and can be substituted for the reference Clostridial NAP in any aspect of the present invention. A non-conservative Clostridial NAP variant can delete one or more amino acids, two or more amino acids, three or more amino acids, four or more amino acids, five or more amino acids, and ten or more amino acids from the reference Clostridial NAP on which the non-conservative Clostridial NAP variant is based. A non-conservative Clostridial NAP variant can add one or more amino acids, two or more amino acids, three or more amino acids, four or more amino acids, five or more amino acids, and ten or more amino acids to the reference Clostridial NAP on which the non-conservative Clostridial NAP variant is based. A non-conservative Clostridial NAP variant may substitute one or more amino acids, two or more amino acids, three or more amino acids, four or more amino acids, five or more amino acids, ten or more amino acids, 20 or more amino acids, 30 or more amino acids, 40 or more amino acids or 50 or more amino acids from the reference Clostridial NAP on which the non-conservative Clostridial NAP variant is based. A non-conservative Clostridial NAP variant can also substitute at least 10 contiguous amino acids, at least 15 contiguous amino acids, at least 20 contiguous amino acids, or at least 25 contiguous amino acids from the reference Clostridial NAP on which the non-conservative Clostridial NAP variant is based, that possess at least 50% amino acid identity, 65% amino acid identity, 75% amino acid identity, 85% amino acid identity or 95% amino acid identity to the reference Clostridial NAP on which the non-conservative Clostridial NAP variant is based. Non-limiting examples of a non-conservative Clostridial NAP variant include, e.g., a non-conservative Clostridial botulinum serotype A HA-33 variant, a non-conservative Clostridial botulinum serotype B HA-33 variant, a non-conservative Clostridial botulinum serotype C1 HA-33 variant, a non-conservative Clostridial botulinum serotype D HA-33 variant, a non-conservative Clostridial botulinum serotype A HA-17 variant, a non-conservative Clostridial botulinum serotype B HA-17 variant, a non-conservative Clostridial botulinum serotype C1 HA-17 variant, a non-conservative Clostridial botulinum serotype D HA-17 variant, a non-conservative Clostridial botulinum serotype A NTNH variant, a non-conservative Clostridial botulinum serotype B NTNH variant, a non-conservative Clostridial botulinum serotype C1 NTNH variant, a non-conservative Clostridial botulinum serotype D NTNH variant, a non-conservative Clostridial botulinum serotype E NTNH variant, a non-conservative Clostridial botulinum serotype F NTNH variant and a non-conservative Clostridial botulinum serotype G NTNH variant.

As used herein, the term “Clostridial NAP chimeric” means a polypeptide comprising at least a portion of a Clostridial NAP and at least a portion of at least one other polypeptide to form an enhanced targeting domain with at least one property different from the reference Clostridial NAP (see Tables 3-6), with the proviso that this Clostridial NAP chimeric can specifically bind to a Clostridial toxin receptor system present in a Clostridial toxin target cell, and thus participate in executing the overall cellular mechanism whereby a Clostridial toxin proteolytically cleaves a substrate.

As used herein, the term “active Clostridial NAP fragment” means any of a variety of Clostridial NAP fragments comprising the enhanced targeting domain can be useful in aspects of the present invention with the proviso that these NAP fragments can specifically bind to a Clostridial toxin receptor system present in a Clostridial toxin target cell, and thus participate in executing the overall cellular mechanism whereby a Clostridial toxin proteolytically cleaves a substrate.

Thus, in an embodiment, a modified Clostridial toxin disclosed in the present specification comprises an enhanced targeting domain comprising a β-trefoil domain derived from a NAP. In another embodiment, a modified Clostridial toxin disclosed in the present specification comprises an enhanced targeting domain comprising a β-trefoil domain with enhanced binding activity derived from a NAP.

In another embodiment, a modified Clostridial toxin disclosed in the present specification comprises an enhanced targeting domain comprising a β-trefoil domain derived from a Clostridial HA-33. In an aspect of this embodiment, a β-trefoil domain derived from a Clostridial HA-33 comprises, e.g., a β-trefoil domain derived from a Clostridial botulinum serotype A HA-33, a β-trefoil domain derived from a Clostridial botulinum serotype B HA-33, a β-trefoil domain derived from a Clostridial botulinum serotype C1 HA-33 or a β-trefoil domain derived from a Clostridial botulinum serotype D HA-33. In another aspect of this embodiment, a β-trefoil domain derived from a Clostridial HA-33 comprises a 1α-fold motif of a β-trefoil domain of a Clostridial botulinum serotype A HA-33, a 1β-fold motif of a β-trefoil domain of a Clostridial botulinum serotype A HA-33, a 1γ-fold motif of a β-trefoil domain of a Clostridial botulinum serotype A HA-33, a 2α-fold motif of a β-trefoil domain of a Clostridial botulinum serotype A HA-33, a 2β-fold motif of a β-trefoil domain of a Clostridial botulinum serotype A HA-33, or a 2γ-fold motif of a β-trefoil domain of a Clostridial botulinum serotype A HA-33.

In another embodiment, a modified Clostridial toxin disclosed in the present specification comprises an enhanced targeting domain comprising a β-trefoil domain with enhanced binding activity derived from a Clostridial HA-33. In an aspect of this embodiment, a β-trefoil domain with enhanced binding activity derived from a Clostridial HA-33 comprises, e.g., a β-trefoil domain with enhanced binding activity derived from a Clostridial botulinum serotype A HA-33, a β-trefoil domain with enhanced binding activity derived from a Clostridial botulinum serotype B HA-33, a β-trefoil domain with enhanced binding activity derived from a Clostridial botulinum serotype C1 HA-33 or a β-trefoil domain with enhanced binding activity derived from a Clostridial botulinum serotype D HA-33. In another aspect of this embodiment, a β-trefoil domain with enhanced binding activity derived from a Clostridial HA-33 comprises a modified 1α-fold motif of a β-trefoil domain of a Clostridial botulinum serotype A HA-33, a modified 1β-fold motif of a β-trefoil domain of a Clostridial botulinum serotype A HA-33, a modified 1γ-fold motif of a β-trefoil domain of a Clostridial botulinum serotype A HA-33, a modified 2α-fold motif of a β-trefoil domain of a Clostridial botulinum serotype A HA-33, a modified 2β-fold motif of a β-trefoil domain of a Clostridial botulinum serotype A HA-33, or a modified 2γ-fold motif of a β-trefoil domain of a Clostridial botulinum serotype A HA-33.

In another embodiment, a β-trefoil domain derived from a Clostridial botulinum serotype A HA-33 comprises a β-trefoil domain derived from a Clostridial botulinum serotype A HA-33 of SEQ ID NO: 9. In another embodiment, a β-trefoil domain derived from a Clostridial botulinum serotype A HA-33 comprises amino acids 10-144 or amino acids 151-293 of SEQ ID NO: 9. In another aspect of this embodiment, a β-trefoil domain derived from a Clostridial botulinum serotype A HA-33 comprises a 1α-fold motif of a β-trefoil domain of a Clostridial botulinum serotype A HA-33, a 1β-fold motif of a β-trefoil domain of a Clostridial botulinum serotype A HA-33, a 1γ-fold motif of a β-trefoil domain of a Clostridial botulinum serotype A HA-33, a 2α-fold motif of a β-trefoil domain of a Clostridial botulinum serotype A HA-33, a 2β-fold motif of a β-trefoil domain of a Clostridial botulinum serotype A HA-33, or a 2γ-fold motif of a β-trefoil domain of a Clostridial botulinum serotype A HA-33 of SEQ ID NO: 9. In another aspect of this embodiment, a β-trefoil domain derived from a Clostridial botulinum serotype A HA-33 comprises amino acids 10-54, amino acids 60-100, amino acids 105-144, amino acids 151-195, amino acids 200-242, or amino acids 249-293 of SEQ ID NO: 9.

In another embodiment, a β-trefoil domain with enhanced binding activity derived from a Clostridial botulinum serotype A HA-33 comprises a β-trefoil domain with enhanced binding activity derived from a Clostridial botulinum serotype A HA-33 of SEQ ID NO: 9. In another embodiment, a β-trefoil domain with enhanced binding activity derived from a Clostridial botulinum serotype A HA-33 comprises amino acids 10-144 or amino acids 151-293 of SEQ ID NO: 9. In another aspect of this embodiment, a β-trefoil domain with enhanced binding activity derived from a Clostridial botulinum serotype A HA-33 comprises a modified 1α-fold motif of a β-trefoil domain of a Clostridial botulinum serotype A HA-33, a modified 1β-fold motif of a β-trefoil domain of a Clostridial botulinum serotype A HA-33, a modified 1γ-fold motif of a β-trefoil domain of a Clostridial botulinum serotype A HA-33, a modified 2α-fold motif of a β-trefoil domain of a Clostridial botulinum serotype A HA-33, a modified 2β-fold motif of a β-trefoil domain of a Clostridial botulinum serotype A HA-33, or a modified 2γ-fold motif of a β-trefoil domain of a Clostridial botulinum serotype A HA-33 of SEQ ID NO: 9. In another aspect of this embodiment, a β-trefoil domain with enhanced binding activity derived from a Clostridial botulinum serotype A HA-33 comprises amino acids 10-54, amino acids 60-100, amino acids 105-144, amino acids 151-195, amino acids 200-242, or amino acids 249-293 of SEQ ID NO: 9.

In other aspects of this embodiment, a Clostridial botulinum serotype A HA-33 comprising a β-trefoil domain with enhanced binding activity comprises a polypeptide having, e.g., at least 70% amino acid identity with amino acids 10-54, amino acids 60-100, amino acids 105-144, amino acids 151-195, amino acids 200-242, or amino acids 249-293 of SEQ ID NO: 9, at least 75% amino acid identity with amino acids 10-54, amino acids 60-100, amino acids 105-144, amino acids 151-195, amino acids 200-242, or amino acids 249-293 of SEQ ID NO: 9, at least 80% amino acid identity with amino acids 10-54, amino acids 60-100, amino acids 105-144, amino acids 151-195, amino acids 200-242, or amino acids 249-293 of SEQ ID NO: 9, at least 85% amino acid identity with amino acids 10-54, amino acids 60-100, amino acids 105-144, amino acids 151-195, amino acids 200-242, or amino acids 249-293 of SEQ ID NO: 9, at least 90% amino acid identity with amino acids 10-54, amino acids 60-100, amino acids 105-144, amino acids 151-195, amino acids 200-242, or amino acids 249-293 of SEQ ID NO: 9 or at least 95% amino acid identity with amino acids 10-54, amino acids 60-100, amino acids 105-144, amino acids 151-195, amino acids 200-242, or amino acids 249-293 of SEQ ID NO: 9. In yet other aspects of this embodiment, a Clostridial botulinum serotype A HA-33 comprising a β-trefoil domain with enhanced binding activity comprises a polypeptide having, e.g., at most 70% amino acid identity with amino acids 10-54, amino acids 60-100, amino acids 105-144, amino acids 151-195, amino acids 200-242, or amino acids 249-293 of SEQ ID NO: 9, at most 75% amino acid identity with amino acids 10-54, amino acids 60-100, amino acids 105-144, amino acids 151-195, amino acids 200-242, or amino acids 249-293 of SEQ ID NO: 9, at most 80% amino acid identity with amino acids 10-54, amino acids 60-100, amino acids 105-144, amino acids 151-195, amino acids 200-242, or amino acids 249-293 of SEQ ID NO: 9, at most 85% amino acid identity with amino acids 10-54, amino acids 60-100, amino acids 105-144, amino acids 151-195, amino acids 200-242, or amino acids 249-293 of SEQ ID NO: 9, at most 90% amino acid identity with amino acids 10-54, amino acids 60-100, amino acids 105-144, amino acids 151-195, amino acids 200-242, or amino acids 249-293 of SEQ ID NO: 9 or at most 95% amino acid identity with amino acids 10-54, amino acids 60-100, amino acids 105-144, amino acids 151-195, amino acids 200-242, or amino acids 249-293 of SEQ ID NO: 9.

In other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 9. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 9. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 9. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 9. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 9. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 9.

In other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 9. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 9. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 9. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 9. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 9. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 9.

In another embodiment, a β-trefoil domain derived from a Clostridial botulinum serotype A HA-33 comprises a 1β4/β5 hairpin turn of a β-trefoil domain of a Clostridial botulinum serotype A HA-33, a 1β8/β9 hairpin turn of a β-trefoil domain of a Clostridial botulinum serotype A HA-33, a 2β4/β5 hairpin turn of a β-trefoil domain of a Clostridial botulinum serotype A HA-33 or a 2β8/β9 hairpin turn of a β-trefoil domain of a Clostridial botulinum serotype A HA-33 of SEQ ID NO: 9. In another aspect of this embodiment, a β-trefoil domain derived from a Clostridial botulinum serotype A HA-33 comprises amino acids 55-59, amino acids 101-104, amino acids 196-199, or amino acids 243-248 of SEQ ID NO: 9.

In another embodiment, a β-trefoil domain with enhanced binding activity derived from a Clostridial botulinum serotype A HA-33 comprises a modifeid 1β4/β5 hairpin turn of a β-trefoil domain of a Clostridial botulinum serotype A HA-33, a modifeid 1β8/β9 hairpin turn of a β-trefoil domain of a Clostridial botulinum serotype A HA-33, a modifeid 2β4/β5 hairpin turn of a β-trefoil domain of a Clostridial botulinum serotype A HA-33 or a modifeid 2β8/β9 hairpin turn of a β-trefoil domain of a Clostridial botulinum serotype A HA-33 of SEQ ID NO: 9. In another aspect of this embodiment, a β-trefoil domain with enhanced binding activity derived from a Clostridial botulinum serotype A HA-33 comprises a modification of amino acids 55-59, amino acids 101-104, amino acids 196-199, or amino acids 243-248 of SEQ ID NO: 9.

In other aspects of this embodiment, a β-trefoil domain with enhanced binding activity derived from a Clostridial botulinum serotype A HA-33 comprises a polypeptide having, e.g., at least 70% amino acid identity with amino acids 55-59, amino acids 101-104, amino acids 196-199, or amino acids 243-248 of SEQ ID NO: 9, at least 75% amino acid identity with amino acids 55-59, amino acids 101-104, amino acids 196-199, or amino acids 243-248 of SEQ ID NO: 9, at least 80% amino acid identity with amino acids 55-59, amino acids 101-104, amino acids 196-199, or amino acids 243-248 of SEQ ID NO: 9, at least 85% amino acid identity with amino acids 55-59, amino acids 101-104, amino acids 196-199, or amino acids 243-248 of SEQ ID NO: 9, at least 90% amino acid identity with amino acids 55-59, amino acids 101-104, amino acids 196-199, or amino acids 243-248 of SEQ ID NO: 9 or at least 95% amino acid identity with amino acids 55-59, amino acids 101-104, amino acids 196-199, or amino acids 243-248 of SEQ ID NO: 9. In yet other aspects of this embodiment, a β-trefoil domain with enhanced binding activity derived from a Clostridial botulinum serotype A HA-33 comprises a polypeptide having, e.g., at most 70% amino acid identity with amino acids 55-59, amino acids 101-104, amino acids 196-199, or amino acids 243-248 of SEQ ID NO: 9, at most 75% amino acid identity with amino acids 55-59, amino acids 101-104, amino acids 196-199, or amino acids 243-248 of SEQ ID NO: 9, at most 80% amino acid identity with amino acids 55-59, amino acids 101-104, amino acids 196-199, or amino acids 243-248 of SEQ ID NO: 9, at most 85% amino acid identity with amino acids 55-59, amino acids 101-104, amino acids 196-199, or amino acids 243-248 of SEQ ID NO: 9, at most 90% amino acid identity with amino acids 55-59, amino acids 101-104, amino acids 196-199, or amino acids 243-248 of SEQ ID NO: 9 or at most 95% amino acid identity with amino acids 55-59, amino acids 101-104, amino acids 196-199, or amino acids 243-248 of SEQ ID NO: 9.

In other aspects of this embodiment, a β-trefoil domain with enhanced binding activity derived from a Clostridial botulinum serotype A HA-33 comprises a polypeptide having, e.g., at most one, two, three or four non-contiguous amino acid substitutions relative to amino acids 55-59, amino acids 101-104, amino acids 196-199, or amino acids 243-248 of SEQ ID NO: 9. In other aspects of this embodiment, a β-trefoil domain with enhanced binding activity derived from a Clostridial botulinum serotype A HA-33 comprises a polypeptide having, e.g., at least one, two, three or four non-contiguous amino acid substitutions relative to amino acids 55-59, amino acids 101-104, amino acids 196-199, or amino acids 243-248 of SEQ ID NO: 9. In other aspects of this embodiment, a non-contiguous amino acid substitution of any amino acid from amino acids 55-59, amino acids 101-104, amino acids 196-199, or amino acids 243-248 of SEQ ID NO: 9 can be replaced with glycine. In other aspects of this embodiment, a non-contiguous amino acid substitution of any hydrophobic amino acid from amino acids 55-59, amino acids 101-104, amino acids 196-199, or amino acids 243-248 of SEQ ID NO: 9 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four non-contiguous amino acid deletions relative to amino acids 55-59, amino acids 101-104, amino acids 196-199, or amino acids 243-248 of SEQ ID NO: 9. In other aspects of this embodiment, a β-trefoil domain with enhanced binding activity derived from a Clostridial botulinum serotype A HA-33 comprises a polypeptide having, e.g., at least one, two, three or four non-contiguous amino acid deletions relative to amino acids 55-59, amino acids 101-104, amino acids 196-199, or amino acids 243-248 of SEQ ID NO: 9. In still other aspects of this embodiment, a β-trefoil domain with enhanced binding activity derived from a Clostridial botulinum serotype A HA-33 comprises a polypeptide having, e.g., at most one, two, three or four non-contiguous amino acid additions relative to amino acids 55-59, amino acids 101-104, amino acids 196-199, or amino acids 243-248 of SEQ ID NO: 9. In other aspects of this embodiment, a β-trefoil domain with enhanced binding activity derived from a Clostridial botulinum serotype A HA-33 comprises a polypeptide having, e.g., at least one, two, three or four non-contiguous amino acid additions relative to amino acids 55-59, amino acids 101-104, amino acids 196-199, or amino acids 243-248 of SEQ ID NO: 9.

In other aspects of this embodiment, a β-trefoil domain with enhanced binding activity derived from a Clostridial botulinum serotype A HA-33 comprises a polypeptide having, e.g., at most one, two, three or four contiguous amino acid substitutions relative to amino acids 55-59, amino acids 101-104, amino acids 196-199, or amino acids 243-248 of SEQ ID NO: 9. In other aspects of this embodiment, a β-trefoil domain with enhanced binding activity derived from a Clostridial botulinum serotype A HA-33 comprises a polypeptide having, e.g., at least one, two, three or four contiguous amino acid substitutions relative to amino acids 55-59, amino acids 101-104, amino acids 196-199, or amino acids 243-248 of SEQ ID NO: 9. In other aspects of this embodiment, contiguous amino acid substitutions of amino acids from amino acids 55-59, amino acids 101-104, amino acids 196-199, or amino acids 243-248 of SEQ ID NO: 9 can be replaced with glycine. In other aspects of this embodiment, contiguous amino acid substitutions of hydrophobic amino acids from amino acids 55-59, amino acids 101-104, amino acids 196-199, or amino acids 243-248 of SEQ ID NO: 9 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four contiguous amino acid deletions relative to amino acids 55-59, amino acids 101-104, amino acids 196-199, or amino acids 243-248 of SEQ ID NO: 9. In other aspects of this embodiment, a β-trefoil domain with enhanced binding activity derived from a Clostridial botulinum serotype A HA-33 comprises a polypeptide having, e.g., at least one, two, three or four contiguous amino acid deletions relative to amino acids 55-59, amino acids 101-104, amino acids 196-199, or amino acids 243-248 of SEQ ID NO: 9. In still other aspects of this embodiment, a β-trefoil domain with enhanced binding activity derived from a Clostridial botulinum serotype A HA-33 comprises a polypeptide having, e.g., at most one, two, three or four contiguous amino acid additions relative to amino acids 55-59, amino acids 101-104, amino acids 196-199, or amino acids 243-248 of SEQ ID NO: 9. In other aspects of this embodiment, a β-trefoil domain with enhanced binding activity derived from a Clostridial botulinum serotype A HA-33 comprises a polypeptide having, e.g., at least one, two, three or four contiguous amino acid additions relative to amino acids 55-59, amino acids 101-104, amino acids 196-199, or amino acids 243-248 of SEQ ID NO: 9.

In another embodiment, a β-trefoil domain derived from a Clostridial botulinum serotype A HA-33 comprises a β-trefoil domain derived from a Clostridial botulinum serotype A HA-33 of SEQ ID NO: 10. In another embodiment, a β-trefoil domain derived from a Clostridial botulinum serotype A HA-33 comprises amino acids 10-144 or amino acids 151-293 of SEQ ID NO: 10. In another aspect of this embodiment, a β-trefoil domain derived from a Clostridial botulinum serotype A HA-33 comprises a 1α-fold motif of a β-trefoil domain of a Clostridial botulinum serotype A HA-33, a 1β-fold motif of a β-trefoil domain of a Clostridial botulinum serotype A HA-33, a 1γ-fold motif of a β-trefoil domain of a Clostridial botulinum serotype A HA-33, a 2α-fold motif of a β-trefoil domain of a Clostridial botulinum serotype A HA-33, a 2β-fold motif of a β-trefoil domain of a Clostridial botulinum serotype A HA-33, or a 2γ-fold motif of a β-trefoil domain of a Clostridial botulinum serotype A HA-33 of SEQ ID NO: 10. In another aspect of this embodiment, a β-trefoil domain derived from a Clostridial botulinum serotype A HA-33 comprises amino acids 10-54, amino acids 60-100, amino acids 105-144, amino acids 151-195, amino acids 200-242, or amino acids 249-293 of SEQ ID NO: 10.

In another embodiment, a β-trefoil domain with enhanced binding activity derived from a Clostridial botulinum serotype A HA-33 comprises a β-trefoil domain with enhanced binding activity derived from a Clostridial botulinum serotype A HA-33 of SEQ ID NO: 10. In another embodiment, a β-trefoil domain with enhanced binding activity derived from a Clostridial botulinum serotype A HA-33 comprises amino acids 10-144 or amino acids 151-293 of SEQ ID NO: 10. In another aspect of this embodiment, a β-trefoil domain with enhanced binding activity derived from a Clostridial botulinum serotype A HA-33 comprises a modified 1α-fold motif of a β-trefoil domain of a Clostridial botulinum serotype A HA-33, a modified 1β-fold motif of a β-trefoil domain of a Clostridial botulinum serotype A HA-33, a modified 1γ-fold motif of a β-trefoil domain of a Clostridial botulinum serotype A HA-33, a modified 2α-fold motif of a β-trefoil domain of a Clostridial botulinum serotype A HA-33, a modified 2β-fold motif of a β-trefoil domain of a Clostridial botulinum serotype A HA-33, or a modified 2γ-fold motif of a β-trefoil domain of a Clostridial botulinum serotype A HA-33 of SEQ ID NO: 10. In another aspect of this embodiment, a β-trefoil domain with enhanced binding activity derived from a Clostridial botulinum serotype A HA-33 comprises amino acids 10-54, amino acids 60-100, amino acids 105-144, amino acids 151-195, amino acids 200-242, or amino acids 249-293 of SEQ ID NO: 10.

In other aspects of this embodiment, a Clostridial botulinum serotype A HA-33 comprising a β-trefoil domain with enhanced binding activity comprises a polypeptide having, e.g., at least 70% amino acid identity with amino acids 10-54, amino acids 60-100, amino acids 105-144, amino acids 151-195, amino acids 200-242, or amino acids 249-293 of SEQ ID NO: 10, at least 75% amino acid identity with amino acids 10-54, amino acids 60-100, amino acids 105-144, amino acids 151-195, amino acids 200-242, or amino acids 249-293 of SEQ ID NO: 10, at least 80% amino acid identity with amino acids 10-54, amino acids 60-100, amino acids 105-144, amino acids 151-195, amino acids 200-242, or amino acids 249-293 of SEQ ID NO: 10, at least 85% amino acid identity with amino acids 10-54, amino acids 60-100, amino acids 105-144, amino acids 151-195, amino acids 200-242, or amino acids 249-293 of SEQ ID NO: 10, at least 90% amino acid identity with amino acids 10-54, amino acids 60-100, amino acids 105-144, amino acids 151-195, amino acids 200-242, or amino acids 249-293 of SEQ ID NO: 10 or at least 95% amino acid identity with amino acids 10-54, amino acids 60-100, amino acids 105-144, amino acids 151-195, amino acids 200-242, or amino acids 249-293 of SEQ ID NO: 10. In yet other aspects of this embodiment, a Clostridial botulinum serotype A HA-33 comprising a β-trefoil domain with enhanced binding activity comprises a polypeptide having, e.g., at most 70% amino acid identity with amino acids 10-54, amino acids 60-100, amino acids 105-144, amino acids 151-195, amino acids 200-242, or amino acids 249-293 of SEQ ID NO: 10, at most 75% amino acid identity with amino acids 10-54, amino acids 60-100, amino acids 105-144, amino acids 151-195, amino acids 200-242, or amino acids 249-293 of SEQ ID NO: 10, at most 80% amino acid identity with amino acids 10-54, amino acids 60-100, amino acids 105-144, amino acids 151-195, amino acids 200-242, or amino acids 249-293 of SEQ ID NO: 10, at most 85% amino acid identity with amino acids 10-54, amino acids 60-100, amino acids 105-144, amino acids 151-195, amino acids 200-242, or amino acids 249-293 of SEQ ID NO: 10, at most 90% amino acid identity with amino acids 10-54, amino acids 60-100, amino acids 105-144, amino acids 151-195, amino acids 200-242, or amino acids 249-293 of SEQ ID NO: 10 or at most 95% amino acid identity with amino acids 10-54, amino acids 60-100, amino acids 105-144, amino acids 151-195, amino acids 200-242, or amino acids 249-293 of SEQ ID NO: 10.

In other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 10. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 10. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 10. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 10. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 10. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 10.

In other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 10. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 10. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 10. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 10. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 10. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 10.

In another embodiment, a β-trefoil domain derived from a Clostridial botulinum serotype A HA-33 comprises a 1β4/β5 hairpin turn of a β-trefoil domain of a Clostridial botulinum serotype A HA-33, a 1β8/β9 hairpin turn of a β-trefoil domain of a Clostridial botulinum serotype A HA-33, a 2β4/β5 hairpin turn of a β-trefoil domain of a Clostridial botulinum serotype A HA-33 or a 2β8/β9 hairpin turn of a β-trefoil domain of a Clostridial botulinum serotype A HA-33 of SEQ ID NO: 10. In another aspect of this embodiment, a β-trefoil domain derived from a Clostridial botulinum serotype A HA-33 comprises amino acids 55-59, amino acids 101-104, amino acids 196-199, or amino acids 243-248 of SEQ ID NO: 10.

In another embodiment, a β-trefoil domain with enhanced binding activity derived from a Clostridial botulinum serotype A HA-33 comprises a modified 1β4/β5 hairpin turn of a β-trefoil domain of a Clostridial botulinum serotype A HA-33, a modified 1β8/β9 hairpin turn of a β-trefoil domain of a Clostridial botulinum serotype A HA-33, a modified 2β4/β5 hairpin turn of a β-trefoil domain of a Clostridial botulinum serotype A HA-33 or a modified 2β8/β9 hairpin turn of a β-trefoil domain of a Clostridial botulinum serotype A HA-33 of SEQ ID NO: 10. In another aspect of this embodiment, a β-trefoil domain with enhanced binding activity derived from a Clostridial botulinum serotype A HA-33 comprises a modification of amino acids 55-59, amino acids 101-104, amino acids 196-199, or amino acids 243-248 of SEQ ID NO: 10.

In other aspects of this embodiment, a β-trefoil domain with enhanced binding activity derived from a Clostridial botulinum serotype A HA-33 comprises a polypeptide having, e.g., at least 70% amino acid identity with amino acids 55-59, amino acids 101-104, amino acids 196-199, or amino acids 243-248 of SEQ ID NO: 10, at least 75% amino acid identity with amino acids 55-59, amino acids 101-104, amino acids 196-199, or amino acids 243-248 of SEQ ID NO: 10, at least 80% amino acid identity with amino acids 55-59, amino acids 101-104, amino acids 196-199, or amino acids 243-248 of SEQ ID NO: 10, at least 85% amino acid identity with amino acids 55-59, amino acids 101-104, amino acids 196-199, or amino acids 243-248 of SEQ ID NO: 10, at least 90% amino acid identity with amino acids 55-59, amino acids 101-104, amino acids 196-199, or amino acids 243-248 of SEQ ID NO: 10 or at least 95% amino acid identity with amino acids 55-59, amino acids 101-104, amino acids 196-199, or amino acids 243-248 of SEQ ID NO: 10. In yet other aspects of this embodiment, a β-trefoil domain with enhanced binding activity derived from a Clostridial botulinum serotype A HA-33 comprises a polypeptide having, e.g., at most 70% amino acid identity with amino acids 55-59, amino acids 101-104, amino acids 196-199, or amino acids 243-248 of SEQ ID NO: 10, at most 75% amino acid identity with amino acids 55-59, amino acids 101-104, amino acids 196-199, or amino acids 243-248 of SEQ ID NO: 10, at most 80% amino acid identity with amino acids 55-59, amino acids 101-104, amino acids 196-199, or amino acids 243-248 of SEQ ID NO: 10, at most 85% amino acid identity with amino acids 55-59, amino acids 101-104, amino acids 196-199, or amino acids 243-248 of SEQ ID NO: 10, at most 90% amino acid identity with amino acids 55-59, amino acids 101-104, amino acids 196-199, or amino acids 243-248 of SEQ ID NO: 10 or at most 95% amino acid identity with amino acids 55-59, amino acids 101-104, amino acids 196-199, or amino acids 243-248 of SEQ ID NO: 10.

In other aspects of this embodiment, a β-trefoil domain with enhanced binding activity derived from a Clostridial botulinum serotype A HA-33 comprises a polypeptide having, e.g., at most one, two, three or four non-contiguous amino acid substitutions relative to amino acids 55-59, amino acids 101-104, amino acids 196-199, or amino acids 243-248 of SEQ ID NO: 10. In other aspects of this embodiment, a β-trefoil domain with enhanced binding activity derived from a Clostridial botulinum serotype A HA-33 comprises a polypeptide having, e.g., at least one, two, three or four non-contiguous amino acid substitutions relative to amino acids 55-59, amino acids 101-104, amino acids 196-199, or amino acids 243-248 of SEQ ID NO: 10. In other aspects of this embodiment, a non-contiguous amino acid substitution of any amino acid from amino acids 55-59, amino acids 101-104, amino acids 196-199, or amino acids 243-248 of SEQ ID NO: 10 can be replaced with glycine. In other aspects of this embodiment, a non-contiguous amino acid substitution of any hydrophobic amino acid from amino acids 55-59, amino acids 101-104, amino acids 196-199, or amino acids 243-248 of SEQ ID NO: 10 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four non-contiguous amino acid deletions relative to amino acids 55-59, amino acids 101-104, amino acids 196-199, or amino acids 243-248 of SEQ ID NO: 10. In other aspects of this embodiment, a β-trefoil domain with enhanced binding activity derived from a Clostridial botulinum serotype A HA-33 comprises a polypeptide having, e.g., at least one, two, three or four non-contiguous amino acid deletions relative to amino acids 55-59, amino acids 101-104, amino acids 196-199, or amino acids 243-248 of SEQ ID NO: 10. In still other aspects of this embodiment, a β-trefoil domain with enhanced binding activity derived from a Clostridial botulinum serotype A HA-33 comprises a polypeptide having, e.g., at most one, two, three or four non-contiguous amino acid additions relative to amino acids 55-59, amino acids 101-104, amino acids 196-199, or amino acids 243-248 of SEQ ID NO: 10. In other aspects of this embodiment, a β-trefoil domain with enhanced binding activity derived from a Clostridial botulinum serotype A HA-33 comprises a polypeptide having, e.g., at least one, two, three or four non-contiguous amino acid additions relative to amino acids 55-59, amino acids 101-104, amino acids 196-199, or amino acids 243-248 of SEQ ID NO: 10.

In other aspects of this embodiment, a β-trefoil domain with enhanced binding activity derived from a Clostridial botulinum serotype A HA-33 comprises a polypeptide having, e.g., at most one, two, three or four contiguous amino acid substitutions relative to amino acids 55-59, amino acids 101-104, amino acids 196-199, or amino acids 243-248 of SEQ ID NO: 10. In other aspects of this embodiment, a β-trefoil domain with enhanced binding activity derived from a Clostridial botulinum serotype A HA-33 comprises a polypeptide having, e.g., at least one, two, three or four contiguous amino acid substitutions relative to amino acids 55-59, amino acids 101-104, amino acids 196-199, or amino acids 243-248 of SEQ ID NO: 10. In other aspects of this embodiment, contiguous amino acid substitutions of amino acids from amino acids 55-59, amino acids 101-104, amino acids 196-199, or amino acids 243-248 of SEQ ID NO: 10 can be replaced with glycine. In other aspects of this embodiment, contiguous amino acid substitutions of hydrophobic amino acids from amino acids 55-59, amino acids 101-104, amino acids 196-199, or amino acids 243-248 of SEQ ID NO: 10 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four contiguous amino acid deletions relative to amino acids 55-59, amino acids 101-104, amino acids 196-199, or amino acids 243-248 of SEQ ID NO: 10. In other aspects of this embodiment, a β-trefoil domain with enhanced binding activity derived from a Clostridial botulinum serotype A HA-33 comprises a polypeptide having, e.g., at least one, two, three or four contiguous amino acid deletions relative to amino acids 55-59, amino acids 101-104, amino acids 196-199, or amino acids 243-248 of SEQ ID NO: 10. In still other aspects of this embodiment, a β-trefoil domain with enhanced binding activity derived from a Clostridial botulinum serotype A HA-33 comprises a polypeptide having, e.g., at most one, two, three or four contiguous amino acid additions relative to amino acids 55-59, amino acids 101-104, amino acids 196-199, or amino acids 243-248 of SEQ ID NO: 10. In other aspects of this embodiment, a β-trefoil domain with enhanced binding activity derived from a Clostridial botulinum serotype A HA-33 comprises a polypeptide having, e.g., at least one, two, three or four contiguous amino acid additions relative to amino acids 55-59, amino acids 101-104, amino acids 196-199, or amino acids 243-248 of SEQ ID NO: 10.

In another embodiment, a β-trefoil domain derived from a Clostridial botulinum serotype A HA-33 comprises a β-trefoil domain derived from a Clostridial botulinum serotype A HA-33 of SEQ ID NO: 11. In another embodiment, a β-trefoil domain derived from a Clostridial botulinum serotype A HA-33 comprises amino acids 10-144 or amino acids 151-293 of SEQ ID NO: 11. In another aspect of this embodiment, a β-trefoil domain derived from a Clostridial botulinum serotype A HA-33 comprises a 1α-fold motif of a β-trefoil domain of a Clostridial botulinum serotype A HA-33, a 1β-fold motif of a β-trefoil domain of a Clostridial botulinum serotype A HA-33, a 1γ-fold motif of a β-trefoil domain of a Clostridial botulinum serotype A HA-33, a 2α-fold motif of a β-trefoil domain of a Clostridial botulinum serotype A HA-33, a 2β-fold motif of a β-trefoil domain of a Clostridial botulinum serotype A HA-33, or a 2γ-fold motif of a β-trefoil domain of a Clostridial botulinum serotype A HA-33 of SEQ ID NO: 11. In another aspect of this embodiment, a β-trefoil domain derived from a Clostridial botulinum serotype A HA-33 comprises amino acids 10-54, amino acids 60-100, amino acids 105-144, amino acids 151-195, amino acids 200-242, or amino acids 249-293 of SEQ ID NO: 11.

In another embodiment, a β-trefoil domain with enhanced binding activity derived from a Clostridial botulinum serotype A HA-33 comprises a β-trefoil domain with enhanced binding activity derived from a Clostridial botulinum serotype A HA-33 of SEQ ID NO: 11. In another embodiment, a β-trefoil domain with enhanced binding activity derived from a Clostridial botulinum serotype A HA-33 comprises amino acids 10-144 or amino acids 151-293 of SEQ ID NO: 11. In another aspect of this embodiment, a β-trefoil domain with enhanced binding activity derived from a Clostridial botulinum serotype A HA-33 comprises a modified 1α-fold motif of a β-trefoil domain of a Clostridial botulinum serotype A HA-33, a modified 1β-fold motif of a β-trefoil domain of a Clostridial botulinum serotype A HA-33, a modified 1γ-fold motif of a β-trefoil domain of a Clostridial botulinum serotype A HA-33, a modified 2α-fold motif of a β-trefoil domain of a Clostridial botulinum serotype A HA-33, a modified 2β-fold motif of a β-trefoil domain of a Clostridial botulinum serotype A HA-33, or a modified 2γ-fold motif of a β-trefoil domain of a Clostridial botulinum serotype A HA-33 of SEQ ID NO: 11. In another aspect of this embodiment, a β-trefoil domain with enhanced binding activity derived from a Clostridial botulinum serotype A HA-33 comprises amino acids 10-54, amino acids 60-100, amino acids 105-144, amino acids 151-195, amino acids 200-242, or amino acids 249-293 of SEQ ID NO: 11.

In other aspects of this embodiment, a Clostridial botulinum serotype A HA-33 comprising a β-trefoil domain with enhanced binding activity comprises a polypeptide having, e.g., at least 70% amino acid identity with amino acids 10-54, amino acids 60-100, amino acids 105-144, amino acids 151-195, amino acids 200-242, or amino acids 249-293 of SEQ ID NO: 11, at least 75% amino acid identity with amino acids 10-54, amino acids 60-100, amino acids 105-144, amino acids 151-195, amino acids 200-242, or amino acids 249-293 of SEQ ID NO: 11, at least 80% amino acid identity with amino acids 10-54, amino acids 60-100, amino acids 105-144, amino acids 151-195, amino acids 200-242, or amino acids 249-293 of SEQ ID NO: 11, at least 85% amino acid identity with amino acids 10-54, amino acids 60-100, amino acids 105-144, amino acids 151-195, amino acids 200-242, or amino acids 249-293 of SEQ ID NO: 11, at least 90% amino acid identity with amino acids 10-54, amino acids 60-100, amino acids 105-144, amino acids 151-195, amino acids 200-242, or amino acids 249-293 of SEQ ID NO: 11 or at least 95% amino acid identity with amino acids 10-54, amino acids 60-100, amino acids 105-144, amino acids 151-195, amino acids 200-242, or amino acids 249-293 of SEQ ID NO: 11. In yet other aspects of this embodiment, a Clostridial botulinum serotype A HA-33 comprising a β-trefoil domain with enhanced binding activity comprises a polypeptide having, e.g., at most 70% amino acid identity with amino acids 10-54, amino acids 60-100, amino acids 105-144, amino acids 151-195, amino acids 200-242, or amino acids 249-293 of SEQ ID NO: 11, at most 75% amino acid identity with amino acids 10-54, amino acids 60-100, amino acids 105-144, amino acids 151-195, amino acids 200-242, or amino acids 249-293 of SEQ ID NO: 11, at most 80% amino acid identity with amino acids 10-54, amino acids 60-100, amino acids 105-144, amino acids 151-195, amino acids 200-242, or amino acids 249-293 of SEQ ID NO: 11, at most 85% amino acid identity with amino acids 10-54, amino acids 60-100, amino acids 105-144, amino acids 151-195, amino acids 200-242, or amino acids 249-293 of SEQ ID NO: 11, at most 90% amino acid identity with amino acids 10-54, amino acids 60-100, amino acids 105-144, amino acids 151-195, amino acids 200-242, or amino acids 249-293 of SEQ ID NO: 11 or at most 95% amino acid identity with amino acids 10-54, amino acids 60-100, amino acids 105-144, amino acids 151-195, amino acids 200-242, or amino acids 249-293 of SEQ ID NO: 11.

In other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 11. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-242, or amino acids 249-293 of SEQ ID NO: 11. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 11. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-242, or amino acids 249-293 of SEQ ID NO: 11. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 11. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-54, amino acids 60-100, amino acids 105-144, amino acids 151-195, amino acids 200-242, or amino acids 249-293 of SEQ ID NO: 11.

In other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 11. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-242, or amino acids 249-293 of SEQ ID NO: 11. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 11. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-242, or amino acids 249-293 of SEQ ID NO: 11. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 11. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-242, or amino acids 249-293 of SEQ ID NO: 11.

In another embodiment, a β-trefoil domain derived from a Clostridial botulinum serotype A HA-33 comprises a 1β4/β5 hairpin turn of a β-trefoil domain of a Clostridial botulinum serotype A HA-33, a 1β8/β9 hairpin turn of a β-trefoil domain of a Clostridial botulinum serotype A HA-33, a 2β4/β5 hairpin turn of a β-trefoil domain of a Clostridial botulinum serotype A HA-33 or a 2β8/β9 hairpin turn of a β-trefoil domain of a Clostridial botulinum serotype A HA-33 of SEQ ID NO: 11. In another aspect of this embodiment, a β-trefoil domain derived from a Clostridial botulinum serotype A HA-33 comprises amino acids 55-59, amino acids 101-104, amino acids 196-199, or amino acids 243-248 of SEQ ID NO: 11.

In another embodiment, a β-trefoil domain with enhanced binding activity derived from a Clostridial botulinum serotype A HA-33 comprises a modified 1β4/β5 hairpin turn of a β-trefoil domain of a Clostridial botulinum serotype A HA-33, a modified 1β8/β9 hairpin turn of a β-trefoil domain of a Clostridial botulinum serotype A HA-33, a modified 2β4/β5 hairpin turn of a β-trefoil domain of a Clostridial botulinum serotype A HA-33 or a modified 2β8/β9 hairpin turn of a β-trefoil domain of a Clostridial botulinum serotype A HA-33 of SEQ ID NO: 11. In another aspect of this embodiment, a β-trefoil domain with enhanced binding activity derived from a Clostridial botulinum serotype A HA-33 comprises a modification of amino acids 55-59, amino acids 101-104, amino acids 196-199, or amino acids 243-248 of SEQ ID NO: 11.

In other aspects of this embodiment, a β-trefoil domain with enhanced binding activity derived from a Clostridial botulinum serotype A HA-33 comprises a polypeptide having, e.g., at least 70% amino acid identity with amino acids 55-59, amino acids 101-104, amino acids 196-199, or amino acids 243-248 of SEQ ID NO: 11, at least 75% amino acid identity with amino acids 55-59, amino acids 101-104, amino acids 196-199, or amino acids 243-248 of SEQ ID NO: 11, at least 80% amino acid identity with amino acids 55-59, amino acids 101-104, amino acids 196-199, or amino acids 243-248 of SEQ ID NO: 11, at least 85% amino acid identity with amino acids 55-59, amino acids 101-104, amino acids 196-199, or amino acids 243-248 of SEQ ID NO: 11, at least 90% amino acid identity with amino acids 55-59, amino acids 101-104, amino acids 196-199, or amino acids 243-248 of SEQ ID NO: 11 or at least 95% amino acid identity with amino acids 55-59, amino acids 101-104, amino acids 196-199, or amino acids 243-248 of SEQ ID NO: 11. In yet other aspects of this embodiment, a β-trefoil domain with enhanced binding activity derived from a Clostridial botulinum serotype A HA-33 comprises a polypeptide having, e.g., at most 70% amino acid identity with amino acids 55-59, amino acids 101-104, amino acids 196-199, or amino acids 243-248 of SEQ ID NO: 11, at most 75% amino acid identity with amino acids 55-59, amino acids 101-104, amino acids 196-199, or amino acids 243-248 of SEQ ID NO: 11, at most 80% amino acid identity with amino acids 55-59, amino acids 101-104, amino acids 196-199, or amino acids 243-248 of SEQ ID NO: 11, at most 85% amino acid identity with amino acids 55-59, amino acids 101-104, amino acids 196-199, or amino acids 243-248 of SEQ ID NO: 11, at most 90% amino acid identity with amino acids 55-59, amino acids 101-104, amino acids 196-199, or amino acids 243-248 of SEQ ID NO: 11 or at most 95% amino acid identity with amino acids 55-59, amino acids 101-104, amino acids 196-199, or amino acids 243-248 of SEQ ID NO: 11.

In other aspects of this embodiment, a β-trefoil domain with enhanced binding activity derived from a Clostridial botulinum serotype A HA-33 comprises a polypeptide having, e.g., at most one, two, three or four non-contiguous amino acid substitutions relative to amino acids 55-59, amino acids 101-104, amino acids 196-199, or amino acids 243-248 of SEQ ID NO: 11. In other aspects of this embodiment, a β-trefoil domain with enhanced binding activity derived from a Clostridial botulinum serotype A HA-33 comprises a polypeptide having, e.g., at least one, two, three or four non-contiguous amino acid substitutions relative to amino acids 55-59, amino acids 101-104, amino acids 196-199, or amino acids 243-248 of SEQ ID NO: 11. In other aspects of this embodiment, a non-contiguous amino acid substitution of any amino acid from amino acids 55-59, amino acids 101-104, amino acids 196-199, or amino acids 243-248 of SEQ ID NO: 11 can be replaced with glycine. In other aspects of this embodiment, a non-contiguous amino acid substitution of any hydrophobic amino acid from amino acids 55-59, amino acids 101-104, amino acids 196-199, or amino acids 243-248 of SEQ ID NO: 11 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four non-contiguous amino acid deletions relative to amino acids 55-59, amino acids 101-104, amino acids 196-199, or amino acids 243-248 of SEQ ID NO: 11. In other aspects of this embodiment, a β-trefoil domain with enhanced binding activity derived from a Clostridial botulinum serotype A HA-33 comprises a polypeptide having, e.g., at least one, two, three or four non-contiguous amino acid deletions relative to amino acids 55-59, amino acids 101-104, amino acids 196-199, or amino acids 243-248 of SEQ ID NO: 11. In still other aspects of this embodiment, a β-trefoil domain with enhanced binding activity derived from a Clostridial botulinum serotype A HA-33 comprises a polypeptide having, e.g., at most one, two, three or four non-contiguous amino acid additions relative to amino acids 55-59, amino acids 101-104, amino acids 196-199, or amino acids 243-248 of SEQ ID NO: 11. In other aspects of this embodiment, a β-trefoil domain with enhanced binding activity derived from a Clostridial botulinum serotype A HA-33 comprises a polypeptide having, e.g., at least one, two, three or four non-contiguous amino acid additions relative to amino acids 55-59, amino acids 101-104, amino acids 196-199, or amino acids 243-248 of SEQ ID NO: 11.

In other aspects of this embodiment, a β-trefoil domain with enhanced binding activity derived from a Clostridial botulinum serotype A HA-33 comprises a polypeptide having, e.g., at most one, two, three or four contiguous amino acid substitutions relative to amino acids 55-59, amino acids 101-104, amino acids 196-199, or amino acids 243-248 of SEQ ID NO: 11. In other aspects of this embodiment, a β-trefoil domain with enhanced binding activity derived from a Clostridial botulinum serotype A HA-33 comprises a polypeptide having, e.g., at least one, two, three or four contiguous amino acid substitutions relative to amino acids 55-59, amino acids 101-104, amino acids 196-199, or amino acids 243-248 of SEQ ID NO: 11. In other aspects of this embodiment, contiguous amino acid substitutions of amino acids from amino acids 55-59, amino acids 101-104, amino acids 196-199, or amino acids 243-248 of SEQ ID NO: 11 can be replaced with glycine. In other aspects of this embodiment, contiguous amino acid substitutions of hydrophobic amino acids from amino acids 55-59, amino acids 101-104, amino acids 196-199, or amino acids 243-248 of SEQ ID NO: 11 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four contiguous amino acid deletions relative to amino acids 55-59, amino acids 101-104, amino acids 196-199, or amino acids 243-248 of SEQ ID NO: 11. In other aspects of this embodiment, a β-trefoil domain with enhanced binding activity derived from a Clostridial botulinum serotype A HA-33 comprises a polypeptide having, e.g., at least one, two, three or four contiguous amino acid deletions relative to amino acids 55-59, amino acids 101-104, amino acids 196-199, or amino acids 243-248 of SEQ ID NO: 11. In still other aspects of this embodiment, a β-trefoil domain with enhanced binding activity derived from a Clostridial botulinum serotype A HA-33 comprises a polypeptide having, e.g., at most one, two, three or four contiguous amino acid additions relative to amino acids 55-59, amino acids 101-104, amino acids 196-199, or amino acids 243-248 of SEQ ID NO: 11. In other aspects of this embodiment, a β-trefoil domain with enhanced binding activity derived from a Clostridial botulinum serotype A HA-33 comprises a polypeptide having, e.g., at least one, two, three or four contiguous amino acid additions relative to amino acids 55-59, amino acids 101-104, amino acids 196-199, or amino acids 243-248 of SEQ ID NO: 11.

In another embodiment, a β-trefoil domain derived from a Clostridial botulinum serotype A HA-33 comprises a β-trefoil domain derived from a Clostridial botulinum serotype A HA-33 of SEQ ID NO: 12. In another embodiment, a β-trefoil domain derived from a Clostridial botulinum serotype A HA-33 comprises amino acids 10-146 or amino acids 153-294 of SEQ ID NO: 12. In another aspect of this embodiment, a β-trefoil domain derived from a Clostridial botulinum serotype A HA-33 comprises a 1α-fold motif of a 13-trefoil domain of a Clostridial botulinum serotype A HA-33, a 1β-fold motif of a β-trefoil domain of a Clostridial botulinum serotype A HA-33, a 1γ-fold motif of a β-trefoil domain of a Clostridial botulinum serotype A HA-33, a 2α-fold motif of a β-trefoil domain of a Clostridial botulinum serotype A HA-33, a 2β-fold motif of a β-trefoil domain of a Clostridial botulinum serotype A HA-33, or a 2γ-fold motif of a β-trefoil domain of a Clostridial botulinum serotype A HA-33 of SEQ ID NO: 12. In another aspect of this embodiment, a β-trefoil domain derived from a Clostridial botulinum serotype A HA-33 comprises amino acids 10-56, amino acids 62-102, amino acids 107-146, amino acids 153-197, amino acids 202-243, or amino acids 250-294 of SEQ ID NO: 12.

In another embodiment, a β-trefoil domain with enhanced binding activity derived from a Clostridial botulinum serotype A HA-33 comprises a β-trefoil domain with enhanced binding activity derived from a Clostridial botulinum serotype A HA-33 of SEQ ID NO: 12. In another embodiment, a β-trefoil domain with enhanced binding activity derived from a Clostridial botulinum serotype A HA-33 comprises amino acids 10-146 or amino acids 153-294 of SEQ ID NO: 12. In another aspect of this embodiment, a β-trefoil domain with enhanced binding activity derived from a Clostridial botulinum serotype A HA-33 comprises a modified 1α-fold motif of a β-trefoil domain of a Clostridial botulinum serotype A HA-33, a modified 1β-fold motif of a β-trefoil domain of a Clostridial botulinum serotype A HA-33, a modified 1γ-fold motif of a β-trefoil domain of a Clostridial botulinum serotype A HA-33, a modified 2α-fold motif of a β-trefoil domain of a Clostridial botulinum serotype A HA-33, a modified 2β-fold motif of a β-trefoil domain of a Clostridial botulinum serotype A HA-33, or a modified 2γ-fold motif of a β-trefoil domain of a Clostridial botulinum serotype A HA-33 of SEQ ID NO: 12. In another aspect of this embodiment, a β-trefoil domain with enhanced binding activity derived from a Clostridial botulinum serotype A HA-33 comprises amino acids 10-56, amino acids 62-102, amino acids 107-146, amino acids 153-197, amino acids 202-243, or amino acids 250-294 of SEQ ID NO: 12.

In other aspects of this embodiment, a Clostridial botulinum serotype A HA-33 comprising a β-trefoil domain with enhanced binding activity comprises a polypeptide having, e.g., at least 70% amino acid identity with amino acids 10-56, amino acids 62-102, amino acids 107-146, amino acids 153-197, amino acids 202-243, or amino acids 250-294 of SEQ ID NO: 12, at least 75% amino acid identity with amino acids 10-56, amino acids 62-102, amino acids 107-146, amino acids 153-197, amino acids 202-243, or amino acids 250-294 of SEQ ID NO: 12, at least 80% amino acid identity with amino acids 10-56, amino acids 62-102, amino acids 107-146, amino acids 153-197, amino acids 202-243, or amino acids 250-294 of SEQ ID NO: 12, at least 85% amino acid identity with amino acids 10-56, amino acids 62-102, amino acids 107-146, amino acids 153-197, amino acids 202-243, or amino acids 250-294 of SEQ ID NO: 12, at least 90% amino acid identity with amino acids 10-56, amino acids 62-102, amino acids 107-146, amino acids 153-197, amino acids 202-243, or amino acids 250-294 of SEQ ID NO: 12 or at least 95% amino acid identity with amino acids 10-56, amino acids 62-102, amino acids 107-146, amino acids 153-197, amino acids 202-243, or amino acids 250-294 of SEQ ID NO: 12. In yet other aspects of this embodiment, a Clostridial botulinum serotype A HA-33 comprising a β-trefoil domain with enhanced binding activity comprises a polypeptide having, e.g., at most 70% amino acid identity with amino acids 10-56, amino acids 62-102, amino acids 107-146, amino acids 153-197, amino acids 202-243, or amino acids 250-294 of SEQ ID NO: 12, at most 75% amino acid identity with amino acids 10-56, amino acids 62-102, amino acids 107-146, amino acids 153-197, amino acids 202-243, or amino acids 250-294 of SEQ ID NO: 12, at most 80% amino acid identity with amino acids 10-56, amino acids 62-102, amino acids 107-146, amino acids 153-197, amino acids 202-243, or amino acids 250-294 of SEQ ID NO: 12, at most 85% amino acid identity with amino acids 10-56, amino acids 62-102, amino acids 107-146, amino acids 153-197, amino acids 202-243, or amino acids 250-294 of SEQ ID NO: 12, at most 90% amino acid identity with amino acids 10-56, amino acids 62-102, amino acids 107-146, amino acids 153-197, amino acids 202-243, or amino acids 250-294 of SEQ ID NO: 12 or at most 95% amino acid identity with amino acids 10-56, amino acids 62-102, amino acids 107-146, amino acids 153-197, amino acids 202-243, or amino acids 250-294 of SEQ ID NO: 12.

In other aspects of this embodiment, a Clostridial botulinum serotype A HA-33 comprising a 11-trefoil domain with enhanced binding activity comprises a polypeptide having, e.g., at most one, two, three, four, five, six, seven, eight, nine, 10 or 20 non-contiguous amino acid substitutions relative to amino acids 10-56, amino acids 62-102, amino acids 107-146, amino acids 153-197, amino acids 202-243, or amino acids 250-294 of SEQ ID NO: 12. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-56, amino acids 62-102, amino acids 107-146, amino acids 153-197, amino acids 202-243, or amino acids 250-294 of SEQ ID NO: 12. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-56, amino acids 62-102, amino acids 107-146, amino acids 153-197, amino acids 202-243, or amino acids 250-294 of SEQ ID NO: 12. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-56, amino acids 62-102, amino acids 107-146, amino acids 153-197, amino acids 202-243, or amino acids 250-294 of SEQ ID NO: 12. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-56, amino acids 62-102, amino acids 107-146, amino acids 153-197, amino acids 202-243, or amino acids 250-294 of SEQ ID NO: 12. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-56, amino acids 62-102, amino acids 107-146, amino acids 153-197, amino acids 202-243, or amino acids 250-294 of SEQ ID NO: 12.

In other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-56, amino acids 62-102, amino acids 107-146, amino acids 153-197, amino acids 202-243, or amino acids 250-294 of SEQ ID NO: 12. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-56, amino acids 62-102, amino acids 107-146, amino acids 153-197, amino acids 202-243, or amino acids 250-294 of SEQ ID NO: 12. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-56, amino acids 62-102, amino acids 107-146, amino acids 153-197, amino acids 202-243, or amino acids 250-294 of SEQ ID NO: 12. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-56, amino acids 62-102, amino acids 107-146, amino acids 153-197, amino acids 202-243, or amino acids 250-294 of SEQ ID NO: 12. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-56, amino acids 62-102, amino acids 107-146, amino acids 153-197, amino acids 202-243, or amino acids 250-294 of SEQ ID NO: 12. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-56, amino acids 62-102, amino acids 107-146, amino acids 153-197, amino acids 202-243, or amino acids 250-294 of SEQ ID NO: 12.

In another embodiment, a β-trefoil domain derived from a Clostridial botulinum serotype A HA-33 comprises a 1β4/β5 hairpin turn of a β-trefoil domain of a Clostridial botulinum serotype A HA-33, a 1β8/β9 hairpin turn of a β-trefoil domain of a Clostridial botulinum serotype A HA-33, a 2β4/β5 hairpin turn of a β-trefoil domain of a Clostridial botulinum serotype A HA-33 or a 2β8/β9 hairpin turn of a β-trefoil domain of a Clostridial botulinum serotype A HA-33 of SEQ ID NO: 12. In another aspect of this embodiment, a β-trefoil domain derived from a Clostridial botulinum serotype A HA-33 comprises amino acids 57-61, amino acids 103-106, amino acids 198-201, or amino acids 244-249 of SEQ ID NO: 12.

In another embodiment, a β-trefoil domain with enhanced binding activity derived from a Clostridial botulinum serotype A HA-33 comprises a modified 1β4/β5 hairpin turn of a β-trefoil domain of a Clostridial botulinum serotype A HA-33, a modified 1β8/β9 hairpin turn of a β-trefoil domain of a Clostridial botulinum serotype A HA-33, a modified 2β4/β5 hairpin turn of a β-trefoil domain of a Clostridial botulinum serotype A HA-33 or a modified 2β8/β9 hairpin turn of a β-trefoil domain of a Clostridial botulinum serotype A HA-33 of SEQ ID NO: 12. In another aspect of this embodiment, a β-trefoil domain with enhanced binding activity derived from a Clostridial botulinum serotype A HA-33 comprises a modification of amino acids 57-61, amino acids 103-106, amino acids 198-201, or amino acids 244-249 of SEQ ID NO: 12.

In other aspects of this embodiment, a β-trefoil domain with enhanced binding activity derived from a Clostridial botulinum serotype A HA-33 comprises a polypeptide having, e.g., at least 70% amino acid identity with amino acids 57-61, amino acids 103-106, amino acids 198-201, or amino acids 244-249 of SEQ ID NO: 12, at least 75% amino acid identity with amino acids 57-61, amino acids 103-106, amino acids 198-201, or amino acids 244-249 of SEQ ID NO: 12, at least 80% amino acid identity with amino acids 57-61, amino acids 103-106, amino acids 198-201, or amino acids 244-249 of SEQ ID NO: 12, at least 85% amino acid identity with amino acids 57-61, amino acids 103-106, amino acids 198-201, or amino acids 244-249 of SEQ ID NO: 12, at least 90% amino acid identity with amino acids 57-61, amino acids 103-106, amino acids 198-201, or amino acids 244-249 of SEQ ID NO: 12 or at least 95% amino acid identity with amino acids 57-61, amino acids 103-106, amino acids 198-201, or amino acids 244-249 of SEQ ID NO: 12. In yet other aspects of this embodiment, a β-trefoil domain with enhanced binding activity derived from a Clostridial botulinum serotype A HA-33 comprises a polypeptide having, e.g., at most 70% amino acid identity with amino acids 57-61, amino acids 103-106, amino acids 198-201, or amino acids 244-249 of SEQ ID NO: 12, at most 75% amino acid identity with amino acids 57-61, amino acids 103-106, amino acids 198-201, or amino acids 244-249 of SEQ ID NO: 12, at most 80% amino acid identity with amino acids 57-61, amino acids 103-106, amino acids 198-201, or amino acids 244-249 of SEQ ID NO: 12, at most 85% amino acid identity with amino acids 57-61, amino acids 103-106, amino acids 198-201, or amino acids 244-249 of SEQ ID NO: 12, at most 90% amino acid identity with amino acids 57-61, amino acids 103-106, amino acids 198-201, or amino acids 244-249 of SEQ ID NO: 12 or at most 95% amino acid identity with amino acids 57-61, amino acids 103-106, amino acids 198-201, or amino acids 244-249 of SEQ ID NO: 12.

In other aspects of this embodiment, a β-trefoil domain with enhanced binding activity derived from a Clostridial botulinum serotype A HA-33 comprises a polypeptide having, e.g., at most one, two, three or four non-contiguous amino acid substitutions relative to amino acids 57-61, amino acids 103-106, amino acids 198-201, or amino acids 244-249 of SEQ ID NO: 12. In other aspects of this embodiment, a β-trefoil domain with enhanced binding activity derived from a Clostridial botulinum serotype A HA-33 comprises a polypeptide having, e.g., at least one, two, three or four non-contiguous amino acid substitutions relative to amino acids 57-61, amino acids 103-106, amino acids 198-201, or amino acids 244-249 of SEQ ID NO: 12. In other aspects of this embodiment, a non-contiguous amino acid substitution of any amino acid from amino acids 57-61, amino acids 103-106, amino acids 198-201, or amino acids 244-249 of SEQ ID NO: 12 can be replaced with glycine. In other aspects of this embodiment, a non-contiguous amino acid substitution of any hydrophobic amino acid from amino acids 57-61, amino acids 103-106, amino acids 198-201, or amino acids 244-249 of SEQ ID NO: 12 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four non-contiguous amino acid deletions relative to amino acids 57-61, amino acids 103-106, amino acids 198-201, or amino acids 244-249 of SEQ ID NO: 12. In other aspects of this embodiment, a β-trefoil domain with enhanced binding activity derived from a Clostridial botulinum serotype A HA-33 comprises a polypeptide having, e.g., at least one, two, three or four non-contiguous amino acid deletions relative to amino acids 57-61, amino acids 103-106, amino acids 198-201, or amino acids 244-249 of SEQ ID NO: 12. In still other aspects of this embodiment, a β-trefoil domain with enhanced binding activity derived from a Clostridial botulinum serotype A HA-33 comprises a polypeptide having, e.g., at most one, two, three or four non-contiguous amino acid additions relative to amino acids 57-61, amino acids 103-106, amino acids 198-201, or amino acids 244-249 of SEQ ID NO: 12. In other aspects of this embodiment, a β-trefoil domain with enhanced binding activity derived from a Clostridial botulinum serotype A HA-33 comprises a polypeptide having, e.g., at least one, two, three or four non-contiguous amino acid additions relative to amino acids 57-61, amino acids 103-106, amino acids 198-201, or amino acids 244-249 of SEQ ID NO: 12.

In other aspects of this embodiment, a β-trefoil domain with enhanced binding activity derived from a Clostridial botulinum serotype A HA-33 comprises a polypeptide having, e.g., at most one, two, three or four contiguous amino acid substitutions relative to amino acids 57-61, amino acids 103-106, amino acids 198-201, or amino acids 244-249 of SEQ ID NO: 12. In other aspects of this embodiment, a β-trefoil domain with enhanced binding activity derived from a Clostridial botulinum serotype A HA-33 comprises a polypeptide having, e.g., at least one, two, three or four contiguous amino acid substitutions relative to amino acids 57-61, amino acids 103-106, amino acids 198-201, or amino acids 244-249 of SEQ ID NO: 12. In other aspects of this embodiment, contiguous amino acid substitutions of amino acids from amino acids 57-61, amino acids 103-106, amino acids 198-201, or amino acids 244-249 of SEQ ID NO: 12 can be replaced with glycine. In other aspects of this embodiment, contiguous amino acid substitutions of hydrophobic amino acids from amino acids 57-61, amino acids 103-106, amino acids 198-201, or amino acids 244-249 of SEQ ID NO: 12 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four contiguous amino acid deletions relative to amino acids 57-61, amino acids 103-106, amino acids 198-201, or amino acids 244-249 of SEQ ID NO: 12. In other aspects of this embodiment, a β-trefoil domain with enhanced binding activity derived from a Clostridial botulinum serotype A HA-33 comprises a polypeptide having, e.g., at least one, two, three or four contiguous amino acid deletions relative to amino acids 57-61, amino acids 103-106, amino acids 198-201, or amino acids 244-249 of SEQ ID NO: 12. In still other aspects of this embodiment, a β-trefoil domain with enhanced binding activity derived from a Clostridial botulinum serotype A HA-33 comprises a polypeptide having, e.g., at most one, two, three or four contiguous amino acid additions relative to amino acids 57-61, amino acids 103-106, amino acids 198-201, or amino acids 244-249 of SEQ ID NO: 12. In other aspects of this embodiment, a β-trefoil domain with enhanced binding activity derived from a Clostridial botulinum serotype A HA-33 comprises a polypeptide having, e.g., at least one, two, three or four contiguous amino acid additions relative to amino acids 57-61, amino acids 103-106, amino acids 198-201, or amino acids 244-249 of SEQ ID NO: 12.

In another embodiment, a β-trefoil domain derived from a Clostridial botulinum serotype A HA-33 comprises a β-trefoil domain derived from a Clostridial botulinum serotype A HA-33 of SEQ ID NO: 13. In another embodiment, a β-trefoil domain derived from a Clostridial botulinum serotype A HA-33 comprises amino acids 10-144 or amino acids 151-293 of SEQ ID NO: 13. In another aspect of this embodiment, a β-trefoil domain derived from a Clostridial botulinum serotype A HA-33 comprises a 1α-fold motif of a β-trefoil domain of a Clostridial botulinum serotype A HA-33, a 1β-fold motif of a β-trefoil domain of a Clostridial botulinum serotype A HA-33, a 1γ-fold motif of a β-trefoil domain of a Clostridial botulinum serotype A HA-33, a 2α-fold motif of a β-trefoil domain of a Clostridial botulinum serotype A HA-33, a 2β-fold motif of a β-trefoil domain of a Clostridial botulinum serotype A HA-33, or a 2γ-fold motif of a β-trefoil domain of a Clostridial botulinum serotype A HA-33 of SEQ ID NO: 13. In another aspect of this embodiment, a β-trefoil domain derived from a Clostridial botulinum serotype A HA-33 comprises amino acids 10-54, amino acids 60-100, amino acids 105-144, amino acids 151-195, amino acids 200-242, or amino acids 249-293 of SEQ ID NO: 13.

In another embodiment, a β-trefoil domain with enhanced binding activity derived from a Clostridial botulinum serotype A HA-33 comprises a β-trefoil domain with enhanced binding activity derived from a Clostridial botulinum serotype A HA-33 of SEQ ID NO: 13. In another embodiment, a β-trefoil domain with enhanced binding activity derived from a Clostridial botulinum serotype A HA-33 comprises amino acids 10-144 or amino acids 151-293 of SEQ ID NO: 13. In another aspect of this embodiment, a β-trefoil domain with enhanced binding activity derived from a Clostridial botulinum serotype A HA-33 comprises a modified 1α-fold motif of a β-trefoil domain of a Clostridial botulinum serotype A HA-33, a modified 1β-fold motif of a β-trefoil domain of a Clostridial botulinum serotype A HA-33, a modified 1γ-fold motif of a β-trefoil domain of a Clostridial botulinum serotype A HA-33, a modified 2α-fold motif of a β-trefoil domain of a Clostridial botulinum serotype A HA-33, a modified 2β-fold motif of a β-trefoil domain of a Clostridial botulinum serotype A HA-33, or a modified 2γ-fold motif of a β-trefoil domain of a Clostridial botulinum serotype A HA-33 of SEQ ID NO: 13. In another aspect of this embodiment, a β-trefoil domain with enhanced binding activity derived from a Clostridial botulinum serotype A HA-33 comprises amino acids 10-54, amino acids 60-100, amino acids 105-144, amino acids 151-195, amino acids 200-242, or amino acids 249-293 of SEQ ID NO: 13.

In other aspects of this embodiment, a Clostridial botulinum serotype A HA-33 comprising a β-trefoil domain with enhanced binding activity comprises a polypeptide having, e.g., at least 70% amino acid identity with amino acids 10-55, amino acids 56-102, amino acids 103-144, amino acids 151-197, amino acids 198-245, or amino acids 246-279 of SEQ ID NO: 13, at least 75% amino acid identity with amino acids 10-55, amino acids 56-102, amino acids 103-144, amino acids 151-197, amino acids 198-245, or amino acids 246-279 of SEQ ID NO: 13, at least 80% amino acid identity with amino acids 10-55, amino acids 56-102, amino acids 103-144, amino acids 151-197, amino acids 198-245, or amino acids 246-279 of SEQ ID NO: 13, at least 85% amino acid identity with amino acids 10-55, amino acids 56-102, amino acids 103-144, amino acids 151-197, amino acids 198-245, or amino acids 246-279 of SEQ ID NO: 13, at least 90% amino acid identity with amino acids 10-55, amino acids 56-102, amino acids 103-144, amino acids 151-197, amino acids 198-245, or amino acids 246-279 of SEQ ID NO: 13 or at least 95% amino acid identity with amino acids 10-55, amino acids 56-102, amino acids 103-144, amino acids 151-197, amino acids 198-245, or amino acids 246-279 of SEQ ID NO: 13. In yet other aspects of this embodiment, a Clostridial botulinum serotype A HA-33 comprising a β-trefoil domain with enhanced binding activity comprises a polypeptide having, e.g., at most 70% amino acid identity with amino acids 10-55, amino acids 56-102, amino acids 103-144, amino acids 151-197, amino acids 198-245, or amino acids 246-279 of SEQ ID NO: 13, at most 75% amino acid identity with amino acids 10-55, amino acids 56-102, amino acids 103-144, amino acids 151-197, amino acids 198-245, or amino acids 246-279 of SEQ ID NO: 13, at most 80% amino acid identity with amino acids 10-55, amino acids 56-102, amino acids 103-144, amino acids 151-197, amino acids 198-245, or amino acids 246-279 of SEQ ID NO: 13, at most 85% amino acid identity with amino acids 10-55, amino acids 56-102, amino acids 103-144, amino acids 151-197, amino acids 198-245, or amino acids 246-279 of SEQ ID NO: 13, at most 90% amino acid identity with amino acids 10-55, amino acids 56-102, amino acids 103-144, amino acids 151-197, amino acids 198-245, or amino acids 246-279 of SEQ ID NO: 13 or at most 95% amino acid identity with amino acids 10-55, amino acids 56-102, amino acids 103-144, amino acids 151-197, amino acids 198-245, or amino acids 246-279 of SEQ ID NO: 13.

In other aspects of this embodiment, a Clostridial botulinum serotype A HA-33 comprising a 11-trefoil domain with enhanced binding activity comprises a polypeptide having, e.g., at most one, two, three, four, five, six, seven, eight, nine, 10 or 20 non-contiguous amino acid substitutions relative to amino acids 10-55, amino acids 56-102, amino acids 103-144, amino acids 151-197, amino acids 198-245, or amino acids 246-279 of SEQ ID NO: 13. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-55, amino acids 56-102, amino acids 103-144, amino acids 151-197, amino acids 198-245, or amino acids 246-279 of SEQ ID NO: 13. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-55, amino acids 56-102, amino acids 103-144, amino acids 151-197, amino acids 198-245, or amino acids 246-279 of SEQ ID NO: 13. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-55, amino acids 56-102, amino acids 103-144, amino acids 151-197, amino acids 198-245, or amino acids 246-279 of SEQ ID NO: 13. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-55, amino acids 56-102, amino acids 103-144, amino acids 151-197, amino acids 198-245, or amino acids 246-279 of SEQ ID NO: 13. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-55, amino acids 56-102, amino acids 103-144, amino acids 151-197, amino acids 198-245, or amino acids 246-279 of SEQ ID NO: 13.

In other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-55, amino acids 56-102, amino acids 103-144, amino acids 151-197, amino acids 198-245, or amino acids 246-279 of SEQ ID NO: 13. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-55, amino acids 56-102, amino acids 103-144, amino acids 151-197, amino acids 198-245, or amino acids 246-279 of SEQ ID NO: 13. In yet other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-55, amino acids 56-102, amino acids 103-144, amino acids 151-197, amino acids 198-245, or amino acids 246-279 of SEQ ID NO: 13. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-55, amino acids 56-102, amino acids 103-144, amino acids 151-197, amino acids 198-245, or amino acids 246-279 of SEQ ID NO: 13. In still other aspects of this embodiment, a Clostridial botulinum serotype A HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-55, amino acids 56-102, amino acids 103-144, amino acids 151-197, amino acids 198-245, or amino acids 246-279 of SEQ ID NO: 13. In other aspects of this embodiment, a Clostridial botulinum serotype A HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-55, amino acids 56-102, amino acids 103-144, amino acids 151-197, amino acids 198-245, or amino acids 246-279 of SEQ ID NO: 13.

In another embodiment, a β-trefoil domain derived from a Clostridial botulinum serotype A HA-33 comprises a 1β4/β5 hairpin turn of a β-trefoil domain of a Clostridial botulinum serotype A HA-33, a 1β8/β9 hairpin turn of a β-trefoil domain of a Clostridial botulinum serotype A HA-33, a 2β4/β5 hairpin turn of a β-trefoil domain of a Clostridial botulinum serotype A HA-33 or a 2β8/β9 hairpin turn of a β-trefoil domain of a Clostridial botulinum serotype A HA-33 of SEQ ID NO: 13. In another aspect of this embodiment, a β-trefoil domain derived from a Clostridial botulinum serotype A HA-33 comprises amino acids 55-59, amino acids 101-104, amino acids 196-199, or amino acids 243-248 of SEQ ID NO: 13.

In another embodiment, a β-trefoil domain with enhanced binding activity derived from a Clostridial botulinum serotype A HA-33 comprises a modified 1β4/β5 hairpin turn of a β-trefoil domain of a Clostridial botulinum serotype A HA-33, a modified 1β8/β9 hairpin turn of a β-trefoil domain of a Clostridial botulinum serotype A HA-33, a modified 2β4/β5 hairpin turn of a β-trefoil domain of a Clostridial botulinum serotype A HA-33 or a modified 2β8/β9 hairpin turn of a β-trefoil domain of a Clostridial botulinum serotype A HA-33 of SEQ ID NO: 13. In another aspect of this embodiment, a β-trefoil domain with enhanced binding activity derived from a Clostridial botulinum serotype A HA-33 comprises a modification of amino acids 55-59, amino acids 101-104, amino acids 196-199, or amino acids 243-248 of SEQ ID NO: 13.

In other aspects of this embodiment, a β-trefoil domain with enhanced binding activity derived from a Clostridial botulinum serotype A HA-33 comprises a polypeptide having, e.g., at least 70% amino acid identity with amino acids 55-59, amino acids 101-104, amino acids 196-199, or amino acids 243-248 of SEQ ID NO: 13, at least 75% amino acid identity with amino acids 55-59, amino acids 101-104, amino acids 196-199, or amino acids 243-248 of SEQ ID NO: 13, at least 80% amino acid identity with amino acids 55-59, amino acids 101-104, amino acids 196-199, or amino acids 243-248 of SEQ ID NO: 13, at least 85% amino acid identity with amino acids 55-59, amino acids 101-104, amino acids 196-199, or amino acids 243-248 of SEQ ID NO: 13, at least 90% amino acid identity with amino acids 55-59, amino acids 101-104, amino acids 196-199, or amino acids 243-248 of SEQ ID NO: 13 or at least 95% amino acid identity with amino acids 55-59, amino acids 101-104, amino acids 196-199, or amino acids 243-248 of SEQ ID NO: 13. In yet other aspects of this embodiment, a β-trefoil domain with enhanced binding activity derived from a Clostridial botulinum serotype A HA-33 comprises a polypeptide having, e.g., at most 70% amino acid identity with amino acids 55-59, amino acids 101-104, amino acids 196-199, or amino acids 243-248 of SEQ ID NO: 13, at most 75% amino acid identity with amino acids 55-59, amino acids 101-104, amino acids 196-199, or amino acids 243-248 of SEQ ID NO: 13, at most 80% amino acid identity with amino acids 55-59, amino acids 101-104, amino acids 196-199, or amino acids 243-248 of SEQ ID NO: 13, at most 85% amino acid identity with amino acids 55-59, amino acids 101-104, amino acids 196-199, or amino acids 243-248 of SEQ ID NO: 13, at most 90% amino acid identity with amino acids 55-59, amino acids 101-104, amino acids 196-199, or amino acids 243-248 of SEQ ID NO: 13 or at most 95% amino acid identity with amino acids 55-59, amino acids 101-104, amino acids 196-199, or amino acids 243-248 of SEQ ID NO: 13.

In other aspects of this embodiment, a β-trefoil domain with enhanced binding activity derived from a Clostridial botulinum serotype A HA-33 comprises a polypeptide having, e.g., at most one, two, three or four non-contiguous amino acid substitutions relative to amino acids 55-59, amino acids 101-104, amino acids 196-199, or amino acids 243-248 of SEQ ID NO: 13. In other aspects of this embodiment, a β-trefoil domain with enhanced binding activity derived from a Clostridial botulinum serotype A HA-33 comprises a polypeptide having, e.g., at least one, two, three or four non-contiguous amino acid substitutions relative to amino acids 55-59, amino acids 101-104, amino acids 196-199, or amino acids 243-248 of SEQ ID NO: 13. In other aspects of this embodiment, a non-contiguous amino acid substitution of any amino acid from amino acids 55-59, amino acids 101-104, amino acids 196-199, or amino acids 243-248 of SEQ ID NO: 13 can be replaced with glycine. In other aspects of this embodiment, a non-contiguous amino acid substitution of any hydrophobic amino acid from amino acids 55-59, amino acids 101-104, amino acids 196-199, or amino acids 243-248 of SEQ ID NO: 13 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four non-contiguous amino acid deletions relative to amino acids 55-59, amino acids 101-104, amino acids 196-199, or amino acids 243-248 of SEQ ID NO: 13. In other aspects of this embodiment, a β-trefoil domain with enhanced binding activity derived from a Clostridial botulinum serotype A HA-33 comprises a polypeptide having, e.g., at least one, two, three or four non-contiguous amino acid deletions relative to amino acids 55-59, amino acids 101-104, amino acids 196-199, or amino acids 243-248 of SEQ ID NO: 13. In still other aspects of this embodiment, a β-trefoil domain with enhanced binding activity derived from a Clostridial botulinum serotype A HA-33 comprises a polypeptide having, e.g., at most one, two, three or four non-contiguous amino acid additions relative to amino acids 55-59, amino acids 101-104, amino acids 196-199, or amino acids 243-248 of SEQ ID NO: 13. In other aspects of this embodiment, a β-trefoil domain with enhanced binding activity derived from a Clostridial botulinum serotype A HA-33 comprises a polypeptide having, e.g., at least one, two, three or four non-contiguous amino acid additions relative to amino acids 55-59, amino acids 101-104, amino acids 196-199, or amino acids 243-248 of SEQ ID NO: 13.

In other aspects of this embodiment, a β-trefoil domain with enhanced binding activity derived from a Clostridial botulinum serotype A HA-33 comprises a polypeptide having, e.g., at most one, two, three or four contiguous amino acid substitutions relative to amino acids 55-59, amino acids 101-104, amino acids 196-199, or amino acids 243-248 of SEQ ID NO: 13. In other aspects of this embodiment, a β-trefoil domain with enhanced binding activity derived from a Clostridial botulinum serotype A HA-33 comprises a polypeptide having, e.g., at least one, two, three or four contiguous amino acid substitutions relative to amino acids 55-59, amino acids 101-104, amino acids 196-199, or amino acids 243-248 of SEQ ID NO: 13. In other aspects of this embodiment, contiguous amino acid substitutions of amino acids from amino acids 55-59, amino acids 101-104, amino acids 196-199, or amino acids 243-248 of SEQ ID NO: 13 can be replaced with glycine. In other aspects of this embodiment, contiguous amino acid substitutions of hydrophobic amino acids from amino acids 55-59, amino acids 101-104, amino acids 196-199, or amino acids 243-248 of SEQ ID NO: 13 can be replaced with phenylalanine. In yet other aspects of this embodiment, a β-trefoil domain with enhanced binding activity derived from a Clostridial botulinum serotype A HA-33 comprises a polypeptide having, e.g., at most one, two, three or four contiguous amino acid deletions relative to amino acids 55-59, amino acids 101-104, amino acids 196-199, or amino acids 243-248 of SEQ ID NO: 13. In other aspects of this embodiment, a β-trefoil domain with enhanced binding activity derived from a Clostridial botulinum serotype A HA-33 comprises a polypeptide having, e.g., at least one, two, three or four contiguous amino acid deletions relative to amino acids 55-59, amino acids 101-104, amino acids 196-199, or amino acids 243-248 of SEQ ID NO: 13. In still other aspects of this embodiment, a β-trefoil domain with enhanced binding activity derived from a Clostridial botulinum serotype A HA-33 comprises a polypeptide having, e.g., at most one, two, three or four contiguous amino acid additions relative to amino acids 55-59, amino acids 101-104, amino acids 196-199, or amino acids 243-248 of SEQ ID NO: 13. In other aspects of this embodiment, a β-trefoil domain with enhanced binding activity derived from a Clostridial botulinum serotype A HA-33 comprises a polypeptide having, e.g., at least one, two, three or four contiguous amino acid additions relative to amino acids 55-59, amino acids 101-104, amino acids 196-199, or amino acids 243-248 of SEQ ID NO: 13.

In another embodiment, a β-trefoil domain derived from a Clostridial botulinum serotype B HA-33 comprises a β-trefoil domain derived from a Clostridial botulinum serotype B HA-33 of SEQ ID NO: 14. In another embodiment, a β-trefoil domain derived from a Clostridial botulinum serotype B HA-33 comprises amino acids 10-144 or amino acids 151-292 of SEQ ID NO: 14. In another aspect of this embodiment, a β-trefoil domain derived from a Clostridial botulinum serotype B HA-33 comprises a 1α-fold motif of a 13-trefoil domain of a Clostridial botulinum serotype B HA-33, a 1β-fold motif of a β-trefoil domain of a Clostridial botulinum serotype B HA-33, a 1γ-fold motif of a β-trefoil domain of a Clostridial botulinum serotype B HA-33, a 2α-fold motif of a β-trefoil domain of a Clostridial botulinum serotype B HA-33, a 2β-fold motif of a β-trefoil domain of a Clostridial botulinum serotype B HA-33, or a 2γ-fold motif of a β-trefoil domain of a Clostridial botulinum serotype B HA-33 of SEQ ID NO: 14. In another aspect of this embodiment, a β-trefoil domain derived from a Clostridial botulinum serotype B HA-33 comprises amino acids 10-54, amino acids 60-100, amino acids 105-144, amino acids 151-195, amino acids 200-241, or amino acids 248-292 of SEQ ID NO: 14.

In another embodiment, a β-trefoil domain with enhanced binding activity derived from a Clostridial botulinum serotype B HA-33 comprises a β-trefoil domain with enhanced binding activity derived from a Clostridial botulinum serotype B HA-33 of SEQ ID NO: 14. In another embodiment, a β-trefoil domain with enhanced binding activity derived from a Clostridial botulinum serotype B HA-33 comprises amino acids 10-144 or amino acids 151-292 of SEQ ID NO: 14. In another aspect of this embodiment, a β-trefoil domain with enhanced binding activity derived from a Clostridial botulinum serotype B HA-33 comprises a modified 1α-fold motif of a β-trefoil domain of a Clostridial botulinum serotype B HA-33, a modified 1β-fold motif of a β-trefoil domain of a Clostridial botulinum serotype B HA-33, a modified 1γ-fold motif of a β-trefoil domain of a Clostridial botulinum serotype B HA-33, a modified 2α-fold motif of a β-trefoil domain of a Clostridial botulinum serotype B HA-33, a modified 2β-fold motif of a β-trefoil domain of a Clostridial botulinum serotype B HA-33, or a modified 2γ-fold motif of a β-trefoil domain of a Clostridial botulinum serotype B HA-33 of SEQ ID NO: 14. In another aspect of this embodiment, a β-trefoil domain with enhanced binding activity derived from a Clostridial botulinum serotype B HA-33 comprises amino acids 10-54, amino acids 60-100, amino acids 105-144, amino acids 151-195, amino acids 200-241, or amino acids 248-292 of SEQ ID NO: 14.

In other aspects of this embodiment, a Clostridial botulinum serotype B HA-33 comprising a β-trefoil domain with enhanced binding activity comprises a polypeptide having, e.g., at least 70% amino acid identity with amino acids 10-54, amino acids 60-100, amino acids 105-144, amino acids 151-195, amino acids 200-241, or amino acids 248-292 of SEQ ID NO: 14, at least 75% amino acid identity with amino acids 10-54, amino acids 60-100, amino acids 105-144, amino acids 151-195, amino acids 200-241, or amino acids 248-292 of SEQ ID NO: 14, at least 80% amino acid identity with amino acids 10-54, amino acids 60-100, amino acids 105-144, amino acids 151-195, amino acids 200-241, or amino acids 248-292 of SEQ ID NO: 14, at least 85% amino acid identity with amino acids 10-54, amino acids 60-100, amino acids 105-144, amino acids 151-195, amino acids 200-241, or amino acids 248-292 of SEQ ID NO: 14, at least 90% amino acid identity with amino acids 10-54, amino acids 60-100, amino acids 105-144, amino acids 151-195, amino acids 200-241, or amino acids 248-292 of SEQ ID NO: 14 or at least 95% amino acid identity with amino acids 10-54, amino acids 60-100, amino acids 105-144, amino acids 151-195, amino acids 200-241, or amino acids 248-292 of SEQ ID NO: 14. In yet other aspects of this embodiment, a Clostridial botulinum serotype B HA-33 comprising a β-trefoil domain with enhanced binding activity comprises a polypeptide having, e.g., at most 70% amino acid identity with amino acids 10-54, amino acids 60-100, amino acids 105-144, amino acids 151-195, amino acids 200-241, or amino acids 248-292 of SEQ ID NO: 14, at most 75% amino acid identity with amino acids 10-54, amino acids 60-100, amino acids 105-144, amino acids 151-195, amino acids 200-241, or amino acids 248-292 of SEQ ID NO: 14, at most 80% amino acid identity with amino acids 10-54, amino acids 60-100, amino acids 105-144, amino acids 151-195, amino acids 200-241, or amino acids 248-292 of SEQ ID NO: 14, at most 85% amino acid identity with amino acids 10-54, amino acids 60-100, amino acids 105-144, amino acids 151-195, amino acids 200-241, or amino acids 248-292 of SEQ ID NO: 14, at most 90% amino acid identity with amino acids 10-54, amino acids 60-100, amino acids 105-144, amino acids 151-195, amino acids 200-241, or amino acids 248-292 of SEQ ID NO: 14 or at most 95% amino acid identity with amino acids 10-54, amino acids 60-100, amino acids 105-144, amino acids 151-195, amino acids 200-241, or amino acids 248-292 of SEQ ID NO: 14.

In other aspects of this embodiment, a Clostridial botulinum serotype B HA-33 comprising a 11-trefoil domain with enhanced binding activity comprises a polypeptide having, e.g., at most one, two, three, four, five, six, seven, eight, nine, 10 or 20 non-contiguous amino acid substitutions relative to amino acids 10-54, amino acids 60-100, amino acids 105-144, amino acids 151-195, amino acids 200-241, or amino acids 248-292 of SEQ ID NO: 14. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-54, amino acids 60-100, amino acids 105-144, amino acids 151-195, amino acids 200-241, or amino acids 248-292 of SEQ ID NO: 14. In yet other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-54, amino acids 60-100, amino acids 105-144, amino acids 151-195, amino acids 200-241, or amino acids 248-292 of SEQ ID NO: 14. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-54, amino acids 60-100, amino acids 105-144, amino acids 151-195, amino acids 200-241, or amino acids 248-292 of SEQ ID NO: 14. In still other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-54, amino acids 60-100, amino acids 105-144, amino acids 151-195, amino acids 200-241, or amino acids 248-292 of SEQ ID NO: 14. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-54, amino acids 60-100, amino acids 105-144, amino acids 151-195, amino acids 200-241, or amino acids 248-292 of SEQ ID NO: 14.

In other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-54, amino acids 60-100, amino acids 105-144, amino acids 151-195, amino acids 200-241, or amino acids 248-292 of SEQ ID NO: 14. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-54, amino acids 60-100, amino acids 105-144, amino acids 151-195, amino acids 200-241, or amino acids 248-292 of SEQ ID NO: 14. In yet other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-54, amino acids 60-100, amino acids 105-144, amino acids 151-195, amino acids 200-241, or amino acids 248-292 of SEQ ID NO: 14. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-54, amino acids 60-100, amino acids 105-144, amino acids 151-195, amino acids 200-241, or amino acids 248-292 of SEQ ID NO: 14. In still other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-54, amino acids 60-100, amino acids 105-144, amino acids 151-195, amino acids 200-241, or amino acids 248-292 of SEQ ID NO: 14. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-54, amino acids 60-100, amino acids 105-144, amino acids 151-195, amino acids 200-241, or amino acids 248-292 of SEQ ID NO: 14.

In another embodiment, a β-trefoil domain derived from a Clostridial botulinum serotype B HA-33 comprises a 1β4/β5 hairpin turn of a β-trefoil domain of a Clostridial botulinum serotype B HA-33, a 1β8/β9 hairpin turn of a β-trefoil domain of a Clostridial botulinum serotype B HA-33, a 2β4/β5 hairpin turn of a β-trefoil domain of a Clostridial botulinum serotype B HA-33 or a 2β8/β9 hairpin turn of a β-trefoil domain of a Clostridial botulinum serotype B HA-33 of SEQ ID NO: 14. In another aspect of this embodiment, a β-trefoil domain derived from a Clostridial botulinum serotype B HA-33 comprises amino acids 55-59, amino acids 101-104, amino acids 196-199, or amino acids 242-247 of SEQ ID NO: 14.

In another embodiment, a β-trefoil domain with enhanced binding activity derived from a Clostridial botulinum serotype B HA-33 comprises a modified 1β4/β5 hairpin turn of a β-trefoil domain of a Clostridial botulinum serotype B HA-33, a modified 1β8/β9 hairpin turn of a β-trefoil domain of a Clostridial botulinum serotype B HA-33, a modified 2β4/β5 hairpin turn of a β-trefoil domain of a Clostridial botulinum serotype B HA-33 or a modified 2β8/β9 hairpin turn of a β-trefoil domain of a Clostridial botulinum serotype B HA-33 of SEQ ID NO: 14. In another aspect of this embodiment, a β-trefoil domain with enhanced binding activity derived from a Clostridial botulinum serotype B HA-33 comprises a modification of amino acids 55-59, amino acids 101-104, amino acids 196-199, or amino acids 242-247 of SEQ ID NO: 14.

In other aspects of this embodiment, a β-trefoil domain with enhanced binding activity derived from a Clostridial botulinum serotype B HA-33 comprises a polypeptide having, e.g., at least 70% amino acid identity with amino acids 55-59, amino acids 101-104, amino acids 196-199, or amino acids 242-247 of SEQ ID NO: 14, at least 75% amino acid identity with amino acids 55-59, amino acids 101-104, amino acids 196-199, or amino acids 242-247 of SEQ ID NO: 14, at least 80% amino acid identity with amino acids 55-59, amino acids 101-104, amino acids 196-199, or amino acids 242-247 of SEQ ID NO: 14, at least 85% amino acid identity with amino acids 55-59, amino acids 101-104, amino acids 196-199, or amino acids 242-247 of SEQ ID NO: 14, at least 90% amino acid identity with amino acids 55-59, amino acids 101-104, amino acids 196-199, or amino acids 242-247 of SEQ ID NO: 14 or at least 95% amino acid identity with amino acids 55-59, amino acids 101-104, amino acids 196-199, or amino acids 242-247 of SEQ ID NO: 14. In yet other aspects of this embodiment, a β-trefoil domain with enhanced binding activity derived from a Clostridial botulinum serotype B HA-33 comprises a polypeptide having, e.g., at most 70% amino acid identity with amino acids 55-59, amino acids 101-104, amino acids 196-199, or amino acids 242-247 of SEQ ID NO: 14, at most 75% amino acid identity with amino acids 55-59, amino acids 101-104, amino acids 196-199, or amino acids 242-247 of SEQ ID NO: 14, at most 80% amino acid identity with amino acids 55-59, amino acids 101-104, amino acids 196-199, or amino acids 242-247 of SEQ ID NO: 14, at most 85% amino acid identity with amino acids 55-59, amino acids 101-104, amino acids 196-199, or amino acids 242-247 of SEQ ID NO: 14, at most 90% amino acid identity with amino acids 55-59, amino acids 101-104, amino acids 196-199, or amino acids 242-247 of SEQ ID NO: 14 or at most 95% amino acid identity with amino acids 55-59, amino acids 101-104, amino acids 196-199, or amino acids 242-247 of SEQ ID NO: 14.

In other aspects of this embodiment, a β-trefoil domain with enhanced binding activity derived from a Clostridial botulinum serotype B HA-33 comprises a polypeptide having, e.g., at most one, two, three or four non-contiguous amino acid substitutions relative to amino acids 55-59, amino acids 101-104, amino acids 196-199, or amino acids 242-247 of SEQ ID NO: 14. In other aspects of this embodiment, a β-trefoil domain with enhanced binding activity derived from a Clostridial botulinum serotype B HA-33 comprises a polypeptide having, e.g., at least one, two, three or four non-contiguous amino acid substitutions relative to amino acids 55-59, amino acids 101-104, amino acids 196-199, or amino acids 242-247 of SEQ ID NO: 14. In other aspects of this embodiment, a non-contiguous amino acid substitution of any amino acid from amino acids 55-59, amino acids 101-104, amino acids 196-199, or amino acids 242-247 of SEQ ID NO: 14 can be replaced with glycine. In other aspects of this embodiment, a non-contiguous amino acid substitution of any hydrophobic amino acid from amino acids 55-59, amino acids 101-104, amino acids 196-199, or amino acids 242-247 of SEQ ID NO: 14 can be replaced with phenylalanine. In yet other aspects of this embodiment, a β-trefoil domain with enhanced binding activity derived from a Clostridial botulinum serotype B HA-33 comprises a polypeptide having, e.g., at most one, two, three or four non-contiguous amino acid deletions relative to amino acids 55-59, amino acids 101-104, amino acids 196-199, or amino acids 242-247 of SEQ ID NO: 14. In other aspects of this embodiment, a β-trefoil domain with enhanced binding activity derived from a Clostridial botulinum serotype B HA-33 comprises a polypeptide having, e.g., at least one, two, three or four non-contiguous amino acid deletions relative to amino acids 55-59, amino acids 101-104, amino acids 196-199, or amino acids 242-247 of SEQ ID NO: 14. In still other aspects of this embodiment, a β-trefoil domain with enhanced binding activity derived from a Clostridial botulinum serotype B HA-33 comprises a polypeptide having, e.g., at most one, two, three or four non-contiguous amino acid additions relative to amino acids 55-59, amino acids 101-104, amino acids 196-199, or amino acids 242-247 of SEQ ID NO: 14. In other aspects of this embodiment, a β-trefoil domain with enhanced binding activity derived from a Clostridial botulinum serotype B HA-33 comprises a polypeptide having, e.g., at least one, two, three or four non-contiguous amino acid additions relative to amino acids 55-59, amino acids 101-104, amino acids 196-199, or amino acids 242-247 of SEQ ID NO: 14.

In other aspects of this embodiment, a β-trefoil domain with enhanced binding activity derived from a Clostridial botulinum serotype B HA-33 comprises a polypeptide having, e.g., at most one, two, three or four contiguous amino acid substitutions relative to amino acids 55-59, amino acids 101-104, amino acids 196-199, or amino acids 242-247 of SEQ ID NO: 14. In other aspects of this embodiment, a β-trefoil domain with enhanced binding activity derived from a Clostridial botulinum serotype B HA-33 comprises a polypeptide having, e.g., at least one, two, three or four contiguous amino acid substitutions relative to amino acids 55-59, amino acids 101-104, amino acids 196-199, or amino acids 242-247 of SEQ ID NO: 14. In other aspects of this embodiment, contiguous amino acid substitutions of amino acids from amino acids 55-59, amino acids 101-104, amino acids 196-199, or amino acids 242-247 of SEQ ID NO: 14 can be replaced with glycine. In other aspects of this embodiment, contiguous amino acid substitutions of hydrophobic amino acids from amino acids 55-59, amino acids 101-104, amino acids 196-199, or amino acids 242-247 of SEQ ID NO: 14 can be replaced with phenylalanine. In yet other aspects of this embodiment, a β-trefoil domain with enhanced binding activity derived from a Clostridial botulinum serotype B HA-33 comprises a polypeptide having, e.g., at most one, two, three or four contiguous amino acid deletions relative to amino acids 55-59, amino acids 101-104, amino acids 196-199, or amino acids 242-247 of SEQ ID NO: 14. In other aspects of this embodiment, a β-trefoil domain with enhanced binding activity derived from a Clostridial botulinum serotype B HA-33 comprises a polypeptide having, e.g., at least one, two, three or four contiguous amino acid deletions relative to amino acids 55-59, amino acids 101-104, amino acids 196-199, or amino acids 242-247 of SEQ ID NO: 14. In still other aspects of this embodiment, a β-trefoil domain with enhanced binding activity derived from a Clostridial botulinum serotype B HA-33 comprises a polypeptide having, e.g., at most one, two, three or four contiguous amino acid additions relative to amino acids 55-59, amino acids 101-104, amino acids 196-199, or amino acids 242-247 of SEQ ID NO: 14. In other aspects of this embodiment, a β-trefoil domain with enhanced binding activity derived from a Clostridial botulinum serotype B HA-33 comprises a polypeptide having, e.g., at least one, two, three or four contiguous amino acid additions relative to amino acids 55-59, amino acids 101-104, amino acids 196-199, or amino acids 242-247 of SEQ ID NO: 14.

In another embodiment, a β-trefoil domain with enhanced binding activity derived from a Clostridial botulinum serotype B HA-33 comprises a β-trefoil domain with enhanced binding activity derived from a Clostridial botulinum serotype B HA-33 of SEQ ID NO: 15. In another aspect of this embodiment, a β-trefoil domain with enhanced binding activity derived from a Clostridial botulinum serotype B HA-33 comprises amino acids 10-56, amino acids 62-102, amino acids 107-146, amino acids 153-197, amino acids 200-242, or amino acids 249-291 of SEQ ID NO: 15.

In other aspects of this embodiment, a Clostridial botulinum serotype B HA-33 comprising a β-trefoil domain with enhanced binding activity comprises a polypeptide having, e.g., at least 70% amino acid identity with amino acids 10-56, amino acids 62-102, amino acids 107-146, amino acids 153-197, amino acids 200-242, or amino acids 249-291 of SEQ ID NO: 15, at least 75% amino acid identity with amino acids 10-56, amino acids 62-102, amino acids 107-146, amino acids 153-197, amino acids 200-242, or amino acids 249-291 of SEQ ID NO: 15, at least 80% amino acid identity with amino acids 10-56, amino acids 62-102, amino acids 107-146, amino acids 153-197, amino acids 200-242, or amino acids 249-291 of SEQ ID NO: 15, at least 85% amino acid identity with amino acids 10-56, amino acids 62-102, amino acids 107-146, amino acids 153-197, amino acids 200-242, or amino acids 249-291 of SEQ ID NO: 15, at least 90% amino acid identity with amino acids 10-56, amino acids 62-102, amino acids 107-146, amino acids 153-197, amino acids 200-242, or amino acids 249-291 of SEQ ID NO: 15 or at least 95% amino acid identity with amino acids 10-56, amino acids 62-102, amino acids 107-146, amino acids 153-197, amino acids 200-242, or amino acids 249-291 of SEQ ID NO: 15. In yet other aspects of this embodiment, a Clostridial botulinum serotype B HA-33 comprising a β-trefoil domain with enhanced binding activity comprises a polypeptide having, e.g., at most 70% amino acid identity with amino acids 10-56, amino acids 62-102, amino acids 107-146, amino acids 153-197, amino acids 200-242, or amino acids 249-291 of SEQ ID NO: 15, at most 75% amino acid identity with amino acids 10-56, amino acids 62-102, amino acids 107-146, amino acids 153-197, amino acids 200-242, or amino acids 249-291 of SEQ ID NO: 15, at most 80% amino acid identity with amino acids 10-56, amino acids 62-102, amino acids 107-146, amino acids 153-197, amino acids 200-242, or amino acids 249-291 of SEQ ID NO: 15, at most 85% amino acid identity with amino acids 10-56, amino acids 62-102, amino acids 107-146, amino acids 153-197, amino acids 200-242, or amino acids 249-291 of SEQ ID NO: 15, at most 90% amino acid identity with amino acids 10-56, amino acids 62-102, amino acids 107-146, amino acids 153-197, amino acids 200-242, or amino acids 249-291 of SEQ ID NO: 15 or at most 95% amino acid identity with amino acids 10-56, amino acids 62-102, amino acids 107-146, amino acids 153-197, amino acids 200-242, or amino acids 249-291 of SEQ ID NO: 15.

In other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 non-contiguous amino acid substitutions relative to amino acids 10-56, amino acids 62-102, amino acids 107-146, amino acids 153-197, amino acids 200-242, or amino acids 249-291 of SEQ ID NO: 15. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-56, amino acids 62-102, amino acids 107-146, amino acids 153-197, amino acids 200-242, or amino acids 249-291 of SEQ ID NO: 15. In yet other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-56, amino acids 62-102, amino acids 107-146, amino acids 153-197, amino acids 200-242, or amino acids 249-291 of SEQ ID NO: 15. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-56, amino acids 62-102, amino acids 107-146, amino acids 153-197, amino acids 200-242, or amino acids 249-291 of SEQ ID NO: 15. In still other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-56, amino acids 62-102, amino acids 107-146, amino acids 153-197, amino acids 200-242, or amino acids 249-291 of SEQ ID NO: 15. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-56, amino acids 62-102, amino acids 107-146, amino acids 153-197, amino acids 200-242, or amino acids 249-291 of SEQ ID NO: 15.

In other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-56, amino acids 62-102, amino acids 107-146, amino acids 153-197, amino acids 200-242, or amino acids 249-291 of SEQ ID NO: 15. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-56, amino acids 62-102, amino acids 107-146, amino acids 153-197, amino acids 200-242, or amino acids 249-291 of SEQ ID NO: 15. In yet other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-56, amino acids 62-102, amino acids 107-146, amino acids 153-197, amino acids 200-242, or amino acids 249-291 of SEQ ID NO: 15. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-56, amino acids 62-102, amino acids 107-146, amino acids 153-197, amino acids 200-242, or amino acids 249-291 of SEQ ID NO: 15. In still other aspects of this embodiment, a Clostridial botulinum serotype B HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-56, amino acids 62-102, amino acids 107-146, amino acids 153-197, amino acids 200-242, or amino acids 249-291 of SEQ ID NO: 15. In other aspects of this embodiment, a Clostridial botulinum serotype B HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-56, amino acids 62-102, amino acids 107-146, amino acids 153-197, amino acids 200-242, or amino acids 249-291 of SEQ ID NO: 15.

In another embodiment, a β-trefoil domain derived from a Clostridial botulinum serotype B HA-33 comprises a 1β4/β5 hairpin turn of a β-trefoil domain of a Clostridial botulinum serotype B HA-33, a 1β8/β9 hairpin turn of a β-trefoil domain of a Clostridial botulinum serotype B HA-33, a 2β4/β5 hairpin turn of a β-trefoil domain of a Clostridial botulinum serotype B HA-33 or a 2β8/β9 hairpin turn of a β-trefoil domain of a Clostridial botulinum serotype B HA-33 of SEQ ID NO: 15. In another aspect of this embodiment, a β-trefoil domain derived from a Clostridial botulinum serotype B HA-33 comprises amino acids 56-61, amino acids 103-106, amino acids 198-201, or amino acids 243-248 of SEQ ID NO: 15.

In another embodiment, a β-trefoil domain with enhanced binding activity derived from a Clostridial botulinum serotype B HA-33 comprises a modified 1β4/β5 hairpin turn of a β-trefoil domain of a Clostridial botulinum serotype B HA-33, a modified 1β8/β9 hairpin turn of a β-trefoil domain of a Clostridial botulinum serotype B HA-33, a modified 2β4/β5 hairpin turn of a β-trefoil domain of a Clostridial botulinum serotype B HA-33 or a modified 2β8/β9 hairpin turn of a β-trefoil domain of a Clostridial botulinum serotype B HA-33 of SEQ ID NO: 15. In another aspect of this embodiment, a β-trefoil domain with enhanced binding activity derived from a Clostridial botulinum serotype B HA-33 comprises a modification of amino acids 56-61, amino acids 103-106, amino acids 198-201, or amino acids 243-248 of SEQ ID NO: 15.

In other aspects of this embodiment, a β-trefoil domain with enhanced binding activity derived from a Clostridial botulinum serotype B HA-33 comprises a polypeptide having, e.g., at least 70% amino acid identity with amino acids 56-61, amino acids 103-106, amino acids 198-201, or amino acids 243-248 of SEQ ID NO: 15, at least 75% amino acid identity with amino acids 56-61, amino acids 103-106, amino acids 198-201, or amino acids 243-248 of SEQ ID NO: 15, at least 80% amino acid identity with amino acids 56-61, amino acids 103-106, amino acids 198-201, or amino acids 243-248 of SEQ ID NO: 15, at least 85% amino acid identity with amino acids 56-61, amino acids 103-106, amino acids 198-201, or amino acids 243-248 of SEQ ID NO: 15, at least 90% amino acid identity with amino acids 56-61, amino acids 103-106, amino acids 198-201, or amino acids 243-248 of SEQ ID NO: 15 or at least 95% amino acid identity with amino acids 56-61, amino acids 103-106, amino acids 198-201, or amino acids 243-248 of SEQ ID NO: 15. In yet other aspects of this embodiment, a β-trefoil domain with enhanced binding activity derived from a Clostridial botulinum serotype B HA-33 comprises a polypeptide having, e.g., at most 70% amino acid identity with amino acids 56-61, amino acids 103-106, amino acids 198-201, or amino acids 243-248 of SEQ ID NO: 15, at most 75% amino acid identity with amino acids 56-61, amino acids 103-106, amino acids 198-201, or amino acids 243-248 of SEQ ID NO: 15, at most 80% amino acid identity with amino acids 56-61, amino acids 103-106, amino acids 198-201, or amino acids 243-248 of SEQ ID NO: 15, at most 85% amino acid identity with amino acids 56-61, amino acids 103-106, amino acids 198-201, or amino acids 243-248 of SEQ ID NO: 15, at most 90% amino acid identity with amino acids 56-61, amino acids 103-106, amino acids 198-201, or amino acids 243-248 of SEQ ID NO: 15 or at most 95% amino acid identity with amino acids 56-61, amino acids 103-106, amino acids 198-201, or amino acids 243-248 of SEQ ID NO: 15.

In other aspects of this embodiment, a β-trefoil domain with enhanced binding activity derived from a Clostridial botulinum serotype B HA-33 comprises a polypeptide having, e.g., at most one, two, three or four non-contiguous amino acid substitutions relative to amino acids 56-61, amino acids 103-106, amino acids 198-201, or amino acids 243-248 of SEQ ID NO: 15. In other aspects of this embodiment, a β-trefoil domain with enhanced binding activity derived from a Clostridial botulinum serotype B HA-33 comprises a polypeptide having, e.g., at least one, two, three or four non-contiguous amino acid substitutions relative to amino acids 56-61, amino acids 103-106, amino acids 198-201, or amino acids 243-248 of SEQ ID NO: 15. In other aspects of this embodiment, a non-contiguous amino acid substitution of any amino acid from amino acids 56-61, amino acids 103-106, amino acids 198-201, or amino acids 243-248 of SEQ ID NO: 15 can be replaced with glycine. In other aspects of this embodiment, a non-contiguous amino acid substitution of any hydrophobic amino acid from amino acids 56-61, amino acids 103-106, amino acids 198-201, or amino acids 243-248 of SEQ ID NO: 15 can be replaced with phenylalanine. In yet other aspects of this embodiment, a β-trefoil domain with enhanced binding activity derived from a Clostridial botulinum serotype B HA-33 comprises a polypeptide having, e.g., at most one, two, three or four non-contiguous amino acid deletions relative to amino acids 56-61, amino acids 103-106, amino acids 198-201, or amino acids 243-248 of SEQ ID NO: 15. In other aspects of this embodiment, a β-trefoil domain with enhanced binding activity derived from a Clostridial botulinum serotype B HA-33 comprises a polypeptide having, e.g., at least one, two, three or four non-contiguous amino acid deletions relative to amino acids 56-61, amino acids 103-106, amino acids 198-201, or amino acids 243-248 of SEQ ID NO: 15. In still other aspects of this embodiment, a β-trefoil domain with enhanced binding activity derived from a Clostridial botulinum serotype B HA-33 comprises a polypeptide having, e.g., at most one, two, three or four non-contiguous amino acid additions relative to amino acids 56-61, amino acids 103-106, amino acids 198-201, or amino acids 243-248 of SEQ ID NO: 15. In other aspects of this embodiment, a β-trefoil domain with enhanced binding activity derived from a Clostridial botulinum serotype B HA-33 comprises a polypeptide having, e.g., at least one, two, three or four non-contiguous amino acid additions relative to amino acids 56-61, amino acids 103-106, amino acids 198-201, or amino acids 243-248 of SEQ ID NO: 15.

In other aspects of this embodiment, a β-trefoil domain with enhanced binding activity derived from a Clostridial botulinum serotype B HA-33 comprises a polypeptide having, e.g., at most one, two, three or four contiguous amino acid substitutions relative to amino acids 56-61, amino acids 103-106, amino acids 198-201, or amino acids 243-248 of SEQ ID NO: 15. In other aspects of this embodiment, a β-trefoil domain with enhanced binding activity derived from a Clostridial botulinum serotype B HA-33 comprises a polypeptide having, e.g., at least one, two, three or four contiguous amino acid substitutions relative to amino acids 56-61, amino acids 103-106, amino acids 198-201, or amino acids 243-248 of SEQ ID NO: 15. In other aspects of this embodiment, contiguous amino acid substitutions of amino acids from amino acids 56-61, amino acids 103-106, amino acids 198-201, or amino acids 243-248 of SEQ ID NO: 15 can be replaced with glycine. In other aspects of this embodiment, contiguous amino acid substitutions of hydrophobic amino acids from amino acids 56-61, amino acids 103-106, amino acids 198-201, or amino acids 243-248 of SEQ ID NO: 15 can be replaced with phenylalanine. In yet other aspects of this embodiment, a β-trefoil domain with enhanced binding activity derived from a Clostridial botulinum serotype B HA-33 comprises a polypeptide having, e.g., at most one, two, three or four contiguous amino acid deletions relative to amino acids 56-61, amino acids 103-106, amino acids 198-201, or amino acids 243-248 of SEQ ID NO: 15. In other aspects of this embodiment, a β-trefoil domain with enhanced binding activity derived from a Clostridial botulinum serotype B HA-33 comprises a polypeptide having, e.g., at least one, two, three or four contiguous amino acid deletions relative to amino acids 56-61, amino acids 103-106, amino acids 198-201, or amino acids 243-248 of SEQ ID NO: 15. In still other aspects of this embodiment, a β-trefoil domain with enhanced binding activity derived from a Clostridial botulinum serotype B HA-33 comprises a polypeptide having, e.g., at most one, two, three or four contiguous amino acid additions relative to amino acids 56-61, amino acids 103-106, amino acids 198-201, or amino acids 243-248 of SEQ ID NO: 15. In other aspects of this embodiment, a β-trefoil domain with enhanced binding activity derived from a Clostridial botulinum serotype B HA-33 comprises a polypeptide having, e.g., at least one, two, three or four contiguous amino acid additions relative to amino acids 56-61, amino acids 103-106, amino acids 198-201, or amino acids 243-248 of SEQ ID NO: 15.

In another embodiment, a β-trefoil domain derived from a Clostridial botulinum serotype C1 HA-33 comprises a β-trefoil domain derived from a Clostridial botulinum serotype C1 HA-33 of SEQ ID NO: 16. In another embodiment, a β-trefoil domain derived from a Clostridial botulinum serotype C1 HA-33 comprises amino acids 10-141 or amino acids 148-285 of SEQ ID NO: 16. In another aspect of this embodiment, a β-trefoil domain derived from a Clostridial botulinum serotype C1 HA-33 comprises a 1α-fold motif of a β-trefoil domain of a Clostridial botulinum serotype C1 HA-33, a 1β-fold motif of a β-trefoil domain of a Clostridial botulinum serotype C1 HA-33, a 1γ-fold motif of a β-trefoil domain of a Clostridial botulinum serotype C1 HA-33, a 2α-fold motif of a β-trefoil domain of a Clostridial botulinum serotype C1 HA-33, a 2β-fold motif of a β-trefoil domain of a Clostridial botulinum serotype C1 HA-33, or a 2γ-fold motif of a β-trefoil domain of a Clostridial botulinum serotype C1 HA-33 of SEQ ID NO: 16. In another aspect of this embodiment, a β-trefoil domain derived from a Clostridial botulinum serotype C1 HA-33 comprises amino acids 10-54, amino acids 60-98, amino acids 103-141, amino acids 148-190, amino acids 195-234, or amino acids 241-285 of SEQ ID NO: 16.

In another embodiment, a β-trefoil domain with enhanced binding activity derived from a Clostridial botulinum serotype C1 HA-33 comprises a β-trefoil domain with enhanced binding activity derived from a Clostridial botulinum serotype C1 HA-33 of SEQ ID NO: 16. In another embodiment, a β-trefoil domain with enhanced binding activity derived from a Clostridial botulinum serotype C1 HA-33 comprises amino acids 10-141 or amino acids 148-285 of SEQ ID NO: 16. In another aspect of this embodiment, a β-trefoil domain with enhanced binding activity derived from a Clostridial botulinum serotype C1 HA-33 comprises a modified 1α-fold motif of a β-trefoil domain of a Clostridial botulinum serotype C1 HA-33, a modified 1β-fold motif of a β-trefoil domain of a Clostridial botulinum serotype C1 HA-33, a modified 1γ-fold motif of a β-trefoil domain of a Clostridial botulinum serotype C1 HA-33, a modified 2α-fold motif of a β-trefoil domain of a Clostridial botulinum serotype C1 HA-33, a modified 2β-fold motif of a β-trefoil domain of a Clostridial botulinum serotype C1 HA-33, or a modified 2γ-fold motif of a β-trefoil domain of a Clostridial botulinum serotype C1 HA-33 of SEQ ID NO: 16. In another aspect of this embodiment, a β-trefoil domain with enhanced binding activity derived from a Clostridial botulinum serotype C1 HA-33 comprises amino acids 10-54, amino acids 60-98, amino acids 103-141, amino acids 148-190, amino acids 195-234, or amino acids 241-285 of SEQ ID NO: 16.

In other aspects of this embodiment, a Clostridial botulinum serotype C1 HA-33 comprising a 11-trefoil domain with enhanced binding activity comprises a polypeptide having, e.g., at least 70% amino acid identity with amino acids 10-54, amino acids 60-98, amino acids 103-141, amino acids 148-190, amino acids 195-234, or amino acids 241-285 of SEQ ID NO: 16, at least 75% amino acid identity with amino acids 10-54, amino acids 60-98, amino acids 103-141, amino acids 148-190, amino acids 195-234, or amino acids 241-285 of SEQ ID NO: 16, at least 80% amino acid identity with amino acids 10-54, amino acids 60-98, amino acids 103-141, amino acids 148-190, amino acids 195-234, or amino acids 241-285 of SEQ ID NO: 16, at least 85% amino acid identity with amino acids 10-54, amino acids 60-98, amino acids 103-141, amino acids 148-190, amino acids 195-234, or amino acids 241-285 of SEQ ID NO: 16, at least 90% amino acid identity with amino acids 10-54, amino acids 60-98, amino acids 103-141, amino acids 148-190, amino acids 195-234, or amino acids 241-285 of SEQ ID NO: 16 or at least 95% amino acid identity with amino acids 10-54, amino acids 60-98, amino acids 103-141, amino acids 148-190, amino acids 195-234, or amino acids 241-285 of SEQ ID NO: 16. In yet other aspects of this embodiment, a Clostridial botulinum serotype C1 HA-33 comprising a β-trefoil domain with enhanced binding activity comprises a polypeptide having, e.g., at most 70% amino acid identity with amino acids 10-54, amino acids 60-98, amino acids 103-141, amino acids 148-190, amino acids 195-234, or amino acids 241-285 of SEQ ID NO: 16, at most 75% amino acid identity with amino acids 10-54, amino acids 60-98, amino acids 103-141, amino acids 148-190, amino acids 195-234, or amino acids 241-285 of SEQ ID NO: 16, at most 80% amino acid identity with amino acids 10-54, amino acids 60-98, amino acids 103-141, amino acids 148-190, amino acids 195-234, or amino acids 241-285 of SEQ ID NO: 16, at most 85% amino acid identity with amino acids 10-54, amino acids 60-98, amino acids 103-141, amino acids 148-190, amino acids 195-234, or amino acids 241-285 of SEQ ID NO: 16, at most 90% amino acid identity with amino acids 10-54, amino acids 60-98, amino acids 103-141, amino acids 148-190, amino acids 195-234, or amino acids 241-285 of SEQ ID NO: 16 or at most 95% amino acid identity with amino acids 10-54, amino acids 60-98, amino acids 103-141, amino acids 148-190, amino acids 195-234, or amino acids 241-285 of SEQ ID NO: 16.

In other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 non-contiguous amino acid substitutions relative to amino acids 10-54, amino acids 60-98, amino acids 103-141, amino acids 148-190, amino acids 195-234, or amino acids 241-285 of SEQ ID NO: 16. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-54, amino acids 60-98, amino acids 103-141, amino acids 148-190, amino acids 195-234, or amino acids 241-285 of SEQ ID NO: 16. In yet other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-54, amino acids 60-98, amino acids 103-141, amino acids 148-190, amino acids 195-234, or amino acids 241-285 of SEQ ID NO: 16. In other aspects of this embodiment, a Clostridial botulinum serotype C1 HA-33 comprising a 11-trefoil domain with enhanced binding activity comprises a polypeptide having, e.g., at least one, two, three, four, five, six, seven, eight, nine, 10 or 20 non-contiguous amino acid deletions relative to amino acids 10-54, amino acids 60-98, amino acids 103-141, amino acids 148-190, amino acids 195-234, or amino acids 241-285 of SEQ ID NO: 16. In still other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-54, amino acids 60-98, amino acids 103-141, amino acids 148-190, amino acids 195-234, or amino acids 241-285 of SEQ ID NO: 16. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-54, amino acids 60-98, amino acids 103-141, amino acids 148-190, amino acids 195-234, or amino acids 241-285 of SEQ ID NO: 16.

In other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-54, amino acids 60-98, amino acids 103-141, amino acids 148-190, amino acids 195-234, or amino acids 241-285 of SEQ ID NO: 16. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-54, amino acids 60-98, amino acids 103-141, amino acids 148-190, amino acids 195-234, or amino acids 241-285 of SEQ ID NO: 16. In yet other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-54, amino acids 60-98, amino acids 103-141, amino acids 148-190, amino acids 195-234, or amino acids 241-285 of SEQ ID NO: 16. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-54, amino acids 60-98, amino acids 103-141, amino acids 148-190, amino acids 195-234, or amino acids 241-285 of SEQ ID NO: 16. In still other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-54, amino acids 60-98, amino acids 103-141, amino acids 148-190, amino acids 195-234, or amino acids 241-285 of SEQ ID NO: 16. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-54, amino acids 60-98, amino acids 103-141, amino acids 148-190, amino acids 195-234, or amino acids 241-285 of SEQ ID NO: 16.

In another embodiment, a β-trefoil domain derived from a Clostridial botulinum serotype C1 HA-33 comprises a 1β4/β5 hairpin turn of a β-trefoil domain of a Clostridial botulinum serotype C1 HA-33, a 1β8/β9 hairpin turn of a β-trefoil domain of a Clostridial botulinum serotype C1 HA-33, a 2β4/β5 hairpin turn of a β-trefoil domain of a Clostridial botulinum serotype C1 HA-33 or a 2β8/β9 hairpin turn of a β-trefoil domain of a Clostridial botulinum serotype C1 HA-33 of SEQ ID NO: 16. In another aspect of this embodiment, a β-trefoil domain derived from a Clostridial botulinum serotype C1 HA-33 comprises amino acids 55-59, amino acids 99-102, amino acids 191-194, or amino acids 235-240 of SEQ ID NO: 16.

In another embodiment, a β-trefoil domain with enhanced binding activity derived from a Clostridial botulinum serotype C1 HA-33 comprises a modified β4/β5 hairpin turn of a β-trefoil domain of a Clostridial botulinum serotype C1 HA-33 or a modified 1β4/β5 hairpin turn of a β-trefoil domain of a Clostridial botulinum serotype C1 HA-33, a modified 1β8/β9 hairpin turn of a β-trefoil domain of a Clostridial botulinum serotype C1 HA-33, a modified 2β4/β5 hairpin turn of a β-trefoil domain of a Clostridial botulinum serotype C1 HA-33 or a modified 2β8/β9 hairpin turn of a β-trefoil domain of a Clostridial botulinum serotype C1 HA-33 of SEQ ID NO: 16. In another aspect of this embodiment, a β-trefoil domain with enhanced binding activity derived from a Clostridial botulinum serotype C1 HA-33 comprises a modification of amino acids 55-59, amino acids 99-102, amino acids 191-194, or amino acids 235-240 of SEQ ID NO: 16.

In other aspects of this embodiment, a β-trefoil domain with enhanced binding activity derived from a Clostridial botulinum serotype C1 HA-33 comprises a polypeptide having, e.g., at least 70% amino acid identity with amino acids 55-59, amino acids 99-102, amino acids 191-194, or amino acids 235-240 of SEQ ID NO: 16, at least 75% amino acid identity with amino acids 55-59, amino acids 99-102, amino acids 191-194, or amino acids 235-240 of SEQ ID NO: 16, at least 80% amino acid identity with amino acids 55-59, amino acids 99-102, amino acids 191-194, or amino acids 235-240 of SEQ ID NO: 16, at least 85% amino acid identity with amino acids 55-59, amino acids 99-102, amino acids 191-194, or amino acids 235-240 of SEQ ID NO: 16, at least 90% amino acid identity with amino acids 55-59, amino acids 99-102, amino acids 191-194, or amino acids 235-240 of SEQ ID NO: 16 or at least 95% amino acid identity with amino acids 55-59, amino acids 99-102, amino acids 191-194, or amino acids 235-240 of SEQ ID NO: 16. In yet other aspects of this embodiment, a β-trefoil domain with enhanced binding activity derived from a Clostridial botulinum serotype C1 HA-33 comprises a polypeptide having, e.g., at most 70% amino acid identity with amino acids 55-59, amino acids 99-102, amino acids 191-194, or amino acids 235-240 of SEQ ID NO: 16, at most 75% amino acid identity with amino acids 55-59, amino acids 99-102, amino acids 191-194, or amino acids 235-240 of SEQ ID NO: 16, at most 80% amino acid identity with amino acids 55-59, amino acids 99-102, amino acids 191-194, or amino acids 235-240 of SEQ ID NO: 16, at most 85% amino acid identity with amino acids 55-59, amino acids 99-102, amino acids 191-194, or amino acids 235-240 of SEQ ID NO: 16, at most 90% amino acid identity with amino acids 55-59, amino acids 99-102, amino acids 191-194, or amino acids 235-240 of SEQ ID NO: 16 or at most 95% amino acid identity with amino acids 55-59, amino acids 99-102, amino acids 191-194, or amino acids 235-240 of SEQ ID NO: 16.

In other aspects of this embodiment, a β-trefoil domain with enhanced binding activity derived from a Clostridial botulinum serotype C1 HA-33 comprises a polypeptide having, e.g., at most one, two, three or four non-contiguous amino acid substitutions relative to amino acids 55-59, amino acids 99-102, amino acids 191-194, or amino acids 235-240 of SEQ ID NO: 16. In other aspects of this embodiment, a β-trefoil domain with enhanced binding activity derived from a Clostridial botulinum serotype C1 HA-33 comprises a polypeptide having, e.g., at least one, two, three or four non-contiguous amino acid substitutions relative to amino acids 55-59, amino acids 99-102, amino acids 191-194, or amino acids 235-240 of SEQ ID NO: 16. In other aspects of this embodiment, a non-contiguous amino acid substitution of any amino acid from amino acids 55-59, amino acids 99-102, amino acids 191-194, or amino acids 235-240 of SEQ ID NO: 16 can be replaced with glycine. In other aspects of this embodiment, a non-contiguous amino acid substitution of any hydrophobic amino acid from amino acids 55-59, amino acids 99-102, amino acids 191-194, or amino acids 235-240 of SEQ ID NO: 16 can be replaced with phenylalanine. In yet other aspects of this embodiment, a β-trefoil domain with enhanced binding activity derived from a Clostridial botulinum serotype C1 HA-33 comprises a polypeptide having, e.g., at most one, two, three or four non-contiguous amino acid deletions relative to amino acids 55-59, amino acids 99-102, amino acids 191-194, or amino acids 235-240 of SEQ ID NO: 16. In other aspects of this embodiment, a β-trefoil domain with enhanced binding activity derived from a Clostridial botulinum serotype C1 HA-33 comprises a polypeptide having, e.g., at least one, two, three or four non-contiguous amino acid deletions relative to amino acids 55-59, amino acids 99-102, amino acids 191-194, or amino acids 235-240 of SEQ ID NO: 16. In still other aspects of this embodiment, a β-trefoil domain with enhanced binding activity derived from a Clostridial botulinum serotype C1 HA-33 comprises a polypeptide having, e.g., at most one, two, three or four non-contiguous amino acid additions relative to amino acids 55-59, amino acids 99-102, amino acids 191-194, or amino acids 235-240 of SEQ ID NO: 16. In other aspects of this embodiment, a β-trefoil domain with enhanced binding activity derived from a Clostridial botulinum serotype C1 HA-33 comprises a polypeptide having, e.g., at least one, two, three or four non-contiguous amino acid additions relative to amino acids 55-59, amino acids 99-102, amino acids 191-194, or amino acids 235-240 of SEQ ID NO: 16.

In other aspects of this embodiment, a β-trefoil domain with enhanced binding activity derived from a Clostridial botulinum serotype C1 HA-33 comprises a polypeptide having, e.g., at most one, two, three or four contiguous amino acid substitutions relative to amino acids 55-59, amino acids 99-102, amino acids 191-194, or amino acids 235-240 of SEQ ID NO: 16. In other aspects of this embodiment, a β-trefoil domain with enhanced binding activity derived from a Clostridial botulinum serotype C1 HA-33 comprises a polypeptide having, e.g., at least one, two, three or four contiguous amino acid substitutions relative to amino acids 55-59, amino acids 99-102, amino acids 191-194, or amino acids 235-240 of SEQ ID NO: 16. In other aspects of this embodiment, contiguous amino acid substitutions of amino acids from amino acids 55-59, amino acids 99-102, amino acids 191-194, or amino acids 235-240 of SEQ ID NO: 16 can be replaced with glycine. In other aspects of this embodiment, contiguous amino acid substitutions of hydrophobic amino acids from amino acids 55-59, amino acids 99-102, amino acids 191-194, or amino acids 235-240 of SEQ ID NO: 16 can be replaced with phenylalanine. In yet other aspects of this embodiment, a β-trefoil domain with enhanced binding activity derived from a Clostridial botulinum serotype C1 HA-33 comprises a polypeptide having, e.g., at most one, two, three or four contiguous amino acid deletions relative to amino acids 55-59, amino acids 99-102, amino acids 191-194, or amino acids 235-240 of SEQ ID NO: 16. In other aspects of this embodiment, a β-trefoil domain with enhanced binding activity derived from a Clostridial botulinum serotype C1 HA-33 comprises a polypeptide having, e.g., at least one, two, three or four contiguous amino acid deletions relative to amino acids 55-59, amino acids 99-102, amino acids 191-194, or amino acids 235-240 of SEQ ID NO: 16. In still other aspects of this embodiment, a β-trefoil domain with enhanced binding activity derived from a Clostridial botulinum serotype C1 HA-33 comprises a polypeptide having, e.g., at most one, two, three or four contiguous amino acid additions relative to amino acids 55-59, amino acids 99-102, amino acids 191-194, or amino acids 235-240 of SEQ ID NO: 16. In other aspects of this embodiment, a β-trefoil domain with enhanced binding activity derived from a Clostridial botulinum serotype C1 HA-33 comprises a polypeptide having, e.g., at least one, two, three or four contiguous amino acid additions relative to amino acids 55-59, amino acids 99-102, amino acids 191-194, or amino acids 235-240 of SEQ ID NO: 16.

In another embodiment, a β-trefoil domain derived from a Clostridial botulinum serotype C1 HA-33 comprises a β-trefoil domain derived from a Clostridial botulinum serotype C1 HA-33 of SEQ ID NO: 17. In another embodiment, a β-trefoil domain derived from a Clostridial botulinum serotype C1 HA-33 comprises amino acids 10-141 or amino acids 148-286 of SEQ ID NO: 17. In another aspect of this embodiment, a β-trefoil domain derived from a Clostridial botulinum serotype C1 HA-33 comprises a 1α-fold motif of a β-trefoil domain of a Clostridial botulinum serotype C1 HA-33, a 1β-fold motif of a β-trefoil domain of a Clostridial botulinum serotype C1 HA-33, a 1γ-fold motif of a β-trefoil domain of a Clostridial botulinum serotype C1 HA-33, a 2α-fold motif of a β-trefoil domain of a Clostridial botulinum serotype C1 HA-33, a 2β-fold motif of a β-trefoil domain of a Clostridial botulinum serotype C1 HA-33, or a 2γ-fold motif of a β-trefoil domain of a Clostridial botulinum serotype C1 HA-33 of SEQ ID NO: 17. In another aspect of this embodiment, a β-trefoil domain derived from a Clostridial botulinum serotype C1 HA-33 comprises amino acids 10-54, amino acids 60-98, amino acids 103-141, amino acids 148-190, amino acids 195-235, or amino acids 242-286 of SEQ ID NO: 17.

In another embodiment, a β-trefoil domain with enhanced binding activity derived from a Clostridial botulinum serotype C1 HA-33 comprises a β-trefoil domain with enhanced binding activity derived from a Clostridial botulinum serotype C1 HA-33 of SEQ ID NO: 17. In another embodiment, a β-trefoil domain with enhanced binding activity derived from a Clostridial botulinum serotype C1 HA-33 comprises amino acids 10-141 or amino acids 148-286 of SEQ ID NO: 17. In another aspect of this embodiment, a β-trefoil domain with enhanced binding activity derived from a Clostridial botulinum serotype C1 HA-33 comprises a modified 1α-fold motif of a β-trefoil domain of a Clostridial botulinum serotype C1 HA-33, a modified 1β-fold motif of a β-trefoil domain of a Clostridial botulinum serotype C1 HA-33, a modified 1γ-fold motif of a β-trefoil domain of a Clostridial botulinum serotype C1 HA-33, a modified 2α-fold motif of a β-trefoil domain of a Clostridial botulinum serotype C1 HA-33, a modified 2β-fold motif of a β-trefoil domain of a Clostridial botulinum serotype C1 HA-33, or a modified 2γ-fold motif of a β-trefoil domain of a Clostridial botulinum serotype C1 HA-33 of SEQ ID NO: 17. In another aspect of this embodiment, a β-trefoil domain with enhanced binding activity derived from a Clostridial botulinum serotype C1 HA-33 comprises amino acids 10-54, amino acids 60-98, amino acids 103-141, amino acids 148-190, amino acids 195-235, or amino acids 242-286 of SEQ ID NO: 17.

In other aspects of this embodiment, a Clostridial botulinum serotype C1 HA-33 comprising a β-trefoil domain with enhanced binding activity comprises a polypeptide having, e.g., at least 70% amino acid identity with amino acids 10-54, amino acids 60-98, amino acids 103-141, amino acids 148-190, amino acids 195-235, or amino acids 242-286 of SEQ ID NO: 17, at least 75% amino acid identity with amino acids 10-54, amino acids 60-98, amino acids 103-141, amino acids 148-190, amino acids 195-235, or amino acids 242-286 of SEQ ID NO: 17, at least 80% amino acid identity with amino acids 10-54, amino acids 60-98, amino acids 103-141, amino acids 148-190, amino acids 195-235, or amino acids 242-286 of SEQ ID NO: 17, at least 85% amino acid identity with amino acids 10-54, amino acids 60-98, amino acids 103-141, amino acids 148-190, amino acids 195-235, or amino acids 242-286 of SEQ ID NO: 17, at least 90% amino acid identity with amino acids 10-54, amino acids 60-98, amino acids 103-141, amino acids 148-190, amino acids 195-235, or amino acids 242-286 of SEQ ID NO: 17 or at least 95% amino acid identity with amino acids 10-54, amino acids 60-98, amino acids 103-141, amino acids 148-190, amino acids 195-235, or amino acids 242-286 of SEQ ID NO: 17. In yet other aspects of this embodiment, a Clostridial botulinum serotype C1 HA-33 comprising a β-trefoil domain with enhanced binding activity comprises a polypeptide having, e.g., at most 70% amino acid identity with amino acids 10-54, amino acids 60-98, amino acids 103-141, amino acids 148-190, amino acids 195-235, or amino acids 242-286 of SEQ ID NO: 17, at most 75% amino acid identity with amino acids 10-54, amino acids 60-98, amino acids 103-141, amino acids 148-190, amino acids 195-235, or amino acids 242-286 of SEQ ID NO: 17, at most 80% amino acid identity with amino acids 10-54, amino acids 60-98, amino acids 103-141, amino acids 148-190, amino acids 195-235, or amino acids 242-286 of SEQ ID NO: 17, at most 85% amino acid identity with amino acids 10-54, amino acids 60-98, amino acids 103-141, amino acids 148-190, amino acids 195-235, or amino acids 242-286 of SEQ ID NO: 17, at most 90% amino acid identity with amino acids 10-54, amino acids 60-98, amino acids 103-141, amino acids 148-190, amino acids 195-235, or amino acids 242-286 of SEQ ID NO: 17 or at most 95% amino acid identity with amino acids 10-54, amino acids 60-98, amino acids 103-141, amino acids 148-190, amino acids 195-235, or amino acids 242-286 of SEQ ID NO: 17.

In other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 non-contiguous amino acid substitutions relative to amino acids 10-54, amino acids 60-98, amino acids 103-141, amino acids 148-190, amino acids 195-235, or amino acids 242-286 of SEQ ID NO: 17. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-54, amino acids 60-98, amino acids 103-141, amino acids 148-190, amino acids 195-235, or amino acids 242-286 of SEQ ID NO: 17. In yet other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-54, amino acids 60-98, amino acids 103-141, amino acids 148-190, amino acids 195-235, or amino acids 242-286 of SEQ ID NO: 17. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-54, amino acids 60-98, amino acids 103-141, amino acids 148-190, amino acids 195-235, or amino acids 242-286 of SEQ ID NO: 17. In still other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-54, amino acids 60-98, amino acids 103-141, amino acids 148-190, amino acids 195-235, or amino acids 242-286 of SEQ ID NO: 17. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-54, amino acids 60-98, amino acids 103-141, amino acids 148-190, amino acids 195-235, or amino acids 242-286 of SEQ ID NO: 17.

In other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-54, amino acids 60-98, amino acids 103-141, amino acids 148-190, amino acids 195-235, or amino acids 242-286 of SEQ ID NO: 17. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-54, amino acids 60-98, amino acids 103-141, amino acids 148-190, amino acids 195-235, or amino acids 242-286 of SEQ ID NO: 17. In yet other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-54, amino acids 60-98, amino acids 103-141, amino acids 148-190, amino acids 195-235, or amino acids 242-286 of SEQ ID NO: 17. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-54, amino acids 60-98, amino acids 103-141, amino acids 148-190, amino acids 195-235, or amino acids 242-286 of SEQ ID NO: 17. In still other aspects of this embodiment, a Clostridial botulinum serotype C1 HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-54, amino acids 60-98, amino acids 103-141, amino acids 148-190, amino acids 195-235, or amino acids 242-286 of SEQ ID NO: 17. In other aspects of this embodiment, a Clostridial botulinum serotype C1 HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-54, amino acids 60-98, amino acids 103-141, amino acids 148-190, amino acids 195-235, or amino acids 242-286 of SEQ ID NO: 17.

In another embodiment, a β-trefoil domain derived from a Clostridial botulinum serotype C1 HA-33 comprises a 1β4/β5 hairpin turn of a β-trefoil domain of a Clostridial botulinum serotype C1 HA-33, a 1β8/β9 hairpin turn of a β-trefoil domain of a Clostridial botulinum serotype C1 HA-33, a 2β4/β5 hairpin turn of a β-trefoil domain of a Clostridial botulinum serotype C1 HA-33 or a 2β8/β9 hairpin turn of a β-trefoil domain of a Clostridial botulinum serotype C1 HA-33 of SEQ ID NO: 17. In another aspect of this embodiment, a β-trefoil domain derived from a Clostridial botulinum serotype C1 HA-33 comprises amino acids 55-59, amino acids 99-102, amino acids 191-194, or amino acids 236-241 of SEQ ID NO: 17.

In another embodiment, a β-trefoil domain with enhanced binding activity derived from a Clostridial botulinum serotype C1 HA-33 comprises a modified 1β4/β5 hairpin turn of a β-trefoil domain of a Clostridial botulinum serotype C1 HA-33, a modified 1β8/β9 hairpin turn of a β-trefoil domain of a Clostridial botulinum serotype C1 HA-33, a modified 2β4/β5 hairpin turn of a β-trefoil domain of a Clostridial botulinum serotype C1 HA-33 or a modified 2β8/β9 hairpin turn of a β-trefoil domain of a Clostridial botulinum serotype C1 HA-33 of SEQ ID NO: 17. In another aspect of this embodiment, a β-trefoil domain with enhanced binding activity derived from a Clostridial botulinum serotype C1 HA-33 comprises a modification of amino acids 55-59, amino acids 99-102, amino acids 191-194, or amino acids 236-241 of SEQ ID NO: 17.

In other aspects of this embodiment, a β-trefoil domain with enhanced binding activity derived from a Clostridial botulinum serotype C1 HA-33 comprises a polypeptide having, e.g., at least 70% amino acid identity with amino acids 55-59, amino acids 99-102, amino acids 191-194, or amino acids 236-241 of SEQ ID NO: 17, at least 75% amino acid identity with amino acids 55-59, amino acids 99-102, amino acids 191-194, or amino acids 236-241 of SEQ ID NO: 17, at least 80% amino acid identity with amino acids 55-59, amino acids 99-102, amino acids 191-194, or amino acids 236-241 of SEQ ID NO: 17, at least 85% amino acid identity with amino acids 55-59, amino acids 99-102, amino acids 191-194, or amino acids 236-241 of SEQ ID NO: 17, at least 90% amino acid identity with amino acids 55-59, amino acids 99-102, amino acids 191-194, or amino acids 236-241 of SEQ ID NO: 17 or at least 95% amino acid identity with amino acids 55-59, amino acids 99-102, amino acids 191-194, or amino acids 236-241 of SEQ ID NO: 17. In yet other aspects of this embodiment, a β-trefoil domain with enhanced binding activity derived from a Clostridial botulinum serotype C1 HA-33 comprises a polypeptide having, e.g., at most 70% amino acid identity with amino acids 55-59, amino acids 99-102, amino acids 191-194, or amino acids 236-241 of SEQ ID NO: 17, at most 75% amino acid identity with amino acids 55-59, amino acids 99-102, amino acids 191-194, or amino acids 236-241 of SEQ ID NO: 17, at most 80% amino acid identity with amino acids 55-59, amino acids 99-102, amino acids 191-194, or amino acids 236-241 of SEQ ID NO: 17, at most 85% amino acid identity with amino acids 55-59, amino acids 99-102, amino acids 191-194, or amino acids 236-241 of SEQ ID NO: 17, at most 90% amino acid identity with amino acids 55-59, amino acids 99-102, amino acids 191-194, or amino acids 236-241 of SEQ ID NO: 17 or at most 95% amino acid identity with amino acids 55-59, amino acids 99-102, amino acids 191-194, or amino acids 236-241 of SEQ ID NO: 17.

In other aspects of this embodiment, a β-trefoil domain with enhanced binding activity derived from a Clostridial botulinum serotype C1 HA-33 comprises a polypeptide having, e.g., at most one, two, three or four non-contiguous amino acid substitutions relative to amino acids 55-59, amino acids 99-102, amino acids 191-194, or amino acids 236-241 of SEQ ID NO: 17. In other aspects of this embodiment, a β-trefoil domain with enhanced binding activity derived from a Clostridial botulinum serotype C1 HA-33 comprises a polypeptide having, e.g., at least one, two, three or four non-contiguous amino acid substitutions relative to amino acids 55-59, amino acids 99-102, amino acids 191-194, or amino acids 236-241 of SEQ ID NO: 17. In other aspects of this embodiment, a non-contiguous amino acid substitution of any amino acid from amino acids 55-59, amino acids 99-102, amino acids 191-194, or amino acids 236-241 of SEQ ID NO: 17 can be replaced with glycine. In other aspects of this embodiment, a non-contiguous amino acid substitution of any hydrophobic amino acid from amino acids 55-59, amino acids 99-102, amino acids 191-194, or amino acids 236-241 of SEQ ID NO: 17 can be replaced with phenylalanine. In yet other aspects of this embodiment, a β-trefoil domain with enhanced binding activity derived from a Clostridial botulinum serotype C1 HA-33 comprises a polypeptide having, e.g., at most one, two, three or four non-contiguous amino acid deletions relative to amino acids 55-59, amino acids 99-102, amino acids 191-194, or amino acids 236-241 of SEQ ID NO: 17. In other aspects of this embodiment, a β-trefoil domain with enhanced binding activity derived from a Clostridial botulinum serotype C1 HA-33 comprises a polypeptide having, e.g., at least one, two, three or four non-contiguous amino acid deletions relative to amino acids 55-59, amino acids 99-102, amino acids 191-194, or amino acids 236-241 of SEQ ID NO: 17. In still other aspects of this embodiment, a β-trefoil domain with enhanced binding activity derived from a Clostridial botulinum serotype C1 HA-33 comprises a polypeptide having, e.g., at most one, two, three or four non-contiguous amino acid additions relative to amino acids 55-59, amino acids 99-102, amino acids 191-194, or amino acids 236-241 of SEQ ID NO: 17. In other aspects of this embodiment, a β-trefoil domain with enhanced binding activity derived from a Clostridial botulinum serotype C1 HA-33 comprises a polypeptide having, e.g., at least one, two, three or four non-contiguous amino acid additions relative to amino acids 55-59, amino acids 99-102, amino acids 191-194, or amino acids 236-241 of SEQ ID NO: 17.

In other aspects of this embodiment, a β-trefoil domain with enhanced binding activity derived from a Clostridial botulinum serotype C1 HA-33 comprises a polypeptide having, e.g., at most one, two, three or four contiguous amino acid substitutions relative to amino acids 55-59, amino acids 99-102, amino acids 191-194, or amino acids 236-241 of SEQ ID NO: 17. In other aspects of this embodiment, a β-trefoil domain with enhanced binding activity derived from a Clostridial botulinum serotype C1 HA-33 comprises a polypeptide having, e.g., at least one, two, three or four contiguous amino acid substitutions relative to amino acids 55-59, amino acids 99-102, amino acids 191-194, or amino acids 236-241 of SEQ ID NO: 17. In other aspects of this embodiment, contiguous amino acid substitutions of amino acids from amino acids 55-59, amino acids 99-102, amino acids 191-194, or amino acids 236-241 of SEQ ID NO: 17 can be replaced with glycine. In other aspects of this embodiment, contiguous amino acid substitutions of hydrophobic amino acids from amino acids 55-59, amino acids 99-102, amino acids 191-194, or amino acids 236-241 of SEQ ID NO: 17 can be replaced with phenylalanine. In yet other aspects of this embodiment, a β-trefoil domain with enhanced binding activity derived from a Clostridial botulinum serotype C1 HA-33 comprises a polypeptide having, e.g., at most one, two, three or four contiguous amino acid deletions relative to amino acids 55-59, amino acids 99-102, amino acids 191-194, or amino acids 236-241 of SEQ ID NO: 17. In other aspects of this embodiment, a β-trefoil domain with enhanced binding activity derived from a Clostridial botulinum serotype C1 HA-33 comprises a polypeptide having, e.g., at least one, two, three or four contiguous amino acid deletions relative to amino acids 55-59, amino acids 99-102, amino acids 191-194, or amino acids 236-241 of SEQ ID NO: 17. In still other aspects of this embodiment, a β-trefoil domain with enhanced binding activity derived from a Clostridial botulinum serotype C1 HA-33 comprises a polypeptide having, e.g., at most one, two, three or four contiguous amino acid additions relative to amino acids 55-59, amino acids 99-102, amino acids 191-194, or amino acids 236-241 of SEQ ID NO: 17. In other aspects of this embodiment, a β-trefoil domain with enhanced binding activity derived from a Clostridial botulinum serotype C1 HA-33 comprises a polypeptide having, e.g., at least one, two, three or four contiguous amino acid additions relative to amino acids 55-59, amino acids 99-102, amino acids 191-194, or amino acids 236-241 of SEQ ID NO: 17.

In another embodiment, a β-trefoil domain derived from a Clostridial botulinum serotype D HA-33 comprises a β-trefoil domain derived from a Clostridial botulinum serotype D HA-33 of SEQ ID NO: 18. In another embodiment, a β-trefoil domain derived from a Clostridial botulinum serotype D HA-33 comprises amino acids 10-141 or amino acids 148-286 of SEQ ID NO: 18. In another aspect of this embodiment, a β-trefoil domain derived from a Clostridial botulinum serotype D HA-33 comprises a 1α-fold motif of a 13-trefoil domain of a Clostridial botulinum serotype D HA-33, a 1β-fold motif of a β-trefoil domain of a Clostridial botulinum serotype D HA-33, a 1γ-fold motif of a β-trefoil domain of a Clostridial botulinum serotype D HA-33, a 2α-fold motif of a β-trefoil domain of a Clostridial botulinum serotype D HA-33, a 2β-fold motif of a β-trefoil domain of a Clostridial botulinum serotype D HA-33, or a 2γ-fold motif of a β-trefoil domain of a Clostridial botulinum serotype D HA-33 of SEQ ID NO: 18. In another aspect of this embodiment, a β-trefoil domain derived from a Clostridial botulinum serotype D HA-33 comprises amino acids 10-54, amino acids 60-98, amino acids 103-141, amino acids 148-190, amino acids 195-235, or amino acids 242-286 of SEQ ID NO: 18.

In another embodiment, a β-trefoil domain with enhanced binding activity derived from a Clostridial botulinum serotype D HA-33 comprises a β-trefoil domain with enhanced binding activity derived from a Clostridial botulinum serotype D HA-33 of SEQ ID NO: 18. In another embodiment, a β-trefoil domain with enhanced binding activity derived from a Clostridial botulinum serotype D HA-33 comprises amino acids 10-141 or amino acids 148-286 of SEQ ID NO: 18. In another aspect of this embodiment, a β-trefoil domain with enhanced binding activity derived from a Clostridial botulinum serotype D HA-33 comprises a modified 1α-fold motif of a β-trefoil domain of a Clostridial botulinum serotype D HA-33, a modified 1β-fold motif of a β-trefoil domain of a Clostridial botulinum serotype D HA-33, a modified 1γ-fold motif of a β-trefoil domain of a Clostridial botulinum serotype D HA-33, a modified 2α-fold motif of a β-trefoil domain of a Clostridial botulinum serotype D HA-33, a modified 2β-fold motif of a β-trefoil domain of a Clostridial botulinum serotype D HA-33, or a modified 2γ-fold motif of a β-trefoil domain of a Clostridial botulinum serotype D HA-33 of SEQ ID NO: 18. In another aspect of this embodiment, a β-trefoil domain with enhanced binding activity derived from a Clostridial botulinum serotype D HA-33 comprises amino acids 10-54, amino acids 60-98, amino acids 103-141, amino acids 148-190, amino acids 195-235, or amino acids 242-286 of SEQ ID NO: 18.

In other aspects of this embodiment, a Clostridial botulinum serotype D HA-33 comprising a β-trefoil domain with enhanced binding activity comprises a polypeptide having, e.g., at least 70% amino acid identity with amino acids 10-54, amino acids 60-98, amino acids 103-141, amino acids 148-190, amino acids 195-235, or amino acids 242-286 of SEQ ID NO: 18, at least 75% amino acid identity with amino acids 10-54, amino acids 60-98, amino acids 103-141, amino acids 148-190, amino acids 195-235, or amino acids 242-286 of SEQ ID NO: 18, at least 80% amino acid identity with amino acids 10-54, amino acids 60-98, amino acids 103-141, amino acids 148-190, amino acids 195-235, or amino acids 242-286 of SEQ ID NO: 18, at least 85% amino acid identity with amino acids 10-54, amino acids 60-98, amino acids 103-141, amino acids 148-190, amino acids 195-235, or amino acids 242-286 of SEQ ID NO: 18, at least 90% amino acid identity with amino acids 10-54, amino acids 60-98, amino acids 103-141, amino acids 148-190, amino acids 195-235, or amino acids 242-286 of SEQ ID NO: 18 or at least 95% amino acid identity with amino acids 10-54, amino acids 60-98, amino acids 103-141, amino acids 148-190, amino acids 195-235, or amino acids 242-286 of SEQ ID NO: 18. In yet other aspects of this embodiment, a Clostridial botulinum serotype D HA-33 comprising a β-trefoil domain with enhanced binding activity comprises a polypeptide having, e.g., at most 70% amino acid identity with amino acids 10-54, amino acids 60-98, amino acids 103-141, amino acids 148-190, amino acids 195-235, or amino acids 242-286 of SEQ ID NO: 18, at most 75% amino acid identity with amino acids 10-54, amino acids 60-98, amino acids 103-141, amino acids 148-190, amino acids 195-235, or amino acids 242-286 of SEQ ID NO: 18, at most 80% amino acid identity with amino acids 10-54, amino acids 60-98, amino acids 103-141, amino acids 148-190, amino acids 195-235, or amino acids 242-286 of SEQ ID NO: 18, at most 85% amino acid identity with amino acids 10-54, amino acids 60-98, amino acids 103-141, amino acids 148-190, amino acids 195-235, or amino acids 242-286 of SEQ ID NO: 18, at most 90% amino acid identity with amino acids 10-54, amino acids 60-98, amino acids 103-141, amino acids 148-190, amino acids 195-235, or amino acids 242-286 of SEQ ID NO: 18 or at most 95% amino acid identity with amino acids 10-54, amino acids 60-98, amino acids 103-141, amino acids 148-190, amino acids 195-235, or amino acids 242-286 of SEQ ID NO: 18.

In other aspects of this embodiment, a Clostridial botulinum serotype D HA-33 comprising a β-trefoil domain with enhanced binding activity comprises a polypeptide having, e.g., at most one, two, three, four, five, six, seven, eight, nine, 10 or 20 non-contiguous amino acid substitutions relative to amino acids 10-54, amino acids 60-98, amino acids 103-141, amino acids 148-190, amino acids 195-235, or amino acids 242-286 of SEQ ID NO: 18. In other aspects of this embodiment, a Clostridial botulinum serotype D HA-33 comprising a β-trefoil domain with enhanced binding activity comprises a polypeptide having, e.g., at least one, two, three, four, five, six, seven, eight, nine, 10 or 20 non-contiguous amino acid substitutions relative to amino acids 10-54, amino acids 60-98, amino acids 103-141, amino acids 148-190, amino acids 195-235, or amino acids 242-286 of SEQ ID NO: 18. In yet other aspects of this embodiment, a Clostridial botulinum serotype D HA-33 comprising a β-trefoil domain with enhanced binding activity comprises a polypeptide having, e.g., at most one, two, three, four, five, six, seven, eight, nine, 10 or 20 non-contiguous amino acid deletions relative to amino acids 10-54, amino acids 60-98, amino acids 103-141, amino acids 148-190, amino acids 195-235, or amino acids 242-286 of SEQ ID NO: 18. In other aspects of this embodiment, a Clostridial botulinum serotype D HA-33 comprising a β-trefoil domain with enhanced binding activity comprises a polypeptide having, e.g., at least one, two, three, four, five, six, seven, eight, nine, 10 or 20 non-contiguous amino acid deletions relative to amino acids 10-54, amino acids 60-98, amino acids 103-141, amino acids 148-190, amino acids 195-235, or amino acids 242-286 of SEQ ID NO: 18. In still other aspects of this embodiment, a Clostridial botulinum serotype D HA-33 comprising a β-trefoil domain with enhanced binding activity comprises a polypeptide having, e.g., at most one, two, three, four, five, six, seven, eight, nine, 10 or 20 non-contiguous amino acid additions relative to amino acids 10-54, amino acids 60-98, amino acids 103-141, amino acids 148-190, amino acids 195-235, or amino acids 242-286 of SEQ ID NO: 18. In other aspects of this embodiment, a Clostridial botulinum serotype D HA-33 comprising a β-trefoil domain with enhanced binding activity comprises a polypeptide having, e.g., at least one, two, three, four, five, six, seven, eight, nine, 10 or 20 non-contiguous amino acid additions relative to amino acids 10-54, amino acids 60-98, amino acids 103-141, amino acids 148-190, amino acids 195-235, or amino acids 242-286 of SEQ ID NO: 18.

In other aspects of this embodiment, a Clostridial botulinum serotype D HA-33 comprising a β-trefoil domain with enhanced binding activity comprises a polypeptide having, e.g., at most one, two, three, four, five, six, seven, eight, nine, 10 or 20 contiguous amino acid substitutions relative to amino acids 10-54, amino acids 60-98, amino acids 103-141, amino acids 148-190, amino acids 195-235, or amino acids 242-286 of SEQ ID NO: 18. In other aspects of this embodiment, a Clostridial botulinum serotype D HA-33 comprising a β-trefoil domain with enhanced binding activity comprises a polypeptide having, e.g., at least one, two, three, four, five, six, seven, eight, nine, 10 or 20 contiguous amino acid substitutions relative to amino acids 10-54, amino acids 60-98, amino acids 103-141, amino acids 148-190, amino acids 195-235, or amino acids 242-286 of SEQ ID NO: 18. In yet other aspects of this embodiment, a Clostridial botulinum serotype D HA-33 comprising a β-trefoil domain with enhanced binding activity comprises a polypeptide having, e.g., at most one, two, three, four, five, six, seven, eight, nine, 10 or 20 contiguous amino acid deletions relative to amino acids 10-54, amino acids 60-98, amino acids 103-141, amino acids 148-190, amino acids 195-235, or amino acids 242-286 of SEQ ID NO: 18. In other aspects of this embodiment, a Clostridial botulinum serotype D HA-33 comprising a β-trefoil domain with enhanced binding activity comprises a polypeptide having, e.g., at least one, two, three, four, five, six, seven, eight, nine, 10 or 20 contiguous amino acid deletions relative to amino acids 10-54, amino acids 60-98, amino acids 103-141, amino acids 148-190, amino acids 195-235, or amino acids 242-286 of SEQ ID NO: 18. In still other aspects of this embodiment, a Clostridial botulinum serotype D HA-33 comprising a β-trefoil domain with enhanced binding activity comprises a polypeptide having, e.g., at most one, two, three, four, five, six, seven, eight, nine, 10 or 20 contiguous amino acid additions relative to amino acids 10-54, amino acids 60-98, amino acids 103-141, amino acids 148-190, amino acids 195-235, or amino acids 242-286 of SEQ ID NO: 18. In other aspects of this embodiment, a Clostridial botulinum serotype D HA-33 comprising a β-trefoil domain with enhanced binding activity comprises a polypeptide having, e.g., at least one, two, three, four, five, six, seven, eight, nine, 10 or 20 contiguous amino acid additions relative to amino acids 10-54, amino acids 60-98, amino acids 103-141, amino acids 148-190, amino acids 195-235, or amino acids 242-286 of SEQ ID NO: 18.

In another embodiment, a β-trefoil domain derived from a Clostridial botulinum serotype D HA-33 comprises a 1β4/β5 hairpin turn of a β-trefoil domain of a Clostridial botulinum serotype D HA-33, a 1β8/β9 hairpin turn of a β-trefoil domain of a Clostridial botulinum serotype D HA-33, a 2β4/β5 hairpin turn of a β-trefoil domain of a Clostridial botulinum serotype D HA-33 or a 2β8/β9 hairpin turn of a β-trefoil domain of a Clostridial botulinum serotype D HA-33 of SEQ ID NO: 18. In another aspect of this embodiment, a β-trefoil domain derived from a Clostridial botulinum serotype D HA-33 comprises amino acids 55-59, amino acids 99-102, amino acids 191-194, or amino acids 236-241 of SEQ ID NO: 18.

In another embodiment, a β-trefoil domain with enhanced binding activity derived from a Clostridial botulinum serotype D HA-33 comprises a modified 1β4/β5 hairpin turn of a β-trefoil domain of a Clostridial botulinum serotype D HA-33, a modified 1β8/β9 hairpin turn of a β-trefoil domain of a Clostridial botulinum serotype D HA-33, a modified 2β4/β5 hairpin turn of a β-trefoil domain of a Clostridial botulinum serotype D HA-33 or a modified 2β8/β9 hairpin turn of a β-trefoil domain of a Clostridial botulinum serotype D HA-33 of SEQ ID NO: 18. In another aspect of this embodiment, a β-trefoil domain with enhanced binding activity derived from a Clostridial botulinum serotype D HA-33 comprises a modification of amino acids 55-59, amino acids 99-102, amino acids 191-194, or amino acids 236-241 of SEQ ID NO: 18.

In other aspects of this embodiment, a β-trefoil domain with enhanced binding activity derived from a Clostridial botulinum serotype D HA-33 comprises a polypeptide having, e.g., at least 70% amino acid identity with amino acids 55-59, amino acids 99-102, amino acids 191-194, or amino acids 236-241 of SEQ ID NO: 18, at least 75% amino acid identity with amino acids 55-59, amino acids 99-102, amino acids 191-194, or amino acids 236-241 of SEQ ID NO: 18, at least 80% amino acid identity with amino acids 55-59, amino acids 99-102, amino acids 191-194, or amino acids 236-241 of SEQ ID NO: 18, at least 85% amino acid identity with amino acids 55-59, amino acids 99-102, amino acids 191-194, or amino acids 236-241 of SEQ ID NO: 18, at least 90% amino acid identity with amino acids 55-59, amino acids 99-102, amino acids 191-194, or amino acids 236-241 of SEQ ID NO: 18 or at least 95% amino acid identity with amino acids 55-59, amino acids 99-102, amino acids 191-194, or amino acids 236-241 of SEQ ID NO: 18. In yet other aspects of this embodiment, a β-trefoil domain with enhanced binding activity derived from a Clostridial botulinum serotype D HA-33 comprises a polypeptide having, e.g., at most 70% amino acid identity with amino acids 55-59, amino acids 99-102, amino acids 191-194, or amino acids 236-241 of SEQ ID NO: 18, at most 75% amino acid identity with amino acids 55-59, amino acids 99-102, amino acids 191-194, or amino acids 236-241 of SEQ ID NO: 18, at most 80% amino acid identity with amino acids 55-59, amino acids 99-102, amino acids 191-194, or amino acids 236-241 of SEQ ID NO: 18, at most 85% amino acid identity with amino acids 55-59, amino acids 99-102, amino acids 191-194, or amino acids 236-241 of SEQ ID NO: 18, at most 90% amino acid identity with amino acids 55-59, amino acids 99-102, amino acids 191-194, or amino acids 236-241 of SEQ ID NO: 18 or at most 95% amino acid identity with amino acids 55-59, amino acids 99-102, amino acids 191-194, or amino acids 236-241 of SEQ ID NO: 18.

In other aspects of this embodiment, a β-trefoil domain with enhanced binding activity derived from a Clostridial botulinum serotype D HA-33 comprises a polypeptide having, e.g., at most one, two, three or four non-contiguous amino acid substitutions relative to amino acids 55-59, amino acids 99-102, amino acids 191-194, or amino acids 236-241 of SEQ ID NO: 18. In other aspects of this embodiment, a β-trefoil domain with enhanced binding activity derived from a Clostridial botulinum serotype D HA-33 comprises a polypeptide having, e.g., at least one, two, three or four non-contiguous amino acid substitutions relative to amino acids 55-59, amino acids 99-102, amino acids 191-194, or amino acids 236-241 of SEQ ID NO: 18. In other aspects of this embodiment, a non-contiguous amino acid substitution of any amino acid from amino acids 55-59, amino acids 99-102, amino acids 191-194, or amino acids 236-241 of SEQ ID NO: 18 can be replaced with glycine. In other aspects of this embodiment, a non-contiguous amino acid substitution of any hydrophobic amino acid from amino acids 55-59, amino acids 99-102, amino acids 191-194, or amino acids 236-241 of SEQ ID NO: 18 can be replaced with phenylalanine. In yet other aspects of this embodiment, a β-trefoil domain with enhanced binding activity derived from a Clostridial botulinum serotype D HA-33 comprises a polypeptide having, e.g., at most one, two, three or four non-contiguous amino acid deletions relative to amino acids 55-59, amino acids 99-102, amino acids 191-194, or amino acids 236-241 of SEQ ID NO: 18. In other aspects of this embodiment, a β-trefoil domain with enhanced binding activity derived from a Clostridial botulinum serotype D HA-33 comprises a polypeptide having, e.g., at least one, two, three or four non-contiguous amino acid deletions relative to amino acids 55-59, amino acids 99-102, amino acids 191-194, or amino acids 236-241 of SEQ ID NO: 18. In still other aspects of this embodiment, a β-trefoil domain with enhanced binding activity derived from a Clostridial botulinum serotype D HA-33 comprises a polypeptide having, e.g., at most one, two, three or four non-contiguous amino acid additions relative to amino acids 55-59, amino acids 99-102, amino acids 191-194, or amino acids 236-241 of SEQ ID NO: 18. In other aspects of this embodiment, a β-trefoil domain with enhanced binding activity derived from a Clostridial botulinum serotype D HA-33 comprises a polypeptide having, e.g., at least one, two, three or four non-contiguous amino acid additions relative to amino acids 55-59, amino acids 99-102, amino acids 191-194, or amino acids 236-241 of SEQ ID NO: 18.

In other aspects of this embodiment, a β-trefoil domain with enhanced binding activity derived from a Clostridial botulinum serotype D HA-33 comprises a polypeptide having, e.g., at most one, two, three or four contiguous amino acid substitutions relative to amino acids 55-59, amino acids 99-102, amino acids 191-194, or amino acids 236-241 of SEQ ID NO: 18. In other aspects of this embodiment, a β-trefoil domain with enhanced binding activity derived from a Clostridial botulinum serotype D HA-33 comprises a polypeptide having, e.g., at least one, two, three or four contiguous amino acid substitutions relative to amino acids 55-59, amino acids 99-102, amino acids 191-194, or amino acids 236-241 of SEQ ID NO: 18. In other aspects of this embodiment, contiguous amino acid substitutions of amino acids from amino acids 55-59, amino acids 99-102, amino acids 191-194, or amino acids 236-241 of SEQ ID NO: 18 can be replaced with glycine. In other aspects of this embodiment, contiguous amino acid substitutions of hydrophobic amino acids from amino acids 55-59, amino acids 99-102, amino acids 191-194, or amino acids 236-241 of SEQ ID NO: 18 can be replaced with phenylalanine. In yet other aspects of this embodiment, a β-trefoil domain with enhanced binding activity derived from a Clostridial botulinum serotype D HA-33 comprises a polypeptide having, e.g., at most one, two, three or four contiguous amino acid deletions relative to amino acids 55-59, amino acids 99-102, amino acids 191-194, or amino acids 236-241 of SEQ ID NO: 18. In other aspects of this embodiment, a β-trefoil domain with enhanced binding activity derived from a Clostridial botulinum serotype D HA-33 comprises a polypeptide having, e.g., at least one, two, three or four contiguous amino acid deletions relative to amino acids 55-59, amino acids 99-102, amino acids 191-194, or amino acids 236-241 of SEQ ID NO: 18. In still other aspects of this embodiment, a β-trefoil domain with enhanced binding activity derived from a Clostridial botulinum serotype D HA-33 comprises a polypeptide having, e.g., at most one, two, three or four contiguous amino acid additions relative to amino acids 55-59, amino acids 99-102, amino acids 191-194, or amino acids 236-241 of SEQ ID NO: 18. In other aspects of this embodiment, a β-trefoil domain with enhanced binding activity derived from a Clostridial botulinum serotype D HA-33 comprises a polypeptide having, e.g., at least one, two, three or four contiguous amino acid additions relative to amino acids 55-59, amino acids 99-102, amino acids 191-194, or amino acids 236-241 of SEQ ID NO: 18.

In an embodiment, a modified Clostridial toxin disclosed in the present specification comprises an enhanced targeting domain comprising a β-trefoil domain derived from a Clostridial HA-17. In an aspect of this embodiment, a β-trefoil domain derived from a Clostridial HA-17 comprises, e.g., a β-trefoil domain derived from a Clostridial botulinum serotype A HA-17, a β-trefoil domain derived from a Clostridial botulinum serotype B HA-17, a β-trefoil domain derived from a Clostridial botulinum serotype C1 HA-17 or a β-trefoil domain derived from a Clostridial botulinum serotype D HA-17. In another aspect of this embodiment, a β-trefoil domain derived from a Clostridial HA-17 comprises a α-fold motif of a β-trefoil domain of a Clostridial HA-17, a β-fold motif of a β-trefoil domain of a Clostridial HA-17 or a γ-fold motif of a β-trefoil domain of a Clostridial HA-17.

In an embodiment, a modified Clostridial toxin disclosed in the present specification comprises an enhanced targeting domain comprising a β-trefoil domain with enhanced binding activity derived from a Clostridial HA-17. In an aspect of this embodiment, a β-trefoil domain with enhanced binding activity derived from a Clostridial HA-17 comprises, e.g., a β-trefoil domain with enhanced binding activity derived from a Clostridial botulinum serotype A HA-17, a β-trefoil domain with enhanced binding activity derived from a Clostridial botulinum serotype B HA-17, a β-trefoil domain with enhanced binding activity derived from a Clostridial botulinum serotype C1 HA-17 or a β-trefoil domain with enhanced binding activity derived from a Clostridial botulinum serotype D HA-17. In another aspect of this embodiment, a β-trefoil domain with enhanced binding activity derived from a Clostridial HA-17 comprises a modified α-fold motif of a β-trefoil domain of a Clostridial HA-17, a modified β-fold motif of a β-trefoil domain of a Clostridial HA-17 or a modified γ-fold motif of a β-trefoil domain of a Clostridial HA-17.

In another embodiment, a β-trefoil domain derived from a Clostridial botulinum serotype A HA-17 comprises a β-trefoil domain derived from a Clostridial botulinum serotype A HA-17 of SEQ ID NO: 19. In another embodiment, a β-trefoil domain derived from a Clostridial botulinum serotype A HA-17 comprises amino acids 9-146 of SEQ ID NO: 19. In another aspect of this embodiment, a β-trefoil domain derived from a Clostridial botulinum serotype A HA-17 comprises a α-fold motif of a β-trefoil domain of a Clostridial botulinum serotype A HA-17, a β-fold motif of a β-trefoil domain of a Clostridial botulinum serotype A HA-17 or a γ-fold motif of a β-trefoil domain of a Clostridial botulinum serotype A HA-17 of SEQ ID NO: 19. In another aspect of this embodiment, a β-trefoil domain derived from a Clostridial botulinum serotype A HA-17 comprises amino acids 9-50, amino acids 55-91, or amino acids 95-146 of SEQ ID NO: 19.

In another embodiment, a β-trefoil domain with enhanced binding activity derived from a Clostridial botulinum serotype A HA-17 comprises a β-trefoil domain with enhanced binding activity derived from a Clostridial botulinum serotype A HA-17 of SEQ ID NO: 19. In another embodiment, a β-trefoil domain with enhanced binding activity derived from a Clostridial botulinum serotype A HA-17 comprises amino acids 9-146 of SEQ ID NO: 19. In another aspect of this embodiment, a β-trefoil domain with enhanced binding activity derived from a Clostridial botulinum serotype A HA-17 comprises a modified α-fold motif of a β-trefoil domain of a Clostridial botulinum serotype A HA-17, a modified β-fold motif of a β-trefoil domain of a Clostridial botulinum serotype A HA-17 or a modified γ-fold motif of a 13-trefoil domain of a Clostridial botulinum serotype A HA-17 of SEQ ID NO: 19. In another aspect of this embodiment, a β-trefoil domain with enhanced binding activity derived from a Clostridial botulinum serotype A HA-17 comprises amino acids 9-50, amino acids 55-91, or amino acids 95-146 of SEQ ID NO: 19.

In other aspects of this embodiment, a Clostridial botulinum serotype A HA-17 comprising a β-trefoil domain with enhanced binding activity comprises a polypeptide having, e.g., at least 70% amino acid identity with amino acids 9-50, amino acids 55-91, or amino acids 95-146 of SEQ ID NO: 19, at least 75% amino acid identity with amino acids 9-50, amino acids 55-91, or amino acids 95-146 of SEQ ID NO: 19, at least 80% amino acid identity with amino acids 9-50, amino acids 55-91, or amino acids 95-146 of SEQ ID NO: 19, at least 85% amino acid identity with amino acids 9-50, amino acids 55-91, or amino acids 95-146 of SEQ ID NO: 19, at least 90% amino acid identity with amino acids 9-50, amino acids 55-91, or amino acids 95-146 of SEQ ID NO: 19 or at least 95% amino acid identity with amino acids 9-50, amino acids 55-91, or amino acids 95-146 of SEQ ID NO: 19. In yet other aspects of this embodiment, a Clostridial botulinum serotype A HA-17 comprising a β-trefoil domain with enhanced binding activity comprises a polypeptide having, e.g., at most 70% amino acid identity with amino acids 9-50, amino acids 55-91, or amino acids 95-146 of SEQ ID NO: 19, at most 75% amino acid identity with amino acids 9-50, amino acids 55-91, or amino acids 95-146 of SEQ ID NO: 19, at most 80% amino acid identity with amino acids 9-50, amino acids 55-91, or amino acids 95-146 of SEQ ID NO: 19, at most 85% amino acid identity with amino acids 9-50, amino acids 55-91, or amino acids 95-146 of SEQ ID NO: 19, at most 90% amino acid identity with amino acids 9-50, amino acids 55-91, or amino acids 95-146 of SEQ ID NO: 19 or at most 95% amino acid identity with amino acids 9-50, amino acids 55-91, or amino acids 95-146 of SEQ ID NO: 19.

In other aspects of this embodiment, a Clostridial botulinum serotype A HA-17 comprising a 11-trefoil domain with enhanced binding activity comprises a polypeptide having, e.g., at most one, two, three, four, five, six, seven, eight, nine, 10 or 20 non-contiguous amino acid substitutions relative to amino acids 9-50, amino acids 55-91, or amino acids 95-146 of SEQ ID NO: 19. In other aspects of this embodiment, a Clostridial botulinum serotype A HA-17 comprising a β-trefoil domain with enhanced binding activity comprises a polypeptide having, e.g., at least one, two, three, four, five, six, seven, eight, nine, 10 or 20 non-contiguous amino acid substitutions relative to amino acids 9-50, amino acids 55-91, or amino acids 95-146 of SEQ ID NO: 19. In yet other aspects of this embodiment, a Clostridial botulinum serotype A HA-17 comprising a β-trefoil domain with enhanced binding activity comprises a polypeptide having, e.g., at most one, two, three, four, five, six, seven, eight, nine, 10 or 20 non-contiguous amino acid deletions relative to amino acids 9-50, amino acids 55-91, or amino acids 95-146 of SEQ ID NO: 19. In other aspects of this embodiment, a Clostridial botulinum serotype A HA-17 comprising a β-trefoil domain with enhanced binding activity comprises a polypeptide having, e.g., at least one, two, three, four, five, six, seven, eight, nine, 10 or 20 non-contiguous amino acid deletions relative to amino acids 9-50, amino acids 55-91, or amino acids 95-146 of SEQ ID NO: 19. In still other aspects of this embodiment, a Clostridial botulinum serotype A HA-17 comprising a β-trefoil domain with enhanced binding activity comprises a polypeptide having, e.g., at most one, two, three, four, five, six, seven, eight, nine, 10 or 20 non-contiguous amino acid additions relative to amino acids 9-50, amino acids 55-91, or amino acids 95-146 of SEQ ID NO: 19. In other aspects of this embodiment, a Clostridial botulinum serotype A HA-17 comprising a β-trefoil domain with enhanced binding activity comprises a polypeptide having, e.g., at least one, two, three, four, five, six, seven, eight, nine, 10 or 20 non-contiguous amino acid additions relative to amino acids 9-50, amino acids 55-91, or amino acids 95-146 of SEQ ID NO: 19.

In other aspects of this embodiment, a Clostridial botulinum serotype A HA-17 comprising a β-trefoil domain with enhanced binding activity comprises a polypeptide having, e.g., at most one, two, three, four, five, six, seven, eight, nine, 10 or 20 contiguous amino acid substitutions relative to amino acids 9-50, amino acids 55-91, or amino acids 95-146 of SEQ ID NO: 19. In other aspects of this embodiment, a Clostridial botulinum serotype A HA-17 comprising a β-trefoil domain with enhanced binding activity comprises a polypeptide having, e.g., at least one, two, three, four, five, six, seven, eight, nine, 10 or 20 contiguous amino acid substitutions relative to amino acids 9-50, amino acids 55-91, or amino acids 95-146 of SEQ ID NO: 19. In yet other aspects of this embodiment, a Clostridial botulinum serotype A HA-17 comprising a β-trefoil domain with enhanced binding activity comprises a polypeptide having, e.g., at most one, two, three, four, five, six, seven, eight, nine, 10 or 20 contiguous amino acid deletions relative to amino acids 9-50, amino acids 55-91, or amino acids 95-146 of SEQ ID NO: 19. In other aspects of this embodiment, a Clostridial botulinum serotype A HA-17 comprising a β-trefoil domain with enhanced binding activity comprises a polypeptide having, e.g., at least one, two, three, four, five, six, seven, eight, nine, 10 or 20 contiguous amino acid deletions relative to amino acids 9-50, amino acids 55-91, or amino acids 95-146 of SEQ ID NO: 19. In still other aspects of this embodiment, a Clostridial botulinum serotype A HA-17 comprising a β-trefoil domain with enhanced binding activity comprises a polypeptide having, e.g., at most one, two, three, four, five, six, seven, eight, nine, 10 or 20 contiguous amino acid additions relative to amino acids 9-50, amino acids 55-91, or amino acids 95-146 of SEQ ID NO: 19. In other aspects of this embodiment, a Clostridial botulinum serotype A HA-17 comprising a β-trefoil domain with enhanced binding activity comprises a polypeptide having, e.g., at least one, two, three, four, five, six, seven, eight, nine, 10 or 20 contiguous amino acid additions relative to amino acids 9-50, amino acids 55-91, or amino acids 95-146 of SEQ ID NO: 19.

In another embodiment, a β-trefoil domain derived from a Clostridial botulinum serotype A HA-17 comprises a β4/β5 hairpin turn of a β-trefoil domain of a Clostridial botulinum serotype A HA-17 or a β8/β9 hairpin turn of a β-trefoil domain of a Clostridial botulinum serotype A HA-17 of SEQ ID NO: 19. In another aspect of this embodiment, a β-trefoil domain derived from a Clostridial botulinum serotype A HA-17 comprises amino acids 51-54 or amino acids 92-94 of SEQ ID NO: 19.

In another embodiment, a β-trefoil domain with enhanced binding activity derived from a Clostridial botulinum serotype A HA-17 comprises a modified β4/β5 hairpin turn of a β-trefoil domain of a Clostridial botulinum serotype A HA-17 or a modified β8/β9 hairpin turn of a β-trefoil domain of a Clostridial botulinum serotype A HA-17 of SEQ ID NO: 19. In another aspect of this embodiment, a β-trefoil domain with enhanced binding activity derived from a Clostridial botulinum serotype A HA-17 comprises a modification of amino acids 51-54 or amino acids 92-94 of SEQ ID NO: 19.

In other aspects of this embodiment, a β-trefoil domain with enhanced binding activity derived from a Clostridial botulinum serotype A HA-17 comprises a polypeptide having, e.g., at least 70% amino acid identity with amino acids 51-54 or amino acids 92-94 of SEQ ID NO: 19, at least 75% amino acid identity with amino acids 51-54 or amino acids 92-94 of SEQ ID NO: 19, at least 80% amino acid identity with amino acids 51-54 or amino acids 92-94 of SEQ ID NO: 19, at least 85% amino acid identity with amino acids 51-54 or amino acids 92-94 of SEQ ID NO: 19, at least 90% amino acid identity with amino acids 51-54 or amino acids 92-94 of SEQ ID NO: 19 or at least 95% amino acid identity with amino acids 51-54 or amino acids 92-94 of SEQ ID NO: 19. In yet other aspects of this embodiment, a β-trefoil domain with enhanced binding activity derived from a Clostridial botulinum serotype A HA-17 comprises a polypeptide having, e.g., at most 70% amino acid identity with amino acids 51-54 or amino acids 92-94 of SEQ ID NO: 19, at most 75% amino acid identity with amino acids 51-54 or amino acids 92-94 of SEQ ID NO: 19, at most 80% amino acid identity with amino acids 51-54 or amino acids 92-94 of SEQ ID NO: 19, at most 85% amino acid identity with amino acids 51-54 or amino acids 92-94 of SEQ ID NO: 19, at most 90% amino acid identity with amino acids 51-54 or amino acids 92-94 of SEQ ID NO: 19 or at most 95% amino acid identity with amino acids 51-54 or amino acids 92-94 of SEQ ID NO: 19.

In other aspects of this embodiment, a β-trefoil domain with enhanced binding activity derived from a Clostridial botulinum serotype A HA-17 comprises a polypeptide having, e.g., at most one, two, three or four non-contiguous amino acid substitutions relative to amino acids 51-54 or amino acids 92-94 of SEQ ID NO: 19. In other aspects of this embodiment, a β-trefoil domain with enhanced binding activity derived from a Clostridial botulinum serotype A HA-17 comprises a polypeptide having, e.g., at least one, two, three or four non-contiguous amino acid substitutions relative to amino acids 51-54 or amino acids 92-94 of SEQ ID NO: 19. In other aspects of this embodiment, a non-contiguous amino acid substitution of any amino acid from amino acids 51-54 or amino acids 92-94 of SEQ ID NO: 19 can be replaced with glycine. In other aspects of this embodiment, a non-contiguous amino acid substitution of any hydrophobic amino acid from amino acids 51-54 or amino acids 92-94 of SEQ ID NO: 19 can be replaced with phenylalanine. In yet other aspects of this embodiment, a β-trefoil domain with enhanced binding activity derived from a Clostridial botulinum serotype A HA-17 comprises a polypeptide having, e.g., at most one, two, three or four non-contiguous amino acid deletions relative to amino acids 51-54 or amino acids 92-94 of SEQ ID NO: 19. In other aspects of this embodiment, a β-trefoil domain with enhanced binding activity derived from a Clostridial botulinum serotype A HA-17 comprises a polypeptide having, e.g., at least one, two, three or four non-contiguous amino acid deletions relative to amino acids 51-54 or amino acids 92-94 of SEQ ID NO: 19. In still other aspects of this embodiment, a β-trefoil domain with enhanced binding activity derived from a Clostridial botulinum serotype A HA-17 comprises a polypeptide having, e.g., at most one, two, three or four non-contiguous amino acid additions relative to amino acids 51-54 or amino acids 92-94 of SEQ ID NO: 19. In other aspects of this embodiment, a β-trefoil domain with enhanced binding activity derived from a Clostridial botulinum serotype A HA-17 comprises a polypeptide having, e.g., at least one, two, three or four non-contiguous amino acid additions relative to amino acids 51-54 or amino acids 92-94 of SEQ ID NO: 19.

In other aspects of this embodiment, a β-trefoil domain with enhanced binding activity derived from a Clostridial botulinum serotype A HA-17 comprises a polypeptide having, e.g., at most one, two, three or four contiguous amino acid substitutions relative to amino acids 51-54 or amino acids 92-94 of SEQ ID NO: 19. In other aspects of this embodiment, a β-trefoil domain with enhanced binding activity derived from a Clostridial botulinum serotype A HA-17 comprises a polypeptide having, e.g., at least one, two, three or four contiguous amino acid substitutions relative to amino acids 51-54 or amino acids 92-94 of SEQ ID NO: 19. In other aspects of this embodiment, contiguous amino acid substitutions of amino acids from amino acids 51-54 or amino acids 92-94 of SEQ ID NO: 19 can be replaced with glycine. In other aspects of this embodiment, contiguous amino acid substitutions of hydrophobic amino acids from amino acids 51-54 or amino acids 92-94 of SEQ ID NO: 19 can be replaced with phenylalanine. In yet other aspects of this embodiment, a β-trefoil domain with enhanced binding activity derived from a Clostridial botulinum serotype A HA-17 comprises a polypeptide having, e.g., at most one, two, three or four contiguous amino acid deletions relative to amino acids 51-54 or amino acids 92-94 of SEQ ID NO: 19. In other aspects of this embodiment, a β-trefoil domain with enhanced binding activity derived from a Clostridial botulinum serotype A HA-17 comprises a polypeptide having, e.g., at least one, two, three or four contiguous amino acid deletions relative to amino acids 51-54 or amino acids 92-94 of SEQ ID NO: 19. In still other aspects of this embodiment, a β-trefoil domain with enhanced binding activity derived from a Clostridial botulinum serotype A HA-17 comprises a polypeptide having, e.g., at most one, two, three or four contiguous amino acid additions relative to amino acids 51-54 or amino acids 92-94 of SEQ ID NO: 19. In other aspects of this embodiment, a β-trefoil domain with enhanced binding activity derived from a Clostridial botulinum serotype A HA-17 comprises a polypeptide having, e.g., at least one, two, three or four contiguous amino acid additions relative to amino acids 51-54 or amino acids 92-94 of SEQ ID NO: 19.

In another embodiment, a β-trefoil domain derived from a Clostridial botulinum serotype B HA-17 comprises a β-trefoil domain derived from a Clostridial botulinum serotype B HA-17 of SEQ ID NO: 20. In another embodiment, a β-trefoil domain derived from a Clostridial botulinum serotype B HA-17 comprises amino acids 9-146 of SEQ ID NO: 20. In another aspect of this embodiment, a β-trefoil domain derived from a Clostridial botulinum serotype B HA-17 comprises a α-fold motif of a β-trefoil domain of a Clostridial botulinum serotype B HA-17, a β-fold motif of a β-trefoil domain of a Clostridial botulinum serotype B HA-17 or a γ-fold motif of a β-trefoil domain of a Clostridial botulinum serotype B HA-17 of SEQ ID NO: 20. In another aspect of this embodiment, a β-trefoil domain derived from a Clostridial botulinum serotype B HA-17 comprises amino acids 9-50, amino acids 55-91, or amino acids 95-146 of SEQ ID NO: 20.

In another embodiment, a β-trefoil domain with enhanced binding activity derived from a Clostridial botulinum serotype B HA-17 comprises a β-trefoil domain with enhanced binding activity derived from a Clostridial botulinum serotype B HA-17 of SEQ ID NO: 20. In another embodiment, a β-trefoil domain with enhanced binding activity derived from a Clostridial botulinum serotype B HA-17 comprises amino acids 9-146 of SEQ ID NO: 20. In another aspect of this embodiment, a β-trefoil domain with enhanced binding activity derived from a Clostridial botulinum serotype B HA-17 comprises a modified α-fold motif of a β-trefoil domain of a Clostridial botulinum serotype B HA-17, a modified β-fold motif of a β-trefoil domain of a Clostridial botulinum serotype B HA-17 or a modified γ-fold motif of a 13-trefoil domain of a Clostridial botulinum serotype B HA-17 of SEQ ID NO: 20. In another aspect of this embodiment, a β-trefoil domain with enhanced binding activity derived from a Clostridial botulinum serotype B HA-17 comprises amino acids 9-50, amino acids 55-91, or amino acids 95-146 of SEQ ID NO: 20.

In other aspects of this embodiment, a Clostridial botulinum serotype B HA-17 comprising a β-trefoil domain with enhanced binding activity comprises a polypeptide having, e.g., at least 70% amino acid identity with amino acids 9-50, amino acids 55-91, or amino acids 95-146 of SEQ ID NO: 20, at least 75% amino acid identity with amino acids 9-50, amino acids 55-91, or amino acids 95-146 of SEQ ID NO: 20, at least 80% amino acid identity with amino acids 9-50, amino acids 55-91, or amino acids 95-146 of SEQ ID NO: 20, at least 85% amino acid identity with amino acids 9-50, amino acids 55-91, or amino acids 95-146 of SEQ ID NO: 20, at least 90% amino acid identity with amino acids 9-50, amino acids 55-91, or amino acids 95-146 of SEQ ID NO: 20 or at least 95% amino acid identity with amino acids 9-50, amino acids 55-91, or amino acids 95-146 of SEQ ID NO: 20. In yet other aspects of this embodiment, a Clostridial botulinum serotype B HA-17 comprising a β-trefoil domain with enhanced binding activity comprises a polypeptide having, e.g., at most 70% amino acid identity with amino acids 9-50, amino acids 55-91, or amino acids 95-146 of SEQ ID NO: 20, at most 75% amino acid identity with amino acids 9-50, amino acids 55-91, or amino acids 95-146 of SEQ ID NO: 20, at most 80% amino acid identity with amino acids 9-50, amino acids 55-91, or amino acids 95-146 of SEQ ID NO: 20, at most 85% amino acid identity with amino acids 9-50, amino acids 55-91, or amino acids 95-146 of SEQ ID NO: 20, at most 90% amino acid identity with amino acids 9-50, amino acids 55-91, or amino acids 95-146 of SEQ ID NO: 20 or at most 95% amino acid identity with amino acids 9-50, amino acids 55-91, or amino acids 95-146 of SEQ ID NO: 20.

In other aspects of this embodiment, a Clostridial botulinum serotype B HA-17 comprising a 11-trefoil domain with enhanced binding activity comprises a polypeptide having, e.g., at most one, two, three, four, five, six, seven, eight, nine, 10 or 20 non-contiguous amino acid substitutions relative to amino acids 9-50, amino acids 55-91, or amino acids 95-146 of SEQ ID NO: 20. In other aspects of this embodiment, a Clostridial botulinum serotype B HA-17 comprising a β-trefoil domain with enhanced binding activity comprises a polypeptide having, e.g., at least one, two, three, four, five, six, seven, eight, nine, 10 or 20 non-contiguous amino acid substitutions relative to amino acids 9-50, amino acids 55-91, or amino acids 95-146 of SEQ ID NO: 20. In yet other aspects of this embodiment, a Clostridial botulinum serotype B HA-17 comprising a β-trefoil domain with enhanced binding activity comprises a polypeptide having, e.g., at most one, two, three, four, five, six, seven, eight, nine, 10 or 20 non-contiguous amino acid deletions relative to amino acids 9-50, amino acids 55-91, or amino acids 95-146 of SEQ ID NO: 20. In other aspects of this embodiment, a Clostridial botulinum serotype B HA-17 comprising a β-trefoil domain with enhanced binding activity comprises a polypeptide having, e.g., at least one, two, three, four, five, six, seven, eight, nine, 10 or 20 non-contiguous amino acid deletions relative to amino acids 9-50, amino acids 55-91, or amino acids 95-146 of SEQ ID NO: 20. In still other aspects of this embodiment, a Clostridial botulinum serotype B HA-17 comprising a β-trefoil domain with enhanced binding activity comprises a polypeptide having, e.g., at most one, two, three, four, five, six, seven, eight, nine, 10 or 20 non-contiguous amino acid additions relative to amino acids 9-50, amino acids 55-91, or amino acids 95-146 of SEQ ID NO: 20. In other aspects of this embodiment, a Clostridial botulinum serotype B HA-17 comprising a β-trefoil domain with enhanced binding activity comprises a polypeptide having, e.g., at least one, two, three, four, five, six, seven, eight, nine, 10 or 20 non-contiguous amino acid additions relative to amino acids 9-50, amino acids 55-91, or amino acids 95-146 of SEQ ID NO: 20.

In other aspects of this embodiment, a Clostridial botulinum serotype B HA-17 comprising a β-trefoil domain with enhanced binding activity comprises a polypeptide having, e.g., at most one, two, three, four, five, six, seven, eight, nine, 10 or 20 contiguous amino acid substitutions relative to amino acids 9-50, amino acids 55-91, or amino acids 95-146 of SEQ ID NO: 20. In other aspects of this embodiment, a Clostridial botulinum serotype B HA-17 comprising a β-trefoil domain with enhanced binding activity comprises a polypeptide having, e.g., at least one, two, three, four, five, six, seven, eight, nine, 10 or 20 contiguous amino acid substitutions relative to amino acids 9-50, amino acids 55-91, or amino acids 95-146 of SEQ ID NO: 20. In yet other aspects of this embodiment, a Clostridial botulinum serotype B HA-17 comprising a β-trefoil domain with enhanced binding activity comprises a polypeptide having, e.g., at most one, two, three, four, five, six, seven, eight, nine, 10 or 20 contiguous amino acid deletions relative to amino acids 9-50, amino acids 55-91, or amino acids 95-146 of SEQ ID NO: 20. In other aspects of this embodiment, a Clostridial botulinum serotype B HA-17 comprising a β-trefoil domain with enhanced binding activity comprises a polypeptide having, e.g., at least one, two, three, four, five, six, seven, eight, nine, 10 or 20 contiguous amino acid deletions relative to amino acids 9-50, amino acids 55-91, or amino acids 95-146 of SEQ ID NO: 20. In still other aspects of this embodiment, a Clostridial botulinum serotype B HA-17 comprising a β-trefoil domain with enhanced binding activity comprises a polypeptide having, e.g., at most one, two, three, four, five, six, seven, eight, nine, 10 or 20 contiguous amino acid additions relative to amino acids 9-50, amino acids 55-91, or amino acids 95-146 of SEQ ID NO: 20. In other aspects of this embodiment, a Clostridial botulinum serotype B HA-17 comprising a β-trefoil domain with enhanced binding activity comprises a polypeptide having, e.g., at least one, two, three, four, five, six, seven, eight, nine, 10 or 20 contiguous amino acid additions relative to amino acids 9-50, amino acids 55-91, or amino acids 95-146 of SEQ ID NO: 20.

In another embodiment, a β-trefoil domain derived from a Clostridial botulinum serotype B HA-17 comprises a β4/β5 hairpin turn of a β-trefoil domain of a Clostridial botulinum serotype B HA-17 or a β8/β9 hairpin turn of a β-trefoil domain of a Clostridial botulinum serotype B HA-17 of SEQ ID NO: 20. In another aspect of this embodiment, a β-trefoil domain derived from a Clostridial botulinum serotype B HA-17 comprises amino acids 51-54 or amino acids 92-94 of SEQ ID NO: 20.

In another embodiment, a β-trefoil domain with enhanced binding activity derived from a Clostridial botulinum serotype B HA-17 comprises a modified β4/β5 hairpin turn of a β-trefoil domain of a Clostridial botulinum serotype B HA-17 or a modified β8/β9 hairpin turn of a β-trefoil domain of a Clostridial botulinum serotype B HA-17 of SEQ ID NO: 20. In another aspect of this embodiment, a β-trefoil domain with enhanced binding activity derived from a Clostridial botulinum serotype B HA-17 comprises a modification of amino acids 51-54 or amino acids 92-94 of SEQ ID NO: 20.

In other aspects of this embodiment, a β-trefoil domain with enhanced binding activity derived from a Clostridial botulinum serotype B HA-17 comprises a polypeptide having, e.g., at least 70% amino acid identity with amino acids 51-54 or amino acids 92-94 of SEQ ID NO: 20, at least 75% amino acid identity with amino acids 51-54 or amino acids 92-94 of SEQ ID NO: 20, at least 80% amino acid identity with amino acids 51-54 or amino acids 92-94 of SEQ ID NO: 20, at least 85% amino acid identity with amino acids 51-54 or amino acids 92-94 of SEQ ID NO: 20, at least 90% amino acid identity with amino acids 51-54 or amino acids 92-94 of SEQ ID NO: 20 or at least 95% amino acid identity with amino acids 51-54 or amino acids 92-94 of SEQ ID NO: 20. In yet other aspects of this embodiment, a β-trefoil domain with enhanced binding activity derived from a Clostridial botulinum serotype B HA-17 comprises a polypeptide having, e.g., at most 70% amino acid identity with amino acids 51-54 or amino acids 92-94 of SEQ ID NO: 20, at most 75% amino acid identity with amino acids 51-54 or amino acids 92-94 of SEQ ID NO: 20, at most 80% amino acid identity with amino acids 51-54 or amino acids 92-94 of SEQ ID NO: 20, at most 85% amino acid identity with amino acids 51-54 or amino acids 92-94 of SEQ ID NO: 20, at most 90% amino acid identity with amino acids 51-54 or amino acids 92-94 of SEQ ID NO: 20 or at most 95% amino acid identity with amino acids 51-54 or amino acids 92-94 of SEQ ID NO: 20.

In other aspects of this embodiment, a β-trefoil domain with enhanced binding activity derived from a Clostridial botulinum serotype B HA-17 comprises a polypeptide having, e.g., at most one, two, three or four non-contiguous amino acid substitutions relative to amino acids 51-54 or amino acids 92-94 of SEQ ID NO: 20. In other aspects of this embodiment, a β-trefoil domain with enhanced binding activity derived from a Clostridial botulinum serotype B HA-17 comprises a polypeptide having, e.g., at least one, two, three or four non-contiguous amino acid substitutions relative to amino acids 51-54 or amino acids 92-94 of SEQ ID NO: 20. In other aspects of this embodiment, a non-contiguous amino acid substitution of any amino acid from amino acids 51-54 or amino acids 92-94 of SEQ ID NO: 20 can be replaced with glycine. In other aspects of this embodiment, a non-contiguous amino acid substitution of any hydrophobic amino acid from amino acids 51-54 or amino acids 92-94 of SEQ ID NO: 20 can be replaced with phenylalanine. In yet other aspects of this embodiment, a β-trefoil domain with enhanced binding activity derived from a Clostridial botulinum serotype B HA-17 comprises a polypeptide having, e.g., at most one, two, three or four non-contiguous amino acid deletions relative to amino acids 51-54 or amino acids 92-94 of SEQ ID NO: 20. In other aspects of this embodiment, a β-trefoil domain with enhanced binding activity derived from a Clostridial botulinum serotype B HA-17 comprises a polypeptide having, e.g., at least one, two, three or four non-contiguous amino acid deletions relative to amino acids 51-54 or amino acids 92-94 of SEQ ID NO: 20. In still other aspects of this embodiment, a β-trefoil domain with enhanced binding activity derived from a Clostridial botulinum serotype B HA-17 comprises a polypeptide having, e.g., at most one, two, three or four non-contiguous amino acid additions relative to amino acids 51-54 or amino acids 92-94 of SEQ ID NO: 20. In other aspects of this embodiment, a β-trefoil domain with enhanced binding activity derived from a Clostridial botulinum serotype B HA-17 comprises a polypeptide having, e.g., at least one, two, three or four non-contiguous amino acid additions relative to amino acids 51-54 or amino acids 92-94 of SEQ ID NO: 20.

In other aspects of this embodiment, a β-trefoil domain with enhanced binding activity derived from a Clostridial botulinum serotype B HA-17 comprises a polypeptide having, e.g., at most one, two, three or four contiguous amino acid substitutions relative to amino acids 51-54 or amino acids 92-94 of SEQ ID NO: 20. In other aspects of this embodiment, a β-trefoil domain with enhanced binding activity derived from a Clostridial botulinum serotype B HA-17 comprises a polypeptide having, e.g., at least one, two, three or four contiguous amino acid substitutions relative to amino acids 51-54 or amino acids 92-94 of SEQ ID NO: 20. In other aspects of this embodiment, contiguous amino acid substitutions of amino acids from amino acids 51-54 or amino acids 92-94 of SEQ ID NO: 20 can be replaced with glycine. In other aspects of this embodiment, contiguous amino acid substitutions of hydrophobic amino acids from amino acids 51-54 or amino acids 92-94 of SEQ ID NO: 20 can be replaced with phenylalanine. In yet other aspects of this embodiment, a β-trefoil domain with enhanced binding activity derived from a Clostridial botulinum serotype B HA-17 comprises a polypeptide having, e.g., at most one, two, three or four contiguous amino acid deletions relative to amino acids 51-54 or amino acids 92-94 of SEQ ID NO: 20. In other aspects of this embodiment, a β-trefoil domain with enhanced binding activity derived from a Clostridial botulinum serotype B HA-17 comprises a polypeptide having, e.g., at least one, two, three or four contiguous amino acid deletions relative to amino acids 51-54 or amino acids 92-94 of SEQ ID NO: 20. In still other aspects of this embodiment, a β-trefoil domain with enhanced binding activity derived from a Clostridial botulinum serotype B HA-17 comprises a polypeptide having, e.g., at most one, two, three or four contiguous amino acid additions relative to amino acids 51-54 or amino acids 92-94 of SEQ ID NO: 20. In other aspects of this embodiment, a β-trefoil domain with enhanced binding activity derived from a Clostridial botulinum serotype B HA-17 comprises a polypeptide having, e.g., at least one, two, three or four contiguous amino acid additions relative to amino acids 51-54 or amino acids 92-94 of SEQ ID NO: 20.

In another embodiment, a β-trefoil domain derived from a Clostridial botulinum serotype C1 HA-17 comprises a β-trefoil domain derived from a Clostridial botulinum serotype C1 HA-17 of SEQ ID NO: 21. In another embodiment, a β-trefoil domain derived from a Clostridial botulinum serotype C1 HA-17 comprises amino acids 9-146 of SEQ ID NO: 21. In another aspect of this embodiment, a β-trefoil domain derived from a Clostridial botulinum serotype C1 HA-17 comprises a α-fold motif of a β-trefoil domain of a Clostridial botulinum serotype C1 HA-17, a β-fold motif of a β-trefoil domain of a Clostridial botulinum serotype C1 HA-17 or a γ-fold motif of a β-trefoil domain of a Clostridial botulinum serotype C1 HA-17 of SEQ ID NO: 21. In another aspect of this embodiment, a β-trefoil domain derived from a Clostridial botulinum serotype C1 HA-17 comprises amino acids 9-50, amino acids 55-91, or amino acids 95-146 of SEQ ID NO: 21.

In another embodiment, a β-trefoil domain with enhanced binding activity derived from a Clostridial botulinum serotype C1 HA-17 comprises a β-trefoil domain with enhanced binding activity derived from a Clostridial botulinum serotype C1 HA-17 of SEQ ID NO: 21. In another embodiment, a β-trefoil domain with enhanced binding activity derived from a Clostridial botulinum serotype C1 HA-17 comprises amino acids 9-146 of SEQ ID NO: 21. In another aspect of this embodiment, a β-trefoil domain with enhanced binding activity derived from a Clostridial botulinum serotype C1 HA-17 comprises a modified α-fold motif of a β-trefoil domain of a Clostridial botulinum serotype C1 HA-17, a modified β-fold motif of a β-trefoil domain of a Clostridial botulinum serotype C1 HA-17 or a modified γ-fold motif of a β-trefoil domain of a Clostridial botulinum serotype C1 HA-17 of SEQ ID NO: 21. In another aspect of this embodiment, a β-trefoil domain with enhanced binding activity derived from a Clostridial botulinum serotype C1 HA-17 comprises amino acids 9-50, amino acids 55-91, or amino acids 95-146 of SEQ ID NO: 21.

In other aspects of this embodiment, a Clostridial botulinum serotype C1 HA-17 comprising a β-trefoil domain with enhanced binding activity comprises a polypeptide having, e.g., at least 70% amino acid identity with amino acids 9-50, amino acids 55-91, or amino acids 95-146 of SEQ ID NO: 21, at least 75% amino acid identity with amino acids 9-50, amino acids 55-91, or amino acids 95-146 of SEQ ID NO: 21, at least 80% amino acid identity with amino acids 9-50, amino acids 55-91, or amino acids 95-146 of SEQ ID NO: 21, at least 85% amino acid identity with amino acids 9-50, amino acids 55-91, or amino acids 95-146 of SEQ ID NO: 21, at least 90% amino acid identity with amino acids 9-50, amino acids 55-91, or amino acids 95-146 of SEQ ID NO: 21 or at least 95% amino acid identity with amino acids 9-50, amino acids 55-91, or amino acids 95-146 of SEQ ID NO: 21. In yet other aspects of this embodiment, a Clostridial botulinum serotype C1 HA-17 comprising a β-trefoil domain with enhanced binding activity comprises a polypeptide having, e.g., at most 70% amino acid identity with amino acids 9-50, amino acids 55-91, or amino acids 95-146 of SEQ ID NO: 21, at most 75% amino acid identity with amino acids 9-50, amino acids 55-91, or amino acids 95-146 of SEQ ID NO: 21, at most 80% amino acid identity with amino acids 9-50, amino acids 55-91, or amino acids 95-146 of SEQ ID NO: 21, at most 85% amino acid identity with amino acids 9-50, amino acids 55-91, or amino acids 95-146 of SEQ ID NO: 21, at most 90% amino acid identity with amino acids 9-50, amino acids 55-91, or amino acids 95-146 of SEQ ID NO: 21 or at most 95% amino acid identity with amino acids 9-50, amino acids 55-91, or amino acids 95-146 of SEQ ID NO: 21.

In other aspects of this embodiment, a Clostridial botulinum serotype C1 HA-17 comprising a 11-trefoil domain with enhanced binding activity comprises a polypeptide having, e.g., at most one, two, three, four, five, six, seven, eight, nine, 10 or 20 non-contiguous amino acid substitutions relative to amino acids 9-50, amino acids 55-91, or amino acids 95-146 of SEQ ID NO: 21. In other aspects of this embodiment, a Clostridial botulinum serotype C1 HA-17 comprising a β-trefoil domain with enhanced binding activity comprises a polypeptide having, e.g., at least one, two, three, four, five, six, seven, eight, nine, 10 or 20 non-contiguous amino acid substitutions relative to amino acids 9-50, amino acids 55-91, or amino acids 95-146 of SEQ ID NO: 21. In yet other aspects of this embodiment, a Clostridial botulinum serotype C1 HA-17 comprising a β-trefoil domain with enhanced binding activity comprises a polypeptide having, e.g., at most one, two, three, four, five, six, seven, eight, nine, 10 or 20 non-contiguous amino acid deletions relative to amino acids 9-50, amino acids 55-91, or amino acids 95-146 of SEQ ID NO: 21. In other aspects of this embodiment, a Clostridial botulinum serotype C1 HA-17 comprising a β-trefoil domain with enhanced binding activity comprises a polypeptide having, e.g., at least one, two, three, four, five, six, seven, eight, nine, 10 or 20 non-contiguous amino acid deletions relative to amino acids 9-50, amino acids 55-91, or amino acids 95-146 of SEQ ID NO: 21. In still other aspects of this embodiment, a Clostridial botulinum serotype C1 HA-17 comprising a β-trefoil domain with enhanced binding activity comprises a polypeptide having, e.g., at most one, two, three, four, five, six, seven, eight, nine, 10 or 20 non-contiguous amino acid additions relative to amino acids 9-50, amino acids 55-91, or amino acids 95-146 of SEQ ID NO: 21. In other aspects of this embodiment, a Clostridial botulinum serotype C1 HA-17 comprising a β-trefoil domain with enhanced binding activity comprises a polypeptide having, e.g., at least one, two, three, four, five, six, seven, eight, nine, 10 or 20 non-contiguous amino acid additions relative to amino acids 9-50, amino acids 55-91, or amino acids 95-146 of SEQ ID NO: 21.

In other aspects of this embodiment, a Clostridial botulinum serotype C1 HA-17 comprising a β-trefoil domain with enhanced binding activity comprises a polypeptide having, e.g., at most one, two, three, four, five, six, seven, eight, nine, 10 or 20 contiguous amino acid substitutions relative to amino acids 9-50, amino acids 55-91, or amino acids 95-146 of SEQ ID NO: 21. In other aspects of this embodiment, a Clostridial botulinum serotype C1 HA-17 comprising a β-trefoil domain with enhanced binding activity comprises a polypeptide having, e.g., at least one, two, three, four, five, six, seven, eight, nine, 10 or 20 contiguous amino acid substitutions relative to amino acids 9-50, amino acids 55-91, or amino acids 95-146 of SEQ ID NO: 21. In yet other aspects of this embodiment, a Clostridial botulinum serotype C1 HA-17 comprising a β-trefoil domain with enhanced binding activity comprises a polypeptide having, e.g., at most one, two, three, four, five, six, seven, eight, nine, 10 or 20 contiguous amino acid deletions relative to amino acids 9-50, amino acids 55-91, or amino acids 95-146 of SEQ ID NO: 21. In other aspects of this embodiment, a Clostridial botulinum serotype C1 HA-17 comprising a β-trefoil domain with enhanced binding activity comprises a polypeptide having, e.g., at least one, two, three, four, five, six, seven, eight, nine, 10 or 20 contiguous amino acid deletions relative to amino acids 9-50, amino acids 55-91, or amino acids 95-146 of SEQ ID NO: 21. In still other aspects of this embodiment, a Clostridial botulinum serotype C1 HA-17 comprising a β-trefoil domain with enhanced binding activity comprises a polypeptide having, e.g., at most one, two, three, four, five, six, seven, eight, nine, 10 or 20 contiguous amino acid additions relative to amino acids 9-50, amino acids 55-91, or amino acids 95-146 of SEQ ID NO: 21. In other aspects of this embodiment, a Clostridial botulinum serotype C1 HA-17 comprising a β-trefoil domain with enhanced binding activity comprises a polypeptide having, e.g., at least one, two, three, four, five, six, seven, eight, nine, 10 or 20 contiguous amino acid additions relative to amino acids 9-50, amino acids 55-91, or amino acids 95-146 of SEQ ID NO: 21.

In another embodiment, a β-trefoil domain derived from a Clostridial botulinum serotype C1 HA-17 comprises a β4/β5 hairpin turn of a β-trefoil domain of a Clostridial botulinum serotype C1 HA-17 or a β8/β9 hairpin turn of a β-trefoil domain of a Clostridial botulinum serotype C1 HA-17 of SEQ ID NO: 21. In another aspect of this embodiment, a β-trefoil domain derived from a Clostridial botulinum serotype C1 HA-17 comprises amino acids 51-54 or amino acids 92-94 of SEQ ID NO: 21.

In another embodiment, a β-trefoil domain with enhanced binding activity derived from a Clostridial botulinum serotype C1 HA-17 comprises a modified β4/β5 hairpin turn of a β-trefoil domain of a Clostridial botulinum serotype C1 HA-17 or a modified β8/β9 hairpin turn of a β-trefoil domain of a Clostridial botulinum serotype C1 HA-17 of SEQ ID NO: 21. In another aspect of this embodiment, a β-trefoil domain with enhanced binding activity derived from a Clostridial botulinum serotype C1 HA-17 comprises a modification of amino acids 51-54 or amino acids 92-94 of SEQ ID NO: 21.

In other aspects of this embodiment, a β-trefoil domain with enhanced binding activity derived from a Clostridial botulinum serotype C1 HA-17 comprises a polypeptide having, e.g., at least 70% amino acid identity with amino acids 51-54 or amino acids 92-94 of SEQ ID NO: 21, at least 75% amino acid identity with amino acids 51-54 or amino acids 92-94 of SEQ ID NO: 21, at least 80% amino acid identity with amino acids 51-54 or amino acids 92-94 of SEQ ID NO: 21, at least 85% amino acid identity with amino acids 51-54 or amino acids 92-94 of SEQ ID NO: 21, at least 90% amino acid identity with amino acids 51-54 or amino acids 92-94 of SEQ ID NO: 21 or at least 95% amino acid identity with amino acids 51-54 or amino acids 92-94 of SEQ ID NO: 21. In yet other aspects of this embodiment, a β-trefoil domain with enhanced binding activity derived from a Clostridial botulinum serotype C1 HA-17 comprises a polypeptide having, e.g., at most 70% amino acid identity with amino acids 51-54 or amino acids 92-94 of SEQ ID NO: 21, at most 75% amino acid identity with amino acids 51-54 or amino acids 92-94 of SEQ ID NO: 21, at most 80% amino acid identity with amino acids 51-54 or amino acids 92-94 of SEQ ID NO: 21, at most 85% amino acid identity with amino acids 51-54 or amino acids 92-94 of SEQ ID NO: 21, at most 90% amino acid identity with amino acids 51-54 or amino acids 92-94 of SEQ ID NO: 21 or at most 95% amino acid identity with amino acids 51-54 or amino acids 92-94 of SEQ ID NO: 21.

In other aspects of this embodiment, a β-trefoil domain with enhanced binding activity derived from a Clostridial botulinum serotype C1 HA-17 comprises a polypeptide having, e.g., at most one, two, three or four non-contiguous amino acid substitutions relative to amino acids 51-54 or amino acids 92-94 of SEQ ID NO: 21. In other aspects of this embodiment, a β-trefoil domain with enhanced binding activity derived from a Clostridial botulinum serotype C1 HA-17 comprises a polypeptide having, e.g., at least one, two, three or four non-contiguous amino acid substitutions relative to amino acids 51-54 or amino acids 92-94 of SEQ ID NO: 21. In other aspects of this embodiment, a non-contiguous amino acid substitution of any amino acid from amino acids 51-54 or amino acids 92-94 of SEQ ID NO: 21 can be replaced with glycine. In other aspects of this embodiment, a non-contiguous amino acid substitution of any hydrophobic amino acid from amino acids 51-54 or amino acids 92-94 of SEQ ID NO: 21 can be replaced with phenylalanine. In yet other aspects of this embodiment, a β-trefoil domain with enhanced binding activity derived from a Clostridial botulinum serotype C1 HA-17 comprises a polypeptide having, e.g., at most one, two, three or four non-contiguous amino acid deletions relative to amino acids 51-54 or amino acids 92-94 of SEQ ID NO: 21. In other aspects of this embodiment, a β-trefoil domain with enhanced binding activity derived from a Clostridial botulinum serotype C1 HA-17 comprises a polypeptide having, e.g., at least one, two, three or four non-contiguous amino acid deletions relative to amino acids 51-54 or amino acids 92-94 of SEQ ID NO: 21. In still other aspects of this embodiment, a β-trefoil domain with enhanced binding activity derived from a Clostridial botulinum serotype C1 HA-17 comprises a polypeptide having, e.g., at most one, two, three or four non-contiguous amino acid additions relative to amino acids 51-54 or amino acids 92-94 of SEQ ID NO: 21. In other aspects of this embodiment, a β-trefoil domain with enhanced binding activity derived from a Clostridial botulinum serotype C1 HA-17 comprises a polypeptide having, e.g., at least one, two, three or four non-contiguous amino acid additions relative to amino acids 51-54 or amino acids 92-94 of SEQ ID NO: 21.

In other aspects of this embodiment, a β-trefoil domain with enhanced binding activity derived from a Clostridial botulinum serotype C1 HA-17 comprises a polypeptide having, e.g., at most one, two, three or four contiguous amino acid substitutions relative to amino acids 51-54 or amino acids 92-94 of SEQ ID NO: 21. In other aspects of this embodiment, a β-trefoil domain with enhanced binding activity derived from a Clostridial botulinum serotype C1 HA-17 comprises a polypeptide having, e.g., at least one, two, three or four contiguous amino acid substitutions relative to amino acids 51-54 or amino acids 92-94 of SEQ ID NO: 21. In other aspects of this embodiment, contiguous amino acid substitutions of amino acids from amino acids 51-54 or amino acids 92-94 of SEQ ID NO: 21 can be replaced with glycine. In other aspects of this embodiment, contiguous amino acid substitutions of hydrophobic amino acids from amino acids 51-54 or amino acids 92-94 of SEQ ID NO: 21 can be replaced with phenylalanine. In yet other aspects of this embodiment, a β-trefoil domain with enhanced binding activity derived from a Clostridial botulinum serotype C1 HA-17 comprises a polypeptide having, e.g., at most one, two, three or four contiguous amino acid deletions relative to amino acids 51-54 or amino acids 92-94 of SEQ ID NO: 21. In other aspects of this embodiment, a β-trefoil domain with enhanced binding activity derived from a Clostridial botulinum serotype C1 HA-17 comprises a polypeptide having, e.g., at least one, two, three or four contiguous amino acid deletions relative to amino acids 51-54 or amino acids 92-94 of SEQ ID NO: 21. In still other aspects of this embodiment, a β-trefoil domain with enhanced binding activity derived from a Clostridial botulinum serotype C1 HA-17 comprises a polypeptide having, e.g., at most one, two, three or four contiguous amino acid additions relative to amino acids 51-54 or amino acids 92-94 of SEQ ID NO: 21. In other aspects of this embodiment, a β-trefoil domain with enhanced binding activity derived from a Clostridial botulinum serotype C1 HA-17 comprises a polypeptide having, e.g., at least one, two, three or four contiguous amino acid additions relative to amino acids 51-54 or amino acids 92-94 of SEQ ID NO: 21.

In another embodiment, a β-trefoil domain derived from a Clostridial botulinum serotype D HA-17 comprises a β-trefoil domain derived from a Clostridial botulinum serotype D HA-17 of SEQ ID NO: 22. In another embodiment, a β-trefoil domain derived from a Clostridial botulinum serotype D HA-17 comprises amino acids 9-146 of SEQ ID NO: 22. In another aspect of this embodiment, a β-trefoil domain derived from a Clostridial botulinum serotype D HA-17 comprises a α-fold motif of a β-trefoil domain of a Clostridial botulinum serotype D HA-17, a β-fold motif of a β-trefoil domain of a Clostridial botulinum serotype D HA-17 or a γ-fold motif of a β-trefoil domain of a Clostridial botulinum serotype D HA-17 of SEQ ID NO: 22. In another aspect of this embodiment, a β-trefoil domain derived from a Clostridial botulinum serotype D HA-17 comprises amino acids 9-50, amino acids 55-91, or amino acids 95-146 of SEQ ID NO: 22.

In another embodiment, a β-trefoil domain with enhanced binding activity derived from a Clostridial botulinum serotype D HA-17 comprises a β-trefoil domain with enhanced binding activity derived from a Clostridial botulinum serotype D HA-17 of SEQ ID NO: 22. In another embodiment, a β-trefoil domain with enhanced binding activity derived from a Clostridial botulinum serotype D HA-17 comprises amino acids 9-146 of SEQ ID NO: 22. In another aspect of this embodiment, a β-trefoil domain with enhanced binding activity derived from a Clostridial botulinum serotype D HA-17 comprises a modified α-fold motif of a β-trefoil domain of a Clostridial botulinum serotype D HA-17, a modified β-fold motif of a β-trefoil domain of a Clostridial botulinum serotype D HA-17 or a modified γ-fold motif of a 13-trefoil domain of a Clostridial botulinum serotype D HA-17 of SEQ ID NO: 22. In another aspect of this embodiment, a β-trefoil domain with enhanced binding activity derived from a Clostridial botulinum serotype D HA-17 comprises amino acids 9-50, amino acids 55-91, or amino acids 95-146 of SEQ ID NO: 22.

In other aspects of this embodiment, a Clostridial botulinum serotype D HA-17 comprising a β-trefoil domain with enhanced binding activity comprises a polypeptide having, e.g., at least 70% amino acid identity with amino acids 9-50, amino acids 55-91, or amino acids 95-146 of SEQ ID NO: 22, at least 75% amino acid identity with amino acids 9-50, amino acids 55-91, or amino acids 95-146 of SEQ ID NO: 22, at least 80% amino acid identity with amino acids 9-50, amino acids 55-91, or amino acids 95-146 of SEQ ID NO: 22, at least 85% amino acid identity with amino acids 9-50, amino acids 55-91, or amino acids 95-146 of SEQ ID NO: 22, at least 90% amino acid identity with amino acids 9-50, amino acids 55-91, or amino acids 95-146 of SEQ ID NO: 22 or at least 95% amino acid identity with amino acids 9-50, amino acids 55-91, or amino acids 95-146 of SEQ ID NO: 22. In yet other aspects of this embodiment, a Clostridial botulinum serotype D HA-17 comprising a β-trefoil domain with enhanced binding activity comprises a polypeptide having, e.g., at most 70% amino acid identity with amino acids 9-50, amino acids 55-91, or amino acids 95-146 of SEQ ID NO: 22, at most 75% amino acid identity with amino acids 9-50, amino acids 55-91, or amino acids 95-146 of SEQ ID NO: 22, at most 80% amino acid identity with amino acids 9-50, amino acids 55-91, or amino acids 95-146 of SEQ ID NO: 22, at most 85% amino acid identity with amino acids 9-50, amino acids 55-91, or amino acids 95-146 of SEQ ID NO: 22, at most 90% amino acid identity with amino acids 9-50, amino acids 55-91, or amino acids 95-146 of SEQ ID NO: 22 or at most 95% amino acid identity with amino acids 9-50, amino acids 55-91, or amino acids 95-146 of SEQ ID NO: 22.

In other aspects of this embodiment, a Clostridial botulinum serotype D HA-17 comprising a 11-trefoil domain with enhanced binding activity comprises a polypeptide having, e.g., at most one, two, three, four, five, six, seven, eight, nine, 10 or 20 non-contiguous amino acid substitutions relative to amino acids 9-50, amino acids 55-91, or amino acids 95-146 of SEQ ID NO: 22. In other aspects of this embodiment, a Clostridial botulinum serotype D HA-17 comprising a β-trefoil domain with enhanced binding activity comprises a polypeptide having, e.g., at least one, two, three, four, five, six, seven, eight, nine, 10 or 20 non-contiguous amino acid substitutions relative to amino acids 9-50, amino acids 55-91, or amino acids 95-146 of SEQ ID NO: 22. In yet other aspects of this embodiment, a Clostridial botulinum serotype D HA-17 comprising a β-trefoil domain with enhanced binding activity comprises a polypeptide having, e.g., at most one, two, three, four, five, six, seven, eight, nine, 10 or 20 non-contiguous amino acid deletions relative to amino acids 9-50, amino acids 55-91, or amino acids 95-146 of SEQ ID NO: 22. In other aspects of this embodiment, a Clostridial botulinum serotype D HA-17 comprising a β-trefoil domain with enhanced binding activity comprises a polypeptide having, e.g., at least one, two, three, four, five, six, seven, eight, nine, 10 or 20 non-contiguous amino acid deletions relative to amino acids 9-50, amino acids 55-91, or amino acids 95-146 of SEQ ID NO: 22. In still other aspects of this embodiment, a Clostridial botulinum serotype D HA-17 comprising a β-trefoil domain with enhanced binding activity comprises a polypeptide having, e.g., at most one, two, three, four, five, six, seven, eight, nine, 10 or 20 non-contiguous amino acid additions relative to amino acids 9-50, amino acids 55-91, or amino acids 95-146 of SEQ ID NO: 22. In other aspects of this embodiment, a Clostridial botulinum serotype D HA-17 comprising a β-trefoil domain with enhanced binding activity comprises a polypeptide having, e.g., at least one, two, three, four, five, six, seven, eight, nine, 10 or 20 non-contiguous amino acid additions relative to amino acids 9-50, amino acids 55-91, or amino acids 95-146 of SEQ ID NO: 22.

In other aspects of this embodiment, a Clostridial botulinum serotype D HA-17 comprising a β-trefoil domain with enhanced binding activity comprises a polypeptide having, e.g., at most one, two, three, four, five, six, seven, eight, nine, 10 or 20 contiguous amino acid substitutions relative to amino acids 9-50, amino acids 55-91, or amino acids 95-146 of SEQ ID NO: 22. In other aspects of this embodiment, a Clostridial botulinum serotype D HA-17 comprising a β-trefoil domain with enhanced binding activity comprises a polypeptide having, e.g., at least one, two, three, four, five, six, seven, eight, nine, 10 or 20 contiguous amino acid substitutions relative to amino acids 9-50, amino acids 55-91, or amino acids 95-146 of SEQ ID NO: 22. In yet other aspects of this embodiment, a Clostridial botulinum serotype D HA-17 comprising a β-trefoil domain with enhanced binding activity comprises a polypeptide having, e.g., at most one, two, three, four, five, six, seven, eight, nine, 10 or 20 contiguous amino acid deletions relative to amino acids 9-50, amino acids 55-91, or amino acids 95-146 of SEQ ID NO: 22. In other aspects of this embodiment, a Clostridial botulinum serotype D HA-17 comprising a β-trefoil domain with enhanced binding activity comprises a polypeptide having, e.g., at least one, two, three, four, five, six, seven, eight, nine, 10 or 20 contiguous amino acid deletions relative to amino acids 9-50, amino acids 55-91, or amino acids 95-146 of SEQ ID NO: 22. In still other aspects of this embodiment, a Clostridial botulinum serotype D HA-17 comprising a β-trefoil domain with enhanced binding activity comprises a polypeptide having, e.g., at most one, two, three, four, five, six, seven, eight, nine, 10 or 20 contiguous amino acid additions relative to amino acids 9-50, amino acids 55-91, or amino acids 95-146 of SEQ ID NO: 22. In other aspects of this embodiment, a Clostridial botulinum serotype D HA-17 comprising a β-trefoil domain with enhanced binding activity comprises a polypeptide having, e.g., at least one, two, three, four, five, six, seven, eight, nine, 10 or 20 contiguous amino acid additions relative to amino acids 9-50, amino acids 55-91, or amino acids 95-146 of SEQ ID NO: 22.

In another embodiment, a β-trefoil domain derived from a Clostridial botulinum serotype D HA-17 comprises a β4/β5 hairpin turn of a β-trefoil domain of a Clostridial botulinum serotype D HA-17 or a β8/β9 hairpin turn of a β-trefoil domain of a Clostridial botulinum serotype D HA-17 of SEQ ID NO: 22. In another aspect of this embodiment, a β-trefoil domain derived from a Clostridial botulinum serotype D HA-17 comprises amino acids 51-54 or amino acids 92-94 of SEQ ID NO: 22.

In another embodiment, a β-trefoil domain with enhanced binding activity derived from a Clostridial botulinum serotype D HA-17 comprises a modified β4/β5 hairpin turn of a β-trefoil domain of a Clostridial botulinum serotype D HA-17 or a modified β8/β9 hairpin turn of a β-trefoil domain of a Clostridial botulinum serotype D HA-17 of SEQ ID NO: 22. In another aspect of this embodiment, a β-trefoil domain with enhanced binding activity derived from a Clostridial botulinum serotype D HA-17 comprises a modification of amino acids 51-54 or amino acids 92-94 of SEQ ID NO: 22.

In other aspects of this embodiment, a β-trefoil domain with enhanced binding activity derived from a Clostridial botulinum serotype D HA-17 comprises a polypeptide having, e.g., at least 70% amino acid identity with amino acids 51-54 or amino acids 92-94 of SEQ ID NO: 22, at least 75% amino acid identity with amino acids 51-54 or amino acids 92-94 of SEQ ID NO: 22, at least 80% amino acid identity with amino acids 51-54 or amino acids 92-94 of SEQ ID NO: 22, at least 85% amino acid identity with amino acids 51-54 or amino acids 92-94 of SEQ ID NO: 22, at least 90% amino acid identity with amino acids 51-54 or amino acids 92-94 of SEQ ID NO: 22 or at least 95% amino acid identity with amino acids 51-54 or amino acids 92-94 of SEQ ID NO: 22. In yet other aspects of this embodiment, a β-trefoil domain with enhanced binding activity derived from a Clostridial botulinum serotype D HA-17 comprises a polypeptide having, e.g., at most 70% amino acid identity with amino acids 51-54 or amino acids 92-94 of SEQ ID NO: 22, at most 75% amino acid identity with amino acids 51-54 or amino acids 92-94 of SEQ ID NO: 22, at most 80% amino acid identity with amino acids 51-54 or amino acids 92-94 of SEQ ID NO: 22, at most 85% amino acid identity with amino acids 51-54 or amino acids 92-94 of SEQ ID NO: 22, at most 90% amino acid identity with amino acids 51-54 or amino acids 92-94 of SEQ ID NO: 22 or at most 95% amino acid identity with amino acids 51-54 or amino acids 92-94 of SEQ ID NO: 22.

In other aspects of this embodiment, a β-trefoil domain with enhanced binding activity derived from a Clostridial botulinum serotype D HA-17 comprises a polypeptide having, e.g., at most one, two, three or four non-contiguous amino acid substitutions relative to amino acids 51-54 or amino acids 92-94 of SEQ ID NO: 22. In other aspects of this embodiment, a β-trefoil domain with enhanced binding activity derived from a Clostridial botulinum serotype D HA-17 comprises a polypeptide having, e.g., at least one, two, three or four non-contiguous amino acid substitutions relative to amino acids 51-54 or amino acids 92-94 of SEQ ID NO: 22. In other aspects of this embodiment, a non-contiguous amino acid substitution of any amino acid from amino acids 51-54 or amino acids 92-94 of SEQ ID NO: 22 can be replaced with glycine. In other aspects of this embodiment, a non-contiguous amino acid substitution of any hydrophobic amino acid from amino acids 51-54 or amino acids 92-94 of SEQ ID NO: 22 can be replaced with phenylalanine. In yet other aspects of this embodiment, a β-trefoil domain with enhanced binding activity derived from a Clostridial botulinum serotype D HA-17 comprises a polypeptide having, e.g., at most one, two, three or four non-contiguous amino acid deletions relative to amino acids 51-54 or amino acids 92-94 of SEQ ID NO: 22. In other aspects of this embodiment, a β-trefoil domain with enhanced binding activity derived from a Clostridial botulinum serotype D HA-17 comprises a polypeptide having, e.g., at least one, two, three or four non-contiguous amino acid deletions relative to amino acids 51-54 or amino acids 92-94 of SEQ ID NO: 22. In still other aspects of this embodiment, a β-trefoil domain with enhanced binding activity derived from a Clostridial botulinum serotype D HA-17 comprises a polypeptide having, e.g., at most one, two, three or four non-contiguous amino acid additions relative to amino acids 51-54 or amino acids 92-94 of SEQ ID NO: 22. In other aspects of this embodiment, a β-trefoil domain with enhanced binding activity derived from a Clostridial botulinum serotype D HA-17 comprises a polypeptide having, e.g., at least one, two, three or four non-contiguous amino acid additions relative to amino acids 51-54 or amino acids 92-94 of SEQ ID NO: 22.

In other aspects of this embodiment, a β-trefoil domain with enhanced binding activity derived from a Clostridial botulinum serotype D HA-17 comprises a polypeptide having, e.g., at most one, two, three or four contiguous amino acid substitutions relative to amino acids 51-54 or amino acids 92-94 of SEQ ID NO: 22. In other aspects of this embodiment, a β-trefoil domain with enhanced binding activity derived from a Clostridial botulinum serotype D HA-17 comprises a polypeptide having, e.g., at least one, two, three or four contiguous amino acid substitutions relative to amino acids 51-54 or amino acids 92-94 of SEQ ID NO: 22. In other aspects of this embodiment, contiguous amino acid substitutions of amino acids from amino acids 51-54 or amino acids 92-94 of SEQ ID NO: 22 can be replaced with glycine. In other aspects of this embodiment, contiguous amino acid substitutions of hydrophobic amino acids from amino acids 51-54 or amino acids 92-94 of SEQ ID NO: 22 can be replaced with phenylalanine. In yet other aspects of this embodiment, a β-trefoil domain with enhanced binding activity derived from a Clostridial botulinum serotype D HA-17 comprises a polypeptide having, e.g., at most one, two, three or four contiguous amino acid deletions relative to amino acids 51-54 or amino acids 92-94 of SEQ ID NO: 22. In other aspects of this embodiment, a β-trefoil domain with enhanced binding activity derived from a Clostridial botulinum serotype D HA-17 comprises a polypeptide having, e.g., at least one, two, three or four contiguous amino acid deletions relative to amino acids 51-54 or amino acids 92-94 of SEQ ID NO: 22. In still other aspects of this embodiment, a β-trefoil domain with enhanced binding activity derived from a Clostridial botulinum serotype D HA-17 comprises a polypeptide having, e.g., at most one, two, three or four contiguous amino acid additions relative to amino acids 51-54 or amino acids 92-94 of SEQ ID NO: 22. In other aspects of this embodiment, a β-trefoil domain with enhanced binding activity derived from a Clostridial botulinum serotype D HA-17 comprises a polypeptide having, e.g., at least one, two, three or four contiguous amino acid additions relative to amino acids 51-54 or amino acids 92-94 of SEQ ID NO: 22.

In an embodiment, a modified Clostridial toxin disclosed in the present specification comprises an enhanced targeting domain comprising a β-trefoil domain derived from a Clostridial NTNH. In an aspect of this embodiment, a β-trefoil domain derived from a Clostridial NTNH comprises, e.g., a β-trefoil domain derived from a Clostridial botulinum serotype A NTNH, a β-trefoil domain derived from a Clostridial botulinum serotype B NTNH, a β-trefoil domain derived from a Clostridial botulinum serotype C1 NTNH, a β-trefoil domain derived from a Clostridial botulinum serotype D NTNH, a β-trefoil domain derived from a Clostridial botulinum serotype E NTNH, a β-trefoil domain derived from a Clostridial botulinum serotype F NTNH or a β-trefoil domain derived from a Clostridial botulinum serotype G NTNH. In another aspect of this embodiment, a β-trefoil domain derived from a Clostridial NTNH comprises a α-fold motif of a β-trefoil domain of a Clostridial NTNH, a β-fold motif of a β-trefoil domain of a Clostridial NTNH or a γ-fold motif of a β-trefoil domain of a Clostridial NTNH.

In an embodiment, a modified Clostridial toxin disclosed in the present specification comprises an enhanced targeting domain comprising a β-trefoil domain with enhanced binding activity derived from a Clostridial NTNH. In an aspect of this embodiment, a β-trefoil domain with enhanced binding activity derived from a Clostridial NTNH comprises, e.g., a β-trefoil domain with enhanced binding activity derived from a Clostridial botulinum serotype A NTNH, a β-trefoil domain with enhanced binding activity derived from a Clostridial botulinum serotype B NTNH, a β-trefoil domain with enhanced binding activity derived from a Clostridial botulinum serotype C1 NTNH, a β-trefoil domain with enhanced binding activity derived from a Clostridial botulinum serotype D NTNH, a β-trefoil domain with enhanced binding activity derived from a Clostridial botulinum serotype E NTNH, a β-trefoil domain with enhanced binding activity derived from a Clostridial botulinum serotype F NTNH or, a β-trefoil domain with enhanced binding activity derived from a Clostridial botulinum serotype G NTNH. In another aspect of this embodiment, a β-trefoil domain with enhanced binding activity derived from a Clostridial NTNH comprises a modified α-fold motif of a β-trefoil domain of a Clostridial NTNH, a modified β-fold motif of a β-trefoil domain of a Clostridial NTNH or a modified γ-fold motif of a β-trefoil domain of a Clostridial NTNH.

In another embodiment, a β-trefoil domain derived from a Clostridial botulinum serotype A NTNH comprises a β-trefoil domain derived from a Clostridial botulinum serotype A NTNH of SEQ ID NO: 23. In another embodiment, a β-trefoil domain derived from a Clostridial botulinum serotype A NTNH comprises amino acids 1050-1194 of SEQ ID NO: 23. In another aspect of this embodiment, a β-trefoil domain derived from a Clostridial botulinum serotype A NTNH comprises a α-fold motif of a β-trefoil domain of a Clostridial botulinum serotype A NTNH, a β-fold motif of a β-trefoil domain of a Clostridial botulinum serotype A NTNH or a γ-fold motif of a β-trefoil domain of a Clostridial botulinum serotype A NTNH of SEQ ID NO: 23. In another aspect of this embodiment, a β-trefoil domain derived from a Clostridial botulinum serotype A NTNH comprises amino acids 1050-1097, amino acids 1111-1138, or amino acids 1149-1194 of SEQ ID NO: 23.

In another embodiment, a β-trefoil domain with enhanced binding activity derived from a Clostridial botulinum serotype A NTNH comprises a β-trefoil domain with enhanced binding activity derived from a Clostridial botulinum serotype A NTNH of SEQ ID NO: 23. In another embodiment, a 11-trefoil domain with enhanced binding activity derived from a Clostridial botulinum serotype A NTNH comprises amino acids 1050-1194 of SEQ ID NO: 23. In another aspect of this embodiment, a β-trefoil domain with enhanced binding activity derived from a Clostridial botulinum serotype A NTNH comprises a modified α-fold motif of a β-trefoil domain of a Clostridial botulinum serotype A NTNH, a modified β-fold motif of a β-trefoil domain of a Clostridial botulinum serotype A NTNH or a modified γ-fold motif of a 13-trefoil domain of a Clostridial botulinum serotype A NTNH of SEQ ID NO: 23. In another aspect of this embodiment, a β-trefoil domain with enhanced binding activity derived from a Clostridial botulinum serotype A NTNH comprises amino acids 1050-1097, amino acids 1111-1138, or amino acids 1149-1194 of SEQ ID NO: 23.

In other aspects of this embodiment, a Clostridial botulinum serotype A NTNH comprising a β-trefoil domain with enhanced binding activity comprises a polypeptide having, e.g., at least 70% amino acid identity with amino acids 1050-1097, amino acids 1111-1138, or amino acids 1149-1194 of SEQ ID NO: 23, at least 75% amino acid identity with amino acids 1050-1097, amino acids 1111-1138, or amino acids 1149-1194 of SEQ ID NO: 23, at least 80% amino acid identity with amino acids 1050-1097, amino acids 1111-1138, or amino acids 1149-1194 of SEQ ID NO: 23, at least 85% amino acid identity with amino acids 1050-1097, amino acids 1111-1138, or amino acids 1149-1194 of SEQ ID NO: 23, at least 90% amino acid identity with amino acids 1050-1097, amino acids 1111-1138, or amino acids 1149-1194 of SEQ ID NO: 23 or at least 95% amino acid identity with amino acids 1050-1097, amino acids 1111-1138, or amino acids 1149-1194 of SEQ ID NO: 23. In yet other aspects of this embodiment, a Clostridial botulinum serotype A NTNH comprising a β-trefoil domain with enhanced binding activity comprises a polypeptide having, e.g., at most 70% amino acid identity with amino acids 1050-1097, amino acids 1111-1138, or amino acids 1149-1194 of SEQ ID NO: 23, at most 75% amino acid identity with amino acids 1050-1097, amino acids 1111-1138, or amino acids 1149-1194 of SEQ ID NO: 23, at most 80% amino acid identity with amino acids 1050-1097, amino acids 1111-1138, or amino acids 1149-1194 of SEQ ID NO: 23, at most 85% amino acid identity with amino acids 1050-1097, amino acids 1111-1138, or amino acids 1149-1194 of SEQ ID NO: 23, at most 90% amino acid identity with amino acids 1050-1097, amino acids 1111-1138, or amino acids 1149-1194 of SEQ ID NO: 23 or at most 95% amino acid identity with amino acids 1050-1097, amino acids 1111-1138, or amino acids 1149-1194 of SEQ ID NO: 23.

In other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 non-contiguous amino acid substitutions relative to amino acids 1050-1097, amino acids 1111-1138, or amino acids 1149-1194 of SEQ ID NO: 23. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1050-1097, amino acids 1111-1138, or amino acids 1149-1194 of SEQ ID NO: 23. In yet other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1050-1097, amino acids 1111-1138, or amino acids 1149-1194 of SEQ ID NO: 23. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1050-1097, amino acids 1111-1138, or amino acids 1149-1194 of SEQ ID NO: 23. In still other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1050-1097, amino acids 1111-1138, or amino acids 1149-1194 of SEQ ID NO: 23. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1050-1097, amino acids 1111-1138, or amino acids 1149-1194 of SEQ ID NO: 23.

In other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1050-1097, amino acids 1111-1138, or amino acids 1149-1194 of SEQ ID NO: 23. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1050-1097, amino acids 1111-1138, or amino acids 1149-1194 of SEQ ID NO: 23. In yet other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1050-1097, amino acids 1111-1138, or amino acids 1149-1194 of SEQ ID NO: 23. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1050-1097, amino acids 1111-1138, or amino acids 1149-1194 of SEQ ID NO: 23. In still other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid additions relative to amino acids 1050-1097, amino acids 1111-1138, or amino acids 1149-1194 of SEQ ID NO: 23. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid additions relative to amino acids 1050-1097, amino acids 1111-1138, or amino acids 1149-1194 of SEQ ID NO: 23.

In another embodiment, a β-trefoil domain derived from a Clostridial botulinum serotype A NTNH comprises a β4/β5 hairpin turn of a β-trefoil domain of a Clostridial botulinum serotype A NTNH or a β8/β9 hairpin turn of a β-trefoil domain of a Clostridial botulinum serotype A NTNH of SEQ ID NO: 23. In another aspect of this embodiment, a β-trefoil domain derived from a Clostridial botulinum serotype A NTNH comprises amino acids 1098-1110 or amino acids 1139-1148 of SEQ ID NO: 23.

In another embodiment, a β-trefoil domain with enhanced binding activity derived from a Clostridial botulinum serotype A NTNH comprises a modified β4/β5 hairpin turn of a β-trefoil domain of a Clostridial botulinum serotype A NTNH or a modified β8/β9 hairpin turn of a β-trefoil domain of a Clostridial botulinum serotype A NTNH of SEQ ID NO: 23. In another aspect of this embodiment, a β-trefoil domain with enhanced binding activity derived from a Clostridial botulinum serotype A NTNH comprises a modification of amino acids 1098-1110 or amino acids 1139-1148 of SEQ ID NO: 23.

In other aspects of this embodiment, a β-trefoil domain with enhanced binding activity derived from a Clostridial botulinum serotype A NTNH comprises a polypeptide having, e.g., at least 70% amino acid identity with amino acids 1098-1110 or amino acids 1139-1148 of SEQ ID NO: 23, at least 75% amino acid identity with amino acids 1098-1110 or amino acids 1139-1148 of SEQ ID NO: 23, at least 80% amino acid identity with amino acids 1098-1110 or amino acids 1139-1148 of SEQ ID NO: 23, at least 85% amino acid identity with amino acids 1098-1110 or amino acids 1139-1148 of SEQ ID NO: 23, at least 90% amino acid identity with amino acids 1098-1110 or amino acids 1139-1148 of SEQ ID NO: 23 or at least 95% amino acid identity with amino acids 1098-1110 or amino acids 1139-1148 of SEQ ID NO: 23. In yet other aspects of this embodiment, a β-trefoil domain with enhanced binding activity derived from a Clostridial botulinum serotype A NTNH comprises a polypeptide having, e.g., at most 70% amino acid identity with amino acids 1098-1110 or amino acids 1139-1148 of SEQ ID NO: 23, at most 75% amino acid identity with amino acids 1098-1110 or amino acids 1139-1148 of SEQ ID NO: 23, at most 80% amino acid identity with amino acids 1098-1110 or amino acids 1139-1148 of SEQ ID NO: 23, at most 85% amino acid identity with amino acids 1098-1110 or amino acids 1139-1148 of SEQ ID NO: 23, at most 90% amino acid identity with amino acids 1098-1110 or amino acids 1139-1148 of SEQ ID NO: 23 or at most 95% amino acid identity with amino acids 1098-1110 or amino acids 1139-1148 of SEQ ID NO: 23.

In other aspects of this embodiment, a β-trefoil domain with enhanced binding activity derived from a Clostridial botulinum serotype A NTNH comprises a polypeptide having, e.g., at most one, two, three or four non-contiguous amino acid substitutions relative to amino acids 1098-1110 or amino acids 1139-1148 of SEQ ID NO: 23. In other aspects of this embodiment, a β-trefoil domain with enhanced binding activity derived from a Clostridial botulinum serotype A NTNH comprises a polypeptide having, e.g., at least one, two, three or four non-contiguous amino acid substitutions relative to amino acids 1098-1110 or amino acids 1139-1148 of SEQ ID NO: 23. In other aspects of this embodiment, a non-contiguous amino acid substitution of any amino acid from amino acids 1098-1110 or amino acids 1139-1148 of SEQ ID NO: 23 can be replaced with glycine. In other aspects of this embodiment, a non-contiguous amino acid substitution of any hydrophobic amino acid from amino acids 1098-1110 or amino acids 1139-1148 of SEQ ID NO: 23 can be replaced with phenylalanine. In yet other aspects of this embodiment, a β-trefoil domain with enhanced binding activity derived from a Clostridial botulinum serotype A NTNH comprises a polypeptide having, e.g., at most one, two, three or four non-contiguous amino acid deletions relative to amino acids 1098-1110 or amino acids 1139-1148 of SEQ ID NO: 23. In other aspects of this embodiment, a β-trefoil domain with enhanced binding activity derived from a Clostridial botulinum serotype A NTNH comprises a polypeptide having, e.g., at least one, two, three or four non-contiguous amino acid deletions relative to amino acids 1098-1110 or amino acids 1139-1148 of SEQ ID NO: 23. In still other aspects of this embodiment, a β-trefoil domain with enhanced binding activity derived from a Clostridial botulinum serotype A NTNH comprises a polypeptide having, e.g., at most one, two, three or four non-contiguous amino acid additions relative to amino acids 1098-1110 or amino acids 1139-1148 of SEQ ID NO: 23. In other aspects of this embodiment, a β-trefoil domain with enhanced binding activity derived from a Clostridial botulinum serotype A NTNH comprises a polypeptide having, e.g., at least one, two, three or four non-contiguous amino acid additions relative to amino acids 1098-1110 or amino acids 1139-1148 of SEQ ID NO: 23.

In other aspects of this embodiment, a β-trefoil domain with enhanced binding activity derived from a Clostridial botulinum serotype A NTNH comprises a polypeptide having, e.g., at most one, two, three or four contiguous amino acid substitutions relative to amino acids 1098-1110 or amino acids 1139-1148 of SEQ ID NO: 23. In other aspects of this embodiment, a β-trefoil domain with enhanced binding activity derived from a Clostridial botulinum serotype A NTNH comprises a polypeptide having, e.g., at least one, two, three or four contiguous amino acid substitutions relative to amino acids 1098-1110 or amino acids 1139-1148 of SEQ ID NO: 23. In other aspects of this embodiment, contiguous amino acid substitutions of amino acids from amino acids 1098-1110 or amino acids 1139-1148 of SEQ ID NO: 23 can be replaced with glycine. In other aspects of this embodiment, contiguous amino acid substitutions of hydrophobic amino acids from amino acids 1098-1110 or amino acids 1139-1148 of SEQ ID NO: 23 can be replaced with phenylalanine. In yet other aspects of this embodiment, a β-trefoil domain with enhanced binding activity derived from a Clostridial botulinum serotype A NTNH comprises a polypeptide having, e.g., at most one, two, three or four contiguous amino acid deletions relative to amino acids 1098-1110 or amino acids 1139-1148 of SEQ ID NO: 23. In other aspects of this embodiment, a β-trefoil domain with enhanced binding activity derived from a Clostridial botulinum serotype A NTNH comprises a polypeptide having, e.g., at least one, two, three or four contiguous amino acid deletions relative to amino acids 1098-1110 or amino acids 1139-1148 of SEQ ID NO: 23. In still other aspects of this embodiment, a β-trefoil domain with enhanced binding activity derived from a Clostridial botulinum serotype A NTNH comprises a polypeptide having, e.g., at most one, two, three or four contiguous amino acid additions relative to amino acids 1098-1110 or amino acids 1139-1148 of SEQ ID NO: 23. In other aspects of this embodiment, a β-trefoil domain with enhanced binding activity derived from a Clostridial botulinum serotype A NTNH comprises a polypeptide having, e.g., at least one, two, three or four contiguous amino acid additions relative to amino acids 1098-1110 or amino acids 1139-1148 of SEQ ID NO: 23.

In another embodiment, a β-trefoil domain derived from a Clostridial botulinum serotype A NTNH comprises a β-trefoil domain derived from a Clostridial botulinum serotype A NTNH of SEQ ID NO: 24. In another embodiment, a β-trefoil domain derived from a Clostridial botulinum serotype A NTNH comprises amino acids 1050-1194 of SEQ ID NO: 24. In another aspect of this embodiment, a β-trefoil domain derived from a Clostridial botulinum serotype A NTNH comprises a α-fold motif of a β-trefoil domain of a Clostridial botulinum serotype A NTNH, a β-fold motif of a β-trefoil domain of a Clostridial botulinum serotype A NTNH or a γ-fold motif of a β-trefoil domain of a Clostridial botulinum serotype A NTNH of SEQ ID NO: 24. In another aspect of this embodiment, a β-trefoil domain derived from a Clostridial botulinum serotype A NTNH comprises amino acids 1050-1097, amino acids 1111-1139, or amino acids 1149-1199 of SEQ ID NO: 24.

In another embodiment, a β-trefoil domain with enhanced binding activity derived from a Clostridial botulinum serotype A NTNH comprises a β-trefoil domain with enhanced binding activity derived from a Clostridial botulinum serotype A NTNH of SEQ ID NO: 24. In another embodiment, a β-trefoil domain with enhanced binding activity derived from a Clostridial botulinum serotype A NTNH comprises amino acids 1050-1194 of SEQ ID NO: 24. In another aspect of this embodiment, a β-trefoil domain with enhanced binding activity derived from a Clostridial botulinum serotype A NTNH comprises a modified α-fold motif of a β-trefoil domain of a Clostridial botulinum serotype A NTNH, a modified β-fold motif of a β-trefoil domain of a Clostridial botulinum serotype A NTNH or a modified γ-fold motif of a 13-trefoil domain of a Clostridial botulinum serotype A NTNH of SEQ ID NO: 24. In another aspect of this embodiment, a β-trefoil domain with enhanced binding activity derived from a Clostridial botulinum serotype A NTNH comprises amino acids 1050-1097, amino acids 1111-1139, or amino acids 1149-1199 of SEQ ID NO: 24.

In other aspects of this embodiment, a Clostridial botulinum serotype A NTNH comprising a β-trefoil domain with enhanced binding activity comprises a polypeptide having, e.g., at least 70% amino acid identity with amino acids 1050-1097, amino acids 1111-1139, or amino acids 1149-1199 of SEQ ID NO: 24, at least 75% amino acid identity with amino acids 1050-1097, amino acids 1111-1139, or amino acids 1149-1199 of SEQ ID NO: 24, at least 80% amino acid identity with amino acids 1050-1097, amino acids 1111-1139, or amino acids 1149-1199 of SEQ ID NO: 24, at least 85% amino acid identity with amino acids 1050-1097, amino acids 1111-1139, or amino acids 1149-1199 of SEQ ID NO: 24, at least 90% amino acid identity with amino acids 1050-1097, amino acids 1111-1139, or amino acids 1149-1199 of SEQ ID NO: 24 or at least 95% amino acid identity with amino acids 1050-1097, amino acids 1111-1139, or amino acids 1149-1199 of SEQ ID NO: 24. In yet other aspects of this embodiment, a Clostridial botulinum serotype A NTNH comprising a β-trefoil domain with enhanced binding activity comprises a polypeptide having, e.g., at most 70% amino acid identity with amino acids 1050-1097, amino acids 1111-1139, or amino acids 1149-1199 of SEQ ID NO: 24, at most 75% amino acid identity with amino acids 1050-1097, amino acids 1111-1139, or amino acids 1149-1199 of SEQ ID NO: 24, at most 80% amino acid identity with amino acids 1050-1097, amino acids 1111-1139, or amino acids 1149-1199 of SEQ ID NO: 24, at most 85% amino acid identity with amino acids 1050-1097, amino acids 1111-1139, or amino acids 1149-1199 of SEQ ID NO: 24, at most 90% amino acid identity with amino acids 1050-1097, amino acids 1111-1139, or amino acids 1149-1199 of SEQ ID NO: 24 or at most 95% amino acid identity with amino acids 1050-1097, amino acids 1111-1139, or amino acids 1149-1199 of SEQ ID NO: 24.

In other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 non-contiguous amino acid substitutions relative to amino acids 1050-1097, amino acids 1111-1139, or amino acids 1149-1199 of SEQ ID NO: 24. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1050-1097, amino acids 1111-1139, or amino acids 1149-1199 of SEQ ID NO: 24. In yet other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1050-1097, amino acids 1111-1139, or amino acids 1149-1199 of SEQ ID NO: 24. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1050-1097, amino acids 1111-1139, or amino acids 1149-1199 of SEQ ID NO: 24. In still other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1050-1097, amino acids 1111-1139, or amino acids 1149-1199 of SEQ ID NO: 24. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1050-1097, amino acids 1111-1139, or amino acids 1149-1199 of SEQ ID NO: 24.

In other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1050-1097, amino acids 1111-1139, or amino acids 1149-1199 of SEQ ID NO: 24. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1050-1097, amino acids 1111-1139, or amino acids 1149-1199 of SEQ ID NO: 24. In yet other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1050-1097, amino acids 1111-1139, or amino acids 1149-1199 of SEQ ID NO: 24. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1050-1097, amino acids 1111-1139, or amino acids 1149-1199 of SEQ ID NO: 24. In still other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid additions relative to amino acids 1050-1097, amino acids 1111-1139, or amino acids 1149-1199 of SEQ ID NO: 24. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid additions relative to amino acids 1050-1097, amino acids 1111-1139, or amino acids 1149-1199 of SEQ ID NO: 24.

In another embodiment, a β-trefoil domain derived from a Clostridial botulinum serotype A NTNH comprises a β4/β5 hairpin turn of a β-trefoil domain of a Clostridial botulinum serotype A NTNH or a β8/β9 hairpin turn of a β-trefoil domain of a Clostridial botulinum serotype A NTNH of SEQ ID NO: 24. In another aspect of this embodiment, a β-trefoil domain derived from a Clostridial botulinum serotype A NTNH comprises amino acids 1098-1110 or amino acids 1140-1148 of SEQ ID NO: 24.

In another embodiment, a β-trefoil domain with enhanced binding activity derived from a Clostridial botulinum serotype A NTNH comprises a modified β4/β5 hairpin turn of a β-trefoil domain of a Clostridial botulinum serotype A NTNH or a modified β8/β9 hairpin turn of a β-trefoil domain of a Clostridial botulinum serotype A NTNH of SEQ ID NO: 24. In another aspect of this embodiment, a β-trefoil domain with enhanced binding activity derived from a Clostridial botulinum serotype A NTNH comprises a modification of amino acids 1098-1110 or amino acids 1140-1148 of SEQ ID NO: 24.

In other aspects of this embodiment, a β-trefoil domain with enhanced binding activity derived from a Clostridial botulinum serotype A NTNH comprises a polypeptide having, e.g., at least 70% amino acid identity with amino acids 1098-1110 or amino acids 1140-1148 of SEQ ID NO: 24, at least 75% amino acid identity with amino acids 1098-1110 or amino acids 1140-1148 of SEQ ID NO: 24, at least 80% amino acid identity with amino acids 1098-1110 or amino acids 1140-1148 of SEQ ID NO: 24, at least 85% amino acid identity with amino acids 1098-1110 or amino acids 1140-1148 of SEQ ID NO: 24, at least 90% amino acid identity with amino acids 1098-1110 or amino acids 1140-1148 of SEQ ID NO: 24 or at least 95% amino acid identity with amino acids 1098-1110 or amino acids 1140-1148 of SEQ ID NO: 24. In yet other aspects of this embodiment, a β-trefoil domain with enhanced binding activity derived from a Clostridial botulinum serotype A NTNH comprises a polypeptide having, e.g., at most 70% amino acid identity with amino acids 1098-1110 or amino acids 1140-1148 of SEQ ID NO: 24, at most 75% amino acid identity with amino acids 1098-1110 or amino acids 1140-1148 of SEQ ID NO: 24, at most 80% amino acid identity with amino acids 1098-1110 or amino acids 1140-1148 of SEQ ID NO: 24, at most 85% amino acid identity with amino acids 1098-1110 or amino acids 1140-1148 of SEQ ID NO: 24, at most 90% amino acid identity with amino acids 1098-1110 or amino acids 1140-1148 of SEQ ID NO: 24 or at most 95% amino acid identity with amino acids 1098-1110 or amino acids 1140-1148 of SEQ ID NO: 24.

In other aspects of this embodiment, a β-trefoil domain with enhanced binding activity derived from a Clostridial botulinum serotype A NTNH comprises a polypeptide having, e.g., at most one, two, three or four non-contiguous amino acid substitutions relative to amino acids 1098-1110 or amino acids 1140-1148 of SEQ ID NO: 24. In other aspects of this embodiment, a β-trefoil domain with enhanced binding activity derived from a Clostridial botulinum serotype A NTNH comprises a polypeptide having, e.g., at least one, two, three or four non-contiguous amino acid substitutions relative to amino acids 1098-1110 or amino acids 1140-1148 of SEQ ID NO: 24. In other aspects of this embodiment, a non-contiguous amino acid substitution of any amino acid from amino acids 1098-1110 or amino acids 1140-1148 of SEQ ID NO: 24 can be replaced with glycine. In other aspects of this embodiment, a non-contiguous amino acid substitution of any hydrophobic amino acid from amino acids 1098-1110 or amino acids 1140-1148 of SEQ ID NO: 24 can be replaced with phenylalanine. In yet other aspects of this embodiment, a β-trefoil domain with enhanced binding activity derived from a Clostridial botulinum serotype A NTNH comprises a polypeptide having, e.g., at most one, two, three or four non-contiguous amino acid deletions relative to amino acids 1098-1110 or amino acids 1140-1148 of SEQ ID NO: 24. In other aspects of this embodiment, a β-trefoil domain with enhanced binding activity derived from a Clostridial botulinum serotype A NTNH comprises a polypeptide having, e.g., at least one, two, three or four non-contiguous amino acid deletions relative to amino acids 1098-1110 or amino acids 1140-1148 of SEQ ID NO: 24. In still other aspects of this embodiment, a β-trefoil domain with enhanced binding activity derived from a Clostridial botulinum serotype A NTNH comprises a polypeptide having, e.g., at most one, two, three or four non-contiguous amino acid additions relative to amino acids 1098-1110 or amino acids 1140-1148 of SEQ ID NO: 24. In other aspects of this embodiment, a β-trefoil domain with enhanced binding activity derived from a Clostridial botulinum serotype A NTNH comprises a polypeptide having, e.g., at least one, two, three or four non-contiguous amino acid additions relative to amino acids 1098-1110 or amino acids 1140-1148 of SEQ ID NO: 24.

In other aspects of this embodiment, a β-trefoil domain with enhanced binding activity derived from a Clostridial botulinum serotype A NTNH comprises a polypeptide having, e.g., at most one, two, three or four contiguous amino acid substitutions relative to amino acids 1098-1110 or amino acids 1140-1148 of SEQ ID NO: 24. In other aspects of this embodiment, a β-trefoil domain with enhanced binding activity derived from a Clostridial botulinum serotype A NTNH comprises a polypeptide having, e.g., at least one, two, three or four contiguous amino acid substitutions relative to amino acids 1098-1110 or amino acids 1140-1148 of SEQ ID NO: 24. In other aspects of this embodiment, contiguous amino acid substitutions of amino acids from amino acids 1098-1110 or amino acids 1140-1148 of SEQ ID NO: 24 can be replaced with glycine. In other aspects of this embodiment, contiguous amino acid substitutions of hydrophobic amino acids from amino acids 1098-1110 or amino acids 1140-1148 of SEQ ID NO: 24 can be replaced with phenylalanine. In yet other aspects of this embodiment, a β-trefoil domain with enhanced binding activity derived from a Clostridial botulinum serotype A NTNH comprises a polypeptide having, e.g., at most one, two, three or four contiguous amino acid deletions relative to amino acids 1098-1110 or amino acids 1140-1148 of SEQ ID NO: 24. In other aspects of this embodiment, a β-trefoil domain with enhanced binding activity derived from a Clostridial botulinum serotype A NTNH comprises a polypeptide having, e.g., at least one, two, three or four contiguous amino acid deletions relative to amino acids 1098-1110 or amino acids 1140-1148 of SEQ ID NO: 24. In still other aspects of this embodiment, a β-trefoil domain with enhanced binding activity derived from a Clostridial botulinum serotype A NTNH comprises a polypeptide having, e.g., at most one, two, three or four contiguous amino acid additions relative to amino acids 1098-1110 or amino acids 1140-1148 of SEQ ID NO: 24. In other aspects of this embodiment, a β-trefoil domain with enhanced binding activity derived from a Clostridial botulinum serotype A NTNH comprises a polypeptide having, e.g., at least one, two, three or four contiguous amino acid additions relative to amino acids 1098-1110 or amino acids 1140-1148 of SEQ ID NO: 24.

In another embodiment, a β-trefoil domain derived from a Clostridial botulinum serotype A NTNH comprises a β-trefoil domain derived from a Clostridial botulinum serotype A NTNH of SEQ ID NO: 25. In another embodiment, a β-trefoil domain derived from a Clostridial botulinum serotype A NTNH comprises amino acids 1050-1194 of SEQ ID NO: 25. In another aspect of this embodiment, a β-trefoil domain derived from a Clostridial botulinum serotype A NTNH comprises a α-fold motif of a β-trefoil domain of a Clostridial botulinum serotype A NTNH, a β-fold motif of a β-trefoil domain of a Clostridial botulinum serotype A NTNH or a γ-fold motif of a β-trefoil domain of a Clostridial botulinum serotype A NTNH of SEQ ID NO: 25. In another aspect of this embodiment, a β-trefoil domain derived from a Clostridial botulinum serotype A NTNH comprises amino acids 1050-1097, amino acids 1111-1138, or amino acids 1149-1194 of SEQ ID NO: 25.

In another embodiment, a β-trefoil domain with enhanced binding activity derived from a Clostridial botulinum serotype A NTNH comprises a β-trefoil domain with enhanced binding activity derived from a Clostridial botulinum serotype A NTNH of SEQ ID NO: 25. In another embodiment, a β-trefoil domain with enhanced binding activity derived from a Clostridial botulinum serotype A NTNH comprises amino acids 1050-1194 of SEQ ID NO: 25. In another aspect of this embodiment, a β-trefoil domain with enhanced binding activity derived from a Clostridial botulinum serotype A NTNH comprises a modified α-fold motif of a β-trefoil domain of a Clostridial botulinum serotype A NTNH, a modified β-fold motif of a β-trefoil domain of a Clostridial botulinum serotype A NTNH or a modified γ-fold motif of a 13-trefoil domain of a Clostridial botulinum serotype A NTNH of SEQ ID NO: 25. In another aspect of this embodiment, a β-trefoil domain with enhanced binding activity derived from a Clostridial botulinum serotype A NTNH comprises amino acids 1050-1097, amino acids 1111-1138, or amino acids 1149-1194 of SEQ ID NO: 25.

In other aspects of this embodiment, a Clostridial botulinum serotype A NTNH comprising a β-trefoil domain with enhanced binding activity comprises a polypeptide having, e.g., at least 70% amino acid identity with amino acids 1050-1097, amino acids 1111-1138, or amino acids 1149-1194 of SEQ ID NO: 25, at least 75% amino acid identity with amino acids 1050-1097, amino acids 1111-1138, or amino acids 1149-1194 of SEQ ID NO: 25, at least 80% amino acid identity with amino acids 1050-1097, amino acids 1111-1138, or amino acids 1149-1194 of SEQ ID NO: 25, at least 85% amino acid identity with amino acids 1050-1097, amino acids 1111-1138, or amino acids 1149-1194 of SEQ ID NO: 25, at least 90% amino acid identity with amino acids 1050-1097, amino acids 1111-1138, or amino acids 1149-1194 of SEQ ID NO: 25 or at least 95% amino acid identity with amino acids 1050-1097, amino acids 1111-1138, or amino acids 1149-1194 of SEQ ID NO: 25. In yet other aspects of this embodiment, a Clostridial botulinum serotype A NTNH comprising a β-trefoil domain with enhanced binding activity comprises a polypeptide having, e.g., at most 70% amino acid identity with amino acids 1050-1097, amino acids 1111-1138, or amino acids 1149-1194 of SEQ ID NO: 25, at most 75% amino acid identity with amino acids 1050-1097, amino acids 1111-1138, or amino acids 1149-1194 of SEQ ID NO: 25, at most 80% amino acid identity with amino acids 1050-1097, amino acids 1111-1138, or amino acids 1149-1194 of SEQ ID NO: 25, at most 85% amino acid identity with amino acids 1050-1097, amino acids 1111-1138, or amino acids 1149-1194 of SEQ ID NO: 25, at most 90% amino acid identity with amino acids 1050-1097, amino acids 1111-1138, or amino acids 1149-1194 of SEQ ID NO: 25 or at most 95% amino acid identity with amino acids 1050-1097, amino acids 1111-1138, or amino acids 1149-1194 of SEQ ID NO: 25.

In other aspects of this embodiment, a Clostridial botulinum serotype A NTNH comprising a 11-trefoil domain with enhanced binding activity comprises a polypeptide having, e.g., at most one, two, three, four, five, six, seven, eight, nine, 10 or 20 non-contiguous amino acid substitutions relative to amino acids 1050-1097, amino acids 1111-1138, or amino acids 1149-1194 of SEQ ID NO: 25. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1050-1097, amino acids 1111-1138, or amino acids 1149-1194 of SEQ ID NO: 25. In yet other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1050-1097, amino acids 1111-1138, or amino acids 1149-1194 of SEQ ID NO: 25. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1050-1097, amino acids 1111-1138, or amino acids 1149-1194 of SEQ ID NO: 25. In still other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1050-1097, amino acids 1111-1138, or amino acids 1149-1194 of SEQ ID NO: 25. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1050-1097, amino acids 1111-1138, or amino acids 1149-1194 of SEQ ID NO: 25.

In other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1050-1097, amino acids 1111-1138, or amino acids 1149-1194 of SEQ ID NO: 25. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1050-1097, amino acids 1111-1138, or amino acids 1149-1194 of SEQ ID NO: 25. In yet other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1050-1097, amino acids 1111-1138, or amino acids 1149-1194 of SEQ ID NO: 25. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1050-1097, amino acids 1111-1138, or amino acids 1149-1194 of SEQ ID NO: 25. In still other aspects of this embodiment, a Clostridial botulinum serotype A NTNH comprising a β-trefoil domain with enhanced binding activity comprises a polypeptide having, e.g., at most one, two, three, four, five, six, seven, eight, nine, 10 or 20 contiguous amino acid additions relative to amino acids 1050-1097, amino acids 1111-1138, or amino acids 1149-1194 of SEQ ID NO: 25. In other aspects of this embodiment, a Clostridial botulinum serotype A NTNH comprising a β-trefoil domain with enhanced binding activity comprises a polypeptide having, e.g., at least one, two, three, four, five, six, seven, eight, nine, 10 or 20 contiguous amino acid additions relative to amino acids 1050-1097, amino acids 1111-1138, or amino acids 1149-1194 of SEQ ID NO: 25.

In another embodiment, a β-trefoil domain derived from a Clostridial botulinum serotype A NTNH comprises a β4/β5 hairpin turn of a β-trefoil domain of a Clostridial botulinum serotype A NTNH or a β8/β9 hairpin turn of a β-trefoil domain of a Clostridial botulinum serotype A NTNH of SEQ ID NO: 25. In another aspect of this embodiment, a β-trefoil domain derived from a Clostridial botulinum serotype A NTNH comprises amino acids 1098-1110 or amino acids 1139-1148 of SEQ ID NO: 25.

In another embodiment, a β-trefoil domain with enhanced binding activity derived from a Clostridial botulinum serotype A NTNH comprises a modified β4/β5 hairpin turn of a β-trefoil domain of a Clostridial botulinum serotype A NTNH or a modified β8/β9 hairpin turn of a β-trefoil domain of a Clostridial botulinum serotype A NTNH of SEQ ID NO: 25. In another aspect of this embodiment, a β-trefoil domain with enhanced binding activity derived from a Clostridial botulinum serotype A NTNH comprises a modification of amino acids 1098-1110 or amino acids 1139-1148 of SEQ ID NO: 25.

In other aspects of this embodiment, a β-trefoil domain with enhanced binding activity derived from a Clostridial botulinum serotype A NTNH comprises a polypeptide having, e.g., at least 70% amino acid identity with amino acids 1098-1110 or amino acids 1139-1148 of SEQ ID NO: 25, at least 75% amino acid identity with amino acids 1098-1110 or amino acids 1139-1148 of SEQ ID NO: 25, at least 80% amino acid identity with amino acids 1098-1110 or amino acids 1139-1148 of SEQ ID NO: 25, at least 85% amino acid identity with amino acids 1098-1110 or amino acids 1139-1148 of SEQ ID NO: 25, at least 90% amino acid identity with amino acids 1098-1110 or amino acids 1139-1148 of SEQ ID NO: 25 or at least 95% amino acid identity with amino acids 1098-1110 or amino acids 1139-1148 of SEQ ID NO: 25. In yet other aspects of this embodiment, a β-trefoil domain with enhanced binding activity derived from a Clostridial botulinum serotype A NTNH comprises a polypeptide having, e.g., at most 70% amino acid identity with amino acids 1098-1110 or amino acids 1139-1148 of SEQ ID NO: 25, at most 75% amino acid identity with amino acids 1098-1110 or amino acids 1139-1148 of SEQ ID NO: 25, at most 80% amino acid identity with amino acids 1098-1110 or amino acids 1139-1148 of SEQ ID NO: 25, at most 85% amino acid identity with amino acids 1098-1110 or amino acids 1139-1148 of SEQ ID NO: 25, at most 90% amino acid identity with amino acids 1098-1110 or amino acids 1139-1148 of SEQ ID NO: 25 or at most 95% amino acid identity with amino acids 1098-1110 or amino acids 1139-1148 of SEQ ID NO: 25.

In other aspects of this embodiment, a β-trefoil domain with enhanced binding activity derived from a Clostridial botulinum serotype A NTNH comprises a polypeptide having, e.g., at most one, two, three or four non-contiguous amino acid substitutions relative to amino acids 1098-1110 or amino acids 1139-1148 of SEQ ID NO: 25. In other aspects of this embodiment, a β-trefoil domain with enhanced binding activity derived from a Clostridial botulinum serotype A NTNH comprises a polypeptide having, e.g., at least one, two, three or four non-contiguous amino acid substitutions relative to amino acids 1098-1110 or amino acids 1139-1148 of SEQ ID NO: 25. In other aspects of this embodiment, a non-contiguous amino acid substitution of any amino acid from amino acids 1098-1110 or amino acids 1139-1148 of SEQ ID NO: 25 can be replaced with glycine. In other aspects of this embodiment, a non-contiguous amino acid substitution of any hydrophobic amino acid from amino acids 1098-1110 or amino acids 1139-1148 of SEQ ID NO: 25 can be replaced with phenylalanine. In yet other aspects of this embodiment, a β-trefoil domain with enhanced binding activity derived from a Clostridial botulinum serotype A NTNH comprises a polypeptide having, e.g., at most one, two, three or four non-contiguous amino acid deletions relative to amino acids 1098-1110 or amino acids 1139-1148 of SEQ ID NO: 25. In other aspects of this embodiment, a β-trefoil domain with enhanced binding activity derived from a Clostridial botulinum serotype A NTNH comprises a polypeptide having, e.g., at least one, two, three or four non-contiguous amino acid deletions relative to amino acids 1098-1110 or amino acids 1139-1148 of SEQ ID NO: 25. In still other aspects of this embodiment, a β-trefoil domain with enhanced binding activity derived from a Clostridial botulinum serotype A NTNH comprises a polypeptide having, e.g., at most one, two, three or four non-contiguous amino acid additions relative to amino acids 1098-1110 or amino acids 1139-1148 of SEQ ID NO: 25. In other aspects of this embodiment, a β-trefoil domain with enhanced binding activity derived from a Clostridial botulinum serotype A NTNH comprises a polypeptide having, e.g., at least one, two, three or four non-contiguous amino acid additions relative to amino acids 1098-1110 or amino acids 1139-1148 of SEQ ID NO: 25.

In other aspects of this embodiment, a β-trefoil domain with enhanced binding activity derived from a Clostridial botulinum serotype A NTNH comprises a polypeptide having, e.g., at most one, two, three or four contiguous amino acid substitutions relative to amino acids 1098-1110 or amino acids 1139-1148 of SEQ ID NO: 25. In other aspects of this embodiment, a β-trefoil domain with enhanced binding activity derived from a Clostridial botulinum serotype A NTNH comprises a polypeptide having, e.g., at least one, two, three or four contiguous amino acid substitutions relative to amino acids 1098-1110 or amino acids 1139-1148 of SEQ ID NO: 25. In other aspects of this embodiment, contiguous amino acid substitutions of amino acids from amino acids 1098-1110 or amino acids 1139-1148 of SEQ ID NO: 25 can be replaced with glycine. In other aspects of this embodiment, contiguous amino acid substitutions of hydrophobic amino acids from amino acids 1098-1110 or amino acids 1139-1148 of SEQ ID NO: 25 can be replaced with phenylalanine. In yet other aspects of this embodiment, a β-trefoil domain with enhanced binding activity derived from a Clostridial botulinum serotype A NTNH comprises a polypeptide having, e.g., at most one, two, three or four contiguous amino acid deletions relative to amino acids 1098-1110 or amino acids 1139-1148 of SEQ ID NO: 25. In other aspects of this embodiment, a β-trefoil domain with enhanced binding activity derived from a Clostridial botulinum serotype A NTNH comprises a polypeptide having, e.g., at least one, two, three or four contiguous amino acid deletions relative to amino acids 1098-1110 or amino acids 1139-1148 of SEQ ID NO: 25. In still other aspects of this embodiment, a β-trefoil domain with enhanced binding activity derived from a Clostridial botulinum serotype A NTNH comprises a polypeptide having, e.g., at most one, two, three or four contiguous amino acid additions relative to amino acids 1098-1110 or amino acids 1139-1148 of SEQ ID NO: 25. In other aspects of this embodiment, a β-trefoil domain with enhanced binding activity derived from a Clostridial botulinum serotype A NTNH comprises a polypeptide having, e.g., at least one, two, three or four contiguous amino acid additions relative to amino acids 1098-1110 or amino acids 1139-1148 of SEQ ID NO: 25.

In another embodiment, a β-trefoil domain derived from a Clostridial botulinum serotype B NTNH comprises a β-trefoil domain derived from a Clostridial botulinum serotype B NTNH of SEQ ID NO: 26. In another embodiment, a β-trefoil domain derived from a Clostridial botulinum serotype B NTNH comprises amino acids 1049-1198 of SEQ ID NO: 26. In another aspect of this embodiment, a β-trefoil domain derived from a Clostridial botulinum serotype B NTNH comprises a α-fold motif of a β-trefoil domain of a Clostridial botulinum serotype B NTNH, a β-fold motif of a β-trefoil domain of a Clostridial botulinum serotype B NTNH or a γ-fold motif of a β-trefoil domain of a Clostridial botulinum serotype B NTNH of SEQ ID NO: 26. In another aspect of this embodiment, a β-trefoil domain derived from a Clostridial botulinum serotype B NTNH comprises amino acids 1049-1096, amino acids 1110-1138, or amino acids 1148-1198 of SEQ ID NO: 26.

In another embodiment, a β-trefoil domain with enhanced binding activity derived from a Clostridial botulinum serotype B NTNH comprises a β-trefoil domain with enhanced binding activity derived from a Clostridial botulinum serotype B NTNH of SEQ ID NO: 26. In another embodiment, a β-trefoil domain with enhanced binding activity derived from a Clostridial botulinum serotype B NTNH comprises amino acids 1049-1198 of SEQ ID NO: 26. In another aspect of this embodiment, a β-trefoil domain with enhanced binding activity derived from a Clostridial botulinum serotype B NTNH comprises a modified α-fold motif of a β-trefoil domain of a Clostridial botulinum serotype B NTNH, a modified β-fold motif of a β-trefoil domain of a Clostridial botulinum serotype B NTNH or a modified γ-fold motif of a 13-trefoil domain of a Clostridial botulinum serotype B NTNH of SEQ ID NO: 26. In another aspect of this embodiment, a β-trefoil domain with enhanced binding activity derived from a Clostridial botulinum serotype B NTNH comprises amino acids 1049-1096, amino acids 1110-1138, or amino acids 1148-1198 of SEQ ID NO: 26.

In other aspects of this embodiment, a Clostridial botulinum serotype B NTNH comprising a β-trefoil domain with enhanced binding activity comprises a polypeptide having, e.g., at least 70% amino acid identity with amino acids 1049-1096, amino acids 1110-1138, or amino acids 1148-1198 of SEQ ID NO: 26, at least 75% amino acid identity with amino acids 1049-1096, amino acids 1110-1138, or amino acids 1148-1198 of SEQ ID NO: 26, at least 80% amino acid identity with amino acids 1049-1096, amino acids 1110-1138, or amino acids 1148-1198 of SEQ ID NO: 26, at least 85% amino acid identity with amino acids 1049-1096, amino acids 1110-1138, or amino acids 1148-1198 of SEQ ID NO: 26, at least 90% amino acid identity with amino acids 1049-1096, amino acids 1110-1138, or amino acids 1148-1198 of SEQ ID NO: 26 or at least 95% amino acid identity with amino acids 1049-1096, amino acids 1110-1138, or amino acids 1148-1198 of SEQ ID NO: 26. In yet other aspects of this embodiment, a Clostridial botulinum serotype B NTNH comprising a β-trefoil domain with enhanced binding activity comprises a polypeptide having, e.g., at most 70% amino acid identity with amino acids 1049-1096, amino acids 1110-1138, or amino acids 1148-1198 of SEQ ID NO: 26, at most 75% amino acid identity with amino acids 1049-1096, amino acids 1110-1138, or amino acids 1148-1198 of SEQ ID NO: 26, at most 80% amino acid identity with amino acids 1049-1096, amino acids 1110-1138, or amino acids 1148-1198 of SEQ ID NO: 26, at most 85% amino acid identity with amino acids 1049-1096, amino acids 1110-1138, or amino acids 1148-1198 of SEQ ID NO: 26, at most 90% amino acid identity with amino acids 1049-1096, amino acids 1110-1138, or amino acids 1148-1198 of SEQ ID NO: 26 or at most 95% amino acid identity with amino acids 1049-1096, amino acids 1110-1138, or amino acids 1148-1198 of SEQ ID NO: 26.

In other aspects of this embodiment, a Clostridial botulinum serotype B NTNH comprising a 11-trefoil domain with enhanced binding activity comprises a polypeptide having, e.g., at most one, two, three, four, five, six, seven, eight, nine, 10 or 20 non-contiguous amino acid substitutions relative to amino acids 1049-1096, amino acids 1110-1138, or amino acids 1148-1198 of SEQ ID NO: 26. In other aspects of this embodiment, a Clostridial botulinum serotype B NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1049-1096, amino acids 1110-1138, or amino acids 1148-1198 of SEQ ID NO: 26. In yet other aspects of this embodiment, a Clostridial botulinum serotype B NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1049-1096, amino acids 1110-1138, or amino acids 1148-1198 of SEQ ID NO: 26. In other aspects of this embodiment, a Clostridial botulinum serotype B NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1049-1096, amino acids 1110-1138, or amino acids 1148-1198 of SEQ ID NO: 26. In still other aspects of this embodiment, a Clostridial botulinum serotype B NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1049-1096, amino acids 1110-1138, or amino acids 1148-1198 of SEQ ID NO: 26. In other aspects of this embodiment, a Clostridial botulinum serotype B NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1049-1096, amino acids 1110-1138, or amino acids 1148-1198 of SEQ ID NO: 26.

In other aspects of this embodiment, a Clostridial botulinum serotype B NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1049-1096, amino acids 1110-1138, or amino acids 1148-1198 of SEQ ID NO: 26. In other aspects of this embodiment, a Clostridial botulinum serotype B NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1049-1096, amino acids 1110-1138, or amino acids 1148-1198 of SEQ ID NO: 26. In yet other aspects of this embodiment, a Clostridial botulinum serotype B NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1049-1096, amino acids 1110-1138, or amino acids 1148-1198 of SEQ ID NO: 26. In other aspects of this embodiment, a Clostridial botulinum serotype B NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1049-1096, amino acids 1110-1138, or amino acids 1148-1198 of SEQ ID NO: 26. In still other aspects of this embodiment, a Clostridial botulinum serotype B NTNH comprising a β-trefoil domain with enhanced binding activity comprises a polypeptide having, e.g., at most one, two, three, four, five, six, seven, eight, nine, 10 or 20 contiguous amino acid additions relative to amino acids 1049-1096, amino acids 1110-1138, or amino acids 1148-1198 of SEQ ID NO: 26. In other aspects of this embodiment, a Clostridial botulinum serotype B NTNH comprising a β-trefoil domain with enhanced binding activity comprises a polypeptide having, e.g., at least one, two, three, four, five, six, seven, eight, nine, 10 or 20 contiguous amino acid additions relative to amino acids 1049-1096, amino acids 1110-1138, or amino acids 1148-1198 of SEQ ID NO: 26.

In another embodiment, a β-trefoil domain derived from a Clostridial botulinum serotype B NTNH comprises a β4/β5 hairpin turn of a β-trefoil domain of a Clostridial botulinum serotype B NTNH or a β8/β9 hairpin turn of a β-trefoil domain of a Clostridial botulinum serotype B NTNH of SEQ ID NO: 26. In another aspect of this embodiment, a β-trefoil domain derived from a Clostridial botulinum serotype B NTNH comprises amino acids 1097-1109 or amino acids 1139-1147 of SEQ ID NO: 26.

In another embodiment, a β-trefoil domain with enhanced binding activity derived from a Clostridial botulinum serotype B NTNH comprises a modified β4/β5 hairpin turn of a β-trefoil domain of a Clostridial botulinum serotype B NTNH or a modified β8/β9 hairpin turn of a β-trefoil domain of a Clostridial botulinum serotype B NTNH of SEQ ID NO: 26. In another aspect of this embodiment, a β-trefoil domain with enhanced binding activity derived from a Clostridial botulinum serotype B NTNH comprises a modification of amino acids 1097-1109 or amino acids 1139-1147 of SEQ ID NO: 26.

In other aspects of this embodiment, a β-trefoil domain with enhanced binding activity derived from a Clostridial botulinum serotype B NTNH comprises a polypeptide having, e.g., at least 70% amino acid identity with amino acids 1097-1109 or amino acids 1139-1147 of SEQ ID NO: 26, at least 75% amino acid identity with amino acids 1097-1109 or amino acids 1139-1147 of SEQ ID NO: 26, at least 80% amino acid identity with amino acids 1097-1109 or amino acids 1139-1147 of SEQ ID NO: 26, at least 85% amino acid identity with amino acids 1097-1109 or amino acids 1139-1147 of SEQ ID NO: 26, at least 90% amino acid identity with amino acids 1097-1109 or amino acids 1139-1147 of SEQ ID NO: 26 or at least 95% amino acid identity with amino acids 1097-1109 or amino acids 1139-1147 of SEQ ID NO: 26. In yet other aspects of this embodiment, a β-trefoil domain with enhanced binding activity derived from a Clostridial botulinum serotype B NTNH comprises a polypeptide having, e.g., at most 70% amino acid identity with amino acids 1097-1109 or amino acids 1139-1147 of SEQ ID NO: 26, at most 75% amino acid identity with amino acids 1097-1109 or amino acids 1139-1147 of SEQ ID NO: 26, at most 80% amino acid identity with amino acids 1097-1109 or amino acids 1139-1147 of SEQ ID NO: 26, at most 85% amino acid identity with amino acids 1097-1109 or amino acids 1139-1147 of SEQ ID NO: 26, at most 90% amino acid identity with amino acids 1097-1109 or amino acids 1139-1147 of SEQ ID NO: 26 or at most 95% amino acid identity with amino acids 1097-1109 or amino acids 1139-1147 of SEQ ID NO: 26.

In other aspects of this embodiment, a β-trefoil domain with enhanced binding activity derived from a Clostridial botulinum serotype B NTNH comprises a polypeptide having, e.g., at most one, two, three or four non-contiguous amino acid substitutions relative to amino acids 1097-1109 or amino acids 1139-1147 of SEQ ID NO: 26. In other aspects of this embodiment, a β-trefoil domain with enhanced binding activity derived from a Clostridial botulinum serotype B NTNH comprises a polypeptide having, e.g., at least one, two, three or four non-contiguous amino acid substitutions relative to amino acids 1097-1109 or amino acids 1139-1147 of SEQ ID NO: 26. In other aspects of this embodiment, a non-contiguous amino acid substitution of any amino acid from amino acids 1097-1109 or amino acids 1139-1147 of SEQ ID NO: 26 can be replaced with glycine. In other aspects of this embodiment, a non-contiguous amino acid substitution of any hydrophobic amino acid from amino acids 1097-1109 or amino acids 1139-1147 of SEQ ID NO: 26 can be replaced with phenylalanine. In yet other aspects of this embodiment, a β-trefoil domain with enhanced binding activity derived from a Clostridial botulinum serotype B NTNH comprises a polypeptide having, e.g., at most one, two, three or four non-contiguous amino acid deletions relative to amino acids 1097-1109 or amino acids 1139-1147 of SEQ ID NO: 26. In other aspects of this embodiment, a β-trefoil domain with enhanced binding activity derived from a Clostridial botulinum serotype B NTNH comprises a polypeptide having, e.g., at least one, two, three or four non-contiguous amino acid deletions relative to amino acids 1097-1109 or amino acids 1139-1147 of SEQ ID NO: 26. In still other aspects of this embodiment, a β-trefoil domain with enhanced binding activity derived from a Clostridial botulinum serotype B NTNH comprises a polypeptide having, e.g., at most one, two, three or four non-contiguous amino acid additions relative to amino acids 1097-1109 or amino acids 1139-1147 of SEQ ID NO: 26. In other aspects of this embodiment, a β-trefoil domain with enhanced binding activity derived from a Clostridial botulinum serotype B NTNH comprises a polypeptide having, e.g., at least one, two, three or four non-contiguous amino acid additions relative to amino acids 1097-1109 or amino acids 1139-1147 of SEQ ID NO: 26.

In other aspects of this embodiment, a β-trefoil domain with enhanced binding activity derived from a Clostridial botulinum serotype B NTNH comprises a polypeptide having, e.g., at most one, two, three or four contiguous amino acid substitutions relative to amino acids 1097-1109 or amino acids 1139-1147 of SEQ ID NO: 26. In other aspects of this embodiment, a β-trefoil domain with enhanced binding activity derived from a Clostridial botulinum serotype B NTNH comprises a polypeptide having, e.g., at least one, two, three or four contiguous amino acid substitutions relative to amino acids 1097-1109 or amino acids 1139-1147 of SEQ ID NO: 26. In other aspects of this embodiment, contiguous amino acid substitutions of amino acids from amino acids 1097-1109 or amino acids 1139-1147 of SEQ ID NO: 26 can be replaced with glycine. In other aspects of this embodiment, contiguous amino acid substitutions of hydrophobic amino acids from amino acids 1097-1109 or amino acids 1139-1147 of SEQ ID NO: 26 can be replaced with phenylalanine. In yet other aspects of this embodiment, a β-trefoil domain with enhanced binding activity derived from a Clostridial botulinum serotype B NTNH comprises a polypeptide having, e.g., at most one, two, three or four contiguous amino acid deletions relative to amino acids 1097-1109 or amino acids 1139-1147 of SEQ ID NO: 26. In other aspects of this embodiment, a β-trefoil domain with enhanced binding activity derived from a Clostridial botulinum serotype B NTNH comprises a polypeptide having, e.g., at least one, two, three or four contiguous amino acid deletions relative to amino acids 1097-1109 or amino acids 1139-1147 of SEQ ID NO: 26. In still other aspects of this embodiment, a β-trefoil domain with enhanced binding activity derived from a Clostridial botulinum serotype B NTNH comprises a polypeptide having, e.g., at most one, two, three or four contiguous amino acid additions relative to amino acids 1097-1109 or amino acids 1139-1147 of SEQ ID NO: 26. In other aspects of this embodiment, a β-trefoil domain with enhanced binding activity derived from a Clostridial botulinum serotype B NTNH comprises a polypeptide having, e.g., at least one, two, three or four contiguous amino acid additions relative to amino acids 1097-1109 or amino acids 1139-1147 of SEQ ID NO: 26.

In another embodiment, a β-trefoil domain derived from a Clostridial botulinum serotype C1 NTNH comprises a β-trefoil domain derived from a Clostridial botulinum serotype C1 NTNH of SEQ ID NO: 27. In another embodiment, a β-trefoil domain derived from a Clostridial botulinum serotype C1 NTNH comprises amino acids 1049-1197 of SEQ ID NO: 27. In another aspect of this embodiment, a β-trefoil domain derived from a Clostridial botulinum serotype C1 NTNH comprises a α-fold motif of a 13-trefoil domain of a Clostridial botulinum serotype C1 NTNH, a β-fold motif of a β-trefoil domain of a Clostridial botulinum serotype C1 NTNH or a γ-fold motif of a β-trefoil domain of a Clostridial botulinum serotype C1 NTNH of SEQ ID NO: 27. In another aspect of this embodiment, a β-trefoil domain derived from a Clostridial botulinum serotype C1 NTNH comprises amino acids 1049-1096, amino acids 1110-1138, or amino acids 1148-1197 of SEQ ID NO: 27.

In another embodiment, a β-trefoil domain with enhanced binding activity derived from a Clostridial botulinum serotype C1 NTNH comprises a β-trefoil domain with enhanced binding activity derived from a Clostridial botulinum serotype C1 NTNH of SEQ ID NO: 27. In another embodiment, a β-trefoil domain with enhanced binding activity derived from a Clostridial botulinum serotype C1 NTNH comprises amino acids 1049-1197 of SEQ ID NO: 27. In another aspect of this embodiment, a β-trefoil domain with enhanced binding activity derived from a Clostridial botulinum serotype C1 NTNH comprises a modified α-fold motif of a β-trefoil domain of a Clostridial botulinum serotype C1 NTNH, a modified β-fold motif of a β-trefoil domain of a Clostridial botulinum serotype C1 NTNH or a modified γ-fold motif of a β-trefoil domain of a Clostridial botulinum serotype C1 NTNH of SEQ ID NO: 27. In another aspect of this embodiment, a β-trefoil domain with enhanced binding activity derived from a Clostridial botulinum serotype C1 NTNH comprises amino acids 1049-1096, amino acids 1110-1138, or amino acids 1148-1197 of SEQ ID NO: 27.

In other aspects of this embodiment, a Clostridial botulinum serotype C1 NTNH comprising a β-trefoil domain with enhanced binding activity comprises a polypeptide having, e.g., at least 70% amino acid identity with amino acids 1049-1096, amino acids 1110-1138, or amino acids 1148-1197 of SEQ ID NO: 27, at least 75% amino acid identity with amino acids 1049-1096, amino acids 1110-1138, or amino acids 1148-1197 of SEQ ID NO: 27, at least 80% amino acid identity with amino acids 1049-1096, amino acids 1110-1138, or amino acids 1148-1197 of SEQ ID NO: 27, at least 85% amino acid identity with amino acids 1049-1096, amino acids 1110-1138, or amino acids 1148-1197 of SEQ ID NO: 27, at least 90% amino acid identity with amino acids 1049-1096, amino acids 1110-1138, or amino acids 1148-1197 of SEQ ID NO: 27 or at least 95% amino acid identity with amino acids 1049-1096, amino acids 1110-1138, or amino acids 1148-1197 of SEQ ID NO: 27. In yet other aspects of this embodiment, a Clostridial botulinum serotype C1 NTNH comprising a β-trefoil domain with enhanced binding activity comprises a polypeptide having, e.g., at most 70% amino acid identity with amino acids 1049-1096, amino acids 1110-1138, or amino acids 1148-1197 of SEQ ID NO: 27, at most 75% amino acid identity with amino acids 1049-1096, amino acids 1110-1138, or amino acids 1148-1197 of SEQ ID NO: 27, at most 80% amino acid identity with amino acids 1049-1096, amino acids 1110-1138, or amino acids 1148-1197 of SEQ ID NO: 27, at most 85% amino acid identity with amino acids 1049-1096, amino acids 1110-1138, or amino acids 1148-1197 of SEQ ID NO: 27, at most 90% amino acid identity with amino acids 1049-1096, amino acids 1110-1138, or amino acids 1148-1197 of SEQ ID NO: 27 or at most 95% amino acid identity with amino acids 1049-1096, amino acids 1110-1138, or amino acids 1148-1197 of SEQ ID NO: 27.

In other aspects of this embodiment, a Clostridial botulinum serotype C1 NTNH comprising a β-trefoil domain with enhanced binding activity comprises a polypeptide having, e.g., at most one, two, three, four, five, six, seven, eight, nine, 10 or 20 non-contiguous amino acid substitutions relative to amino acids 1049-1096, amino acids 1110-1138, or amino acids 1148-1197 of SEQ ID NO: 27. In other aspects of this embodiment, a Clostridial botulinum serotype C1 NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1049-1096, amino acids 1110-1138, or amino acids 1148-1197 of SEQ ID NO: 27. In yet other aspects of this embodiment, a Clostridial botulinum serotype C1 NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1049-1096, amino acids 1110-1138, or amino acids 1148-1197 of SEQ ID NO: 27. In other aspects of this embodiment, a Clostridial botulinum serotype C1 NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1049-1096, amino acids 1110-1138, or amino acids 1148-1197 of SEQ ID NO: 27. In still other aspects of this embodiment, a Clostridial botulinum serotype C1 NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1049-1096, amino acids 1110-1138, or amino acids 1148-1197 of SEQ ID NO: 27. In other aspects of this embodiment, a Clostridial botulinum serotype C1 NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1049-1096, amino acids 1110-1138, or amino acids 1148-1197 of SEQ ID NO: 27.

In other aspects of this embodiment, a Clostridial botulinum serotype C1 NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1049-1096, amino acids 1110-1138, or amino acids 1148-1197 of SEQ ID NO: 27. In other aspects of this embodiment, a Clostridial botulinum serotype C1 NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1049-1096, amino acids 1110-1138, or amino acids 1148-1197 of SEQ ID NO: 27. In yet other aspects of this embodiment, a Clostridial botulinum serotype C1 NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1049-1096, amino acids 1110-1138, or amino acids 1148-1197 of SEQ ID NO: 27. In other aspects of this embodiment, a Clostridial botulinum serotype C1 NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1049-1096, amino acids 1110-1138, or amino acids 1148-1197 of SEQ ID NO: 27. In still other aspects of this embodiment, a Clostridial botulinum serotype C1 NTNH comprising a β-trefoil domain with enhanced binding activity comprises a polypeptide having, e.g., at most one, two, three, four, five, six, seven, eight, nine, 10 or 20 contiguous amino acid additions relative to amino acids 1049-1096, amino acids 1110-1138, or amino acids 1148-1197 of SEQ ID NO: 27. In other aspects of this embodiment, a Clostridial botulinum serotype C1 NTNH comprising a β-trefoil domain with enhanced binding activity comprises a polypeptide having, e.g., at least one, two, three, four, five, six, seven, eight, nine, 10 or 20 contiguous amino acid additions relative to amino acids 1049-1096, amino acids 1110-1138, or amino acids 1148-1197 of SEQ ID NO: 27.

In another embodiment, a β-trefoil domain derived from a Clostridial botulinum serotype C1 NTNH comprises a β4/β5 hairpin turn of a β-trefoil domain of a Clostridial botulinum serotype C1 NTNH or a β8/β9 hairpin turn of a β-trefoil domain of a Clostridial botulinum serotype C1 NTNH of SEQ ID NO: 27. In another aspect of this embodiment, a β-trefoil domain derived from a Clostridial botulinum serotype C1 NTNH comprises amino acids 1097-1109 or amino acids 1139-1147 of SEQ ID NO: 27.

In another embodiment, a β-trefoil domain with enhanced binding activity derived from a Clostridial botulinum serotype C1 NTNH comprises a modified β4/β5 hairpin turn of a β-trefoil domain of a Clostridial botulinum serotype C1 NTNH or a modified β8/β9 hairpin turn of a β-trefoil domain of a Clostridial botulinum serotype C1 NTNH of SEQ ID NO: 27. In another aspect of this embodiment, a β-trefoil domain with enhanced binding activity derived from a Clostridial botulinum serotype C1 NTNH comprises a modification of amino acids 1097-1109 or amino acids 1139-1147 of SEQ ID NO: 27.

In other aspects of this embodiment, a β-trefoil domain with enhanced binding activity derived from a Clostridial botulinum serotype C1 NTNH comprises a polypeptide having, e.g., at least 70% amino acid identity with amino acids 1097-1109 or amino acids 1139-1147 of SEQ ID NO: 27, at least 75% amino acid identity with amino acids 1097-1109 or amino acids 1139-1147 of SEQ ID NO: 27, at least 80% amino acid identity with amino acids 1097-1109 or amino acids 1139-1147 of SEQ ID NO: 27, at least 85% amino acid identity with amino acids 1097-1109 or amino acids 1139-1147 of SEQ ID NO: 27, at least 90% amino acid identity with amino acids 1097-1109 or amino acids 1139-1147 of SEQ ID NO: 27 or at least 95% amino acid identity with amino acids 1097-1109 or amino acids 1139-1147 of SEQ ID NO: 27. In yet other aspects of this embodiment, a β-trefoil domain with enhanced binding activity derived from a Clostridial botulinum serotype C1 NTNH comprises a polypeptide having, e.g., at most 70% amino acid identity with amino acids 1097-1109 or amino acids 1139-1147 of SEQ ID NO: 27, at most 75% amino acid identity with amino acids 1097-1109 or amino acids 1139-1147 of SEQ ID NO: 27, at most 80% amino acid identity with amino acids 1097-1109 or amino acids 1139-1147 of SEQ ID NO: 27, at most 85% amino acid identity with amino acids 1097-1109 or amino acids 1139-1147 of SEQ ID NO: 27, at most 90% amino acid identity with amino acids 1097-1109 or amino acids 1139-1147 of SEQ ID NO: 27 or at most 95% amino acid identity with amino acids 1097-1109 or amino acids 1139-1147 of SEQ ID NO: 27.

In other aspects of this embodiment, a β-trefoil domain with enhanced binding activity derived from a Clostridial botulinum serotype C1 NTNH comprises a polypeptide having, e.g., at most one, two, three or four non-contiguous amino acid substitutions relative to amino acids 1097-1109 or amino acids 1139-1147 of SEQ ID NO: 27. In other aspects of this embodiment, a β-trefoil domain with enhanced binding activity derived from a Clostridial botulinum serotype C1 NTNH comprises a polypeptide having, e.g., at least one, two, three or four non-contiguous amino acid substitutions relative to amino acids 1097-1109 or amino acids 1139-1147 of SEQ ID NO: 27. In other aspects of this embodiment, a non-contiguous amino acid substitution of any amino acid from amino acids 1097-1109 or amino acids 1139-1147 of SEQ ID NO: 27 can be replaced with glycine. In other aspects of this embodiment, a non-contiguous amino acid substitution of any hydrophobic amino acid from amino acids 1097-1109 or amino acids 1139-1147 of SEQ ID NO: 27 can be replaced with phenylalanine. In yet other aspects of this embodiment, a β-trefoil domain with enhanced binding activity derived from a Clostridial botulinum serotype C1 NTNH comprises a polypeptide having, e.g., at most one, two, three or four non-contiguous amino acid deletions relative to amino acids 1097-1109 or amino acids 1139-1147 of SEQ ID NO: 27. In other aspects of this embodiment, a β-trefoil domain with enhanced binding activity derived from a Clostridial botulinum serotype C1 NTNH comprises a polypeptide having, e.g., at least one, two, three or four non-contiguous amino acid deletions relative to amino acids 1097-1109 or amino acids 1139-1147 of SEQ ID NO: 27. In still other aspects of this embodiment, a β-trefoil domain with enhanced binding activity derived from a Clostridial botulinum serotype C1 NTNH comprises a polypeptide having, e.g., at most one, two, three or four non-contiguous amino acid additions relative to amino acids 1097-1109 or amino acids 1139-1147 of SEQ ID NO: 27. In other aspects of this embodiment, a β-trefoil domain with enhanced binding activity derived from a Clostridial botulinum serotype C1 NTNH comprises a polypeptide having, e.g., at least one, two, three or four non-contiguous amino acid additions relative to amino acids 1097-1109 or amino acids 1139-1147 of SEQ ID NO: 27.

In other aspects of this embodiment, a β-trefoil domain with enhanced binding activity derived from a Clostridial botulinum serotype C1 NTNH comprises a polypeptide having, e.g., at most one, two, three or four contiguous amino acid substitutions relative to amino acids 1097-1109 or amino acids 1139-1147 of SEQ ID NO: 27. In other aspects of this embodiment, a β-trefoil domain with enhanced binding activity derived from a Clostridial botulinum serotype C1 NTNH comprises a polypeptide having, e.g., at least one, two, three or four contiguous amino acid substitutions relative to amino acids 1097-1109 or amino acids 1139-1147 of SEQ ID NO: 27. In other aspects of this embodiment, contiguous amino acid substitutions of amino acids from amino acids 1097-1109 or amino acids 1139-1147 of SEQ ID NO: 27 can be replaced with glycine. In other aspects of this embodiment, contiguous amino acid substitutions of hydrophobic amino acids from amino acids 1097-1109 or amino acids 1139-1147 of SEQ ID NO: 27 can be replaced with phenylalanine. In yet other aspects of this embodiment, a β-trefoil domain with enhanced binding activity derived from a Clostridial botulinum serotype C1 NTNH comprises a polypeptide having, e.g., at most one, two, three or four contiguous amino acid deletions relative to amino acids 1097-1109 or amino acids 1139-1147 of SEQ ID NO: 27. In other aspects of this embodiment, a β-trefoil domain with enhanced binding activity derived from a Clostridial botulinum serotype C1 NTNH comprises a polypeptide having, e.g., at least one, two, three or four contiguous amino acid deletions relative to amino acids 1097-1109 or amino acids 1139-1147 of SEQ ID NO: 27. In still other aspects of this embodiment, a β-trefoil domain with enhanced binding activity derived from a Clostridial botulinum serotype C1 NTNH comprises a polypeptide having, e.g., at most one, two, three or four contiguous amino acid additions relative to amino acids 1097-1109 or amino acids 1139-1147 of SEQ ID NO: 27. In other aspects of this embodiment, a β-trefoil domain with enhanced binding activity derived from a Clostridial botulinum serotype C1 NTNH comprises a polypeptide having, e.g., at least one, two, three or four contiguous amino acid additions relative to amino acids 1097-1109 or amino acids 1139-1147 of SEQ ID NO: 27.

In another embodiment, a β-trefoil domain derived from a Clostridial botulinum serotype D NTNH comprises a β-trefoil domain derived from a Clostridial botulinum serotype D NTNH of SEQ ID NO: 28. In another embodiment, a β-trefoil domain derived from a Clostridial botulinum serotype D NTNH comprises amino acids 1049-1197 of SEQ ID NO: 28. In another aspect of this embodiment, a β-trefoil domain derived from a Clostridial botulinum serotype D NTNH comprises a α-fold motif of a β-trefoil domain of a Clostridial botulinum serotype D NTNH, a β-fold motif of a β-trefoil domain of a Clostridial botulinum serotype D NTNH or a γ-fold motif of a β-trefoil domain of a Clostridial botulinum serotype D NTNH of SEQ ID NO: 28. In another aspect of this embodiment, a β-trefoil domain derived from a Clostridial botulinum serotype D NTNH comprises amino acids 1049-1096, amino acids 1110-1138, or amino acids 1148-1197 of SEQ ID NO: 28.

In another embodiment, a β-trefoil domain with enhanced binding activity derived from a Clostridial botulinum serotype D NTNH comprises a β-trefoil domain with enhanced binding activity derived from a Clostridial botulinum serotype D NTNH of SEQ ID NO: 28. In another embodiment, a β-trefoil domain with enhanced binding activity derived from a Clostridial botulinum serotype D NTNH comprises amino acids 1049-1197 of SEQ ID NO: 28. In another aspect of this embodiment, a β-trefoil domain with enhanced binding activity derived from a Clostridial botulinum serotype D NTNH comprises a modified α-fold motif of a β-trefoil domain of a Clostridial botulinum serotype D NTNH, a modified β-fold motif of a β-trefoil domain of a Clostridial botulinum serotype D NTNH or a modified γ-fold motif of a (3-trefoil domain of a Clostridial botulinum serotype D NTNH of SEQ ID NO: 28. In another aspect of this embodiment, a β-trefoil domain with enhanced binding activity derived from a Clostridial botulinum serotype D NTNH comprises amino acids 1049-1096, amino acids 1110-1138, or amino acids 1148-1197 of SEQ ID NO: 28.

In other aspects of this embodiment, a Clostridial botulinum serotype D NTNH comprising a 11-trefoil domain with enhanced binding activity comprises a polypeptide having, e.g., at least 70% amino acid identity with amino acids 1049-1096, amino acids 1110-1138, or amino acids 1148-1197 of SEQ ID NO: 28, at least 75% amino acid identity with amino acids 1049-1096, amino acids 1110-1138, or amino acids 1148-1197 of SEQ ID NO: 28, at least 80% amino acid identity with amino acids 1049-1096, amino acids 1110-1138, or amino acids 1148-1197 of SEQ ID NO: 28, at least 85% amino acid identity with amino acids 1049-1096, amino acids 1110-1138, or amino acids 1148-1197 of SEQ ID NO: 28, at least 90% amino acid identity with amino acids 1049-1096, amino acids 1110-1138, or amino acids 1148-1197 of SEQ ID NO: 28 or at least 95% amino acid identity with amino acids 1049-1096, amino acids 1110-1138, or amino acids 1148-1197 of SEQ ID NO: 28. In yet other aspects of this embodiment, a Clostridial botulinum serotype D NTNH comprising a β-trefoil domain with enhanced binding activity comprises a polypeptide having, e.g., at most 70% amino acid identity with amino acids 1049-1096, amino acids 1110-1138, or amino acids 1148-1197 of SEQ ID NO: 28, at most 75% amino acid identity with amino acids 1049-1096, amino acids 1110-1138, or amino acids 1148-1197 of SEQ ID NO: 28, at most 80% amino acid identity with amino acids 1049-1096, amino acids 1110-1138, or amino acids 1148-1197 of SEQ ID NO: 28, at most 85% amino acid identity with amino acids 1049-1096, amino acids 1110-1138, or amino acids 1148-1197 of SEQ ID NO: 28, at most 90% amino acid identity with amino acids 1049-1096, amino acids 1110-1138, or amino acids 1148-1197 of SEQ ID NO: 28 or at most 95% amino acid identity with amino acids 1049-1096, amino acids 1110-1138, or amino acids 1148-1197 of SEQ ID NO: 28.

In other aspects of this embodiment, a Clostridial botulinum serotype D NTNH comprising a β-trefoil domain with enhanced binding activity comprises a polypeptide having, e.g., at most one, two, three, four, five, six, seven, eight, nine, 10 or 20 non-contiguous amino acid substitutions relative to amino acids 1049-1096, amino acids 1110-1138, or amino acids 1148-1197 of SEQ ID NO: 28. In other aspects of this embodiment, a Clostridial botulinum serotype D NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1049-1096, amino acids 1110-1138, or amino acids 1148-1197 of SEQ ID NO: 28. In yet other aspects of this embodiment, a Clostridial botulinum serotype D NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1049-1096, amino acids 1110-1138, or amino acids 1148-1197 of SEQ ID NO: 28. In other aspects of this embodiment, a Clostridial botulinum serotype D NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1049-1096, amino acids 1110-1138, or amino acids 1148-1197 of SEQ ID NO: 28. In still other aspects of this embodiment, a Clostridial botulinum serotype D NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1049-1096, amino acids 1110-1138, or amino acids 1148-1197 of SEQ ID NO: 28. In other aspects of this embodiment, a Clostridial botulinum serotype D NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1049-1096, amino acids 1110-1138, or amino acids 1148-1197 of SEQ ID NO: 28.

In other aspects of this embodiment, a Clostridial botulinum serotype D NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1049-1096, amino acids 1110-1138, or amino acids 1148-1197 of SEQ ID NO: 28. In other aspects of this embodiment, a Clostridial botulinum serotype D NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1049-1096, amino acids 1110-1138, or amino acids 1148-1197 of SEQ ID NO: 28. In yet other aspects of this embodiment, a Clostridial botulinum serotype D NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1049-1096, amino acids 1110-1138, or amino acids 1148-1197 of SEQ ID NO: 28. In other aspects of this embodiment, a Clostridial botulinum serotype D NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1049-1096, amino acids 1110-1138, or amino acids 1148-1197 of SEQ ID NO: 28. In still other aspects of this embodiment, a Clostridial botulinum serotype D NTNH comprising a β-trefoil domain with enhanced binding activity comprises a polypeptide having, e.g., at most one, two, three, four, five, six, seven, eight, nine, 10 or 20 contiguous amino acid additions relative to amino acids 1049-1096, amino acids 1110-1138, or amino acids 1148-1197 of SEQ ID NO: 28. In other aspects of this embodiment, a Clostridial botulinum serotype D NTNH comprising a β-trefoil domain with enhanced binding activity comprises a polypeptide having, e.g., at least one, two, three, four, five, six, seven, eight, nine, 10 or 20 contiguous amino acid additions relative to amino acids 1049-1096, amino acids 1110-1138, or amino acids 1148-1197 of SEQ ID NO: 28.

In another embodiment, a β-trefoil domain derived from a Clostridial botulinum serotype D NTNH comprises a β4/β5 hairpin turn of a β-trefoil domain of a Clostridial botulinum serotype D NTNH or a β8/β9 hairpin turn of a β-trefoil domain of a Clostridial botulinum serotype D NTNH of SEQ ID NO: 28. In another aspect of this embodiment, a β-trefoil domain derived from a Clostridial botulinum serotype D NTNH comprises amino acids 1097-1109 or amino acids 1139-1147 of SEQ ID NO: 28.

In another embodiment, a β-trefoil domain with enhanced binding activity derived from a Clostridial botulinum serotype D NTNH comprises a modified β4/β5 hairpin turn of a β-trefoil domain of a Clostridial botulinum serotype D NTNH or a modified β8/β9 hairpin turn of a β-trefoil domain of a Clostridial botulinum serotype D NTNH of SEQ ID NO: 28. In another aspect of this embodiment, a β-trefoil domain with enhanced binding activity derived from a Clostridial botulinum serotype D NTNH comprises a modification of amino acids 1097-1109 or amino acids 1139-1147 of SEQ ID NO: 28.

In other aspects of this embodiment, a β-trefoil domain with enhanced binding activity derived from a Clostridial botulinum serotype D NTNH comprises a polypeptide having, e.g., at least 70% amino acid identity with amino acids 1097-1109 or amino acids 1139-1147 of SEQ ID NO: 28, at least 75% amino acid identity with amino acids 1097-1109 or amino acids 1139-1147 of SEQ ID NO: 28, at least 80% amino acid identity with amino acids 1097-1109 or amino acids 1139-1147 of SEQ ID NO: 28, at least 85% amino acid identity with amino acids 1097-1109 or amino acids 1139-1147 of SEQ ID NO: 28, at least 90% amino acid identity with amino acids 1097-1109 or amino acids 1139-1147 of SEQ ID NO: 28 or at least 95% amino acid identity with amino acids 1097-1109 or amino acids 1139-1147 of SEQ ID NO: 28. In yet other aspects of this embodiment, a β-trefoil domain with enhanced binding activity derived from a Clostridial botulinum serotype D NTNH comprises a polypeptide having, e.g., at most 70% amino acid identity with amino acids 1097-1109 or amino acids 1139-1147 of SEQ ID NO: 28, at most 75% amino acid identity with amino acids 1097-1109 or amino acids 1139-1147 of SEQ ID NO: 28, at most 80% amino acid identity with amino acids 1097-1109 or amino acids 1139-1147 of SEQ ID NO: 28, at most 85% amino acid identity with amino acids 1097-1109 or amino acids 1139-1147 of SEQ ID NO: 28, at most 90% amino acid identity with amino acids 1097-1109 or amino acids 1139-1147 of SEQ ID NO: 28 or at most 95% amino acid identity with amino acids 1097-1109 or amino acids 1139-1147 of SEQ ID NO: 28.

In other aspects of this embodiment, a β-trefoil domain with enhanced binding activity derived from a Clostridial botulinum serotype D NTNH comprises a polypeptide having, e.g., at most one, two, three or four non-contiguous amino acid substitutions relative to amino acids 1097-1109 or amino acids 1139-1147 of SEQ ID NO: 28. In other aspects of this embodiment, a β-trefoil domain with enhanced binding activity derived from a Clostridial botulinum serotype D NTNH comprises a polypeptide having, e.g., at least one, two, three or four non-contiguous amino acid substitutions relative to amino acids 1097-1109 or amino acids 1139-1147 of SEQ ID NO: 28. In other aspects of this embodiment, a non-contiguous amino acid substitution of any amino acid from amino acids 1097-1109 or amino acids 1139-1147 of SEQ ID NO: 28 can be replaced with glycine. In other aspects of this embodiment, a non-contiguous amino acid substitution of any hydrophobic amino acid from amino acids 1097-1109 or amino acids 1139-1147 of SEQ ID NO: 28 can be replaced with phenylalanine. In yet other aspects of this embodiment, a β-trefoil domain with enhanced binding activity derived from a Clostridial botulinum serotype D NTNH comprises a polypeptide having, e.g., at most one, two, three or four non-contiguous amino acid deletions relative to amino acids 1097-1109 or amino acids 1139-1147 of SEQ ID NO: 28. In other aspects of this embodiment, a β-trefoil domain with enhanced binding activity derived from a Clostridial botulinum serotype D NTNH comprises a polypeptide having, e.g., at least one, two, three or four non-contiguous amino acid deletions relative to amino acids 1097-1109 or amino acids 1139-1147 of SEQ ID NO: 28. In still other aspects of this embodiment, a β-trefoil domain with enhanced binding activity derived from a Clostridial botulinum serotype D NTNH comprises a polypeptide having, e.g., at most one, two, three or four non-contiguous amino acid additions relative to amino acids 1097-1109 or amino acids 1139-1147 of SEQ ID NO: 28. In other aspects of this embodiment, a β-trefoil domain with enhanced binding activity derived from a Clostridial botulinum serotype D NTNH comprises a polypeptide having, e.g., at least one, two, three or four non-contiguous amino acid additions relative to amino acids 1097-1109 or amino acids 1139-1147 of SEQ ID NO: 28.

In other aspects of this embodiment, a β-trefoil domain with enhanced binding activity derived from a Clostridial botulinum serotype D NTNH comprises a polypeptide having, e.g., at most one, two, three or four contiguous amino acid substitutions relative to amino acids 1097-1109 or amino acids 1139-1147 of SEQ ID NO: 28. In other aspects of this embodiment, a β-trefoil domain with enhanced binding activity derived from a Clostridial botulinum serotype D NTNH comprises a polypeptide having, e.g., at least one, two, three or four contiguous amino acid substitutions relative to amino acids 1097-1109 or amino acids 1139-1147 of SEQ ID NO: 28. In other aspects of this embodiment, contiguous amino acid substitutions of amino acids from amino acids 1097-1109 or amino acids 1139-1147 of SEQ ID NO: 28 can be replaced with glycine. In other aspects of this embodiment, contiguous amino acid substitutions of hydrophobic amino acids from amino acids 1097-1109 or amino acids 1139-1147 of SEQ ID NO: 28 can be replaced with phenylalanine. In yet other aspects of this embodiment, a β-trefoil domain with enhanced binding activity derived from a Clostridial botulinum serotype D NTNH comprises a polypeptide having, e.g., at most one, two, three or four contiguous amino acid deletions relative to amino acids 1097-1109 or amino acids 1139-1147 of SEQ ID NO: 28. In other aspects of this embodiment, a β-trefoil domain with enhanced binding activity derived from a Clostridial botulinum serotype D NTNH comprises a polypeptide having, e.g., at least one, two, three or four contiguous amino acid deletions relative to amino acids 1097-1109 or amino acids 1139-1147 of SEQ ID NO: 28. In still other aspects of this embodiment, a β-trefoil domain with enhanced binding activity derived from a Clostridial botulinum serotype D NTNH comprises a polypeptide having, e.g., at most one, two, three or four contiguous amino acid additions relative to amino acids 1097-1109 or amino acids 1139-1147 of SEQ ID NO: 28. In other aspects of this embodiment, a β-trefoil domain with enhanced binding activity derived from a Clostridial botulinum serotype D NTNH comprises a polypeptide having, e.g., at least one, two, three or four contiguous amino acid additions relative to amino acids 1097-1109 or amino acids 1139-1147 of SEQ ID NO: 28.

In another embodiment, a β-trefoil domain derived from a Clostridial botulinum serotype E NTNH comprises a β-trefoil domain derived from a Clostridial botulinum serotype E NTNH of SEQ ID NO: 29. In another embodiment, a β-trefoil domain derived from a Clostridial botulinum serotype E NTNH comprises amino acids 1014-1163 of SEQ ID NO: 29.

In another aspect of this embodiment, a β-trefoil domain derived from a Clostridial botulinum serotype E NTNH comprises a α-fold motif of a β-trefoil domain of a Clostridial botulinum serotype E NTNH, a β-fold motif of a β-trefoil domain of a Clostridial botulinum serotype E NTNH or a γ-fold motif of a β-trefoil domain of a Clostridial botulinum serotype E NTNH of SEQ ID NO: 29. In another aspect of this embodiment, a β-trefoil domain derived from a Clostridial botulinum serotype E NTNH comprises amino acids 1014-1061, amino acids 1075-1103, or amino acids 1114-1163 of SEQ ID NO: 29.

In another embodiment, a β-trefoil domain with enhanced binding activity derived from a Clostridial botulinum serotype E NTNH comprises a β-trefoil domain with enhanced binding activity derived from a Clostridial botulinum serotype E NTNH of SEQ ID NO: 29. In another embodiment, a β-trefoil domain with enhanced binding activity derived from a Clostridial botulinum serotype E NTNH comprises amino acids 1014-1163 of SEQ ID NO: 29. In another aspect of this embodiment, a β-trefoil domain with enhanced binding activity derived from a Clostridial botulinum serotype E NTNH comprises a modified α-fold motif of a β-trefoil domain of a Clostridial botulinum serotype E NTNH, a modified β-fold motif of a β-trefoil domain of a Clostridial botulinum serotype E NTNH or a modified γ-fold motif of a 13-trefoil domain of a Clostridial botulinum serotype E NTNH of SEQ ID NO: 29. In another aspect of this embodiment, a β-trefoil domain with enhanced binding activity derived from a Clostridial botulinum serotype E NTNH comprises amino acids 1014-1061, amino acids 1075-1103, or amino acids 1114-1163 of SEQ ID NO: 29.

In other aspects of this embodiment, a Clostridial botulinum serotype E NTNH comprising a β-trefoil domain with enhanced binding activity comprises a polypeptide having, e.g., at least 70% amino acid identity with amino acids 1014-1061, amino acids 1075-1103, or amino acids 1114-1163 of SEQ ID NO: 29, at least 75% amino acid identity with amino acids 1014-1061, amino acids 1075-1103, or amino acids 1114-1163 of SEQ ID NO: 29, at least 80% amino acid identity with amino acids 1014-1061, amino acids 1075-1103, or amino acids 1114-1163 of SEQ ID NO: 29, at least 85% amino acid identity with amino acids 1014-1061, amino acids 1075-1103, or amino acids 1114-1163 of SEQ ID NO: 29, at least 90% amino acid identity with amino acids 1014-1061, amino acids 1075-1103, or amino acids 1114-1163 of SEQ ID NO: 29 or at least 95% amino acid identity with amino acids 1014-1061, amino acids 1075-1103, or amino acids 1114-1163 of SEQ ID NO: 29. In yet other aspects of this embodiment, a Clostridial botulinum serotype E NTNH comprising a β-trefoil domain with enhanced binding activity comprises a polypeptide having, e.g., at most 70% amino acid identity with amino acids 1014-1061, amino acids 1075-1103, or amino acids 1114-1163 of SEQ ID NO: 29, at most 75% amino acid identity with amino acids 1014-1061, amino acids 1075-1103, or amino acids 1114-1163 of SEQ ID NO: 29, at most 80% amino acid identity with amino acids 1014-1061, amino acids 1075-1103, or amino acids 1114-1163 of SEQ ID NO: 29, at most 85% amino acid identity with amino acids 1014-1061, amino acids 1075-1103, or amino acids 1114-1163 of SEQ ID NO: 29, at most 90% amino acid identity with amino acids 1014-1061, amino acids 1075-1103, or amino acids 1114-1163 of SEQ ID NO: 29 or at most 95% amino acid identity with amino acids 1014-1061, amino acids 1075-1103, or amino acids 1114-1163 of SEQ ID NO: 29.

In other aspects of this embodiment, a Clostridial botulinum serotype E NTNH comprising a β-trefoil domain with enhanced binding activity comprises a polypeptide having, e.g., at most one, two, three, four, five, six, seven, eight, nine, 10 or 20 non-contiguous amino acid substitutions relative to amino acids 1014-1061, amino acids 1075-1103, or amino acids 1114-1163 of SEQ ID NO: 29. In other aspects of this embodiment, a Clostridial botulinum serotype E NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1014-1061, amino acids 1075-1103, or amino acids 1114-1163 of SEQ ID NO: 29. In yet other aspects of this embodiment, a Clostridial botulinum serotype E NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1014-1061, amino acids 1075-1103, or amino acids 1114-1163 of SEQ ID NO: 29. In other aspects of this embodiment, a Clostridial botulinum serotype E NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1014-1061, amino acids 1075-1103, or amino acids 1114-1163 of SEQ ID NO: 29. In still other aspects of this embodiment, a Clostridial botulinum serotype E NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1014-1061, amino acids 1075-1103, or amino acids 1114-1163 of SEQ ID NO: 29. In other aspects of this embodiment, a Clostridial botulinum serotype E NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1014-1061, amino acids 1075-1103, or amino acids 1114-1163 of SEQ ID NO: 29.

In other aspects of this embodiment, a Clostridial botulinum serotype E NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1014-1061, amino acids 1075-1103, or amino acids 1114-1163 of SEQ ID NO: 29. In other aspects of this embodiment, a Clostridial botulinum serotype E NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1014-1061, amino acids 1075-1103, or amino acids 1114-1163 of SEQ ID NO: 29. In yet other aspects of this embodiment, a Clostridial botulinum serotype E NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1014-1061, amino acids 1075-1103, or amino acids 1114-1163 of SEQ ID NO: 29. In other aspects of this embodiment, a Clostridial botulinum serotype E NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1014-1061, amino acids 1075-1103, or amino acids 1114-1163 of SEQ ID NO: 29. In still other aspects of this embodiment, a Clostridial botulinum serotype E NTNH comprising a β-trefoil domain with enhanced binding activity comprises a polypeptide having, e.g., at most one, two, three, four, five, six, seven, eight, nine, 10 or 20 contiguous amino acid additions relative to amino acids 1014-1061, amino acids 1075-1103, or amino acids 1114-1163 of SEQ ID NO: 29. In other aspects of this embodiment, a Clostridial botulinum serotype E NTNH comprising a β-trefoil domain with enhanced binding activity comprises a polypeptide having, e.g., at least one, two, three, four, five, six, seven, eight, nine, 10 or 20 contiguous amino acid additions relative to amino acids 1014-1061, amino acids 1075-1103, or amino acids 1114-1163 of SEQ ID NO: 29.

In another embodiment, a β-trefoil domain derived from a Clostridial botulinum serotype E NTNH comprises a β4/β5 hairpin turn of a β-trefoil domain of a Clostridial botulinum serotype E NTNH or a β8/β9 hairpin turn of a β-trefoil domain of a Clostridial botulinum serotype E NTNH of SEQ ID NO: 29. In another aspect of this embodiment, a β-trefoil domain derived from a Clostridial botulinum serotype E NTNH comprises amino acids 1062-1074 or amino acids 1104-1113 of SEQ ID NO: 29.

In another embodiment, a β-trefoil domain with enhanced binding activity derived from a Clostridial botulinum serotype E NTNH comprises a modified β4/β5 hairpin turn of a β-trefoil domain of a Clostridial botulinum serotype E NTNH or a modified β8/β9 hairpin turn of a β-trefoil domain of a Clostridial botulinum serotype E NTNH of SEQ ID NO: 29. In another aspect of this embodiment, a β-trefoil domain with enhanced binding activity derived from a Clostridial botulinum serotype E NTNH comprises a modification of amino acids 1062-1074 or amino acids 1104-1113 of SEQ ID NO: 29.

In other aspects of this embodiment, a β-trefoil domain with enhanced binding activity derived from a Clostridial botulinum serotype E NTNH comprises a polypeptide having, e.g., at least 70% amino acid identity with amino acids 1062-1074 or amino acids 1104-1113 of SEQ ID NO: 29, at least 75% amino acid identity with amino acids 1062-1074 or amino acids 1104-1113 of SEQ ID NO: 29, at least 80% amino acid identity with amino acids 1062-1074 or amino acids 1104-1113 of SEQ ID NO: 29, at least 85% amino acid identity with amino acids 1062-1074 or amino acids 1104-1113 of SEQ ID NO: 29, at least 90% amino acid identity with amino acids 1062-1074 or amino acids 1104-1113 of SEQ ID NO: 29 or at least 95% amino acid identity with amino acids 1062-1074 or amino acids 1104-1113 of SEQ ID NO: 29. In yet other aspects of this embodiment, a β-trefoil domain with enhanced binding activity derived from a Clostridial botulinum serotype E NTNH comprises a polypeptide having, e.g., at most 70% amino acid identity with amino acids 1062-1074 or amino acids 1104-1113 of SEQ ID NO: 29, at most 75% amino acid identity with amino acids 1062-1074 or amino acids 1104-1113 of SEQ ID NO: 29, at most 80% amino acid identity with amino acids 1062-1074 or amino acids 1104-1113 of SEQ ID NO: 29, at most 85% amino acid identity with amino acids 1062-1074 or amino acids 1104-1113 of SEQ ID NO: 29, at most 90% amino acid identity with amino acids 1062-1074 or amino acids 1104-1113 of SEQ ID NO: 29 or at most 95% amino acid identity with amino acids 1062-1074 or amino acids 1104-1113 of SEQ ID NO: 29.

In other aspects of this embodiment, a β-trefoil domain with enhanced binding activity derived from a Clostridial botulinum serotype E NTNH comprises a polypeptide having, e.g., at most one, two, three or four non-contiguous amino acid substitutions relative to amino acids 1062-1074 or amino acids 1104-1113 of SEQ ID NO: 29. In other aspects of this embodiment, a β-trefoil domain with enhanced binding activity derived from a Clostridial botulinum serotype E NTNH comprises a polypeptide having, e.g., at least one, two, three or four non-contiguous amino acid substitutions relative to amino acids 1062-1074 or amino acids 1104-1113 of SEQ ID NO: 29. In other aspects of this embodiment, a non-contiguous amino acid substitution of any amino acid from amino acids 1062-1074 or amino acids 1104-1113 of SEQ ID NO: 29 can be replaced with glycine. In other aspects of this embodiment, a non-contiguous amino acid substitution of any hydrophobic amino acid from amino acids 1062-1074 or amino acids 1104-1113 of SEQ ID NO: 29 can be replaced with phenylalanine. In yet other aspects of this embodiment, a β-trefoil domain with enhanced binding activity derived from a Clostridial botulinum serotype E NTNH comprises a polypeptide having, e.g., at most one, two, three or four non-contiguous amino acid deletions relative to amino acids 1062-1074 or amino acids 1104-1113 of SEQ ID NO: 29. In other aspects of this embodiment, a β-trefoil domain with enhanced binding activity derived from a Clostridial botulinum serotype E NTNH comprises a polypeptide having, e.g., at least one, two, three or four non-contiguous amino acid deletions relative to amino acids 1062-1074 or amino acids 1104-1113 of SEQ ID NO: 29. In still other aspects of this embodiment, a β-trefoil domain with enhanced binding activity derived from a Clostridial botulinum serotype E NTNH comprises a polypeptide having, e.g., at most one, two, three or four non-contiguous amino acid additions relative to amino acids 1062-1074 or amino acids 1104-1113 of SEQ ID NO: 29. In other aspects of this embodiment, a β-trefoil domain with enhanced binding activity derived from a Clostridial botulinum serotype E NTNH comprises a polypeptide having, e.g., at least one, two, three or four non-contiguous amino acid additions relative to amino acids 1062-1074 or amino acids 1104-1113 of SEQ ID NO: 29.

In other aspects of this embodiment, a β-trefoil domain with enhanced binding activity derived from a Clostridial botulinum serotype E NTNH comprises a polypeptide having, e.g., at most one, two, three or four contiguous amino acid substitutions relative to amino acids 1062-1074 or amino acids 1104-1113 of SEQ ID NO: 29. In other aspects of this embodiment, a β-trefoil domain with enhanced binding activity derived from a Clostridial botulinum serotype E NTNH comprises a polypeptide having, e.g., at least one, two, three or four contiguous amino acid substitutions relative to amino acids 1062-1074 or amino acids 1104-1113 of SEQ ID NO: 29. In other aspects of this embodiment, contiguous amino acid substitutions of amino acids from amino acids 1062-1074 or amino acids 1104-1113 of SEQ ID NO: 29 can be replaced with glycine. In other aspects of this embodiment, contiguous amino acid substitutions of hydrophobic amino acids from amino acids 1062-1074 or amino acids 1104-1113 of SEQ ID NO: 29 can be replaced with phenylalanine. In yet other aspects of this embodiment, a β-trefoil domain with enhanced binding activity derived from a Clostridial botulinum serotype E NTNH comprises a polypeptide having, e.g., at most one, two, three or four contiguous amino acid deletions relative to amino acids 1062-1074 or amino acids 1104-1113 of SEQ ID NO: 29. In other aspects of this embodiment, a β-trefoil domain with enhanced binding activity derived from a Clostridial botulinum serotype E NTNH comprises a polypeptide having, e.g., at least one, two, three or four contiguous amino acid deletions relative to amino acids 1062-1074 or amino acids 1104-1113 of SEQ ID NO: 29. In still other aspects of this embodiment, a β-trefoil domain with enhanced binding activity derived from a Clostridial botulinum serotype E NTNH comprises a polypeptide having, e.g., at most one, two, three or four contiguous amino acid additions relative to amino acids 1062-1074 or amino acids 1104-1113 of SEQ ID NO: 29. In other aspects of this embodiment, a β-trefoil domain with enhanced binding activity derived from a Clostridial botulinum serotype E NTNH comprises a polypeptide having, e.g., at least one, two, three or four contiguous amino acid additions relative to amino acids 1062-1074 or amino acids 1104-1113 of SEQ ID NO: 29.

In another embodiment, a β-trefoil domain derived from a Clostridial botulinum serotype F NTNH comprises a β-trefoil domain derived from a Clostridial botulinum serotype F NTNH of SEQ ID NO: 30. In another embodiment, a β-trefoil domain derived from a Clostridial botulinum serotype F NTNH comprises amino acids 1016-1160 of SEQ ID NO: 30. In another aspect of this embodiment, a β-trefoil domain derived from a Clostridial botulinum serotype F NTNH comprises a α-fold motif of a 8-trefoil domain of a Clostridial botulinum serotype F NTNH, a β-fold motif of a β-trefoil domain of a Clostridial botulinum serotype F NTNH or a γ-fold motif of a β-trefoil domain of a Clostridial botulinum serotype F NTNH of SEQ ID NO: 30. In another aspect of this embodiment, a β-trefoil domain derived from a Clostridial botulinum serotype F NTNH comprises amino acids 1016-1063, amino acids 1077-1104, or amino acids 1115-1160 of SEQ ID NO: 30.

In another embodiment, a β-trefoil domain with enhanced binding activity derived from a Clostridial botulinum serotype F NTNH comprises a β-trefoil domain with enhanced binding activity derived from a Clostridial botulinum serotype F NTNH of SEQ ID NO: 30. In another embodiment, a β-trefoil domain with enhanced binding activity derived from a Clostridial botulinum serotype F NTNH comprises amino acids 1016-1160 of SEQ ID NO: 30. In another aspect of this embodiment, a β-trefoil domain with enhanced binding activity derived from a Clostridial botulinum serotype F NTNH comprises a modified α-fold motif of a β-trefoil domain of a Clostridial botulinum serotype F NTNH, a modified β-fold motif of a β-trefoil domain of a Clostridial botulinum serotype F NTNH or a modified γ-fold motif of a 13-trefoil domain of a Clostridial botulinum serotype F NTNH of SEQ ID NO: 30. In another aspect of this embodiment, a β-trefoil domain with enhanced binding activity derived from a Clostridial botulinum serotype F NTNH comprises amino acids 1016-1063, amino acids 1077-1104, or amino acids 1115-1160 of SEQ ID NO: 30.

In other aspects of this embodiment, a Clostridial botulinum serotype F NTNH comprising a β-trefoil domain with enhanced binding activity comprises a polypeptide having, e.g., at least 70% amino acid identity with amino acids 1016-1063, amino acids 1077-1104, or amino acids 1115-1160 of SEQ ID NO: 30, at least 75% amino acid identity with amino acids 1016-1063, amino acids 1077-1104, or amino acids 1115-1160 of SEQ ID NO: 30, at least 80% amino acid identity with amino acids 1016-1063, amino acids 1077-1104, or amino acids 1115-1160 of SEQ ID NO: 30, at least 85% amino acid identity with amino acids 1016-1063, amino acids 1077-1104, or amino acids 1115-1160 of SEQ ID NO: 30, at least 90% amino acid identity with amino acids 1016-1063, amino acids 1077-1104, or amino acids 1115-1160 of SEQ ID NO: 30 or at least 95% amino acid identity with amino acids 1016-1063, amino acids 1077-1104, or amino acids 1115-1160 of SEQ ID NO: 30. In yet other aspects of this embodiment, a Clostridial botulinum serotype F NTNH comprising a β-trefoil domain with enhanced binding activity comprises a polypeptide having, e.g., at most 70% amino acid identity with amino acids 1016-1063, amino acids 1077-1104, or amino acids 1115-1160 of SEQ ID NO: 30, at most 75% amino acid identity with amino acids 1016-1063, amino acids 1077-1104, or amino acids 1115-1160 of SEQ ID NO: 30, at most 80% amino acid identity with amino acids 1016-1063, amino acids 1077-1104, or amino acids 1115-1160 of SEQ ID NO: 30, at most 85% amino acid identity with amino acids 1016-1063, amino acids 1077-1104, or amino acids 1115-1160 of SEQ ID NO: 30, at most 90% amino acid identity with amino acids 1016-1063, amino acids 1077-1104, or amino acids 1115-1160 of SEQ ID NO: 30 or at most 95% amino acid identity with amino acids 1016-1063, amino acids 1077-1104, or amino acids 1115-1160 of SEQ ID NO: 30.

In other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 non-contiguous amino acid substitutions relative to amino acids 1016-1063, amino acids 1077-1104, or amino acids 1115-1160 of SEQ ID NO: 30. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1016-1063, amino acids 1077-1104, or amino acids 1115-1160 of SEQ ID NO: 30. In yet other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1016-1063, amino acids 1077-1104, or amino acids 1115-1160 of SEQ ID NO: 30. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1016-1063, amino acids 1077-1104, or amino acids 1115-1160 of SEQ ID NO: 30. In still other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1016-1063, amino acids 1077-1104, or amino acids 1115-1160 of SEQ ID NO: 30. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1016-1063, amino acids 1077-1104, or amino acids 1115-1160 of SEQ ID NO: 30.

In other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1016-1063, amino acids 1077-1104, or amino acids 1115-1160 of SEQ ID NO: 30. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1016-1063, amino acids 1077-1104, or amino acids 1115-1160 of SEQ ID NO: 30. In yet other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1016-1063, amino acids 1077-1104, or amino acids 1115-1160 of SEQ ID NO: 30. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1016-1063, amino acids 1077-1104, or amino acids 1115-1160 of SEQ ID NO: 30. In still other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 contiguous amino acid additions relative to amino acids 1016-1063, amino acids 1077-1104, or amino acids 1115-1160 of SEQ ID NO: 30. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 contiguous amino acid additions relative to amino acids 1016-1063, amino acids 1077-1104, or amino acids 1115-1160 of SEQ ID NO: 30.

In another embodiment, a β-trefoil domain derived from a Clostridial botulinum serotype F NTNH comprises a β4/β5 hairpin turn of a β-trefoil domain of a Clostridial botulinum serotype F NTNH or a β8/β9 hairpin turn of a β-trefoil domain of a Clostridial botulinum serotype F NTNH of SEQ ID NO: 30. In another aspect of this embodiment, a β-trefoil domain derived from a Clostridial botulinum serotype F NTNH comprises amino acids 1064-1076 or amino acids 1105-1114 of SEQ ID NO: 30.

In another embodiment, a β-trefoil domain with enhanced binding activity derived from a Clostridial botulinum serotype F NTNH comprises a modified β4/β5 hairpin turn of a β-trefoil domain of a Clostridial botulinum serotype F NTNH or a modified β8/β9 hairpin turn of a β-trefoil domain of a Clostridial botulinum serotype F NTNH of SEQ ID NO: 30. In another aspect of this embodiment, a β-trefoil domain with enhanced binding activity derived from a Clostridial botulinum serotype F NTNH comprises a modification of amino acids 1064-1076 or amino acids 1105-1114 of SEQ ID NO: 30.

In other aspects of this embodiment, a β-trefoil domain with enhanced binding activity derived from a Clostridial botulinum serotype F NTNH comprises a polypeptide having, e.g., at least 70% amino acid identity with amino acids 1064-1076 or amino acids 1105-1114 of SEQ ID NO: 30, at least 75% amino acid identity with amino acids 1064-1076 or amino acids 1105-1114 of SEQ ID NO: 30, at least 80% amino acid identity with amino acids 1064-1076 or amino acids 1105-1114 of SEQ ID NO: 30, at least 85% amino acid identity with amino acids 1064-1076 or amino acids 1105-1114 of SEQ ID NO: 30, at least 90% amino acid identity with amino acids 1064-1076 or amino acids 1105-1114 of SEQ ID NO: 30 or at least 95% amino acid identity with amino acids 1064-1076 or amino acids 1105-1114 of SEQ ID NO: 30. In yet other aspects of this embodiment, a β-trefoil domain with enhanced binding activity derived from a Clostridial botulinum serotype F NTNH comprises a polypeptide having, e.g., at most 70% amino acid identity with amino acids 1064-1076 or amino acids 1105-1114 of SEQ ID NO: 30, at most 75% amino acid identity with amino acids 1064-1076 or amino acids 1105-1114 of SEQ ID NO: 30, at most 80% amino acid identity with amino acids 1064-1076 or amino acids 1105-1114 of SEQ ID NO: 30, at most 85% amino acid identity with amino acids 1064-1076 or amino acids 1105-1114 of SEQ ID NO: 30, at most 90% amino acid identity with amino acids 1064-1076 or amino acids 1105-1114 of SEQ ID NO: 30 or at most 95% amino acid identity with amino acids 1064-1076 or amino acids 1105-1114 of SEQ ID NO: 30.

In other aspects of this embodiment, a β-trefoil domain with enhanced binding activity derived from a Clostridial botulinum serotype F NTNH comprises a polypeptide having, e.g., at most one, two, three or four non-contiguous amino acid substitutions relative to amino acids 1064-1076 or amino acids 1105-1114 of SEQ ID NO: 30. In other aspects of this embodiment, a β-trefoil domain with enhanced binding activity derived from a Clostridial botulinum serotype F NTNH comprises a polypeptide having, e.g., at least one, two, three or four non-contiguous amino acid substitutions relative to amino acids 1064-1076 or amino acids 1105-1114 of SEQ ID NO: 30. In other aspects of this embodiment, a non-contiguous amino acid substitution of any amino acid from amino acids 1064-1076 or amino acids 1105-1114 of SEQ ID NO: 30 can be replaced with glycine. In other aspects of this embodiment, a non-contiguous amino acid substitution of any hydrophobic amino acid from amino acids 1064-1076 or amino acids 1105-1114 of SEQ ID NO: 30 can be replaced with phenylalanine. In yet other aspects of this embodiment, a β-trefoil domain with enhanced binding activity derived from a Clostridial botulinum serotype F NTNH comprises a polypeptide having, e.g., at most one, two, three or four non-contiguous amino acid deletions relative to amino acids 1064-1076 or amino acids 1105-1114 of SEQ ID NO: 30. In other aspects of this embodiment, a β-trefoil domain with enhanced binding activity derived from a Clostridial botulinum serotype F NTNH comprises a polypeptide having, e.g., at least one, two, three or four non-contiguous amino acid deletions relative to amino acids 1064-1076 or amino acids 1105-1114 of SEQ ID NO: 30. In still other aspects of this embodiment, a β-trefoil domain with enhanced binding activity derived from a Clostridial botulinum serotype F NTNH comprises a polypeptide having, e.g., at most one, two, three or four non-contiguous amino acid additions relative to amino acids 1064-1076 or amino acids 1105-1114 of SEQ ID NO: 30. In other aspects of this embodiment, a β-trefoil domain with enhanced binding activity derived from a Clostridial botulinum serotype F NTNH comprises a polypeptide having, e.g., at least one, two, three or four non-contiguous amino acid additions relative to amino acids 1064-1076 or amino acids 1105-1114 of SEQ ID NO: 30.

In other aspects of this embodiment, a β-trefoil domain with enhanced binding activity derived from a Clostridial botulinum serotype F NTNH comprises a polypeptide having, e.g., at most one, two, three or four contiguous amino acid substitutions relative to amino acids 1064-1076 or amino acids 1105-1114 of SEQ ID NO: 30. In other aspects of this embodiment, a β-trefoil domain with enhanced binding activity derived from a Clostridial botulinum serotype F NTNH comprises a polypeptide having, e.g., at least one, two, three or four contiguous amino acid substitutions relative to amino acids 1064-1076 or amino acids 1105-1114 of SEQ ID NO: 30. In other aspects of this embodiment, contiguous amino acid substitutions of amino acids from amino acids 1064-1076 or amino acids 1105-1114 of SEQ ID NO: 30 can be replaced with glycine. In other aspects of this embodiment, contiguous amino acid substitutions of hydrophobic amino acids from amino acids 1064-1076 or amino acids 1105-1114 of SEQ ID NO: 30 can be replaced with phenylalanine. In yet other aspects of this embodiment, a β-trefoil domain with enhanced binding activity derived from a Clostridial botulinum serotype F NTNH comprises a polypeptide having, e.g., at most one, two, three or four contiguous amino acid deletions relative to amino acids 1064-1076 or amino acids 1105-1114 of SEQ ID NO: 30. In other aspects of this embodiment, a β-trefoil domain with enhanced binding activity derived from a Clostridial botulinum serotype F NTNH comprises a polypeptide having, e.g., at least one, two, three or four contiguous amino acid deletions relative to amino acids 1064-1076 or amino acids 1105-1114 of SEQ ID NO: 30. In still other aspects of this embodiment, a β-trefoil domain with enhanced binding activity derived from a Clostridial botulinum serotype F NTNH comprises a polypeptide having, e.g., at most one, two, three or four contiguous amino acid additions relative to amino acids 1064-1076 or amino acids 1105-1114 of SEQ ID NO: 30. In other aspects of this embodiment, a β-trefoil domain with enhanced binding activity derived from a Clostridial botulinum serotype F NTNH comprises a polypeptide having, e.g., at least one, two, three or four contiguous amino acid additions relative to amino acids 1064-1076 or amino acids 1105-1114 of SEQ ID NO: 30.

In another embodiment, a β-trefoil domain derived from a Clostridial botulinum serotype F NTNH comprises a β-trefoil domain derived from a Clostridial botulinum serotype F NTNH of SEQ ID NO: 31. In another embodiment, a β-trefoil domain derived from a Clostridial botulinum serotype F NTNH comprises amino acids 1017-1166 of SEQ ID NO: 31. In another aspect of this embodiment, a β-trefoil domain derived from a Clostridial botulinum serotype F NTNH comprises a α-fold motif of a β-trefoil domain of a Clostridial botulinum serotype F NTNH, a β-fold motif of a β-trefoil domain of a Clostridial botulinum serotype F NTNH or a γ-fold motif of a β-trefoil domain of a Clostridial botulinum serotype F NTNH of SEQ ID NO: 31. In another aspect of this embodiment, a β-trefoil domain derived from a Clostridial botulinum serotype F NTNH comprises amino acids 1017-1064, amino acids 1078-1106, or amino acids 1117-1166 of SEQ ID NO: 31.

In another embodiment, a β-trefoil domain with enhanced binding activity derived from a Clostridial botulinum serotype F NTNH comprises a β-trefoil domain with enhanced binding activity derived from a Clostridial botulinum serotype F NTNH of SEQ ID NO: 31. In another embodiment, a β-trefoil domain with enhanced binding activity derived from a Clostridial botulinum serotype F NTNH comprises amino acids 1017-1166 of SEQ ID NO: 31. In another aspect of this embodiment, a β-trefoil domain with enhanced binding activity derived from a Clostridial botulinum serotype F NTNH comprises a modified α-fold motif of a β-trefoil domain of a Clostridial botulinum serotype F NTNH, a modified β-fold motif of a β-trefoil domain of a Clostridial botulinum serotype F NTNH or a modified γ-fold motif of a 13-trefoil domain of a Clostridial botulinum serotype F NTNH of SEQ ID NO: 31. In another aspect of this embodiment, a β-trefoil domain with enhanced binding activity derived from a Clostridial botulinum serotype F NTNH comprises amino acids 1017-1064, amino acids 1078-1106, or amino acids 1117-1166 of SEQ ID NO: 31.

In other aspects of this embodiment, a Clostridial botulinum serotype F NTNH comprising a β-trefoil domain with enhanced binding activity comprises a polypeptide having, e.g., at least 70% amino acid identity with amino acids 1017-1064, amino acids 1078-1106, or amino acids 1117-1166 of SEQ ID NO: 31, at least 75% amino acid identity with amino acids 1017-1064, amino acids 1078-1106, or amino acids 1117-1166 of SEQ ID NO: 31, at least 80% amino acid identity with amino acids 1017-1064, amino acids 1078-1106, or amino acids 1117-1166 of SEQ ID NO: 31, at least 85% amino acid identity with amino acids 1017-1064, amino acids 1078-1106, or amino acids 1117-1166 of SEQ ID NO: 31, at least 90% amino acid identity with amino acids 1017-1064, amino acids 1078-1106, or amino acids 1117-1166 of SEQ ID NO: 31 or at least 95% amino acid identity with amino acids 1017-1064, amino acids 1078-1106, or amino acids 1117-1166 of SEQ ID NO: 31. In yet other aspects of this embodiment, a Clostridial botulinum serotype F NTNH comprising a β-trefoil domain with enhanced binding activity comprises a polypeptide having, e.g., at most 70% amino acid identity with amino acids 1017-1064, amino acids 1078-1106, or amino acids 1117-1166 of SEQ ID NO: 31, at most 75% amino acid identity with amino acids 1017-1064, amino acids 1078-1106, or amino acids 1117-1166 of SEQ ID NO: 31, at most 80% amino acid identity with amino acids 1017-1064, amino acids 1078-1106, or amino acids 1117-1166 of SEQ ID NO: 31, at most 85% amino acid identity with amino acids 1017-1064, amino acids 1078-1106, or amino acids 1117-1166 of SEQ ID NO: 31, at most 90% amino acid identity with amino acids 1017-1064, amino acids 1078-1106, or amino acids 1117-1166 of SEQ ID NO: 31 or at most 95% amino acid identity with amino acids 1017-1064, amino acids 1078-1106, or amino acids 1117-1166 of SEQ ID NO: 31.

In other aspects of this embodiment, a Clostridial botulinum serotype F NTNH comprising a 11-trefoil domain with enhanced binding activity comprises a polypeptide having, e.g., at most one, two, three, four, five, six, seven, eight, nine, 10 or 20 non-contiguous amino acid substitutions relative to amino acids 1017-1064, amino acids 1078-1106, or amino acids 1117-1166 of SEQ ID NO: 31. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1017-1064, amino acids 1078-1106, or amino acids 1117-1166 of SEQ ID NO: 31. In yet other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1017-1064, amino acids 1078-1106, or amino acids 1117-1166 of SEQ ID NO: 31. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1017-1064, amino acids 1078-1106, or amino acids 1117-1166 of SEQ ID NO: 31. In still other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1017-1064, amino acids 1078-1106, or amino acids 1117-1166 of SEQ ID NO: 31. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1017-1064, amino acids 1078-1106, or amino acids 1117-1166 of SEQ ID NO: 31.

In other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1017-1064, amino acids 1078-1106, or amino acids 1117-1166 of SEQ ID NO: 31. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1017-1064, amino acids 1078-1106, or amino acids 1117-1166 of SEQ ID NO: 31. In yet other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1017-1064, amino acids 1078-1106, or amino acids 1117-1166 of SEQ ID NO: 31. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1017-1064, amino acids 1078-1106, or amino acids 1117-1166 of SEQ ID NO: 31. In still other aspects of this embodiment, a Clostridial botulinum serotype F NTNH comprising a β-trefoil domain with enhanced binding activity comprises a polypeptide having, e.g., at most one, two, three, four, five, six, seven, eight, nine, 10 or 20 contiguous amino acid additions relative to amino acids 1017-1064, amino acids 1078-1106, or amino acids 1117-1166 of SEQ ID NO: 31. In other aspects of this embodiment, a Clostridial botulinum serotype F NTNH comprising a β-trefoil domain with enhanced binding activity comprises a polypeptide having, e.g., at least one, two, three, four, five, six, seven, eight, nine, 10 or 20 contiguous amino acid additions relative to amino acids 1017-1064, amino acids 1078-1106, or amino acids 1117-1166 of SEQ ID NO: 31.

In another embodiment, a β-trefoil domain derived from a Clostridial botulinum serotype F NTNH comprises a β4/β5 hairpin turn of a β-trefoil domain of a Clostridial botulinum serotype F NTNH or a β8/β9 hairpin turn of a β-trefoil domain of a Clostridial botulinum serotype F NTNH of SEQ ID NO: 31. In another aspect of this embodiment, a β-trefoil domain derived from a Clostridial botulinum serotype F NTNH comprises amino acids 1065-1077 or amino acids 1107-1116 of SEQ ID NO: 31.

In another embodiment, a β-trefoil domain with enhanced binding activity derived from a Clostridial botulinum serotype F NTNH comprises a modified β4/β5 hairpin turn of a β-trefoil domain of a Clostridial botulinum serotype F NTNH or a modified β8/β9 hairpin turn of a β-trefoil domain of a Clostridial botulinum serotype F NTNH of SEQ ID NO: 31. In another aspect of this embodiment, a β-trefoil domain with enhanced binding activity derived from a Clostridial botulinum serotype F NTNH comprises a modification of amino acids 1065-1077 or amino acids 1107-1116 of SEQ ID NO: 31.

In other aspects of this embodiment, a β-trefoil domain with enhanced binding activity derived from a Clostridial botulinum serotype F NTNH comprises a polypeptide having, e.g., at least 70% amino acid identity with amino acids 1065-1077 or amino acids 1107-1116 of SEQ ID NO: 31, at least 75% amino acid identity with amino acids 1065-1077 or amino acids 1107-1116 of SEQ ID NO: 31, at least 80% amino acid identity with amino acids 1065-1077 or amino acids 1107-1116 of SEQ ID NO: 31, at least 85% amino acid identity with amino acids 1065-1077 or amino acids 1107-1116 of SEQ ID NO: 31, at least 90% amino acid identity with amino acids 1065-1077 or amino acids 1107-1116 of SEQ ID NO: 31 or at least 95% amino acid identity with amino acids 1065-1077 or amino acids 1107-1116 of SEQ ID NO: 31. In yet other aspects of this embodiment, a β-trefoil domain with enhanced binding activity derived from a Clostridial botulinum serotype F NTNH comprises a polypeptide having, e.g., at most 70% amino acid identity with amino acids 1065-1077 or amino acids 1107-1116 of SEQ ID NO: 31, at most 75% amino acid identity with amino acids 1065-1077 or amino acids 1107-1116 of SEQ ID NO: 31, at most 80% amino acid identity with amino acids 1065-1077 or amino acids 1107-1116 of SEQ ID NO: 31, at most 85% amino acid identity with amino acids 1065-1077 or amino acids 1107-1116 of SEQ ID NO: 31, at most 90% amino acid identity with amino acids 1065-1077 or amino acids 1107-1116 of SEQ ID NO: 31 or at most 95% amino acid identity with amino acids 1065-1077 or amino acids 1107-1116 of SEQ ID NO: 31.

In other aspects of this embodiment, a β-trefoil domain with enhanced binding activity derived from a Clostridial botulinum serotype F NTNH comprises a polypeptide having, e.g., at most one, two, three or four non-contiguous amino acid substitutions relative to amino acids 1065-1077 or amino acids 1107-1116 of SEQ ID NO: 31. In other aspects of this embodiment, a β-trefoil domain with enhanced binding activity derived from a Clostridial botulinum serotype F NTNH comprises a polypeptide having, e.g., at least one, two, three or four non-contiguous amino acid substitutions relative to amino acids 1065-1077 or amino acids 1107-1116 of SEQ ID NO: 31. In other aspects of this embodiment, a non-contiguous amino acid substitution of any amino acid from amino acids 1065-1077 or amino acids 1107-1116 of SEQ ID NO: 31 can be replaced with glycine. In other aspects of this embodiment, a non-contiguous amino acid substitution of any hydrophobic amino acid from amino acids 1065-1077 or amino acids 1107-1116 of SEQ ID NO: 31 can be replaced with phenylalanine. In yet other aspects of this embodiment, a β-trefoil domain with enhanced binding activity derived from a Clostridial botulinum serotype F NTNH comprises a polypeptide having, e.g., at most one, two, three or four non-contiguous amino acid deletions relative to amino acids 1065-1077 or amino acids 1107-1116 of SEQ ID NO: 31. In other aspects of this embodiment, a β-trefoil domain with enhanced binding activity derived from a Clostridial botulinum serotype F NTNH comprises a polypeptide having, e.g., at least one, two, three or four non-contiguous amino acid deletions relative to amino acids 1065-1077 or amino acids 1107-1116 of SEQ ID NO: 31. In still other aspects of this embodiment, a β-trefoil domain with enhanced binding activity derived from a Clostridial botulinum serotype F NTNH comprises a polypeptide having, e.g., at most one, two, three or four non-contiguous amino acid additions relative to amino acids 1065-1077 or amino acids 1107-1116 of SEQ ID NO: 31. In other aspects of this embodiment, a β-trefoil domain with enhanced binding activity derived from a Clostridial botulinum serotype F NTNH comprises a polypeptide having, e.g., at least one, two, three or four non-contiguous amino acid additions relative to amino acids 1065-1077 or amino acids 1107-1116 of SEQ ID NO: 31.

In other aspects of this embodiment, a β-trefoil domain with enhanced binding activity derived from a Clostridial botulinum serotype F NTNH comprises a polypeptide having, e.g., at most one, two, three or four contiguous amino acid substitutions relative to amino acids 1065-1077 or amino acids 1107-1116 of SEQ ID NO: 31. In other aspects of this embodiment, a β-trefoil domain with enhanced binding activity derived from a Clostridial botulinum serotype F NTNH comprises a polypeptide having, e.g., at least one, two, three or four contiguous amino acid substitutions relative to amino acids 1065-1077 or amino acids 1107-1116 of SEQ ID NO:

31. In other aspects of this embodiment, contiguous amino acid substitutions of amino acids from amino acids 1065-1077 or amino acids 1107-1116 of SEQ ID NO: 31 can be replaced with glycine. In other aspects of this embodiment, contiguous amino acid substitutions of hydrophobic amino acids from amino acids 1065-1077 or amino acids 1107-1116 of SEQ ID NO: 31 can be replaced with phenylalanine. In yet other aspects of this embodiment, a β-trefoil domain with enhanced binding activity derived from a Clostridial botulinum serotype F NTNH comprises a polypeptide having, e.g., at most one, two, three or four contiguous amino acid deletions relative to amino acids 1065-1077 or amino acids 1107-1116 of SEQ ID NO: 31. In other aspects of this embodiment, a β-trefoil domain with enhanced binding activity derived from a Clostridial botulinum serotype F NTNH comprises a polypeptide having, e.g., at least one, two, three or four contiguous amino acid deletions relative to amino acids 1065-1077 or amino acids 1107-1116 of SEQ ID NO: 31. In still other aspects of this embodiment, a β-trefoil domain with enhanced binding activity derived from a Clostridial botulinum serotype F NTNH comprises a polypeptide having, e.g., at most one, two, three or four contiguous amino acid additions relative to amino acids 1065-1077 or amino acids 1107-1116 of SEQ ID NO: 31. In other aspects of this embodiment, a β-trefoil domain with enhanced binding activity derived from a Clostridial botulinum serotype F NTNH comprises a polypeptide having, e.g., at least one, two, three or four contiguous amino acid additions relative to amino acids 1065-1077 or amino acids 1107-1116 of SEQ ID NO: 31.

In another embodiment, a β-trefoil domain derived from a Clostridial botulinum serotype G NTNH comprises a β-trefoil domain derived from a Clostridial botulinum serotype G NTNH of SEQ ID NO: 32. In another embodiment, a β-trefoil domain derived from a Clostridial botulinum serotype G NTNH comprises amino acids 1050-1199 of SEQ ID NO: 32. In another aspect of this embodiment, a β-trefoil domain derived from a Clostridial botulinum serotype G NTNH comprises a α-fold motif of a 8-trefoil domain of a Clostridial botulinum serotype G NTNH, a β-fold motif of a β-trefoil domain of a Clostridial botulinum serotype G NTNH or a γ-fold motif of a β-trefoil domain of a Clostridial botulinum serotype G NTNH of SEQ ID NO: 32. In another aspect of this embodiment, a β-trefoil domain derived from a Clostridial botulinum serotype G NTNH comprises amino acids 1050-1097, amino acids 1111-1139, or amino acids 1150-1199 of SEQ ID NO: 32.

In another embodiment, a β-trefoil domain with enhanced binding activity derived from a Clostridial botulinum serotype G NTNH comprises a β-trefoil domain with enhanced binding activity derived from a Clostridial botulinum serotype G NTNH of SEQ ID NO: 32. In another embodiment, a β-trefoil domain with enhanced binding activity derived from a Clostridial botulinum serotype G NTNH comprises amino acids 1050-1199 of SEQ ID NO: 32. In another aspect of this embodiment, a β-trefoil domain with enhanced binding activity derived from a Clostridial botulinum serotype G NTNH comprises a modified α-fold motif of a β-trefoil domain of a Clostridial botulinum serotype G NTNH, a modified β-fold motif of a β-trefoil domain of a Clostridial botulinum serotype G NTNH or a modified γ-fold motif of a β-trefoil domain of a Clostridial botulinum serotype G NTNH of SEQ ID NO: 32. In another aspect of this embodiment, a β-trefoil domain with enhanced binding activity derived from a Clostridial botulinum serotype G NTNH comprises amino acids 1050-1097, amino acids 1111-1139, or amino acids 1150-1199 of SEQ ID NO: 32.

In other aspects of this embodiment, a Clostridial botulinum serotype G NTNH comprising a β-trefoil domain with enhanced binding activity comprises a polypeptide having, e.g., at least 70% amino acid identity with amino acids 1050-1097, amino acids 1111-1139, or amino acids 1150-1199 of SEQ ID NO: 32, at least 75% amino acid identity with amino acids 1050-1097, amino acids 1111-1139, or amino acids 1150-1199 of SEQ ID NO: 32, at least 80% amino acid identity with amino acids 1050-1097, amino acids 1111-1139, or amino acids 1150-1199 of SEQ ID NO: 32, at least 85% amino acid identity with amino acids 1050-1097, amino acids 1111-1139, or amino acids 1150-1199 of SEQ ID NO: 32, at least 90% amino acid identity with amino acids 1050-1097, amino acids 1111-1139, or amino acids 1150-1199 of SEQ ID NO: 32 or at least 95% amino acid identity with amino acids 1050-1097, amino acids 1111-1139, or amino acids 1150-1199 of SEQ ID NO: 32. In yet other aspects of this embodiment, a Clostridial botulinum serotype G NTNH comprising a β-trefoil domain with enhanced binding activity comprises a polypeptide having, e.g., at most 70% amino acid identity with amino acids 1050-1097, amino acids 1111-1139, or amino acids 1150-1199 of SEQ ID NO: 32, at most 75% amino acid identity with amino acids 1050-1097, amino acids 1111-1139, or amino acids 1150-1199 of SEQ ID NO: 32, at most 80% amino acid identity with amino acids 1050-1097, amino acids 1111-1139, or amino acids 1150-1199 of SEQ ID NO: 32, at most 85% amino acid identity with amino acids 1050-1097, amino acids 1111-1139, or amino acids 1150-1199 of SEQ ID NO: 32, at most 90% amino acid identity with amino acids 1050-1097, amino acids 1111-1139, or amino acids 1150-1199 of SEQ ID NO: 32 or at most 95% amino acid identity with amino acids 1050-1097, amino acids 1111-1139, or amino acids 1150-1199 of SEQ ID NO: 32.

In other aspects of this embodiment, a Clostridial botulinum serotype G NTNH comprising a 11-trefoil domain with enhanced binding activity comprises a polypeptide having, e.g., at most one, two, three, four, five, six, seven, eight, nine, 10 or 20 non-contiguous amino acid substitutions relative to amino acids 1050-1097, amino acids 1111-1139, or amino acids 1150-1199 of SEQ ID NO: 32. In other aspects of this embodiment, a Clostridial botulinum serotype G NTNH comprising a β-trefoil domain with enhanced binding activity comprises a polypeptide having, e.g., at least one, two, three, four, five, six, seven, eight, nine, 10 or 20 non-contiguous amino acid substitutions relative to amino acids 1050-1097, amino acids 1111-1139, or amino acids 1150-1199 of SEQ ID NO: 32. In yet other aspects of this embodiment, a Clostridial botulinum serotype G NTNH comprising a β-trefoil domain with enhanced binding activity comprises a polypeptide having, e.g., at most one, two, three, four, five, six, seven, eight, nine, 10 or 20 non-contiguous amino acid deletions relative to amino acids 1050-1097, amino acids 1111-1139, or amino acids 1150-1199 of SEQ ID NO: 32. In other aspects of this embodiment, a Clostridial botulinum serotype G NTNH comprising a β-trefoil domain with enhanced binding activity comprises a polypeptide having, e.g., at least one, two, three, four, five, six, seven, eight, nine, 10 or 20 non-contiguous amino acid deletions relative to amino acids 1050-1097, amino acids 1111-1139, or amino acids 1150-1199 of SEQ ID NO: 32. In still other aspects of this embodiment, a Clostridial botulinum serotype G NTNH comprising a β-trefoil domain with enhanced binding activity comprises a polypeptide having, e.g., at most one, two, three, four, five, six, seven, eight, nine, 10 or 20 non-contiguous amino acid additions relative to amino acids 1050-1097, amino acids 1111-1139, or amino acids 1150-1199 of SEQ ID NO: 32. In other aspects of this embodiment, a Clostridial botulinum serotype G NTNH comprising a β-trefoil domain with enhanced binding activity comprises a polypeptide having, e.g., at least one, two, three, four, five, six, seven, eight, nine, 10 or 20 non-contiguous amino acid additions relative to amino acids 1050-1097, amino acids 1111-1139, or amino acids 1150-1199 of SEQ ID NO: 32.

In other aspects of this embodiment, a Clostridial botulinum serotype G NTNH comprising a β-trefoil domain with enhanced binding activity comprises a polypeptide having, e.g., at most one, two, three, four, five, six, seven, eight, nine, 10 or 20 contiguous amino acid substitutions relative to amino acids 1050-1097, amino acids 1111-1139, or amino acids 1150-1199 of SEQ ID NO: 32. In other aspects of this embodiment, a Clostridial botulinum serotype G NTNH comprising a β-trefoil domain with enhanced binding activity comprises a polypeptide having, e.g., at least one, two, three, four, five, six, seven, eight, nine, 10 or 20 contiguous amino acid substitutions relative to amino acids 1050-1097, amino acids 1111-1139, or amino acids 1150-1199 of SEQ ID NO: 32. In yet other aspects of this embodiment, a Clostridial botulinum serotype G NTNH comprising a β-trefoil domain with enhanced binding activity comprises a polypeptide having, e.g., at most one, two, three, four, five, six, seven, eight, nine, 10 or 20 contiguous amino acid deletions relative to amino acids 1050-1097, amino acids 1111-1139, or amino acids 1150-1199 of SEQ ID NO: 32. In other aspects of this embodiment, a Clostridial botulinum serotype G NTNH comprising a β-trefoil domain with enhanced binding activity comprises a polypeptide having, e.g., at least one, two, three, four, five, six, seven, eight, nine, 10 or 20 contiguous amino acid deletions relative to amino acids 1050-1097, amino acids 1111-1139, or amino acids 1150-1199 of SEQ ID NO: 32. In still other aspects of this embodiment, a Clostridial botulinum serotype G NTNH comprising a β-trefoil domain with enhanced binding activity comprises a polypeptide having, e.g., at most one, two, three, four, five, six, seven, eight, nine, 10 or 20 contiguous amino acid additions relative to amino acids 1050-1097, amino acids 1111-1139, or amino acids 1150-1199 of SEQ ID NO: 32. In other aspects of this embodiment, a Clostridial botulinum serotype G NTNH comprising a β-trefoil domain with enhanced binding activity comprises a polypeptide having, e.g., at least one, two, three, four, five, six, seven, eight, nine, 10 or 20 contiguous amino acid additions relative to amino acids 1050-1097, amino acids 1111-1139, or amino acids 1150-1199 of SEQ ID NO: 32.

In another embodiment, a β-trefoil domain derived from a Clostridial botulinum serotype G NTNH comprises a β4/β5 hairpin turn of a β-trefoil domain of a Clostridial botulinum serotype G NTNH or a β8/β9 hairpin turn of a β-trefoil domain of a Clostridial botulinum serotype G NTNH of SEQ ID NO: 32. In another aspect of this embodiment, a β-trefoil domain derived from a Clostridial botulinum serotype G NTNH comprises amino acids 1098-1110 or amino acids 1140-1149 of SEQ ID NO: 32.

In another embodiment, a β-trefoil domain with enhanced binding activity derived from a Clostridial botulinum serotype G NTNH comprises a modified β4/β5 hairpin turn of a β-trefoil domain of a Clostridial botulinum serotype G NTNH or a modified β8/β9 hairpin turn of a β-trefoil domain of a Clostridial botulinum serotype G NTNH of SEQ ID NO: 32. In another aspect of this embodiment, a β-trefoil domain with enhanced binding activity derived from a Clostridial botulinum serotype G NTNH comprises a modification of amino acids 1098-1110 or amino acids 1140-1149 of SEQ ID NO: 32.

In other aspects of this embodiment, a β-trefoil domain with enhanced binding activity derived from a Clostridial botulinum serotype G NTNH comprises a polypeptide having, e.g., at least 70% amino acid identity with amino acids 1098-1110 or amino acids 1140-1149 of SEQ ID NO: 32, at least 75% amino acid identity with amino acids 1098-1110 or amino acids 1140-1149 of SEQ ID NO: 32, at least 80% amino acid identity with amino acids 1098-1110 or amino acids 1140-1149 of SEQ ID NO: 32, at least 85% amino acid identity with amino acids 1098-1110 or amino acids 1140-1149 of SEQ ID NO: 32, at least 90% amino acid identity with amino acids 1098-1110 or amino acids 1140-1149 of SEQ ID NO: 32 or at least 95% amino acid identity with amino acids 1098-1110 or amino acids 1140-1149 of SEQ ID NO: 32. In yet other aspects of this embodiment, a β-trefoil domain with enhanced binding activity derived from a Clostridial botulinum serotype G NTNH comprises a polypeptide having, e.g., at most 70% amino acid identity with amino acids 1098-1110 or amino acids 1140-1149 of SEQ ID NO: 32, at most 75% amino acid identity with amino acids 1098-1110 or amino acids 1140-1149 of SEQ ID NO: 32, at most 80% amino acid identity with amino acids 1098-1110 or amino acids 1140-1149 of SEQ ID NO: 32, at most 85% amino acid identity with amino acids 1098-1110 or amino acids 1140-1149 of SEQ ID NO: 32, at most 90% amino acid identity with amino acids 1098-1110 or amino acids 1140-1149 of SEQ ID NO: 32 or at most 95% amino acid identity with amino acids 1098-1110 or amino acids 1140-1149 of SEQ ID NO: 32.

In other aspects of this embodiment, a β-trefoil domain with enhanced binding activity derived from a Clostridial botulinum serotype G NTNH comprises a polypeptide having, e.g., at most one, two, three or four non-contiguous amino acid substitutions relative to amino acids 1098-1110 or amino acids 1140-1149 of SEQ ID NO: 32. In other aspects of this embodiment, a β-trefoil domain with enhanced binding activity derived from a Clostridial botulinum serotype G NTNH comprises a polypeptide having, e.g., at least one, two, three or four non-contiguous amino acid substitutions relative to amino acids 1098-1110 or amino acids 1140-1149 of SEQ ID NO: 32. In other aspects of this embodiment, a non-contiguous amino acid substitution of any amino acid from amino acids 1098-1110 or amino acids 1140-1149 of SEQ ID NO: 32 can be replaced with glycine. In other aspects of this embodiment, a non-contiguous amino acid substitution of any hydrophobic amino acid from amino acids 1098-1110 or amino acids 1140-1149 of SEQ ID NO: 32 can be replaced with phenylalanine. In yet other aspects of this embodiment, a β-trefoil domain with enhanced binding activity derived from a Clostridial botulinum serotype G NTNH comprises a polypeptide having, e.g., at most one, two, three or four non-contiguous amino acid deletions relative to amino acids 1098-1110 or amino acids 1140-1149 of SEQ ID NO: 32. In other aspects of this embodiment, a β-trefoil domain with enhanced binding activity derived from a Clostridial botulinum serotype G NTNH comprises a polypeptide having, e.g., at least one, two, three or four non-contiguous amino acid deletions relative to amino acids 1098-1110 or amino acids 1140-1149 of SEQ ID NO: 32. In still other aspects of this embodiment, a β-trefoil domain with enhanced binding activity derived from a Clostridial botulinum serotype G NTNH comprises a polypeptide having, e.g., at most one, two, three or four non-contiguous amino acid additions relative to amino acids 1098-1110 or amino acids 1140-1149 of SEQ ID NO: 32. In other aspects of this embodiment, a β-trefoil domain with enhanced binding activity derived from a Clostridial botulinum serotype G NTNH comprises a polypeptide having, e.g., at least one, two, three or four non-contiguous amino acid additions relative to amino acids 1098-1110 or amino acids 1140-1149 of SEQ ID NO: 32.

In other aspects of this embodiment, a β-trefoil domain with enhanced binding activity derived from a Clostridial botulinum serotype G NTNH comprises a polypeptide having, e.g., at most one, two, three or four contiguous amino acid substitutions relative to amino acids 1098-1110 or amino acids 1140-1149 of SEQ ID NO: 32. In other aspects of this embodiment, a β-trefoil domain with enhanced binding activity derived from a Clostridial botulinum serotype G NTNH comprises a polypeptide having, e.g., at least one, two, three or four contiguous amino acid substitutions relative to amino acids 1098-1110 or amino acids 1140-1149 of SEQ ID NO: 32. In other aspects of this embodiment, contiguous amino acid substitutions of amino acids from amino acids 1098-1110 or amino acids 1140-1149 of SEQ ID NO: 32 can be replaced with glycine. In other aspects of this embodiment, contiguous amino acid substitutions of hydrophobic amino acids from amino acids 1098-1110 or amino acids 1140-1149 of SEQ ID NO: 32 can be replaced with phenylalanine. In yet other aspects of this embodiment, a β-trefoil domain with enhanced binding activity derived from a Clostridial botulinum serotype G NTNH comprises a polypeptide having, e.g., at most one, two, three or four contiguous amino acid deletions relative to amino acids 1098-1110 or amino acids 1140-1149 of SEQ ID NO: 32. In other aspects of this embodiment, a β-trefoil domain with enhanced binding activity derived from a Clostridial botulinum serotype G NTNH comprises a polypeptide having, e.g., at least one, two, three or four contiguous amino acid deletions relative to amino acids 1098-1110 or amino acids 1140-1149 of SEQ ID NO: 32. In still other aspects of this embodiment, a β-trefoil domain with enhanced binding activity derived from a Clostridial botulinum serotype G NTNH comprises a polypeptide having, e.g., at most one, two, three or four contiguous amino acid additions relative to amino acids 1098-1110 or amino acids 1140-1149 of SEQ ID NO: 32. In other aspects of this embodiment, a β-trefoil domain with enhanced binding activity derived from a Clostridial botulinum serotype G NTNH comprises a polypeptide having, e.g., at least one, two, three or four contiguous amino acid additions relative to amino acids 1098-1110 or amino acids 1140-1149 of SEQ ID NO: 32.

Another example of an enhanced targeting domain that increases binding activity for an endogenous Clostridial toxin receptor system present on a naturally-occurring Clostridial toxin target cell, includes, without limitation, ligands that bind the same receptor systems as naturally-occurring Clostridial toxins. Recent studies are revealing components of the endogenous receptor systems used by a Clostridial toxin during the intoxication process. As a non-limiting example, fibroblast growth factor 3 receptor (FGFR3) serves as a BoNT/A receptor, see, e.g., Ester Fernandez-Salas et al., Botulinum Toxin Screening Assays, PCT Patent Application No. 2005/006421 (Sep. 9, 2005). As another non-limiting example, synaptotagmin I serves as a BoNT/B receptor and as a BoNT/G receptor, see, e.g., Min Dong et al., *Synaptotagmins I and II mediate entry of botulinum neurotoxin B into cells,* 162(7) J. Cell Biol. 1293-1303 (2003); and Andreas Rummel et al., *Synaptotagmins I and II act as nerve cell receptors for botulinum neurotoxin G,* 279(29) J. Biol. Chem. 30865-30870 (2004). As yet another non-limiting example, synaptotagmin II serves as a BoNT/B receptor and as a BoNT/G receptor, see, e.g., Min Dong et al., supra, (2003); and Andreas Rummel et al., supra, (2004). The selection of a ligand domain as an enhanced binding region will depend on the Clostridial toxin being modified. As non-limiting examples, ligands that selectively bind to a FGFR3 could be used as an enhanced targeting domain for a modified BoNT/A, whereas ligands that selectively bind a Synaptotagmin I or Synaptotagmin II could be used as an enhanced targeting domain for a modified BoNT/B or a modified BoNT/G.

Fibroblast growth factors (FGF) participate in many developmental, differentiation and growth and repair processes of cells through complex combinatorial signaling pathways. Presently, at least 23 ligands (FGF1-23) are known to signal through a family of five transmembrane tyrosine kinase FGF receptors (FGFR1-5). Affinity of FGFRs for their ligands is highly diverse with different affinities for each family member of growth factors, see, e.g., C. J. Powers et al., *Fibroblast growth factors, their receptors and signaling,* 7(3) Endocr. Relat. Cancer. 165-197 (2000). This diversity is achieved in part by the generation of alternatively spliced variants encoding distinct receptor isoforms, see, e.g., Bernhard Reuss & Oliver von Bohlen and Halbach, *Fibroblast growth factors and their receptors in the central nervous system,* 313(2) Cell Tissue Res. 139-157 (2003). The protein region that appears to have the highest influence on ligand binding selectivity is a portion of the IgIII domain, for which isoforms encoded by three different splice variants have been identified. These three isoforms, designated IgIIIa, IgIIIb and IgIIIc, have relative binding affinities for different FGFR family members. Alternative splicing in the FGFR ligand binding domain, designated a and b, generates additional receptor isoforms with novel ligand affinities. Isoforms for IgIIIa, IgIIIb and IgIIIc have been identified for both FGFR1 and FGFR2. Thus far, the IgIIIa isoform of FGFR3 and the IgIIIa and IgIIIb isoforms of FGFR4 and FGFR5 have not been reported.

Currently, several FGFs have been shown to selectively bind FGFR3, such as, e.g., FGF-1, FGF-2, FGF-4, FGF-8, FGF-9, FGF-17 and FGF-18, see, e.g., Hecht et al., 1995; Ornitz et al., 1996; and Xu et al., 2000. Additional studies have revealed that FGF-1 and FGF9 preferentially bind FGFR3IIIb, whereas FGF-1 FGF-2, FGF-4, FGF-8, and FGF9 preferentially bind FGFR3IIIc. Studies have shown that each of these ligands is present in various vertebrate species with a high degree of sequence identity which suggests functional equivalence or similarity. As a non-limiting example, FGF-8 is found in fish, birds and mammals and each of these FGF-8 ligands have over 80% amino acid sequence identity. As another non-limiting example, FGF-18 is found in fish, birds and mammals and each of these FGF-18 ligands have over 70% amino acid sequence identity. Crystallographic studies have revealed that all FGFs are structurally organized into a β-trefoil domain. The amino acid sequences comprising the β-trefoil domains found in various FGF ligands that bind FGFR3 are shown in Table 7.

TABLE 7

| β-trefoil Domains of FGFs | | | | | | | |
|---|---|---|---|---|---|---|---|
| | | Amino Acid Sequence Region of Carbohydrate Binding Moieties | | | | | |
| Ligand | SEQ ID NO: | α-fold | β4/β5 β-hairpin turn | β-fold | β8/β9 β-hairpin turn | γ-fold |
| FGF-1 | 33 | 26-64 | 65-67 | 68-105 | 106-108 | 109-155 |
| FGF-2 | 34 | 29-67 | 68-70 | 71-111 | 112-114 | 115-155 |
| FGF-4 | 35 | 83-121 | 122-124 | 125-162 | 163-165 | 166-206 |
| FGF-8 | 36 | 43-80 | 81-83 | 84-123 | 124-126 | 127-172 |
| FGF-9 | 37 | 63-100 | 101-103 | 104-144 | 145-147 | 148-196 |
| FGF-17 | 38 | 55-91 | 92-94 | 95-134 | 135-137 | 138-183 |
| FGF-18 | 39 | 54-91 | 92-94 | 95-134 | 135-137 | 138-183 |

As used herein, the term "Fibroblast Growth Factor" is synonymous with "FGF" and means a polypeptide with selective binding activity, such as, e.g., a binding affinity or a binding specificity, for a receptor system, including endogenous Clostridial toxin receptor systems such as, e.g., a receptor system comprising FGFR3. It is envisioned that both naturally occurring FGFs as well as FGFs with enhanced binding activity can be used to practice aspects of the present invention. As used herein, the term "FGF with enhanced binding activity" means a FGF with enhanced binding activity for an endogenous Clostridial toxin receptor system, such as, e.g., a binding affinity or a binding specificity, to a statistically significantly degree relative to an unmodified naturally occurring Clostridial toxin binding domain from a Clostridial toxin. By definition, a FGF with enhanced binding activity has at least one amino acid change from the corresponding region of the disclosed reference sequences (see Table 7) and can be described in percent identity to the corresponding region of that reference sequence.

Any of a variety of sequence alignment methods can be used to determine percent identity of a modified FGF relative to a naturally-occurring FGF, including, without limitation, global methods, local methods and hybrid methods, such as, e.g., segment approach methods. Protocols to determine percent identity are routine procedures within the scope of one skilled in the art and from the teaching herein.

Approaches well known to one skilled in the art on how to modify a FGF in order to increase its binding activity for an endogenous Clostridial toxin receptor system present on a naturally-occurring Clostridial toxin target cell. As described above, one approach involves identifying amino acids using computational protein design algorithims; changing specifically-identified amino acids using, without limitation, site-directed mutagenesis, oligonucleotide-directed mutagenesis and site-specific mutagenesis; and testing the binding activity of modified Clostridial toxins comprising a modified FGF with enhanced binding activity using, e.g., heterogeneous assays, homogeneous assays and non-separating homogeneous assays. It is further envisioned that the binding activity of a modified Clostridial toxin with enhanced binding activity disclosed in the present specification can be determined by affinity chromotography using immobilized receptors and interfacial optical assays. In another approach described above, a binding activity of a modified FGF for a naturally-occurring Clostridial toxin receptor system present on a naturally-occurring Clostridial toxin target cell can be achieved using directed-evolution methods.

A FGF includes, without limitation, naturally occurring FGF variants, such as, e.g., FGF isoforms and FGF subtypes; non-naturally occurring FGF variants, such as, e.g., conservative FGF variants, non-conservative FGF variants, FGF chimerics, active FGF fragments thereof, or any combination thereof.

As used herein, the term "FGF variant," whether naturally-occurring or non-naturally-occurring, means a FGF that has at least one amino acid change from the corresponding region of the disclosed reference sequences (see Tables 7) and can be described in percent identity to the corresponding region of that reference sequence. Unless expressly indicated, all FGF variants disclosed in the present specification are capable of executing the cell binding step of the intoxication process.

It is recognized by those of skill in the art that within each Clostridial bacterium there can be naturally occurring FGF variants that differ somewhat in their amino acid sequence, and also in the nucleic acids encoding these proteins. For example, there are presently at least four FGF-8 variants, FGF-8A, FGF-8A, FGF-8B, FGF-8E and FGF-8F, with specific FGF-8 variants showing various degrees of amino acid divergence when compared to another FGF-8 variant. As another example, there are presently at least two FGF-2 variants, FGF-2-1 and FGF-2-1, with the FGF-2-1 variant showing an amino acid divergence when compared to the FGF-2-2 variant. As used herein, the term "naturally occurring FGF variant" means any FGF produced by a naturally-occurring process, including, without limitation, FGF isoforms produced from alternatively-spliced transcripts, FGF isoforms produced by spontaneous mutation and FGF subtypes. A naturally occurring FGF variant can function in substantially the same manner as the reference FGF on which the naturally occurring FGF variant is based, and can be substituted for the reference FGF in any aspect of the present invention. A naturally occurring FGF variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference FGF on which the naturally occurring FGF variant is based. A naturally occurring FGF variant can also substitute at least 10 contiguous amino acids, at least 15 contiguous amino acids, at least 20 contiguous amino acids, or at least 25 contiguous amino acids from the reference FGF on which the naturally occurring FGF variant is based, that possess at least 50% amino acid identity, 65% amino acid identity, 75% amino acid identity, 85% amino acid identity or 95% amino acid identity to the reference FGF on which the naturally occurring FGF variant is based.

A non-limiting examples of a naturally occurring FGF variant is a FGF isoform such as, e.g., a FGF-1 isoform, a FGF-2 isoform, a FGF-4 isoform, a FGF-8 isoform, a FGF-9 isoform, a FGF-17 isoform and a FGF-18 isoform. A FGF isoform can function in substantially the same manner as the reference FGF on which the FGF isoform is based, and can be substituted for the reference FGF in any aspect of the present invention.

Another non-limiting examples of a naturally occurring FGF variant is a FGF subtype such as, e.g., a FGF-1 subtype, a FGF-2 subtype, a FGF-4 subtype, a FGF-8 subtype, a FGF-9 subtype, a FGF-17 subtype and a FGF-18 subtype. A FGF subtype can function in substantially the same manner as the reference FGF on which the FGF subtype is based, and can be substituted for the reference FGF in any aspect of the present invention.

As used herein, the term "non-naturally occurring FGF variant" means any FGF produced with the aid of human manipulation, including, without limitation, FGFs produced by genetic engineering using random mutagenesis or rational design and FGFs produced by chemical synthesis. Non-limiting examples of non-naturally occurring FGF variants include, e.g., conservative FGF variants, non-conservative FGF variants, FGF chimeric variants and active FGF fragments.

As used herein, the term "conservative FGF variant" means a FGF that has at least one amino acid substituted by another amino acid or an amino acid analog that has at least one property similar to that of the original amino acid from the reference FGF sequence (see Table 7). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative FGF variant can function in substantially the same manner as the reference FGF on which the conservative FGF variant is based, and can be substituted for the reference FGF in any aspect of the present invention. A conservative FGF variant may substitute one or more amino acids, two or more amino acids, three or more amino acids, four or more amino acids, five or more amino acids, ten or more amino acids, 20 or more amino acids, 30 or more amino acids, 40 or more amino acids or 50 or more amino acids from the reference FGF on which the conservative FGF variant is based. A conservative FGF variant can also substitute at least 10 contiguous amino acids, at least 15 contiguous amino acids, at least 20 contiguous amino acids, or at least 25 contiguous amino acids from the reference FGF on which the conservative FGF variant is based, that possess at least 50% amino acid identity, 65% amino acid identity, 75% amino acid identity, 85% amino acid identity or 95% amino acid identity to the reference FGF on which the conservative FGF variant is based. Non-limiting examples of a conservative FGF variant include, e.g., a conservative FGF-1 variant, a conservative FGF-2 variant, a conservative FGF-4 variant, a conservative FGF-8 variant, a conservative FGF-9 variant, a conservative FGF-17 variant and a conservative FGF-18 variant.

As used herein, the term "non-conservative FGF variant" means a FGF in which 1) at least one amino acid is deleted from the reference FGF on which the non-conservative FGF variant is based; 2) at least one amino acid added to the reference FGF on which the non-conservative FGF is based; or 3) at least one amino acid is substituted by another amino acid or an amino acid analog that does not share any property similar to that of the original amino acid from the reference FGF sequence (see Table 7). A non-conservative FGF variant can function in substantially the same manner as the reference FGF on which the non-conservative FGF variant is based, and can be substituted for the reference FGF in any aspect of the present invention. A non-conservative FGF variant can delete one or more amino acids, two or more amino acids, three or more amino acids, four or more amino acids, five or more amino acids, and ten or more amino acids from the reference FGF on which the non-conservative FGF variant is based. A non-conservative FGF variant can add one or more amino acids, two or more amino acids, three or more amino acids, four or more amino acids, five or more amino acids, and ten or more amino acids to the reference FGF on which the non-conservative FGF variant is based. A non-conservative FGF variant may substitute one or more amino acids, two or more amino acids, three or more amino acids, four or more amino acids, five or more amino acids, ten or more amino acids, 20 or more amino acids, 30 or more amino acids, 40 or more amino acids or 50 or more amino acids from the reference FGF on which the non-conservative FGF variant is based. A non-conservative FGF variant can also substitute at least 10 contiguous amino acids, at least 15 contiguous amino acids, at least 20 contiguous amino acids, or at least 25 contiguous amino acids from the reference FGF on which the non-conservative FGF variant is based, that possess at least 50% amino acid identity, 65% amino acid identity, 75% amino acid identity, 85% amino acid identity or 95% amino acid identity to the reference FGF on which the non-conservative FGF variant is based. Non-limiting examples of a non-conservative FGF variant include, e.g., a non-conservative FGF-1 variant, a non-conservative FGF-2 variant, a non-conservative FGF-4 variant, a non-conservative FGF-8 variant, a non-conservative FGF-9 variant, a non-conservative FGF-17 variant and a non-conservative FGF-18 variant.

As used herein, the term "FGF chimeric" means a polypeptide comprising at least a portion of a FGF and at least a portion of at least one other polypeptide to form an enhanced targeting domain with at least one property different from the reference FGF (see Tables 7), with the proviso that this FGF chimeric can specifically bind to an endogenous Clostridial toxin receptor system present in a Clostridial toxin target cell, and thus participate in executing the overall cellular mechanism whereby a Clostridial toxin proteolytically cleaves a substrate.

Thus, in an embodiment, a modified Clostridial toxin disclosed in the present specification comprises an enhanced targeting domain comprising a β-trefoil domain derived from a FGF. In an aspect of this embodiment, a β-trefoil domain derived from a FGF comprises, e.g., a β-trefoil domain derived from a FGF-1, a β-trefoil domain derived from a FGF-2, a β-trefoil domain derived from FGF-4, a β-trefoil domain derived from a FGF-8, a β-trefoil domain derived from a FGF-9, a β-trefoil domain derived from a FGF-17 or a β-trefoil domain derived from a FGF-18. In another aspect of this embodiment, a β-trefoil domain derived from a FGF comprises a α-fold motif of a β-trefoil domain of a FGF, a β-fold motif of a β-trefoil domain of a FGF or a γ-fold motif of a β-trefoil domain of a FGF.

In an embodiment, a modified Clostridial toxin disclosed in the present specification comprises an enhanced targeting domain comprising a β-trefoil domain with enhanced binding activity derived from a FGF. In an aspect of this embodiment, a β-trefoil domain with enhanced binding activity derived from a FGF comprises, e.g., a β-trefoil domain with enhanced binding activity derived from a FGF-1, a β-trefoil domain with enhanced binding activity derived from a FGF-2, a β-trefoil domain with enhanced binding activity derived from a FGF-4, a β-trefoil domain with enhanced binding activity derived from a FGF-8, a β-trefoil domain with enhanced binding activity derived from a FGF-9, a β-trefoil domain with enhanced binding activity derived from a FGF-17 or a β-trefoil domain with enhanced binding activity derived from a FGF-18. In another aspect of this embodiment, a β-trefoil domain with enhanced binding activity derived from a FGF comprises a modified α-fold motif of a β-trefoil domain of a FGF, a modified β-fold motif of a β-trefoil domain of a FGF or a modified γ-fold motif of a β-trefoil domain of a FGF.

In another embodiment, a β-trefoil domain derived from a FGF-1 comprises a β-trefoil domain derived from a FGF-1 of SEQ ID NO: 33. In another embodiment, a β-trefoil domain derived from a FGF-1 comprises amino acids 26-155 of SEQ ID NO: 33. In another aspect of this embodiment, a β-trefoil domain derived from a FGF-1 comprises a α-fold motif of a β-trefoil domain of a FGF-1, a β-fold motif of a β-trefoil domain of a FGF-1 or a γ-fold motif of a β-trefoil domain of a FGF-1 of SEQ ID NO: 33. In another aspect of this embodiment, a β-trefoil domain derived from a FGF-1 comprises amino acids 26-64, amino acids 68-105, or amino acids 109-155 of SEQ ID NO: 33.

In another embodiment, a β-trefoil domain with enhanced binding activity derived from a FGF-1 comprises a β-trefoil domain with enhanced binding activity derived from a FGF-1 of SEQ ID NO: 33. In another embodiment, a β-trefoil domain with enhanced binding activity derived from a FGF-1 comprises amino acids 26-155 of SEQ ID NO: 33. In another aspect of this embodiment, a β-trefoil domain with enhanced binding activity derived from a FGF-1 comprises a modified α-fold motif of a β-trefoil domain of a FGF-1, a modified β-fold motif of a β-trefoil domain of a FGF-1 or a modified γ-fold motif of a β-trefoil domain of a FGF-1 of SEQ ID NO: 33. In another aspect of this embodiment, a β-trefoil domain with enhanced binding activity derived from a FGF-1 comprises amino acids 26-64, amino acids 68-105, or amino acids 109-155 of SEQ ID NO: 33.

In other aspects of this embodiment, a FGF-1 comprising a β-trefoil domain with enhanced binding activity comprises a polypeptide having, e.g., at least 70% amino acid identity with amino acids 26-64, amino acids 68-105, or amino acids 109-155 of SEQ ID NO: 33, at least 75% amino acid identity with amino acids 26-64, amino acids 68-105, or amino acids 109-155 of SEQ ID NO: 33, at least 80% amino acid identity with amino acids 26-64, amino acids 68-105, or amino acids 109-155 of SEQ ID NO: 33, at least 85% amino acid identity with amino acids 26-64, amino acids 68-105, or amino acids 109-155 of SEQ ID NO: 33, at least 90% amino acid identity with amino acids 26-64, amino acids 68-105, or amino acids 109-155 of SEQ ID NO: 33 or at least 95% amino acid identity with amino acids 26-64, amino acids 68-105, or amino acids 109-155 of SEQ ID NO: 33. In yet other aspects of this embodiment, a FGF-1 comprising a β-trefoil domain with enhanced binding activity comprises a polypeptide having, e.g., at most 70% amino acid identity with amino acids 26-64, amino acids 68-105, or amino acids 109-155 of SEQ ID NO: 33, at most 75% amino acid identity with amino acids 26-64, amino acids 68-105, or amino acids 109-155 of SEQ ID NO: 33, at most 80% amino acid identity with amino acids 26-64, amino acids 68-105, or amino acids 109-155 of SEQ ID NO: 33, at most 85% amino acid identity with amino acids 26-64, amino acids 68-105, or amino acids 109-155 of SEQ ID NO: 33, at most 90% amino acid identity with amino acids 26-64, amino acids 68-105, or amino acids 109-155 of SEQ ID NO: 33 or at most 95% amino acid identity with amino acids 26-64, amino acids 68-105, or amino acids 109-155 of SEQ ID NO: 33.

In other aspects of this embodiment, a FGF-1 comprising a β-trefoil domain with enhanced binding activity comprises a polypeptide having, e.g., at most one, two, three, four, five, six, seven, eight, nine, 10 or 20 non-contiguous amino acid substitutions relative to amino acids 26-64, amino acids 68-105, or amino acids 109-155 of SEQ ID NO: 33. In other aspects of this embodiment, a FGF-1 comprising a β-trefoil domain with enhanced binding activity comprises a polypeptide having, e.g., at least one, two, three, four, five, six, seven, eight, nine, 10 or 20 non-contiguous amino acid substitutions relative to amino acids 26-64, amino acids 68-105, or amino acids 109-155 of SEQ ID NO: 33. In yet other aspects of this embodiment, a FGF-1 comprising a β-trefoil domain with enhanced binding activity comprises a polypeptide having, e.g., at most one, two, three, four, five, six, seven, eight, nine, 10 or 20 non-contiguous amino acid deletions relative to amino acids 26-64, amino acids 68-105, or amino acids 109-155 of SEQ ID NO: 33. In other aspects of this embodiment, a FGF-1 comprising a β-trefoil domain with enhanced binding activity comprises a polypeptide having, e.g., at least one, two, three, four, five, six, seven, eight, nine, 10 or 20 non-contiguous amino acid deletions relative to amino acids 26-64, amino acids 68-105, or amino acids 109-155 of SEQ ID NO: 33. In still other aspects of this embodiment, a FGF-1 comprising a β-trefoil domain with enhanced binding activity comprises a polypeptide having, e.g., at most one, two, three, four, five, six, seven, eight, nine, 10 or 20 non-contiguous amino acid additions relative to amino acids 26-64, amino acids 68-105, or amino acids 109-155 of SEQ ID NO: 33. In other aspects of this embodiment, a FGF-1 comprising a β-trefoil domain with enhanced binding activity comprises a polypeptide having, e.g., at least one, two, three, four, five, six, seven, eight, nine, 10 or 20 non-contiguous amino acid additions relative to amino acids 26-64, amino acids 68-105, or amino acids 109-155 of SEQ ID NO: 33.

In other aspects of this embodiment, a FGF-1 comprising a β-trefoil domain with enhanced binding activity comprises a polypeptide having, e.g., at most one, two, three, four, five, six, seven, eight, nine, 10 or 20 contiguous amino acid substitutions relative to amino acids 26-64, amino acids 68-105, or amino acids 109-155 of SEQ ID NO: 33. In other aspects of this embodiment, a FGF-1 comprising a β-trefoil domain with enhanced binding activity comprises a polypeptide having, e.g., at least one, two, three, four, five, six, seven, eight, nine, 10 or 20 contiguous amino acid substitutions relative to amino acids 26-64, amino acids 68-105, or amino acids 109-155 of SEQ ID NO: 33. In yet other aspects of this embodiment, a FGF-1 comprising a β-trefoil domain with enhanced binding activity comprises a polypeptide having, e.g., at most one, two, three, four, five, six, seven, eight, nine, 10 or 20 contiguous amino acid deletions relative to amino acids 26-64, amino acids 68-105, or amino acids 109-155 of SEQ ID NO: 33. In other aspects of this embodiment, a FGF-1 comprising a β-trefoil domain with enhanced binding activity comprises a polypeptide having, e.g., at least one, two, three, four, five, six, seven, eight, nine, 10 or 20 contiguous amino acid deletions relative to amino acids 26-64, amino acids 68-105, or amino acids 109-155 of SEQ ID NO: 33. In still other aspects of this embodiment, a FGF-1 comprising a β-trefoil domain with enhanced binding activity comprises a polypeptide having, e.g., at most one, two, three, four, five, six, seven, eight, nine, 10 or 20 contiguous amino acid additions relative to amino acids 26-64, amino acids 68-105, or amino acids 109-155 of SEQ ID NO: 33. In other aspects of this embodiment, a FGF-1 comprising a β-trefoil domain with enhanced binding activity comprises a polypeptide having, e.g., at least one, two, three, four, five, six, seven, eight, nine, 10 or 20 contiguous amino acid additions relative to amino acids 26-64, amino acids 68-105, or amino acids 109-155 of SEQ ID NO: 33.

In another embodiment, a β-trefoil domain derived from a FGF-1 comprises a β4/β5 hairpin turn of a β-trefoil domain of a FGF-1 or a β8/β9 hairpin turn of a β-trefoil domain of a FGF-1 of SEQ ID NO: 33. In another aspect of this embodiment, a β-trefoil domain derived from a FGF-1 comprises amino acids 65-67 or amino acids 106-108 of SEQ ID NO: 33.

In another embodiment, a β-trefoil domain with enhanced binding activity derived from a FGF-1 comprises a modified β4/β5 hairpin turn of a β-trefoil domain of a FGF-1 or a modified β8/β9 hairpin turn of a β-trefoil domain of a FGF-1 of SEQ ID NO: 33. In another aspect of this embodiment, a β-trefoil domain with enhanced binding activity derived from a FGF-1 comprises a modification of amino acids 65-67 or amino acids 106-108 of SEQ ID NO: 33.

In other aspects of this embodiment, a β-trefoil domain with enhanced binding activity derived from a FGF-1 comprises a polypeptide having, e.g., at least 70% amino acid identity with amino acids 65-67 or amino acids 106-108 of SEQ ID NO: 33, at least 75% amino acid identity with amino acids 65-67 or amino acids 106-108 of SEQ ID NO: 33, at least 80% amino acid identity with amino acids 65-67 or amino acids 106-108 of SEQ ID NO: 33, at least 85% amino acid identity with amino acids 65-67 or amino acids 106-108 of SEQ ID NO: 33, at least 90% amino acid identity with amino acids 65-67 or amino acids 106-108 of SEQ ID NO: 33 or at least 95% amino acid identity with amino acids 65-67 or amino acids 106-108 of SEQ ID NO: 33. In yet other aspects of this embodiment, a β-trefoil domain with enhanced binding activity derived from a FGF-1 comprises a polypeptide having, e.g., at most 70% amino acid identity with amino acids 65-67 or amino acids 106-108 of SEQ ID NO: 33, at most 75% amino acid identity with amino acids 65-67 or amino acids 106-108 of SEQ ID NO: 33, at most 80% amino acid identity with amino acids 65-67 or amino acids 106-108 of SEQ ID NO: 33, at most 85% amino acid identity with amino acids 65-67 or amino acids 106-108 of SEQ ID NO: 33, at most 90% amino acid identity with amino acids 65-67 or amino acids 106-108 of SEQ ID NO: 33 or at most 95% amino acid identity with amino acids 65-67 or amino acids 106-108 of SEQ ID NO: 33.

In other aspects of this embodiment, a β-trefoil domain with enhanced binding activity derived from a FGF-1 comprises a polypeptide having, e.g., at most one, two, three or four non-contiguous amino acid substitutions relative to amino acids 65-67 or amino acids 106-108 of SEQ ID NO: 33. In other aspects of this embodiment, a β-trefoil domain with enhanced binding activity derived from a FGF-1 comprises a polypeptide having, e.g., at least one, two, three or four non-contiguous amino acid substitutions relative to amino acids 65-67 or amino acids 106-108 of SEQ ID NO: 33. In other aspects of this embodiment, a non-contiguous amino acid substitution of any amino acid from amino acids 65-67 or amino acids 106-108 of SEQ ID NO: 33 can be replaced with glycine. In other aspects of this embodiment, a non-contiguous amino acid substitution of any hydrophobic amino acid from amino acids 65-67 or amino acids 106-108 of SEQ ID NO: 33 can be replaced with phenylalanine. In yet other aspects of this embodiment, a β-trefoil domain with enhanced binding activity derived from a FGF-1 comprises a polypeptide having, e.g., at most one, two, three or four non-contiguous amino acid deletions relative to amino acids 65-67 or amino acids 106-108 of SEQ ID NO: 33. In other aspects of this embodiment, a β-trefoil domain with enhanced binding activity derived from a FGF-1 comprises a polypeptide having, e.g., at least one, two, three or four non-contiguous amino acid deletions relative to amino acids 65-67 or amino acids 106-108 of SEQ ID NO: 33. In still other aspects of this embodiment, a β-trefoil domain with enhanced binding activity derived from a FGF-1 comprises a polypeptide having, e.g., at most one, two, three or four non-contiguous amino acid additions relative to amino acids 65-67 or amino acids 106-108 of SEQ ID NO: 33. In other aspects of this embodiment, a β-trefoil domain with enhanced binding activity derived from a FGF-1 comprises a polypeptide having, e.g., at least one, two, three or four non-contiguous amino acid additions relative to amino acids 65-67 or amino acids 106-108 of SEQ ID NO: 33.

In other aspects of this embodiment, a β-trefoil domain with enhanced binding activity derived from a FGF-1 comprises a polypeptide having, e.g., at most one, two, three or four contiguous amino acid substitutions relative to amino acids 65-67 or amino acids 106-108 of SEQ ID NO: 33. In other aspects of this embodiment, a β-trefoil domain with enhanced binding activity derived from a FGF-1 comprises a polypeptide having, e.g., at least one, two, three or four contiguous amino acid substitutions relative to amino acids 65-67 or amino acids 106-108 of SEQ ID NO: 33. In other aspects of this embodiment, contiguous amino acid substitutions of amino acids from amino acids 65-67 or amino acids 106-108 of SEQ ID NO: 33 can be replaced with glycine. In other aspects of this embodiment, contiguous amino acid substitutions of hydrophobic amino acids from amino acids 65-67 or amino acids 106-108 of SEQ ID NO: 33 can be replaced with phenylalanine. In yet other aspects of this embodiment, a β-trefoil domain with enhanced binding activity derived from a FGF-1 comprises a polypeptide having, e.g., at most one, two, three or four contiguous amino acid deletions relative to amino acids 65-67 or amino acids 106-108 of SEQ ID NO: 33. In other aspects of this embodiment, a β-trefoil domain with enhanced binding activity derived from a FGF-1 comprises a polypeptide having, e.g., at least one, two, three or four contiguous amino acid deletions relative to amino acids 65-67 or amino acids 106-108 of SEQ ID NO: 33. In still other aspects of this embodiment, a β-trefoil domain with enhanced binding activity derived from a FGF-1 comprises a polypeptide having, e.g., at most one, two, three or four contiguous amino acid additions relative to amino acids 65-67 or amino acids 106-108 of SEQ ID NO: 33. In other aspects of this embodiment, a β-trefoil domain with enhanced binding activity derived from a FGF-1 comprises a polypeptide having, e.g., at least one, two, three or four contiguous amino acid additions relative to amino acids 65-67 or amino acids 106-108 of SEQ ID NO: 33.

In another embodiment, a β-trefoil domain derived from a FGF-2 comprises a β-trefoil domain derived from a FGF-2 of SEQ ID NO: 34. In another embodiment, a β-trefoil domain derived from a FGF-2 comprises amino acids 29-155 of SEQ ID NO: 34. In another aspect of this embodiment, a β-trefoil domain derived from a FGF-2 comprises a α-fold motif of a β-trefoil domain of a FGF-2, a β-fold motif of a β-trefoil domain of a FGF-2 or a γ-fold motif of a β-trefoil domain of a FGF-2 of SEQ ID NO: 34. In another aspect of this embodiment, a β-trefoil domain derived from a FGF-2 comprises amino acids 29-67, amino acids 71-111, or amino acids 115-155 of SEQ ID NO: 34.

In another embodiment, a β-trefoil domain with enhanced binding activity derived from a FGF-2 comprises a β-trefoil domain with enhanced binding activity derived from a FGF-2 of SEQ ID NO: 34. In another embodiment, a β-trefoil domain with enhanced binding activity derived from a FGF-2 comprises amino acids 29-155 of SEQ ID NO: 34. In another aspect of this embodiment, a β-trefoil domain with enhanced binding activity derived from a FGF-2 comprises a modified α-fold motif of a β-trefoil domain of a FGF-2, a modified β-fold motif of a β-trefoil domain of a FGF-2 or a modified γ-fold motif of a β-trefoil domain of a FGF-2 of SEQ ID NO:

34. In another aspect of this embodiment, a β-trefoil domain with enhanced binding activity derived from a FGF-2 comprises amino acids 29-67, amino acids 71-111, or amino acids 115-155 of SEQ ID NO: 34.

In other aspects of this embodiment, a FGF-2 comprising a β-trefoil domain with enhanced binding activity comprises a polypeptide having, e.g., at least 70% amino acid identity with amino acids 29-67, amino acids 71-111, or amino acids 115-155 of SEQ ID NO: 34, at least 75% amino acid identity with amino acids 29-67, amino acids 71-111, or amino acids 115-155 of SEQ ID NO: 34, at least 80% amino acid identity with amino acids 29-67, amino acids 71-111, or amino acids 115-155 of SEQ ID NO: 34, at least 85% amino acid identity with amino acids 29-67, amino acids 71-111, or amino acids 115-155 of SEQ ID NO: 34, at least 90% amino acid identity with amino acids 29-67, amino acids 71-111, or amino acids 115-155 of SEQ ID NO: 34 or at least 95% amino acid identity with amino acids 29-67, amino acids 71-111, or amino acids 115-155 of SEQ ID NO: 34. In yet other aspects of this embodiment, a FGF-2 comprising a β-trefoil domain with enhanced binding activity comprises a polypeptide having, e.g., at most 70% amino acid identity with amino acids 29-67, amino acids 71-111, or amino acids 115-155 of SEQ ID NO: 34, at most 75% amino acid identity with amino acids 29-67, amino acids 71-111, or amino acids 115-155 of SEQ ID NO: 34, at most 80% amino acid identity with amino acids 29-67, amino acids 71-111, or amino acids 115-155 of SEQ ID NO: 34, at most 85% amino acid identity with amino acids 29-67, amino acids 71-111, or amino acids 115-155 of SEQ ID NO: 34, at most 90% amino acid identity with amino acids 29-67, amino acids 71-111, or amino acids 115-155 of SEQ ID NO: 34 or at most 95% amino acid identity with amino acids 29-67, amino acids 71-111, or amino acids 115-155 of SEQ ID NO: 34.

In other aspects of this embodiment, a FGF-2 comprising a β-trefoil domain with enhanced binding activity comprises a polypeptide having, e.g., at most one, two, three, four, five, six, seven, eight, nine, 10 or 20 non-contiguous amino acid substitutions relative to amino acids 29-67, amino acids 71-111, or amino acids 115-155 of SEQ ID NO: 34. In other aspects of this embodiment, a FGF-2 comprising a β-trefoil domain with enhanced binding activity comprises a polypeptide having, e.g., at least one, two, three, four, five, six, seven, eight, nine, 10 or 20 non-contiguous amino acid substitutions relative to amino acids 29-67, amino acids 71-111, or amino acids 115-155 of SEQ ID NO: 34. In yet other aspects of this embodiment, a FGF-2 comprising a β-trefoil domain with enhanced binding activity comprises a polypeptide having, e.g., at most one, two, three, four, five, six, seven, eight, nine, 10 or 20 non-contiguous amino acid deletions relative to amino acids 29-67, amino acids 71-111, or amino acids 115-155 of SEQ ID NO: 34. In other aspects of this embodiment, a FGF-2 comprising a β-trefoil domain with enhanced binding activity comprises a polypeptide having, e.g., at least one, two, three, four, five, six, seven, eight, nine, 10 or 20 non-contiguous amino acid deletions relative to amino acids 29-67, amino acids 71-111, or amino acids 115-155 of SEQ ID NO: 34. In still other aspects of this embodiment, a FGF-2 comprising a β-trefoil domain with enhanced binding activity comprises a polypeptide having, e.g., at most one, two, three, four, five, six, seven, eight, nine, 10 or 20 non-contiguous amino acid additions relative to amino acids 29-67, amino acids 71-111, or amino acids 115-155 of SEQ ID NO: 34. In other aspects of this embodiment, a FGF-2 comprising a β-trefoil domain with enhanced binding activity comprises a polypeptide having, e.g., at least one, two, three, four, five, six, seven, eight, nine, 10 or 20 non-contiguous amino acid additions relative to amino acids 29-67, amino acids 71-111, or amino acids 115-155 of SEQ ID NO: 34.

In other aspects of this embodiment, a FGF-2 comprising a β-trefoil domain with enhanced binding activity comprises a polypeptide having, e.g., at most one, two, three, four, five, six, seven, eight, nine, 10 or 20 contiguous amino acid substitutions relative to amino acids 29-67, amino acids 71-111, or amino acids 115-155 of SEQ ID NO: 34. In other aspects of this embodiment, a FGF-2 comprising a β-trefoil domain with enhanced binding activity comprises a polypeptide having, e.g., at least one, two, three, four, five, six, seven, eight, nine, 10 or 20 contiguous amino acid substitutions relative to amino acids 29-67, amino acids 71-111, or amino acids 115-155 of SEQ ID NO: 34. In yet other aspects of this embodiment, a FGF-2 comprising a β-trefoil domain with enhanced binding activity comprises a polypeptide having, e.g., at most one, two, three, four, five, six, seven, eight, nine, 10 or 20 contiguous amino acid deletions relative to amino acids 29-67, amino acids 71-111, or amino acids 115-155 of SEQ ID NO: 34. In other aspects of this embodiment, a FGF-2 comprising a β-trefoil domain with enhanced binding activity comprises a polypeptide having, e.g., at least one, two, three, four, five, six, seven, eight, nine, 10 or 20 contiguous amino acid deletions relative to amino acids 29-67, amino acids 71-111, or amino acids 115-155 of SEQ ID NO: 34. In still other aspects of this embodiment, a FGF-2 comprising a β-trefoil domain with enhanced binding activity comprises a polypeptide having, e.g., at most one, two, three, four, five, six, seven, eight, nine, 10 or 20 contiguous amino acid additions relative to amino acids 29-67, amino acids 71-111, or amino acids 115-155 of SEQ ID NO: 34. In other aspects of this embodiment, a FGF-2 comprising a β-trefoil domain with enhanced binding activity comprises a polypeptide having, e.g., at least one, two, three, four, five, six, seven, eight, nine, 10 or 20 contiguous amino acid additions relative to amino acids 29-67, amino acids 71-111, or amino acids 115-155 of SEQ ID NO: 34.

In another embodiment, a β-trefoil domain derived from a FGF-2 comprises a β4/β5 hairpin turn of a β-trefoil domain of a FGF-2 or a β8/β9 hairpin turn of a β-trefoil domain of a FGF-2 of SEQ ID NO: 34. In another aspect of this embodiment, a β-trefoil domain derived from a FGF-2 comprises amino acids 68-70 or amino acids 112-114 of SEQ ID NO: 34.

In another embodiment, a β-trefoil domain with enhanced binding activity derived from a FGF-2 comprises a modified β4/β5 hairpin turn of a β-trefoil domain of a FGF-2 or a modified β8/β9 hairpin turn of a β-trefoil domain of a FGF-2 of SEQ ID NO: 34. In another aspect of this embodiment, a β-trefoil domain with enhanced binding activity derived from a FGF-2 comprises a modification of amino acids 68-70 or amino acids 112-114 of SEQ ID NO: 34.

In other aspects of this embodiment, a β-trefoil domain with enhanced binding activity derived from a FGF-2 comprises a polypeptide having, e.g., at least 70% amino acid identity with amino acids 68-70 or amino acids 112-114 of SEQ ID NO: 34, at least 75% amino acid identity with amino acids 68-70 or amino acids 112-114 of SEQ ID NO: 34, at least 80% amino acid identity with amino acids 68-70 or amino acids 112-114 of SEQ ID NO: 34, at least 85% amino acid identity with amino acids 68-70 or amino acids 112-114 of SEQ ID NO: 34, at least 90% amino acid identity with amino acids 68-70 or amino acids 112-114 of SEQ ID NO: 34 or at least 95% amino acid identity with amino acids 68-70 or amino acids 112-114 of SEQ ID NO: 34. In yet other aspects of this embodiment, a β-trefoil domain with enhanced binding activity derived from a FGF-2 comprises a polypeptide having, e.g., at most 70% amino acid identity with amino acids 68-70 or amino acids 112-114 of SEQ ID NO: 34, at most 75% amino acid identity with amino acids 68-70 or amino acids 112-114 of SEQ ID NO: 34, at most 80% amino acid identity with amino acids 68-70 or amino acids 112-114 of SEQ ID NO: 34, at most 85% amino acid identity with amino acids 68-70 or amino acids 112-114 of SEQ ID NO: 34, at most 90% amino acid identity with amino acids 68-70 or amino acids 112-114 of SEQ ID NO: 34 or at most 95% amino acid identity with amino acids 68-70 or amino acids 112-114 of SEQ ID NO: 34.

In other aspects of this embodiment, a β-trefoil domain with enhanced binding activity derived from a FGF-2 comprises a polypeptide having, e.g., at most one, two, three or four non-contiguous amino acid substitutions relative to amino acids 68-70 or amino acids 112-114 of SEQ ID NO: 34. In other aspects of this embodiment, a β-trefoil domain with enhanced binding activity derived from a FGF-2 comprises a polypeptide having, e.g., at least one, two, three or four non-contiguous amino acid substitutions relative to amino acids 68-70 or amino acids 112-114 of SEQ ID NO: 34. In other aspects of this embodiment, a non-contiguous amino acid substitution of any amino acid from amino acids 68-70 or amino acids 112-114 of SEQ ID NO: 34 can be replaced with glycine. In other aspects of this embodiment, a non-contiguous amino acid substitution of any hydrophobic amino acid from amino acids 68-70 or amino acids 112-114 of SEQ ID NO: 34 can be replaced with phenylalanine. In yet other aspects of this embodiment, a β-trefoil domain with enhanced binding activity derived from a FGF-2 comprises a polypeptide having, e.g., at most one, two, three or four non-contiguous amino acid deletions relative to amino acids 68-70 or amino acids 112-114 of SEQ ID NO: 34. In other aspects of this embodiment, a β-trefoil domain with enhanced binding activity derived from a FGF-2 comprises a polypeptide having, e.g., at least one, two, three or four non-contiguous amino acid deletions relative to amino acids 68-70 or amino acids 112-114 of SEQ ID NO: 34. In still other aspects of this embodiment, a β-trefoil domain with enhanced binding activity derived from a FGF-2 comprises a polypeptide having, e.g., at most one, two, three or four non-contiguous amino acid additions relative to amino acids 68-70 or amino acids 112-114 of SEQ ID NO: 34. In other aspects of this embodiment, a β-trefoil domain with enhanced binding activity derived from a FGF-2 comprises a polypeptide having, e.g., at least one, two, three or four non-contiguous amino acid additions relative to amino acids 68-70 or amino acids 112-114 of SEQ ID NO: 34.

In other aspects of this embodiment, a β-trefoil domain with enhanced binding activity derived from a FGF-2 comprises a polypeptide having, e.g., at most one, two, three or four contiguous amino acid substitutions relative to amino acids 68-70 or amino acids 112-114 of SEQ ID NO: 34. In other aspects of this embodiment, a β-trefoil domain with enhanced binding activity derived from a FGF-2 comprises a polypeptide having, e.g., at least one, two, three or four contiguous amino acid substitutions relative to amino acids 68-70 or amino acids 112-114 of SEQ ID NO: 34. In other aspects of this embodiment, contiguous amino acid substitutions of amino acids from amino acids 68-70 or amino acids 112-114 of SEQ ID NO: 34 can be replaced with glycine. In other aspects of this embodiment, contiguous amino acid substitutions of hydrophobic amino acids from amino acids 68-70 or amino acids 112-114 of SEQ ID NO: 34 can be replaced with phenylalanine. In yet other aspects of this embodiment, a β-trefoil domain with enhanced binding activity derived from a FGF-2 comprises a polypeptide having, e.g., at most one, two, three or four contiguous amino acid deletions relative to amino acids 68-70 or amino acids 112-114 of SEQ ID NO: 34. In other aspects of this embodiment, a β-trefoil domain with enhanced binding activity derived from a FGF-2 comprises a polypeptide having, e.g., at least one, two, three or four contiguous amino acid deletions relative to amino acids 68-70 or amino acids 112-114 of SEQ ID NO: 34. In still other aspects of this embodiment, a β-trefoil domain with enhanced binding activity derived from a FGF-2 comprises a polypeptide having, e.g., at most one, two, three or four contiguous amino acid additions relative to amino acids 68-70 or amino acids 112-114 of SEQ ID NO: 34. In other aspects of this embodiment, a β-trefoil domain with enhanced binding activity derived from a FGF-2 comprises a polypeptide having, e.g., at least one, two, three or four contiguous amino acid additions relative to amino acids 68-70 or amino acids 112-114 of SEQ ID NO: 34.

In another embodiment, a β-trefoil domain derived from a FGF-4 comprises a β-trefoil domain derived from a FGF-4 of SEQ ID NO: 35. In another embodiment, a β-trefoil domain derived from a FGF-4 comprises amino acids 83-206 of SEQ ID NO: 35. In another aspect of this embodiment, a β-trefoil domain derived from a FGF-4 comprises a α-fold motif of a β-trefoil domain of a FGF-4, a β-fold motif of a β-trefoil domain of a FGF-4 or a γ-fold motif of a β-trefoil domain of a FGF-4 of SEQ ID NO: 35. In another aspect of this embodiment, a β-trefoil domain derived from a FGF-4 comprises amino acids 83-121, amino acids 125-162, or amino acids 166-206 of SEQ ID NO: 35.

In another embodiment, a β-trefoil domain with enhanced binding activity derived from a FGF-4 comprises a β-trefoil domain with enhanced binding activity derived from a FGF-4 of SEQ ID NO: 35. In another embodiment, a β-trefoil domain with enhanced binding activity derived from a FGF-4 comprises amino acids 83-206 of SEQ ID NO: 35. In another aspect of this embodiment, a β-trefoil domain with enhanced binding activity derived from a FGF-4 comprises a modified α-fold motif of a β-trefoil domain of a FGF-4, a modified β-fold motif of a β-trefoil domain of a FGF-4 or a modified γ-fold motif of a β-trefoil domain of a FGF-4 of SEQ ID NO: 35. In another aspect of this embodiment, a β-trefoil domain with enhanced binding activity derived from a FGF-4 comprises amino acids 83-121, amino acids 125-162, or amino acids 166-206 of SEQ ID NO: 35.

In other aspects of this embodiment, a FGF-4 comprising a β-trefoil domain with enhanced binding activity comprises a polypeptide having, e.g., at least 70% amino acid identity with amino acids 83-121, amino acids 125-162, or amino acids 166-206 of SEQ ID NO: 35, at least 75% amino acid identity with amino acids 83-121, amino acids 125-162, or amino acids 166-206 of SEQ ID NO: 35, at least 80% amino acid identity with amino acids 83-121, amino acids 125-162, or amino acids 166-206 of SEQ ID NO: 35, at least 85% amino acid identity with amino acids 83-121, amino acids 125-162, or amino acids 166-206 of SEQ ID NO: 35, at least 90% amino acid identity with amino acids 83-121, amino acids 125-162, or amino acids 166-206 of SEQ ID NO: 35 or at least 95% amino acid identity with amino acids 83-121, amino acids 125-162, or amino acids 166-206 of SEQ ID NO: 35. In yet other aspects of this embodiment, a FGF-4 comprising a β-trefoil domain with enhanced binding activity comprises a polypeptide having, e.g., at most 70% amino acid identity with amino acids 83-121, amino acids 125-162, or amino acids 166-206 of SEQ ID NO: 35, at most 75% amino acid identity with amino acids 83-121, amino acids 125-162, or amino acids 166-206 of SEQ ID NO: 35, at most 80% amino acid identity with amino acids 83-121, amino acids 125-162, or amino acids 166-206 of SEQ ID NO: 35, at most 85% amino acid identity with amino acids 83-121, amino acids 125-162, or amino acids 166-206 of SEQ ID NO: 35, at most 90% amino acid identity with amino acids 83-121, amino acids 125-162, or amino acids 166-206 of SEQ ID NO: 35 or at most 95% amino acid identity with amino acids 83-121, amino acids 125-162, or amino acids 166-206 of SEQ ID NO: 35.

In other aspects of this embodiment, a FGF-4 comprising a β-trefoil domain with enhanced binding activity comprises a polypeptide having, e.g., at most one, two, three, four, five, six, seven, eight, nine, 10 or 20 non-contiguous amino acid substitutions relative to amino acids 83-121, amino acids 125-162, or amino acids 166-206 of SEQ ID NO: 35. In other aspects of this embodiment, a FGF-4 comprising a β-trefoil domain with enhanced binding activity comprises a polypeptide having, e.g., at least one, two, three, four, five, six, seven, eight, nine, 10 or 20 non-contiguous amino acid substitutions relative to amino acids 83-121, amino acids 125-162, or amino acids 166-206 of SEQ ID NO: 35. In yet other aspects of this embodiment, a FGF-4 comprising a β-trefoil domain with enhanced binding activity comprises a polypeptide having, e.g., at most one, two, three, four, five, six, seven, eight, nine, 10 or 20 non-contiguous amino acid deletions relative to amino acids 83-121, amino acids 125-162, or amino acids 166-206 of SEQ ID NO: 35. In other aspects of this embodiment, a FGF-4 comprising a β-trefoil domain with enhanced binding activity comprises a polypeptide having, e.g., at least one, two, three, four, five, six, seven, eight, nine, 10 or 20 non-contiguous amino acid deletions relative to amino acids 83-121, amino acids 125-162, or amino acids 166-206 of SEQ ID NO: 35. In still other aspects of this embodiment, a FGF-4 comprising a β-trefoil domain with enhanced binding activity comprises a polypeptide having, e.g., at most one, two, three, four, five, six, seven, eight, nine, 10 or 20 non-contiguous amino acid additions relative to amino acids 83-121, amino acids 125-162, or amino acids 166-206 of SEQ ID NO: 35. In other aspects of this embodiment, a FGF-4 comprising a β-trefoil domain with enhanced binding activity comprises a polypeptide having, e.g., at least one, two, three, four, five, six, seven, eight, nine, 10 or 20 non-contiguous amino acid additions relative to amino acids 83-121, amino acids 125-162, or amino acids 166-206 of SEQ ID NO: 35.

In other aspects of this embodiment, a FGF-4 comprising a β-trefoil domain with enhanced binding activity comprises a polypeptide having, e.g., at most one, two, three, four, five, six, seven, eight, nine, 10 or 20 contiguous amino acid substitutions relative to amino acids 83-121, amino acids 125-162, or amino acids 166-206 of SEQ ID NO: 35. In other aspects of this embodiment, a FGF-4 comprising a β-trefoil domain with enhanced binding activity comprises a polypeptide having, e.g., at least one, two, three, four, five, six, seven, eight, nine, 10 or 20 contiguous amino acid substitutions relative to amino acids 83-121, amino acids 125-162, or amino acids 166-206 of SEQ ID NO: 35. In yet other aspects of this embodiment, a FGF-4 comprising a β-trefoil domain with enhanced binding activity comprises a polypeptide having, e.g., at most one, two, three, four, five, six, seven, eight, nine, 10 or 20 contiguous amino acid deletions relative to amino acids 83-121, amino acids 125-162, or amino acids 166-206 of SEQ ID NO: 35. In other aspects of this embodiment, a FGF-4 comprising a β-trefoil domain with enhanced binding activity comprises a polypeptide having, e.g., at least one, two, three, four, five, six, seven, eight, nine, 10 or 20 contiguous amino acid deletions relative to amino acids 83-121, amino acids 125-162, or amino acids 166-206 of SEQ ID NO: 35. In still other aspects of this embodiment, a FGF-4 comprising a β-trefoil domain with enhanced binding activity comprises a polypeptide having, e.g., at most one, two, three, four, five, six, seven, eight, nine, 10 or 20 contiguous amino acid additions relative to amino acids 83-121, amino acids 125-162, or amino acids 166-206 of SEQ ID NO: 35. In other aspects of this embodiment, a FGF-4 comprising a β-trefoil domain with enhanced binding activity comprises a polypeptide having, e.g., at least one, two, three, four, five, six, seven, eight, nine, 10 or 20 contiguous amino acid additions relative to amino acids 83-121, amino acids 125-162, or amino acids 166-206 of SEQ ID NO: 35.

In another embodiment, a β-trefoil domain derived from a FGF-4 comprises a β4/β5 hairpin turn of a β-trefoil domain of a FGF-4 or a β8/β9 hairpin turn of a β-trefoil domain of a FGF-4 of SEQ ID NO: 35. In another aspect of this embodiment, a β-trefoil domain derived from a FGF-4 comprises amino acids 122-124 or amino acids 163-165 of SEQ ID NO: 35.

In another embodiment, a β-trefoil domain with enhanced binding activity derived from a FGF-4 comprises a modified β4/β5 hairpin turn of a β-trefoil domain of a FGF-4 or a modified β8/β9 hairpin turn of a β-trefoil domain of a FGF-4 of SEQ ID NO: 35. In another aspect of this embodiment, a β-trefoil domain with enhanced binding activity derived from a FGF-4 comprises a modification of amino acids 122-124 or amino acids 163-165 of SEQ ID NO: 35.

In other aspects of this embodiment, a β-trefoil domain with enhanced binding activity derived from a FGF-4 comprises a polypeptide having, e.g., at least 70% amino acid identity with amino acids 122-124 or amino acids 163-165 of SEQ ID NO: 35, at least 75% amino acid identity with amino acids 122-124 or amino acids 163-165 of SEQ ID NO: 35, at least 80% amino acid identity with amino acids 122-124 or amino acids 163-165 of SEQ ID NO: 35, at least 85% amino acid identity with amino acids 122-124 or amino acids 163-165 of SEQ ID NO: 35, at least 90% amino acid identity with amino acids 122-124 or amino acids 163-165 of SEQ ID NO: 35 or at least 95% amino acid identity with amino acids 122-124 or amino acids 163-165 of SEQ ID NO: 35. In yet other aspects of this embodiment, a β-trefoil domain with enhanced binding activity derived from a FGF-4 comprises a polypeptide having, e.g., at most 70% amino acid identity with amino acids 122-124 or amino acids 163-165 of SEQ ID NO: 35, at most 75% amino acid identity with amino acids 122-124 or amino acids 163-165 of SEQ ID NO: 35, at most 80% amino acid identity with amino acids 122-124 or amino acids 163-165 of SEQ ID NO: 35, at most 85% amino acid identity with amino acids 122-124 or amino acids 163-165 of SEQ ID NO: 35, at most 90% amino acid identity with amino acids 122-124 or amino acids 163-165 of SEQ ID NO: 35 or at most 95% amino acid identity with amino acids 122-124 or amino acids 163-165 of SEQ ID NO: 35.

In other aspects of this embodiment, a β-trefoil domain with enhanced binding activity derived from a FGF-4 comprises a polypeptide having, e.g., at most one, two, three or four non-contiguous amino acid substitutions relative to amino acids 122-124 or amino acids 163-165 of SEQ ID NO: 35. In other aspects of this embodiment, a β-trefoil domain with enhanced binding activity derived from a FGF-4 comprises a polypeptide having, e.g., at least one, two, three or four non-contiguous amino acid substitutions relative to amino acids 122-124 or amino acids 163-165 of SEQ ID NO: 35. In other aspects of this embodiment, a non-contiguous amino acid substitution of any amino acid from amino acids 122-124 or amino acids 163-165 of SEQ ID NO: 35 can be replaced with glycine. In other aspects of this embodiment, a non-contiguous amino acid substitution of any hydrophobic amino acid from amino acids 122-124 or amino acids 163-165 of SEQ ID NO: 35 can be replaced with phenylalanine. In yet other aspects of this embodiment, a β-trefoil domain with enhanced binding activity derived from a FGF-4 comprises a polypeptide having, e.g., at most one, two, three or four non-contiguous amino acid deletions relative to amino acids 122-124 or amino acids 163-165 of SEQ ID NO: 35. In other aspects of this embodiment, a β-trefoil domain with enhanced binding activity derived from a FGF-4 comprises a polypeptide having, e.g., at least one, two, three or four non-contiguous amino acid deletions relative to amino acids 122-124 or amino acids 163-165 of SEQ ID NO: 35. In still other aspects of this embodiment, a β-trefoil domain with enhanced binding activity derived from a FGF-4 comprises a polypeptide having, e.g., at most one, two, three or four non-contiguous amino acid additions relative to amino acids 122-124 or amino acids 163-165 of SEQ ID NO: 35. In other aspects of this embodiment, a β-trefoil domain with enhanced binding activity derived from a FGF-4 comprises a polypeptide having, e.g., at least one, two, three or four non-contiguous amino acid additions relative to amino acids 122-124 or amino acids 163-165 of SEQ ID NO: 35.

In other aspects of this embodiment, a β-trefoil domain with enhanced binding activity derived from a FGF-4 comprises a polypeptide having, e.g., at most one, two, three or four contiguous amino acid substitutions relative to amino acids 122-124 or amino acids 163-165 of SEQ ID NO: 35. In other aspects of this embodiment, a β-trefoil domain with enhanced binding activity derived from a FGF-4 comprises a polypeptide having, e.g., at least one, two, three or four contiguous amino acid substitutions relative to amino acids 122-124 or amino acids 163-165 of SEQ ID NO: 35. In other aspects of this embodiment, contiguous amino acid substitutions of amino acids from amino acids 122-124 or amino acids 163-165 of SEQ ID NO: 35 can be replaced with glycine. In other aspects of this embodiment, contiguous amino acid substitutions of hydrophobic amino acids from amino acids 122-124 or amino acids 163-165 of SEQ ID NO: 35 can be replaced with phenylalanine. In yet other aspects of this embodiment, a β-trefoil domain with enhanced binding activity derived from a FGF-4 comprises a polypeptide having, e.g., at most one, two, three or four contiguous amino acid deletions relative to amino acids 122-124 or amino acids 163-165 of SEQ ID NO: 35. In other aspects of this embodiment, a β-trefoil domain with enhanced binding activity derived from a FGF-4 comprises a polypeptide having, e.g., at least one, two, three or four contiguous amino acid deletions relative to amino acids 122-124 or amino acids 163-165 of SEQ ID NO: 35. In still other aspects of this embodiment, a β-trefoil domain with enhanced binding activity derived from a FGF-4 comprises a polypeptide having, e.g., at most one, two, three or four contiguous amino acid additions relative to amino acids 122-124 or amino acids 163-165 of SEQ ID NO: 35. In other aspects of this embodiment, a β-trefoil domain with enhanced binding activity derived from a FGF-4 comprises a polypeptide having, e.g., at least one, two, three or four contiguous amino acid additions relative to amino acids 122-124 or amino acids 163-165 of SEQ ID NO: 35.

In another embodiment, a β-trefoil domain derived from a FGF-8 comprises a β-trefoil domain derived from a FGF-8 of SEQ ID NO: 36. In another embodiment, a β-trefoil domain derived from a FGF-8 comprises amino acids 43-172 of SEQ ID NO: 36. In another aspect of this embodiment, a β-trefoil domain derived from a FGF-8 comprises a α-fold motif of a β-trefoil domain of a FGF-8, a β-fold motif of a β-trefoil domain of a FGF-8 or a γ-fold motif of a β-trefoil domain of a FGF-8 of SEQ ID NO: 36. In another aspect of this embodiment, a β-trefoil domain derived from a FGF-8 comprises amino acids 43-80, amino acids 84-123, or amino acids 127-172 of SEQ ID NO: 36.

In another embodiment, a β-trefoil domain with enhanced binding activity derived from a FGF-8 comprises a β-trefoil domain with enhanced binding activity derived from a FGF-8 of SEQ ID NO: 36. In another embodiment, a β-trefoil domain with enhanced binding activity derived from a FGF-8 comprises amino acids 43-172 of SEQ ID NO: 36. In another aspect of this embodiment, a β-trefoil domain with enhanced binding activity derived from a FGF-8 comprises a modified α-fold motif of a β-trefoil domain of a FGF-8, a modified β-fold motif of a β-trefoil domain of a FGF-8 or a modified γ-fold motif of a β-trefoil domain of a FGF-8 of SEQ ID NO: 36. In another aspect of this embodiment, a β-trefoil domain with enhanced binding activity derived from a FGF-8 comprises amino acids 43-80, amino acids 84-123, or amino acids 127-172 of SEQ ID NO: 36.

In other aspects of this embodiment, a FGF-8 comprising a β-trefoil domain with enhanced binding activity comprises a polypeptide having, e.g., at least 70% amino acid identity with amino acids 43-80, amino acids 84-123, or amino acids 127-172 of SEQ ID NO: 36, at least 75% amino acid identity with amino acids 43-80, amino acids 84-123, or amino acids 127-172 of SEQ ID NO: 36, at least 80% amino acid identity with amino acids 43-80, amino acids 84-123, or amino acids 127-172 of SEQ ID NO: 36, at least 85% amino acid identity with amino acids 43-80, amino acids 84-123, or amino acids 127-172 of SEQ ID NO: 36, at least 90% amino acid identity with amino acids 43-80, amino acids 84-123, or amino acids 127-172 of SEQ ID NO: 36 or at least 95% amino acid identity with amino acids 43-80, amino acids 84-123, or amino acids 127-172 of SEQ ID NO: 36. In yet other aspects of this embodiment, a FGF-8 comprising a β-trefoil domain with enhanced binding activity comprises a polypeptide having, e.g., at most 70% amino acid identity with amino acids 43-80, amino acids 84-123, or amino acids 127-172 of SEQ ID NO: 36, at most 75% amino acid identity with amino acids 43-80, amino acids 84-123, or amino acids 127-172 of SEQ ID NO: 36, at most 80% amino acid identity with amino acids 43-80, amino acids 84-123, or amino acids 127-172 of SEQ ID NO: 36, at most 85% amino acid identity with amino acids 43-80, amino acids 84-123, or amino acids 127-172 of SEQ ID NO: 36, at most 90% amino acid identity with amino acids 43-80, amino acids 84-123, or amino acids 127-172 of SEQ ID NO: 36 or at most 95% amino acid identity with amino acids 43-80, amino acids 84-123, or amino acids 127-172 of SEQ ID NO: 36.

In other aspects of this embodiment, a FGF-8 comprising a β-trefoil domain with enhanced binding activity comprises a polypeptide having, e.g., at most one, two, three, four, five, six, seven, eight, nine, 10 or 20 non-contiguous amino acid substitutions relative to amino acids 43-80, amino acids 84-123, or amino acids 127-172 of SEQ ID NO: 36. In other aspects of this embodiment, a FGF-8 comprising a β-trefoil domain with enhanced binding activity comprises a polypeptide having, e.g., at least one, two, three, four, five, six, seven, eight, nine, 10 or 20 non-contiguous amino acid substitutions relative to amino acids 43-80, amino acids 84-123, or amino acids 127-172 of SEQ ID NO: 36. In yet other aspects of this embodiment, a FGF-8 comprising a β-trefoil domain with enhanced binding activity comprises a polypeptide having, e.g., at most one, two, three, four, five, six, seven, eight, nine, 10 or 20 non-contiguous amino acid deletions relative to amino acids 43-80, amino acids 84-123, or amino acids 127-172 of SEQ ID NO: 36. In other aspects of this embodiment, a FGF-8 comprising a β-trefoil domain with enhanced binding activity comprises a polypeptide having, e.g., at least one, two, three, four, five, six, seven, eight, nine, 10 or 20 non-contiguous amino acid deletions relative to amino acids 43-80, amino acids 84-123, or amino acids 127-172 of SEQ ID NO: 36. In still other aspects of this embodiment, a FGF-8 comprising a β-trefoil domain with enhanced binding activity comprises a polypeptide having, e.g., at most one, two, three, four, five, six, seven, eight, nine, 10 or 20 non-contiguous amino acid additions relative to amino acids 43-80, amino acids 84-123, or amino acids 127-172 of SEQ ID NO: 36. In other aspects of this embodiment, a FGF-8 comprising a β-trefoil domain with enhanced binding activity comprises a polypeptide having, e.g., at least one, two, three, four, five, six, seven, eight, nine, 10 or 20 non-contiguous amino acid additions relative to amino acids 43-80, amino acids 84-123, or amino acids 127-172 of SEQ ID NO: 36.

In other aspects of this embodiment, a FGF-8 comprising a β-trefoil domain with enhanced binding activity comprises a polypeptide having, e.g., at most one, two, three, four, five, six, seven, eight, nine, 10 or 20 contiguous amino acid substitutions relative to amino acids 43-80, amino acids 84-123, or amino acids 127-172 of SEQ ID NO: 36. In other aspects of this embodiment, a FGF-8 comprising a β-trefoil domain with enhanced binding activity comprises a polypeptide having, e.g., at least one, two, three, four, five, six, seven, eight, nine, 10 or 20 contiguous amino acid substitutions relative to amino acids 43-80, amino acids 84-123, or amino acids 127-172 of SEQ ID NO: 36. In yet other aspects of this embodiment, a FGF-8 comprising a β-trefoil domain with enhanced binding activity comprises a polypeptide having, e.g., at most one, two, three, four, five, six, seven, eight, nine, 10 or 20 contiguous amino acid deletions relative to amino acids 43-80, amino acids 84-123, or amino acids 127-172 of SEQ ID NO: 36. In other aspects of this embodiment, a FGF-8 comprising a β-trefoil domain with enhanced binding activity comprises a polypeptide having, e.g., at least one, two, three, four, five, six, seven, eight, nine, 10 or 20 contiguous amino acid deletions relative to amino acids 43-80, amino acids 84-123, or amino acids 127-172 of SEQ ID NO: 36. In still other aspects of this embodiment, a FGF-8 comprising a β-trefoil domain with enhanced binding activity comprises a polypeptide having, e.g., at most one, two, three, four, five, six, seven, eight, nine, 10 or 20 contiguous amino acid additions relative to amino acids 43-80, amino acids 84-123, or amino acids 127-172 of SEQ ID NO: 36. In other aspects of this embodiment, a FGF-8 comprising a β-trefoil domain with enhanced binding activity comprises a polypeptide having, e.g., at least one, two, three, four, five, six, seven, eight, nine, 10 or 20 contiguous amino acid additions relative to amino acids 43-80, amino acids 84-123, or amino acids 127-172 of SEQ ID NO: 36.

In another embodiment, a β-trefoil domain derived from a FGF-8 comprises a β4/β5 hairpin turn of a β-trefoil domain of a FGF-8 or a β8/β9 hairpin turn of a β-trefoil domain of a FGF-8 of SEQ ID NO: 36. In another aspect of this embodiment, a β-trefoil domain derived from a FGF-8 comprises amino acids 81-83 or amino acids 124-126 of SEQ ID NO: 36.

In another embodiment, a β-trefoil domain with enhanced binding activity derived from a FGF-8 comprises a modified β4/β5 hairpin turn of a β-trefoil domain of a FGF-8 or a modified β8/β9 hairpin turn of a β-trefoil domain of a FGF-8 of SEQ ID NO: 36. In another aspect of this embodiment, a β-trefoil domain with enhanced binding activity derived from a FGF-8 comprises a modification of amino acids 81-83 or amino acids 124-126 of SEQ ID NO: 36.

In other aspects of this embodiment, a β-trefoil domain with enhanced binding activity derived from a FGF-8 comprises a polypeptide having, e.g., at least 70% amino acid identity with amino acids 81-83 or amino acids 124-126 of SEQ ID NO: 36, at least 75% amino acid identity with amino acids 81-83 or amino acids 124-126 of SEQ ID NO: 36, at least 80% amino acid identity with amino acids 81-83 or amino acids 124-126 of SEQ ID NO: 36, at least 85% amino acid identity with amino acids 81-83 or amino acids 124-126 of SEQ ID NO: 36, at least 90% amino acid identity with amino acids 81-83 or amino acids 124-126 of SEQ ID NO: 36 or at least 95% amino acid identity with amino acids 81-83 or amino acids 124-126 of SEQ ID NO: 36. In yet other aspects of this embodiment, a β-trefoil domain with enhanced binding activity derived from a FGF-8 comprises a polypeptide having, e.g., at most 70% amino acid identity with amino acids 81-83 or amino acids 124-126 of SEQ ID NO: 36, at most 75% amino acid identity with amino acids 81-83 or amino acids 124-126 of SEQ ID NO: 36, at most 80% amino acid identity with amino acids 81-83 or amino acids 124-126 of SEQ ID NO: 36, at most 85% amino acid identity with amino acids 81-83 or amino acids 124-126 of SEQ ID NO: 36, at most 90% amino acid identity with amino acids 81-83 or amino acids 124-126 of SEQ ID NO: 36 or at most 95% amino acid identity with amino acids 81-83 or amino acids 124-126 of SEQ ID NO: 36.

In other aspects of this embodiment, a β-trefoil domain with enhanced binding activity derived from a FGF-8 comprises a polypeptide having, e.g., at most one, two, three or four non-contiguous amino acid substitutions relative to amino acids 81-83 or amino acids 124-126 of SEQ ID NO: 36. In other aspects of this embodiment, a β-trefoil domain with enhanced binding activity derived from a FGF-8 comprises a polypeptide having, e.g., at least one, two, three or four non-contiguous amino acid substitutions relative to amino acids 81-83 or amino acids 124-126 of SEQ ID NO: 36. In other aspects of this embodiment, a non-contiguous amino acid substitution of any amino acid from amino acids 81-83 or amino acids 124-126 of SEQ ID NO: 36 can be replaced with glycine. In other aspects of this embodiment, a non-contiguous amino acid substitution of any hydrophobic amino acid from amino acids 81-83 or amino acids 124-126 of SEQ ID NO: 36 can be replaced with phenylalanine. In yet other aspects of this embodiment, a β-trefoil domain with enhanced binding activity derived from a FGF-8 comprises a polypeptide having, e.g., at most one, two, three or four non-contiguous amino acid deletions relative to amino acids 81-83 or amino acids 124-126 of SEQ ID NO: 36. In other aspects of this embodiment, a β-trefoil domain with enhanced binding activity derived from a FGF-8 comprises a polypeptide having, e.g., at least one, two, three or four non-contiguous amino acid deletions relative to amino acids 81-83 or amino acids 124-126 of SEQ ID NO: 36. In still other aspects of this embodiment, a β-trefoil domain with enhanced binding activity derived from a FGF-8 comprises a polypeptide having, e.g., at most one, two, three or four non-contiguous amino acid additions relative to amino acids 81-83 or amino acids 124-126 of SEQ ID NO: 36. In other aspects of this embodiment, a β-trefoil domain with enhanced binding activity derived from a FGF-8 comprises a polypeptide having, e.g., at least one, two, three or four non-contiguous amino acid additions relative to amino acids 81-83 or amino acids 124-126 of SEQ ID NO: 36.

In other aspects of this embodiment, a β-trefoil domain with enhanced binding activity derived from a FGF-8 comprises a polypeptide having, e.g., at most one, two, three or four contiguous amino acid substitutions relative to amino acids 81-83 or amino acids 124-126 of SEQ ID NO: 36. In other aspects of this embodiment, a β-trefoil domain with enhanced binding activity derived from a FGF-8 comprises a polypeptide having, e.g., at least one, two, three or four contiguous amino acid substitutions relative to amino acids 81-83 or amino acids 124-126 of SEQ ID NO: 36. In other aspects of this embodiment, contiguous amino acid substitutions of amino acids from amino acids 81-83 or amino acids 124-126 of SEQ ID NO: 36 can be replaced with glycine. In other aspects of this embodiment, contiguous amino acid substitutions of hydrophobic amino acids from amino acids 81-83 or amino acids 124-126 of SEQ ID NO: 36 can be replaced with phenylalanine. In yet other aspects of this embodiment, a β-trefoil domain with enhanced binding activity derived from a FGF-8 comprises a polypeptide having, e.g., at most one, two, three or four contiguous amino acid deletions relative to amino acids 81-83 or amino acids 124-126 of SEQ ID NO: 36. In other aspects of this embodiment, a β-trefoil domain with enhanced binding activity derived from a FGF-8 comprises a polypeptide having, e.g., at least one, two, three or four contiguous amino acid deletions relative to amino acids 81-83 or amino acids 124-126 of SEQ ID NO: 36. In still other aspects of this embodiment, a β-trefoil domain with enhanced binding activity derived from a FGF-8 comprises a polypeptide having, e.g., at most one, two, three or four contiguous amino acid additions relative to amino acids 81-83 or amino acids 124-126 of SEQ ID NO: 36. In other aspects of this embodiment, a β-trefoil domain with enhanced binding activity derived from a FGF-8 comprises a polypeptide having, e.g., at least one, two, three or four contiguous amino acid additions relative to amino acids 81-83 or amino acids 124-126 of SEQ ID NO: 36.

In another embodiment, a β-trefoil domain derived from a FGF-9 comprises a β-trefoil domain derived from a FGF-9 of SEQ ID NO: 37. In another embodiment, a β-trefoil domain derived from a FGF-9 comprises amino acids 63-196 of SEQ ID NO: 37. In another aspect of this embodiment, a β-trefoil domain derived from a FGF-9 comprises a α-fold motif of a β-trefoil domain of a FGF-9, a β-fold motif of a β-trefoil domain of a FGF-9 or a γ-fold motif of a β-trefoil domain of a FGF-9 of SEQ ID NO: 37. In another aspect of this embodiment, a β-trefoil domain derived from a FGF-9 comprises amino acids 63-100, amino acids 104-144, or amino acids 148-196 of SEQ ID NO: 37.

In another embodiment, a β-trefoil domain with enhanced binding activity derived from a FGF-9 comprises a β-trefoil domain with enhanced binding activity derived from a FGF-9 of SEQ ID NO: 37. In another embodiment, a β-trefoil domain with enhanced binding activity derived from a FGF-9 comprises amino acids 63-196 of SEQ ID NO: 37. In another aspect of this embodiment, a β-trefoil domain with enhanced binding activity derived from a FGF-9 comprises a modified α-fold motif of a β-trefoil domain of a FGF-9, a modified β-fold motif of a β-trefoil domain of a FGF-9 or a modified γ-fold motif of a β-trefoil domain of a FGF-9 of SEQ ID NO: 37. In another aspect of this embodiment, a β-trefoil domain with enhanced binding activity derived from a FGF-9 comprises amino acids 63-100, amino acids 104-144, or amino acids 148-196 of SEQ ID NO: 37.

In other aspects of this embodiment, a FGF-9 comprising a β-trefoil domain with enhanced binding activity comprises a polypeptide having, e.g., at least 70% amino acid identity with amino acids 63-100, amino acids 104-144, or amino acids 148-196 of SEQ ID NO: 37, at least 75% amino acid identity with amino acids 63-100, amino acids 104-144, or amino acids 148-196 of SEQ ID NO: 37, at least 80% amino acid identity with amino acids 63-100, amino acids 104-144, or amino acids 148-196 of SEQ ID NO: 37, at least 85% amino acid identity with amino acids 63-100, amino acids 104-144, or amino acids 148-196 of SEQ ID NO: 37, at least 90% amino acid identity with amino acids 63-100, amino acids 104-144, or amino acids 148-196 of SEQ ID NO: 37 or at least 95% amino acid identity with amino acids 63-100, amino acids 104-144, or amino acids 148-196 of SEQ ID NO: 37. In yet other aspects of this embodiment, a FGF-9 comprising a β-trefoil domain with enhanced binding activity comprises a polypeptide having, e.g., at most 70% amino acid identity with amino acids 63-100, amino acids 104-144, or amino acids 148-196 of SEQ ID NO: 37, at most 75% amino acid identity with amino acids 63-100, amino acids 104-144, or amino acids 148-196 of SEQ ID NO: 37, at most 80% amino acid identity with amino acids 63-100, amino acids 104-144, or amino acids 148-196 of SEQ ID NO: 37, at most 85% amino acid identity with amino acids 63-100, amino acids 104-144, or amino acids 148-196 of SEQ ID NO: 37, at most 90% amino acid identity with amino acids 63-100, amino acids 104-144, or amino acids 148-196 of SEQ ID NO: 37 or at most 95% amino acid identity with amino acids 63-100, amino acids 104-144, or amino acids 148-196 of SEQ ID NO: 37.

In other aspects of this embodiment, a FGF-9 comprising a β-trefoil domain with enhanced binding activity comprises a polypeptide having, e.g., at most one, two, three, four, five, six, seven, eight, nine, 10 or 20 non-contiguous amino acid substitutions relative to amino acids 63-100, amino acids 104-144, or amino acids 148-196 of SEQ ID NO: 37. In other aspects of this embodiment, a FGF-9 comprising a β-trefoil domain with enhanced binding activity comprises a polypeptide having, e.g., at least one, two, three, four, five, six, seven, eight, nine, 10 or 20 non-contiguous amino acid substitutions relative to amino acids 63-100, amino acids 104-144, or amino acids 148-196 of SEQ ID NO: 37. In yet other aspects of this embodiment, a FGF-9 comprising a β-trefoil domain with enhanced binding activity comprises a polypeptide having, e.g., at most one, two, three, four, five, six, seven, eight, nine, 10 or 20 non-contiguous amino acid deletions relative to amino acids 63-100, amino acids 104-144, or amino acids 148-196 of SEQ ID NO: 37. In other aspects of this embodiment, a FGF-9 comprising a β-trefoil domain with enhanced binding activity comprises a polypeptide having, e.g., at least one, two, three, four, five, six, seven, eight, nine, 10 or 20 non-contiguous amino acid deletions relative to amino acids 63-100, amino acids 104-144, or amino acids 148-196 of SEQ ID NO: 37. In still other aspects of this embodiment, a FGF-9 comprising a β-trefoil domain with enhanced binding activity comprises a polypeptide having, e.g., at most one, two, three, four, five, six, seven, eight, nine, 10 or 20 non-contiguous amino acid additions relative to amino acids 63-100, amino acids 104-144, or amino acids 148-196 of SEQ ID NO: 37. In other aspects of this embodiment, a FGF-9 comprising a β-trefoil domain with enhanced binding activity comprises a polypeptide having, e.g., at least one, two, three, four, five, six, seven, eight, nine, 10 or 20 non-contiguous amino acid additions relative to amino acids 63-100, amino acids 104-144, or amino acids 148-196 of SEQ ID NO: 37.

In other aspects of this embodiment, a FGF-9 comprising a β-trefoil domain with enhanced binding activity comprises a polypeptide having, e.g., at most one, two, three, four, five, six, seven, eight, nine, 10 or 20 contiguous amino acid substitutions relative to amino acids 63-100, amino acids 104-144, or amino acids 148-196 of SEQ ID NO: 37. In other aspects of this embodiment, a FGF-9 comprising a β-trefoil domain with enhanced binding activity comprises a polypeptide having, e.g., at least one, two, three, four, five, six, seven, eight, nine, 10 or 20 contiguous amino acid substitutions relative to amino acids 63-100, amino acids 104-144, or amino acids 148-196 of SEQ ID NO: 37. In yet other aspects of this embodiment, a FGF-9 comprising a β-trefoil domain with enhanced binding activity comprises a polypeptide having, e.g., at most one, two, three, four, five, six, seven, eight, nine, 10 or 20 contiguous amino acid deletions relative to amino acids 63-100, amino acids 104-144, or amino acids 148-196 of SEQ ID NO: 37. In other aspects of this embodiment, a FGF-9 comprising a β-trefoil domain with enhanced binding activity comprises a polypeptide having, e.g., at least one, two, three, four, five, six, seven, eight, nine, 10 or 20 contiguous amino acid deletions relative to amino acids 63-100, amino acids 104-144, or amino acids 148-196 of SEQ ID NO: 37. In still other aspects of this embodiment, a FGF-9 comprising a β-trefoil domain with enhanced binding activity comprises a polypeptide having, e.g., at most one, two, three, four, five, six, seven, eight, nine, 10 or 20 contiguous amino acid additions relative to amino acids 63-100, amino acids 104-144, or amino acids 148-196 of SEQ ID NO: 37. In other aspects of this embodiment, a FGF-9 comprising a β-trefoil domain with enhanced binding activity comprises a polypeptide having, e.g., at least one, two, three, four, five, six, seven, eight, nine, 10 or 20 contiguous amino acid additions relative to amino acids 63-100, amino acids 104-144, or amino acids 148-196 of SEQ ID NO: 37.

In another embodiment, a β-trefoil domain derived from a FGF-9 comprises a β4/β5 hairpin turn of a β-trefoil domain of a FGF-9 or a β8/β9 hairpin turn of a β-trefoil domain of a FGF-9 of SEQ ID NO: 37. In another aspect of this embodiment, a β-trefoil domain derived from a FGF-9 comprises amino acids 101-103 or amino acids 145-147 of SEQ ID NO: 37.

In another embodiment, a β-trefoil domain with enhanced binding activity derived from a FGF-9 comprises a modified β4/β5 hairpin turn of a β-trefoil domain of a FGF-9 or a modified β8/β9 hairpin turn of a β-trefoil domain of a FGF-9 of SEQ ID NO: 37. In another aspect of this embodiment, a β-trefoil domain with enhanced binding activity derived from a FGF-9 comprises a modification of amino acids 101-103 or amino acids 145-147 of SEQ ID NO: 37.

In other aspects of this embodiment, a β-trefoil domain with enhanced binding activity derived from a FGF-9 comprises a polypeptide having, e.g., at least 70% amino acid identity with amino acids 101-103 or amino acids 145-147 of SEQ ID NO: 37, at least 75% amino acid identity with amino acids 101-103 or amino acids 145-147 of SEQ ID NO: 37, at least 80% amino acid identity with amino acids 101-103 or amino acids 145-147 of SEQ ID NO: 37, at least 85% amino acid identity with amino acids 101-103 or amino acids 145-147 of SEQ ID NO: 37, at least 90% amino acid identity with amino acids 101-103 or amino acids 145-147 of SEQ ID NO: 37 or at least 95% amino acid identity with amino acids 101-103 or amino acids 145-147 of SEQ ID NO: 37. In yet other aspects of this embodiment, a β-trefoil domain with enhanced binding activity derived from a FGF-9 comprises a polypeptide having, e.g., at most 70% amino acid identity with amino acids 101-103 or amino acids 145-147 of SEQ ID NO: 37, at most 75% amino acid identity with amino acids 101-103 or amino acids 145-147 of SEQ ID NO: 37, at most 80% amino acid identity with amino acids 101-103 or amino acids 145-147 of SEQ ID NO: 37, at most 85% amino acid identity with amino acids 101-103 or amino acids 145-147 of SEQ ID NO: 37, at most 90% amino acid identity with amino acids 101-103 or amino acids 145-147 of SEQ ID NO: 37 or at most 95% amino acid identity with amino acids 101-103 or amino acids 145-147 of SEQ ID NO: 37.

In other aspects of this embodiment, a β-trefoil domain with enhanced binding activity derived from a FGF-9 comprises a polypeptide having, e.g., at most one, two, three or four non-contiguous amino acid substitutions relative to amino acids 101-103 or amino acids 145-147 of SEQ ID NO: 37. In other aspects of this embodiment, a β-trefoil domain with enhanced binding activity derived from a FGF-9 comprises a polypeptide having, e.g., at least one, two, three or four non-contiguous amino acid substitutions relative to amino acids 101-103 or amino acids 145-147 of SEQ ID NO: 37. In other aspects of this embodiment, a non-contiguous amino acid substitution of any amino acid from amino acids 101-103 or amino acids 145-147 of SEQ ID NO: 37 can be replaced with glycine. In other aspects of this embodiment, a non-contiguous amino acid substitution of any hydrophobic amino acid from amino acids 101-103 or amino acids 145-147 of SEQ ID NO: 37 can be replaced with phenylalanine. In yet other aspects of this embodiment, a β-trefoil domain with enhanced binding activity derived from a FGF-9 comprises a polypeptide having, e.g., at most one, two, three or four non-contiguous amino acid deletions relative to amino acids 101-103 or amino acids 145-147 of SEQ ID NO: 37. In other aspects of this embodiment, a β-trefoil domain with enhanced binding activity derived from a FGF-9 comprises a polypeptide having, e.g., at least one, two, three or four non-contiguous amino acid deletions relative to amino acids 101-103 or amino acids 145-147 of SEQ ID NO: 37. In still other aspects of this embodiment, a β-trefoil domain with enhanced binding activity derived from a FGF-9 comprises a polypeptide having, e.g., at most one, two, three or four non-contiguous amino acid additions relative to amino acids 101-103 or amino acids 145-147 of SEQ ID NO: 37. In other aspects of this embodiment, a β-trefoil domain with enhanced binding activity derived from a FGF-9 comprises a polypeptide having, e.g., at least one, two, three or four non-contiguous amino acid additions relative to amino acids 101-103 or amino acids 145-147 of SEQ ID NO: 37.

In other aspects of this embodiment, a β-trefoil domain with enhanced binding activity derived from a FGF-9 comprises a polypeptide having, e.g., at most one, two, three or four contiguous amino acid substitutions relative to amino acids 101-103 or amino acids 145-147 of SEQ ID NO: 37. In other aspects of this embodiment, a β-trefoil domain with enhanced binding activity derived from a FGF-9 comprises a polypeptide having, e.g., at least one, two, three or four contiguous amino acid substitutions relative to amino acids 101-103 or amino acids 145-147 of SEQ ID NO: 37. In other aspects of this embodiment, contiguous amino acid substitutions of amino acids from amino acids 101-103 or amino acids 145-147 of SEQ ID NO: 37 can be replaced with glycine. In other aspects of this embodiment, contiguous amino acid substitutions of hydrophobic amino acids from amino acids 101-103 or amino acids 145-147 of SEQ ID NO: 37 can be replaced with phenylalanine. In yet other aspects of this embodiment, a β-trefoil domain with enhanced binding activity derived from a FGF-9 comprises a polypeptide having, e.g., at most one, two, three or four contiguous amino acid deletions relative to amino acids 101-103 or amino acids 145-147 of SEQ ID NO: 37. In other aspects of this embodiment, a β-trefoil domain with enhanced binding activity derived from a FGF-9 comprises a polypeptide having, e.g., at least one, two, three or four contiguous amino acid deletions relative to amino acids 101-103 or amino acids 145-147 of SEQ ID NO: 37. In still other aspects of this embodiment, a β-trefoil domain with enhanced binding activity derived from a FGF-9 comprises a polypeptide having, e.g., at most one, two, three or four contiguous amino acid additions relative to amino acids 101-103 or amino acids 145-147 of SEQ ID NO: 37. In other aspects of this embodiment, a β-trefoil domain with enhanced binding activity derived from a FGF-9 comprises a polypeptide having, e.g., at least one, two, three or four contiguous amino acid additions relative to amino acids 101-103 or amino acids 145-147 of SEQ ID NO: 37.

In another embodiment, a β-trefoil domain derived from a FGF-17 comprises a β-trefoil domain derived from a FGF-17 of SEQ ID NO: 38. In another embodiment, a β-trefoil domain derived from a FGF-17 comprises amino acids 55-183 of SEQ ID NO: 38. In another aspect of this embodiment, a β-trefoil domain derived from a FGF-17 comprises a α-fold motif of a β-trefoil domain of a FGF-17, a β-fold motif of a β-trefoil domain of a FGF-17 or a γ-fold motif of a β-trefoil domain of a FGF-17 of SEQ ID NO: 38. In another aspect of this embodiment, a β-trefoil domain derived from a FGF-17 comprises amino acids 55-91, amino acids 95-134, or amino acids 138-183 of SEQ ID NO: 38.

In another embodiment, a β-trefoil domain with enhanced binding activity derived from a FGF-17 comprises a β-trefoil domain with enhanced binding activity derived from a FGF-17 of SEQ ID NO: 38. In another embodiment, a β-trefoil domain with enhanced binding activity derived from a FGF-17 comprises amino acids 55-183 of SEQ ID NO: 38. In another aspect of this embodiment, a β-trefoil domain with enhanced binding activity derived from a FGF-17 comprises a modified α-fold motif of a β-trefoil domain of a FGF-17, a modified β-fold motif of a β-trefoil domain of a FGF-17 or a modified γ-fold motif of a β-trefoil domain of a FGF-17 of SEQ ID NO: 38. In another aspect of this embodiment, a β-trefoil domain with enhanced binding activity derived from a FGF-17 comprises amino acids 55-91, amino acids 95-134, or amino acids 138-183 of SEQ ID NO: 38.

In other aspects of this embodiment, a FGF-17 comprising a β-trefoil domain with enhanced binding activity comprises a polypeptide having, e.g., at least 70% amino acid identity with amino acids 55-91, amino acids 95-134, or amino acids 138-183 of SEQ ID NO: 38, at least 75% amino acid identity with amino acids 55-91, amino acids 95-134, or amino acids 138-183 of SEQ ID NO: 38, at least 80% amino acid identity with amino acids 55-91, amino acids 95-134, or amino acids 138-183 of SEQ ID NO: 38, at least 85% amino acid identity with amino acids 55-91, amino acids 95-134, or amino acids 138-183 of SEQ ID NO: 38, at least 90% amino acid identity with amino acids 55-91, amino acids 95-134, or amino acids 138-183 of SEQ ID NO: 38 or at least 95% amino acid identity with amino acids 55-91, amino acids 95-134, or amino acids 138-183 of SEQ ID NO: 38. In yet other aspects of this embodiment, a FGF-17 comprising a β-trefoil domain with enhanced binding activity comprises a polypeptide having, e.g., at most 70% amino acid identity with amino acids 55-91, amino acids 95-134, or amino acids 138-183 of SEQ ID NO: 38, at most 75% amino acid identity with amino acids 55-91, amino acids 95-134, or amino acids 138-183 of SEQ ID NO: 38, at most 80% amino acid identity with amino acids 55-91, amino acids 95-134, or amino acids 138-183 of SEQ ID NO: 38, at most 85% amino acid identity with amino acids 55-91, amino acids 95-134, or amino acids 138-183 of SEQ ID NO: 38, at most 90% amino acid identity with amino acids 55-91, amino acids 95-134, or amino acids 138-183 of SEQ ID NO: 38 or at most 95% amino acid identity with amino acids 55-91, amino acids 95-134, or amino acids 138-183 of SEQ ID NO: 38.

In other aspects of this embodiment, a FGF-17 comprising a β-trefoil domain with enhanced binding activity comprises a polypeptide having, e.g., at most one, two, three, four, five, six, seven, eight, nine, 10 or 20 non-contiguous amino acid substitutions relative to amino acids 55-91, amino acids 95-134, or amino acids 138-183 of SEQ ID NO: 38. In other aspects of this embodiment, a FGF-17 comprising a β-trefoil domain with enhanced binding activity comprises a polypeptide having, e.g., at least one, two, three, four, five, six, seven, eight, nine, 10 or 20 non-contiguous amino acid substitutions relative to amino acids 55-91, amino acids 95-134, or amino acids 138-183 of SEQ ID NO: 38. In yet other aspects of this embodiment, a FGF-17 comprising a β-trefoil domain with enhanced binding activity comprises a polypeptide having, e.g., at most one, two, three, four, five, six, seven, eight, nine, 10 or 20 non-contiguous amino acid deletions relative to amino acids 55-91, amino acids 95-134, or amino acids 138-183 of SEQ ID NO: 38. In other aspects of this embodiment, a FGF-17 comprising a β-trefoil domain with enhanced binding activity comprises a polypeptide having, e.g., at least one, two, three, four, five, six, seven, eight, nine, 10 or 20 non-contiguous amino acid deletions relative to amino acids 55-91, amino acids 95-134, or amino acids 138-183 of SEQ ID NO: 38. In still other aspects of this embodiment, a FGF-17 comprising a β-trefoil domain with enhanced binding activity comprises a polypeptide having, e.g., at most one, two, three, four, five, six, seven, eight, nine, 10 or 20 non-contiguous amino acid additions relative to amino acids 55-91, amino acids 95-134, or amino acids 138-183 of SEQ ID NO: 38. In other aspects of this embodiment, a FGF-17 comprising a β-trefoil domain with enhanced binding activity comprises a polypeptide having, e.g., at least one, two, three, four, five, six, seven, eight, nine, 10 or 20 non-contiguous amino acid additions relative to amino acids 55-91, amino acids 95-134, or amino acids 138-183 of SEQ ID NO: 38.

In other aspects of this embodiment, a FGF-17 comprising a β-trefoil domain with enhanced binding activity comprises a polypeptide having, e.g., at most one, two, three, four, five, six, seven, eight, nine, 10 or 20 contiguous amino acid substitutions relative to amino acids 55-91, amino acids 95-134, or amino acids 138-183 of SEQ ID NO: 38. In other aspects of this embodiment, a FGF-17 comprising a β-trefoil domain with enhanced binding activity comprises a polypeptide having, e.g., at least one, two, three, four, five, six, seven, eight, nine, 10 or 20 contiguous amino acid substitutions relative to amino acids 55-91, amino acids 95-134, or amino acids 138-183 of SEQ ID NO: 38. In yet other aspects of this embodiment, a FGF-17 comprising a β-trefoil domain with enhanced binding activity comprises a polypeptide having, e.g., at most one, two, three, four, five, six, seven, eight, nine, 10 or 20 contiguous amino acid deletions relative to amino acids 55-91, amino acids 95-134, or amino acids 138-183 of SEQ ID NO: 38. In other aspects of this embodiment, a FGF-17 comprising a β-trefoil domain with enhanced binding activity comprises a polypeptide having, e.g., at least one, two, three, four, five, six, seven, eight, nine, 10 or 20 contiguous amino acid deletions relative to amino acids 55-91, amino acids 95-134, or amino acids 138-183 of SEQ ID NO: 38. In still other aspects of this embodiment, a FGF-17 comprising a β-trefoil domain with enhanced binding activity comprises a polypeptide having, e.g., at most one, two, three, four, five, six, seven, eight, nine, 10 or 20 contiguous amino acid additions relative to amino acids 55-91, amino acids 95-134, or amino acids 138-183 of SEQ ID NO: 38. In other aspects of this embodiment, a FGF-17 comprising a β-trefoil domain with enhanced binding activity comprises a polypeptide having, e.g., at least one, two, three, four, five, six, seven, eight, nine, 10 or 20 contiguous amino acid additions relative to amino acids 55-91, amino acids 95-134, or amino acids 138-183 of SEQ ID NO: 38.

In another embodiment, a β-trefoil domain derived from a FGF-17 comprises a β4/β5 hairpin turn of a β-trefoil domain of a FGF-17 or a β8/β9 hairpin turn of a β-trefoil domain of a FGF-17 of SEQ ID NO: 38. In another aspect of this embodiment, a β-trefoil domain derived from a FGF-17 comprises amino acids 92-94 or amino acids 135-137 of SEQ ID NO: 38.

In another embodiment, a β-trefoil domain with enhanced binding activity derived from a FGF-17 comprises a modified β4/β5 hairpin turn of a β-trefoil domain of a FGF-17 or a modified β8/β9 hairpin turn of a β-trefoil domain of a FGF-17 of SEQ ID NO: 38. In another aspect of this embodiment, a β-trefoil domain with enhanced binding activity derived from a FGF-17 comprises a modification of amino acids 92-94 or amino acids 135-137 of SEQ ID NO: 38.

In other aspects of this embodiment, a β-trefoil domain with enhanced binding activity derived from a FGF-17 comprises a polypeptide having, e.g., at least 70% amino acid identity with amino acids 92-94 or amino acids 135-137 of SEQ ID NO: 38, at least 75% amino acid identity with amino acids 92-94 or amino acids 135-137 of SEQ ID NO: 38, at least 80% amino acid identity with amino acids 92-94 or amino acids 135-137 of SEQ ID NO: 38, at least 85% amino acid identity with amino acids 92-94 or amino acids 135-137 of SEQ ID NO: 38, at least 90% amino acid identity with amino acids 92-94 or amino acids 135-137 of SEQ ID NO: 38 or at least 95% amino acid identity with amino acids 92-94 or amino acids 135-137 of SEQ ID NO: 38. In yet other aspects of this embodiment, a β-trefoil domain with enhanced binding activity derived from a FGF-17 comprises a polypeptide having, e.g., at most 70% amino acid identity with amino acids 92-94 or amino acids 135-137 of SEQ ID NO: 38, at most 75% amino acid identity with amino acids 92-94 or amino acids 135-137 of SEQ ID NO: 38, at most 80% amino acid identity with amino acids 92-94 or amino acids 135-137 of SEQ ID NO: 38, at most 85% amino acid identity with amino acids 92-94 or amino acids 135-137 of SEQ ID NO: 38, at most 90% amino acid identity with amino acids 92-94 or amino acids 135-137 of SEQ ID NO: 38 or at most 95% amino acid identity with amino acids 92-94 or amino acids 135-137 of SEQ ID NO: 38.

In other aspects of this embodiment, a β-trefoil domain with enhanced binding activity derived from a FGF-17 comprises a polypeptide having, e.g., at most one, two, three or four non-contiguous amino acid substitutions relative to amino acids 92-94 or amino acids 135-137 of SEQ ID NO: 38. In other aspects of this embodiment, a β-trefoil domain with enhanced binding activity derived from a FGF-17 comprises a polypeptide having, e.g., at least one, two, three or four non-contiguous amino acid substitutions relative to amino acids 92-94 or amino acids 135-137 of SEQ ID NO: 38. In other aspects of this embodiment, a non-contiguous amino acid substitution of any amino acid from amino acids 92-94 or amino acids 135-137 of SEQ ID NO: 38 can be replaced with glycine. In other aspects of this embodiment, a non-contiguous amino acid substitution of any hydrophobic amino acid from amino acids 92-94 or amino acids 135-137 of SEQ ID NO: 38 can be replaced with phenylalanine. In yet other aspects of this embodiment, a β-trefoil domain with enhanced binding activity derived from a FGF-17 comprises a polypeptide having, e.g., at most one, two, three or four non-contiguous amino acid deletions relative to amino acids 92-94 or amino acids 135-137 of SEQ ID NO: 38. In other aspects of this embodiment, a β-trefoil domain with enhanced binding activity derived from a FGF-17 comprises a polypeptide having, e.g., at least one, two, three or four non-contiguous amino acid deletions relative to amino acids 92-94 or amino acids 135-137 of SEQ ID NO: 38. In still other aspects of this embodiment, a β-trefoil domain with enhanced binding activity derived from a FGF-17 comprises a polypeptide having, e.g., at most one, two, three or four non-contiguous amino acid additions relative to amino acids 92-94 or amino acids 135-137 of SEQ ID NO: 38. In other aspects of this embodiment, a β-trefoil domain with enhanced binding activity derived from a FGF-17 comprises a polypeptide having, e.g., at least one, two, three or four non-contiguous amino acid additions relative to amino acids 92-94 or amino acids 135-137 of SEQ ID NO: 38.

In other aspects of this embodiment, a β-trefoil domain with enhanced binding activity derived from a FGF-17 comprises a polypeptide having, e.g., at most one, two, three or four contiguous amino acid substitutions relative to amino acids 92-94 or amino acids 135-137 of SEQ ID NO: 38. In other aspects of this embodiment, a β-trefoil domain with enhanced binding activity derived from a FGF-17 comprises a polypeptide having, e.g., at least one, two, three or four contiguous amino acid substitutions relative to amino acids 92-94 or amino acids 135-137 of SEQ ID NO: 38. In other aspects of this embodiment, contiguous amino acid substitutions of amino acids from amino acids 92-94 or amino acids 135-137 of SEQ ID NO: 38 can be replaced with glycine. In other aspects of this embodiment, contiguous amino acid substitutions of hydrophobic amino acids from amino acids 92-94 or amino acids 135-137 of SEQ ID NO: 38 can be replaced with phenylalanine. In yet other aspects of this embodiment, a β-trefoil domain with enhanced binding activity derived from a FGF-17 comprises a polypeptide having, e.g., at most one, two, three or four contiguous amino acid deletions relative to amino acids 92-94 or amino acids 135-137 of SEQ ID NO: 38. In other aspects of this embodiment, a β-trefoil domain with enhanced binding activity derived from a FGF-17 comprises a polypeptide having, e.g., at least one, two, three or four contiguous amino acid deletions relative to amino acids 92-94 or amino acids 135-137 of SEQ ID NO: 38. In still other aspects of this embodiment, a β-trefoil domain with enhanced binding activity derived from a FGF-17 comprises a polypeptide having, e.g., at most one, two, three or four contiguous amino acid additions relative to amino acids 92-94 or amino acids 135-137 of SEQ ID NO: 38. In other aspects of this embodiment, a β-trefoil domain with enhanced binding activity derived from a FGF-17 comprises a polypeptide having, e.g., at least one, two, three or four contiguous amino acid additions relative to amino acids 92-94 or amino acids 135-137 of SEQ ID NO: 38.

In another embodiment, a β-trefoil domain derived from a FGF-18 comprises a β-trefoil domain derived from a FGF-18 of SEQ ID NO: 39. In another embodiment, a β-trefoil domain derived from a FGF-18 comprises amino acids 54-183 of SEQ ID NO: 39. In another aspect of this embodiment, a β-trefoil domain derived from a FGF-18 comprises a α-fold motif of a β-trefoil domain of a FGF-18, a β-fold motif of a β-trefoil domain of a FGF-18 or a γ-fold motif of a β-trefoil domain of a FGF-18 of SEQ ID NO: 39. In another aspect of this embodiment, a β-trefoil domain derived from a FGF-18 comprises amino acids 54-91, amino acids 95-134, or amino acids 138-183 of SEQ ID NO: 39.

In another embodiment, a β-trefoil domain with enhanced binding activity derived from a FGF-18 comprises a β-trefoil domain with enhanced binding activity derived from a FGF-18 of SEQ ID NO: 39. In another embodiment, a β-trefoil domain with enhanced binding activity derived from a FGF-18 comprises amino acids 54-183 of SEQ ID NO: 39. In another aspect of this embodiment, a β-trefoil domain with enhanced binding activity derived from a FGF-18 comprises a modified α-fold motif of a β-trefoil domain of a FGF-18, a modified β-fold motif of a β-trefoil domain of a FGF-18 or a modified γ-fold motif of a β-trefoil domain of a FGF-18 of SEQ ID NO: 39. In another aspect of this embodiment, a β-trefoil domain with enhanced binding activity derived from a FGF-18 comprises amino acids 54-91, amino acids 95-134, or amino acids 138-183 of SEQ ID NO: 39.

In other aspects of this embodiment, a FGF-18 comprising a β-trefoil domain with enhanced binding activity comprises a polypeptide having, e.g., at least 70% amino acid identity with amino acids 54-91, amino acids 95-134, or amino acids 138-183 of SEQ ID NO: 39, at least 75% amino acid identity with amino acids 54-91, amino acids 95-134, or amino acids 138-183 of SEQ ID NO: 39, at least 80% amino acid identity with amino acids 54-91, amino acids 95-134, or amino acids 138-183 of SEQ ID NO: 39, at least 85% amino acid identity with amino acids 54-91, amino acids 95-134, or amino acids 138-183 of SEQ ID NO: 39, at least 90% amino acid identity with amino acids 54-91, amino acids 95-134, or amino acids 138-183 of SEQ ID NO: 39 or at least 95% amino acid identity with amino acids 54-91, amino acids 95-134, or amino acids 138-183 of SEQ ID NO: 39. In yet other aspects of this embodiment, a FGF-18 comprising a β-trefoil domain with enhanced binding activity comprises a polypeptide having, e.g., at most 70% amino acid identity with amino acids 54-91, amino acids 95-134, or amino acids 138-183 of SEQ ID NO: 39, at most 75% amino acid identity with amino acids 54-91, amino acids 95-134, or amino acids 138-183 of SEQ ID NO: 39, at most 80% amino acid identity with amino acids 54-91, amino acids 95-134, or amino acids 138-183 of SEQ ID NO: 39, at most 85% amino acid identity with amino acids 54-91, amino acids 95-134, or amino acids 138-183 of SEQ ID NO: 39, at most 90% amino acid identity with amino acids 54-91, amino acids 95-134, or amino acids 138-183 of SEQ ID NO: 39 or at most 95% amino acid identity with amino acids 54-91, amino acids 95-134, or amino acids 138-183 of SEQ ID NO: 39.

In other aspects of this embodiment, a FGF-18 comprising a β-trefoil domain with enhanced binding activity comprises a polypeptide having, e.g., at most one, two, three, four, five, six, seven, eight, nine, 10 or 20 non-contiguous amino acid substitutions relative to amino acids 54-91, amino acids 95-134, or amino acids 138-183 of SEQ ID NO: 39. In other aspects of this embodiment, a FGF-18 comprising a β-trefoil domain with enhanced binding activity comprises a polypeptide having, e.g., at least one, two, three, four, five, six, seven, eight, nine, 10 or 20 non-contiguous amino acid substitutions relative to amino acids 54-91, amino acids 95-134, or amino acids 138-183 of SEQ ID NO: 39. In yet other aspects of this embodiment, a FGF-18 comprising a β-trefoil domain with enhanced binding activity comprises a polypeptide having, e.g., at most one, two, three, four, five, six, seven, eight, nine, 10 or 20 non-contiguous amino acid deletions relative to amino acids 54-91, amino acids 95-134, or amino acids 138-183 of SEQ ID NO: 39. In other aspects of this embodiment, a FGF-18 comprising a β-trefoil domain with enhanced binding activity comprises a polypeptide having, e.g., at least one, two, three, four, five, six, seven, eight, nine, 10 or 20 non-contiguous amino acid deletions relative to amino acids 54-91, amino acids 95-134, or amino acids 138-183 of SEQ ID NO: 39. In still other aspects of this embodiment, a FGF-18 comprising a β-trefoil domain with enhanced binding activity comprises a polypeptide having, e.g., at most one, two, three, four, five, six, seven, eight, nine, 10 or 20 non-contiguous amino acid additions relative to amino acids 54-91, amino acids 95-134, or amino acids 138-183 of SEQ ID NO: 39. In other aspects of this embodiment, a FGF-18 comprising a β-trefoil domain with enhanced binding activity comprises a polypeptide having, e.g., at least one, two, three, four, five, six, seven, eight, nine, 10 or 20 non-contiguous amino acid additions relative to amino acids 54-91, amino acids 95-134, or amino acids 138-183 of SEQ ID NO: 39.

In other aspects of this embodiment, a FGF-18 comprising a β-trefoil domain with enhanced binding activity comprises a polypeptide having, e.g., at most one, two, three, four, five, six, seven, eight, nine, 10 or 20 contiguous amino acid substitutions relative to amino acids 54-91, amino acids 95-134, or amino acids 138-183 of SEQ ID NO: 39. In other aspects of this embodiment, a FGF-18 comprising a β-trefoil domain with enhanced binding activity comprises a polypeptide having, e.g., at least one, two, three, four, five, six, seven, eight, nine, 10 or 20 contiguous amino acid substitutions relative to amino acids 54-91, amino acids 95-134, or amino acids 138-183 of SEQ ID NO: 39. In yet other aspects of this embodiment, a FGF-18 comprising a β-trefoil domain with enhanced binding activity comprises a polypeptide having, e.g., at most one, two, three, four, five, six, seven, eight, nine, 10 or 20 contiguous amino acid deletions relative to amino acids 54-91, amino acids 95-134, or amino acids 138-183 of SEQ ID NO: 39. In other aspects of this embodiment, a FGF-18 comprising a β-trefoil domain with enhanced binding activity comprises a polypeptide having, e.g., at least one, two, three, four, five, six, seven, eight, nine, 10 or 20 contiguous amino acid deletions relative to amino acids 54-91, amino acids 95-134, or amino acids 138-183 of SEQ ID NO: 39. In still other aspects of this embodiment, a FGF-18 comprising a β-trefoil domain with enhanced binding activity comprises a polypeptide having, e.g., at most one, two, three, four, five, six, seven, eight, nine, 10 or 20 contiguous amino acid additions relative to amino acids 54-91, amino acids 95-134, or amino acids 138-183 of SEQ ID NO: 39. In other aspects of this embodiment, a FGF-18 comprising a β-trefoil domain with enhanced binding activity comprises a polypeptide having, e.g., at least one, two, three, four, five, six, seven, eight, nine, 10 or 20 contiguous amino acid additions relative to amino acids 54-91, amino acids 95-134, or amino acids 138-183 of SEQ ID NO: 39.

In another embodiment, a β-trefoil domain derived from a FGF-18 comprises a β4/β5 hairpin turn of a β-trefoil domain of a FGF-18 or a β8/β9 hairpin turn of a β-trefoil domain of a FGF-18 of SEQ ID NO: 39. In another aspect of this embodiment, a β-trefoil domain derived from a FGF-18 comprises amino acids 92-94 or amino acids 135-137 of SEQ ID NO: 39.

In another embodiment, a β-trefoil domain with enhanced binding activity derived from a FGF-18 comprises a modified β4/β5 hairpin turn of a β-trefoil domain of a FGF-18 or a modified β8/β9 hairpin turn of a β-trefoil domain of a FGF-18 of SEQ ID NO: 39. In another aspect of this embodiment, a β-trefoil domain with enhanced binding activity derived from a FGF-18 comprises a modification of amino acids 92-94 or amino acids 135-137 of SEQ ID NO: 39.

In other aspects of this embodiment, a β-trefoil domain with enhanced binding activity derived from a FGF-18 comprises a polypeptide having, e.g., at least 70% amino acid identity with amino acids 92-94 or amino acids 135-137 of SEQ ID NO: 39, at least 75% amino acid identity with amino acids 92-94 or amino acids 135-137 of SEQ ID NO: 39, at least 80% amino acid identity with amino acids 92-94 or amino acids 135-137 of SEQ ID NO: 39, at least 85% amino acid identity with amino acids 92-94 or amino acids 135-137 of SEQ ID NO: 39, at least 90% amino acid identity with amino acids 92-94 or amino acids 135-137 of SEQ ID NO: 39 or at least 95% amino acid identity with amino acids 92-94 or amino acids 135-137 of SEQ ID NO: 39. In yet other aspects of this embodiment, a β-trefoil domain with enhanced binding activity derived from a FGF-18 comprises a polypeptide having, e.g., at most 70% amino acid identity with amino acids 92-94 or amino acids 135-137 of SEQ ID NO: 39, at most 75% amino acid identity with amino acids 92-94 or amino acids 135-137 of SEQ ID NO: 39, at most 80% amino acid identity with amino acids 92-94 or amino acids 135-137 of SEQ ID NO: 39, at most 85% amino acid identity with amino acids 92-94 or amino acids 135-137 of SEQ ID NO: 39, at most 90% amino acid identity with amino acids 92-94 or amino acids 135-137 of SEQ ID NO: 39 or at most 95% amino acid identity with amino acids 92-94 or amino acids 135-137 of SEQ ID NO: 39.

In other aspects of this embodiment, a β-trefoil domain with enhanced binding activity derived from a FGF-18 comprises a polypeptide having, e.g., at most one, two, three or four non-contiguous amino acid substitutions relative to amino acids 92-94 or amino acids 135-137 of SEQ ID NO: 39. In other aspects of this embodiment, a β-trefoil domain with enhanced binding activity derived from a FGF-18 comprises a polypeptide having, e.g., at least one, two, three or four non-contiguous amino acid substitutions relative to amino acids 92-94 or amino acids 135-137 of SEQ ID NO: 39. In other aspects of this embodiment, a non-contiguous amino acid substitution of any amino acid from amino acids 92-94 or amino acids 135-137 of SEQ ID NO: 39 can be replaced with glycine. In other aspects of this embodiment, a non-contiguous amino acid substitution of any hydrophobic amino acid from amino acids 92-94 or amino acids 135-137 of SEQ ID NO: 39 can be replaced with phenylalanine. In yet other aspects of this embodiment, a β-trefoil domain with enhanced binding activity derived from a FGF-18 comprises a polypeptide having, e.g., at most one, two, three or four non-contiguous amino acid deletions relative to amino acids 92-94 or amino acids 135-137 of SEQ ID NO: 39. In other aspects of this embodiment, a β-trefoil domain with enhanced binding activity derived from a FGF-18 comprises a polypeptide having, e.g., at least one, two, three or four non-contiguous amino acid deletions relative to amino acids 92-94 or amino acids 135-137 of SEQ ID NO: 39. In still other aspects of this embodiment, a β-trefoil domain with enhanced binding activity derived from a FGF-18 comprises a polypeptide having, e.g., at most one, two, three or four non-contiguous amino acid additions relative to amino acids 92-94 or amino acids 135-137 of SEQ ID NO: 39. In other aspects of this embodiment, a β-trefoil domain with enhanced binding activity derived from a FGF-18 comprises a polypeptide having, e.g., at least one, two, three or four non-contiguous amino acid additions relative to amino acids 92-94 or amino acids 135-137 of SEQ ID NO: 39.

In other aspects of this embodiment, a β-trefoil domain with enhanced binding activity derived from a FGF-18 comprises a polypeptide having, e.g., at most one, two, three or four contiguous amino acid substitutions relative to amino acids 92-94 or amino acids 135-137 of SEQ ID NO: 39. In other aspects of this embodiment, a β-trefoil domain with enhanced binding activity derived from a FGF-18 comprises a polypeptide having, e.g., at least one, two, three or four contiguous amino acid substitutions relative to amino acids 92-94 or amino acids 135-137 of SEQ ID NO: 39. In other aspects of this embodiment, contiguous amino acid substitutions of amino acids from amino acids 92-94 or amino acids 135-137 of SEQ ID NO: 39 can be replaced with glycine. In other aspects of this embodiment, contiguous amino acid substitutions of hydrophobic amino acids from amino acids 92-94 or amino acids 135-137 of SEQ ID NO: 39 can be replaced with phenylalanine. In yet other aspects of this embodiment, a β-trefoil domain with enhanced binding activity derived from a FGF-18 comprises a polypeptide having, e.g., at most one, two, three or four contiguous amino acid deletions relative to amino acids 92-94 or amino acids 135-137 of SEQ ID NO: 39. In other aspects of this embodiment, a β-trefoil domain with enhanced binding activity derived from a FGF-18 comprises a polypeptide having, e.g., at least one, two, three or four contiguous amino acid deletions relative to amino acids 92-94 or amino acids 135-137 of SEQ ID NO: 39. In still other aspects of this embodiment, a β-trefoil domain with enhanced binding activity derived from a FGF-18 comprises a polypeptide having, e.g., at most one, two, three or four contiguous amino acid additions relative to amino acids 92-94 or amino acids 135-137 of SEQ ID NO: 39. In other aspects of this embodiment, a β-trefoil domain with enhanced binding activity derived from a FGF-18 comprises a polypeptide having, e.g., at least one, two, three or four contiguous amino acid additions relative to amino acids 92-94 or amino acids 135-137 of SEQ ID NO: 39.

Because of the modular nature of the β-trefoil domain, it is envisioned that any combination of α-folds, β-folds, γ-folds, β4/β5 β-hairpin turns, β8/β9 β-hairpin turns, or any combination thereof from a β-trefoil domain of a Clostridial toxin binding domain, a β-trefoil domain of a modified Clostridial toxin binding domain, a β-trefoil domain of a NAP or a β-trefoil domain, a β-trefoil domain of a modified NAP, a β-trefoil domain of an FGF ligand, a β-trefoil domain of a modified FGF ligand, or any combination thereof, can be used to practice aspect of the present invention. As a non-limiting example, a modified Clostridial toxin disclosed in the present specification can comprise an enhanced targeting domain comprising a α-fold from a BoNT/A binding domain, a β-fold from a FGF-18 and a 2γ-fold from a Clostridial botulinum serotype A HA-33. As another non-limiting example, a modified Clostridial toxin disclosed in the present specification can comprise an enhanced targeting domain comprising a α-fold from a Clostridial botulinum serotype A HA-17, a β-fold from a Clostridial botulinum serotype E NTNH and a γ-fold from a modified BoNT/C1 binding domain with enhanced binding activity.

In another aspect of the invention, a modified Clostridial toxin with enhanced binding activity comprises, in part, a protease cleavage site is located within a di-chain loop region. As used herein, the term "di-chain loop region" means the amino acid sequence of a Clostridial toxin containing a protease cleavage site used to convert the single-chain form of a Clostridial toxin into the di-chain form. Non-limiting examples of a Clostridial toxin di-chain loop region, include, a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; and a di-chain loop region of TeNT comprising amino acids 439-467 of SEQ ID NO: 8 (Table 8).

TABLE 8

Di-chain Loop Region of Clostridial Toxins

| Toxin | SEQ ID NO: | Light Chain Region | Di-chain Loop Region Containing the Naturally-occurring Protease Cleavage Site | Heavy Chain Region |
|---|---|---|---|---|
| BoNT/A | 1 | NMNFTKLKNFTGLFEFYKLL | CVRGIITSKTKSLDKGYNK*----ALNDLC | IKVNNWDL |
| BoNT/B | 2 | KQAYEEISKEHLAVYKIQM | CKSVK*-------------------APGIC | IDVDNEDL |
| BoNT/C1 | 3 | PALRKVNPENMLYLFTKF | CHKAIDGRSLYNK*------------TLDC | RELLVKNTDL |
| BoNT/D | 4 | PALQKLSSESVVDLFTKV | CLRLTKNSR*---------------DDSTC | IKVKNNRL |
| BoNT/E | 5 | IITPITGRGLVKKIIRF | CKNIVSVKGIR*--------------KSIC | IEINNGEL |
| BoNT/F | 6 | IIDSIPDKGLVEKIVKF | CKSVIPRKGTK*------------APPRLC | IRVNNSEL |
| BoNT/G | 7 | KEAYEEISLEHLVIYRIAM | CKPVMYKNTGK*--------------SEQC | IIVNNEDL |
| TeNT | 8 | TNAFRNVDGSGLVSKLIGL | CKKIIPPTNIRENLYNRTA*SLTDLGGELC | IKIKNEDL |

The amino acid sequence displayed are as follows: BoNT/A, residues 325-462 of SEQ ID No: 1; BoNT/B, residues 332-454 of SEQ ID No: 2; BoNT/C1, residues 334-463 of SEQ ID No: 3; BoNT/D, residues 334-458 of SEQ ID No: 4; BoNT/E, residues 311-434 of SEQ ID No: 5; BoNT/F, residues 328-453 of SEQ ID No: 6; BoNT/G, residues 331-458 of SEQ ID No: 7; and TeNT, residues 334-474 of SEQ ID No: 8. An asterisks (*) indicates the peptide bond that is cleaved by a Clostridial toxin protease.

In is envisioned that any and all protease cleavage sites can be used to convert the single-chain polypeptide form of a Clostridial toxin into the di-chain form, including, without limitation, endogenous di-chain loop protease cleavage sites and exogenous protease cleavage sites.

As used herein, the term "endogenous di-chain loop protease cleavage site" is synonymous with a "naturally occurring di-chain loop protease cleavage site" and means a naturally occurring protease cleavage site found within the di-chain loop region of a naturally occurring Clostridial toxin and includes, without limitation, naturally occurring Clostridial toxin di-chain loop protease cleavage site variants, such as, e.g., Clostridial toxin di-chain loop protease cleavage site isoforms and Clostridial toxin di-chain loop protease cleavage site subtypes. Non-limiting examples of an endogenous protease cleavage site, include, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

As mentioned above, Clostridial toxins are translated as a single-chain polypeptide of approximately 150 kDa that is subsequently cleaved by proteolytic scission within a disulfide loop by a naturally-occurring protease. This posttranslational processing yields a di-chain molecule comprising an approximately 50 kDa light chain (LC) and an approximately 100 kDa heavy chain (HC) held together by a single disulphide bond and noncovalent interactions. While the identity of the protease is currently unknown, the di-chain loop protease cleavage site for many Clostridial toxins has been determined. In BoNTs, cleavage at K448-A449 converts the single polypeptide form of BoNT/A into the di-chain form; cleavage at K441-A442 converts the single polypeptide form of BoNT/B into the di-chain form; cleavage at K449-T450 converts the single polypeptide form of BoNT/C1 into the di-chain form; cleavage at R445-D446 converts the single polypeptide form of BoNT/D into the di-chain form; cleavage at R422-K423 converts the single polypeptide form of BoNT/E into the di-chain form; cleavage at K439-A440 converts the single polypeptide form of BoNT/F into the di-chain form; and cleavage at K446-5447 converts the single polypeptide form of BoNT/G into the di-chain form. Proteolytic cleavage of the single polypeptide form of TeNT at A457-5458 results in the di-chain form. Such a di-chain loop protease cleavage site is operably-linked in-frame to a modified Clostridial toxin as a fusion protein. However, it should also be noted that additional cleavage sites within the di-chain loop also appear to be cleaved resulting in the generation of a small peptide fragment being lost. As a non-limiting example, BoNT/A single-chain polypeptide cleave ultimately results in the loss of a ten amino acid fragment within the di-chain loop.

Thus, in an embodiment, a protease cleavage site comprising an endogenous Clostridial toxin di-chain loop protease cleavage site is used to convert the single-chain toxin into the di-chain form. In aspects of this embodiment, conversion into the di-chain form by proteolytic cleavage occurs from a site comprising, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site or a TeNT di-chain loop protease cleavage site.

In other aspects of this embodiment, conversion into the di-chain form by proteolytic cleavage occurs from a site comprising, e.g., a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; or a di-chain loop region of TeNT comprising amino acids 439-467 of SEQ ID NO: 8.

It is also envisioned that an exogenous protease cleavage site can be used to convert the single-chain polypeptide form of a modified Clostridial toxin disclosed in the present specification into the di-chain form. As used herein, the term "exogenous protease cleavage site" is synonymous with a "non-naturally occurring protease cleavage site" and means a protease cleavage site that is not normally present in a di-chain loop region from a naturally occurring Clostridial toxin. Non-limiting examples of exogenous protease cleavage sites include, e.g., an enterokinase cleavage site (Table 9); a Thrombin cleavage site (Table 9); a Factor Xa cleavage site (Table 9); a human rhinovirus 3C protease cleavage site (Table 9); a tobacco etch virus (TEV) protease cleavage site (Table 9); a dipeptidyl aminopeptidase cleavage site; a small ubiquitin-like modifier (SUMO)/ubiquitin-like protein-1 (ULP-1) protease cleavage site, such as, e.g., MADSEVNQEAKPEVKPEVKPETHINLKVSDGSSEIFFKIKKTTPLRRLMEAFAKRQGK EMDSLRFLYDGIRIQADQTPEDLDMEDNDIIEAHREQIGG (SEQ ID. NO: 57); and a Clostridial toxin substrate cleavage site.

Similarly, an addition of an exogenous protease cleavage site in the di-chain loop region will also enable cleavage of a modified Clostridial toxin disclosed in the present specification when expressed in an organism that does not produce the naturally-occurring protease used to cleave the di-chain loop region of a toxin.

It is envisioned that an exogenous protease cleavage site of any and all lengths can be useful in aspects of the present invention with the proviso that the exogenous protease cleavage site is capable of being cleaved by its respective protease. Thus, in aspects of this embodiment, an exogenous protease cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, an exogenous protease cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at

TABLE 9

Exogenous Protease Cleavage Sites

| Protease Cleavage Site | Consensus Sequence | Non-limiting Examples | SED ID NO: |
|---|---|---|---|
| Bovine enterokinase | DDDDK* | DDDDK* | 40 |
| Tobacco Etch Virus (TEV) | E $P^5$ $P^4YP^2Q$*(G/S), where $P^2$, $P^4$ and $P^5$ can be any amino acid | ENLYFQ*G | 41 |
| | | ENLYFQ*S | 42 |
| | | ENIYTQ*G | 43 |
| | | ENIYTQ*S | 44 |
| | | ENIYLQ*G | 45 |
| | | ENIYLQ*S | 46 |
| | | ENVYFQ*G | 47 |
| | | ENVYSQ*S | 48 |
| | | ENVYSQ*G | 49 |
| | | ENVYSQ*S | 50 |
| Human Rhinovirus 3C | $P^5P^4$LFQ*GP where $P^4$ is G, A, V, L, I, M, S or T and $P^5$ can any amino acid, with D or E preferred. | EALFQ*GP | 51 |
| | | EVLFQ*GP | 52 |
| | | ELLFQ*GP | 53 |
| | | DALFQ*GP | 54 |
| | | DVLFQ*GP | 55 |
| | | DLLFQ*GP | 56 |
| SUMO/ULP-1 | Tertiary structure | polypeptide-G* | 57 |
| Thrombin | $P^3P^2$(R/K)*$P^{1'}$, where $P^3$ is any amino acid and $P^2$ or $P^{1'}$ is G with the other position being any amino acid | GVR*G | 58 |
| | | SAR*G | 59 |
| | | SLR*G | 60 |
| | | DGR*I | 61 |
| | | QGK*I | 62 |
| Thrombin | $P^4P^3$P(R/K)*$P^{1'}P^{2'}$ where $P^{1'}$ and $P^{2'}$ can be any amino acid except for acidic amino acids like D or E; and $P^3$ and $P^4$ are hydrophobic amino acids like F, L, I, Y, W, V, M, P, C or A | LVPR*GS | 63 |
| | | LVPK*GS | 64 |
| | | FIPR*TF | 65 |
| | | VLPR*SF | 66 |
| | | IVPR*SF | 67 |
| | | IVPR*GY | 68 |
| | | VVPR*GV | 69 |
| | | VLPR*LI | 70 |
| | | VMPR*SL | 71 |
| | | MFPR*SL | 72 |
| Coagulation Factor Xa | I(E/D)GR* | IDGR* | 73 |
| | | IEGR* | 74 |

An asterisks (*) indicates the peptide bond that is cleaved by the indicated protease.

As mentioned above, a Clostridial toxin is converted from a single polypeptide form into a di-chain molecule by proteolytic cleavage. While the naturally-occurring protease is currently not known, cleavage occurs within the di-chain loop region between the two cysteine residues that form the disulfide bridge (see Table 8). Replacement of an endogenous protease cleavage site with an exogenous protease cleavage site will enable cleavage of a modified Clostridial toxin disclosed in the present specification when expressed in an organism that does not produce the naturally-occurring protease used to cleave the di-chain loop region of a toxin.

most 30 amino acids in length, at most 40 amino acids in length, at most 50 amino acids in length or at most 60 amino acids in length.

In aspects of this embodiment, a di-chain loop region can be modified to substitute a naturally-occurring protease cleavage site for an exogenous protease cleavage site. In this type of modification, the naturally-occurring protease cleavage site is made inoperable and thus can not be cleaved by its protease. Only the exogenous protease cleavage site can be cleaved by its corresponding exogenous protease. In this type of modification, the exogenous protease site is operably-linked in-frame to a modified Clostridial toxin as a fusion protein and the site can be cleaved by its respective exogenous protease. As a non-limiting example, a single-chain modified BoNT/A comprising an exogenous protease cleavage site in the di-chain loop region can be cleaved by its respective exogenous protease to produce the di-chain form of the toxin.

In other aspects of this embodiment, a di-chain loop region can be modified to include an exogenous protease cleavage site in addition to the naturally-occurring protease cleavage site. In this type of modification, both cleavage sites are operably-linked in-frame to a modified Clostridial toxin as a fusion protein and both sites can be cleaved by their respective proteases. As a non-limiting example, a single-chain modified BoNT/A that comprises a di-chain loop containing both the naturally-occurring BoNT/A di-chain loop protease cleavage site and an exogenous protease cleavage site can be cleaved by either the naturally occurring di-chain loop protease or by the appropriate exogenous protease to produce the di-chain form of the toxin.

A naturally-occurring protease cleavage site can be made inoperable by altering at least the two amino acids flanking the peptide bond cleaved by the naturally-occurring di-chain loop protease. More extensive alterations can be made, with the proviso that the two cysteine residues of the di-chain loop region remain intact and can still form the disulfide bridge. Non-limiting examples of an amino acid alteration include deletion of an amino acid or replacement of the original amino acid with a different amino acid. Thus, in one embodiment, a naturally-occurring protease cleavage site is made inoperable by altering the two amino acids flanking the peptide bond cleaved by a naturally-occurring protease. In other aspects of this embodiment, a naturally-occurring protease cleavage site is made inoperable by altering, e.g., at least three amino acids including the two amino acids flanking the peptide bond cleaved by a naturally-occurring protease; at least four amino acids including the two amino acids flanking the peptide bond cleaved by a naturally-occurring protease; at least five amino acids including the two amino acids flanking the peptide bond cleaved by a naturally-occurring protease; at least six amino acids including the two amino acids flanking the peptide bond cleaved by a naturally-occurring protease; at least seven amino acids including the two amino acids flanking the peptide bond cleaved by a naturally-occurring protease; at least eight amino acids including the two amino acids flanking the peptide bond cleaved by a naturally-occurring protease; at least nine amino acids including the two amino acids flanking the peptide bond cleaved by a naturally-occurring protease; at least ten amino acids including the two amino acids flanking the peptide bond cleaved by a naturally-occurring protease; at least 15 amino acids including the two amino acids flanking the peptide bond cleaved by a naturally-occurring protease; or at least 20 amino acids including the two amino acids flanking the peptide bond cleaved by a naturally-occurring protease.

In still other aspects of this embodiment, a naturally-occurring di-chain protease cleavage site is made inoperable by altering, e.g., at most three amino acids including the two amino acids flanking the peptide bond cleaved by a naturally-occurring protease; at most four amino acids including the two amino acids flanking the peptide bond cleaved by a naturally-occurring protease; at most five amino acids including the two amino acids flanking the peptide bond cleaved by a naturally-occurring protease; at most six amino acids including the two amino acids flanking the peptide bond cleaved by a naturally-occurring protease; at most seven amino acids including the two amino acids flanking the peptide bond cleaved by a naturally-occurring protease; at most eight amino acids including the two amino acids flanking the peptide bond cleaved by a naturally-occurring protease; at most nine amino acids including the two amino acids flanking the peptide bond cleaved by a naturally-occurring protease; at most ten amino acids including the two amino acids flanking the peptide bond cleaved by a naturally-occurring protease; at most 15 amino acids including the two amino acids flanking the peptide bond cleaved by a naturally-occurring protease; or at most 20 amino acids including the two amino acids flanking the peptide bond cleaved by a naturally-occurring protease.

In an embodiment, an exogenous protease cleavage site is located within the di-chain loop of a modified Clostridial toxin. In aspects of this embodiment, a modified Clostridial toxin comprises an exogenous protease cleavage site comprises, e.g., a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site or a Factor Xa protease cleavage site. In other aspects of this embodiment, an exogenous protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In an aspect of this embodiment, an exogenous protease cleavage site can be, e.g., a bovine enterokinase cleavage site is located within the di-chain loop of a modified Clostridial toxin. In other aspects of the embodiment, an exogenous protease cleavage site can be, e.g., a bovine enterokinase protease cleavage site located within the di-chain loop of a modified Clostridial toxin comprises SEQ ID NO: 40. Is still other aspects of this embodiment, a bovine enterokinase protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In another aspect of this embodiment, an exogenous protease cleavage site can be, e.g., a Tobacco Etch Virus protease cleavage site is located within the di-chain loop of a modified Clostridial toxin. In other aspects of the embodiment, an exogenous protease cleavage site can be, e.g., a Tobacco Etch Virus protease cleavage site located within the di-chain loop of a modified Clostridial toxin comprises SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49 or SEQ ID NO: 50. Is still other aspects of this embodiment, a Tobacco Etch Virus protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In still another aspect of this embodiment, an exogenous protease cleavage site can be, e.g., a Human Rhinovirus 3C protease cleavage site is located within the di-chain loop of a modified Clostridial toxin. In other aspects of the embodiment, an exogenous protease cleavage site can be, e.g., a Human Rhinovirus 3C protease cleavage site located within the di-chain loop of a modified Clostridial toxin comprises SEQ ID NO: 51, SEQ ID NO: 52, SEQ ID NO: 53, SEQ ID NO: 54, SEQ ID NO: 55 or SEQ ID NO: 56. Is still other aspects of this embodiment, a Human Rhinovirus 3C protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In yet another aspect of this embodiment, an exogenous protease cleavage site can be, e.g., a SUMO/ULP-1 protease cleavage site is located within the di-chain loop of a modified Clostridial toxin. In other aspects of the embodiment, an exogenous protease cleavage site can be, e.g., a SUMO/ULP-1 protease cleavage site located within the di-chain loop of a modified Clostridial toxin comprises SEQ ID NO: 57. Is still other aspects of this embodiment, a SUMO/ULP-1 protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In a further aspect of this embodiment, an exogenous protease cleavage site can be, e.g., a Thrombin protease cleavage site is located within the di-chain loop of a modified Clostridial toxin. In other aspects of the embodiment, an exogenous protease cleavage site can be, e.g., a Thrombin protease cleavage site located within the di-chain loop of a modified Clostridial toxin comprises SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71 or SEQ ID NO: 72. Is still other aspects of this embodiment, a Thrombin protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In another aspect of this embodiment, an exogenous protease cleavage site can be, e.g., a Coagulation Factor Xa protease cleavage site is located within the di-chain loop of a modified Clostridial toxin. In other aspects of the embodiment, an exogenous protease cleavage site can be, e.g., a Coagulation Factor Xa protease cleavage site located within the di-chain loop of a modified Clostridial toxin comprises SEQ ID NO: 73 or SEQ ID NO: 74. Is still other aspects of this embodiment, a Coagulation Factor Xa protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G or a modified TeNT.

In another embodiment, an exogenous protease site comprises a Clostridial toxin substrate cleavage site. As used herein, the term "Clostridial toxin substrate cleavage site" means a scissile bond together with adjacent or non-adjacent recognition elements, or both, sufficient for detectable proteolysis at the scissile bond by a Clostridial toxin under conditions suitable for Clostridial toxin protease activity. By definition, a Clostridial toxin substrate cleavage site is susceptible to cleavage by at least one Clostridial toxin under conditions suitable for Clostridial toxin protease activity. Non-limiting examples of Clostridial toxin substrate cleavage site are disclosed in, e.g., Steward, L. E. et al., Self-Activating Clostridial Toxins, U.S. Patent Application 60/718,616 (Sep. 19, 2005).

It is understood that a modified Clostridial toxin disclosed in the present specification can optionally include one or more additional components. As a non-limiting example of an optional component, a modified Clostridial toxin can further comprise a flexible region comprising a flexible spacer. Non-limiting examples of a flexible spacer include, e.g., a G-spacer GGGGS (SEQ ID NO: 75) or an A-spacer EAAAK (SEQ ID NO: 76). A flexible region comprising flexible spacers can be used to adjust the length of a polypeptide region in order to optimize a characteristic, attribute or property of a polypeptide. Such a flexible region is operably-linked in-frame to the modified Clostridial toxin as a fusion protein. As a non-limiting example, a polypeptide region comprising one or more flexible spacers in tandem can be use to better expose a protease cleavage site thereby facilitating cleavage of that site by a protease. As another non-limiting example, a polypeptide region comprising one or more flexible spacers in tandem can be use to better present an enhanced targeting domain, thereby facilitating the binding of that enhanced targeting domain to its receptor system.

Thus, in an embodiment, a modified Clostridial toxin disclosed in the present specification can further comprise a flexible region comprising a flexible spacer. In another embodiment, a modified Clostridial toxin disclosed in the present specification can further comprise flexible region comprising a plurality of flexible spacers in tandem. In aspects of this embodiment, a flexible region can comprise in tandem, e.g., at least 1 G-spacer, at least 2 G-spacers, at least 3 G-spacers, at least 4 G-spacers or at least 5 G-spacers. In other aspects of this embodiment, a flexible region can comprise in tandem, e.g., at most 1 G-spacer, at most 2 G-spacers, at most 3 G-spacers, at most 4 G-spacers or at most 5 G-spacers. In still other aspects of this embodiment, a flexible region can comprise in tandem, e.g., at least 1 A-spacer, at least 2 A-spacers, at least 3 A-spacers, at least 4 A-spacers or at least 5 A-spacers. In still other aspects of this embodiment, a flexible region can comprise in tandem, e.g., at most 1 A-spacer, at most 2 A-spacers, at most 3 A-spacers, at most 4 A-spacers or at most 5 A-spacers. In another aspect of this embodiment, a modified Clostridial toxin can comprise a flexible region comprising one or more copies of the same flexible spacers, one or more copies of different flexible-spacer regions, or any combination thereof.

In aspects of this embodiment, a modified Clostridial toxin comprising a flexible spacer can be, e.g., a modified BoNT/A, a modified BoNT/B, a modified BoNT/C1, a modified BoNT/D, a modified BoNT/E, a modified BoNT/F, a modified BoNT/G or a modified TeNT.

It is envisioned that a modified Clostridial toxin disclosed in the present specification can comprise a flexible spacer in any and all locations with the proviso that modified Clostridial toxin is capable of performing the intoxication process. In aspects of this embodiment, a flexible spacer is positioned between, e.g., an enzymatic domain and a translocation domain, an enzymatic domain and an enhanced targeting domain, an enzymatic domain and a protease cleavage site. In other aspects of this embodiment, a G-spacer is positioned between, e.g., an enzymatic domain and a translocation domain, an enzymatic domain and an enhanced targeting domain, an enzymatic domain and a protease cleavage site. In other aspects of this embodiment, a A-spacer is positioned between, e.g., an enzymatic domain and a translocation domain, an enzymatic domain and an enhanced targeting domain, an enzymatic domain and a protease cleavage site.

In other aspects of this embodiment, a flexible spacer is positioned between, e.g., an enhanced targeting domain and a translocation domain, an enhanced targeting domain and an enzymatic domain, an enhanced targeting domain and a protease cleavage site. In other aspects of this embodiment, a G-spacer is positioned between, e.g., an enhanced targeting domain and a translocation domain, an enhanced targeting domain and an enzymatic domain, an enhanced targeting domain and a protease cleavage site. In other aspects of this embodiment, a A-spacer is positioned between, e.g., an enhanced targeting domain and a translocation domain, an enhanced targeting domain and an enzymatic domain, an enhanced targeting domain and a protease cleavage site.

In yet other aspects of this embodiment, a flexible spacer is positioned between, e.g., a translocation domain and an enzymatic domain, an translocation domain and an enhanced targeting domain, an translocation domain and a protease cleavage site. In other aspects of this embodiment, a G-spacer is positioned between, e.g., a translocation domain and an enzymatic domain, an translocation domain and an enhanced targeting domain, an translocation domain and a protease cleavage site. In other aspects of this embodiment, a A-spacer is positioned between, e.g., a translocation domain and an enzymatic domain, an translocation domain and an enhanced targeting domain, a translocation domain and a protease cleavage site.

As another non-limiting example of an optional component, a modified Clostridial toxin can further comprise an epitope-binding region. An epitope-binding region can be used in a wide variety of procedures involving, e.g., protein purification and protein visualization. Such an epitope-binding region is operably-linked in-frame to a modified Clostridial toxin as a fusion protein. Non-limiting examples of an epitope-binding region include, e.g., FLAG, Express™ (SEQ ID NO: 77), human Influenza virus hemagluttinin (HA) (SEQ ID NO: 78), human p62$^{c\text{-}Myc}$ protein (c-MYC) (SEQ ID NO: 79), Vesicular Stomatitis Virus Glycoprotein (VSV-G) (SEQ ID NO: 80), Substance P (SEQ ID NO: 81), glycoprotein-D precursor of Herpes simplex virus (HSV) (SEQ ID NO: 82), V5 (SEQ ID NO: 83), AU1 (SEQ ID NO: 84) and AU5 (SEQ ID NO: 85); affinity-binding, such as. e.g., polyhistidine (HIS) (SEQ ID NO: 86), streptavidin binding peptide (strep), and biotin or a biotinylation sequence; peptide-binding regions, such as. e.g., the glutathione binding domain of glutathione-S-transferase, the calmodulin binding domain of the calmodulin binding protein, and the maltose binding domain of the maltose binding protein. Non-limiting examples of specific protocols for selecting, making and using an appropriate binding peptide are described in, e.g., Epitope Tagging, pp. 17.90-17.93 (Sambrook and Russell, eds., Molecular Cloning A Laboratory Manual, Vol. 3, 3$^{rd}$ ed. 2001); Antibodies: A Laboratory Manual (Edward Harlow & David Lane, eds., Cold Spring Harbor Laboratory Press, 2$^{nd}$ ed. 1998); and Using Antibodies: A Laboratory Manual: Portable Protocol No. I (Edward Harlow & David Lane, Cold Spring Harbor Laboratory Press, 1998). In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Thus, in an embodiment, a modified Clostridial toxin disclosed in the present specification can further comprise an epitope-binding region. In another embodiment, a modified Clostridial toxin disclosed in the present specification can further comprises a plurality of epitope-binding regions. In aspects of this embodiment, a modified Clostridial toxin can comprise, e.g., at least 1 epitope-binding region, at least 2 epitope-binding regions, at least 3 epitope-binding regions, at least 4 epitope-binding regions or at least 5 epitope-binding regions. In other aspects of this embodiment, a modified Clostridial toxin can comprise, e.g., at most 1 epitope-binding region, at most 2 epitope-binding regions, at most 3 epitope-binding regions, at most 4 epitope-binding regions or at most 5 epitope-binding regions. In another aspect of this embodiment, a modified Clostridial toxin can comprise one or more copies of the same epitope-binding region, one or more copies of different epitope-binding regions, or any combination thereof.

The location of an epitope-binding region can be in various positions, including, without limitation, at the amino terminus of a modified Clostridial toxin, within a modified Clostridial toxin, or at the carboxyl terminus of a modified Clostridial toxin. Thus, in an embodiment, an epitope-binding region is located at the amino-terminus of a modified Clostridial toxin. In such a location, a start methionine should be placed in front of the epitope-binding region. In addition, it is known in the art that when adding a polypeptide that is operationally-linked to the amino terminus of another polypeptide comprising the start methionine that the original methionine residue can be deleted. This is due to the fact that the added polypeptide will contain a new start methionine and that the original start methionine may reduce optimal expression of the fusion protein. In aspects of this embodiment, an epitope-binding region located at the amino-terminus of a modified Clostridial toxin disclosed in the present specification can be, e.g., a FLAG, Express™ epitope-binding region, a human Influenza virus hemagluttinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

In another embodiment, an epitope-binding region is located at the carboxyl-terminus of a modified Clostridial toxin. In aspects of this embodiment, an epitope-binding region located at the carboxyl-terminus of a modified Clostridial toxin disclosed in the present specification can be, e.g., a FLAG, Express™ epitope-binding region, a human Influenza virus hemagluttinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

Figure 3A:
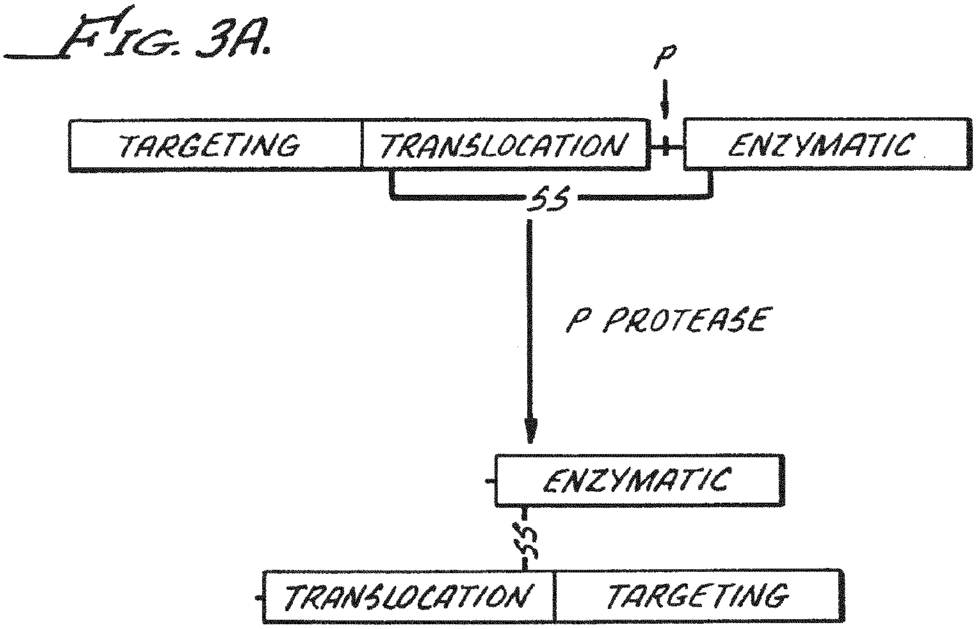
FIG. 3A depicts the single polypeptide form of a modified Clostridial toxin with an amino to carboxyl linear organization comprising an enhanced targeting domain, an enzymatic domain and a translocation domain, with the di-chain loop region depicted by the double SS bracket. A proteolytic cleavage site (P) within a di-chain loop region is located between the translocation and enzymatic domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the targeting and translocation domains, the translocation and enzymatic domains or any combination thereof.
Figure 3B:
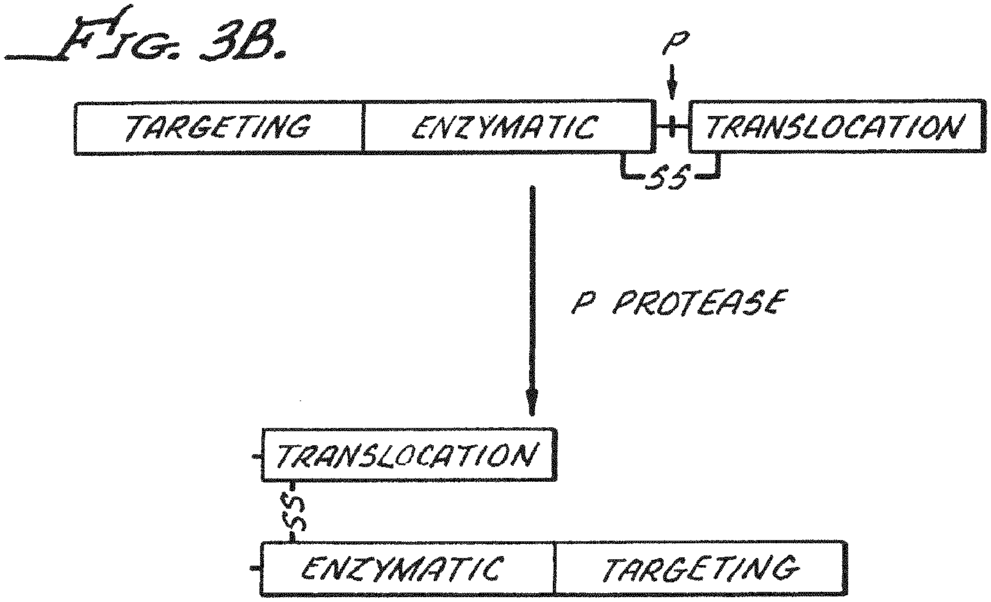
FIG. 3B depicts the single polypeptide form of a modified Clostridial toxin with an amino to carboxyl linear organization comprising an enhanced targeting domain, an enzymatic domain and a translocation domain, with the di-chain loop region depicted by the double SS bracket. A proteolytic cleavage site (P) within a di-chain loop region is located between the enzymatic and translocation domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the targeting and enzymatic domains, the enzymatic and translocation domains or any combination thereof.
Figure 4A:
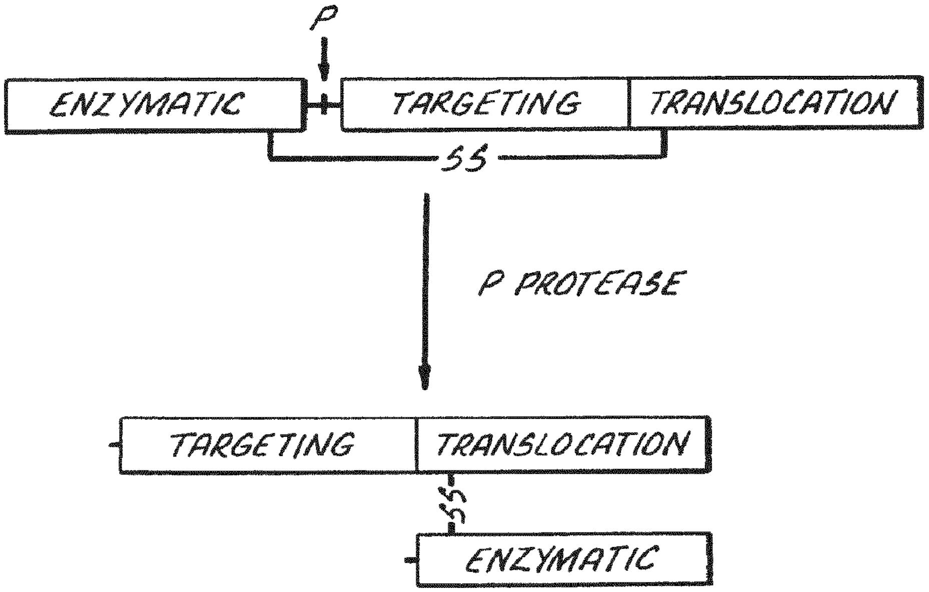
FIG. 4A depicts the single polypeptide form of a modified Clostridial toxin with an amino to carboxyl linear organization comprising an enzymatic domain, an enhanced targeting domain and a translocation domain, with the di-chain loop region depicted by the double SS bracket. A proteolytic cleavage site (P) within a di-chain loop region is located between the enzymatic and targeting domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the enzymatic and targeting domains, the targeting and translocation domains or any combination thereof.
Figure 4B:
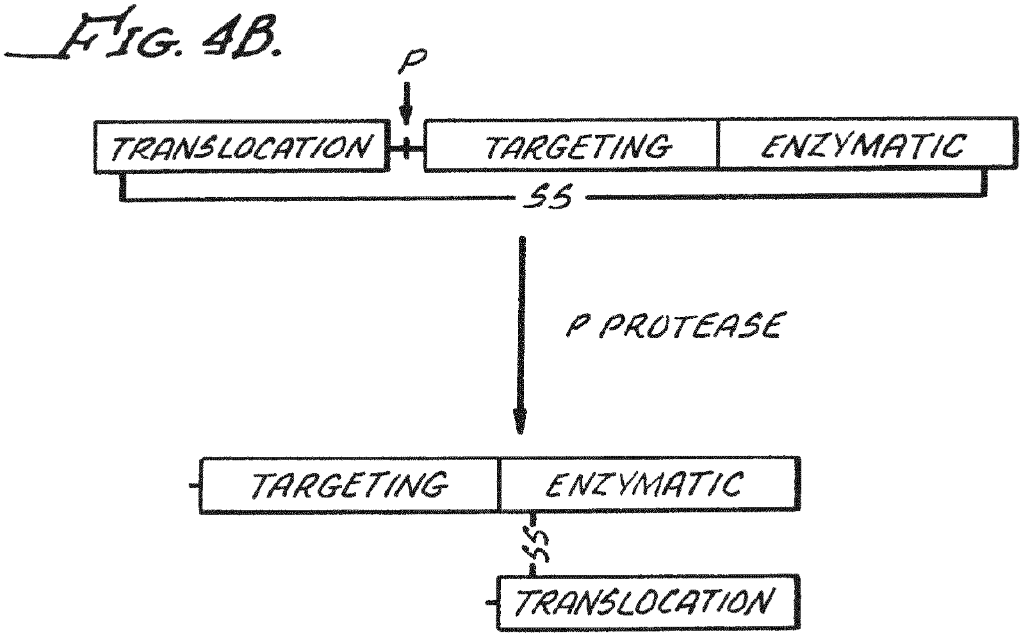
FIG. 4B depicts the single polypeptide form of a modified Clostridial toxin with an amino to carboxyl linear organization comprising a translocation domain, an enhanced targeting domain and an enzymatic domain, with the di-chain loop region depicted by the double SS bracket. A proteolytic cleavage site (P) within a di-chain loop region is located between the translocation and targeting domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the translocation and targeting domains, the targeting and enzymatic domains or any combination thereof.
Figure 5A:
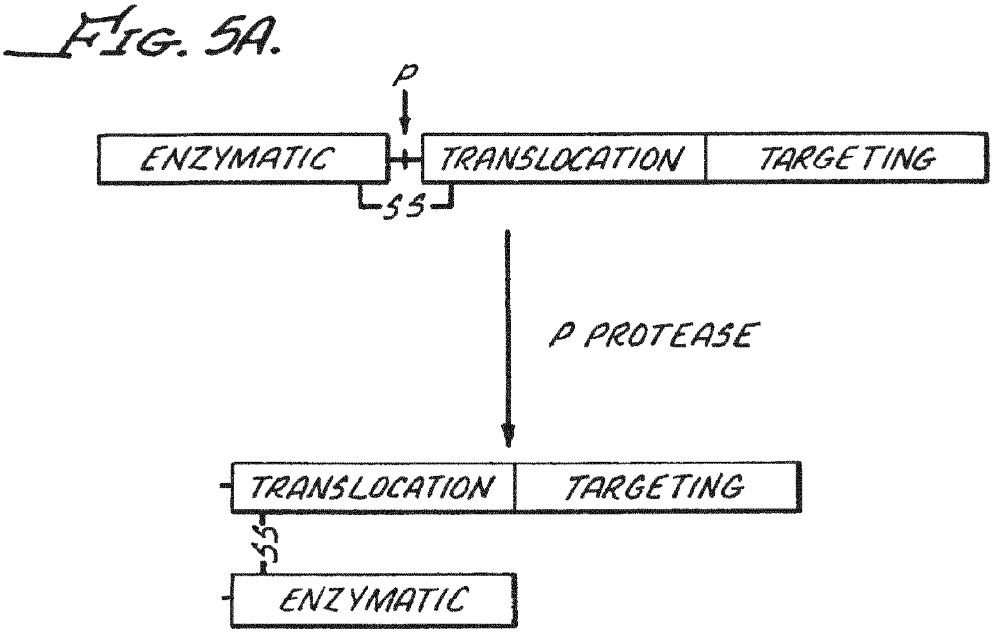
FIG. 5A depicts the single polypeptide form of a modified Clostridial toxin with an amino to carboxyl linear organization comprising an enzymatic domain, a translocation domain and an enhanced targeting domain, with the di-chain loop region depicted by the double SS bracket. A proteolytic cleavage site (P) within a di-chain loop region is located between the enzymatic and translocation domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the enzymatic and translocation domains, the translocation and targeting domains or any combination thereof.
Figure 5B:
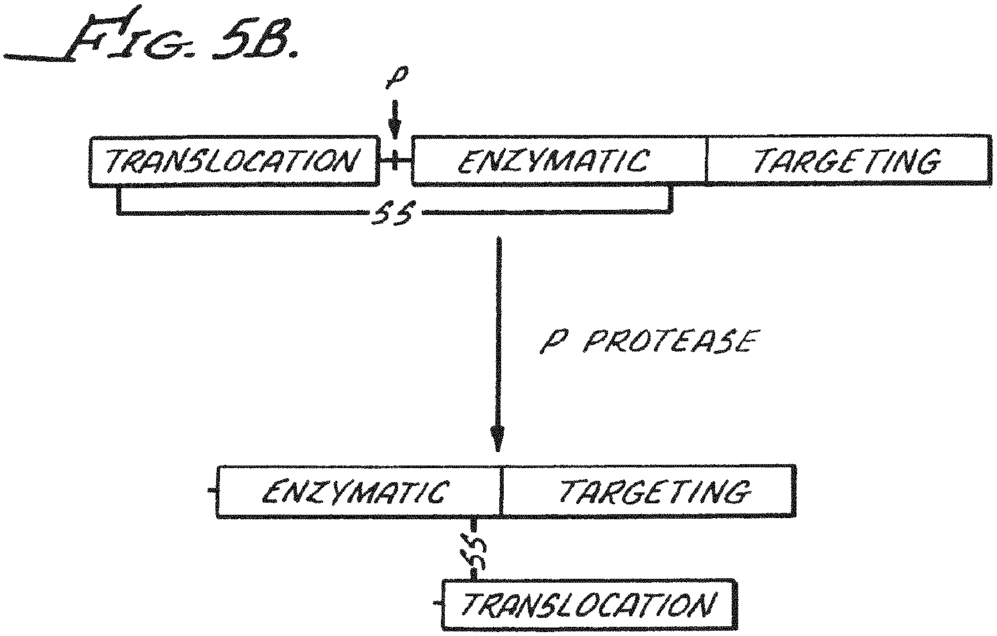
FIG. 5B depicts the single polypeptide form of a modified Clostridial toxin with an amino to carboxyl linear organization comprising a translocation domain, an enzymatic domain and an enhanced targeting domain, with the di-chain loop region depicted by the double SS bracket. A proteolytic cleavage site (P) within a di-chain loop region is located between the translocation and enzymatic domains. Upon proteolytic cleavage with a P protease, the single chain form of the toxin is converted to the di-chain form. The P protease site can be a Clostridial toxin endogenous protease cleavage site or a non-Clostridial toxin exogenous protease cleavage site. Spacers can be placed between the translocation and enzymatic domains, the enzymatic and targeting domains or any combination thereof.

It is envisioned that a modified Clostridial toxin disclosed in the present specification can comprise an enhance binding domain in any and all locations with the proviso that modified Clostridial toxin is capable of performing the intoxication process. Non-limiting examples include, locating an enhance binding domain at the amino terminus of a modified Clostridial toxin (FIG. 3); locating an enhance binding domain between a Clostridial toxin enzymatic domain and a Clostridial toxin translocation domain of a modified Clostridial toxin (FIG. 4); and locating an enhance binding domain at the carboxyl terminus of a modified Clostridial toxin (FIG. 5).

Thus, in an embodiment, a modified Clostridial toxin can comprise an amino to carboxyl single polypeptide linear order comprising a Clostridial toxin enzymatic domain, a Clostridial toxin translocation domain and an enhanced targeting domain. In an aspect of this embodiment, a modified Clostridial toxin can comprise an amino to carboxyl single polypeptide linear order comprising a Clostridial toxin enzymatic domain, a protease cleavage site, a Clostridial toxin translocation domain and an enhanced targeting domain. In another aspect of this embodiment, a modified Clostridial toxin can comprise an amino to carboxyl single polypeptide linear order comprising a Clostridial toxin enzymatic domain, an endogenous protease cleavage site, a Clostridial toxin translocation domain and an enhanced targeting domain. In another aspect of this embodiment, a modified Clostridial toxin can comprise an amino to carboxyl single polypeptide linear order comprising a Clostridial toxin enzymatic domain, an exogenous protease cleavage site, a Clostridial toxin translocation domain and an enhanced targeting domain.

In another embodiment, a modified Clostridial toxin can comprise an amino to carboxyl single polypeptide linear order comprising a Clostridial toxin enzymatic domain, an enhanced targeting domain and a Clostridial toxin translocation domain. In an aspect of this embodiment, a modified Clostridial toxin can comprise an amino to carboxyl single polypeptide linear order comprising a Clostridial toxin enzymatic domain, a protease cleavage site, an enhanced targeting domain and a Clostridial toxin translocation domain. In another aspect of this embodiment, a modified Clostridial toxin can comprise an amino to carboxyl single polypeptide linear order comprising a Clostridial toxin enzymatic domain, an endogenous protease cleavage site, an enhanced targeting domain and a Clostridial toxin translocation domain. In another aspect of this embodiment, a modified Clostridial toxin can comprise an amino to carboxyl single polypeptide linear order comprising a Clostridial toxin enzymatic domain, an exogenous protease cleavage site, an enhanced targeting domain and a Clostridial toxin translocation domain.

In another embodiment, a modified Clostridial toxin can comprise an amino to carboxyl single polypeptide linear order comprising an enhanced targeting domain, a Clostridial toxin translocation domain, and a Clostridial toxin enzymatic domain. In an aspect of this embodiment, a modified Clostridial toxin can comprise an amino to carboxyl single polypeptide linear order comprising an enhanced targeting domain, a Clostridial toxin translocation domain, a protease cleavage site and a Clostridial toxin enzymatic domain. In another aspect of this embodiment, a modified Clostridial toxin can comprise an amino to carboxyl single polypeptide linear order comprising an enhanced targeting domain, a Clostridial toxin translocation domain, an endogenous protease cleavage site and a Clostridial toxin enzymatic domain. In another aspect of this embodiment, a modified Clostridial toxin can comprise an amino to carboxyl single polypeptide linear order comprising an enhanced targeting domain, a Clostridial toxin translocation domain, an exogenous protease cleavage site and a Clostridial toxin enzymatic domain.

In another embodiment, a modified Clostridial toxin can comprise an amino to carboxyl single polypeptide linear order comprising an enhanced targeting domain, a Clostridial toxin enzymatic domain and a Clostridial toxin translocation domain. In an aspect of this embodiment, a modified Clostridial toxin can comprise an amino to carboxyl single polypeptide linear order comprising an enhanced targeting domain, a Clostridial toxin enzymatic domain, a protease cleavage site and a Clostridial toxin translocation domain. In another aspect of this embodiment, a modified Clostridial toxin can comprise an amino to carboxyl single polypeptide linear order comprising an enhanced targeting domain, a Clostridial toxin enzymatic domain, an endogenous protease cleavage site and a Clostridial toxin translocation domain. In another aspect of this embodiment, a modified Clostridial toxin can comprise an amino to carboxyl single polypeptide linear order comprising an enhanced targeting domain, a Clostridial toxin enzymatic domain, an exogenous protease cleavage site and a Clostridial toxin translocation domain.

In another embodiment, a modified Clostridial toxin can comprise an amino to carboxyl single polypeptide linear order comprising a Clostridial toxin translocation domain, a Clostridial toxin enzymatic domain and an enhanced targeting domain. In an aspect of this embodiment, a modified Clostridial toxin can comprise an amino to carboxyl single polypeptide linear order comprising a Clostridial toxin translocation domain, a protease cleavage site, a Clostridial toxin enzymatic domain and an enhanced targeting domain. In another aspect of this embodiment, a modified Clostridial toxin can comprise an amino to carboxyl single polypeptide linear order comprising a Clostridial toxin translocation domain, an endogenous protease cleavage site, a Clostridial toxin enzymatic domain and an enhanced targeting domain. In another aspect of this embodiment, a modified Clostridial toxin can comprise an amino to carboxyl single polypeptide linear order comprising a Clostridial toxin translocation domain, an exogenous protease cleavage site, a Clostridial toxin enzymatic domain and an enhanced targeting domain.

Aspects of the present invention provide, in part modified Clostridial toxins. Non-limiting examples of Clostridial toxin modifications disclosed in the present specification include, e.g., addition of an enhanced targeting domain, addition of a protease cleavage site, rearrangement of the enzymatic, translocation and binding domains and addition of a spacer region. It is understood that all such modifications do not substantially affect the ability of a modified Clostridial toxin to intoxicate a cell. As used herein, the term "do not substantially affect" means a modified Clostridial toxin can still execute the overall cellular mechanism whereby a Clostridial toxin enters a neuron and inhibits neurotransmitter release and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate. In aspects of this embodiment, the modified Clostridial toxin is, e.g., at least 10% as toxic as a naturally-occurring Clostridial toxin, at least 20% as toxic as a naturally-occurring Clostridial toxin, at least 30% as toxic as a naturally-occurring Clostridial toxin, at least 40% as toxic as a naturally-occurring Clostridial toxin, at least 50% as toxic as a naturally-occurring Clostridial toxin, at least 60% as toxic as a naturally-occurring Clostridial toxin, at least 70% as toxic as a naturally-occurring Clostridial toxin, at least 80% as toxic as a naturally-occurring Clostridial toxin, at least 90% as toxic as a naturally-occurring Clostridial toxin or at least 95% as toxic as a naturally-occurring Clostridial toxin. In aspects of this embodiment, the modified Clostridial toxin is, e.g., at most 10% as toxic as a naturally-occurring Clostridial toxin, at most 20% as toxic as a naturally-occurring Clostridial toxin, at most 30% as toxic as a naturally-occurring Clostridial toxin, at most 40% as toxic as a naturally-occurring Clostridial toxin, at most 50% as toxic as a naturally-occurring Clostridial toxin, at most 60% as toxic as a naturally-occurring Clostridial toxin, at most 70% as toxic as a naturally-occurring Clostridial toxin, at most 80% as toxic as a naturally-occurring Clostridial toxin, at most 90% as toxic as a naturally-occurring Clostridial toxin or at most 95% as toxic as a naturally-occurring Clostridial toxin.

Another aspect of the present invention provides polynucleotide molecules encoding modified Clostridial toxins disclosed in the present specification. It is envisioned that any and all modified Clostridial toxin disclosed in the present specification can be encoded by a polynucleotide molecule.

Aspects of the present invention provide, in part polynucleotide molecules. As used herein, the term "polynucleotide molecule" is synonymous with "nucleic acid molecule" and means a polymeric form of nucleotides, such as, e.g., ribonucleotides and deoxyribonucleotides, of any length. It is envisioned that any and all polynucleotide molecules that can encode a modified Clostridial toxin disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagmid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

Thus, in an embodiment, a polynucleotide molecule encodes a modified Clostridial toxin disclosed in the present specification.

In another embodiment, a polynucleotide molecule encodes, in part, a modified Clostridial toxin comprising a Clostridial toxin enzymatic domain disclosed in the present specification. In an aspect of this embodiment, a polynucleotide molecule encoding a modified Clostridial toxin enzymatic domain comprises a naturally occurring Clostridial toxin enzymatic domain variant, such as, e.g., a Clostridial toxin enzymatic domain isoform or a Clostridial toxin enzymatic domain subtype. In another aspect of this embodiment, a polynucleotide molecule encoding a Clostridial toxin enzymatic domain comprises a non-naturally occurring Clostridial toxin enzymatic domain variant, such as, e.g., a conservative Clostridial toxin enzymatic domain variant, a non-conservative Clostridial toxin enzymatic domain variant or an active Clostridial toxin enzymatic domain fragment, or any combination thereof. In other aspects of this embodiment, a polynucleotide molecule encoding a Clostridial toxin enzymatic domain comprises a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, or active fragment thereof.

In another embodiment, a polynucleotide molecule encodes, in part, a modified Clostridial toxin comprising a Clostridial toxin translocation domain disclosed in the present specification. In an aspect of this embodiment, a polynucleotide molecule encoding a modified Clostridial toxin translocation domain comprises a naturally occurring Clostridial toxin translocation domain variant, such as, e.g., a Clostridial toxin translocation domain isoform or a Clostridial toxin translocation domain subtype. In another aspect of this embodiment, a polynucleotide molecule encoding a Clostridial toxin translocation domain comprises a non-naturally occurring Clostridial toxin translocation domain variant, such as, e.g., a conservative Clostridial toxin translocation domain variant, a non-conservative Clostridial toxin translocation domain variant or an active Clostridial toxin translocation domain fragment, or any combination thereof. In other aspects of this embodiment, a polynucleotide molecule encoding a Clostridial toxin translocation domain comprises a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, or active fragment thereof.

In another embodiment, a polynucleotide molecule encodes, in part, a modified Clostridial toxin comprising an enhanced targeting domain disclosed in the present specification. In an aspect of this embodiment, a polynucleotide molecule encoding an enhanced targeting domain comprises a Clostridial toxin binding domain with enhanced binding activity disclosed in the present specification. In an aspect of this embodiment, a polynucleotide molecule encoding a modified Clostridial toxin binding domain with enhanced binding activity comprises a non-naturally occurring Clostridial toxin binding domain variant with enhanced binding activity, such as, e.g., a conservative Clostridial toxin binding domain variant with enhanced binding activity, a non-conservative Clostridial toxin binding domain variant with enhanced binding activity or an active Clostridial toxin binding domain fragment with enhanced binding activity, or any combination thereof. In other aspects of this embodiment, a polynucleotide molecule encoding a Clostridial toxin binding domain with enhanced binding activity comprises a BoNT/A binding domain with enhanced binding activity, a BoNT/B binding domain with enhanced binding activity, a BoNT/C1 binding domain with enhanced binding activity, a BoNT/D binding domain with enhanced binding activity, a BoNT/E binding domain with enhanced binding activity, a BoNT/F binding domain with enhanced binding activity, a BoNT/G binding domain with enhanced binding activity, a TeNT binding domain with enhanced binding activity, or active fragment thereof.

In an aspect of this embodiment, an enhanced targeting domain comprises a Clostridial NAP disclosed in the present specification. In an aspect of this embodiment, a polynucleotide molecule encoding a Clostridial NAP comprises a naturally occurring Clostridial NAP variant, such as, e.g., a Clostridial NAP isoform or a Clostridial NAP subtype. In an aspect of this embodiment, a polynucleotide molecule encoding a NAP comprises a non-naturally occurring Clostridial NAP variant, such as, e.g., a conservative Clostridial NAP variant, a non-conservative Clostridial NAP variant or an active Clostridial NAP fragment, or any combination thereof. In other aspects of this embodiment, a polynucleotide molecule encoding a Clostridial NAP comprises a Clostridial botulinum serotype A HA-33, a Clostridial botulinum serotype B HA-33, a Clostridial botulinum serotype C1 HA-33, a Clostridial botulinum serotype D HA-33, a Clostridial botulinum serotype A HA-17, a Clostridial botulinum serotype B HA-17, a Clostridial botulinum serotype C1 HA-17, a Clostridial botulinum serotype D HA-17, a Clostridial botulinum serotype A NTNH, a Clostridial botulinum serotype B NTNH, a Clostridial botulinum serotype C1 NTNH, a Clostridial botulinum serotype D NTNH, a Clostridial botulinum serotype E NTNH, a Clostridial botulinum serotype F NTNH and a Clostridial botulinum serotype G NTNH.

In an aspect of this embodiment, an enhanced targeting domain comprises a Clostridial NAP with enhanced binding activity disclosed in the present specification. In an aspect of this embodiment, a polynucleotide molecule encoding a NAP with enhanced binding activity comprises a non-naturally occurring Clostridial NAP variant with enhanced binding activity, such as, e.g., a conservative Clostridial NAP variant with enhanced binding activity, a non-conservative Clostridial NAP variant with enhanced binding activity or an active Clostridial NAP fragment with enhanced binding activity, or any combination thereof. In other aspects of this embodiment, a polynucleotide molecule encoding a Clostridial NAP comprises a Clostridial botulinum serotype A HA-33 with enhanced binding activity, a Clostridial botulinum serotype B HA-33 with enhanced binding activity, a Clostridial botulinum serotype C1 HA-33 with enhanced binding activity, a Clostridial botulinum serotype D HA-33 with enhanced binding activity, a Clostridial botulinum serotype A HA-17 with enhanced binding activity, a Clostridial botulinum serotype B HA-17 with enhanced binding activity, a Clostridial botulinum serotype C1 HA-17 with enhanced binding activity, a Clostridial botulinum serotype D HA-17 with enhanced binding activity, a Clostridial botulinum serotype A NTNH with enhanced binding activity, a Clostridial botulinum serotype B NTNH with enhanced binding activity, a Clostridial botulinum serotype C1 NTNH with enhanced binding activity, a Clostridial botulinum serotype D NTNH with enhanced binding activity, a Clostridial botulinum serotype E NTNH with enhanced binding activity, a Clostridial botulinum serotype F NTNH with enhanced binding activity and a Clostridial botulinum serotype G NTNH with enhanced binding activity.

In an aspect of this embodiment, an enhanced targeting domain comprises a FGF disclosed in the present specification. In an aspect of this embodiment, a polynucleotide molecule encoding a FGF comprises a naturally occurring FGF variant, such as, e.g., a FGF isoform or a FGF subtype. In an aspect of this embodiment, a polynucleotide molecule encoding a FGF comprises a non-naturally occurring FGF variant, such as, e.g., a conservative FGF variant, a non-conservative FGF variant or an active FGF fragment, or any combination thereof. In other aspects of this embodiment, a polynucleotide molecule encoding a FGF comprises a FGF-1, a FGF-2, a FGF-4, a FGF-8, a FGF-9, a FGF-17 and a FGF-18.

In an aspect of this embodiment, an enhanced targeting domain comprises a FGF with enhanced binding activity disclosed in the present specification. In an aspect of this embodiment, a polynucleotide molecule encoding a FGF with enhanced binding activity comprises a non-naturally occurring FGF variant with enhanced binding activity, such as, e.g., a conservative FGF variant with enhanced binding activity, a non-conservative FGF variant with enhanced binding activity or an active FGF fragment with enhanced binding activity, or any combination thereof. In other aspects of this embodiment, a polynucleotide molecule encoding a FGF with enhanced binding activity comprises a FGF-1 with enhanced binding activity, a FGF-2 with enhanced binding activity, a FGF-4 with enhanced binding activity, a FGF-8 with enhanced binding activity, a FGF-9 with enhanced binding activity, a FGF-17 with enhanced binding activity and a FGF-18 with enhanced binding activity.

In another embodiment, a polynucleotide molecule encodes, in part, a modified Clostridial toxin comprising a protease cleavage site disclosed in the present specification. In an aspect of this embodiment, a polynucleotide molecule encoding a protease cleavage site comprises an endogenous Clostridial toxin protease site. In aspects of this embodiment, a polynucleotide molecule encoding an endogenous Clostridial toxin protease site can be, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site or a TeNT di-chain loop protease cleavage site. In another aspect of this embodiment, a polynucleotide molecule encoding a protease cleavage site comprises an exogenous Clostridial toxin protease site. In aspects of this embodiment, a polynucleotide molecule encoding an exogenous Clostridial toxin protease site can be, e.g., a bovine enterokinase protease cleavage site, a Tobacco Etch Virus protease cleavage site, a Human Rhinovirus 3C protease cleavage site, a SUMO/ULP-1 protease cleavage site, a Thrombin protease cleavage site, a Coagulation Factor Xa protease cleavage site or a Clostridial toxin substrate cleavage site, such as, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site or a TeNT substrate cleavage site.

In another embodiment, a polynucleotide molecule encodes, in part, a modified Clostridial toxin comprising a flexible spacer disclosed in the present specification. In an aspect of this embodiment, a polynucleotide molecule encoding a flexible spacer can comprise a G-spacer, a A-spacer or any combination thereof.

In another embodiment, a polynucleotide molecule encodes, in part, a modified Clostridial toxin comprising an epitope-binding region disclosed in the present specification. In an aspect of this embodiment, a polynucleotide molecule encoding an epitope-binding region can comprise a FLAG, Express™, a human Influenza virus hemagluttinin (HA), a human p62$^{c\text{-}Myc}$ protein (c-MYC), a Vesicular Stomatitis Virus Glycoprotein (VSV-G), a Substance P, a glycoprotein-D precursor of Herpes simplex virus (HSV), a V5, a AU1, a AU5 (SEQ ID NO: 85), a polyhistidine (HIS), or any combination thereof.

Well-established molecular biology techniques that may be necessary to make a polynucleotide molecule encoding a modified Clostridial toxin disclosed in the present specification including, but not limited to, procedures involving polymerase chain reaction (PCR) amplification, restriction enzyme reactions, agarose gel electrophoresis, nucleic acid ligation, bacterial transformation, nucleic acid purification, nucleic acid sequencing and recombination-based techniques are routine procedures well within the scope of one skilled in the art and from the teaching herein. Non-limiting examples of specific protocols necessary to make a polynucleotide molecule encoding a modified Clostridial toxin are described in e.g., Molecular Cloning A Laboratory Manual, supra, (2001); and Current Protocols in Molecular Biology (Frederick M. Ausubel et al., eds. John Wiley & Sons, 2004). Additionally, a variety of commercially available products useful for making a polynucleotide molecule encoding a modified Clostridial toxin are widely available. These protocols are routine procedures well within the scope of one skilled in the art and from the teaching herein.

Another aspect of the present invention provides a method of producing a modified Clostridial toxin disclosed in the present specification, such method comprising the step of expressing a polynucleotide molecule encoding a modified Clostridial toxin in a cell. Another aspect of the present invention provides a method of producing a modified Clostridial toxin disclosed in the present specification, such method comprising the steps of introducing an expression construct comprising a polynucleotide molecule encoding a modified Clostridial toxin into a cell and expressing the expression construct in the cell.

The methods disclosed in the present specification include, in part, a modified Clostridial toxin. It is envisioned that any and all modified Clostridial toxins disclosed in the present specification can be produced using the methods disclosed in the present specification. It is also envisioned that any and all polynucleotide molecules encoding a modified Clostridial toxins disclosed in the present specification can be useful in producing a modified Clostridial toxins disclosed in the present specification using the methods disclosed in the present specification.

The methods disclosed in the present specification include, in part, an expression construct. An expression construct comprises a polynucleotide molecule disclosed in the present specification operably-linked to an expression vector useful for expressing the polynucleotide molecule in a cell or cell-free extract. A wide variety of expression vectors can be employed for expressing a polynucleotide molecule encoding a modified Clostridial toxin, including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors useful to practice aspects of these methods may include those which express a modified Clostridial toxin under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

Thus, aspects of this embodiment include, without limitation, a viral expression vector operably-linked to a polynucleotide molecule encoding a modified Clostridial toxin; a prokaryotic expression vector operably-linked to a polynucleotide molecule encoding a modified Clostridial toxin; a yeast expression vector operably-linked to a polynucleotide molecule encoding a modified Clostridial toxin; an insect expression vector operably-linked to a polynucleotide molecule encoding a modified Clostridial toxin; and a mammalian expression vector operably-linked to a polynucleotide molecule encoding a modified Clostridial toxin. Other aspects of this embodiment include, without limitation, expression constructs suitable for expressing a modified Clostridial toxin disclosed in the present specification using a cell-free extract comprising a cell-free extract expression vector operably linked to a polynucleotide molecule encoding a modified Clostridial toxin. Other aspects of this embodiment include, without limitation, expression constructs comprising polynucleotide molecules comprising any one of SEQ ID NO: 109 through SEQ ID NO: 132 and SEQ ID NO: 136 through SEQ ID NO: 159. Other aspects of this embodiment include, without limitation, expression constructs comprising polynucleotide molecules encoding a modified Clostridial toxin comprising any one of SEQ ID NO: 85 through SEQ ID NO: 108.

The methods disclosed in the present specification include, in part, a cell. It is envisioned that any and all cells can be used. Thus, aspects of this embodiment include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, 4th ed. 2000); ANIMAL CELL CULTURE: A PRACTICAL APPROACH (John R. W. Masters ed., Oxford University Press, 3rd ed. 2000); MOLECULAR CLONING A LABORATORY MANUAL, supra, (2001); BASIC CELL CULTURE: A PRACTICAL APPROACH (John M. Davis, Oxford Press, 2nd ed. 2002); and CURRENT PROTOCOLS IN MOLECULAR BIOLOGY, supra, (2004). These protocols are routine procedures within the scope of one skilled in the art and from the teaching herein.

The methods disclosed in the present specification include, in part, introducing into a cell a polynucleotide molecule. A polynucleotide molecule introduced into a cell can be transiently or stably maintained by that cell. Stably-maintained polynucleotide molecules may be extra-chromosomal and replicate autonomously, or they may be integrated into the chromosomal material of the cell and replicate non-autonomously. It is envisioned that any and all methods for introducing a polynucleotide molecule disclosed in the present specification into a cell can be used. Methods useful for introducing a nucleic acid molecule into a cell include, without limitation, chemical-mediated transfection such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated tranfection, such as, e.g., biolistic particle delivery, microinjection, protoplast fusion and electroporation; and viral-mediated transfection, such as, e.g., retroviral-mediated transfection, see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

In an aspect of this embodiment, a chemical-mediated method, termed transfection, is used to introduce a polynucleotide molecule encoding a modified Clostridial toxin into a cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, Transfection of adherent and suspended cells by calcium phosphate, 33(2) Methods 136-143 (2004); diethyl-aminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., Polyethylenimine strategies for plasmid delivery to brain-derived cells, 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physical-mediated method is used to introduce a polynucleotide molecule encoding a modified Clostridial toxin into a cell. Physical techniques include, without limitation, electroporation, biolistic and microinjection. Biolistics and microinjection techniques perforate the cell wall in order to introduce the nucleic acid molecule into the cell, see, e.g., Jeike E. Biewenga et al., Plasmid-mediated gene transfer in neurons using the biolistics technique, 71(1) J. Neurosci. Methods. 67-75 (1997); and John O'Brien & Sarah C. R. Lummis, Biolistic and diolistic transfection: using the gene gun to deliver DNA and lipophilic dyes into mammalian cells, 33(2) Methods 121-125 (2004). Electroporation, also termed electropermeabilization, uses brief, high-voltage, electrical pulses to create transient pores in the membrane through which the nucleic acid molecules enter and can be used effectively for stable and transient transfections of all cell types, see, e.g., M. Golzio et al., In vitro and in vivo electric field-mediated permeabilization, gene transfer, and expression, 33(2) Methods 126-135 (2004); and Oliver Gresch et al., New non-viral method for gene transfer into primary cells, 33(2) Methods 151-163 (2004).

In another aspect of this embodiment, a viral-mediated method, termed transduction, is used to introduce a polynucleotide molecule encoding a modified Clostridial toxin into a cell. In viral-mediated methods of transient transduction, the process by which viral particles infect and replicate in a host cell has been manipulated in order to use this mechanism to introduce a nucleic acid molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, Lentiviral and MLV based retroviral vectors for ex vivo and in vivo gene transfer, 33(2) Methods 164-172 (2004); and Maurizio Federico, From lentiviruses to lentivirus vectors, 229 Methods Mol. Biol. 3-15 (2003); E. M. Poeschla, Non-primate lentiviral vectors, 5(5) Curr. Opin. Mol. Ther. 529-540 (2003); Karim Benihoud et al, Adenovirus vectors for gene delivery, 10(5) Curr. Opin. Biotechnol. 440-447 (1999); H. Bueler, Adeno-associated viral vectors for gene transfer and gene therapy, 380(6) Biol. Chem. 613-622 (1999); Chooi M. Lai et al., Adenovirus and adeno-associated virus vectors, 21(12) DNA Cell Biol. 895-913 (2002); Edward A. Burton et al., Gene delivery using herpes simplex virus vectors, 21(12) DNA Cell Biol. 915-936 (2002); Paola Grandi et al., Targeting HSV amplicon vectors, 33(2) Methods 179-186 (2004); Ilya Frolov et al., Alphavirus-based expression vectors: strategies and applications, 93(21) Proc. Natl. Acad. Sci. U.S.A. 11371-11377 (1996); Markus U. Ehrengruber, Alphaviral gene transfer in neurobiology, 59(1) Brain Res. Bull. 13-22 (2002); Thomas A. Kost & J. Patrick Condreay, Recombinant baculoviruses as mammalian cell gene-delivery vectors, 20(4) Trends Biotechnol. 173-180 (2002); and A. Huser & C. Hofmann, Baculovirus vectors: novel mammalian cell gene-delivery vehicles and their applications, 3(1) Am. J. Pharmacogenomics 53-63 (2003).

Adenoviruses, which are non-enveloped, double-stranded DNA viruses, are often selected for mammalian cell transduction because adenoviruses handle relatively large polynucleotide molecules of about 36 kb, are produced at high titer, and can efficiently infect a wide variety of both dividing and non-dividing cells, see, e.g., Wim T. J. M. C. Hermens et al., Transient gene transfer to neurons and glia: analysis of adenoviral vector performance in the CNS and PNS, 71(1) J. Neurosci. Methods 85-98 (1997); and Hiroyuki Mizuguchi et al., Approaches for generating recombinant adenovirus vectors, 52(3) Adv. Drug Deliv. Rev. 165-176 (2001). Transduction using adenoviral-based system do not support prolonged protein expression because the nucleic acid molecule is carried from an episome in the cell nucleus, rather than being integrated into the host cell chromosome. Adenoviral vector systems and specific protocols for how to use such vectors are disclosed in, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEasy™ Adenoviral Vector System (Stratagene, Inc., La Jolla, Calif.) and AdEasy™ Adenoviral Vector System Instruction Manual 064004f, Stratagene, Inc.

Nucleic acid molecule delivery can also use single-stranded RNA retroviruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., Transient production of retroviral- and lentiviral-based vectors for the transduction of Mammalian cells, 285 Methods Mol. Biol. 141-148 (2004); Armin Blesch, Lentiviral and MLV based retroviral vectors for ex vivo and in vivo gene transfer, 33(2) Methods 164-172 (2004); Felix Recillas-Targa, Gene transfer and expression in mammalian cell lines and transgenic animals, 267 Methods Mol. Biol. 417-433 (2004); and Roland Wolkowicz et al., Lentiviral vectors for the delivery of DNA into mammalian cells, 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persistent expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., In vivo gene delivery and stable transduction of non-dividing cells by a lentiviral vector, 272 (5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., U.S. patent Nos. Manfred Gossen & Hermann Bujard, Tight control of gene expression in eukaryotic cells by tetracycline-responsive promoters, U.S. Pat. No. 5,464,758 (Nov. 7, 1995) and Hermann Bujard & Manfred Gossen, Methods for regulating gene expression, U.S. Pat. No. 5,814,618 (Sep. 29, 1998) David S. Hogness, Polynucleotides encoding insect steroid hormone receptor polypeptides and cells transformed with same, U.S. Pat. No. 5,514,578 (May 7, 1996) and David S. Hogness, Polynucleotide encoding insect ecdysone receptor, U.S. Pat. No. 6,245,531 (Jun. 12, 2001); Elisabetta Vegeto et al., Progesterone receptor having C. terminal hormone binding domain truncations, U.S. Pat. No. 5,364,791 (Nov. 15, 1994), Elisabetta Vegeto et al., Mutated steroid hormone receptors, methods for their use and molecular switch for gene therapy, U.S. Pat. No. 5,874,534 (Feb. 23, 1999) and Elisabetta Vegeto et al., Mutated steroid hormone receptors, methods for their use and molecular switch for gene therapy, U.S. Pat. No. 5,935,934 (Aug. 10, 1999). Furthermore, such viral delivery systems can be prepared by standard methods and are commercially available, see, e.g., BD™ Tet-Off and Tet-On Gene Expression Systems (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

The methods disclosed in the present specification include, in part, expressing a modified Clostridial toxin from a polynucleotide molecule. It is envisioned that any of a variety of expression systems may be useful for expressing a modified Clostridial toxin from a polynucleotide molecule disclosed in the present specification, including, without limitation, cell-based systems and cell-free expression systems. Cell-based systems include, without limitation, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts and generally are equivalent to the method disclosed herein. Expression of a polynucleotide molecule using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH(S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins,* 80(9) CURRENT SCIENCE 1121-1128, (2001). These protocols are routine procedures well within the scope of one skilled in the art and from the teaching herein.

A variety of cell-based expression procedures are useful for expressing a modified Clostridial toxin encoded by polynucleotide molecule disclosed in the present specification. Examples included, without limitation, viral expression systems, prokaryotic expression systems, yeast expression systems, baculoviral expression systems, insect expression systems and mammalian expression systems. Viral expression systems include, without limitation, the ViraPower™ Lentiviral (Invitrogen, Inc., Carlsbad, Calif.), the Adenoviral Expression Systems (Invitrogen, Inc., Carlsbad, Calif.), the AdEasy™ XL Adenoviral Vector System (Stratagene, La Jolla, Calif.) and the ViraPort® Retroviral Gene Expression System (Stratagene, La Jolla, Calif.). Non-limiting examples of prokaryotic expression systems include the Champion™ pET Expression System (EMD Biosciences-Novagen, Madison, Wis.), the TriEx™ Bacterial Expression System (EMD Biosciences-Novagen, Madison, Wis.), the QIAexpress® Expression System (QIAGEN, Inc.), and the Affinity® Protein Expression and Purification System (Stratagene, La Jolla, Calif.). Yeast expression systems include, without limitation, the EasySelect™ *Pichia* Expression Kit (Invitrogen, Inc., Carlsbad, Calif.), the YES-Echo™ Expression Vector Kits (Invitrogen, Inc., Carlsbad, Calif.) and the SpECTRA™ *S. pombe* Expression System (Invitrogen, Inc., Carlsbad, Calif.). Non-limiting examples of baculoviral expression systems include the BaculoDirect™ (Invitrogen, Inc., Carlsbad, Calif.), the BactoBac® (Invitrogen, Inc., Carlsbad, Calif.), and the BD BaculoGold™ (BD Biosciences-Pharmigen, San Diego, Calif.). Insect expression systems include, without limitation, the *Drosophila* Expression System (DES®) (Invitrogen, Inc., Carlsbad, Calif.), InsectSelect™ System (Invitrogen, Inc., Carlsbad, Calif.) and InsectDirect™ System (EMD Biosciences-Novagen, Madison, Wis.). Non-limiting examples of mammalian expression systems include the T-REx™ (Tetracycline-Regulated Expression) System (Invitrogen, Inc., Carlsbad, Calif.), the Flp-In™ T-REx™ System (Invitrogen, Inc., Carlsbad, Calif.), the pcDNA™ system (Invitrogen, Inc., Carlsbad, Calif.), the pSecTag2 system (Invitrogen, Inc., Carlsbad, Calif.), the Exchanger® System, InterPlay™ Mammalian TAP System (Stratagene, La Jolla, Calif.), Complete Control® Inducible Mammalian Expression System (Stratagene, La Jolla, Calif.) and LacSwitch® II Inducible Mammalian Expression System (Stratagene, La Jolla, Calif.).

Another procedure of expressing a modified Clostridial toxin encoded by polynucleotide molecule disclosed in the present specification employs a cell-free expression system such as, without limitation, prokaryotic extracts and eukaryotic extracts. Non-limiting examples of prokaryotic cell extracts include the RTS 100 *E. coli* HY Kit (Roche Applied Science, Indianapolis, Ind.), the ActivePro In Vitro Translation Kit (Ambion, Inc., Austin, Tex.), the EcoPro™ System (EMD Biosciences-Novagen, Madison, Wis.) and the Expressway™ Plus Expression System (Invitrogen, Inc., Carlsbad, Calif.). Eukaryotic cell extract include, without limitation, the RTS 100 Wheat Germ CECF Kit (Roche Applied Science, Indianapolis, Ind.), the TnT® Coupled Wheat Germ Extract Systems (Promega Corp., Madison, Wis.), the Wheat Germ IVT™ Kit (Ambion, Inc., Austin, Tex.), the Retic Lysate IVT™ Kit (Ambion, Inc., Austin, Tex.), the PROTEINscript® II System (Ambion, Inc., Austin, Tex.) and the TnT® Coupled Reticulocyte Lysate Systems (Promega Corp., Madison, Wis.).

Aspects of the present invention can also be described as follows:

1. A modified Clostridial toxin comprising: a) a Clostridial toxin enzymatic domain capable of executing an enzymatic target modification step of a Clostridial toxin intoxication process; b) a Clostridial toxin translocation domain capable of executing a translocation step of a Clostridial toxin intoxication process; c) an enhanced targeting domain comprising a modified Clostridial binding domain capable of executing a cell binding step of a Clostridial toxin intoxication process; and d) a protease cleavage site; wherein cleavage of the protease cleavage site converts the single-chain form of the modified Clostridial toxin into the di-chain form; and wherein the modified Clostridial binding domain exhibits enhanced binding activity for an endogenous Clostridial toxin receptor system relative to the binding activity of a naturally-occurring Clostridial binding domain from which the modified Clostridial binding domain is derived.
2. The modified Clostridial toxin according to 1, wherein the modified Clostridial toxin comprises, in a linear amino-to-carboxyl single polypeptide order, the Clostridial toxin enzymatic domain, the protease cleavage site, the Clostridial toxin translocation domain and the enhanced targeting domain.
3. The modified Clostridial toxin according to 1, wherein the modified Clostridial toxin comprises, in a linear amino-to-carboxyl single polypeptide order, the Clostridial toxin enzymatic domain, the protease cleavage site, the enhanced targeting domain and the Clostridial toxin translocation domain.
4. The modified Clostridial toxin according to 1, wherein the modified Clostridial toxin comprises, in a linear amino-to-carboxyl single polypeptide order, the enhanced targeting domain, the Clostridial toxin translocation domain, the protease cleavage site and the Clostridial toxin enzymatic domain.
5. The modified Clostridial toxin according to 1, wherein the modified Clostridial toxin comprises, in a linear amino-to-carboxyl single polypeptide order, the enhanced targeting domain, the Clostridial toxin enzymatic domain, the protease cleavage site and the Clostridial toxin translocation domain.
6. The modified Clostridial toxin according to 1, wherein the modified Clostridial toxin comprises, in a linear amino-to-carboxyl single polypeptide order, the Clostridial toxin translocation domain, the protease cleavage site, the Clostridial toxin enzymatic domain and the enhanced targeting domain.
7. The modified Clostridial toxin according to 1, wherein the modified Clostridial toxin comprises, in a linear amino-to-carboxyl single polypeptide order, the Clostridial toxin translocation domain, the protease cleavage site, the enhanced targeting domain and the Clostridial toxin enzymatic domain.
8. The modified Clostridial toxin according to 1, wherein the Clostridial toxin enzymatic domain is selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain and a TeNT enzymatic domain.
9. The modified Clostridial toxin according to 1, wherein the Clostridial toxin translocation domain is selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain and a TeNT translocation domain.
10. The modified Clostridial toxin according to 1, wherein the modified Clostridial toxin binding domain is selected from the group consisting of a modified BoNT/A binding domain, a modified BoNT/B binding domain, a modified BoNT/C1 binding domain, a modified BoNT/D binding domain, a modified BoNT/E binding domain, a modified BoNT/F binding domain, a modified BoNT/G binding domain and a modified TeNT binding domain.
11. The modified Clostridial toxin according to 10, wherein the modified BoNT/A binding domain comprises an amino acid substitution at a position selected from the group consisting of Trp 1101, Gly 1102, Leu 1105, Tyr 1111, Tyr 1112, Gly 1158, Ile 1163, Asp 1179, Glu 1203, Phe 1252, Ser 1264, Trp 1266, Tyr 1267, Gln 1270, Gly 1279 and Trp 1282 of SEQ ID NO: 1, and any combination thereof; wherein the amino acid substitution enhances the binding activity of the modified BoNT/A binding domain for a BoNT/A receptor system.
12. The modified Clostridial toxin according to 10, wherein the modified BoNT/B binding domain comprises an amino acid substitution at a position selected from the group consisting of Trp 1088, Gly 1089, Leu 1092, Tyr 1098, Tyr 1099, Gly 1142, Ile 1147, Asp 1165, Glu 1191, Ile 1240, Ser 1260, Trp 1262, Tyr 1263, Glu 1266, Gly 1277 and Trp 1280 of SEQ ID NO: 2, and any combination thereof; wherein the amino acid substitution enhances the binding activity of the modified BoNT/B binding domain for a BoNT/B receptor system.
13. The modified Clostridial toxin according to 10, wherein the modified BoNT/C1 binding domain comprises an amino acid substitution at a position selected from the group consisting of Trp 1102, Gly 1103, Leu 1106, Tyr 1112, Tyr 1113, Gly 1145, Ile 1150, Asp 1166, Glu 1196, Ile 1247, Gly 1256, Trp 1258, Tyr 1259, His 1261, Gly 1281 and Trp 1284 of SEQ ID NO: 3, and any combination thereof; wherein the amino acid substitution enhances the binding activity of the modified BoNT/C1 binding domain for a BoNT/C1 receptor system.
14. The modified Clostridial toxin according to 10, wherein the modified BoNT/D binding domain comprises an amino acid substitution at a position selected from the group consisting of Trp 1089, Gly 1090, Leu 1093, Tyr 1099, Tyr 1100, Gly 1132, Ile 1137, Asp 1153, Asn 1186, Lys 1236, Trp 1238, Arg 1239, Phe 1242, Ser 1262 and Trp 1265 of SEQ ID NO: 4, and any combination thereof; wherein the amino acid substitution enhances the binding activity of the modified BoNT/D binding domain for a BoNT/D receptor system.

15. The modified Clostridial toxin according to 10, wherein the modified BoNT/E binding domain comprises an amino acid substitution at a position selected from the group consisting of Trp 1076, Gly 1077, Leu 1080, Tyr 1086, Tyr 1087, Gly 1124, Ile 1129, Asp 1146, Glu 1172, Phe 1213, Ser 1221, Trp 1223, Tyr 1224, His 1227, Gly 1236 and Trp 1239 of SEQ ID NO: 5, and any combination thereof; wherein the amino acid substitution enhances the binding activity of the modified BoNT/E binding domain for a BoNT/E receptor system.

16. The modified Clostridial toxin according to 10, wherein the modified BoNT/F binding domain comprises an amino acid substitution at a position selected from the group consisting of Trp 1096, Gly 1097, Leu 1100, Tyr 1106, Tyr 1107, Gly 1147, Ile 1152, Asp 1171, Glu 1195, Phe 1237, Ser 1245, Trp 1247, Tyr 1248, Asn 1251, Gly 1260 and Trp 1263 of SEQ ID NO: 6, and any combination thereof; wherein the amino acid substitution enhances the binding activity of the modified BoNT/F binding domain for a BoNT/F receptor system.

17. The modified Clostridial toxin according to 10, wherein the modified BoNT/G binding domain comprises an amino acid substitution at a position selected from the group consisting of Trp 1096, Gly 1097, Leu 1100, Tyr 1106, Tyr 1107, Gly 1148, Ile 1153, Asp 1172, Gln 1198, Ile 1245, Ser 1266, Trp 1268, Tyr 1269, Arg 1272, Gly 1283 and Trp 1285 of SEQ ID NO: 7, and any combination thereof; wherein the amino acid substitution enhances the binding activity of the modified BoNT/G binding domain for a BoNT/G receptor system.

18. The modified Clostridial toxin according to 10, wherein the modified TeNT binding domain comprises an amino acid substitution at a position selected from the group consisting of Trp 1118, Gly 1119, Leu 1122, Tyr 1128, Tyr 1129, Gly 1172, Ile 1177, Asp 1194, Asp 1222, Thr 1270, Ser 1287, Trp 1289, Tyr 1290, His 1293, Gly 1300 and Trp 1303 of SEQ ID NO: 8, and any combination thereof; wherein the amino acid substitution enhances the binding activity of the modified TeNT binding domain for a TeNT receptor system.

19. The modified Clostridial toxin according to 1, wherein the modified Clostridial toxin binding domain comprises at least one amino acid substitution in a β-trefoil domain.

20. The modified Clostridial toxin according to 19, wherein the amino acid substitution is located within an α-fold, a β-fold or a γ-fold of the β-trefoil domain.

21. The modified Clostridial toxin according to 19, wherein the amino acid substitution is located within a β4/β5 β-hairpin turn or a β8/β9 β-hairpin turn of the β-trefoil domain.

22. The modified Clostridial toxin according to 21, wherein the amino acid substitution is a glycine or a phenylalanine.

23. The modified Clostridial toxin according to 1, wherein the modified Clostridial toxin binding domain comprises a substitution of a Clostridial toxin binding domain α-fold for an α-fold selected from the group consisting of a Clostridial botulinum serotype A HA-33 1α-fold, a Clostridial botulinum serotype B HA-33 1α-fold, a Clostridial botulinum serotype C1 HA-33 1α-fold, a Clostridial botulinum serotype D HA-33 1α-fold, a Clostridial botulinum serotype A HA-33 2α-fold, a Clostridial botulinum serotype B HA-33 2α-fold, a Clostridial botulinum serotype C1 HA-33 2α-fold, a Clostridial botulinum serotype D HA-33 2α-fold, a Clostridial botulinum serotype A HA-17 α-fold, a Clostridial botulinum serotype B HA-17 α-fold, a Clostridial botulinum serotype C1 HA-17 α-fold, a Clostridial botulinum serotype D HA-17 α-fold, a Clostridial botulinum serotype A NTNH α-fold, a Clostridial botulinum serotype B NTNH α-fold, a Clostridial botulinum serotype C1 NTNH α-fold, a Clostridial botulinum serotype D NTNH α-fold, a Clostridial botulinum serotype E NTNH α-fold, a Clostridial botulinum serotype F NTNH α-fold, a Clostridial botulinum serotype G NTNH α-fold, a FGF-1α-fold, a FGF-2 α-fold, a FGF-4 α-fold, a FGF-8 α-fold, a FGF-9 α-fold, a FGF-17 α-fold and a FGF-18 α-fold.

24. The modified Clostridial toxin according to 1, wherein the modified Clostridial toxin binding domain comprises a substitution of a Clostridial toxin binding domain β-fold for a β-fold selected from the group consisting of a Clostridial botulinum serotype A HA-33 1β-fold, a Clostridial botulinum serotype B HA-33 1β-fold, a Clostridial botulinum serotype C1 HA-33 1β-fold, a Clostridial botulinum serotype D HA-33 1β-fold, a Clostridial botulinum serotype A HA-33 2β-fold, a Clostridial botulinum serotype B HA-33 2β-fold, a Clostridial botulinum serotype C1 HA-33 2β-fold, a Clostridial botulinum serotype D HA-33 2β-fold, a Clostridial botulinum serotype A HA-17 β-fold, a Clostridial botulinum serotype B HA-17 β-fold, a Clostridial botulinum serotype C1 HA-17 β-fold, a Clostridial botulinum serotype D HA-17 β-fold, a Clostridial botulinum serotype A NTNH β-fold, a Clostridial botulinum serotype B NTNH β-fold, a Clostridial botulinum serotype C1 NTNH β-fold, a Clostridial botulinum serotype D NTNH β-fold, a Clostridial botulinum serotype E NTNH β-fold, a Clostridial botulinum serotype F NTNH β-fold, a Clostridial botulinum serotype G NTNH β-fold, a FGF-1 β-fold, a FGF-2 β-fold, a FGF-4 β-fold, a FGF-8 β-fold, a FGF-9 β-fold, a FGF-17 β-fold and a FGF-18 β-fold.

25. The modified Clostridial toxin according to 1, wherein the modified Clostridial toxin binding domain comprises a substitution of a Clostridial toxin binding domain γ-fold for a γ-fold selected from the group consisting of a Clostridial botulinum serotype A HA-33 1γ-fold, a Clostridial botulinum serotype B HA-33 1γ-fold, a Clostridial botulinum serotype C1 HA-33 1γ-fold, a Clostridial botulinum serotype D HA-33 1γ-fold, a Clostridial botulinum serotype A HA-33 2γ-fold, a Clostridial botulinum serotype B HA-33 2γ-fold, a Clostridial botulinum serotype C1 HA-33 2γ-fold, a Clostridial botulinum serotype D HA-33 2γ-fold, a Clostridial botulinum serotype A HA-17 γ-fold, a Clostridial botulinum serotype B HA-17 γ-fold, a Clostridial botulinum serotype C1 HA-17 γ-fold, a Clostridial botulinum serotype D HA-17 γ-fold, a Clostridial botulinum serotype A NTNH γ-fold, a Clostridial botulinum serotype B NTNH γ-fold, a Clostridial botulinum serotype C1 NTNH γ-fold, a Clostridial botulinum serotype D NTNH γ-fold, a Clostridial botulinum serotype E NTNH γ-fold, a Clostridial botulinum serotype F NTNH γ-fold, a Clostridial botulinum serotype G NTNH γ-fold, a FGF-1 γ-fold, a FGF-2 γ-fold, a FGF-4 γ-fold, a FGF-8 γ-fold, a FGF-9 γ-fold, a FGF-17 γ-fold and a FGF-18 γ-fold.

26. The modified Clostridial toxin according to 1, wherein the modified Clostridial toxin binding domain comprises a substitution of a Clostridial toxin binding domain β4/β5 6-hairpin turn for a β4/β5 6-hairpin turn selected from the group consisting of a Clostridial botulinum serotype A HA-33 β4/β5 β-hairpin turn, a Clostridial botulinum serotype B HA-33 1β4/β5 β-hairpin turn, a Clostridial botulinum serotype C1 HA-33 1β4/β5 β-hairpin turn, a Clostridial botulinum serotype D HA-33 1β4/β5 β-hairpin turn, a Clostridial botulinum serotype A HA-33 2β4/β5 β-hairpin turn, a Clostridial botulinum serotype B HA-33 2β4/β5 β-hairpin turn, a Clostridial botulinum serotype C1 HA-33 2β4/β5 β-hairpin turn, a Clostridial botulinum serotype D HA-33 2β4/β5 β-hairpin turn, a Clostridial botulinum serotype A HA-17 β4/β5 β-hairpin turn, a Clostridial botulinum serotype B HA-17 β4/β5 β-hairpin turn, a Clostridial botulinum serotype C1 HA-17 β4/β5 β-hairpin turn, a Clostridial botulinum serotype D HA-17 β4/β5 β-hairpin turn, a Clostridial botulinum serotype A NTNH β4/β5 6-hairpin turn, a Clostridial botulinum serotype B NTNH β4/β5 6-hairpin turn, a Clostridial botulinum serotype C1 NTNH β4/β5 6-hairpin turn, a Clostridial botulinum serotype D NTNH β4/β5 β-hairpin turn, a Clostridial botulinum serotype E NTNH β4/β5 6-hairpin turn, a Clostridial botulinum serotype F NTNH β4/β5 6-hairpin turn, a Clostridial botulinum serotype G NTNH β4/β5 6-hairpin turn, a FGF-1 β4/β5 β-hairpin turn, a FGF-2 β4/β5 β-hairpin turn, a FGF-4 β4/β5 β-hairpin turn, a FGF-8 β4/β5 β-hairpin turn, a FGF-9 β4/β5 β-hairpin turn, a FGF-17 β4/β5 β-hairpin turn and a FGF-18 β4/β5 β-hairpin turn.

27. The modified Clostridial toxin according to 1, wherein the modified Clostridial toxin binding domain comprises a substitution of a Clostridial toxin binding domain β8/β9 6-hairpin turn for a β8/β9 6-hairpin turn selected from the group consisting of a Clostridial botulinum serotype A HA-33 β8/β9 β-hairpin turn, a Clostridial botulinum serotype B HA-33 1β8/β9 β-hairpin turn, a Clostridial botulinum serotype C1 HA-33 1β8/β9 β-hairpin turn, a Clostridial botulinum serotype D HA-33 1β8/β9 β-hairpin turn, a Clostridial botulinum serotype A HA-33 2β8/β9 β-hairpin turn, a Clostridial botulinum serotype B HA-33 2β8/β9 β-hairpin turn, a Clostridial botulinum serotype C1 HA-33 2β8/β9 β-hairpin turn, a Clostridial botulinum serotype D HA-33 2β8/β9 β-hairpin turn, a Clostridial botulinum serotype A HA-17 β8/β9 β-hairpin turn, a Clostridial botulinum serotype B HA-17 β8/β9 β-hairpin turn, a Clostridial botulinum serotype C1 HA-17 β8/β9 β-hairpin turn, a Clostridial botulinum serotype D HA-17 β8/β9 β-hairpin turn, a Clostridial botulinum serotype A NTNH β8/β9 6-hairpin turn, a Clostridial botulinum serotype B NTNH β8/β9 6-hairpin turn, a Clostridial botulinum serotype C1 NTNH β8/β9 6-hairpin turn, a Clostridial botulinum serotype D NTNH β8/β9 6-hairpin turn, a Clostridial botulinum serotype E NTNH β8/β9 6-hairpin turn, a Clostridial botulinum serotype F NTNH β8/β9 6-hairpin turn, a Clostridial botulinum serotype G NTNH β8/β9 6-hairpin turn, a FGF-1 β8/β9 β-hairpin turn, a FGF-2 β8/β9 β-hairpin turn, a FGF-4 β8/β9 β-hairpin turn, a FGF-8 β8/β9 β-hairpin turn, a FGF-9 β8/β9 β-hairpin turn, a FGF-17 β8/β9 β-hairpin turn and a FGF-18 β8/β9 β-hairpin turn.

28. The modified Clostridial toxin according to 1, wherein the protease cleavage site is an endogenous Clostridial toxin di-chain loop protease cleavage site or an exogenous cleavage site.

29. The modified Clostridial toxin according to 28, wherein the endogenous Clostridial toxin di-chain loop protease cleavage site is selected from the group consisting of a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

30. The modified Clostridial toxin according to 28, wherein the exogenous protease cleavage site is selected from the group consisting of an enterokinase cleavage site, a Thrombin cleavage site, a Factor Xa cleavage site, a human rhinovirus 3C protease cleavage site, a tobacco etch virus protease cleavage site, a dipeptidyl aminopeptidase cleavage site, a small ubiquitin-like modifier (SUMO)/ubiquitin-like protein-1(ULP-1) protease cleavage site, and a Clostridial toxin substrate cleavage site.

31. The modified Clostridial toxin according to 30, wherein the Clostridial toxin substrate cleavage site is selected from the group consisting of a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site and a TeNT substrate cleavage site.

32. A modified Clostridial toxin comprising: a) a Clostridial toxin enzymatic domain capable of executing an enzymatic target modification step of a Clostridial toxin intoxication process; b) a Clostridial toxin translocation domain capable of executing a translocation step of a Clostridial toxin intoxication process; c) an enhanced targeting domain comprising a Clostridial non-toxin associated protein β-trefoil domain capable of executing a cell binding step of a Clostridial toxin intoxication process; and d) a protease cleavage site; wherein cleavage of the protease cleavage site converts the single-chain form of the modified Clostridial toxin into the di-chain form.

33. The modified Clostridial toxin according to 32, wherein the modified Clostridial toxin comprises, in a linear amino-to-carboxyl single polypeptide order, the Clostridial toxin enzymatic domain, the protease cleavage site, the Clostridial toxin translocation domain and the enhanced targeting domain.

34. The modified Clostridial toxin according to 32, wherein the modified Clostridial toxin comprises, in a linear amino-to-carboxyl single polypeptide order, the Clostridial toxin enzymatic domain, the protease cleavage site, the enhanced targeting domain and the Clostridial toxin translocation domain.

35. The modified Clostridial toxin according to 32, wherein the modified Clostridial toxin comprises, in a linear amino-to-carboxyl single polypeptide order, the enhanced targeting domain, the Clostridial toxin translocation domain, the protease cleavage site and the Clostridial toxin enzymatic domain.

36. The modified Clostridial toxin according to 32, wherein the modified Clostridial toxin comprises, in a linear amino-to-carboxyl single polypeptide order, the enhanced targeting domain, the Clostridial toxin enzymatic domain, the protease cleavage site and the Clostridial toxin translocation domain.

37. The modified Clostridial toxin according to 32, wherein the modified Clostridial toxin comprises, in a linear amino-to-carboxyl single polypeptide order, the Clostridial toxin translocation domain, the protease cleavage site, the Clostridial toxin enzymatic domain and the enhanced targeting domain.

38. The modified Clostridial toxin according to 32, wherein the modified Clostridial toxin comprises, in a linear amino-to-carboxyl single polypeptide order, the Clostridial toxin translocation domain, the protease cleavage site, the enhanced targeting domain and the Clostridial toxin enzymatic domain.

39. The modified Clostridial toxin according to 32, wherein the Clostridial toxin enzymatic domain is selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain and a TeNT enzymatic domain.

40. The modified Clostridial toxin according to 32, wherein the Clostridial toxin translocation domain is selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain and a TeNT translocation domain.

41. The modified Clostridial toxin according to 32, wherein the Clostridial non-toxin associated protein 13-trefoil domain is selected from the group consisting of a Clostridial botulinum serotype A HA-33 β-trefoil domain, a Clostridial botulinum serotype B HA-33 β-trefoil domain, a Clostridial botulinum serotype C1 HA-33 β-trefoil domain, a Clostridial botulinum serotype D HA-33 β-trefoil domain, a Clostridial botulinum serotype A HA-17 β-trefoil domain, a Clostridial botulinum serotype B HA-17 β-trefoil domain, a Clostridial botulinum serotype C1 HA-17 β-trefoil domain, a Clostridial botulinum serotype D HA-17 β-trefoil domain, a Clostridial botulinum serotype A NTNH β-trefoil domain, a Clostridial botulinum serotype B NTNH β-trefoil domain, a Clostridial botulinum serotype C1 NTNH β-trefoil domain, a Clostridial botulinum serotype D NTNH β-trefoil domain, a Clostridial botulinum serotype E NTNH β-trefoil domain, a Clostridial botulinum serotype F NTNH β-trefoil domain and a Clostridial botulinum serotype G NTNH β-trefoil domain.

42. The modified Clostridial toxin according to 32, wherein the protease cleavage site is an endogenous Clostridial toxin di-chain loop protease cleavage site or an exogenous cleavage site.

43. The modified Clostridial toxin according to 42, wherein the endogenous Clostridial toxin di-chain loop protease cleavage site is selected from the group consisting of a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

44. The modified Clostridial toxin according to 42, wherein the exogenous protease cleavage site is selected from the group consisting of an enterokinase cleavage site, a Thrombin cleavage site, a Factor Xa cleavage site, a human rhinovirus 3C protease cleavage site, a tobacco etch virus protease cleavage site, a dipeptidyl aminopeptidase cleavage site, a small ubiquitin-like modifier (SUMO)/ubiquitin-like protein-1(ULP-1) protease cleavage site, and a Clostridial toxin substrate cleavage site.

45. The modified Clostridial toxin according to 44, wherein the Clostridial toxin substrate cleavage site is selected from the group consisting of a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site and a TeNT substrate cleavage site.

46. A modified Clostridial toxin comprising: a) a Clostridial toxin enzymatic domain capable of executing an enzymatic target modification step of a Clostridial toxin intoxication process; b) a Clostridial toxin translocation domain capable of executing a translocation step of a Clostridial toxin intoxication process; c) an enhanced targeting domain comprising a FGF β-trefoil domain capable of selectively binding an FGFR3; and d) a protease cleavage site; wherein cleavage of the protease cleavage site converts the single-chain form of the modified Clostridial toxin into the di-chain form.

47. The modified Clostridial toxin according to 46, wherein the modified Clostridial toxin comprises, in a linear amino-to-carboxyl single polypeptide order, the Clostridial toxin enzymatic domain, the protease cleavage site, the Clostridial toxin translocation domain and the enhanced targeting domain.

48. The modified Clostridial toxin according to 46, wherein the modified Clostridial toxin comprises, in a linear amino-to-carboxyl single polypeptide order, the Clostridial toxin enzymatic domain, the protease cleavage site, the enhanced targeting domain and the Clostridial toxin translocation domain.

49. The modified Clostridial toxin according to 46, wherein the modified Clostridial toxin comprises, in a linear amino-to-carboxyl single polypeptide order, the enhanced targeting domain, the Clostridial toxin translocation domain, the protease cleavage site and the Clostridial toxin enzymatic domain.

50. The modified Clostridial toxin according to 46, wherein the modified Clostridial toxin comprises, in a linear amino-to-carboxyl single polypeptide order, the enhanced targeting domain, the Clostridial toxin enzymatic domain, the protease cleavage site and the Clostridial toxin translocation domain.

51. The modified Clostridial toxin according to 46, wherein the modified Clostridial toxin comprises, in a linear amino-to-carboxyl single polypeptide order, the Clostridial toxin translocation domain, the protease cleavage site, the Clostridial toxin enzymatic domain and the enhanced targeting domain.

52. The modified Clostridial toxin according to 46, wherein the modified Clostridial toxin comprises, in a linear amino-to-carboxyl single polypeptide order, the Clostridial toxin translocation domain, the protease cleavage site, the enhanced targeting domain and the Clostridial toxin enzymatic domain.

53. The modified Clostridial toxin according to 46, wherein the Clostridial toxin enzymatic domain is selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain and a TeNT enzymatic domain.

54. The modified Clostridial toxin according to 46, wherein the Clostridial toxin translocation domain is selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain and a TeNT translocation domain.

55. The modified Clostridial toxin according to 46, wherein the FGF β-trefoil domain is selected from the group consisting of a FGF-1 β-trefoil domain, a FGF-2 β-trefoil domain, a FGF-4 β-trefoil domain, a FGF-8 β-trefoil domain, a FGF-9 β-trefoil domain, a FGF-17 β-trefoil domain and a FGF-18 β-trefoil domain.
56. The modified Clostridial toxin according to 46, wherein the protease cleavage site is an endogenous Clostridial toxin di-chain loop protease cleavage site or an exogenous cleavage site.
57. The modified Clostridial toxin according to 56, wherein the endogenous Clostridial toxin di-chain loop protease cleavage site is selected from the group consisting of a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.
58. The modified Clostridial toxin according to 56, wherein the exogenous protease cleavage site is selected from the group consisting of an enterokinase cleavage site, a Thrombin cleavage site, a Factor Xa cleavage site, a human rhinovirus 3C protease cleavage site, a tobacco etch virus protease cleavage site, a dipeptidyl aminopeptidase cleavage site, a small ubiquitin-like modifier (SUMO)/ubiquitin-like protein-1(ULP-1) protease cleavage site, and a Clostridial toxin substrate cleavage site.
59. The modified Clostridial toxin according to 58, wherein the Clostridial toxin substrate cleavage site is selected from the group consisting of a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site and a TeNT substrate cleavage site.
60. A polynucleotide molecule encoding a modified Clostridial toxin, the polynucleotide molecule comprising: a) a polynucleotide molecule encoding a Clostridial toxin enzymatic domain capable of executing an enzymatic target modification step of a Clostridial toxin intoxication process; b) a polynucleotide molecule encoding a Clostridial toxin translocation domain capable of executing a translocation step of a Clostridial toxin intoxication process; c) a polynucleotide molecule encoding an enhanced targeting domain comprising a modified Clostridial binding domain capable of executing a cell binding step of a Clostridial toxin intoxication process; and d) a polynucleotide molecule encoding a protease cleavage site; wherein cleavage of the protease cleavage site converts the single-chain form of the modified Clostridial toxin into the di-chain form; and wherein the modified Clostridial binding domain exhibits enhanced binding activity for an endogenous Clostridial toxin receptor system relative to the binding activity of a naturally-occurring Clostridial binding domain from which the modified Clostridial binding domain is derived.
61. The polynucleotide molecule according to 60, wherein the polynucleotide molecule encodes the modified Clostridial toxin of any one of Claims 2-7.

62. The polynucleotide molecule according to 60, wherein the polynucleotide molecule encodes a Clostridial toxin enzymatic domain selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain and a TeNT enzymatic domain.
63. The polynucleotide molecule according to 60, wherein the polynucleotide molecule encodes a Clostridial toxin translocation domain selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain and a TeNT translocation domain.
64. The polynucleotide molecule according to 60, wherein the polynucleotide molecule encodes a modified Clostridial toxin binding domain selected from the group consisting of a modified BoNT/A binding domain, a modified BoNT/B binding domain, a modified BoNT/C1 binding domain, a modified BoNT/D binding domain, a modified BoNT/E binding domain, a modified BoNT/F binding domain, a modified BoNT/G binding domain and a modified TeNT binding domain.
65. The polynucleotide molecule according to 60, wherein the polynucleotide molecule encodes a modified Clostridial toxin binding domain comprising a substitution of a Clostridial toxin binding domain α-fold for an α-fold selected from the group consisting of a Clostridial botulinum serotype A HA-33 1α-fold, a Clostridial botulinum serotype B HA-33 1α-fold, a Clostridial botulinum serotype C1 HA-33 1α-fold, a Clostridial botulinum serotype D HA-33 1α-fold, a Clostridial botulinum serotype A HA-33 2α-fold, a Clostridial botulinum serotype B HA-33 2α-fold, a Clostridial botulinum serotype C1 HA-33 2α-fold, a Clostridial botulinum serotype D HA-33 2α-fold, a Clostridial botulinum serotype A HA-17 α-fold, a Clostridial botulinum serotype B HA-17 α-fold, a Clostridial botulinum serotype C1 HA-17 α-fold, a Clostridial botulinum serotype D HA-17 α-fold, a Clostridial botulinum serotype A NTNH α-fold, a Clostridial botulinum serotype B NTNH α-fold, a Clostridial botulinum serotype C1 NTNH α-fold, a Clostridial botulinum serotype D NTNH α-fold, a Clostridial botulinum serotype E NTNH α-fold, a Clostridial botulinum serotype F NTNH α-fold, a Clostridial botulinum serotype G NTNH α-fold, a FGF-1 α-fold, a FGF-2 α-fold, a FGF-4 α-fold, a FGF-8 α-fold, a FGF-9 α-fold, a FGF-17 α-fold and a FGF-18 α-fold.
66. The polynucleotide molecule according to 60, wherein the polynucleotide molecule encodes a modified Clostridial toxin binding domain comprising a substitution of a Clostridial toxin binding domain β-fold for a β-fold selected from the group consisting of a Clostridial botulinum serotype A HA-33 1β-fold, a Clostridial botulinum serotype B HA-33 1β-fold, a Clostridial botulinum serotype C1 HA-33 1β-fold, a Clostridial botulinum serotype D HA-33 1β-fold, a Clostridial botulinum serotype A HA-33 2β-fold, a Clostridial botulinum serotype B HA-33 2β-fold, a Clostridial botulinum serotype C1 HA-33 2β-fold, a Clostridial botulinum serotype D HA-33 2β-fold, a Clostridial botulinum serotype A HA-17 β-fold, a Clostridial botulinum serotype B HA-17 β-fold, a Clostridial botulinum serotype C1 HA-17 β-fold, a Clostridial botulinum serotype D HA-17 β-fold, a Clostridial botulinum serotype A NTNH β-fold, a Clostridial botulinum serotype B NTNH β-fold, a Clostridial botulinum serotype C1 NTNH β-fold, a Clostridial botulinum serotype D NTNH β-fold, a Clostridial botulinum serotype E NTNH β-fold, a Clostridial botulinum serotype F NTNH β-fold, a Clostridial botulinum serotype G NTNH β-fold, a FGF-1

β-fold, a FGF-2 β-fold, a FGF-4 β-fold, a FGF-8 β-fold, a FGF-9 β-fold, a FGF-17 β-fold and a FGF-18 β-fold.

67. The polynucleotide molecule according to 60, wherein the polynucleotide molecule encodes a modified Clostridial toxin binding domain comprising a substitution of a Clostridial toxin binding domain γ-fold for a γ-fold selected from the group consisting of a Clostridial botulinum serotype A HA-33 1γ-fold, a Clostridial botulinum serotype B HA-33 1γ-fold, a Clostridial botulinum serotype C1 HA-33 1γ-fold, a Clostridial botulinum serotype D HA-33 1γ-fold, a Clostridial botulinum serotype A HA-33 2γ-fold, a Clostridial botulinum serotype B HA-33 2γ-fold, a Clostridial botulinum serotype C1 HA-33 2γ-fold, a Clostridial botulinum serotype D HA-33 2γ-fold, a Clostridial botulinum serotype A HA-17 γ-fold, a Clostridial botulinum serotype B HA-17 γ-fold, a Clostridial botulinum serotype C1 HA-17 γ-fold, a Clostridial botulinum serotype D HA-17 γ-fold, a Clostridial botulinum serotype A NTNH γ-fold, a Clostridial botulinum serotype B NTNH γ-fold, a Clostridial botulinum serotype C1 NTNH γ-fold, a Clostridial botulinum serotype D NTNH γ-fold, a Clostridial botulinum serotype E NTNH γ-fold, a Clostridial botulinum serotype F NTNH γ-fold, a Clostridial botulinum serotype G NTNH γ-fold, a FGF-1 γ-fold, a FGF-2 γ-fold, a FGF-4 γ-fold, a FGF-8 γ-fold, a FGF-9 γ-fold, a FGF-17 γ-fold and a FGF-18 γ-fold.

68. The polynucleotide molecule according to 60, wherein the polynucleotide molecule encodes a modified Clostridial toxin binding domain comprising a substitution of a Clostridial toxin binding domain β4/β5 β-hairpin turn for a β4/β5 β-hairpin turn selected from the group consisting of a Clostridial botulinum serotype A HA-33 β4/β5 β-hairpin turn, a Clostridial botulinum serotype B HA-33 1β4/β5 β-hairpin turn, a Clostridial botulinum serotype C1 HA-33 1β4/β5 β-hairpin turn, a Clostridial botulinum serotype D HA-33 1β4/β5 β-hairpin turn, a Clostridial botulinum serotype A HA-33 2β4/β5 β-hairpin turn, a Clostridial botulinum serotype B HA-33 2β4/β5 β-hairpin turn, a Clostridial botulinum serotype C1 HA-33 2β4/β5 β-hairpin turn, a Clostridial botulinum serotype D HA-33 2β4/β5 β-hairpin turn, a Clostridial botulinum serotype A HA-17 β4/β5 β-hairpin turn, a Clostridial botulinum serotype B HA-17 β4/β5 β-hairpin turn, a Clostridial botulinum serotype C1 HA-17 β4/β5 β-hairpin turn, a Clostridial botulinum serotype D HA-17 β4/β5 β-hairpin turn, a Clostridial botulinum serotype A NTNH β4/β5 β-hairpin turn, a Clostridial botulinum serotype B NTNH β4/β5 β-hairpin turn, a Clostridial botulinum serotype C1 NTNH β4/β5 β-hairpin turn, a Clostridial botulinum serotype D NTNH β4/β5 β-hairpin turn, a Clostridial botulinum serotype E NTNH β4/β5 β-hairpin turn, a Clostridial botulinum serotype F NTNH β4/β5 β-hairpin turn, a Clostridial botulinum serotype G NTNH β4/β5 β-hairpin turn, a FGF-1 β4/β5 β-hairpin turn, a FGF-2 β4/β5 β-hairpin turn, a FGF-4 β4/β5 β-hairpin turn, a FGF-8 β4/β5 β-hairpin turn, a FGF-9 β4/β5 β-hairpin turn, a FGF-17 β4/β5 β-hairpin turn and a FGF-18 β4/β5 β-hairpin turn.

69. The polynucleotide molecule according to 60, wherein the polynucleotide molecule encodes a modified Clostridial toxin binding domain comprising a substitution of a Clostridial toxin binding domain β8/β9 β-hairpin turn for a β8/β9 β-hairpin turn selected from the group consisting of a Clostridial botulinum serotype A HA-33 β8/β9 β-hairpin turn, a Clostridial botulinum serotype B HA-33 1β8/β9 β-hairpin turn, a Clostridial botulinum serotype C1 HA-33 1β8/β9 β-hairpin turn, a Clostridial botulinum serotype D HA-33 1β8/β9 β-hairpin turn, a Clostridial botulinum serotype A HA-33 2β8/β9 β-hairpin turn, a Clostridial botulinum serotype B HA-33 2β8/β9 β-hairpin turn, a Clostridial botulinum serotype C1 HA-33 2β8/β9 β-hairpin turn, a Clostridial botulinum serotype D HA-33 2β8/β9 β-hairpin turn, a Clostridial botulinum serotype A HA-17 β8/β9 β-hairpin turn, a Clostridial botulinum serotype B HA-17 β8/β9 β-hairpin turn, a Clostridial botulinum serotype C1 HA-17 β8/β9 β-hairpin turn, a Clostridial botulinum serotype D HA-17 β8/β9 β-hairpin turn, a Clostridial botulinum serotype A NTNH β8/β9 β-hairpin turn, a Clostridial botulinum serotype B NTNH β8/β9 β-hairpin turn, a Clostridial botulinum serotype C1 NTNH β8/β9 β-hairpin turn, a Clostridial botulinum serotype D NTNH β8/β9 β-hairpin turn, a Clostridial botulinum serotype E NTNH β8/β9 β-hairpin turn, a Clostridial botulinum serotype F NTNH β8/β9 β-hairpin turn, a Clostridial botulinum serotype G NTNH β8/β9 β-hairpin turn, a FGF-1 β8/β9 β-hairpin turn, a FGF-2 β8/β9 β-hairpin turn, a FGF-4 β8/β9 β-hairpin turn, a FGF-8 β8/β9 β-hairpin turn, a FGF-9 β8/β9 β-hairpin turn, a FGF-17 β8/β9 β-hairpin turn and a FGF-18 β8/β9 β-hairpin turn.

70. The polynucleotide molecule according to 60, wherein the polynucleotide molecule encoding the protease cleavage site is an endogenous Clostridial toxin di-chain loop protease cleavage site or an exogenous cleavage site.

71. The polynucleotide molecule according to 60, wherein the polynucleotide molecule comprises an expression vector.

72. A polynucleotide molecule encoding a modified Clostridial toxin, the polynucleotide molecule comprising: a) a polynucleotide molecule encoding a Clostridial toxin enzymatic domain capable of executing an enzymatic target modification step of a Clostridial toxin intoxication process; b) a polynucleotide molecule encoding a Clostridial toxin translocation domain capable of executing a translocation step of a Clostridial toxin intoxication process; c) a polynucleotide molecule encoding an enhanced targeting domain comprising a Clostridial non-toxin associated protein β-trefoil domain capable of executing a cell binding step of a Clostridial toxin intoxication process; and d) a polynucleotide molecule encoding a protease cleavage site; wherein cleavage of the protease cleavage site converts the single-chain form of the modified Clostridial toxin into the di-chain form.

73. The polynucleotide molecule according to 72, wherein the polynucleotide molecule encodes a modified Clostridial toxin of any one of Claims 33-38.

74. The polynucleotide molecule according to 72, wherein the polynucleotide molecule encodes a Clostridial toxin enzymatic domain selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain and a TeNT enzymatic domain.

75. The polynucleotide molecule according to 72, wherein the polynucleotide molecule encodes a Clostridial toxin translocation domain selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain and a TeNT translocation domain.

76. The polynucleotide molecule according to 72, wherein the polynucleotide molecule encodes a Clostridial non-toxin associated protein β-trefoil domain selected from the group consisting of a Clostridial botulinum serotype A HA-33 β-trefoil domain, a Clostridial botulinum serotype B HA-33 β-trefoil domain, a Clostridial botulinum serotype C1 HA-33 β-trefoil domain, a Clostridial botulinum serotype D HA-33 β-trefoil domain, a Clostridial botulinum serotype A HA-17 β-trefoil domain, a Clostridial botulinum serotype B HA-17 β-trefoil domain, a Clostridial botulinum serotype C1 HA-17 β-trefoil domain, a Clostridial botulinum serotype D HA-17 β-trefoil domain, a Clostridial botulinum serotype A NTNH β-trefoil domain, a Clostridial botulinum serotype B NTNH β-trefoil domain, a Clostridial botulinum serotype C1 NTNH (3-trefoil domain, a Clostridial botulinum serotype D NTNH β-trefoil domain, a Clostridial botulinum serotype E NTNH β-trefoil domain, a Clostridial botulinum serotype F NTNH β-trefoil domain and a Clostridial botulinum serotype G NTNH β-trefoil domain.

77. The polynucleotide molecule according to 72, wherein the polynucleotide molecule encoding the protease cleavage site is an endogenous Clostridial toxin di-chain loop protease cleavage site or an exogenous cleavage site.

78. The polynucleotide molecule according to 60, wherein the polynucleotide molecule comprises an expression vector.

79. A polynucleotide molecule encoding a modified Clostridial toxin, the polynucleotide molecule comprising: a) a polynucleotide molecule encoding a Clostridial toxin enzymatic domain capable of executing an enzymatic target modification step of a Clostridial toxin intoxication process; b) a polynucleotide molecule encoding a Clostridial toxin translocation domain capable of executing a translocation step of a Clostridial toxin intoxication process; c) a polynucleotide molecule encoding an enhanced targeting domain comprising a FGF β-trefoil domain capable of selectively binding an FGFR3; and d) a polynucleotide molecule encoding a protease cleavage site; wherein cleavage of the protease cleavage site converts the single-chain form of the modified Clostridial toxin into the di-chain form.

80. The polynucleotide molecule according to 79, wherein the polynucleotide molecule encodes a modified Clostridial toxin of any one of Claims 47-52.

81. The polynucleotide molecule according to 79, wherein the polynucleotide molecule encodes a Clostridial toxin enzymatic domain selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain and a TeNT enzymatic domain.

82. The polynucleotide molecule according to 79, wherein the polynucleotide molecule encodes a Clostridial toxin translocation domain selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain and a TeNT translocation domain.

83. The polynucleotide molecule according to 79, wherein the polynucleotide molecule encodes a FGF β-trefoil domain selected from the group consisting of a FGF-1 β-trefoil domain, a FGF-2 β-trefoil domain, a FGF-4 β-trefoil domain, a FGF-8 β-trefoil domain, a FGF-9 β-trefoil domain, a FGF-17 β-trefoil domain and a FGF-18 β-trefoil domain.

84. The polynucleotide molecule according to 79, wherein the polynucleotide molecule encoding the protease cleavage site is an endogenous Clostridial toxin di-chain loop protease cleavage site or an exogenous cleavage site.

85. The polynucleotide molecule according to 79, wherein the polynucleotide molecule comprises an expression vector.

86. A method of producing a modified Clostridial toxin comprising the step of expressing a polynucleotide molecule encoding a modified Clostridial toxin in a cell, the polynucleotide molecule comprising: a) a polynucleotide molecule encoding a Clostridial toxin enzymatic domain capable of executing an enzymatic target modification step of a Clostridial toxin intoxication process; b) a polynucleotide molecule encoding a Clostridial toxin translocation domain capable of executing a translocation step of a Clostridial toxin intoxication process; c) a polynucleotide molecule encoding an enhanced targeting domain comprising a modified Clostridial binding domain capable of executing a cell binding step of a Clostridial toxin intoxication process; and d) a polynucleotide molecule encoding a protease cleavage site; wherein cleavage of the protease cleavage site converts the single-chain form of the modified Clostridial toxin into the di-chain form; and wherein the modified Clostridial binding domain exhibits enhanced binding activity for an endogenous Clostridial toxin receptor system relative to the binding activity of a naturally-occurring Clostridial binding domain from which the modified Clostridial binding domain is derived.

87. A method of producing a modified Clostridial toxin comprising the step of expressing a polynucleotide molecule encoding a modified Clostridial toxin in a cell, the polynucleotide molecule comprising: a) a polynucleotide molecule encoding a Clostridial toxin enzymatic domain capable of executing an enzymatic target modification step of a Clostridial toxin intoxication process; b) a polynucleotide molecule encoding a Clostridial toxin translocation domain capable of executing a translocation step of a Clostridial toxin intoxication process; c) a polynucleotide molecule encoding an enhanced targeting domain comprising a Clostridial non-toxin associated protein β-trefoil domain capable of executing a cell binding step of a Clostridial toxin intoxication process; and d) a polynucleotide molecule encoding a protease cleavage site; wherein cleavage of the protease cleavage site converts the single-chain form of the modified Clostridial toxin into the di-chain form.

88. A method of producing a modified Clostridial toxin comprising the step of expressing a polynucleotide molecule encoding a modified Clostridial toxin in a cell, the polynucleotide molecule comprising: a) a polynucleotide molecule encoding a Clostridial toxin enzymatic domain capable of executing an enzymatic target modification step of a Clostridial toxin intoxication process; b) a polynucleotide molecule encoding a Clostridial toxin translocation domain capable of executing a translocation step of a Clostridial toxin intoxication process; c) a polynucleotide molecule encoding an enhanced targeting domain comprising a FGF β-trefoil domain capable of selectively binding an FGFR3; and d) a polynucleotide molecule encoding a protease cleavage site; wherein cleavage of the protease cleavage site converts the single-chain form of the modified Clostridial toxin into the di-chain form.

89. A method of producing a modified Clostridial toxin comprising the steps of: a) introducing into a cell a polynucleotide molecule encoding a modified Clostridial toxin, the polynucleotide molecule comprising: i) a polynucleotide molecule encoding a Clostridial toxin enzymatic domain capable of executing an enzymatic target modification step of a Clostridial toxin intoxication process; ii) a polynucleotide molecule encoding a Clostridial toxin translocation domain capable of executing a translocation step of a Clostridial toxin intoxication process; iii) a polynucleotide molecule encoding an enhanced targeting domain comprising a modified Clostridial binding domain capable of executing a cell binding step of a Clostridial toxin intoxication process; and iv) a polynucleotide molecule encoding a protease cleavage site; wherein cleavage of the protease cleavage site converts the single-chain form of the modified Clostridial toxin into the di-chain form; and wherein the modified Clostridial binding domain exhibits enhanced binding activity for an endogenous Clostridial toxin receptor system relative to the binding activity of a naturally-occurring Clostridial binding domain from which the modified Clostridial binding domain is derived; and b) expressing the modified Clostridial toxin encoded by the polynucleotide molecule.

90. A method of producing a modified Clostridial toxin comprising the steps of: a) introducing into a cell a polynucleotide molecule encoding a modified Clostridial toxin, the polynucleotide molecule comprising: i) a polynucleotide molecule encoding a Clostridial toxin enzymatic domain capable of executing an enzymatic target modification step of a Clostridial toxin intoxication process; ii) a polynucleotide molecule encoding a Clostridial toxin translocation domain capable of executing a translocation step of a Clostridial toxin intoxication process; iii) a polynucleotide molecule encoding an enhanced targeting domain comprising a Clostridial non-toxin associated protein β-trefoil domain capable of executing a cell binding step of a Clostridial toxin intoxication process; and iv) a polynucleotide molecule encoding a protease cleavage site; wherein cleavage of the protease cleavage site converts the single-chain form of the modified Clostridial toxin into the di-chain form; and b) expressing the modified Clostridial toxin encoded by the polynucleotide molecule.

91. A method of producing a modified Clostridial toxin comprising the steps of: a) introducing into a cell a polynucleotide molecule encoding a modified Clostridial toxin, the polynucleotide molecule comprising: i) a polynucleotide molecule encoding a Clostridial toxin enzymatic domain capable of executing an enzymatic target modification step of a Clostridial toxin intoxication process; ii) a polynucleotide molecule encoding a Clostridial toxin translocation domain capable of executing a translocation step of a Clostridial toxin intoxication process; iii) a polynucleotide molecule encoding an enhanced targeting domain comprising a FGF β-trefoil domain capable of selectively binding an FGFR3; and iv) a polynucleotide molecule encoding a protease cleavage site; wherein cleavage of the protease cleavage site converts the single-chain form of the modified Clostridial toxin into the di-chain form; and b) expressing the modified Clostridial toxin encoded by the polynucleotide molecule.

EXAMPLES

The following non-limiting examples are provided for illustrative purposes only in order to facilitate a more complete understanding of disclosed embodiments and are in no way intended to limit any of the embodiments disclosed in the present specification.

Example 1

Construction of a Modified Clostridial Toxin Comprising a Modified Clostridial Toxin Binding Domain with Enhanced Binding Activity This example illustrates how to make a modified Clostridial toxin comprising a modified Clostridial toxin binding domain with enhanced binding activity using site-directed mutagenesis.

A polynucleotide molecule encoding BoNT/A (SEQ ID NO: 1) is synthesized using standard procedures (BlueHeron® Biotechnology, Bothell, Wash.). Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-ED-PAR1Tb. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule encoding BoNT/A (SEQ ID NO: 1) can be synthesized in order to improve expression in an *Escherichia coli* strain. The polynucleotide molecule encoding the BoNT/A can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, PCT Patent Serial No. 2005/020578 (Jun. 9, 2005); Lance E. Steward et al. Optimizing Expression of Active Botulinum Toxin Type A, PCT Patent Serial No. 2005/027917 (Aug. 3, 2005). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). Is so desired, optimization to a different organism, such as, e.g., a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005).

A similar cloning strategy is used to make pUCBHB1 cloning constructs comprising a polynucleotide molecule encoding BoNT/B of SEQ ID NO: 2; a polynucleotide molecule encoding BoNT/C1 of SEQ ID NO: 3; a polynucleotide molecule encoding BoNT/D of SEQ ID NO: 4; a polynucleotide molecule encoding BoNT/E of SEQ ID NO: 5; a polynucleotide molecule encoding BoNT/F of SEQ ID NO: 6; a polynucleotide molecule encoding BoNT/G of SEQ ID NO: 7; and a polynucleotide molecule encoding TeNT of SEQ ID NO: 8. In addition, one skilled in the art can modify Clostridial toxins, such as, e.g., to include an exogenous protease cleavage site within the di-chain loop region, or flexible spacer regions.

To construct pET29/BoNT/A, a pUCBHB1/BoNT/A construct is digested with restriction endonucleases that 1) excise the insert comprising the open reading frame of SEQ ID NO: 1 encoding BoNT/A; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding the BoNT/A of SEQ ID NO: 1 operably-linked to a carboxyl terminal polyhistidine affinity binding peptide.

A similar cloning strategy is used to make pET29 expression constructs comprising a polynucleotide molecule encoding BoNT/B of SEQ ID NO: 2; a polynucleotide molecule encoding BoNT/C1 of SEQ ID NO: 3; a polynucleotide molecule encoding BoNT/D of SEQ ID NO: 4; a polynucleotide molecule encoding BoNT/E of SEQ ID NO: 5; a polynucleotide molecule encoding BoNT/F of SEQ ID NO: 6; a polynucleotide molecule encoding BoNT/G of SEQ ID NO: 7; and a polynucleotide molecule encoding TeNT of SEQ ID NO: 8.

To construct a modified BoNT/A comprising a modified binding domain with enhanced binding activity, specific amino acids influencing binding activity will be changed. It is already known that amino acids Trp 1101, Gly 1102, Leu 1105, Tyr 1111, Tyr 1112, Gly 1158, Ile 1163, Asp 1179, Glu 1203, Phe 1252, Ser 1264, Trp 1266, Tyr 1267, Gln 1270, Gly 1279 and Trp 1282 of SEQ ID NO: 1 are important for function. To determine which amino acid substitutions could enhance the binding activity of a BoNT/A binding domain, computational protein design algorithims will generate novel proteins with optimized properties. The crystal structure of a BoNT/A binding domain will be used as the starting template for computational calculations. Potential amino acid candidates will be identified using a combined output from Protein Design Automation® (PDA®) and Sequence Prediction Algorithm™ (SPA™) calculations. For PDA calculations, the conformations of amino acids at variable positions will be represented as a set of backbone-independent side chain rotamers derived from the rotamer library. The energies of all possible combinations of the considered amino acids at the chosen variable positions will be calculated using a force field containing terms describing van der Waals, solvation, electrostatic, and hydrogen bond interactions. The optimal (ground state) sequence will be determined using a Dead End Elimination (DEE) algorithm, and a Monte Carlo (MC) algorithm will be used to evaluate the energies of similar sequences around the predicted ground state. SPA calculations utilize a genetic algorithm to screen for low energy sequences, with energies being calculated during each round of "evolution" for those sequences being sampled. The conformations of amino acids will be represented as a set of side chain rotamers derived from a backbone-independent rotamer library using a flexible rotamer model. SPA calculations will generate sequences which will be subsequently clustered computationally into groups of similar sequences using a nearest neighbor single linkage hierarchical clustering algorithm. Critical contact amino acids will be fixed in both sequence and conformation and calculations will be carried out to evaluate single and combinatorial substitutions at variable amino acids. All amino acids in contact with these residues will be floated, that is the amino acid conformation but not the amino acid identity will be allowed to vary to allow for conformational adjustments. Final experimental substitutions will be chosen based on their predicted energies relative to the naturally occurring BoNT/A binding domain and their occupancy, that is the number times the substitution occurred in the set of 1000 MC or genetic algorithm sequences. Two sets of design calculations will be carried out using Rosetta to identify substitutions predicted to stabilize the BoNT/A binding domain. In the first round, only single amino acid substitutions will be modeled. In a second round, interface amino acids will be allowed to change to all 20 naturally occurring amino acids including the native amino acid type, but excluding cysteine, simultaneously. In each case, amino acid side chains contacting the substituted amino acid side chains will be repacked (allowing all rotamers of the native amino acid type). Sequences and conformations with low energies will be selected using a Monte-Carlo simulated annealing procedure. All resulting protein complex models will be rescored by computing a predicted binding energy. Final sequences were selected for the lowest binding energy Identified candidate amino acids will be changed using site-directed in vitro mutagenesis. A 50 μL reaction will be assembled using pET29/BoNT/A as a template, sense and antisense oligonucleotides encoding the desired amino acid change identified above, and reagents included with the QuickChange®II XL Site-Directed Mutagenesis kit (Stratagene, La Jolla, Calif.). The polymerase chain reaction (PCR) mix will contain 5 μL of 10× Buffer, 1 μL of deoxyribonucleotides (dNTPs), 1 μL of PfuUltra™ High Fidelity DNA polymerase (2.5 units/μL), 125 ng of each primer, 100 ng of template DNA, and nuclease-free water to a final volume of 50 μL. The thermocycler conditions will be: one cycle of 95° C. for 60 seconds; 16 cycles of 95° C. for 30 seconds, 55° C. for 60 seconds, and 72° C. for 10 minutes; one cycle of 72° C. for 5 minutes; and 4° C. to hold. Following thermocycling, 1 μL of DpnI restriction enzyme (Stratagene, La Jolla, Calif.) will be added to the reaction and will be incubated for 1 hour at 37° C. to digest the template DNA. The reaction will be purified by QIAquick kit (QIAGEN, Inc., Valencia, Calif.) and will be analysis by agarose gel electrophoresis to determine that the reaction produced full-length plasmid. The mutagenesis products will be transformed into chemically competent *E. coli* DH5α cells (Invitrogen, Inc, Carlsbad, Calif.) using a heat shock method, plated on 1.5% Luria-Bertani agar plates (pH 7.0) containing 100 μg/mL of Ampicillin, and will be placed in a 37° C. incubator for overnight growth. Candidate mutagenesis constructs will be isolated as Ampicillin resistant colonies and will be analyzed using an alkaline lysis plasmid mini-preparation procedure to isolate the expression construct and restriction endonuclease digests to determine the presence of the insert. The incorporation of the point mutation will be determined by sequence analysis of candidate plasmid constructs.

To test the binding activity of modified BoNT/A candidates with enhanced binding activity, the soluble portion of FGFR3 will be expressed recombinantly for use in surface plasmon resonance (SPR) binding assays, e.g., Biacore® (Biacore Inc., Piscataway, N.J.). The soluble portion of FGFR3 will be expressed as a fusion to streptavidin and the receptor will then be immobilized on an appropriate sensor chip. Utilizing a Biacore® instrument, changes in local refractive index as a result of receptor binding will be measured as a change in the SPR angle. The rates of change in the SPR angle will then be analyzed to determine association rate ($K_{on}$), dissociation rate ($K_{off}$) and the dissociation equilibrium constant ($K_D$=$K_{off}$/$K_{on}$). Modified BoNT/A candidates with enhanced binding activity will exhibit either an increased association rate, a decreased dissociation rate, both an increased association rate and a decreased dissociation rate, or a decreased dissociation equilibrium constant relative to the measurements obtained from the naturally occurring BoNT/A from which the modifeid BoNT/A with enhanced binding activity was derived.

Example 2

Construction of a Modified Clostridial Toxin Comprising a Non-Toxin Associated Protein The following example illustrates how to make a modified Clostridial toxin comprising an enhanced targeting domain comprising a non-toxin associated protein.

A polynucleotide molecule encoding BoNT/A-33/A is synthesized using standard procedures (BlueHeron® Biotechnology, Bothell, Wash.), as described in Example 1. BoNT/A-33/A is a BoNT/A modified to replace amino acids 1111-1296 of SEQ ID NO: 1, a BoNT/A 8-trefoil domain, with amino acids 151 to 293 of SEQ ID NO: 9, a HA-33 β-trefoil domain from a Clostridial botulinum serotype A strain. If desired, an expression optimized polynucleotide molecule encoding BoNT/A-33/A can be synthesized in order to improve expression in to a different organism, such as, e.g., an *Escherichia coli* strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for BoNT/B-33/A, a modified BoNT/B where amino acids 1098-1291 of SEQ ID NO: 2 are replaced with amino acids 151 to 293 of SEQ ID NO: 9; BoNT/C1-33/A, a modified BoNT/C1 where amino acids 1112-1291 of SEQ ID NO: 3 are replaced with amino acids 151 to 293 of SEQ ID NO: 9; BoNT/D-33/A, a modified BoNT/D where amino acids 1099-1276 of SEQ ID NO: 4 are replaced with amino acids 151 to 293 of SEQ ID NO: 9; BoNT/E-33/A, a modified BoNT/E where amino acids 1086-1252 of SEQ ID NO: 5 are replaced with amino acids 151 to 293 of SEQ ID NO: 9; BoNT/F-33/A, a modified BoNT/F where amino acids 1106-1274 of SEQ ID NO: 6 are replaced with amino acids 151 to 293 of SEQ ID NO: 9; BoNT/G-33/A, a modified BoNT/G where amino acids 1106-1297 of SEQ ID NO: 7 are replaced with amino acids 151 to 293 of SEQ ID NO: 9; and TeNT-33/A, a modified TeNT where amino acids 1128-1315 of SEQ ID NO: 8 are replaced with amino acids 151 to 293 of SEQ ID NO: 9. Similarly, the β-trefoil domain from a Clostridial toxin indicated above can be replaced with a non-toxin associated protein β-trefoil domain comprising amino acids 10-144 of SEQ ID NO: 9; amino acids 10-144 of SEQ ID NO: 10; amino acids 10-144 of SEQ ID NO: 11; amino acids 10-146 of SEQ ID NO: 12; amino acids 10-144 of SEQ ID NO: 13; amino acids 10-144 of SEQ ID NO: 14; amino acids 10-146 of SEQ ID NO: 15; amino acids 10-141 of SEQ ID NO: 16; amino acids 10-141 of SEQ ID NO: 17; amino acids 10-141 of SEQ ID NO: 18; 151-293 of SEQ ID NO: 10; 151-293 of SEQ ID NO: 11; 153-294 of SEQ ID NO: 12; 151-279 of SEQ ID NO: 13; 151-292 of SEQ ID NO: 14; 153-291 of SEQ ID NO: 15; 148-285 of SEQ ID NO: 16; 148-286 of SEQ ID NO: 17; 148-286 of SEQ ID NO: 18; 9-146 of SEQ ID NO: 19; 9-146 of SEQ ID NO: 20; 9-146 of SEQ ID NO: 21; 9-146 of SEQ ID NO: 22; 1050-1194 of SEQ ID NO: 23; 1050-1199 of SEQ ID NO: 24; 1050-1194 of SEQ ID NO: 25; 1049-1198 of SEQ ID NO: 26; 1049-1197 of SEQ ID NO: 27; 1049-1197 of SEQ ID NO: 28; 1014-1163 of SEQ ID NO: 29; 1016-1160 of SEQ ID NO: 30; 1017-1166 of SEQ ID NO: 31; and 1050-1199 of SEQ ID NO: 32.

To construct pET29/BoNT/A-33/A, a pUCBHB1/BoNT/A-33/A construct is digested with restriction endonucleases that 1) excise the insert comprising the open reading frame encoding BoNT/A-33/A; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-33/A. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding BoNT/A-33/A operably-linked to a carboxyl terminal polyhistidine affinity binding peptide.

A similar cloning strategy is used to make pET29 expression constructs comprising a polynucleotide molecule encoding for BoNT/B-33/A, BoNT/C1-33/A, BoNT/D-33/A, BoNT/E-33/A, BoNT/F-33/A, BoNT/G-33/A, TeNT-33/A, as well as the modified Clostridial toxin indicated above comprising amino acids 10-144 of SEQ ID NO: 9; amino acids 10-144 of SEQ ID NO: 10; amino acids 10-144 of SEQ ID NO: 11; amino acids 10-146 of SEQ ID NO: 12; amino acids 10-144 of SEQ ID NO: 13; amino acids 10-144 of SEQ ID NO: 14; amino acids 10-146 of SEQ ID NO: 15; amino acids 10-141 of SEQ ID NO: 16; amino acids 10-141 of SEQ ID NO: 17; amino acids 10-141 of SEQ ID NO: 18; 151-293 of SEQ ID NO: 10; 151-293 of SEQ ID NO: 11; 153-294 of SEQ ID NO: 12; 151-279 of SEQ ID NO: 13; 151-292 of SEQ ID NO: 14; 153-291 of SEQ ID NO: 15; 148-285 of SEQ ID NO: 16; 148-286 of SEQ ID NO: 17; 148-286 of SEQ ID NO: 18; 9-146 of SEQ ID NO: 19; 9-146 of SEQ ID NO: 20; 9-146 of SEQ ID NO: 21; 9-146 of SEQ ID NO: 22; 1050-1194 of SEQ ID NO: 23; 1050-1199 of SEQ ID NO: 24; 1050-1194 of SEQ ID NO: 25; 1049-1198 of SEQ ID NO: 26; 1049-1197 of SEQ ID NO: 27; 1049-1197 of SEQ ID NO: 28; 1014-1163 of SEQ ID NO: 29; 1016-1160 of SEQ ID NO: 30; 1017-1166 of SEQ ID NO: 31; and 1050-1199 of SEQ ID NO: 32.

Example 3

Construction of a Modified Clostridial Toxin Comprising a Non-Toxin Associated Protein Fold The following example illustrates how to make a modified Clostridial toxin comprising an enhanced targeting domain comprising a non-toxin associated protein fold.

A polynucleotide molecule encoding BoNT/A-17γ/A is synthesized using standard procedures (BlueHeron® Biotechnology, Bothell, Wash.), as described in Example 1. BoNT/A-17γ/A is a BoNT/A modified to replace amino acids 1237-1296 of SEQ ID NO: 1, a γ-fold from a BoNT/A β-trefoil domain, with amino acids 95 to 146 of SEQ ID NO: 19, a γ-fold from a HA-17 β-trefoil domain from a Clostridial botulinum serotype A strain. If desired, an expression optimized polynucleotide molecule encoding BoNT/A-17γ/A can be synthesized in order to improve expression in to a different organism, such as, e.g., an *Escherichia coli* strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for BoNT/B-17γ/A, a modified BoNT/B where amino acids 1223-1291 of SEQ ID NO: 2 are replaced with amino acids 95 to 146 of SEQ ID NO: 19; BoNT/C1-F18γ, a modified BoNT/C1 where amino acids 1230-1291 of SEQ ID NO: 3 are replaced with amino acids 95 to 146 of SEQ ID NO: 19; BoNT/D-17γ/A, a modified BoNT/D where amino acids 1219-1276 of SEQ ID NO: 4 are replaced with amino acids 95 to 146 of SEQ ID NO: 19; BoNT/E-17γ/A, a modified BoNT/E where amino acids 1199-1252 of SEQ ID NO: 5 are replaced with amino acids 95 to 146 of SEQ ID NO: 19; BoNT/F-17γ/A, a modified BoNT/F where amino acids 1222-1274 of SEQ ID NO: 6 are replaced with amino acids 95 to 146 of SEQ ID NO: 19; BoNT/G-17γ/A, a modified BoNT/G where amino acids 1231-1297 of SEQ ID NO: 7 are replaced with amino acids 95 to 146 of SEQ ID NO: 19; and TeNT-17γ/A, a modified TeNT where amino acids 1255-1315 of SEQ ID NO: 8 are replaced with amino acids 95 to 146 of SEQ ID NO: 19.

Similarly, the γ-fold from a HA-17/A β-trefoil domain can replace amino acids 1111-1162 of SEQ ID NO: 1, an α-fold from a BoNT/A β-trefoil domain; amino acids 1098-1147 of SEQ ID NO: 2, an α-fold from a BoNT/B β-trefoil domain; amino acids 1112-1150 of SEQ ID NO: 3, an α-fold from a BoNT/C1 trefoil domain; amino acids 1099-1137 of SEQ ID NO: 4, an α-fold from a BoNT/D β-trefoil domain; amino acids 1086-1129 of SEQ ID NO: 5, an α-fold from a BoNT/E β-trefoil domain; amino acids 1106-1152 of SEQ ID NO: 6, an α-fold from a BoNT/F β-trefoil domain; amino acids 1106-1153 of SEQ ID NO: 7, an α-fold from a BoNT/G β-trefoil domain; or amino acids 1128-1177 of SEQ ID NO: 8, an α-fold from a TeNT β-trefoil domain. Similarly, the γ-fold from a HA-17/Aβ-trefoil domain can replace amino acids 1179-1223 of SEQ ID NO: 1, a β-fold from a BoNT/A β-trefoil domain; amino acids 1166-1210 of SEQ ID NO: 2, a β-fold from a BoNT/B β-trefoil domain; amino acids 1167-1218 of SEQ ID NO: 3, a β-fold from a BoNT/C1 β-trefoil domain; amino acids 1154-1207 of SEQ ID NO: 4, a β-fold from a BoNT/D β-trefoil domain; amino acids 1147-1190 of SEQ ID NO: 5, a β-fold from a BoNT/E β-trefoil domain; amino acids 1172-1213 of SEQ ID NO: 6, a β-fold from a BoNT/F β-trefoil domain; amino acids 1173-1218 of SEQ ID NO: 7, a β-fold from a BoNT/G β-trefoil domain; or amino acids 1195-1240 of SEQ ID NO: 8, a β-fold from a TeNT β-trefoil domain.

Similarly, an α-fold, β-fold or γ-fold from a β-trefoil domain from a Clostridial toxin indicated above can be replaced with a HA-17 γ-fold comprising amino acids 95-146 of SEQ ID NO: 20, amino acids 95-146 of SEQ ID NO: 21, or amino acids 95-146 of SEQ ID NO: 22; a HA-33 γ-fold comprising amino acids 105-144 of SEQ ID NO: 9, amino acids 105-144 of SEQ ID NO: 10, amino acids 105-144 of SEQ ID NO: 11, amino acids 107-146 of SEQ ID NO: 12, amino acids 105-144 of SEQ ID NO: 13, amino acids 105-144 of SEQ ID NO: 14, amino acids 107-146 of SEQ ID NO: 15, amino acids 103-141 of SEQ ID NO: 16, amino acids 103-141 of SEQ ID NO: 17, amino acids 103-141 of SEQ ID NO: 18, amino acids 249-293 of SEQ ID NO: 9, amino acids 249-293 of SEQ ID NO: 10, amino acids 249-293 of SEQ ID NO: 11, amino acids 250-294 of SEQ ID NO: 12, amino acids 249-279 of SEQ ID NO: 13, amino acids 248-292 of SEQ ID NO: 14, amino acids 249-291 of SEQ ID NO: 15, amino acids 241-285 of SEQ ID NO: 16, amino acids 242-286 of SEQ ID NO: 17, or amino acids 242-286 of SEQ ID NO: 18; or a NTNH γ-fold comprising amino acids 1149-1194 of SEQ ID NO: 23, amino acids 1149-1199 of SEQ ID NO: 24, amino acids 1149-1194 of SEQ ID NO: 25, amino acids 1148-1198 of SEQ ID NO: 26, amino acids 1148-1197 of SEQ ID NO: 27, amino acids 1148-1197 of SEQ ID NO: 28, amino acids 1114-1163 of SEQ ID NO: 29, amino acids 1115-1160 of SEQ ID NO: 30, amino acids 1117-1166 of SEQ ID NO: 31, or amino acids 1150-1199 of SEQ ID NO: 32.

Likewise, an α-fold, β-fold or γ-fold from a β-trefoil domain from a Clostridial toxin indicated above can be replaced with a HA-17 α-fold comprising amino acids 9-50 of SEQ ID NO: 19, amino acids 9-50 of SEQ ID NO: 20, amino acids 9-50 of SEQ ID NO: 21, or amino acids 9-50 of SEQ ID NO: 22; a HA-33 α-fold comprising amino acids 10-54 of SEQ ID NO: 9, amino acids 10-54 of SEQ ID NO: 10, amino acids 10-54 of SEQ ID NO: 11, amino acids 10-56 of SEQ ID NO: 12, amino acids 10-54 of SEQ ID NO: 13, amino acids 10-54 of SEQ ID NO: 14, amino acids 10-56 of SEQ ID NO: 15, amino acids 10-54 of SEQ ID NO: 16, amino acids 10-54 of SEQ ID NO: 17, amino acids 10-54 of SEQ ID NO: 18, amino acids 151-195 of SEQ ID NO: 9, amino acids 151-195 of SEQ ID NO: 10, amino acids 151-195 of SEQ ID NO: 11, amino acids 153-197 of SEQ ID NO: 12, amino acids 151-195 of SEQ ID NO: 13, amino acids 151-195 of SEQ ID NO: 14, amino acids 153-197 of SEQ ID NO: 15, amino acids 148-190 of SEQ ID NO: 16, amino acids 148-190 of SEQ ID NO: 17, or amino acids 148-190 of SEQ ID NO: 18; or a NTNH α-fold comprising amino acids 1050-1097 of SEQ ID NO: 23, amino acids 1050-1097 of SEQ ID NO: 24, amino acids 1050-1097 of SEQ ID NO: 25, amino acids 1049-1096 of SEQ ID NO: 26, amino acids 1049-1096 of SEQ ID NO: 27, amino acids 1049-1096 of SEQ ID NO: 28, amino acids 1014-1061 of SEQ ID NO: 29, amino acids 1016-1063 of SEQ ID NO: 30, amino acids 1017-1064 of SEQ ID NO: 31, or amino acids 1050-1097 of SEQ ID NO: 32.

Further, an α-fold, β-fold or γ-fold from a β-trefoil domain from a Clostridial toxin indicated above can be replaced with a HA-17 β-fold comprising amino acids 55-91 of SEQ ID NO: 19, amino acids 55-91 of SEQ ID NO: 20, amino acids 55-91 of SEQ ID NO: 21, or amino acids 55-91 of SEQ ID NO: 22; a HA-33 β-fold comprising amino acids 60-100 of SEQ ID NO: 9, amino acids 60-100 of SEQ ID NO: 10, amino acids 60-100 of SEQ ID NO: 11, amino acids 62-102 of SEQ ID NO: 12, amino acids 60-100 of SEQ ID NO: 13, amino acids 60-100 of SEQ ID NO: 14, amino acids 62-102 of SEQ ID NO: 15, amino acids 60-98 of SEQ ID NO: 16, amino acids 60-98 of SEQ ID NO: 17, amino acids 60-98 of SEQ ID NO: 18, amino acids 200-242 of SEQ ID NO: 9, amino acids 200-242 of SEQ ID NO: 10, amino acids 200-242 of SEQ ID NO: 11, amino acids 202-243 of SEQ ID NO: 12, amino acids 200-242 of SEQ ID NO: 13, amino acids 200-241 of SEQ ID NO: 14, amino acids 200-242 of SEQ ID NO: 15, amino acids 195-234 of SEQ ID NO: 16, amino acids 195-235 of SEQ ID NO: 17, or amino acids 195-235 of SEQ ID NO: 18; or a NTNH β-fold comprising amino acids 1111-1138 of SEQ ID NO: 23, amino acids 1111-1139 of SEQ ID NO: 24, amino acids 1111-1138 of SEQ ID NO: 25, amino acids 1110-1138 of SEQ ID NO: 26, amino acids 1110-1138 of SEQ ID NO: 27, amino acids 1110-1138 of SEQ ID NO: 28, amino acids 1075-1103 of SEQ ID NO: 29, amino acids 1077-1104 of SEQ ID NO: 30, amino acids 1078-1106 of SEQ ID NO: 31, or amino acids 1111-1139 of SEQ ID NO: 32.

To construct pET29/BoNT/A-17γ/A, a pUCBHB1/BoNT/A-17γ/A construct is digested with restriction endonucleases that 1) excise the insert comprising the open reading frame encoding BoNT/A-17γ/A; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-17γ/A. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding BoNT/A-17γ/A operably-linked to a carboxyl terminal polyhistidine affinity binding peptide.

A similar cloning strategy is used to make pET29 expression constructs comprising a polynucleotide molecule encoding BoNT/B-17γ/A, BoNT/C1-17γ/A, BoNT/D-17γ/A, BoNT/E-17γ/A, BoNT/F-17γ/A, BoNT/G-17γ/A, TeNT-17γ/A, BoNT/A-33-1γ/A, BoNT/B-33-1γ/A, BoNT/C1-33-1γ/A, BoNT/D-33-1γ/A, BoNT/E-33-1γ/A, BoNT/F-33-1γ/A, BoNT/G-33-1γ/A, TeNT-33-1γ/A, BoNT/A-33-2γ/A, BoNT/B-33-2γ/A, BoNT/C1-33-2γ/A, BoNT/D-33-2γ/A, BoNT/E-33-2γ/A, BoNT/F-33-2γ/A, BoNT/G-33-2γ/A, TeNT-33-2γ/A, BoNT/B-NTNHγ/A, BoNT/B-NTNHγ/A, BoNT/C1-NTNHγ/A, BoNT/D-NTNHγ/A, BoNT/E-NTNHγ/A, BoNT/F-NTNHγ/A, BoNT/G-NTNHγ/A, TeNT-NTNHγ/A, BoNT/A-17α/A, BoNT/B-17α/A, BoNT/C1-17α/A, BoNT/D-17α/A, BoNT/E-17α/A, BoNT/F-17α/A, BoNT/G-17α/A, TeNT-17α/A, BoNT/A-33-1α/A, BoNT/B-33-1α/A, BoNT/C1-33-1α/A, BoNT/D-33-1α/A, BoNT/E-33-1α/A, BoNT/F-33-1α/A, BoNT/G-33-1α/A, TeNT-33-1α/A, BoNT/A-33-2α/A, BoNT/B-33-2α/A, BoNT/C1-33-2α/A, BoNT/D-33-2α/A, BoNT/E-33-2α/A, BoNT/F-33-2α/A, BoNT/G-33-2α/A, TeNT-33-2α/A, BoNT/B-NTNHα/A, BoNT/B-NTNHα/A, BoNT/C1-NTNHα/A, BoNT/D-NTNHα/A, BoNT/E-NTNHα/A, BoNT/F-NTNHα/A, BoNT/G-NTNHα/A, TeNT-NTNHα, BoNT/A-17β/A, BoNT/B-17β/A, BoNT/C1-17β/A, BoNT/D-17β/A, BoNT/E-17β/A, BoNT/F-17β/A, BoNT/G-17β/A, TeNT-17β/A, BoNT/A-33-1β/A, BoNT/B-33-1β/A, BoNT/C1-33-1β/A, BoNT/D-33-1β/A, BoNT/E-33-1β/A, BoNT/F-33-1β/A, BoNT/G-33-1β/A, TeNT-33-1β/A, BoNT/A-33-2β/A, BoNT/B-33-2β/A, BoNT/C1-33-2β/A, BoNT/D-33-2β/A, BoNT/E-33-2β/A, BoNT/F-33-2β/A, BoNT/G-33-2β/A, TeNT-33-2β/A, BoNT/B-NTNHβ/A, BoNT/B-NTNHβ/A, BoNT/C1-NTNHβ/A, BoNT/D-NTNHβ/A, BoNT/E-NTNHβ/A, BoNT/F-NTNHβ/A, BoNT/G-NTNHβ/A, TeNT-NTNHβ, A similar cloning strategy is also used to make pET29 expression constructs comprising a polynucleotide molecule encoding a modified Clostridial toxin indicated above that has its α-fold or β-fold replaced by amino acids comprising a HA-17 α-fold, β-fold or γ-fold; amino acids comprising a HA-33 la-fold, 1β-fold, 1γ-fold, 2α-fold, 2β-fold, or 2γ-fold; or amino acids comprising a NTNH α-fold, β-fold or γ-fold.

Example 4

Construction of a Modified Clostridial Toxin Comprising a FGF that Selectively Binds to a FGFR3

The following example illustrates how to make a modified Clostridial toxin comprising an enhanced targeting domain comprising a FGF that selectively binds to a FGFR3.

A polynucleotide molecule encoding BoNT/A-F18 is synthesized using standard procedures (BlueHeron® Biotechnology, Bothell, Wash.), as described in Example 1. BoNT/A-F18 is a BoNT/A modified to replace amino acids 1111-1296 of SEQ ID NO: 1, a BoNT/A β-trefoil domain, with amino acids 54 to 183 of SEQ ID NO: 39, a FGF-18 β-trefoil domain. If desired, an expression optimized polynucleotide molecule encoding BoNT/A-F18 can be synthesized in order to improve expression in to a different organism, such as, e.g., an *Escherichia coli* strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for BoNT/B-F18, a modified BoNT/B where amino acids 1098-1291 of SEQ ID NO: 2 are replaced with amino acids 54 to 183 of SEQ ID NO: 39; BoNT/C1-F18, a modified BoNT/C1 where amino acids 1112-1291 of SEQ ID NO: 3 are replaced with amino acids 54 to 183 of SEQ ID NO: 39; BoNT/D-F18, a modified BoNT/D where amino acids 1099-1276 of SEQ ID NO: 4 are replaced with amino acids 54 to 183 of SEQ ID NO: 39; BoNT/E-F18, a modified BoNT/E where amino acids 1086-1252 of SEQ ID NO: 5 are replaced with amino acids 54 to 183 of SEQ ID NO: 39; BoNT/F-F18, a modified BoNT/F where amino acids 1106-1274 of SEQ ID NO: 6 are replaced with amino acids 54 to 183 of SEQ ID NO: 39; BoNT/G-F18, a modified BoNT/G where amino acids 1106-1297 of SEQ ID NO: 7 are replaced with amino acids 54 to 183 of SEQ ID NO: 39; and TeNT-F18, a modified TeNT where amino acids 1128-1315 of SEQ ID NO: 8 are replaced with amino acids 54 to 183 of SEQ ID NO: 39. Similarly, the β-trefoil domain from a Clostridial toxin indicated above can be replaced with a FGF β-trefoil domain comprising amino acids 26-155 of SEQ ID NO: 33; amino acids 29-155 of SEQ ID NO: 34; amino acids 83-206 of SEQ ID NO: 35; amino acids 43-172 of SEQ ID NO: 36; amino acids 63-196 of SEQ ID NO: 37; amino acids 55-183 of SEQ ID NO: 38; and amino acids 54-183 of SEQ ID NO: 39.

To construct pET29/BoNT/A-F18, a pUCBHB1/BoNT/A-F18 construct is digested with restriction endonucleases that 1) excise the insert comprising the open reading frame encoding BoNT/A-F18; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-F18.

The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding BoNT/A-F18 operably-linked to a carboxyl terminal polyhistidine affinity binding peptide.

A similar cloning strategy is used to make pET29 expression constructs comprising a polynucleotide molecule encoding for BoNT/B-F18, BoNT/C1-F18, BoNT/D-F18, BoNT/E-F18, BoNT/F-F18, BoNT/G-F18, TeNT-F18, as well as the modified Clostridial toxin indicated above comprising amino acids 26-155 of SEQ ID NO: 33; amino acids 29-155 of SEQ ID NO: 34; amino acids 83-206 of SEQ ID NO: 35; amino acids 43-172 of SEQ ID NO: 36; amino acids 63-196 of SEQ ID NO: 37; amino acids 55-183 of SEQ ID NO: 38; and amino acids 54-183 of SEQ ID NO: 39.

Example 5

Construction of a Modified Clostridial Toxin Comprising a FGF Fold that Selectively Binds to a FGFR3

The following example illustrates how to make a modified Clostridial toxin comprising an enhanced targeting domain comprising a FGF fold that selectively binds to a FGFR3.

A polynucleotide molecule encoding BoNT/A-F18γ is synthesized using standard procedures (BlueHeron® Biotechnology, Bothell, Wash.), as described in Example 1. BoNT/A-F18γ is a BoNT/A modified to replace amino acids 1237-1296 of SEQ ID NO: 1, a γ-fold from a BoNT/A β-trefoil domain, with amino acids 138 to 183 of SEQ ID NO: 39, a γ-fold from a FGF-18 β-trefoil domain. If desired, an expression optimized polynucleotide molecule encoding BoNT/A-F18γ can be synthesized in order to improve expression in to a different organism, such as, e.g., an *Escherichia coli* strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for BoNT/B-F18γ, a modified BoNT/B where amino acids 1223-1291 of SEQ ID NO: 2 are replaced with amino acids 138 to 183 of SEQ ID NO: 39; BoNT/C1-F18γ, a modified BoNT/C1 where amino acids 1230-1291 of SEQ ID NO: 3 are replaced with amino acids 138 to 183 of SEQ ID NO: 39; BoNT/D-F18γ, a modified BoNT/D where amino acids 1219-1276 of SEQ ID NO: 4 are replaced with amino acids 138 to 183 of SEQ ID NO: 39; BoNT/E-F18γ, a modified BoNT/E where amino acids 1199-1252 of SEQ ID NO: 5 are replaced with amino acids 138 to 183 of SEQ ID NO: 39; BoNT/F-F18γ, a modified BoNT/F where amino acids 1222-1274 of SEQ ID NO: 6 are replaced with amino acids 138 to 183 of SEQ ID NO: 39; BoNT/G-F18γ, a modified BoNT/G where amino acids 1231-1297 of SEQ ID NO: 7 are replaced with amino acids 138 to 183 of SEQ ID NO: 39; and TeNT-F18γ, a modified TeNT where amino acids 1255-1315 of SEQ ID NO: 8 are replaced with amino acids 138 to 183 of SEQ ID NO: 39. Similarly, the γ-fold from a FGF-18 β-trefoil domain can replace amino acids 1111-1162 of SEQ ID NO: 1, an α-fold from a BoNT/A β-trefoil domain; amino acids 1098-1147 of SEQ ID NO: 2, an α-fold from a BoNT/B β-trefoil domain; amino acids 1112-1150 of SEQ ID NO: 3, an α-fold from a BoNT/C1 β-trefoil domain; amino acids 1099-1137 of SEQ ID NO: 4, an α-fold from a BoNT/D β-trefoil domain; amino acids 1086-1129 of SEQ ID NO: 5, an α-fold from a BoNT/E β-trefoil domain; amino acids 1106-1152 of SEQ ID NO: 6, an α-fold from a BoNT/F β-trefoil domain; amino acids 1106-1153 of SEQ ID NO: 7, an α-fold from a BoNT/G β-trefoil domain; or amino acids 1128-1177 of SEQ ID NO: 8, an α-fold from a TeNT β-trefoil domain. Similarly, the γ-fold from a FGF-18 β-trefoil domain can replace amino acids 1179-1223 of SEQ ID NO: 1, a β-fold from a BoNT/A 13-trefoil domain; amino acids 1166-1210 of SEQ ID NO: 2, a β-fold from a BoNT/B β-trefoil domain; amino acids 1167-1218 of SEQ ID NO: 3, a β-fold from a BoNT/C1 β-trefoil domain; amino acids 1154-1207 of SEQ ID NO: 4, a β-fold from a BoNT/D β-trefoil domain; amino acids 1147-1190 of SEQ ID NO: 5, a β-fold from a BoNT/E β-trefoil domain; amino acids 1172-1213 of SEQ ID NO: 6, a β-fold from a BoNT/F trefoil domain; amino acids 1173-1218 of SEQ ID NO: 7, a β-fold from a BoNT/G β-trefoil domain; or amino acids 1195-1240 of SEQ ID NO: 8, a β-fold from a TeNT β-trefoil domain.

Similarly, an α-fold, β-fold or γ-fold from a β-trefoil domain from a Clostridial toxin indicated above can be replaced with a FGF γ-fold comprising amino acids 109-155 of SEQ ID NO: 33; amino acids 115-155 of SEQ ID NO: 34; amino acids 166-206 of SEQ ID NO: 35; amino acids 127-172 of SEQ ID NO: 36; amino acids 148-196 of SEQ ID NO: 37; or amino acids 138-183 of SEQ ID NO: 38. Likewise, an α-fold, β-fold or γ-fold from a β-trefoil domain from a Clostridial toxin indicated above can be replaced with a FGF α-fold comprising amino acids 26-64 of SEQ ID NO: 33; amino acids 29-67 of SEQ ID NO: 34; amino acids 83-121 of SEQ ID NO: 35; amino acids 43-80 of SEQ ID NO: 36; amino acids 63-100 of SEQ ID NO: 37; amino acids 55-91 of SEQ ID NO: 38; or amino acids 54-91 of SEQ ID NO: 39. Further, an α-fold, β-fold or γ-fold from a β-trefoil domain from a Clostridial toxin indicated above can be replaced with a FGF β-fold comprising amino acids 68-105 of SEQ ID NO: 33; amino acids 71-111 of SEQ ID NO: 34; amino acids 125-162 of SEQ ID NO: 35; amino acids 84-123 of SEQ ID NO: 36; amino acids 104-144 of SEQ ID NO: 37; amino acids 95-134 of SEQ ID NO: 38; or amino acids 95-134 of SEQ ID NO: 39.

To construct pET29/BoNT/A-F18, a pUCBHB1/BoNT/A-F18γ construct is digested with restriction endonucleases that 1) excise the insert comprising the open reading frame encoding BoNT/A-F18γ; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-F18γ. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding BoNT/A-F18γ operably-linked to a carboxyl terminal polyhistidine affinity binding peptide.

A similar cloning strategy is used to make pET29 expression constructs comprising a polynucleotide molecule encoding for BoNT/B-F18γ, BoNT/C1-F18γ, BoNT/D-F18γ, BoNT/E-F18γ, BoNT/F-F18γ, BoNT/G-F18γ, TeNT-F18γ, BoNT/A-F18α, BoNT/B-F18α, BoNT/C1-F18α, BoNT/D-F18α, BoNT/E-F18α, BoNT/F-F18α, BoNT/G-F18α, TeNT-F18α, BoNT/A-F18β, BoNT/B-F18β, BoNT/C1-F18β, BoNT/D-F18β, BoNT/E-F18β, BoNT/F-F18β, BoNT/G-F18β, or TeNT-F18β, as well as the modified Clostridial toxin indicated above comprising amino acids 109-155 of SEQ ID NO: 33; amino acids 115-155 of SEQ ID NO: 34; amino acids 166-206 of SEQ ID NO: 35; amino acids 127-172 of SEQ ID NO: 36; amino acids 148-196 of SEQ ID NO: 37; amino acids 138-183 of SEQ ID NO: 38; amino acids 26-64 of SEQ ID NO: 33; amino acids 29-67 of SEQ ID NO: 34; amino acids 83-121 of SEQ ID NO: 35; amino acids 43-80 of SEQ ID NO: 36; amino acids 63-100 of SEQ ID NO: 37; amino acids 55-91 of SEQ ID NO: 38; amino acids 54-91 of SEQ ID NO: 39; amino acids 68-105 of SEQ ID NO: 33; amino acids 71-111 of SEQ ID NO: 34; amino acids 125-162 of SEQ ID NO: 35; amino acids 84-123 of SEQ ID NO: 36; amino acids 104-144 of SEQ ID NO: 37; amino acids 95-134 of SEQ ID NO: 38; or amino acids 95-134 of SEQ ID NO: 39.

Example 6

Expression of Modified Clostridial Toxins in a Bacterial Cell

The following example illustrates a procedure useful for expressing any of the modified Clostridial toxins disclosed in the present specification in a bacterial cell.

An expression construct, such as, e.g., any of the expression constructs in Examples 1-5, is introduced into chemically competent *E. coli* BL21 (DE3) cells (Invitrogen, Inc, Carlsbad, Calif.) using a heat-shock transformation protocol. The heat-shock reaction is plated onto 1.5% Luria-Bertani agar plates (pH 7.0) containing 50 μg/mL of Kanamycin and is placed in a 37° C. incubator for overnight growth. Kanamycin-resistant colonies of transformed *E. coli* containing the expression construct are used to inoculate a baffled flask containing 3.0 mL of PA-0.5G media containing 50 μg/mL of Kanamycin which is then placed in a 37° C. incubator, shaking at 250 rpm, for overnight growth. The resulting overnight starter culture is in turn used to inoculate a 3 L baffled flask containing ZYP-5052 autoinducing media containing 50 μg/mL of Kanamycin at a dilution of 1:1000. Culture volumes ranged from about 600 mL (20% flask volume) to about 750 mL (25% flask volume). These cultures are grown in a 37° C. incubator shaking at 250 rpm for approximately 5.5 hours and are then transferred to a 16° C. incubator shaking at 250 rpm for overnight expression. Cells are harvested by centrifugation (4,000 rpm at 4° C. for 20-30 minutes) and are used immediately, or stored dry at −80° C. until needed.

Example 7

Purification and Quantification of Modified Clostridial Toxins

The following example illustrates methods useful for purification and quantification of any modified Clostridial toxins disclosed in the present specification.

For immobilized metal affinity chromatography (IMAC) protein purification, *E. coli* BL21 (DE3) cell pellets used to express a modified Clostridial toxin, as described in Example 7, are resuspended in Column Binding Buffer (25 mM N-(2-hydroxyethyl)piperazine-N'-(2-ethanesulfonic acid) (HEPES), pH 7.8; 500 mM sodium chloride; 10 mM imidazole; 2× Protease Inhibitor Cocktail Set III (EMD Biosciences-Calbiochem, San Diego Calif.); 5 units/mL of Benzonase (EMD Biosciences-Novagen, Madison, Wis.); 0.1% (v/v) Triton-X® 100, 4-octylphenol polyethoxylate; 10% (v/v) glycerol), and then are transferred to a cold Oakridge centrifuge tube. The cell suspension is sonicated on ice (10-12 pulses of 10 seconds at 40% amplitude with 60 seconds cooling intervals on a Branson Digital Sonifier) in order to lyse the cells and then is centrifuged (16,000 rpm at 4° C. for 20 minutes) to clarify the lysate. An immobilized metal affinity chromatography column is prepared using a 20 mL Econo-Pac column support (Bio-Rad Laboratories, Hercules, Calif.) packed with 2.5-5.0 mL of TALON™ SuperFlow $Co^{2+}$ affinity resin (BD Biosciences-Clontech, Palo Alto, Calif.), which is then equilibrated by rinsing with 5 column volumes of deionized, distilled water, followed by 5 column volumes of Column Binding Buffer. The clarified lysate is applied slowly to the equilibrated column by gravity flow (approximately 0.25-0.3 mL/minute). The column is then washed with 5 column volumes of Column Wash Buffer (N-(2-hydroxyethyl)piperazine-N'-(2-ethanesulfonic acid) (HEPES), pH 7.8; 500 mM sodium chloride; 10 mM imidazole; 0.1% (v/v) Triton-X® 100, 4-octylphenol polyethoxylate; 10% (v/v) glycerol). The modified Clostridial toxin is eluted with 20-30 mL of Column Elution Buffer (25 mM N-(2-hydroxyethyl)piperazine-N'-(2-ethanesulfonic acid) (HEPES), pH 7.8; 500 mM sodium chloride; 500 mM imidazole; 0.1% (v/v) Triton-X® 100, 4-octylphenol polyethoxylate; 10% (v/v) glycerol) and is collected in approximately twelve 1 mL fractions. The amount of modified Clostridial toxin contained in each elution fraction is determined by a Bradford dye assay. In this procedure, 20 μL aliquots of each 1.0 mL fraction is combined with 200 μL of Bio-Rad Protein Reagent (Bio-Rad Laboratories, Hercules, Calif.), diluted 1 to 4 with deionized, distilled water, and then the intensity of the colorimetric signal is measured using a spectrophotometer. The five fractions with the strongest signal are considered the elution peak and are combined together. Total protein yield is determined by estimating the total protein concentration of the pooled peak elution fractions using bovine gamma globulin as a standard (Bio-Rad Laboratories, Hercules, Calif.).

For purification of a modified Clostridial toxin using a FPLC desalting column, a HiPrep™ 26/10 size exclusion column (Amersham Biosciences, Piscataway, N.J.) is pre-equilibrated with 80 mL of 4° C. Column Buffer (50 mM sodium phosphate, pH 6.5). After the column is equilibrated, a modified Clostridial toxin sample is applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted modified Clostridial toxin sample is collected as a single fraction of approximately 7-12 mL.

For purification of a modified Clostridial toxin using a FPLC ion exchange column, a modified Clostridial toxin sample that has been desalted following elution from an IMAC column is applied to a 1 mL Q1™ anion exchange column (Bio-Rad Laboratories, Hercules, Calif.) using a BioLogic DuoFlow chromatography system (Bio-Rad Laboratories, Hercules, Calif.). The sample is applied to the column in 4° C. Column Buffer (50 mM sodium phosphate, pH 6.5) and is eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of modified Clostridial toxin from the column is monitored at 280, 260, and 214 nm, and peaks absorbing above a minimum threshold (0.01 au) at 280 nm are collected. Most of the modified Clostridial toxin will elute at a sodium chloride concentration of approximately 100 to 200 mM. Average total yields of modified Clostridial toxin will be determined by a Bradford assay.

Expression of a modified Clostridial toxin is analyzed by polyacrylamide gel electrophoresis. Samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels are stained with SYPRO® Ruby (Bio-Rad Laboratories, Hercules, Calif.) and the separated polypeptides are imaged using a Fluor-S MAX MultiImager (Bio-Rad Laboratories, Hercules, Calif.) for quantification of modified Clostridial toxin expression levels. The size and amount of modified Clostridial toxin is determined by comparison to MagicMark™ protein molecular weight standards (Invitrogen, Inc, Carlsbad, Calif.).

Expression of modified Clostridial toxin is also analyzed by Western blot analysis. Protein samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated polypeptides are transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes are blocked by incubating at room temperature for 2 hours in a solution containing 25 mM Tris-Buffered Saline (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes are incubated at 4° C. for overnight in Tris-Buffered Saline TWEEN-20® (25 mM Tris-Buffered Saline, 0.1% TWEEN-20®, polyoxyethylene (20) sorbitan monolaureate) containing appropriate primary antibodies as a probe. Primary antibody probed blots are washed three times for 15 minutes each time in Tris-Buffered Saline TWEEN-20®. Washed membranes are incubated at room temperature for 2 hours in Tris-Buffered Saline TWEEN-20® containing an appropriate immunoglobulin G antibody conjugated to horseradish peroxidase as a secondary antibody. Secondary antibody-probed blots are washed three times for 15 minutes each time in Tris-Buffered Saline TWEEN-20®. Signal detection of the labeled modified Clostridial toxin are visualized using the ECL Plus™ Western Blot Detection System (Amersham Biosciences, Piscataway, N.J.) and are imaged with a Typhoon 9410 Variable Mode Imager (Amersham Biosciences, Piscataway, N.J.) for quantification of modified Clostridial toxin expression levels.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

What is claimed:

1. A modified di-chain Clostridial toxin comprising:

a) a first chain comprising a Clostridial toxin enzymatic domain that executes an enzymatic target modification step of a Clostridial toxin intoxication process; and, b) a second chain comprising a Clostridial toxin translocation domain that executes a translocation step of a Clostridial toxin intoxication process and an enhanced targeting domain comprising a Fibroblast Growth Factor (FGF) β-trefoil domain that selectively binds a Fibroblast Growth Factor Receptor-3 (FGFR3);

wherein the modification is a substitution of a Clostridial toxin β-trefoil domain with the Fibroblast Growth Factor (FGF) β-trefoil domain; and wherein the modified Clostridial toxin exhibits enhanced binding activity for an endogenous Clostridial toxin receptor system relative to the binding activity of a Clostridial toxin without the modification.

2. A polynucleotide molecule encoding the modified Clostridial toxin according to claim 1.

3. An expression vector comprising the polynucleotide molecule according to claim 2.

* * * * *